US011945856B2

(12) United States Patent
O'Connor-McCourt et al.

(10) Patent No.: US 11,945,856 B2
(45) Date of Patent: Apr. 2, 2024

(54) ACTIVIN RECEPTOR TYPE IIB VARIANTS AND USES THEREOF

(71) Applicant: 35PHARMA Inc., Montreal (CA)

(72) Inventors: Maureen O'Connor-McCourt, Montreal (CA); Vannakambadi K. Ganesh, Montreal (CA); Gilles Tremblay, Montreal (CA); Gauthier Schang, Montreal (CA)

(73) Assignee: 35PHARMA Inc., Montreal (CA)

( * ) Notice: Subject to any disclaimer, the term of this patent is extended or adjusted under 35 U.S.C. 154(b) by 0 days.

(21) Appl. No.: 18/160,787

(22) Filed: Jan. 27, 2023

(65) Prior Publication Data

US 2023/0287084 A1 Sep. 14, 2023

Related U.S. Application Data

(60) Provisional application No. 63/420,999, filed on Oct. 31, 2022, provisional application No. 63/416,852, filed on Oct. 17, 2022, provisional application No. 63/397,773, filed on Aug. 12, 2022, provisional application No. 63/304,478, filed on Jan. 28, 2022.

(51) Int. Cl.
*C07K 14/71* (2006.01)
*A61P 9/12* (2006.01)

(52) U.S. Cl.
CPC ................ *C07K 14/71* (2013.01); *A61P 9/12* (2018.01); *C07K 2319/30* (2013.01)

(58) Field of Classification Search
CPC ........ C07K 14/71; C07K 2319/30; A61P 9/12
See application file for complete search history.

(56) References Cited

U.S. PATENT DOCUMENTS

| | | | |
|---|---|---|---|
| 5,693,607 | A | 12/1997 | Segarini et al. |
| 7,612,041 | B2 | 11/2009 | Knopf et al. |
| 7,709,605 | B2 | 5/2010 | Knopf et al. |
| 7,842,663 | B2 | 11/2010 | Knopf et al. |
| 7,951,771 | B2 | 5/2011 | Knopf et al. |
| 7,988,973 | B2 | 8/2011 | Sherman |
| 8,007,809 | B2 | 8/2011 | Sherman |
| 8,058,229 | B2 | 11/2011 | Seehra et al. |
| 8,216,997 | B2 | 7/2012 | Seehra et al. |
| 8,252,900 | B2 | 8/2012 | Knopf et al. |
| 8,318,135 | B2 | 11/2012 | O'Connor-McCourt et al. |
| 8,343,933 | B2 | 1/2013 | Knopf et al. |
| 8,361,957 | B2 | 1/2013 | Seehra et al. |
| 8,629,109 | B2 | 1/2014 | Knopf et al. |
| 8,658,135 | B2 | 2/2014 | O'Connor-McCourt et al. |
| 8,703,927 | B2 | 4/2014 | Seehra et al. |
| 8,815,247 | B2 | 8/2014 | Govindappa et al. |
| 8,895,016 | B2 | 11/2014 | Sherman et al. |
| 9,138,459 | B2 | 9/2015 | Knopf et al. |
| 9,163,075 | B2 | 10/2015 | Knopf et al. |
| 9,399,669 | B2 | 7/2016 | Knopf et al. |
| 9,439,945 | B2 | 9/2016 | Seehra et al. |
| 9,932,379 | B2 | 4/2018 | Seehra et al. |
| 10,131,700 | B2 | 11/2018 | Seehra et al. |
| 10,259,861 | B2 | 4/2019 | Knopf et al. |
| 10,550,170 | B2 | 2/2020 | Sherman et al. |
| 10,689,427 | B2 | 6/2020 | Seehra et al. |
| 10,829,532 | B2 | 11/2020 | Seehra et al. |
| 11,524,990 | B2 | 12/2022 | Sherman et al. |
| 2005/0203022 | A1 | 9/2005 | Gotwals et al. |
| 2007/0244042 | A1 | 10/2007 | Sun et al. |
| 2015/0056199 | A1 | 2/2015 | Kumar et al. |
| 2015/0225483 | A1 | 8/2015 | Lo |
| 2017/0291935 | A1 | 10/2017 | Sherman et al. |
| 2018/0148491 | A1* | 5/2018 | Han ..................... C07K 14/705 |
| 2020/0055919 | A1 | 2/2020 | Kumar et al. |
| 2020/0071383 | A1 | 3/2020 | Sherman et al. |
| 2020/0407415 | A1 | 12/2020 | Seehra et al. |
| 2022/0306724 | A1 | 9/2022 | Kumar et al. |
| 2023/0079602 | A1 | 3/2023 | Seehra et al. |
| 2023/0087128 | A1 | 3/2023 | Seehra et al. |
| 2023/0129812 | A1 | 4/2023 | Kumar |
| 2023/0183319 | A1 | 6/2023 | Kumar et al. |

FOREIGN PATENT DOCUMENTS

| | | | |
|---|---|---|---|
| EP | 3523328 | A1 | 8/2019 |
| EP | 3737406 | A1 | 11/2020 |
| EP | 4100430 | A1 | 12/2022 |

(Continued)

OTHER PUBLICATIONS

Abdulkadyrov et al., "Sotatercept in patients with osteolytic lesions of multiple myeloma", Br J Haematol. Jun. 2014; 165(6): 814-823. Epub Mar. 21, 2014.
Austin and Lloyd, "Genetics and Mediators in Pulmonary Arterial Hypertension", Clinics in Chest Medicine Mar. 2007; 28(1): 43-57.
Calvier et al., "LRP1 Deficiency in Vascular SMC Leads To Pulmonary Arterial Hypertension That Is Reversed By PPARγ Activation", Circ Res. Jun. 7, 2019; 124(12): 1778-1785. Epub Apr. 26, 2019.
Campbell et al., "Myostatin Inhibitor ACE-031 Treatment of Ambulatory Boys With Duchenne Muscular Dystrophy: Results of a Randomized, Placebo-Controlled Clinical Trial", Muscle Nerve. Apr. 2017; 55(4): 458-464. Epub Dec. 23, 2016.
Cappellini et al., "Sotatercept, a novel transforming growth factor ß ligand trap, improves anemia in ß-thalassemia: a phase II, open-label, dose-finding study", Haematologica. Mar. 2019; 104(3): 477-484. Epub Oct. 18, 2018.
Coyne et al., "Sotatercept Safety and Effects on Hemoglobin, Bone, and Vascular Calcification", Kidney Int Rep. Aug. 13, 2019; 4(11): 1585-1597. eCollection Nov. 2019.

(Continued)

*Primary Examiner* — Li N Komatsu
(74) *Attorney, Agent, or Firm* — COOLEY LLP

(57) ABSTRACT

There are provided polypeptides that include an Activin receptor type IIB (ActRIIB) ectodomain (ECD) variant. In some embodiments, a polypeptide of the disclosure includes an ActRIIB-ECD variant fused to an Fc domain moiety. The disclosure also provides pharmaceutical compositions and methods of using the polypeptides to treat diseases and conditions associated with TGFβ superfamily ligand signaling, such as pulmonary hypertension, fibrosis, muscle weakness and atrophy, metabolic disorders and/or cardiometabolic disease, bone damage, and/or low red blood cell levels (such as anemia).

33 Claims, 132 Drawing Sheets

Specification includes a Sequence Listing.

(56) References Cited

FOREIGN PATENT DOCUMENTS

| | | | |
|---|---|---|---|
| EP | 4100431 | A1 | 12/2022 |
| EP | 4121078 | A1 | 1/2023 |
| EP | 4121088 | A1 | 1/2023 |
| EP | 4221736 | A1 | 8/2023 |
| WO | WO-0183525 | A2 | 11/2001 |
| WO | WO-2005028517 | A2 | 3/2005 |
| WO | WO-2008113185 | A1 | 9/2008 |
| WO | WO-2008157367 | A1 | 12/2008 |
| WO | WO-2010031168 | A1 | 3/2010 |
| WO | WO-2010099219 | A2 | 9/2010 |
| WO | WO-2012071649 | A1 | 6/2012 |
| WO | WO-2012142515 | A2 | 10/2012 |
| WO | WO-2013000234 | A1 | 1/2013 |
| WO | WO-2017037634 | A1 | 3/2017 |
| WO | WO-2017091706 | A1 | 6/2017 |
| WO | WO-2018067874 | A1 | 4/2018 |
| WO | WO-2018158727 | A1 | 9/2018 |
| WO | WO-2019140283 | A1 | 7/2019 |
| WO | WO-2021158675 | A1 | 8/2021 |
| WO | WO-2021158695 | A1 | 8/2021 |
| WO | WO-2021189010 | A1 | 9/2021 |
| WO | WO-2021189019 | A1 | 9/2021 |
| WO | WO-2022072882 | A1 | 4/2022 |
| WO | WO-2022150590 | A1 | 7/2022 |
| WO | WO-2022271571 | A1 | 12/2022 |
| WO | WO-2022271716 | A2 | 12/2022 |
| WO | WO-2023022968 | A2 | 2/2023 |
| WO | WO-2023023345 | A2 | 2/2023 |

OTHER PUBLICATIONS

Desroches-Castan et al., "BMP9 and BMP10: Two close vascular quiescence partners that stand out", Dev Dyn. Jan. 2022; 251(1): 158-177.

Humbert et al., "Sotatercept for the Treatment of Pulmonary Arterial Hypertension", N Engl J Med. Apr. 1, 2021; 384(13): 1204-1215.

Humbert, Marc, "Update in Pulmonary Hypertension 2008", Am J Respir Crit Care Med. Apr. 15, 2009; 179(8): 650-656.

International Search Report and Written Opinion for International Application No. PCT/CA2023/050116 dated Apr. 5, 2023, 18 pages.

Invitation to Pay for International Application No. PCT/CA2023/050116 dated Feb. 15, 2023, 3 pages.

Komrokji et al., "Sotatercept with long-term extension for the treatment of anaemia in patients with lower-risk myelodysplastic syndromes: a phase 2, dose-ranging trial", Lancet Haematol. Feb. 2018; 5(2): e63-e72. Epub Jan. 10, 2018.

Li et al., "Elevated Plasma Connective Tissue Growth Factor Levels in Children with Pulmonary Arterial Hypertension Associated with Congenital Heart Disease", Pediatr Cardiol. Apr. 2016; 37(4): 714-721. Epub Dec. 29, 2015.

Pi et al., "Vascular Endothelial Cell-Specific Connective Tissue Growth Factor (CTGF) Is Necessary for Development of Chronic Hypoxia-Induced Pulmonary Hypertension", Front Physiol. Feb. 27, 2018; 9: 138, 13 pages. eCollection 2018.

Quarck and Perros, "Rescuing BMPR2-driven endothelial dysfunction in PAH: a novel treatment strategy for the future?", Stem Cell Investig. Jun. 14, 2017; 4: 56, 3 pages. eCollection 2017.

Raftopoulos et al., "Sotatercept (ACE-011) for the treatment of chemotherapy-induced anemia in patients with metastatic breast cancer or advanced or metastatic solid tumors treated with platinum-based chemotherapeutic regimens: results from two phase 2 studies", Support Care Cancer Apr. 2016; 24(4): 1517-1525. Epub Sep. 14, 2015.

Ruckle et al., "Single-Dose, Randomized, Double-Blind, Placebo-Controlled Study of ACE-011 (ActRIIA-IgG1) in Postmenopausal Women", J Bone Miner Res. Apr. 2009; 24(4): 744-752.

Ryanto et al., "An endothelial activin A-bone morphogenetic protein receptor type 2 link is overdriven in pulmonary hypertension", Nature Communications. Mar. 19, 2021; 12(1): 1720, 14 pages.

Sevilla-Pérez et al., "Shroom expression is attenuated in pulmonary arterial hypertension", Eur Respir J. Oct. 2008; 32(4): 871-880. Epub Jun. 11, 2008.

Sherman et al., "Multiple-Dose, Safety, Pharmacokinetic, and Pharmacodynamic Study of Sotatercept (ActRIIA-IgG1), a Novel Erythropoietic Agent, in Healthy Postmenopausal Women", J Clin Pharmacol. Nov. 2013; 53(11): 1121-1130. Epub Sep. 9, 2013.

Tam et al., "Selective deletion of connective tissue growth factor attenuates experimentally-induced pulmonary fibrosis and pulmonary arterial hypertension", Int J Biochem Cell Biol. May 2021; 134: 105961, 12 pages. Epub Mar. 1, 2021.

Yung et al., "ACTRIIA-Fc rebalances activin/GDF versus BMP signaling in pulmonary hypertension", Sci Transl Med. May 13, 2020; 12(543): eaaz5660, 13 pages.

* cited by examiner

Activin A + GDF-11

Activin A + GDF-8

SEQUENCE LISTING

```
Sequence total quantity: 345
SEQ ID NO: 1            moltype = AA  length = 19
FEATURE                 Location/Qualifiers
source                  1..19
                        mol_type = protein
                        organism = synthetic construct
SEQUENCE: 1
MDWTWRILFL VAAATGTHA                                                19

SEQ ID NO: 2            moltype = AA  length = 107
FEATURE                 Location/Qualifiers
source                  1..107
                        mol_type = protein
                        organism = synthetic construct
SEQUENCE: 2
ETRECIYYNA NWELERTNQS GLERCEGEQD KRLHCYASWR NSSGTIELVK KGCWLDDFNC  60
YDRQECVATE ENPQVYFCCC EGNFCNERFT HLPEAGGPEV TYEPPPT                 107

SEQ ID NO: 3            moltype = AA  length = 116
FEATURE                 Location/Qualifiers
source                  1..116
                        mol_type = protein
                        organism = synthetic construct
SEQUENCE: 3
ILGRSETQEC LFFNANWEKD RTNQTGVEPC YGDKDKRRHC FATWKNISGS IEIVKQGCWL  60
DDINCYDRTD CVEKKDSPEV YFCCCEGNMC NEKFSYFPEM EVTQPTSNPV TPKPPT      116

SEQ ID NO: 4            moltype = AA  length = 107
FEATURE                 Location/Qualifiers
source                  1..107
                        mol_type = protein
                        organism = synthetic construct
SEQUENCE: 4
ETRECIYYNA NWELERTNQS GLERCEGEQD KRLHCYASWR NSSGTIELVK KGCWLDEFNC  60
YDRQECVATE ENPQVYFCCC EGNFCNERFT HLPEAGGPEV TYEPPPT                 107

SEQ ID NO: 5            moltype = AA  length = 107
FEATURE                 Location/Qualifiers
source                  1..107
                        mol_type = protein
                        organism = synthetic construct
SEQUENCE: 5
ETRECIYYNA NWELERTNQS GLERCEGEQD KRLHCYASWR NSSGTIELVK KGCWLDDENC  60
YDRQECVATE ENPQVYFCCC EGNFCNERFT HLPEAGGPEV TYEPPPT                 107

SEQ ID NO: 6            moltype = AA  length = 107
FEATURE                 Location/Qualifiers
source                  1..107
                        mol_type = protein
                        organism = synthetic construct
SEQUENCE: 6
ETRECIYYNA NWELERTNQS GLERCEGEQD KRLHCYASWR NSSGTIELVK KGCWLDDDNC  60
YDRQECVATE ENPQVYFCCC EGNFCNERFT HLPEAGGPEV TYEPPPT                 107

SEQ ID NO: 7            moltype = AA  length = 107
FEATURE                 Location/Qualifiers
source                  1..107
                        mol_type = protein
                        organism = synthetic construct
SEQUENCE: 7
ETRECIYYNA NWELERTNQS GLERCEGEQD KRLHCYASWR NSSGTIELVK KGCWLDDYNC  60
YDRQECVATE ENPQVYFCCC EGNFCNERFT HLPEAGGPEV TYEPPPT                 107

SEQ ID NO: 8            moltype = AA  length = 107
FEATURE                 Location/Qualifiers
source                  1..107
                        mol_type = protein
                        organism = synthetic construct
SEQUENCE: 8
ETRECIYYNA NWELERTNQS GLERCEGEQD KRLHCYASWR NSSGTIELVK KGCWLDDKNC  60
YDRQECVATE ENPQVYFCCC EGNFCNERFT HLPEAGGPEV TYEPPPT                 107

SEQ ID NO: 9            moltype = AA  length = 107
FEATURE                 Location/Qualifiers
source                  1..107
                        mol_type = protein
                        organism = synthetic construct
SEQUENCE: 9
```

-continued

```
ETRECIYYNA NWELERTNQS GLERCEGEQD KRLHCYASWR NSSGTIELVK KGCWLDDQNC  60
YDRQECVATE ENPQVYFCCC EGNFCNERFT HLPEAGGPEV TYEPPPT               107

SEQ ID NO: 10          moltype = AA  length = 107
FEATURE                Location/Qualifiers
source                 1..107
                       mol_type = protein
                       organism = synthetic construct
SEQUENCE: 10
ETRECIYYNA NWELERTNQS GLERCEGEQD KRLHCYASWR NSSGTIELVK KGCWLDDWNC  60
YDRQECVATE ENPQVYFCCC EGNFCNERFT HLPEAGGPEV TYEPPPT               107

SEQ ID NO: 11          moltype = AA  length = 107
FEATURE                Location/Qualifiers
source                 1..107
                       mol_type = protein
                       organism = synthetic construct
SEQUENCE: 11
ETRECIYYNA NWELERTNQS GLERCEGEQD KRLHCYASWR NSSGTIELVK KGCWLDDNNC  60
YDRQECVATE ENPQVYFCCC EGNFCNERFT HLPEAGGPEV TYEPPPT               107

SEQ ID NO: 12          moltype = AA  length = 107
FEATURE                Location/Qualifiers
source                 1..107
                       mol_type = protein
                       organism = synthetic construct
SEQUENCE: 12
ETRECIYYNA NWELERTNQS GLERCEGEQD KRLHCYASWR NSSGTIELVK KGCWLDDRNC  60
YDRQECVATE ENPQVYFCCC EGNFCNERFT HLPEAGGPEV TYEPPPT               107

SEQ ID NO: 13          moltype = AA  length = 107
FEATURE                Location/Qualifiers
source                 1..107
                       mol_type = protein
                       organism = synthetic construct
SEQUENCE: 13
ETRECIYYNA NWELERTNQS GLERCEGEQD KRLHCYASWR NSSGTIELVK KGCWLDDHNC  60
YDRQECVATE ENPQVYFCCC EGNFCNERFT HLPEAGGPEV TYEPPPT               107

SEQ ID NO: 14          moltype = AA  length = 107
FEATURE                Location/Qualifiers
source                 1..107
                       mol_type = protein
                       organism = synthetic construct
SEQUENCE: 14
ETRECIYYNA NWELERTNQS GLERCEGEYD KRLHCYASWR NSSGTIELVK KGCWLDDFNC  60
YDRQECVATE ENPQVYFCCC EGNFCNERFT HLPEAGGPEV TYEPPPT               107

SEQ ID NO: 15          moltype = AA  length = 107
FEATURE                Location/Qualifiers
source                 1..107
                       mol_type = protein
                       organism = synthetic construct
SEQUENCE: 15
ETRECIYYNA NWELERTNQS GLERCEGEQQ KRLHCYASWR NSSGTIELVK KGCWLDDFNC  60
YDRQECVATE ENPQVYFCCC EGNFCNERFT HLPEAGGPEV TYEPPPT               107

SEQ ID NO: 16          moltype = AA  length = 107
FEATURE                Location/Qualifiers
source                 1..107
                       mol_type = protein
                       organism = synthetic construct
SEQUENCE: 16
ETRECIYYNA NWELERTNQS GLERCEGEQD YRLHCYASWR NSSGTIELVK KGCWLDDFNC  60
YDRQECVATE ENPQVYFCCC EGNFCNERFT HLPEAGGPEV TYEPPPT               107

SEQ ID NO: 17          moltype = AA  length = 107
FEATURE                Location/Qualifiers
source                 1..107
                       mol_type = protein
                       organism = synthetic construct
SEQUENCE: 17
ETRECIYYNA NWELERTNQS GLERCEGEQD KRLHCYARWR NSSGTIELVK KGCWLDDFNC  60
YDRQECVATE ENPQVYFCCC EGNFCNERFT HLPEAGGPEV TYEPPPT               107

SEQ ID NO: 18          moltype = AA  length = 107
FEATURE                Location/Qualifiers
source                 1..107
                       mol_type = protein
```

```
                         organism = synthetic construct
SEQUENCE: 18
ETRECIYYNA NWELERTNQS GLERCEGEQD KRLHCYASWR NSSGTIELVK KGCWLDDFNC  60
YDRQECVATE ENPQQYFCCC EGNFCNERFT HLPEAGGPEV TYEPPPT                107

SEQ ID NO: 19            moltype = AA  length = 107
FEATURE                  Location/Qualifiers
source                   1..107
                         mol_type = protein
                         organism = synthetic construct
SEQUENCE: 19
ETRECIYYNA NWELERTNQS GLERCEGEQD KRLHCYASWR NSSGTIELVK KGCWLDDFNC  60
YDRQECVATE ENPQVYDCCC EGNFCNERFT HLPEAGGPEV TYEPPPT                107

SEQ ID NO: 20            moltype = AA  length = 107
FEATURE                  Location/Qualifiers
source                   1..107
                         mol_type = protein
                         organism = synthetic construct
SEQUENCE: 20
ETRECIYYNA NWELERTNQS GLERCEDEQD KRLHCYASWR NSSGTIELVK KGCWLDDFNC  60
YDRQECVATE ENPQVYFCCC EGNFCNERFT HLPEAGGPEV TYEPPPT                107

SEQ ID NO: 21            moltype = AA  length = 107
FEATURE                  Location/Qualifiers
source                   1..107
                         mol_type = protein
                         organism = synthetic construct
SEQUENCE: 21
ETRECIYYNA NWELERTNQS GLERCEGEQD KRLHCYASWR NSSGTIELVK KGCWLDEENC  60
YDRQECVATE ENPQVYFCCC EGNFCNERFT HLPEAGGPEV TYEPPPT                107

SEQ ID NO: 22            moltype = AA  length = 107
FEATURE                  Location/Qualifiers
source                   1..107
                         mol_type = protein
                         organism = synthetic construct
SEQUENCE: 22
ETRECIYYNA NWELERTNQS GLERCEGEYD KRLHCYASWR NSSGTIELVK KGCWLDDENC  60
YDRQECVATE ENPQVYFCCC EGNFCNERFT HLPEAGGPEV TYEPPPT                107

SEQ ID NO: 23            moltype = AA  length = 5
FEATURE                  Location/Qualifiers
source                   1..5
                         mol_type = protein
                         organism = synthetic construct
SEQUENCE: 23
GRGEA                                                              5

SEQ ID NO: 24            moltype = AA  length = 112
FEATURE                  Location/Qualifiers
source                   1..112
                         mol_type = protein
                         organism = synthetic construct
SEQUENCE: 24
GRGEAETREC IYYNANWELE RTNQSGLERC EGEQDKRLHC YASWRNSSGT IELVKKGCWL  60
DDFNCYDRQE CVATEENPQV YFCCCEGNFC NERFTHLPEA GGPEVTYEPP PT          112

SEQ ID NO: 25            moltype = AA  length = 111
FEATURE                  Location/Qualifiers
source                   1..111
                         mol_type = protein
                         organism = synthetic construct
SEQUENCE: 25
RGEAETRECI YYNANWELER TNQSGLERCE GEQDKRLHCY ASWRNSSGTI ELVKKGCWLD  60
DFNCYDRQEC VATEENPQVY FCCCEGNFCN ERFTHLPEAG GPEVTYEPPP T           111

SEQ ID NO: 26            moltype = AA  length = 110
FEATURE                  Location/Qualifiers
source                   1..110
                         mol_type = protein
                         organism = synthetic construct
SEQUENCE: 26
GEAETRECIY YNANWELERT NQSGLERCEG EQDKRLHCYA SWRNSSGTIE LVKKGCWLDD  60
FNCYDRQECV ATEENPQVYF CCCEGNFCNE RFTHLPEAGG PEVTYEPPPT             110

SEQ ID NO: 27            moltype = AA  length = 109
FEATURE                  Location/Qualifiers
source                   1..109
```

```
                        mol_type = protein
                        organism = synthetic construct
SEQUENCE: 27
EAETRECIYY NANWELERTN QSGLERCEGE QDKRLHCYAS WRNSSGTIEL VKKGCWLDDF  60
NCYDRQECVA TEENPQVYFC CCEGNFCNER FTHLPEAGGP EVTYEPPPT              109

SEQ ID NO: 28           moltype = AA  length = 108
FEATURE                 Location/Qualifiers
source                  1..108
                        mol_type = protein
                        organism = synthetic construct
SEQUENCE: 28
AETRECIYYN ANWELERTNQ SGLERCEGEQ DKRLHCYASW RNSSGTIELV KKGCWLDDFN  60
CYDRQECVAT EENPQVYFCC CEGNFCNERF THLPEAGGPE VTYEPPPT               108

SEQ ID NO: 29           moltype = AA  length = 112
FEATURE                 Location/Qualifiers
source                  1..112
                        mol_type = protein
                        organism = synthetic construct
SEQUENCE: 29
GRGEAETREC IYYNANWELE RTNQSGLERC EGEQDKRLHC YASWRNSSGT IELVKKGCWL  60
DDENCYDRQE CVATEENPQV YFCCCEGNFC NERFTHLPEA GGPEVTYEPP PT          112

SEQ ID NO: 30           moltype = AA  length = 111
FEATURE                 Location/Qualifiers
source                  1..111
                        mol_type = protein
                        organism = synthetic construct
SEQUENCE: 30
RGEAETRECI YYNANWELER TNQSGLERCE GEQDKRLHCY ASWRNSSGTI ELVKKGCWLD  60
DENCYDRQEC VATEENPQVY FCCCEGNFCN ERFTHLPEAG GPEVTYEPPP T           111

SEQ ID NO: 31           moltype = AA  length = 110
FEATURE                 Location/Qualifiers
source                  1..110
                        mol_type = protein
                        organism = synthetic construct
SEQUENCE: 31
GEAETRECIY YNANWELERT NQSGLERCEG EQDKRLHCYA SWRNSSGTIE LVKKGCWLDD  60
ENCYDRQECV ATEENPQVYF CCCEGNFCNE RFTHLPEAGG PEVTYEPPPT             110

SEQ ID NO: 32           moltype = AA  length = 109
FEATURE                 Location/Qualifiers
source                  1..109
                        mol_type = protein
                        organism = synthetic construct
SEQUENCE: 32
EAETRECIYY NANWELERTN QSGLERCEGE QDKRLHCYAS WRNSSGTIEL VKKGCWLDDE  60
NCYDRQECVA TEENPQVYFC CCEGNFCNER FTHLPEAGGP EVTYEPPPT              109

SEQ ID NO: 33           moltype = AA  length = 108
FEATURE                 Location/Qualifiers
source                  1..108
                        mol_type = protein
                        organism = synthetic construct
SEQUENCE: 33
AETRECIYYN ANWELERTNQ SGLERCEGEQ DKRLHCYASW RNSSGTIELV KKGCWLDDEN  60
CYDRQECVAT EENPQVYFCC CEGNFCNERF THLPEAGGPE VTYEPPPT               108

SEQ ID NO: 34           moltype = AA  length = 39
FEATURE                 Location/Qualifiers
source                  1..39
                        mol_type = protein
                        organism = synthetic construct
SEQUENCE: 34
GGGGSGGGGS GGGGSGGGGS GGGGSGGGGS GGGGSGGGG                         39

SEQ ID NO: 35           moltype = AA  length = 38
FEATURE                 Location/Qualifiers
source                  1..38
                        mol_type = protein
                        organism = synthetic construct
SEQUENCE: 35
GGGGSGGGGS GGGGSGGGGS GGGGSGGGGS GGGGSGGG                          38

SEQ ID NO: 36           moltype = AA  length = 37
FEATURE                 Location/Qualifiers
source                  1..37
```

```
                        mol_type = protein
                        organism = synthetic construct
SEQUENCE: 36
GGGGSGGGGS GGGGSGGGGS GGGGSGGGGS GGGGSGG                            37

SEQ ID NO: 37           moltype = AA  length = 36
FEATURE                 Location/Qualifiers
source                  1..36
                        mol_type = protein
                        organism = synthetic construct
SEQUENCE: 37
GGGGSGGGGS GGGGSGGGGS GGGGSGGGGS GGGGSG                             36

SEQ ID NO: 38           moltype = AA  length = 35
FEATURE                 Location/Qualifiers
source                  1..35
                        mol_type = protein
                        organism = synthetic construct
SEQUENCE: 38
GGGGSGGGGS GGGGSGGGGS GGGGSGGGGS GGGGS                              35

SEQ ID NO: 39           moltype = AA  length = 34
FEATURE                 Location/Qualifiers
source                  1..34
                        mol_type = protein
                        organism = synthetic construct
SEQUENCE: 39
GGGGSGGGGS GGGGSGGGGS GGGGSGGGGS GGGG                               34

SEQ ID NO: 40           moltype = AA  length = 33
FEATURE                 Location/Qualifiers
source                  1..33
                        mol_type = protein
                        organism = synthetic construct
SEQUENCE: 40
GGGGSGGGGS GGGGSGGGGS GGGGSGGGGS GGG                                33

SEQ ID NO: 41           moltype = AA  length = 32
FEATURE                 Location/Qualifiers
source                  1..32
                        mol_type = protein
                        organism = synthetic construct
SEQUENCE: 41
GGGGSGGGGS GGGGSGGGGS GGGGSGGGGS GG                                 32

SEQ ID NO: 42           moltype = AA  length = 31
FEATURE                 Location/Qualifiers
source                  1..31
                        mol_type = protein
                        organism = synthetic construct
SEQUENCE: 42
GGGGSGGGGS GGGGSGGGGS GGGGSGGGGS G                                  31

SEQ ID NO: 43           moltype = AA  length = 30
FEATURE                 Location/Qualifiers
source                  1..30
                        mol_type = protein
                        organism = synthetic construct
SEQUENCE: 43
GGGGSGGGGS GGGGSGGGGS GGGGSGGGGS                                    30

SEQ ID NO: 44           moltype = AA  length = 29
FEATURE                 Location/Qualifiers
source                  1..29
                        mol_type = protein
                        organism = synthetic construct
SEQUENCE: 44
GGGGSGGGGS GGGGSGGGGS GGGGSGGGG                                     29

SEQ ID NO: 45           moltype = AA  length = 28
FEATURE                 Location/Qualifiers
source                  1..28
                        mol_type = protein
                        organism = synthetic construct
SEQUENCE: 45
GGGGSGGGGS GGGGSGGGGS GGGGSGGG                                      28

SEQ ID NO: 46           moltype = AA  length = 27
FEATURE                 Location/Qualifiers
```

```
source                 1..27
                       mol_type = protein
                       organism = synthetic construct
SEQUENCE: 46
GGGGSGGGGS GGGGSGGGGS GGGGSGG                                          27

SEQ ID NO: 47          moltype = AA  length = 26
FEATURE                Location/Qualifiers
source                 1..26
                       mol_type = protein
                       organism = synthetic construct
SEQUENCE: 47
GGGGSGGGGS GGGGSGGGGS GGGGSG                                           26

SEQ ID NO: 48          moltype = AA  length = 25
FEATURE                Location/Qualifiers
source                 1..25
                       mol_type = protein
                       organism = synthetic construct
SEQUENCE: 48
GGGGSGGGGS GGGGSGGGGS GGGGS                                            25

SEQ ID NO: 49          moltype = AA  length = 24
FEATURE                Location/Qualifiers
source                 1..24
                       mol_type = protein
                       organism = synthetic construct
SEQUENCE: 49
GGGGSGGGGS GGGGSGGGGS GGGG                                             24

SEQ ID NO: 50          moltype = AA  length = 23
FEATURE                Location/Qualifiers
source                 1..23
                       mol_type = protein
                       organism = synthetic construct
SEQUENCE: 50
GGGGSGGGGS GGGGSGGGGS GGG                                              23

SEQ ID NO: 51          moltype = AA  length = 22
FEATURE                Location/Qualifiers
source                 1..22
                       mol_type = protein
                       organism = synthetic construct
SEQUENCE: 51
GGGGSGGGGS GGGGSGGGGS GG                                               22

SEQ ID NO: 52          moltype = AA  length = 21
FEATURE                Location/Qualifiers
source                 1..21
                       mol_type = protein
                       organism = synthetic construct
SEQUENCE: 52
GGGGSGGGGS GGGGSGGGGS G                                                21

SEQ ID NO: 53          moltype = AA  length = 20
FEATURE                Location/Qualifiers
source                 1..20
                       mol_type = protein
                       organism = synthetic construct
SEQUENCE: 53
GGGGSGGGGS GGGGSGGGGS                                                  20

SEQ ID NO: 54          moltype = AA  length = 19
FEATURE                Location/Qualifiers
source                 1..19
                       mol_type = protein
                       organism = synthetic construct
SEQUENCE: 54
GGGGSGGGGS GGGGSGGGG                                                   19

SEQ ID NO: 55          moltype = AA  length = 18
FEATURE                Location/Qualifiers
source                 1..18
                       mol_type = protein
                       organism = synthetic construct
SEQUENCE: 55
GGGGSGGGGS GGGGSGGG                                                    18

SEQ ID NO: 56          moltype = AA  length = 17
```

-continued

```
FEATURE                Location/Qualifiers
source                 1..17
                       mol_type = protein
                       organism = synthetic construct
SEQUENCE: 56
GGGGSGGGGS GGGGSGG                                              17

SEQ ID NO: 57          moltype = AA  length = 16
FEATURE                Location/Qualifiers
source                 1..16
                       mol_type = protein
                       organism = synthetic construct
SEQUENCE: 57
GGGGSGGGGS GGGGSG                                               16

SEQ ID NO: 58          moltype = AA  length = 15
FEATURE                Location/Qualifiers
source                 1..15
                       mol_type = protein
                       organism = synthetic construct
SEQUENCE: 58
GGGGSGGGGS GGGGS                                                15

SEQ ID NO: 59          moltype = AA  length = 14
FEATURE                Location/Qualifiers
source                 1..14
                       mol_type = protein
                       organism = synthetic construct
SEQUENCE: 59
GGGGSGGGGS GGGG                                                 14

SEQ ID NO: 60          moltype = AA  length = 13
FEATURE                Location/Qualifiers
source                 1..13
                       mol_type = protein
                       organism = synthetic construct
SEQUENCE: 60
GGGGSGGGGS GGG                                                  13

SEQ ID NO: 61          moltype = AA  length = 12
FEATURE                Location/Qualifiers
source                 1..12
                       mol_type = protein
                       organism = synthetic construct
SEQUENCE: 61
GGGGSGGGGS GG                                                   12

SEQ ID NO: 62          moltype = AA  length = 11
FEATURE                Location/Qualifiers
source                 1..11
                       mol_type = protein
                       organism = synthetic construct
SEQUENCE: 62
GGGGSGGGGS G                                                    11

SEQ ID NO: 63          moltype = AA  length = 10
FEATURE                Location/Qualifiers
source                 1..10
                       mol_type = protein
                       organism = synthetic construct
SEQUENCE: 63
GGGGSGGGGS                                                      10

SEQ ID NO: 64          moltype = AA  length = 9
FEATURE                Location/Qualifiers
source                 1..9
                       mol_type = protein
                       organism = synthetic construct
SEQUENCE: 64
GGGGSGGGG                                                       9

SEQ ID NO: 65          moltype = AA  length = 8
FEATURE                Location/Qualifiers
source                 1..8
                       mol_type = protein
                       organism = synthetic construct
SEQUENCE: 65
GGGGSGGG                                                        8
```

-continued

```
SEQ ID NO: 66           moltype = AA  length = 7
FEATURE                 Location/Qualifiers
source                  1..7
                        mol_type = protein
                        organism = synthetic construct
SEQUENCE: 66
GGGGSGG                                                               7

SEQ ID NO: 67           moltype = AA  length = 6
FEATURE                 Location/Qualifiers
source                  1..6
                        mol_type = protein
                        organism = synthetic construct
SEQUENCE: 67
GGGGSG                                                                6

SEQ ID NO: 68           moltype = AA  length = 5
FEATURE                 Location/Qualifiers
source                  1..5
                        mol_type = protein
                        organism = synthetic construct
SEQUENCE: 68
GGGGS                                                                 5

SEQ ID NO: 69           moltype = AA  length = 4
FEATURE                 Location/Qualifiers
source                  1..4
                        mol_type = protein
                        organism = synthetic construct
SEQUENCE: 69
GGGG                                                                  4

SEQ ID NO: 70           moltype =   length =
SEQUENCE: 70
000

SEQ ID NO: 71           moltype =   length =
SEQUENCE: 71
000

SEQ ID NO: 72           moltype = AA  length = 40
FEATURE                 Location/Qualifiers
source                  1..40
                        mol_type = protein
                        organism = synthetic construct
SEQUENCE: 72
GGGGSGGGGS GGGGSGGGGS GGGGSGGGGS GGGGSGGGGS                           40

SEQ ID NO: 73           moltype = AA  length = 4
FEATURE                 Location/Qualifiers
source                  1..4
                        mol_type = protein
                        organism = synthetic construct
SEQUENCE: 73
TGGG                                                                  4

SEQ ID NO: 74           moltype = AA  length = 5
FEATURE                 Location/Qualifiers
source                  1..5
                        mol_type = protein
                        organism = synthetic construct
SEQUENCE: 74
TGGGG                                                                 5

SEQ ID NO: 75           moltype = AA  length = 5
FEATURE                 Location/Qualifiers
source                  1..5
                        mol_type = protein
                        organism = synthetic construct
SEQUENCE: 75
SGGGG                                                                 5

SEQ ID NO: 76           moltype = AA  length = 4
FEATURE                 Location/Qualifiers
source                  1..4
                        mol_type = protein
                        organism = synthetic construct
SEQUENCE: 76
SGGG                                                                  4
```

```
SEQ ID NO: 77           moltype = AA  length = 11
FEATURE                 Location/Qualifiers
source                  1..11
                        mol_type = protein
                        organism = synthetic construct
SEQUENCE: 77
TGGGGSGGGG S                                                        11

SEQ ID NO: 78           moltype = AA  length = 16
FEATURE                 Location/Qualifiers
source                  1..16
                        mol_type = protein
                        organism = synthetic construct
SEQUENCE: 78
TGGGGSGGGG SGGGGS                                                   16

SEQ ID NO: 79           moltype = AA  length = 21
FEATURE                 Location/Qualifiers
source                  1..21
                        mol_type = protein
                        organism = synthetic construct
SEQUENCE: 79
TGGGGSGGGG SGGGGSGGGG S                                             21

SEQ ID NO: 80           moltype = AA  length = 26
FEATURE                 Location/Qualifiers
source                  1..26
                        mol_type = protein
                        organism = synthetic construct
SEQUENCE: 80
TGGGGSGGGG SGGGGSGGGG SGGGGS                                        26

SEQ ID NO: 81           moltype = AA  length = 31
FEATURE                 Location/Qualifiers
source                  1..31
                        mol_type = protein
                        organism = synthetic construct
SEQUENCE: 81
TGGGGSGGGG SGGGGSGGGG SGGGGSGGGG S                                  31

SEQ ID NO: 82           moltype = AA  length = 36
FEATURE                 Location/Qualifiers
source                  1..36
                        mol_type = protein
                        organism = synthetic construct
SEQUENCE: 82
TGGGGSGGGG SGGGGSGGGG SGGGGSGGGG SGGGGS                             36

SEQ ID NO: 83           moltype = AA  length = 10
FEATURE                 Location/Qualifiers
source                  1..10
                        mol_type = protein
                        organism = synthetic construct
SEQUENCE: 83
TGGGPKSCDK                                                          10

SEQ ID NO: 84           moltype =   length =
SEQUENCE: 84
000

SEQ ID NO: 85           moltype =   length =
SEQUENCE: 85
000

SEQ ID NO: 86           moltype = AA  length = 4
FEATURE                 Location/Qualifiers
source                  1..4
                        mol_type = protein
                        organism = synthetic construct
SEQUENCE: 86
AGGG                                                                4

SEQ ID NO: 87           moltype = AA  length = 4
FEATURE                 Location/Qualifiers
source                  1..4
                        mol_type = protein
                        organism = synthetic construct
SEQUENCE: 87
```

-continued

```
GGSG                                                          4

SEQ ID NO: 88          moltype = AA  length = 4
FEATURE                Location/Qualifiers
source                 1..4
                       mol_type = protein
                       organism = synthetic construct
SEQUENCE: 88
GGAG                                                          4

SEQ ID NO: 89          moltype = AA  length = 5
FEATURE                Location/Qualifiers
source                 1..5
                       mol_type = protein
                       organism = synthetic construct
SEQUENCE: 89
GGGGG                                                         5

SEQ ID NO: 90          moltype = AA  length = 5
FEATURE                Location/Qualifiers
source                 1..5
                       mol_type = protein
                       organism = synthetic construct
SEQUENCE: 90
GGGGA                                                         5

SEQ ID NO: 91          moltype = AA  length = 4
FEATURE                Location/Qualifiers
source                 1..4
                       mol_type = protein
                       organism = synthetic construct
SEQUENCE: 91
GGGS                                                          4

SEQ ID NO: 92          moltype = AA  length = 4
FEATURE                Location/Qualifiers
source                 1..4
                       mol_type = protein
                       organism = synthetic construct
SEQUENCE: 92
GGGA                                                          4

SEQ ID NO: 93          moltype =   length =
SEQUENCE: 93
000

SEQ ID NO: 94          moltype =   length =
SEQUENCE: 94
000

SEQ ID NO: 95          moltype = AA  length = 4
FEATURE                Location/Qualifiers
source                 1..4
                       mol_type = protein
                       organism = synthetic construct
SEQUENCE: 95
GSGS                                                          4

SEQ ID NO: 96          moltype = AA  length = 6
FEATURE                Location/Qualifiers
source                 1..6
                       mol_type = protein
                       organism = synthetic construct
SEQUENCE: 96
GAGAGA                                                        6

SEQ ID NO: 97          moltype = AA  length = 6
FEATURE                Location/Qualifiers
source                 1..6
                       mol_type = protein
                       organism = synthetic construct
SEQUENCE: 97
GSGSGS                                                        6

SEQ ID NO: 98          moltype = AA  length = 8
FEATURE                Location/Qualifiers
source                 1..8
                       mol_type = protein
                       organism = synthetic construct
```

-continued

```
SEQUENCE: 98
GAGAGAGA                                                         8

SEQ ID NO: 99            moltype = AA  length = 8
FEATURE                  Location/Qualifiers
source                   1..8
                         mol_type = protein
                         organism = synthetic construct
SEQUENCE: 99
GSGSGSGS                                                         8

SEQ ID NO: 100           moltype = AA  length = 10
FEATURE                  Location/Qualifiers
source                   1..10
                         mol_type = protein
                         organism = synthetic construct
SEQUENCE: 100
GAGAGAGAGA                                                       10

SEQ ID NO: 101           moltype = AA  length = 10
FEATURE                  Location/Qualifiers
source                   1..10
                         mol_type = protein
                         organism = synthetic construct
SEQUENCE: 101
GSGSGSGSGS                                                       10

SEQ ID NO: 102           moltype = AA  length = 12
FEATURE                  Location/Qualifiers
source                   1..12
                         mol_type = protein
                         organism = synthetic construct
SEQUENCE: 102
GAGAGAGAGA GA                                                    12

SEQ ID NO: 103           moltype = AA  length = 4
FEATURE                  Location/Qualifiers
source                   1..4
                         mol_type = protein
                         organism = synthetic construct
SEQUENCE: 103
GAGA                                                             4

SEQ ID NO: 104           moltype = AA  length = 12
FEATURE                  Location/Qualifiers
source                   1..12
                         mol_type = protein
                         organism = synthetic construct
SEQUENCE: 104
GSGSGSGSGS GS                                                    12

SEQ ID NO: 105           moltype = AA  length = 6
FEATURE                  Location/Qualifiers
source                   1..6
                         mol_type = protein
                         organism = synthetic construct
SEQUENCE: 105
GGAGGA                                                           6

SEQ ID NO: 106           moltype = AA  length = 6
FEATURE                  Location/Qualifiers
source                   1..6
                         mol_type = protein
                         organism = synthetic construct
SEQUENCE: 106
GGSGGS                                                           6

SEQ ID NO: 107           moltype = AA  length = 9
FEATURE                  Location/Qualifiers
source                   1..9
                         mol_type = protein
                         organism = synthetic construct
SEQUENCE: 107
GGAGGAGGA                                                        9

SEQ ID NO: 108           moltype = AA  length = 9
FEATURE                  Location/Qualifiers
source                   1..9
                         mol_type = protein
```

```
                     organism = synthetic construct
SEQUENCE: 108
GGSGGSGGS                                                      9

SEQ ID NO: 109       moltype = AA  length = 12
FEATURE              Location/Qualifiers
source               1..12
                     mol_type = protein
                     organism = synthetic construct
SEQUENCE: 109
GGAGGAGGAG GA                                                  12

SEQ ID NO: 110       moltype = AA  length = 12
FEATURE              Location/Qualifiers
source               1..12
                     mol_type = protein
                     organism = synthetic construct
SEQUENCE: 110
GGSGGSGGSG GS                                                  12

SEQ ID NO: 111       moltype = AA  length = 4
FEATURE              Location/Qualifiers
source               1..4
                     mol_type = protein
                     organism = synthetic construct
SEQUENCE: 111
GGAG                                                           4

SEQ ID NO: 112       moltype = AA  length = 4
FEATURE              Location/Qualifiers
source               1..4
                     mol_type = protein
                     organism = synthetic construct
SEQUENCE: 112
GGSG                                                           4

SEQ ID NO: 113       moltype = AA  length = 8
FEATURE              Location/Qualifiers
source               1..8
                     mol_type = protein
                     organism = synthetic construct
SEQUENCE: 113
GGAGGGAG                                                       8

SEQ ID NO: 114       moltype = AA  length = 8
FEATURE              Location/Qualifiers
source               1..8
                     mol_type = protein
                     organism = synthetic construct
SEQUENCE: 114
GGSGGGSG                                                       8

SEQ ID NO: 115       moltype = AA  length = 12
FEATURE              Location/Qualifiers
source               1..12
                     mol_type = protein
                     organism = synthetic construct
SEQUENCE: 115
GGAGGGAGGG AG                                                  12

SEQ ID NO: 116       moltype = AA  length = 12
FEATURE              Location/Qualifiers
source               1..12
                     mol_type = protein
                     organism = synthetic construct
SEQUENCE: 116
GGSGGGSGGG SG                                                  12

SEQ ID NO: 117       moltype = AA  length = 15
FEATURE              Location/Qualifiers
source               1..15
                     mol_type = protein
                     organism = synthetic construct
SEQUENCE: 117
GGGGAGGGGA GGGGA                                               15

SEQ ID NO: 118       moltype = AA  length = 4
FEATURE              Location/Qualifiers
source               1..4
```

```
                         mol_type = protein
                         organism = synthetic construct
SEQUENCE: 118
AAAL                                                                         4

SEQ ID NO: 119           moltype = AA  length = 4
FEATURE                  Location/Qualifiers
source                   1..4
                         mol_type = protein
                         organism = synthetic construct
SEQUENCE: 119
AAAK                                                                         4

SEQ ID NO: 120           moltype = AA  length = 4
FEATURE                  Location/Qualifiers
source                   1..4
                         mol_type = protein
                         organism = synthetic construct
SEQUENCE: 120
AAAR                                                                         4

SEQ ID NO: 121           moltype = AA  length = 14
FEATURE                  Location/Qualifiers
source                   1..14
                         mol_type = protein
                         organism = synthetic construct
SEQUENCE: 121
EGKSSGSGSE SKST                                                              14

SEQ ID NO: 122           moltype = AA  length = 12
FEATURE                  Location/Qualifiers
source                   1..12
                         mol_type = protein
                         organism = synthetic construct
SEQUENCE: 122
GSAGSAAGSG EF                                                                12

SEQ ID NO: 123           moltype = AA  length = 12
FEATURE                  Location/Qualifiers
source                   1..12
                         mol_type = protein
                         organism = synthetic construct
SEQUENCE: 123
AEAAAKEAAA KA                                                                12

SEQ ID NO: 124           moltype = AA  length = 18
FEATURE                  Location/Qualifiers
source                   1..18
                         mol_type = protein
                         organism = synthetic construct
SEQUENCE: 124
KESGSVSSEQ LAQFRSLD                                                          18

SEQ ID NO: 125           moltype = AA  length = 10
FEATURE                  Location/Qualifiers
source                   1..10
                         mol_type = protein
                         organism = synthetic construct
SEQUENCE: 125
GENLYFQSGG                                                                   10

SEQ ID NO: 126           moltype = AA  length = 8
FEATURE                  Location/Qualifiers
source                   1..8
                         mol_type = protein
                         organism = synthetic construct
SEQUENCE: 126
SACYCELS                                                                     8

SEQ ID NO: 127           moltype = AA  length = 5
FEATURE                  Location/Qualifiers
source                   1..5
                         mol_type = protein
                         organism = synthetic construct
SEQUENCE: 127
RSIAT                                                                        5

SEQ ID NO: 128           moltype = AA  length = 17
FEATURE                  Location/Qualifiers
```

```
source                  1..17
                        mol_type = protein
                        organism = synthetic construct
SEQUENCE: 128
RPACKIPNDL KQKVMNH                                                17

SEQ ID NO: 129          moltype = AA  length = 36
FEATURE                 Location/Qualifiers
source                  1..36
                        mol_type = protein
                        organism = synthetic construct
SEQUENCE: 129
GGSAGGSGSG SSGGSSGASG TGTAGGTGSG SGTGSG                           36

SEQ ID NO: 130          moltype = AA  length = 17
FEATURE                 Location/Qualifiers
source                  1..17
                        mol_type = protein
                        organism = synthetic construct
SEQUENCE: 130
AAANSSIDLI SVPVDSR                                                17

SEQ ID NO: 131          moltype = AA  length = 36
FEATURE                 Location/Qualifiers
source                  1..36
                        mol_type = protein
                        organism = synthetic construct
SEQUENCE: 131
GGSGGGSEGG GSEGGGSEGG GSEGGGSEGG GSGGGS                           36

SEQ ID NO: 132          moltype = AA  length = 5
FEATURE                 Location/Qualifiers
source                  1..5
                        mol_type = protein
                        organism = synthetic construct
SEQUENCE: 132
EAAAK                                                             5

SEQ ID NO: 133          moltype = AA  length = 5
FEATURE                 Location/Qualifiers
source                  1..5
                        mol_type = protein
                        organism = synthetic construct
SEQUENCE: 133
PAPAP                                                             5

SEQ ID NO: 134          moltype = AA  length = 224
FEATURE                 Location/Qualifiers
source                  1..224
                        mol_type = protein
                        organism = synthetic construct
SEQUENCE: 134
THTCPPCPAP ELLGGPSVFL FPPKPKDTLM ISRTPEVTCV VVDVSHEDPE VKFNWYVDGV  60
EVHNAKTKPR EEQYNSTYRV VSVLTVLHQD WLNGKEYKCK VSNKALPAPI EKTISKAKGQ  120
PREPQVYTLP PSREEMTKNQ VSLTCLVKGF YPSDIAVEWE SNGQPENNYK TTPPVLDSDG  180
SFFLYSKLTV DKSRWQQGNV FSCSVMHEAL HNHYTQKSLS LSPG                  224

SEQ ID NO: 135          moltype = AA  length = 224
FEATURE                 Location/Qualifiers
source                  1..224
                        mol_type = protein
                        organism = synthetic construct
SEQUENCE: 135
THTCPPCPAP ELLGGPSVFL FPPKPKDTLM ISRTPEVTCV VVDVSHEDPE VKFNWYVDGV  60
EVHNAKTKPR EEQYNSTYRV VSVLTVLHQD WLNGKEYKCK VSNKALPAPI EKTISKAKGQ  120
PREPQVYTLP PSRDELTKNQ VSLTCLVKGF YPSDIAVEWE SNGQPENNYK TTPPVLDSDG  180
SFFLYSKLTV DKSRWQQGNV FSCSVMHEAL HNHYTQKSLS LSPG                  224

SEQ ID NO: 136          moltype = AA  length = 224
FEATURE                 Location/Qualifiers
source                  1..224
                        mol_type = protein
                        organism = synthetic construct
SEQUENCE: 136
THTCPPCPAP ELLGGPSVFL FPPKPKDTLY ITREPEVTCV VVDVSHEDPE VKFNWYVDGV  60
EVHNAKTKPR EEQYNSTYRV VSVLTVLHQD WLNGKEYKCK VSNKALPAPI EKTISKAKGQ  120
PREPQVYTLP PSREEMTKNQ VSLTCLVKGF YPSDIAVEWE SNGQPENNYK TTPPVLDSDG  180
SFFLYSKLTV DKSRWQQGNV FSCSVMHEAL HNHYTQKSLS LSPG                  224
```

-continued

```
SEQ ID NO: 137         moltype = AA  length = 224
FEATURE                Location/Qualifiers
source                 1..224
                       mol_type = protein
                       organism = synthetic construct
SEQUENCE: 137
THTCPPCPAP ELLGGPSVFL FPPKPKDTLY ITREPEVTCV VVDVSHEDPE VKFNWYVDGV  60
EVHNAKTKPR EEQYNSTYRV VSVLTVLHQD WLNGKEYKCK VSNKALPAPI EKTISKAKGQ  120
PREPQVYTLP PSRDELTKNQ VSLTCLVKGF YPSDIAVEWE SNGQPENNYK TTPPVLDSDG  180
SFFLYSKLTV DKSRWQQGNV FSCSVMHEAL HNHYTQKSLS LSPG                  224

SEQ ID NO: 138         moltype = AA  length = 224
FEATURE                Location/Qualifiers
source                 1..224
                       mol_type = protein
                       organism = synthetic construct
SEQUENCE: 138
THTCPPCPAP ELLGGPSVFL FPPKPKDTLY ISRTPEVTCV VVDVSHEDPE VKFNWYVDGV  60
EVHNAKTKPR EEQYNSTYRV VSVLTVLHQD WLNGKEYKCK VSNKALPAPI EKTISKAKGQ  120
PREPQVYTLP PSRDELTKNQ VSLTCLVKGF YPSDIAVEWE SNGQPENNYK TTPPVLDSDG  180
SFFLYSKLTV DKSRWQQGNV FSCSVMHEAL HNHYTQKSLS LSPG                  224

SEQ ID NO: 139         moltype = AA  length = 217
FEATURE                Location/Qualifiers
source                 1..217
                       mol_type = protein
                       organism = synthetic construct
SEQUENCE: 139
APELLGGPSV FLFPPKPKDT LMISRTPEVT CVVVDVSHED PEVKFNWYVD GVEVHNAKTK  60
PREEQYNSTY RVVSVLTVLH QDWLNGKEYK CKVSNKALPA PIEKTISKAK GQPREPQVYT  120
LPPSRDELTK NQVSLTCLVK GFYPSDIAVE WESNGQPENN YKTTPPVLDS DGSFFLYSKL  180
TVDKSRWQQG NVFSCSVMHE ALHNHYTQKS LSLSPGK                          217

SEQ ID NO: 140         moltype = AA  length = 216
FEATURE                Location/Qualifiers
source                 1..216
                       mol_type = protein
                       organism = synthetic construct
SEQUENCE: 140
APELLGGPSV FLFPPKPKDT LMISRTPEVT CVVVDVSHED PEVKFNWYVD GVEVHNAKTK  60
PREEQYNSTY RVVSVLTVLH QDWLNGKEYK CKVSNKALPA PIEKTISKAK GQPREPQVYT  120
LPPSRDELTK NQVSLTCLVK GFYPSDIAVE WESNGQPENN YKTTPPVLDS DGSFFLYSKL  180
TVDKSRWQQG NVFSCSVMHE ALHNHYTQKS LSLSPG                           216

SEQ ID NO: 141         moltype = AA  length = 220
FEATURE                Location/Qualifiers
source                 1..220
                       mol_type = protein
                       organism = synthetic construct
SEQUENCE: 141
PPCPAPELLG GPSVFLFPPK PKDTLMISRT PEVTCVVVDV SHEDPEVKFN WYVDGVEVHN  60
AKTKPREEQY NSTYRVVSVL TVLHQDWLNG KEYKCKVSNK ALPAPIEKTI SKAKGQPREP  120
QVYTLPPSRD ELTKNQVSLT CLVKGFYPSD IAVEWESNGQ PENNYKTTPP VLDSDGSFFL  180
YSKLTVDKSR WQQGNVFSCS VMHEALHNHY TQKSLSLSPG                       220

SEQ ID NO: 142         moltype = AA  length = 226
FEATURE                Location/Qualifiers
source                 1..226
                       mol_type = protein
                       organism = synthetic construct
SEQUENCE: 142
DKTHTCPPCP APELLGGPSV FLFPPKPKDT LMISRTPEVT CVVVDVSHED PEVKFNWYVD  60
GVEVHNAKTK PREEQYNSTY RVVSVLTVLH QDWLNGKEYK CKVSNKALPA PIEKTISKAK  120
GQPREPQVYT LPPSRDELTK NQVSLTCLVK GFYPSDIAVE WESNGQPENN YKTTPPVLDS  180
DGSFFLYSKL TVDKSRWQQG NVFSCSVMHE ALHNHYTQKS LSLSPG                226

SEQ ID NO: 143         moltype = AA  length = 231
FEATURE                Location/Qualifiers
source                 1..231
                       mol_type = protein
                       organism = synthetic construct
SEQUENCE: 143
EPKSSDKTHT CPPCPAPELL GGPSVFLFPP KPKDTLMISR TPEVTCVVVD VSHEDPEVKF  60
NWYVDGVEVH NAKTKPREEQ YNSTYRVVSV LTVLHQDWLN GKEYKCKVSN KALPAPIEKT  120
ISKAKGQPRE PQVYTLPPSR DELTKNQVSL TCLVKGFYPS DIAVEWESNG QPENNYKTTP  180
PVLDSDGSFF LYSKLTVDKS RWQQGNVFSC SVMHEALHNH YTQKSLSLSP G          231

SEQ ID NO: 144         moltype = AA  length = 231
FEATURE                Location/Qualifiers
```

-continued

```
source                  1..231
                        mol_type = protein
                        organism = synthetic construct
SEQUENCE: 144
EPKSSDKTHT SPPSPAPELL GGPSVFLFPP KPKDTLMISR TPEVTCVVVD VSHEDPEVKF  60
NWYVDGVEVH NAKTKPREEQ YNSTYRVVSV LTVLHQDWLN GKEYKCKVSN KALPAPIEKT  120
ISKAKGQPRE PQVYTLPPSR DELTKNQVSL TCLVKGFYPS DIAVEWESNG QPENNYKTTP  180
PVLDSDGSFF LYSKLTVDKS RWQQGNVFSC SVMHEALHNH YTQKSLSLSP G           231

SEQ ID NO: 145          moltype = AA  length = 224
FEATURE                 Location/Qualifiers
source                  1..224
                        mol_type = protein
                        organism = synthetic construct
SEQUENCE: 145
THTCPPCPAP ELLGGPSVFL FPPKPKDTLY ISRTPEVTCV VVDVSHEDPE VKFNWYVDGV  60
EVHNAKTKPR EEQYNSTYRV VSVLTVLHQD WLNGKEYKCK VSNKALPAPI EKTISKAKGQ  120
PREPQVYTLP PSREEMTKNQ VSLTCLVKGF YPSDIAVEWE SNGQPENNYK TTPPVLDSDG  180
SFFLYSKLTV DKSRWQQGNV FSCSVMHEAL HNHYTQKSLS LSPG                  224

SEQ ID NO: 146          moltype = AA  length = 224
FEATURE                 Location/Qualifiers
source                  1..224
                        mol_type = protein
                        organism = synthetic construct
SEQUENCE: 146
THTCPPCPAP ELLGGPSVFL FPPKPKDTLM ISRTPEVTCV VVDVSHEDPE VKFNWYVDGV  60
EVHNAKTKPR EEQYNSTYRV VSVLTVLHQD WLNGKEYKCK VSNKALPVPI EKTISKAKGQ  120
PREPQVYTLP PSRDELTKNQ VSLTCLVKGF YPSDIAVEWE SNGQPENNYK TTPPVLDSDG  180
SFFLYSKLTV DKSRWQQGNV FSCSVMHEAL HNHYTQKSLS LSPG                  224

SEQ ID NO: 147          moltype = AA  length = 224
FEATURE                 Location/Qualifiers
source                  1..224
                        mol_type = protein
                        organism = synthetic construct
SEQUENCE: 147
THTCPPCPAP ELLGGPSVFL FPPKPKDTLM ISRTPEVTCV VVDVSHEDPE VKFNWYVDGV  60
EVHNAKTKPR EEQYNSTYRV VSVLTVLHQD WLNGKEYKCK VSNKALPVPI EKTISKAKGQ  120
PREPQVYTLP PSREEMTKNQ VSLTCLVKGF YPSDIAVEWE SNGQPENNYK TTPPVLDSDG  180
SFFLYSKLTV DKSRWQQGNV FSCSVMHEAL HNHYTQKSLS LSPG                  224

SEQ ID NO: 148          moltype = AA  length = 216
FEATURE                 Location/Qualifiers
source                  1..216
                        mol_type = protein
                        organism = synthetic construct
SEQUENCE: 148
APPVAGPSVF LFPPKPKDTL MISRTPEVTC VVVDVSHEDP EVQFNWYVDG VEVHNAKTKP  60
REEQFNSTFR VVSVLTVVHQ DWLNGKEYKC KVSNKGLPAP IEKTISKTKG QPREPQVYTL  120
PPSREEMTKN QVSLTCLVKG FYPSDISVEW ESNGQPENNY KTTPPMLDSD GSFFLYSKLT  180
VDKSRWQQGN VFSCSVMHEA LHNHYTQKSL SLSPGK                            216

SEQ ID NO: 149          moltype = AA  length = 223
FEATURE                 Location/Qualifiers
source                  1..223
                        mol_type = protein
                        organism = synthetic construct
SEQUENCE: 149
VECPPCPAPP VAGPSVFLFP PKPKDTLMIS RTPEVTCVVV DVSHEDPEVQ FNWYVDGVEV  60
HNAKTKPREE QFNSTFRVVS VLTVVHQDWL NGKEYKCKVS NKGLPAPIEK TISKTKGQPR  120
EPQVYTLPPS REEMTKNQVS LTCLVKGFYP SDIAVEWESN GQPENNYKTT PPMLDSDGSF  180
FLYSKLTVDK SRWQQGNVFS CSVMHEALHN HYTQKSLSLS PGK                   223

SEQ ID NO: 150          moltype = AA  length = 228
FEATURE                 Location/Qualifiers
source                  1..228
                        mol_type = protein
                        organism = synthetic construct
SEQUENCE: 150
ERKCCVECPP CPAPPVAGPS VFLFPPKPKD TLMISRTPEV TCVVVDVSHE DPEVQFNWYV  60
DGVEVHNAKT KPREEQFNST FRVVSVLTVV HQDWLNGKEY KCKVSNKGLP APIEKTISKT  120
KGQPREPQVY TLPPSREEMT KNQVSLTCLV KGFYPSDISV EWESNGQPEN NYKTTPPMLD  180
SDGSFFLYSK LTVDKSRWQQ GNVFSCSVMH EALHNHYTQK SLSLSPGK              228

SEQ ID NO: 151          moltype = AA  length = 227
FEATURE                 Location/Qualifiers
source                  1..227
                        mol_type = protein
```

```
                         organism = synthetic construct
SEQUENCE: 151
ERKSSVECPP CPAPPVAGPS VFLFPPKPKD TLMISRTPEV TCVVVDVSHE DPEVQFNWYV  60
DGVEVHNAKT KPREEQFNST FRVVSVLTVV HQDWLNGKEY KCKVSNKGLP APIEKTISKT  120
KGQPREPQVY TLPPSREEMT KNQVSLTCLV KGFYPSDISV EWESNGQPEN NYKTTPPMLD  180
SDGSFFLYSK LTVDKSRWQQ GNVFSCSVMH EALHNHYTQK SLSLSPG               227

SEQ ID NO: 152           moltype = AA  length = 227
FEATURE                  Location/Qualifiers
source                   1..227
                         mol_type = protein
                         organism = synthetic construct
SEQUENCE: 152
ERKSSVESPP CPAPPVAGPS VFLFPPKPKD TLMISRTPEV TCVVVDVSHE DPEVQFNWYV  60
DGVEVHNAKT KPREEQFNST FRVVSVLTVV HQDWLNGKEY KCKVSNKGLP APIEKTISKT  120
KGQPREPQVY TLPPSREEMT KNQVSLTCLV KGFYPSDISV EWESNGQPEN NYKTTPPMLD  180
SDGSFFLYSK LTVDKSRWQQ GNVFSCSVMH EALHNHYTQK SLSLSPG               227

SEQ ID NO: 153           moltype = AA  length = 227
FEATURE                  Location/Qualifiers
source                   1..227
                         mol_type = protein
                         organism = synthetic construct
SEQUENCE: 153
ERKSSVESPP SPAPPVAGPS VFLFPPKPKD TLMISRTPEV TCVVVDVSHE DPEVQFNWYV  60
DGVEVHNAKT KPREEQFNST FRVVSVLTVV HQDWLNGKEY KCKVSNKGLP APIEKTISKT  120
KGQPREPQVY TLPPSREEMT KNQVSLTCLV KGFYPSDISV EWESNGQPEN NYKTTPPMLD  180
SDGSFFLYSK LTVDKSRWQQ GNVFSCSVMH EALHNHYTQK SLSLSPG               227

SEQ ID NO: 154           moltype = AA  length = 215
FEATURE                  Location/Qualifiers
source                   1..215
                         mol_type = protein
                         organism = synthetic construct
SEQUENCE: 154
APPVAGPSVF LFPPKPKDTL MISRTPEVTC VVVDVSHEDP EVQFNWYVDG VEVHNAKTKP  60
REEQFNSTFR VVSVLTVVHQ DWLNGKEYKC KVSNKGLPAP IEKTISKTKG QPREPQVYTL  120
PPSREEMTKN QVSLTCLVKG FYPSDISVEW ESNGQPENNY KTTPPMLDSD GSFFLYSKLT  180
VDKSRWQQGN VFSCSVMHEA LHNHYTQKSL SLSPG                            215

SEQ ID NO: 155           moltype = AA  length = 219
FEATURE                  Location/Qualifiers
source                   1..219
                         mol_type = protein
                         organism = synthetic construct
SEQUENCE: 155
PPCPAPPVAG PSVFLFPPKP KDTLMISRTP EVTCVVVDVS HEDPEVQFNW YVDGVEVHNA  60
KTKPREEQFN STFRVVSVLT VVHQDWLNGK EYKCKVSNKG LPAPIEKTIS KTKGQPREPQ  120
VYTLPPSREE MTKNQVSLTC LVKGFYPSDI SVEWESNGQP ENNYKTTPPM LDSDGSFFLY  180
SKLTVDKSRW QQGNVFSCSV MHEALHNHYT QKSLSLSPG                        219

SEQ ID NO: 156           moltype = AA  length = 222
FEATURE                  Location/Qualifiers
source                   1..222
                         mol_type = protein
                         organism = synthetic construct
SEQUENCE: 156
VECPPCPAPP VAGPSVFLFP PKPKDTLMIS RTPEVTCVVV DVSHEDPEVQ FNWYVDGVEV  60
HNAKTKPREE QFNSTFRVVS VLTVVHQDWL NGKEYKCKVS NKGLPAPIEK TISKTKGQPR  120
EPQVYTLPPS REEMTKNQVS LTCLVKGFYP SDISVEWESN GQPENNYKTT PPMLDSDGSF  180
FLYSKLTVDK SRWQQGNVFS CSVMHEALHN HYTQKSLSLS PG                    222

SEQ ID NO: 157           moltype = AA  length = 224
FEATURE                  Location/Qualifiers
source                   1..224
                         mol_type = protein
                         organism = synthetic construct
SEQUENCE: 157
PCPPCKCPAP NLLGGPSVFI FPPKIKDVLM ISLSPIVTCV VVDVSEDDPD VQISWFVNNV  60
EVHTAQTQTH REDYNSTLRV VSALPIQHQD WMSGKEFKCK VNNKDLPAPI ERTISKPKGS  120
VRAPQVYVLP PPEEEMTKKQ VTLTCMVTDF MPEDIYVEWT NNGKTELNYK NTEPVLDSDG  180
SYFMYSKLRV EKKNWVERNS YSCSVVHEGL HNHHTTKSFS RTPG                  224

SEQ ID NO: 158           moltype = AA  length = 217
FEATURE                  Location/Qualifiers
source                   1..217
                         mol_type = protein
                         organism = synthetic construct
SEQUENCE: 158
```

-continued

```
APELLGGPSV FLFPPKPKDT LMISRTPEVT CVVVDVSHED PEVQFKWYVD GVEVHNAKTK  60
PREEQYNSTF RVVSVLTVLH QDWLNGKEYK CKVSNKALPA PIEKTISKTK GQPREPQVYT  120
LPPSREEMTK NQVSLTCLVK GFYPSDIAVE WESSGQPENN YNTTPPMLDS DGSFFLYSKL  180
TVDKSRWQQG NIFSCSVMHE ALHNRFTQKS LSLSPGK                          217

SEQ ID NO: 159          moltype = AA  length = 216
FEATURE                 Location/Qualifiers
source                  1..216
                        mol_type = protein
                        organism = synthetic construct
SEQUENCE: 159
APELLGGPSV FLFPPKPKDT LMISRTPEVT CVVVDVSHED PEVQFKWYVD GVEVHNAKTK  60
PREEQYNSTF RVVSVLTVLH QDWLNGKEYK CKVSNKALPA PIEKTISKTK GQPREPQVYT  120
LPPSREEMTK NQVSLTCLVK GFYPSDIAVE WESSGQPENN YNTTPPMLDS DGSFFLYSKL  180
TVDKSRWQQG NIFSCSVMHE ALHNRFTQKS LSLSPG                           216

SEQ ID NO: 160          moltype = AA  length = 220
FEATURE                 Location/Qualifiers
source                  1..220
                        mol_type = protein
                        organism = synthetic construct
SEQUENCE: 160
PRCPAPELLG GPSVFLFPPK PKDTLMISRT PEVTCVVVDV SHEDPEVQFK WYVDGVEVHN  60
AKTKPREEQY NSTFRVVSVL TVLHQDWLNG KEYKCKVSNK ALPAPIEKTI SKTKGQPREP  120
QVYTLPPSRE EMTKNQVSLT CLVKGFYPSD IAVEWESSGQ PENNYNTTPP MLDSDGSFFL  180
YSKLTVDKSR WQQGNIFSCS VMHEALHNRF TQKSLSLSPG                       220

SEQ ID NO: 161          moltype = AA  length = 226
FEATURE                 Location/Qualifiers
source                  1..226
                        mol_type = protein
                        organism = synthetic construct
SEQUENCE: 161
DTPPPCPRCP APELLGGPSV FLFPPKPKDT LMISRTPEVT CVVVDVSHED PEVQFKWYVD  60
GVEVHNAKTK PREEQYNSTF RVVSVLTVLH QDWLNGKEYK CKVSNKALPA PIEKTISKTK  120
GQPREPQVYT LPPSREEMTK NQVSLTCLVK GFYPSDIAVE WESSGQPENN YNTTPPMLDS  180
DGSFFLYSKL TVDKSRWQQG NIFSCSVMHE ALHNRFTQKS LSLSPG                226

SEQ ID NO: 162          moltype = AA  length = 231
FEATURE                 Location/Qualifiers
source                  1..231
                        mol_type = protein
                        organism = synthetic construct
SEQUENCE: 162
EPKSSDTPPP CPRCPAPELL GGPSVFLFPP KPKDTLMISR TPEVTCVVVD VSHEDPEVQF  60
KWYVDGVEVH NAKTKPREEQ YNSTFRVVSV LTVLHQDWLN GKEYKCKVSN KALPAPIEKT  120
ISKTKGQPRE PQVYTLPPSR EEMTKNQVSL TCLVKGFYPS DIAVEWESSG QPENNYNTTP  180
PMLDSDGSFF LYSKLTVDKS RWQQGNIFSC SVMHEALHNR FTQKSLSLSP G          231

SEQ ID NO: 163          moltype = AA  length = 231
FEATURE                 Location/Qualifiers
source                  1..231
                        mol_type = protein
                        organism = synthetic construct
SEQUENCE: 163
EPKSSDTPPP SPRCPAPELL GGPSVFLFPP KPKDTLMISR TPEVTCVVVD VSHEDPEVQF  60
KWYVDGVEVH NAKTKPREEQ YNSTFRVVSV LTVLHQDWLN GKEYKCKVSN KALPAPIEKT  120
ISKTKGQPRE PQVYTLPPSR EEMTKNQVSL TCLVKGFYPS DIAVEWESSG QPENNYNTTP  180
PMLDSDGSFF LYSKLTVDKS RWQQGNIFSC SVMHEALHNR FTQKSLSLSP G          231

SEQ ID NO: 164          moltype = AA  length = 231
FEATURE                 Location/Qualifiers
source                  1..231
                        mol_type = protein
                        organism = synthetic construct
SEQUENCE: 164
EPKSSDTPPP SPRSPAPELL GGPSVFLFPP KPKDTLMISR TPEVTCVVVD VSHEDPEVQF  60
KWYVDGVEVH NAKTKPREEQ YNSTFRVVSV LTVLHQDWLN GKEYKCKVSN KALPAPIEKT  120
ISKTKGQPRE PQVYTLPPSR EEMTKNQVSL TCLVKGFYPS DIAVEWESSG QPENNYNTTP  180
PMLDSDGSFF LYSKLTVDKS RWQQGNIFSC SVMHEALHNR FTQKSLSLSP G          231

SEQ ID NO: 165          moltype = AA  length = 217
FEATURE                 Location/Qualifiers
source                  1..217
                        mol_type = protein
                        organism = synthetic construct
SEQUENCE: 165
APEFLGGPSV FLFPPKPKDT LMISRTPEVT CVVVDVSQED PEVQFNWYVD GVEVHNAKTK  60
PREEQFNSTY RVVSVLTVLH QDWLNGKEYK CKVSNKGLPS SIEKTISKAK GQPREPQVYT  120
```

-continued

```
LPPSQEEMTK NQVSLTCLVK GFYPSDIAVE WESNGQPENN YKTTPPVLDS DGSFFLYSRL  180
TVDKSRWQEG NVFSCSVMHE ALHNHYTQKS LSLSLGK                           217

SEQ ID NO: 166          moltype = AA  length = 224
FEATURE                 Location/Qualifiers
source                  1..224
                        mol_type = protein
                        organism = synthetic construct
SEQUENCE: 166
GPPCPPCPAP EFLGGPSVFL FPPKPKDTLM ISRTPEVTCV VVDVSQEDPE VQFNWYVDGV  60
EVHNAKTKPR EEQFNSTYRV VSVLTVLHQD WLNGKEYKCK VSNKGLPSSI EKTISKAKGQ  120
PREPQVYTLP PSQEEMTKNQ VSLTCLVKGF YPSDIAVEWE SNGQPENNYK TTPPVLDSDG  180
SFFLYSRLTV DKSRWQEGNV FSCSVMHEAL HNHYTQKSLS LSLG                   224

SEQ ID NO: 167          moltype = AA  length = 216
FEATURE                 Location/Qualifiers
source                  1..216
                        mol_type = protein
                        organism = synthetic construct
SEQUENCE: 167
APEFLGGPSV FLFPPKPKDT LMISRTPEVT CVVVDVSQED PEVQFNWYVD GVEVHNAKTK  60
PREEQFNSTY RVVSVLTVLH QDWLNGKEYK CKVSNKGLPS SIEKTISKAK GQPREPQVYT  120
LPPSQEEMTK NQVSLTCLVK GFYPSDIAVE WESNGQPENN YKTTPPVLDS DGSFFLYSRL  180
TVDKSRWQEG NVFSCSVMHE ALHNHYTQKS LSLSLG                            216

SEQ ID NO: 168          moltype = AA  length = 220
FEATURE                 Location/Qualifiers
source                  1..220
                        mol_type = protein
                        organism = synthetic construct
SEQUENCE: 168
PSCPAPEFLG GPSVFLFPPK PKDTLMISRT PEVTCVVVDV SQEDPEVQFN WYVDGVEVHN  60
AKTKPREEQF NSTYRVVSVL TVLHQDWLNG KEYKCKVSNK GLPSSIEKTI SKAKGQPREP  120
QVYTLPPSQE EMTKNQVSLT CLVKGFYPSD IAVEWESNGQ PENNYKTTPP VLDSDGSFFL  180
YSRLTVDKSR WQEGNVFSCS VMHEALHNHY TQKSLSLSLG                        220

SEQ ID NO: 169          moltype = AA  length = 228
FEATURE                 Location/Qualifiers
source                  1..228
                        mol_type = protein
                        organism = synthetic construct
SEQUENCE: 169
ESKYGPPCPS CPAPEFLGGP SVFLFPPKPK DTLMISRTPE VTCVVVDVSQ EDPEVQFNWY  60
VDGVEVHNAK TKPREEQFNS TYRVVSVLTV LHQDWLNGKE YKCKVSNKGL PSSIEKTISK  120
AKGQPREPQV YTLPPSQEEM TKNQVSLTCL VKGFYPSDIA VEWESNGQPE NNYKTTPPVL  180
DSDGSFFLYS RLTVDKSRWQ EGNVFSCSVM HEALHNHYTQ KSLSLSLG               228

SEQ ID NO: 170          moltype = AA  length = 228
FEATURE                 Location/Qualifiers
source                  1..228
                        mol_type = protein
                        organism = synthetic construct
SEQUENCE: 170
ESKYGPPCPP CPAPEFLGGP SVFLFPPKPK DTLMISRTPE VTCVVVDVSQ EDPEVQFNWY  60
VDGVEVHNAK TKPREEQFNS TYRVVSVLTV LHQDWLNGKE YKCKVSNKGL PSSIEKTISK  120
AKGQPREPQV YTLPPSQEEM TKNQVSLTCL VKGFYPSDIA VEWESNGQPE NNYKTTPPVL  180
DSDGSFFLYS RLTVDKSRWQ EGNVFSCSVM HEALHNHYTQ KSLSLSLG               228

SEQ ID NO: 171          moltype = AA  length = 228
FEATURE                 Location/Qualifiers
source                  1..228
                        mol_type = protein
                        organism = synthetic construct
SEQUENCE: 171
ESKYGPPCPP CPAPEFLGGP SVFLFPPKPK DTLMISRTPE VTCVVVDVSQ EDPEVQFNWY  60
VDGVEVHNAK TKPREEQFNS TYRVVSVLTV LHQDWLNGKE YKCKVSNKGL PSSIEKTISK  120
AKGQPREPQV YTLPPSQEEM TKNQVSLTCL VKGFYPSDIA VEWESNGQPE NNYKTTPPVL  180
DSDGSFFLYS KLTVDKSRWQ EGNVFSCSVM HEALHNHYTQ KSLSLSLG               228

SEQ ID NO: 172          moltype = AA  length = 228
FEATURE                 Location/Qualifiers
source                  1..228
                        mol_type = protein
                        organism = synthetic construct
SEQUENCE: 172
ESKYGPPSPS CPAPEFLGGP SVFLFPPKPK DTLMISRTPE VTCVVVDVSQ EDPEVQFNWY  60
VDGVEVHNAK TKPREEQFNS TYRVVSVLTV LHQDWLNGKE YKCKVSNKGL PSSIEKTISK  120
AKGQPREPQV YTLPPSQEEM TKNQVSLTCL VKGFYPSDIA VEWESNGQPE NNYKTTPPVL  180
DSDGSFFLYS RLTVDKSRWQ EGNVFSCSVM HEALHNHYTQ KSLSLSLG               228
```

```
SEQ ID NO: 173          moltype = AA  length = 228
FEATURE                 Location/Qualifiers
source                  1..228
                        mol_type = protein
                        organism = synthetic construct
SEQUENCE: 173
ESKYGPPSPS SPAPEFLGGP SVFLFPPKPK DTLMISRTPE VTCVVVDVSQ EDPEVQFNWY  60
VDGVEVHNAK TKPREEQFNS TYRVVSVLTV LHQDWLNGKE YKCKVSNKGL PSSIEKTISK  120
AKGQPREPQV YTLPPSQEEM TKNQVSLTCL VKGFYPSDIA VEWESNGQPE NNYKTTPPVL  180
DSDGSFFLYS RLTVDKSRWQ EGNVFSCSVM HEALHNHYTQ KSLSLSLG               228

SEQ ID NO: 174          moltype = AA  length = 334
FEATURE                 Location/Qualifiers
source                  1..334
                        mol_type = protein
                        organism = synthetic construct
SEQUENCE: 174
ETRECIYYNA NWELERTNQS GLERCEGEQD KRLHCYASWR NSSGTIELVK KGCWLDDFNC  60
YDRQECVATE ENPQVYFCCC EGNFCNERFT HLPEAGGPEV TYEPPPTGGG THTCPPCPAP  120
ELLGGPSVFL FPPKPKDTLM ISRTPEVTCV VVDVSHEDPE VKFNWYVDGV EVHNAKTKPR  180
EEQYNSTYRV VSVLTVLHQD WLNGKEYKCK VSNKALPAPI EKTISKAKGQ PREPQVYTLP  240
PSRDELTKNQ VSLTCLVKGF YPSDIAVEWE SNGQPENNYK TTPPVLDSDG SFFLYSKLTV  300
DKSRWQQGNV FSCSVMHEAL HNHYTQKSLS LSPG                              334

SEQ ID NO: 175          moltype = AA  length = 345
FEATURE                 Location/Qualifiers
source                  1..345
                        mol_type = protein
                        organism = synthetic construct
SEQUENCE: 175
ETRECIYYNA NWELERTNQS GLERCEGEQD KRLHCYASWR NSSGTIELVK KGCWLDDFNC  60
YDRQECVATE ENPQVYFCCC EGNFCNERFT HLPEAGGPEV TYEPPPTGGG GSGGGGSGGG  120
GTHTCPPCPA PELLGGPSVF LFPPKPKDTL MISRTPEVTC VVVDVSHEDP EVKFNWYVDG  180
VEVHNAKTKP REEQYNSTYR VVSVLTVLHQ DWLNGKEYKC KVSNKALPAP IEKTISKAKG  240
QPREPQVYTL PPSRDELTKN QVSLTCLVKG FYPSDIAVEW ESNGQPENNY KTTPPVLDSD  300
GSFFLYSKLT VDKSRWQQGN VFSCSVMHEA LHNHYTQKSL SLSPG                  345

SEQ ID NO: 176          moltype = AA  length = 343
FEATURE                 Location/Qualifiers
source                  1..343
                        mol_type = protein
                        organism = synthetic construct
SEQUENCE: 176
ILGRSETQEC LFFNANWEKD RTNQTGVEPC YGDKDKRRHC FATWKNISGS IEIVKQGCWL  60
DDINCYDRTD CVEKKDSPEV YFCCCEGNMC NEKFSYFPEM EVTQPTSNPV TPKPPTGGGT  120
HTCPPCPAPE LLGGPSVFLF PPKPKDTLMI SRTPEVTCVV VDVSHEDPEV KFNWYVDGVE  180
VHNAKTKPRE EQYNSTYRVV SVLTVLHQDW LNGKEYKCKV SNKALPVPIE KTISKAKGQP  240
REPQVYTLPP SREEMTKNQV SLTCLVKGFY PSDIAVEWES NGQPENNYKT TPPVLDSDGS  300
FFLYSKLTVD KSRWQQGNVF SCSVMHEALH NHYTQKSLSL SPG                    343

SEQ ID NO: 177          moltype = AA  length = 334
FEATURE                 Location/Qualifiers
source                  1..334
                        mol_type = protein
                        organism = synthetic construct
SEQUENCE: 177
ETRECIYYNA NWELERTNQS GLERCEDEQD KRLHCYASWR NSSGTIELVK KGCWLDDFNC  60
YDRQECVATE ENPQVYFCCC EGNFCNERFT HLPEAGGPEV TYEPPPTGGG THTCPPCPAP  120
ELLGGPSVFL FPPKPKDTLM ISRTPEVTCV VVDVSHEDPE VKFNWYVDGV EVHNAKTKPR  180
EEQYNSTYRV VSVLTVLHQD WLNGKEYKCK VSNKALPAPI EKTISKAKGQ PREPQVYTLP  240
PSREEMTKNQ VSLTCLVKGF YPSDIAVEWE SNGQPENNYK TTPPVLDSDG SFFLYSKLTV  300
DKSRWQQGNV FSCSVMHEAL HNHYTQKSLS LSPG                              334

SEQ ID NO: 178          moltype = AA  length = 334
FEATURE                 Location/Qualifiers
source                  1..334
                        mol_type = protein
                        organism = synthetic construct
SEQUENCE: 178
ETRECIYYNA NWELERTNQS GLERCEGEQD KRLHCYASWR NSSGTIELVK KGCWLDEFNC  60
YDRQECVATE ENPQVYFCCC EGNFCNERFT HLPEAGGPEV TYEPPPTGGG THTCPPCPAP  120
ELLGGPSVFL FPPKPKDTLM ISRTPEVTCV VVDVSHEDPE VKFNWYVDGV EVHNAKTKPR  180
EEQYNSTYRV VSVLTVLHQD WLNGKEYKCK VSNKALPAPI EKTISKAKGQ PREPQVYTLP  240
PSREEMTKNQ VSLTCLVKGF YPSDIAVEWE SNGQPENNYK TTPPVLDSDG SFFLYSKLTV  300
DKSRWQQGNV FSCSVMHEAL HNHYTQKSLS LSPG                              334

SEQ ID NO: 179          moltype = AA  length = 334
FEATURE                 Location/Qualifiers
```

```
source                  1..334
                        mol_type = protein
                        organism = synthetic construct
SEQUENCE: 179
ETRECIYYNA NWELERTNQS GLERCEGEQD KRLHCYASWR NSSGTIELVK KGCWLDDENC  60
YDRQECVATE ENPQVYFCCC EGNFCNERFT HLPEAGGPEV TYEPPPTGGG THTCPPCPAP  120
ELLGGPSVFL FPPKPKDTLM ISRTPEVTCV VVDVSHEDPE VKFNWYVDGV EVHNAKTKPR  180
EEQYNSTYRV VSVLTVLHQD WLNGKEYKCK VSNKALPAPI EKTISKAKGQ PREPQVYTLP  240
PSREEMTKNQ VSLTCLVKGF YPSDIAVEWE SNGQPENNYK TTPPVLDSDG SFFLYSKLTV  300
DKSRWQQGNV FSCSVMHEAL HNHYTQKSLS LSPG                              334

SEQ ID NO: 180          moltype = AA  length = 334
FEATURE                 Location/Qualifiers
source                  1..334
                        mol_type = protein
                        organism = synthetic construct
SEQUENCE: 180
ETRECIYYNA NWELERTNQS GLERCEGEYD KRLHCYASWR NSSGTIELVK KGCWLDDFNC  60
YDRQECVATE ENPQVYFCCC EGNFCNERFT HLPEAGGPEV TYEPPPTGGG THTCPPCPAP  120
ELLGGPSVFL FPPKPKDTLM ISRTPEVTCV VVDVSHEDPE VKFNWYVDGV EVHNAKTKPR  180
EEQYNSTYRV VSVLTVLHQD WLNGKEYKCK VSNKALPAPI EKTISKAKGQ PREPQVYTLP  240
PSREEMTKNQ VSLTCLVKGF YPSDIAVEWE SNGQPENNYK TTPPVLDSDG SFFLYSKLTV  300
DKSRWQQGNV FSCSVMHEAL HNHYTQKSLS LSPG                              334

SEQ ID NO: 181          moltype = AA  length = 334
FEATURE                 Location/Qualifiers
source                  1..334
                        mol_type = protein
                        organism = synthetic construct
SEQUENCE: 181
ETRECIYYNA NWELERTNQS GLERCEGEQQ KRLHCYASWR NSSGTIELVK KGCWLDDFNC  60
YDRQECVATE ENPQVYFCCC EGNFCNERFT HLPEAGGPEV TYEPPPTGGG THTCPPCPAP  120
ELLGGPSVFL FPPKPKDTLM ISRTPEVTCV VVDVSHEDPE VKFNWYVDGV EVHNAKTKPR  180
EEQYNSTYRV VSVLTVLHQD WLNGKEYKCK VSNKALPAPI EKTISKAKGQ PREPQVYTLP  240
PSREEMTKNQ VSLTCLVKGF YPSDIAVEWE SNGQPENNYK TTPPVLDSDG SFFLYSKLTV  300
DKSRWQQGNV FSCSVMHEAL HNHYTQKSLS LSPG                              334

SEQ ID NO: 182          moltype = AA  length = 334
FEATURE                 Location/Qualifiers
source                  1..334
                        mol_type = protein
                        organism = synthetic construct
SEQUENCE: 182
ETRECIYYNA NWELERTNQS GLERCEGEQD YRLHCYASWR NSSGTIELVK KGCWLDDFNC  60
YDRQECVATE ENPQVYFCCC EGNFCNERFT HLPEAGGPEV TYEPPPTGGG THTCPPCPAP  120
ELLGGPSVFL FPPKPKDTLM ISRTPEVTCV VVDVSHEDPE VKFNWYVDGV EVHNAKTKPR  180
EEQYNSTYRV VSVLTVLHQD WLNGKEYKCK VSNKALPAPI EKTISKAKGQ PREPQVYTLP  240
PSREEMTKNQ VSLTCLVKGF YPSDIAVEWE SNGQPENNYK TTPPVLDSDG SFFLYSKLTV  300
DKSRWQQGNV FSCSVMHEAL HNHYTQKSLS LSPG                              334

SEQ ID NO: 183          moltype = AA  length = 334
FEATURE                 Location/Qualifiers
source                  1..334
                        mol_type = protein
                        organism = synthetic construct
SEQUENCE: 183
ETRECIYYNA NWELERTNQS GLERCEGEQD KRLHCYARWR NSSGTIELVK KGCWLDDFNC  60
YDRQECVATE ENPQVYFCCC EGNFCNERFT HLPEAGGPEV TYEPPPTGGG THTCPPCPAP  120
ELLGGPSVFL FPPKPKDTLM ISRTPEVTCV VVDVSHEDPE VKFNWYVDGV EVHNAKTKPR  180
EEQYNSTYRV VSVLTVLHQD WLNGKEYKCK VSNKALPAPI EKTISKAKGQ PREPQVYTLP  240
PSREEMTKNQ VSLTCLVKGF YPSDIAVEWE SNGQPENNYK TTPPVLDSDG SFFLYSKLTV  300
DKSRWQQGNV FSCSVMHEAL HNHYTQKSLS LSPG                              334

SEQ ID NO: 184          moltype = AA  length = 334
FEATURE                 Location/Qualifiers
source                  1..334
                        mol_type = protein
                        organism = synthetic construct
SEQUENCE: 184
ETRECIYYNA NWELERTNQS GLERCEGEQD KRLHCYASWR NSSGTIELVK KGCWLDDFNC  60
YDRQECVATE ENPQQYFCCC EGNFCNERFT HLPEAGGPEV TYEPPPTGGG THTCPPCPAP  120
ELLGGPSVFL FPPKPKDTLM ISRTPEVTCV VVDVSHEDPE VKFNWYVDGV EVHNAKTKPR  180
EEQYNSTYRV VSVLTVLHQD WLNGKEYKCK VSNKALPAPI EKTISKAKGQ PREPQVYTLP  240
PSREEMTKNQ VSLTCLVKGF YPSDIAVEWE SNGQPENNYK TTPPVLDSDG SFFLYSKLTV  300
DKSRWQQGNV FSCSVMHEAL HNHYTQKSLS LSPG                              334

SEQ ID NO: 185          moltype = AA  length = 334
FEATURE                 Location/Qualifiers
source                  1..334
```

```
                        mol_type = protein
                        organism = synthetic construct
SEQUENCE: 185
ETRECIYYNA NWELERTNQS GLERCEGEQD KRLHCYASWR NSSGTIELVK KGCWLDDFNC  60
YDRQECVATE ENPQVYDCCC EGNFCNERFT HLPEAGGPEV TYEPPPTGGG THTCPPCPAP  120
ELLGGPSVFL FPPKPKDTLM ISRTPEVTCV VVDVSHEDPE VKFNWYVDGV EVHNAKTKPR  180
EEQYNSTYRV VSVLTVLHQD WLNGKEYKCK VSNKALPAPI EKTISKAKGQ PREPQVYTLP  240
PSREEMTKNQ VSLTCLVKGF YPSDIAVEWE SNGQPENNYK TTPPVLDSDG SFFLYSKLTV  300
DKSRWQQGNV FSCSVMHEAL HNHYTQKSLS LSPG                             334

SEQ ID NO: 186          moltype = AA  length = 345
FEATURE                 Location/Qualifiers
source                  1..345
                        mol_type = protein
                        organism = synthetic construct
SEQUENCE: 186
ETRECIYYNA NWELERTNQS GLERCEGEQD KRLHCYASWR NSSGTIELVK KGCWLDDENC  60
YDRQECVATE ENPQVYFCCC EGNFCNERFT HLPEAGGPEV TYEPPPTGGG GSGGGGSGGG  120
GTHTCPPCPA PELLGGPSVF LFPPKPKDTL MISRTPEVTC VVVDVSHEDP EVKFNWYVDG  180
VEVHNAKTKP REEQYNSTYR VVSVLTVLHQ DWLNGKEYKC KVSNKALPAP IEKTISKAKG  240
QPREPQVYTL PPSRDELTKN QVSLTCLVKG FYPSDIAVEW ESNGQPENNY KTTPPVLDSD  300
GSFFLYSKLT VDKSRWQQGN VFSCSVMHEA LHNHYTQKSL SLSPG                  345

SEQ ID NO: 187          moltype = AA  length = 334
FEATURE                 Location/Qualifiers
source                  1..334
                        mol_type = protein
                        organism = synthetic construct
SEQUENCE: 187
ETRECIYYNA NWELERTNQS GLERCEGEQD KRLHCYASWR NSSGTIELVK KGCWLDDENC  60
YDRQECVATE ENPQVYFCCC EGNFCNERFT HLPEAGGPEV TYEPPPTGGG THTCPPCPAP  120
ELLGGPSVFL FPPKPKDTLM ISRTPEVTCV VVDVSHEDPE VKFNWYVDGV EVHNAKTKPR  180
EEQYNSTYRV VSVLTVLHQD WLNGKEYKCK VSNKALPAPI EKTISKAKGQ PREPQVYTLP  240
PSRDELTKNQ VSLTCLVKGF YPSDIAVEWE SNGQPENNYK TTPPVLDSDG SFFLYSKLTV  300
DKSRWQQGNV FSCSVMHEAL HNHYTQKSLS LSPG                             334

SEQ ID NO: 188          moltype = AA  length = 334
FEATURE                 Location/Qualifiers
source                  1..334
                        mol_type = protein
                        organism = synthetic construct
SEQUENCE: 188
ETRECIYYNA NWELERTNQS GLERCEGEQD KRLHCYASWR NSSGTIELVK KGCWLDDENC  60
YDRQECVATE ENPQVYFCCC EGNFCNERFT HLPEAGGPEV TYEPPPTGGG THTCPPCPAP  120
ELLGGPSVFL FPPKPKDTLY ISRTPEVTCV VVDVSHEDPE VKFNWYVDGV EVHNAKTKPR  180
EEQYNSTYRV VSVLTVLHQD WLNGKEYKCK VSNKALPAPI EKTISKAKGQ PREPQVYTLP  240
PSRDELTKNQ VSLTCLVKGF YPSDIAVEWE SNGQPENNYK TTPPVLDSDG SFFLYSKLTV  300
DKSRWQQGNV FSCSVMHEAL HNHYTQKSLS LSPG                             334

SEQ ID NO: 189          moltype = AA  length = 334
FEATURE                 Location/Qualifiers
source                  1..334
                        mol_type = protein
                        organism = synthetic construct
SEQUENCE: 189
ETRECIYYNA NWELERTNQS GLERCEGEQD KRLHCYASWR NSSGTIELVK KGCWLDDENC  60
YDRQECVATE ENPQVYFCCC EGNFCNERFT HLPEAGGPEV TYEPPPTGGG THTCPPCPAP  120
ELLGGPSVFL FPPKPKDTLY ITREPEVTCV VVDVSHEDPE VKFNWYVDGV EVHNAKTKPR  180
EEQYNSTYRV VSVLTVLHQD WLNGKEYKCK VSNKALPAPI EKTISKAKGQ PREPQVYTLP  240
PSRDELTKNQ VSLTCLVKGF YPSDIAVEWE SNGQPENNYK TTPPVLDSDG SFFLYSKLTV  300
DKSRWQQGNV FSCSVMHEAL HNHYTQKSLS LSPG                             334

SEQ ID NO: 190          moltype = AA  length = 350
FEATURE                 Location/Qualifiers
source                  1..350
                        mol_type = protein
                        organism = synthetic construct
SEQUENCE: 190
ETRECIYYNA NWELERTNQS GLERCEGEQD KRLHCYASWR NSSGTIELVK KGCWLDDENC  60
YDRQECVATE ENPQVYFCCC EGNFCNERFT HLPEAGGPEV TYEPPPTGGG GSGGGGSGGG  120
GSGGGGTHTC PPCPAPELLG GPSVFLFPPK PKDTLMISRT PEVTCVVVDV SHEDPEVKFN  180
WYVDGVEVHN AKTKPREEQY NSTYRVVSVL TVLHQDWLNG KEYKCKVSNK ALPAPIEKTI  240
SKAKGQPREP QVYTLPPSRD ELTKNQVSLT CLVKGFYPSD IAVEWESNGQ PENNYKTTPP  300
VLDSDGSFFL YSKLTVDKSR WQQGNVFSCS VMHEALHNHY TQKSLSLSPG             350

SEQ ID NO: 191          moltype = AA  length = 370
FEATURE                 Location/Qualifiers
source                  1..370
                        mol_type = protein
```

```
                         organism = synthetic construct
SEQUENCE: 191
ETRECIYYNA NWELERTNQS GLERCEGEQD KRLHCYASWR NSSGTIELVK KGCWLDDENC  60
YDRQECVATE ENPQVYFCCC EGNFCNERFT HLPEAGGPEV TYEPPPTGGG GSGGGGSGGG  120
GSGGGGSGGG GSGGGGSGGG GSGGGGTHTC PPCPAPELLG GPSVFLFPPK PKDTLMISRT  180
PEVTCVVVDV SHEDPEVKFN WYVDGVEVHN AKTKPREEQY NSTYRVVSVL TVLHQDWLNG  240
KEYKCKVSNK ALPAPIEKTI SKAKGQPREP QVYTLPPSRD ELTKNQVSLT CLVKGFYPSD  300
IAVEWESNGQ PENNYKTTPP VLDSDGSFFL YSKLTVDKSR WQQGNVFSCS VMHEALHNHY  360
TQKSLSLSPG                                                        370

SEQ ID NO: 192           moltype = AA  length = 345
FEATURE                  Location/Qualifiers
source                   1..345
                         mol_type = protein
                         organism = synthetic construct
SEQUENCE: 192
ETRECIYYNA NWELERTNQS GLERCEGEQD KRLHCYASWR NSSGTIELVK KGCWLDDENC  60
YDRQECVATE ENPQVYFCCC EGNFCNERFT HLPEAGGPEV TYEPPPTGGG GSGGGGSGGG  120
GPCPPCKCPA PNLLGGPSVF IFPPKIKDVL MISLSPIVTC VVVDVSEDDP DVQISWFVNN  180
VEVHTAQTQT HREDYNSTLR VVSALPIQHQ DWMSGKEFKC KVNNKDLPAP IERTISKPKG  240
SVRAPQVYVL PPPEEEMTKK QVTLTCMVTD FMPEDIYVEW TNNGKTELNY KNTEPVLDSD  300
GSYFMYSKLR VEKKNWVERN SYSCSVVHEG LHNHHTTKSF SRTPG                 345

SEQ ID NO: 193           moltype = AA  length = 350
FEATURE                  Location/Qualifiers
source                   1..350
                         mol_type = protein
                         organism = synthetic construct
SEQUENCE: 193
ETRECIYYNA NWELERTNQS GLERCEGEQD KRLHCYASWR NSSGTIELVK KGCWLDDENC  60
YDRQECVATE ENPQVYFCCC EGNFCNERFT HLPEAGGPEV TYEPPPTGGG GSGGGGSGGG  120
GSGGGGPCPP CKCPAPNLLG GPSVFIFPPK IKDVLMISLS PIVTCVVVDV SEDDPDVQIS  180
WFVNNVEVHT AQTQTHREDY NSTLRVVSAL PIQHQDWMSG KEFKCKVNNK DLPAPIERTI  240
SKPKGSVRAP QVYVLPPPEE EMTKKQVTLT CMVTDFMPED IYVEWTNNGK TELNYKNTEP  300
VLDSDGSYFM YSKLRVEKKN WVERNSYSCS VVHEGLHNHH TTKSFSRTPG            350

SEQ ID NO: 194           moltype = AA  length = 370
FEATURE                  Location/Qualifiers
source                   1..370
                         mol_type = protein
                         organism = synthetic construct
SEQUENCE: 194
ETRECIYYNA NWELERTNQS GLERCEGEQD KRLHCYASWR NSSGTIELVK KGCWLDDENC  60
YDRQECVATE ENPQVYFCCC EGNFCNERFT HLPEAGGPEV TYEPPPTGGG GSGGGGSGGG  120
GSGGGGSGGG GSGGGGSGGG GSGGGGPCPP CKCPAPNLLG GPSVFIFPPK IKDVLMISLS  180
PIVTCVVVDV SEDDPDVQIS WFVNNVEVHT AQTQTHREDY NSTLRVVSAL PIQHQDWMSG  240
KEFKCKVNNK DLPAPIERTI SKPKGSVRAP QVYVLPPPEE EMTKKQVTLT CMVTDFMPED  300
IYVEWTNNGK TELNYKNTEP VLDSDGSYFM YSKLRVEKKN WVERNSYSCS VVHEGLHNHH  360
TTKSFSRTPG                                                        370

SEQ ID NO: 195           moltype = AA  length = 334
FEATURE                  Location/Qualifiers
source                   1..334
                         mol_type = protein
                         organism = synthetic construct
SEQUENCE: 195
ETRECIYYNA NWELERTNQS GLERCEGEQD KRLHCYASWR NSSGTIELVK KGCWLDDENC  60
YDRQECVATE ENPQVYFCCC EGNFCNERFT HLPEAGGPEV TYEPPPTGGG PCPPCKCPAP  120
NLLGGPSVFI FPPKIKDVLM ISLSPIVTCV VVDVSEDDPD VQISWFVNNV EVHTAQTQTH  180
REDYNSTLRV VSALPIQHQD WMSGKEFKCK VNNKDLPAPI ERTISKPKGS VRAPQVYVLP  240
PPEEEMTKKQ VTLTCMVTDF MPEDIYVEWT NNGKTELNYK NTEPVLDSDG SYFMYSKLRV  300
EKKNWVERNS YSCSVVHEGL HNHHTTKSFS RTPG                             334

SEQ ID NO: 196           moltype = AA  length = 334
FEATURE                  Location/Qualifiers
source                   1..334
                         mol_type = protein
                         organism = synthetic construct
SEQUENCE: 196
ETRECIYYNA NWELERTNQS GLERCEGEQD KRLHCYASWR NSSGTIELVK KGCWLDDDNC  60
YDRQECVATE ENPQVYFCCC EGNFCNERFT HLPEAGGPEV TYEPPPTGGG THTCPPCPAP  120
ELLGGPSVFL FPPKPKDTLM ISRTPEVTCV VVDVSHEDPE VKFNWYVDGV EVHNAKTKPR  180
EEQYNSTYRV VSVLTVLHQD WLNGKEYKCK VSNKALPAPI EKTISKAKGQ PREPQVYTLP  240
PSREEMTKNQ VSLTCLVKGF YPSDIAVEWE SNGQPENNYK TTPPVLDSDG SFFLYSKLTV  300
DKSRWQQGNV FSCSVMHEAL HNHYTQKSLS LSPG                             334

SEQ ID NO: 197           moltype = AA  length = 334
FEATURE                  Location/Qualifiers
source                   1..334
```

```
                         mol_type = protein
                         organism = synthetic construct
SEQUENCE: 197
ETRECIYYNA NWELERTNQS GLERCEGEQD KRLHCYASWR NSSGTIELVK KGCWLDDDNC  60
YDRQECVATE ENPQVYFCCC EGNFCNERFT HLPEAGGPEV TYEPPPTGGG THTCPPCPAP  120
ELLGGPSVFL FPPKPKDTLM ISRTPEVTCV VVDVSHEDPE VKFNWYVDGV EVHNAKTKPR  180
EEQYNSTYRV VSVLTVLHQD WLNGKEYKCK VSNKALPAPI EKTISKAKGQ PREPQVYTLP  240
PSRDELTKNQ VSLTCLVKGF YPSDIAVEWE SNGQPENNYK TTPPVLDSDG SFFLYSKLTV  300
DKSRWQQGNV FSCSVMHEAL HNHYTQKSLS LSPG                              334

SEQ ID NO: 198          moltype = AA  length = 334
FEATURE                 Location/Qualifiers
source                  1..334
                         mol_type = protein
                         organism = synthetic construct
SEQUENCE: 198
ETRECIYYNA NWELERTNQS GLERCEGEQD KRLHCYASWR NSSGTIELVK KGCWLDDDNC  60
YDRQECVATE ENPQVYFCCC EGNFCNERFT HLPEAGGPEV TYEPPPTGGG PCPPCKCPAP  120
NLLGGPSVFI FPPKIKDVLM ISLSPIVTCV VVDVSEDDPD VQISWFVNNV EVHTAQTQTH  180
REDYNSTLRV VSALPIQHQD WMSGKEFKCK VNNKDLPAPI ERTISKPKGS VRAPQVYVLP  240
PPEEEMTKKQ VTLTCMVTDF MPEDIYVEWT NNGKTELNYK NTEPVLDSDG SYFMYSKLRV  300
EKKNWVERNS YSCSVVHEGL HNHHTTKSFS RTPG                              334

SEQ ID NO: 199          moltype = AA  length = 345
FEATURE                 Location/Qualifiers
source                  1..345
                         mol_type = protein
                         organism = synthetic construct
SEQUENCE: 199
ETRECIYYNA NWELERTNQS GLERCEGEQD KRLHCYASWR NSSGTIELVK KGCWLDDDNC  60
YDRQECVATE ENPQVYFCCC EGNFCNERFT HLPEAGGPEV TYEPPPTGGG GSGGGGSGGG  120
GTHTCPPCPA PELLGGPSVF LFPPKPKDTL MISRTPEVTC VVVDVSHEDP EVKFNWYVDG  180
VEVHNAKTKP REEQYNSTYR VVSVLTVLHQ DWLNGKEYKC KVSNKALPAP IEKTISKAKG  240
QPREPQVYTL PPSREEMTKN QVSLTCLVKG FYPSDIAVEW ESNGQPENNY KTTPPVLDSD  300
GSFFLYSKLT VDKSRWQQGN VFSCSVMHEA LHNHYTQKSL SLSPG                  345

SEQ ID NO: 200          moltype = AA  length = 345
FEATURE                 Location/Qualifiers
source                  1..345
                         mol_type = protein
                         organism = synthetic construct
SEQUENCE: 200
ETRECIYYNA NWELERTNQS GLERCEGEQD KRLHCYASWR NSSGTIELVK KGCWLDDDNC  60
YDRQECVATE ENPQVYFCCC EGNFCNERFT HLPEAGGPEV TYEPPPTGGG GSGGGGSGGG  120
GTHTCPPCPA PELLGGPSVF LFPPKPKDTL MISRTPEVTC VVVDVSHEDP EVKFNWYVDG  180
VEVHNAKTKP REEQYNSTYR VVSVLTVLHQ DWLNGKEYKC KVSNKALPAP IEKTISKAKG  240
QPREPQVYTL PPSRDELTKN QVSLTCLVKG FYPSDIAVEW ESNGQPENNY KTTPPVLDSD  300
GSFFLYSKLT VDKSRWQQGN VFSCSVMHEA LHNHYTQKSL SLSPG                  345

SEQ ID NO: 201          moltype = AA  length = 370
FEATURE                 Location/Qualifiers
source                  1..370
                         mol_type = protein
                         organism = synthetic construct
SEQUENCE: 201
ETRECIYYNA NWELERTNQS GLERCEGEQD KRLHCYASWR NSSGTIELVK KGCWLDDDNC  60
YDRQECVATE ENPQVYFCCC EGNFCNERFT HLPEAGGPEV TYEPPPTGGG GSGGGGSGGG  120
GSGGGGSGGG GSGGGGSGGG GSGGGGTHTC PPCPAPELLG GPSVFLFPPK PKDTLMISRT  180
PEVTCVVVDV SHEDPEVKFN WYVDGVEVHN AKTKPREEQY NSTYRVVSVL TVLHQDWLNG  240
KEYKCKVSNK ALPAPIEKTI SKAKGQPREP QVYTLPPSRD ELTKNQVSLT CLVKGFYPSD  300
IAVEWESNGQ PENNYKTTPP VLDSDGSFFL YSKLTVDKSR WQQGNVFSCS VMHEALHNHY  360
TQKSLSLSPG                                                         370

SEQ ID NO: 202          moltype = AA  length = 370
FEATURE                 Location/Qualifiers
source                  1..370
                         mol_type = protein
                         organism = synthetic construct
SEQUENCE: 202
ETRECIYYNA NWELERTNQS GLERCEGEQD KRLHCYASWR NSSGTIELVK KGCWLDDDNC  60
YDRQECVATE ENPQVYFCCC EGNFCNERFT HLPEAGGPEV TYEPPPTGGG GSGGGGSGGG  120
GSGGGGSGGG GSGGGGSGGG GSGGGGPCPP CKCPAPNLLG GPSVFIFPPK IKDVLMISLS  180
PIVTCVVVDV SEDDPDVQIS WFVNNVEVHT AQTQTHREDY NSTLRVVSAL PIQHQDWMSG  240
KEFKCKVNNK DLPAPIERTI SKPKGSVRAP QVYVLPPPEE EMTKKQVTLT CMVTDFMPED  300
IYVEWTNNGK TELNYKNTEP VLDSDGSYFM YSKLRVEKKN WVERNSYSCS VVHEGLHNHH  360
TTKSFSRTPG                                                         370

SEQ ID NO: 203          moltype = AA  length = 334
FEATURE                 Location/Qualifiers
```

-continued

```
source                  1..334
                        mol_type = protein
                        organism = synthetic construct
SEQUENCE: 203
ETRECIYYNA NWELERTNQS GLERCEGEQD KRLHCYASWR NSSGTIELVK KGCWLDDYNC  60
YDRQECVATE ENPQVYFCCC EGNFCNERFT HLPEAGGPEV TYEPPPTGGG THTCPPCPAP  120
ELLGGPSVFL FPPKPKDTLM ISRTPEVTCV VVDVSHEDPE VKFNWYVDGV EVHNAKTKPR  180
EEQYNSTYRV VSVLTVLHQD WLNGKEYKCK VSNKALPAPI EKTISKAKGQ PREPQVYTLP  240
PSREEMTKNQ VSLTCLVKGF YPSDIAVEWE SNGQPENNYK TTPPVLDSDG SFFLYSKLTV  300
DKSRWQQGNV FSCSVMHEAL HNHYTQKSLS LSPG                              334

SEQ ID NO: 204          moltype = AA  length = 334
FEATURE                 Location/Qualifiers
source                  1..334
                        mol_type = protein
                        organism = synthetic construct
SEQUENCE: 204
ETRECIYYNA NWELERTNQS GLERCEGEQD KRLHCYASWR NSSGTIELVK KGCWLDDYNC  60
YDRQECVATE ENPQVYFCCC EGNFCNERFT HLPEAGGPEV TYEPPPTGGG THTCPPCPAP  120
ELLGGPSVFL FPPKPKDTLM ISRTPEVTCV VVDVSHEDPE VKFNWYVDGV EVHNAKTKPR  180
EEQYNSTYRV VSVLTVLHQD WLNGKEYKCK VSNKALPAPI EKTISKAKGQ PREPQVYTLP  240
PSRDELTKNQ VSLTCLVKGF YPSDIAVEWE SNGQPENNYK TTPPVLDSDG SFFLYSKLTV  300
DKSRWQQGNV FSCSVMHEAL HNHYTQKSLS LSPG                              334

SEQ ID NO: 205          moltype = AA  length = 334
FEATURE                 Location/Qualifiers
source                  1..334
                        mol_type = protein
                        organism = synthetic construct
SEQUENCE: 205
ETRECIYYNA NWELERTNQS GLERCEGEQD KRLHCYASWR NSSGTIELVK KGCWLDDYNC  60
YDRQECVATE ENPQVYFCCC EGNFCNERFT HLPEAGGPEV TYEPPPTGGG PCPPCKCPAP  120
NLLGGPSVFI FPPKIKDVLM ISLSPIVTCV VVDVSEDDPD VQISWFVNNV EVHTAQTQTH  180
REDYNSTLRV VSALPIQHQD WMSGKEFKCK VNNKDLPAPI ERTISKPKGS VRAPQVYVLP  240
PPEEEMTKKQ VTLTCMVTDF MPEDIYVEWT NNGKTELNYK NTEPVLDSDG SYFMYSKLRV  300
EKKNWVERNS YSCSVVHEGL HNHHTTKSFS RTPG                              334

SEQ ID NO: 206          moltype = AA  length = 345
FEATURE                 Location/Qualifiers
source                  1..345
                        mol_type = protein
                        organism = synthetic construct
SEQUENCE: 206
ETRECIYYNA NWELERTNQS GLERCEGEQD KRLHCYASWR NSSGTIELVK KGCWLDDYNC  60
YDRQECVATE ENPQVYFCCC EGNFCNERFT HLPEAGGPEV TYEPPPTGGG GSGGGGSGGG  120
GTHTCPPCPA PELLGGPSVF LFPPKPKDTL MISRTPEVTC VVVDVSHEDP EVKFNWYVDG  180
VEVHNAKTKP REEQYNSTYR VVSVLTVLHQ DWLNGKEYKC KVSNKALPAP IEKTISKAKG  240
QPREPQVYTL PPSREEMTKN QVSLTCLVKG FYPSDIAVEW ESNGQPENNY KTTPPVLDSD  300
GSFFLYSKLT VDKSRWQQGN VFSCSVMHEA LHNHYTQKSL SLSPG                  345

SEQ ID NO: 207          moltype = AA  length = 345
FEATURE                 Location/Qualifiers
source                  1..345
                        mol_type = protein
                        organism = synthetic construct
SEQUENCE: 207
ETRECIYYNA NWELERTNQS GLERCEGEQD KRLHCYASWR NSSGTIELVK KGCWLDDYNC  60
YDRQECVATE ENPQVYFCCC EGNFCNERFT HLPEAGGPEV TYEPPPTGGG GSGGGGSGGG  120
GTHTCPPCPA PELLGGPSVF LFPPKPKDTL MISRTPEVTC VVVDVSHEDP EVKFNWYVDG  180
VEVHNAKTKP REEQYNSTYR VVSVLTVLHQ DWLNGKEYKC KVSNKALPAP IEKTISKAKG  240
QPREPQVYTL PPSRDELTKN QVSLTCLVKG FYPSDIAVEW ESNGQPENNY KTTPPVLDSD  300
GSFFLYSKLT VDKSRWQQGN VFSCSVMHEA LHNHYTQKSL SLSPG                  345

SEQ ID NO: 208          moltype = AA  length = 370
FEATURE                 Location/Qualifiers
source                  1..370
                        mol_type = protein
                        organism = synthetic construct
SEQUENCE: 208
ETRECIYYNA NWELERTNQS GLERCEGEQD KRLHCYASWR NSSGTIELVK KGCWLDDYNC  60
YDRQECVATE ENPQVYFCCC EGNFCNERFT HLPEAGGPEV TYEPPPTGGG GSGGGGSGGG  120
GSGGGGSGGG GSGGGGSGGG GSGGGGTHTC PPCPAPELLG GPSVFLFPPK PKDTLMISRT  180
PEVTCVVVDV SHEDPEVKFN WYVDGVEVHN AKTKPREEQY NSTYRVVSVL TVLHQDWLNG  240
KEYKCKVSNK ALPAPIEKTI SKAKGQPREP QVYTLPPSRD ELTKNQVSLT CLVKGFYPSD  300
IAVEWESNGQ PENNYKTTPP VLDSDGSFFL YSKLTVDKSR WQQGNVFSCS VMHEALHNHY  360
TQKSLSLSPG                                                         370

SEQ ID NO: 209          moltype = AA  length = 370
FEATURE                 Location/Qualifiers
```

-continued

```
source                  1..370
                        mol_type = protein
                        organism = synthetic construct
SEQUENCE: 209
ETRECIYYNA NWELERTNQS GLERCEGEQD KRLHCYASWR NSSGTIELVK KGCWLDDYNC  60
YDRQECVATE ENPQVYFCCC EGNFCNERFT HLPEAGGPEV TYEPPPTGGG GSGGGGSGGG  120
GSGGGGSGGG GSGGGGSGGG GSGGGGPCPP CKCPAPNLLG GPSVFIFPPK IKDVLMISLS  180
PIVTCVVVDV SEDDPDVQIS WFVNNVEVHT AQTQTHREDY NSTLRVVSAL PIQHQDWMSG  240
KEFKCKVNNK DLPAPIERTI SKPKGSVRAP QVYVLPPPEE EMTKKQVTLT CMVTDFMPED  300
IYVEWTNNGK TELNYKNTEP VLDSDGSYFM YSKLRVEKKN WVERNSYSCS VVHEGLHNHH  360
TTKSFSRTPG                                                        370

SEQ ID NO: 210          moltype = AA  length = 334
FEATURE                 Location/Qualifiers
source                  1..334
                        mol_type = protein
                        organism = synthetic construct
SEQUENCE: 210
ETRECIYYNA NWELERTNQS GLERCEGEQD KRLHCYASWR NSSGTIELVK KGCWLDDKNC  60
YDRQECVATE ENPQVYFCCC EGNFCNERFT HLPEAGGPEV TYEPPPTGGG THTCPPCPAP  120
ELLGGPSVFL FPPKPKDTLM ISRTPEVTCV VVDVSHEDPE VKFNWYVDGV EVHNAKTKPR  180
EEQYNSTYRV VSVLTVLHQD WLNGKEYKCK VSNKALPAPI EKTISKAKGQ PREPQVYTLP  240
PSREEMTKNQ VSLTCLVKGF YPSDIAVEWE SNGQPENNYK TTPPVLDSDG SFFLYSKLTV  300
DKSRWQQGNV FSCSVMHEAL HNHYTQKSLS LSPG                              334

SEQ ID NO: 211          moltype = AA  length = 334
FEATURE                 Location/Qualifiers
source                  1..334
                        mol_type = protein
                        organism = synthetic construct
SEQUENCE: 211
ETRECIYYNA NWELERTNQS GLERCEGEQD KRLHCYASWR NSSGTIELVK KGCWLDDKNC  60
YDRQECVATE ENPQVYFCCC EGNFCNERFT HLPEAGGPEV TYEPPPTGGG THTCPPCPAP  120
ELLGGPSVFL FPPKPKDTLM ISRTPEVTCV VVDVSHEDPE VKFNWYVDGV EVHNAKTKPR  180
EEQYNSTYRV VSVLTVLHQD WLNGKEYKCK VSNKALPAPI EKTISKAKGQ PREPQVYTLP  240
PSRDELTKNQ VSLTCLVKGF YPSDIAVEWE SNGQPENNYK TTPPVLDSDG SFFLYSKLTV  300
DKSRWQQGNV FSCSVMHEAL HNHYTQKSLS LSPG                              334

SEQ ID NO: 212          moltype = AA  length = 334
FEATURE                 Location/Qualifiers
source                  1..334
                        mol_type = protein
                        organism = synthetic construct
SEQUENCE: 212
ETRECIYYNA NWELERTNQS GLERCEGEQD KRLHCYASWR NSSGTIELVK KGCWLDDKNC  60
YDRQECVATE ENPQVYFCCC EGNFCNERFT HLPEAGGPEV TYEPPPTGGG PCPPCKCPAP  120
NLLGGPSVFI FPPKIKDVLM ISLSPIVTCV VVDVSEDDPD VQISWFVNNV EVHTAQTQTH  180
REDYNSTLRV VSALPIQHQD WMSGKEFKCK VNNKDLPAPI ERTISKPKGS VRAPQVYVLP  240
PPEEEMTKKQ VTLTCMVTDF MPEDIYVEWT NNGKTELNYK NTEPVLDSDG SYFMYSKLRV  300
EKKNWVERNS YSCSVVHEGL HNHHTTKSFS RTPG                              334

SEQ ID NO: 213          moltype = AA  length = 345
FEATURE                 Location/Qualifiers
source                  1..345
                        mol_type = protein
                        organism = synthetic construct
SEQUENCE: 213
ETRECIYYNA NWELERTNQS GLERCEGEQD KRLHCYASWR NSSGTIELVK KGCWLDDKNC  60
YDRQECVATE ENPQVYFCCC EGNFCNERFT HLPEAGGPEV TYEPPPTGGG GSGGGGSGGG  120
GTHTCPPCPA PELLGGPSVF LFPPKPKDTL MISRTPEVTC VVVDVSHEDP EVKFNWYVDG  180
VEVHNAKTKP REEQYNSTYR VVSVLTVLHQ DWLNGKEYKC KVSNKALPAP IEKTISKAKG  240
QPREPQVYTL PPSREEMTKN QVSLTCLVKG FYPSDIAVEW ESNGQPENNY KTTPPVLDSD  300
GSFFLYSKLT VDKSRWQQGN VFSCSVMHEA LHNHYTQKSL SLSPG                  345

SEQ ID NO: 214          moltype = AA  length = 345
FEATURE                 Location/Qualifiers
source                  1..345
                        mol_type = protein
                        organism = synthetic construct
SEQUENCE: 214
ETRECIYYNA NWELERTNQS GLERCEGEQD KRLHCYASWR NSSGTIELVK KGCWLDDKNC  60
YDRQECVATE ENPQVYFCCC EGNFCNERFT HLPEAGGPEV TYEPPPTGGG GSGGGGSGGG  120
GTHTCPPCPA PELLGGPSVF LFPPKPKDTL MISRTPEVTC VVVDVSHEDP EVKFNWYVDG  180
VEVHNAKTKP REEQYNSTYR VVSVLTVLHQ DWLNGKEYKC KVSNKALPAP IEKTISKAKG  240
QPREPQVYTL PPSRDELTKN QVSLTCLVKG FYPSDIAVEW ESNGQPENNY KTTPPVLDSD  300
GSFFLYSKLT VDKSRWQQGN VFSCSVMHEA LHNHYTQKSL SLSPG                  345

SEQ ID NO: 215          moltype = AA  length = 370
FEATURE                 Location/Qualifiers
```

```
source                  1..370
                        mol_type = protein
                        organism = synthetic construct
SEQUENCE: 215
ETRECIYYNA NWELERTNQS GLERCEGEQD KRLHCYASWR NSSGTIELVK KGCWLDDKNC  60
YDRQECVATE ENPQVYFCCC EGNFCNERFT HLPEAGGPEV TYEPPPTGGG GSGGGGSGGG  120
GSGGGGSGGG GSGGGGSGGG GSGGGGTHTC PPCPAPELLG GPSVFLFPPK PKDTLMISRT  180
PEVTCVVVDV SHEDPEVKFN WYVDGVEVHN AKTKPREEQY NSTYRVVSVL TVLHQDWLNG  240
KEYKCKVSNK ALPAPIEKTI SKAKGQPREP QVYTLPPSRD ELTKNQVSLT CLVKGFYPSD  300
IAVEWESNGQ PENNYKTTPP VLDSDGSFFL YSKLTVDKSR WQQGNVFSCS VMHEALHNHY  360
TQKSLSLSPG                                                        370

SEQ ID NO: 216          moltype = AA  length = 370
FEATURE                 Location/Qualifiers
source                  1..370
                        mol_type = protein
                        organism = synthetic construct
SEQUENCE: 216
ETRECIYYNA NWELERTNQS GLERCEGEQD KRLHCYASWR NSSGTIELVK KGCWLDDKNC  60
YDRQECVATE ENPQVYFCCC EGNFCNERFT HLPEAGGPEV TYEPPPTGGG GSGGGGSGGG  120
GSGGGGSGGG GSGGGGSGGG GSGGGGPCPP CKCPAPNLLG GPSVFIFPPK IKDVLMISLS  180
PIVTCVVVDV SEDDPDVQIS WFVNNVEVHT AQTQTHREDY NSTLRVVSAL PIQHQDWMSG  240
KEFKCKVNNK DLPAPIERTI SKPKGSVRAP QVYVLPPPEE EMTKKQVTLT CMVTDFMPED  300
IYVEWTNNGK TELNYKNTEP VLDSDGSYFM YSKLRVEKKN WVERNSYSCS VVHEGLHNHH  360
TTKSFSRTPG                                                        370

SEQ ID NO: 217          moltype = AA  length = 334
FEATURE                 Location/Qualifiers
source                  1..334
                        mol_type = protein
                        organism = synthetic construct
SEQUENCE: 217
ETRECIYYNA NWELERTNQS GLERCEGEQD KRLHCYASWR NSSGTIELVK KGCWLDDQNC  60
YDRQECVATE ENPQVYFCCC EGNFCNERFT HLPEAGGPEV TYEPPPTGGG THTCPPCPAP  120
ELLGGPSVFL FPPKPKDTLM ISRTPEVTCV VVDVSHEDPE VKFNWYVDGV EVHNAKTKPR  180
EEQYNSTYRV VSVLTVLHQD WLNGKEYKCK VSNKALPAPI EKTISKAKGQ PREPQVYTLP  240
PSREEMTKNQ VSLTCLVKGF YPSDIAVEWE SNGQPENNYK TTPPVLDSDG SFFLYSKLTV  300
DKSRWQQGNV FSCSVMHEAL HNHYTQKSLS LSPG                             334

SEQ ID NO: 218          moltype = AA  length = 334
FEATURE                 Location/Qualifiers
source                  1..334
                        mol_type = protein
                        organism = synthetic construct
SEQUENCE: 218
ETRECIYYNA NWELERTNQS GLERCEGEQD KRLHCYASWR NSSGTIELVK KGCWLDDQNC  60
YDRQECVATE ENPQVYFCCC EGNFCNERFT HLPEAGGPEV TYEPPPTGGG THTCPPCPAP  120
ELLGGPSVFL FPPKPKDTLM ISRTPEVTCV VVDVSHEDPE VKFNWYVDGV EVHNAKTKPR  180
EEQYNSTYRV VSVLTVLHQD WLNGKEYKCK VSNKALPAPI EKTISKAKGQ PREPQVYTLP  240
PSRDELTKNQ VSLTCLVKGF YPSDIAVEWE SNGQPENNYK TTPPVLDSDG SFFLYSKLTV  300
DKSRWQQGNV FSCSVMHEAL HNHYTQKSLS LSPG                             334

SEQ ID NO: 219          moltype = AA  length = 334
FEATURE                 Location/Qualifiers
source                  1..334
                        mol_type = protein
                        organism = synthetic construct
SEQUENCE: 219
ETRECIYYNA NWELERTNQS GLERCEGEQD KRLHCYASWR NSSGTIELVK KGCWLDDQNC  60
YDRQECVATE ENPQVYFCCC EGNFCNERFT HLPEAGGPEV TYEPPPTGGG PCPPCKCPAP  120
NLLGGPSVFI FPPKIKDVLM ISLSPIVTCV VVDVSEDDPD VQISWFVNNV EVHTAQTQTH  180
REDYNSTLRV VSALPIQHQD WMSGKEFKCK VNNKDLPAPI ERTISKPKGS VRAPQVYVLP  240
PPEEEMTKKQ VTLTCMVTDF MPEDIYVEWT NNGKTELNYK NTEPVLDSDG SYFMYSKLRV  300
EKKNWVERNS YSCSVVHEGL HNHHTTKSFS RTPG                             334

SEQ ID NO: 220          moltype = AA  length = 345
FEATURE                 Location/Qualifiers
source                  1..345
                        mol_type = protein
                        organism = synthetic construct
SEQUENCE: 220
ETRECIYYNA NWELERTNQS GLERCEGEQD KRLHCYASWR NSSGTIELVK KGCWLDDQNC  60
YDRQECVATE ENPQVYFCCC EGNFCNERFT HLPEAGGPEV TYEPPPTGGG GSGGGGSGGG  120
GTHTCPPCPA PELLGGPSVF LFPPKPKDTL MISRTPEVTC VVVDVSHEDP EVKFNWYVDG  180
VEVHNAKTKP REEQYNSTYR VVSVLTVLHQ DWLNGKEYKC KVSNKALPAP IEKTISKAKG  240
QPREPQVYTL PPSREEMTKN QVSLTCLVKG FYPSDIAVEW ESNGQPENNY KTTPPVLDSD  300
GSFFLYSKLT VDKSRWQQGN VFSCSVMHEA LHNHYTQKSL SLSPG                  345

SEQ ID NO: 221          moltype = AA  length = 345
```

```
FEATURE                 Location/Qualifiers
source                  1..345
                        mol_type = protein
                        organism = synthetic construct
SEQUENCE: 221
ETRECIYYNA NWELERTNQS GLERCEGEQD KRLHCYASWR NSSGTIELVK KGCWLDDQNC  60
YDRQECVATE ENPQVYFCCC EGNFCNERFT HLPEAGGPEV TYEPPPTGGG GSGGGGSGGG  120
GTHTCPPCPA PELLGGPSVF LFPPKPKDTL MISRTPEVTC VVVDVSHEDP EVKFNWYVDG  180
VEVHNAKTKP REEQYNSTYR VVSVLTVLHQ DWLNGKEYKC KVSNKALPAP IEKTISKAKG  240
QPREPQVYTL PPSRDELTKN QVSLTCLVKG FYPSDIAVEW ESNGQPENNY KTTPPVLDSD  300
GSFFLYSKLT VDKSRWQQGN VFSCSVMHEA LHNHYTQKSL SLSPG                  345

SEQ ID NO: 222          moltype = AA  length = 370
FEATURE                 Location/Qualifiers
source                  1..370
                        mol_type = protein
                        organism = synthetic construct
SEQUENCE: 222
ETRECIYYNA NWELERTNQS GLERCEGEQD KRLHCYASWR NSSGTIELVK KGCWLDDQNC  60
YDRQECVATE ENPQVYFCCC EGNFCNERFT HLPEAGGPEV TYEPPPTGGG GSGGGGSGGG  120
GSGGGGSGGG GSGGGGSGGG GSGGGGTHTC PPCPAPELLG GPSVFLFPPK PKDTLMISRT  180
PEVTCVVVDV SHEDPEVKFN WYVDGVEVHN AKTKPREEQY NSTYRVVSVL TVLHQDWLNG  240
KEYKCKVSNK ALPAPIEKTI SKAKGQPREP QVYTLPPSRD ELTKNQVSLT CLVKGFYPSD  300
IAVEWESNGQ PENNYKTTPP VLDSDGSFFL YSKLTVDKSR WQQGNVFSCS VMHEALHNHY  360
TQKSLSLSPG                                                         370

SEQ ID NO: 223          moltype = AA  length = 370
FEATURE                 Location/Qualifiers
source                  1..370
                        mol_type = protein
                        organism = synthetic construct
SEQUENCE: 223
ETRECIYYNA NWELERTNQS GLERCEGEQD KRLHCYASWR NSSGTIELVK KGCWLDDQNC  60
YDRQECVATE ENPQVYFCCC EGNFCNERFT HLPEAGGPEV TYEPPPTGGG GSGGGGSGGG  120
GSGGGGSGGG GSGGGGSGGG GSGGGGPCPP CKCPAPNLLG GPSVFIFPPK IKDVLMISLS  180
PIVTCVVVDV SEDDPDVQIS WFVNNVEVHT AQTQTHREDY NSTLRVVSAL PIQHQDWMSG  240
KEFKCKVNNK DLPAPIERTI SKPKGSVRAP QVYVLPPPEE EMTKKQVTLT CMVTDFMPED  300
IYVEWTNNGK TELNYKNTEP VLDSDGSYFM YSKLRVEKKN WVERNSYSCS VVHEGLHNHH  360
TTKSFSRTPG                                                         370

SEQ ID NO: 224          moltype = AA  length = 334
FEATURE                 Location/Qualifiers
source                  1..334
                        mol_type = protein
                        organism = synthetic construct
SEQUENCE: 224
ETRECIYYNA NWELERTNQS GLERCEGEQD KRLHCYASWR NSSGTIELVK KGCWLDDWNC  60
YDRQECVATE ENPQVYFCCC EGNFCNERFT HLPEAGGPEV TYEPPPTGGG THTCPPCPAP  120
ELLGGPSVFL FPPKPKDTLM ISRTPEVTCV VVDVSHEDPE VKFNWYVDGV EVHNAKTKPR  180
EEQYNSTYRV VSVLTVLHQD WLNGKEYKCK VSNKALPAPI EKTISKAKGQ PREPQVYTLP  240
PSREEMTKNQ VSLTCLVKGF YPSDIAVEWE SNGQPENNYK TTPPVLDSDG SFFLYSKLTV  300
DKSRWQQGNV FSCSVMHEAL HNHYTQKSLS LSPG                              334

SEQ ID NO: 225          moltype = AA  length = 334
FEATURE                 Location/Qualifiers
source                  1..334
                        mol_type = protein
                        organism = synthetic construct
SEQUENCE: 225
ETRECIYYNA NWELERTNQS GLERCEGEQD KRLHCYASWR NSSGTIELVK KGCWLDDWNC  60
YDRQECVATE ENPQVYFCCC EGNFCNERFT HLPEAGGPEV TYEPPPTGGG THTCPPCPAP  120
ELLGGPSVFL FPPKPKDTLM ISRTPEVTCV VVDVSHEDPE VKFNWYVDGV EVHNAKTKPR  180
EEQYNSTYRV VSVLTVLHQD WLNGKEYKCK VSNKALPAPI EKTISKAKGQ PREPQVYTLP  240
PSRDELTKNQ VSLTCLVKGF YPSDIAVEWE SNGQPENNYK TTPPVLDSDG SFFLYSKLTV  300
DKSRWQQGNV FSCSVMHEAL HNHYTQKSLS LSPG                              334

SEQ ID NO: 226          moltype = AA  length = 334
FEATURE                 Location/Qualifiers
source                  1..334
                        mol_type = protein
                        organism = synthetic construct
SEQUENCE: 226
ETRECIYYNA NWELERTNQS GLERCEGEQD KRLHCYASWR NSSGTIELVK KGCWLDDWNC  60
YDRQECVATE ENPQVYFCCC EGNFCNERFT HLPEAGGPEV TYEPPPTGGG PCPPCKCPAP  120
NLLGGPSVFI FPPKIKDVLM ISLSPIVTCV VVDVSEDDPD VQISWFVNNV EVHTAQTQTH  180
REDYNSTLRV VSALPIQHQD WMSGKEFKCK VNNKDLPAPI ERTISKPKGS VRAPQVYVLP  240
PPEEEMTKKQ VTLTCMVTDF MPEDIYVEWT NNGKTELNYK NTEPVLDSDG SYFMYSKLRV  300
EKKNWVERNS YSCSVVHEGL HNHHTTKSFS RTPG                              334
```

```
SEQ ID NO: 227          moltype = AA  length = 345
FEATURE                 Location/Qualifiers
source                  1..345
                        mol_type = protein
                        organism = synthetic construct
SEQUENCE: 227
ETRECIYYNA NWELERTNQS GLERCEGEQD KRLHCYASWR NSSGTIELVK KGCWLDDWNC  60
YDRQECVATE ENPQVYFCCC EGNFCNERFT HLPEAGGPEV TYEPPPTGGG GSGGGGSGGG  120
GTHTCPPCPA PELLGGPSVF LFPPKPKDTL MISRTPEVTC VVVDVSHEDP EVKFNWYVDG  180
VEVHNAKTKP REEQYNSTYR VVSVLTVLHQ DWLNGKEYKC KVSNKALPAP IEKTISKAKG  240
QPREPQVYTL PPSREEMTKN QVSLTCLVKG FYPSDIAVEW ESNGQPENNY KTTPPVLDSD  300
GSFFLYSKLT VDKSRWQQGN VFSCSVMHEA LHNHYTQKSL SLSPG                  345

SEQ ID NO: 228          moltype = AA  length = 345
FEATURE                 Location/Qualifiers
source                  1..345
                        mol_type = protein
                        organism = synthetic construct
SEQUENCE: 228
ETRECIYYNA NWELERTNQS GLERCEGEQD KRLHCYASWR NSSGTIELVK KGCWLDDWNC  60
YDRQECVATE ENPQVYFCCC EGNFCNERFT HLPEAGGPEV TYEPPPTGGG GSGGGGSGGG  120
GTHTCPPCPA PELLGGPSVF LFPPKPKDTL MISRTPEVTC VVVDVSHEDP EVKFNWYVDG  180
VEVHNAKTKP REEQYNSTYR VVSVLTVLHQ DWLNGKEYKC KVSNKALPAP IEKTISKAKG  240
QPREPQVYTL PPSRDELTKN QVSLTCLVKG FYPSDIAVEW ESNGQPENNY KTTPPVLDSD  300
GSFFLYSKLT VDKSRWQQGN VFSCSVMHEA LHNHYTQKSL SLSPG                  345

SEQ ID NO: 229          moltype = AA  length = 370
FEATURE                 Location/Qualifiers
source                  1..370
                        mol_type = protein
                        organism = synthetic construct
SEQUENCE: 229
ETRECIYYNA NWELERTNQS GLERCEGEQD KRLHCYASWR NSSGTIELVK KGCWLDDWNC  60
YDRQECVATE ENPQVYFCCC EGNFCNERFT HLPEAGGPEV TYEPPPTGGG GSGGGGSGGG  120
GSGGGGSGGG GSGGGGSGGG GSGGGGTHTC PPCPAPELLG GPSVFLFPPK PKDTLMISRT  180
PEVTCVVVDV SHEDPEVKFN WYVDGVEVHN AKTKPREEQY NSTYRVVSVL TVLHQDWLNG  240
KEYKCKVSNK ALPAPIEKTI SKAKGQPREP QVYTLPPSRD ELTKNQVSLT CLVKGFYPSD  300
IAVEWESNGQ PENNYKTTPP VLDSDGSFFL YSKLTVDKSR WQQGNVFSCS VMHEALHNHY  360
TQKSLSLSPG                                                         370

SEQ ID NO: 230          moltype = AA  length = 370
FEATURE                 Location/Qualifiers
source                  1..370
                        mol_type = protein
                        organism = synthetic construct
SEQUENCE: 230
ETRECIYYNA NWELERTNQS GLERCEGEQD KRLHCYASWR NSSGTIELVK KGCWLDDWNC  60
YDRQECVATE ENPQVYFCCC EGNFCNERFT HLPEAGGPEV TYEPPPTGGG GSGGGGSGGG  120
GSGGGGSGGG GSGGGGSGGG GSGGGGPCPP CKCPAPNLLG GPSVFIFPPK IKDVLMISLS  180
PIVTCVVVDV SEDDPDVQIS WFVNNVEVHT AQTQTHREDY NSTLRVVSAL PIQHQDWMSG  240
KEFKCKVNNK DLPAPIERTI SKPKGSVRAP QVYVLPPPEE EMTKKQVTLT CMVTDFMPED  300
IYVEWTNNGK TELNYKNTEP VLDSDGSYFM YSKLRVEKKN WVERNSYSCS VVHEGLHNHH  360
TTKSFSRTPG                                                         370

SEQ ID NO: 231          moltype = AA  length = 334
FEATURE                 Location/Qualifiers
source                  1..334
                        mol_type = protein
                        organism = synthetic construct
SEQUENCE: 231
ETRECIYYNA NWELERTNQS GLERCEGEQD KRLHCYASWR NSSGTIELVK KGCWLDEENC  60
YDRQECVATE ENPQVYFCCC EGNFCNERFT HLPEAGGPEV TYEPPPTGGG THTCPPCPAP  120
ELLGGPSVFL FPPKPKDTLM ISRTPEVTCV VVDVSHEDPE VKFNWYVDGV EVHNAKTKPR  180
EEQYNSTYRV VSVLTVLHQD WLNGKEYKCK VSNKALPAPI EKTISKAKGQ PREPQVYTLP  240
PSRDELTKNQ VSLTCLVKGF YPSDIAVEWE SNGQPENNYK TTPPVLDSDG SFFLYSKLTV  300
DKSRWQQGNV FSCSVMHEAL HNHYTQKSLS LSPG                              334

SEQ ID NO: 232          moltype = AA  length = 345
FEATURE                 Location/Qualifiers
source                  1..345
                        mol_type = protein
                        organism = synthetic construct
SEQUENCE: 232
ETRECIYYNA NWELERTNQS GLERCEGEYD KRLHCYASWR NSSGTIELVK KGCWLDDENC  60
YDRQECVATE ENPQVYFCCC EGNFCNERFT HLPEAGGPEV TYEPPPTGGG GSGGGGSGGG  120
GTHTCPPCPA PELLGGPSVF LFPPKPKDTL MISRTPEVTC VVVDVSHEDP EVKFNWYVDG  180
VEVHNAKTKP REEQYNSTYR VVSVLTVLHQ DWLNGKEYKC KVSNKALPAP IEKTISKAKG  240
QPREPQVYTL PPSRDELTKN QVSLTCLVKG FYPSDIAVEW ESNGQPENNY KTTPPVLDSD  300
GSFFLYSKLT VDKSRWQQGN VFSCSVMHEA LHNHYTQKSL SLSPG                  345
```

```
SEQ ID NO: 233          moltype = AA  length = 345
FEATURE                 Location/Qualifiers
source                  1..345
                        mol_type = protein
                        organism = synthetic construct
SEQUENCE: 233
ETRECIYYNA NWELERTNQS GLERCEGEQQ KRLHCYASWR NSSGTIELVK KGCWLDDENC  60
YDRQECVATE ENPQVYFCCC EGNFCNERFT HLPEAGGPEV TYEPPPTGGG GSGGGGSGGG  120
GTHTCPPCPA PELLGGPSVF LFPPKPKDTL MISRTPEVTC VVVDVSHEDP EVKFNWYVDG  180
VEVHNAKTKP REEQYNSTYR VVSVLTVLHQ DWLNGKEYKC KVSNKALPAP IEKTISKAKG  240
QPREPQVYTL PPSRDELTKN QVSLTCLVKG FYPSDIAVEW ESNGQPENNY KTTPPVLDSD  300
GSFFLYSKLT VDKSRWQQGN VFSCSVMHEA LHNHYTQKSL SLSPG                  345

SEQ ID NO: 234          moltype = AA  length = 334
FEATURE                 Location/Qualifiers
source                  1..334
                        mol_type = protein
                        organism = synthetic construct
SEQUENCE: 234
ETRECIYYNA NWELERTNQS GLERCEDEQD KRLHCYASWR NSSGTIELVK KGCWLDDENC  60
YDRQECVATE ENPQVYFCCC EGNFCNERFT HLPEAGGPEV TYEPPPTGGG THTCPPCPAP  120
ELLGGPSVFL FPPKPKDTLM ISRTPEVTCV VVDVSHEDPE VKFNWYVDGV EVHNAKTKPR  180
EEQYNSTYRV VSVLTVLHQD WLNGKEYKCK VSNKALPAPI EKTISKAKGQ PREPQVYTLP  240
PSREEMTKNQ VSLTCLVKGF YPSDIAVEWE SNGQPENNYK TTPPVLDSDG SFFLYSKLTV  300
DKSRWQQGNV FSCSVMHEAL HNHYTQKSLS LSPG                             334

SEQ ID NO: 235          moltype = AA  length = 350
FEATURE                 Location/Qualifiers
source                  1..350
                        mol_type = protein
                        organism = synthetic construct
SEQUENCE: 235
GRGEAETREC IYYNANWELE RTNQSGLERC EGEQDKRLHC YASWRNSSGT IELVKKGCWL  60
DDENCYDRQE CVATEENPQV YFCCCEGNFC NERFTHLPEA GGPEVTYEPP PTGGGGSGGG  120
GSGGGGTHTC PPCPAPELLG GPSVFLFPPK PKDTLMISRT PEVTCVVVDV SHEDPEVKFN  180
WYVDGVEVHN AKTKPREEQY NSTYRVVSVL TVLHQDWLNG KEYKCKVSNK ALPAPIEKTI  240
SKAKGQPREP QVYTLPPSRD ELTKNQVSLT CLVKGFYPSD IAVEWESNGQ PENNYKTTPP  300
VLDSDGSFFL YSKLTVDKSR WQQGNVFSCS VMHEALHNHY TQKSLSLSPG            350

SEQ ID NO: 236          moltype = AA  length = 349
FEATURE                 Location/Qualifiers
source                  1..349
                        mol_type = protein
                        organism = synthetic construct
SEQUENCE: 236
RGEAETRECI YYNANWELER TNQSGLERCE GEQDKRLHCY ASWRNSSGTI ELVKKGCWLD  60
DENCYDRQEC VATEENPQVY FCCCEGNFCN ERFTHLPEAG GPEVTYEPPP TGGGGSGGGG  120
SGGGGTHTCP PCPAPELLGG PSVFLFPPKP KDTLMISRTP EVTCVVVDVS HEDPEVKFNW  180
YVDGVEVHNA KTKPREEQYN STYRVVSVLT VLHQDWLNGK EYKCKVSNKA LPAPIEKTIS  240
KAKGQPREPQ VYTLPPSRDE LTKNQVSLTC LVKGFYPSDI AVEWESNGQP ENNYKTTPPV  300
LDSDGSFFLY SKLTVDKSRW QQGNVFSCSV MHEALHNHYT QKSLSLSPG             349

SEQ ID NO: 237          moltype = AA  length = 348
FEATURE                 Location/Qualifiers
source                  1..348
                        mol_type = protein
                        organism = synthetic construct
SEQUENCE: 237
GEAETRECIY YNANWELERT NQSGLERCEG EQDKRLHCYA SWRNSSGTIE LVKKGCWLDD  60
ENCYDRQECV ATEENPQVYF CCCEGNFCNE RFTHLPEAGG PEVTYEPPPT GGGGSGGGGS  120
GGGGTHTCPP CPAPELLGGP SVFLFPPKPK DTLMISRTPE VTCVVVDVSH EDPEVKFNWY  180
VDGVEVHNAK TKPREEQYNS TYRVVSVLTV LHQDWLNGKE YKCKVSNKAL PAPIEKTISK  240
AKGQPREPQV YTLPPSRDEL TKNQVSLTCL VKGFYPSDIA VEWESNGQPE NNYKTTPPVL  300
DSDGSFFLYS KLTVDKSRWQ QGNVFSCSVM HEALHNHYTQ KSLSLSPG              348

SEQ ID NO: 238          moltype = AA  length = 347
FEATURE                 Location/Qualifiers
source                  1..347
                        mol_type = protein
                        organism = synthetic construct
SEQUENCE: 238
EAETRECIYY NANWELERTN QSGLERCEGE QDKRLHCYAS WRNSSGTIEL VKKGCWLDDE  60
NCYDRQECVA TEENPQVYFC CCEGNFCNER FTHLPEAGGP EVTYEPPPTG GGGSGGGGSG  120
GGGTHTCPPC PAPELLGGPS VFLFPPKPKD TLMISRTPEV TCVVVDVSHE DPEVKFNWYV  180
DGVEVHNAKT KPREEQYNST YRVVSVLTVL HQDWLNGKEY KCKVSNKALP APIEKTISKA  240
KGQPREPQVY TLPPSRDELT KNQVSLTCLV KGFYPSDIAV EWESNGQPEN NYKTTPPVLD  300
SDGSFFLYSK LTVDKSRWQQ GNVFSCSVMH EALHNHYTQK SLSLSPG               347
```

```
SEQ ID NO: 239          moltype = AA  length = 346
FEATURE                 Location/Qualifiers
source                  1..346
                        mol_type = protein
                        organism = synthetic construct
SEQUENCE: 239
AETRECIYYN ANWELERTNQ SGLERCEGEQ DKRLHCYASW RNSSGTIELV KKGCWLDDEN  60
CYDRQECVAT EENPQVYFCC CEGNFCNERF THLPEAGGPE VTYEPPPTGG GGSGGGGSGG  120
GGTHTCPPCP APELLGGPSV FLFPPKPKDT LMISRTPEVT CVVVDVSHED PEVKFNWYVD  180
GVEVHNAKTK PREEQYNSTY RVVSVLTVLH QDWLNGKEYK CKVSNKALPA PIEKTISKAK  240
GQPREPQVYT LPPSRDELTK NQVSLTCLVK GFYPSDIAVE WESNGQPENN YKTTPPVLDS  300
DGSFFLYSKL TVDKSRWQQG NVFSCSVMHE ALHNHYTQKS LSLSPG                 346

SEQ ID NO: 240          moltype = AA  length = 345
FEATURE                 Location/Qualifiers
source                  1..345
                        mol_type = protein
                        organism = synthetic construct
SEQUENCE: 240
ETRECIYYNA NWELERTNQS GLERCEDEQD KRLHCYASWR NSSGTIELVK KGCWLDDFNC  60
YDRQECVATE ENPQVYFCCC EGNFCNERFT HLPEAGGPEV TYEPPPTGGG GSGGGGSGGG  120
GTHTCPPCPA PELLGGPSVF LFPPKPKDTL MISRTPEVTC VVVDVSHEDP EVKFNWYVDG  180
VEVHNAKTKP REEQYNSTYR VVSVLTVLHQ DWLNGKEYKC KVSNKALPAP IEKTISKAKG  240
QPREPQVYTL PPSRDELTKN QVSLTCLVKG FYPSDIAVEW ESNGQPENNY KTTPPVLDSD  300
GSFFLYSKLT VDKSRWQQGN VFSCSVMHEA LHNHYTQKSL SLSPG                  345

SEQ ID NO: 241          moltype = AA  length = 337
FEATURE                 Location/Qualifiers
source                  1..337
                        mol_type = protein
                        organism = synthetic construct
SEQUENCE: 241
ETRECIYYNA NWELERTNQS GLERCEGEQD KRLHCYASWR NSSGTIELVK KGCWLDDKNC  60
YDRQECVATE ENPQVYFCCC EGNFCNERFT HLPEAGGPEV TYEPPPTGGG GSGTHTCPPC  120
PAPELLGGPS VFLFPPKPKD TLMISRTPEV TCVVVDVSHE DPEVKFNWYV DGVEVHNAKT  180
KPREEQYNST YRVVSVLTVL HQDWLNGKEY KCKVSNKALP APIEKTISKA KGQPREPQVY  240
TLPPSRDELT KNQVSLTCLV KGFYPSDIAV EWESNGQPEN NYKTTPPVLD SDGSFFLYSK  300
LTVDKSRWQQ GNVFSCSVMH EALHNHYTQK SLSLSPG                           337

SEQ ID NO: 242          moltype = AA  length = 341
FEATURE                 Location/Qualifiers
source                  1..341
                        mol_type = protein
                        organism = synthetic construct
SEQUENCE: 242
ETRECIYYNA NWELERTNQS GLERCEGEQD KRLHCYASWR NSSGTIELVK KGCWLDDKNC  60
YDRQECVATE ENPQVYFCCC EGNFCNERFT HLPEAGGPEV TYEPPPTGGG GSGGGGSTHT  120
CPPCPAPELL GGPSVFLFPP KPKDTLMISR TPEVTCVVVD VSHEDPEVKF NWYVDGVEVH  180
NAKTKPREEQ YNSTYRVVSV LTVLHQDWLN GKEYKCKVSN KALPAPIEKT ISKAKGQPRE  240
PQVYTLPPSR DELTKNQVSL TCLVKGFYPS DIAVEWESNG QPENNYKTTP PVLDSDGSFF  300
LYSKLTVDKS RWQQGNVFSC SVMHEALHNH YTQKSLSLSP G                      341

SEQ ID NO: 243          moltype = AA  length = 350
FEATURE                 Location/Qualifiers
source                  1..350
                        mol_type = protein
                        organism = synthetic construct
SEQUENCE: 243
ETRECIYYNA NWELERTNQS GLERCEGEQD KRLHCYASWR NSSGTIELVK KGCWLDDKNC  60
YDRQECVATE ENPQVYFCCC EGNFCNERFT HLPEAGGPEV TYEPPPTGGG GSGGGGSGGG  120
GSGGGGTHTC PPCPAPELLG GPSVFLFPPK PKDTLMISRT PEVTCVVVDV SHEDPEVKFN  180
WYVDGVEVHN AKTKPREEQY NSTYRVVSVL TVLHQDWLNG KEYKCKVSNK ALPAPIEKTI  240
SKAKGQPREP QVYTLPPSRD ELTKNQVSLT CLVKGFYPSD IAVEWESNGQ PENNYKTTPP  300
VLDSDGSFFL YSKLTVDKSR WQQGNVFSCS VMHEALHNHY TQKSLSLSPG             350

SEQ ID NO: 244          moltype = AA  length = 370
FEATURE                 Location/Qualifiers
source                  1..370
                        mol_type = protein
                        organism = synthetic construct
SEQUENCE: 244
ETRECIYYNA NWELERTNQS GLERCEGEQD KRLHCYASWR NSSGTIELVK KGCWLDDKNC  60
YDRQECVATE ENPQVYFCCC EGNFCNERFT HLPEAGGPEV TYEPPPTGGG GSGGGGSGGG  120
GSGGGGSGGG GSGGGGSGGG GSGGGGTHTC PPCPAPELLG GPSVFLFPPK PKDTLMISRT  180
PEVTCVVVDV SHEDPEVKFN WYVDGVEVHN AKTKPREEQY NSTYRVVSVL TVLHQDWLNG  240
KEYKCKVSNK ALPAPIEKTI SKAKGQPREP QVYTLPPSRD ELTKNQVSLT CLVKGFYPSD  300
IAVEWESNGQ PENNYKTTPP VLDSDGSFFL YSKLTVDKSR WQQGNVFSCS VMHEALHNHY  360
TQKSLSLSPG                                                         370
```

-continued

```
SEQ ID NO: 245         moltype =   length =
SEQUENCE: 245
000

SEQ ID NO: 246         moltype = AA  length = 337
FEATURE                Location/Qualifiers
source                 1..337
                       mol_type = protein
                       organism = synthetic construct
SEQUENCE: 246
ETRECIYYNA NWELERTNQS GLERCEGEQD KRLHCYASWR NSSGTIELVK KGCWLDDENC  60
YDRQECVATE ENPQVYFCCC EGNFCNERFT HLPEAGGPEV TYEPPPTGGG GSGTHTCPPC  120
PAPELLGGPS VFLFPPKPKD TLMISRTPEV TCVVVDVSHE DPEVKFNWYV DGVEVHNAKT  180
KPREEQYNST YRVVSVLTVL HQDWLNGKEY KCKVSNKALP APIEKTISKA KGQPREPQVY  240
TLPPSRDELT KNQVSLTCLV KGFYPSDIAV EWESNGQPEN NYKTTPPVLD SDGSFFLYSK  300
LTVDKSRWQQ GNVFSCSVMH EALHNHYTQK SLSLSPG                          337

SEQ ID NO: 247         moltype = AA  length = 341
FEATURE                Location/Qualifiers
source                 1..341
                       mol_type = protein
                       organism = synthetic construct
SEQUENCE: 247
ETRECIYYNA NWELERTNQS GLERCEGEQD KRLHCYASWR NSSGTIELVK KGCWLDDENC  60
YDRQECVATE ENPQVYFCCC EGNFCNERFT HLPEAGGPEV TYEPPPTGGG GSGGGGSTHT  120
CPPCPAPELL GGPSVFLFPP KPKDTLMISR TPEVTCVVVD VSHEDPEVKF NWYVDGVEVH  180
NAKTKPREEQ YNSTYRVVSV LTVLHQDWLN GKEYKCKVSN KALPAPIEKT ISKAKGQPRE  240
PQVYTLPPSR DELTKNQVSL TCLVKGFYPS DIAVEWESNG QPENNYKTTP PVLDSDGSFF  300
LYSKLTVDKS RWQQGNVFSC SVMHEALHNH YTQKSLSLSP G                     341

SEQ ID NO: 248         moltype = AA  length = 348
FEATURE                Location/Qualifiers
source                 1..348
                       mol_type = protein
                       organism = synthetic construct
SEQUENCE: 248
ETRECIYYNA NWELERTNQS GLERCEGEQD KRLHCYASWR NSSGTIELVK KGCWLDDENC  60
YDRQECVATE ENPQVYFCCC EGNFCNERFT HLPEAGGPEV TYEPPPTAPT GGGGSGGGGS  120
GGGGTHTCPP CPAPELLGGP SVFLFPPKPK DTLMISRTPE VTCVVVDVSH EDPEVKFNWY  180
VDGVEVHNAK TKPREEQYNS TYRVVSVLTV LHQDWLNGKE YKCKVSNKAL PAPIEKTISK  240
AKGQPREPQV YTLPPSRDEL TKNQVSLTCL VKGFYPSDIA VEWESNGQPE NNYKTTPPVL  300
DSDGSFFLYS KLTVDKSRWQ QGNVFSCSVM HEALHNHYTQ KSLSLSPG              348

SEQ ID NO: 249         moltype = AA  length = 345
FEATURE                Location/Qualifiers
source                 1..345
                       mol_type = protein
                       organism = synthetic construct
SEQUENCE: 249
ETRECIYYNA NWELERTNQS GLERCEGEQD KRLHCYASWR NSSGTIELVK KGCWLDDNNC  60
YDRQECVATE ENPQVYFCCC EGNFCNERFT HLPEAGGPEV TYEPPPTGGG GSGGGGSGGG  120
GTHTCPPCPA PELLGGPSVF LFPPKPKDTL MISRTPEVTC VVVDVSHEDP EVKFNWYVDG  180
VEVHNAKTKP REEQYNSTYR VVSVLTVLHQ DWLNGKEYKC KVSNKALPAP IEKTISKAKG  240
QPREPQVYTL PPSRDELTKN QVSLTCLVKG FYPSDIAVEW ESNGQPENNY KTTPPVLDSD  300
GSFFLYSKLT VDKSRWQQGN VFSCSVMHEA LHNHYTQKSL SLSPG                 345

SEQ ID NO: 250         moltype = AA  length = 345
FEATURE                Location/Qualifiers
source                 1..345
                       mol_type = protein
                       organism = synthetic construct
SEQUENCE: 250
ETRECIYYNA NWELERTNQS GLERCEGEQD KRLHCYASWR NSSGTIELVK KGCWLDDRNC  60
YDRQECVATE ENPQVYFCCC EGNFCNERFT HLPEAGGPEV TYEPPPTGGG GSGGGGSGGG  120
GTHTCPPCPA PELLGGPSVF LFPPKPKDTL MISRTPEVTC VVVDVSHEDP EVKFNWYVDG  180
VEVHNAKTKP REEQYNSTYR VVSVLTVLHQ DWLNGKEYKC KVSNKALPAP IEKTISKAKG  240
QPREPQVYTL PPSRDELTKN QVSLTCLVKG FYPSDIAVEW ESNGQPENNY KTTPPVLDSD  300
GSFFLYSKLT VDKSRWQQGN VFSCSVMHEA LHNHYTQKSL SLSPG                 345

SEQ ID NO: 251         moltype = AA  length = 345
FEATURE                Location/Qualifiers
source                 1..345
                       mol_type = protein
                       organism = synthetic construct
SEQUENCE: 251
ETRECIYYNA NWELERTNQS GLERCEGEQD KRLHCYASWR NSSGTIELVK KGCWLDDHNC  60
YDRQECVATE ENPQVYFCCC EGNFCNERFT HLPEAGGPEV TYEPPPTGGG GSGGGGSGGG  120
GTHTCPPCPA PELLGGPSVF LFPPKPKDTL MISRTPEVTC VVVDVSHEDP EVKFNWYVDG  180
VEVHNAKTKP REEQYNSTYR VVSVLTVLHQ DWLNGKEYKC KVSNKALPAP IEKTISKAKG  240
```

-continued

```
QPREPQVYTL PPSRDELTKN QVSLTCLVKG FYPSDIAVEW ESNGQPENNY KTTPPVLDSD  300
GSFFLYSKLT VDKSRWQQGN VFSCSVMHEA LHNHYTQKSL SLSPG                  345

SEQ ID NO: 252          moltype = AA  length = 337
FEATURE                 Location/Qualifiers
source                  1..337
                        mol_type = protein
                        organism = synthetic construct
SEQUENCE: 252
ETRECIYYNA NWELERTNQS GLERCEGEQD KRLHCYASWR NSSGTIELVK KGCWLDDQNC  60
YDRQECVATE ENPQVYFCCC EGNFCNERFT HLPEAGGPEV TYEPPPTGGG GSGTHTCPPC  120
PAPELLGGPS VFLFPPKPKD TLMISRTPEV TCVVVDVSHE DPEVKFNWYV DGVEVHNAKT  180
KPREEQYNST YRVVSVLTVL HQDWLNGKEY KCKVSNKALP APIEKTISKA KGQPREPQVY  240
TLPPSRDELT KNQVSLTCLV KGFYPSDIAV EWESNGQPEN NYKTTPPVLD SDGSFFLYSK  300
LTVDKSRWQQ GNVFSCSVMH EALHNHYTQK SLSLSPG                           337

SEQ ID NO: 253          moltype = AA  length = 341
FEATURE                 Location/Qualifiers
source                  1..341
                        mol_type = protein
                        organism = synthetic construct
SEQUENCE: 253
ETRECIYYNA NWELERTNQS GLERCEGEQD KRLHCYASWR NSSGTIELVK KGCWLDDQNC  60
YDRQECVATE ENPQVYFCCC EGNFCNERFT HLPEAGGPEV TYEPPPTGGG GSGGGGSTHT  120
CPPCPAPELL GGPSVFLFPP KPKDTLMISR TPEVTCVVVD VSHEDPEVKF NWYVDGVEVH  180
NAKTKPREEQ YNSTYRVVSV LTVLHQDWLN GKEYKCKVSN KALPAPIEKT ISKAKGQPRE  240
PQVYTLPPSR DELTKNQVSL TCLVKGFYPS DIAVEWESNG QPENNYKTTP PVLDSDGSFF  300
LYSKLTVDKS RWQQGNVFSC SVMHEALHNH YTQKSLSLSP G                      341

SEQ ID NO: 254          moltype = AA  length = 350
FEATURE                 Location/Qualifiers
source                  1..350
                        mol_type = protein
                        organism = synthetic construct
SEQUENCE: 254
ETRECIYYNA NWELERTNQS GLERCEGEQD KRLHCYASWR NSSGTIELVK KGCWLDDQNC  60
YDRQECVATE ENPQVYFCCC EGNFCNERFT HLPEAGGPEV TYEPPPTGGG GSGGGGSGGG  120
GSGGGGTHTC PPCPAPELLG GPSVFLFPPK PKDTLMISRT PEVTCVVVDV SHEDPEVKFN  180
WYVDGVEVHN AKTKPREEQY NSTYRVVSVL TVLHQDWLNG KEYKCKVSNK ALPAPIEKTI  240
SKAKGQPREP QVYTLPPSRD ELTKNQVSLT CLVKGFYPSD IAVEWESNGQ PENNYKTTPP  300
VLDSDGSFFL YSKLTVDKSR WQQGNVFSCS VMHEALHNHY TQKSLSLSPG             350

SEQ ID NO: 255          moltype = DNA  length = 63
FEATURE                 Location/Qualifiers
source                  1..63
                        mol_type = other DNA
                        organism = synthetic construct
SEQUENCE: 255
gccaccatgg actggacctg gagaatcctg ttcctggtgg ctgctgctac cggaacacac  60
gct                                                                63

SEQ ID NO: 256          moltype = DNA  length = 1002
FEATURE                 Location/Qualifiers
source                  1..1002
                        mol_type = other DNA
                        organism = synthetic construct
SEQUENCE: 256
gagaccaggg agtgtatcta ctataacgcc aattgggagc tggagaggac aaaccagtcc  60
ggactggagc ggtgtgaggg agagcaggac aagagactgc attgctacgc tagctggcgc  120
aattccagcg gcaccatcga gctggtgaag aagggctgtt ggctggacga tttcaactgt  180
tacgatagac aggagtgcgt ggccaccgag gagaatcctc aggtgtattt ttgctgttgc  240
gagggcaact tctgcaatga gaggttcacc cacctgccag aggctggagg accagaggtg  300
acctatgagc cacctccaac aggaggagga acccatacat gtccaccttg cccagctcca  360
gagctgctgg gaggcccttc cgtgttcctg tttccaccca agccaaagga caccctgatg  420
atctctagga ccccagaggt gacatgcgtg gtggtggacg tgtcccacga ggaccccgag  480
gtgaagttta actggtacgt ggatggcgtg gaggtgcata atgctaagac aaagccaagg  540
gaggagcagt acaactccac ctatcgggtg gtgagcgtgc tgacagtgct gcaccaggat  600
tggctgaacg gcaaggagta taagtgtaag gtgagcaata aggctctgcc tgccccaatc  660
gagaagacca tctctaaggc taagggccag cccagagagc ctcaggtgta cacactgcct  720
ccatcccgcg acgagctgac caagaaccag gtgagcctga catgcctggt gaagggcttc  780
tatcccagcg acatcgccgt ggagtgggag tctaatggcc agcctgagaa caattacaag  840
accacacccc ctgtgctgga cagcgatggc tctttctttc tgtattctaa gctgaccgtg  900
gataagtccc ggtggcagca gggcaacgtg ttttcttgtt ccgtgatgca tgaggccctg  960
cacaatcatt acacacagaa gagcctgtct ctgtcccctg gc                     1002

SEQ ID NO: 257          moltype = DNA  length = 1035
FEATURE                 Location/Qualifiers
source                  1..1035
                        mol_type = other DNA
```

```
                         organism = synthetic construct
SEQUENCE: 257
gagaccaggg agtgtatcta ctataacgcc aattgggagc tggagaggac aaaccagtcc  60
ggactggagc ggtgtgaggg cgagcaggac aagagactgc attgctacgc tagctggcgc  120
aattccagcg gcaccatcga gctggtgaag aagggctgtt ggctggacga tttcaactgt  180
tacgatagac aggagtgcgt ggccaccgag gagaatcctc aggtgtattt ttgctgttgc  240
gagggcaact tctgcaatga gaggttcacc cacctgccag aggctggagg accagaggtg  300
acctatgagc cacctccaac aggaggagga ggctctggag gaggaggctc cggaggagga  360
ggaacccata catgtccacc ttgcccagct ccagagctgc tgggaggccc ttccgtgttc  420
ctgtttccac ccaagccaaa ggacaccctg atgatctcta ggaccccaga ggtgacatgc  480
gtggtggtgg acgtgtccca cgaggacccc gaggtgaagt ttaactggta cgtggatggc  540
gtggaggtgc ataatgctaa gacaaagcca agggaggagc agtacaactc cacctatcgg  600
gtggtgagcg tgctgacagt gctgcaccag gattggctga acggcaagga gtataagtgt  660
aaggtgagca ataaggctct gcctgcccca atcgagaaga ccatctctaa ggctaagggc  720
cagcccagag agcctcaggt gtacacactg cctccatccc gcgacgagct gaccaagaac  780
caggtgagcc tgacatgcct ggtgaagggc ttctatccca gcgacatcgc cgtggagtgg  840
gagtctaatg gccagcctga gaacaattac aagaccacac cccctgtgct ggacagcgat  900
ggctctttct ttctgtattc taagctgacc gtggataagt cccggtggca gcagggcaac  960
gtgttttctt gttccgtgat gcatgaggcc ctgcacaatc attacacaca gaagagcctg  1020
tctctgtccc ctggc                                                    1035

SEQ ID NO: 258          moltype = DNA  length = 1029
FEATURE                 Location/Qualifiers
source                  1..1029
                        mol_type = other DNA
                        organism = synthetic construct
SEQUENCE: 258
atcctgggcc gcagcgagac acaggagtgt ctgttcttta acgccaattg ggagaaggat  60
aggaccaacc agacaggcgt ggagccatgt tatggcgaca aggataagag gcggcattgc  120
ttcgctacct ggaagaacat ctccggcagc atcgagatcg tgaagcaggg ctgttggctg  180
gacgatatca attgttacga ccggacagat tgcgtggaga agaaggactc tcccgaggtg  240
tatttttgct gttgcgaggg caacatgtgc aatgagaagt tctcttactt tcccgagatg  300
gaggtgaccc agcctacatc caatccagtg accccaaagc cacctacagg aggaggaacc  360
cacacatgtc caccatgccc tgctccagag ctgctgggag gaccatccgt gttcctgttt  420
cctccaaagc ccaaggacac cctgatgatc agcagaaccc ccgaggtgac atgcgtggtg  480
gtggacgtgt ctcacgagga ccccgaggtg aagtttaact ggtacgtgga tggcgtggag  540
gtgcataatg ccaagaccaa gcctagagag gagcagtaca actccaccta tcgcgtggtg  600
agcgtgctga cagtgctgca tcaggattgg ctgaacggca aggagtacaa gtgtaaggtg  660
tccaataagg ctctgcccgt gcctatcgag aagaccatca gcaaggccaa gggccagcct  720
agggagccac aggtgtatac actgcccccct tcccgggagg agatgaccaa gaaccaggtg  780
agcctgacat gcctggtgaa gggcttctac cctagcgaca tcgctgtgga gtgggagtct  840
aatggccagc cagagaacaa ttataagacc acaccacccg tgctggacag cgatggctct  900
ttctttctgt actctaagct gaccgtggat aagtcccgct ggcagcaggg caacgtgttt  960
tcttgttccg tgatgcacga ggccctgcac aatcattaca cacagaagag cctgtctctg  1020
tccccaggc                                                           1029

SEQ ID NO: 259          moltype = DNA  length = 1005
FEATURE                 Location/Qualifiers
source                  1..1005
                        mol_type = other DNA
                        organism = synthetic construct
SEQUENCE: 259
gagaccaggg agtgtatcta ctataacgcc aattgggagc tggagaggac aaaccagtcc  60
ggactggagc ggtgtgagga cgagcaggac aagagactgc attgctacgc tagctggcgc  120
aattccagcg gcaccatcga gctggtgaag aagggctgtt ggctggacga tttcaactgt  180
tacgatagac aggagtgcgt ggccaccgag gagaatcctc aggtgtattt ttgctgttgc  240
gagggcaact tctgcaatga gaggttcacc cacctgccag aggctggagg accagaggtg  300
acctatgagc cacctccaac aggaggagga acccatacat gtccaccttg cccagctcca  360
gagctgctgg gaggcccttc cgtgttcctg tttccaccca agccaaagga caccctgatg  420
atctctagga ccccagaggt gacatgcgtg gtggtggacg tgtcccacga ggaccccgag  480
gtgaagttta actggtacgt ggatggcgtg gaggtgcata atgctaagac aaagccaagg  540
gaggagcagt acaactccac ctatcgggtg gtgagcgtgc tgacagtgct gcaccaggat  600
tggctgaacg gcaaggagta taagtgtaag gtgagcaata aggctctgcc tgccccaatc  660
gagaagacca tctctaaggc taagggccag cccagagagc ctcaggtgta cacactgcct  720
ccatcccgcg aggagatgac caagaaccag gtgagcctga catgcctggt gaagggcttc  780
tatcccagcg acatcgccgt ggagtgggag tctaatggcc agcctgagaa caattacaag  840
accacacccc ctgtgctgga cagcgatggc tctttctttc tgtattctaa gctgaccgtg  900
gataagtccc ggtggcagca gggcaacgtg ttttcttgtt ccgtgatgca tgaggccctg  960
cacaatcatt acacacagaa gagcctgtct ctgtcccctg gcaag                  1005

SEQ ID NO: 260          moltype = DNA  length = 1005
FEATURE                 Location/Qualifiers
source                  1..1005
                        mol_type = other DNA
                        organism = synthetic construct
SEQUENCE: 260
gagaccaggg agtgtatcta ctataacgcc aattgggagc tggagaggac aaaccagtcc  60
ggactggagc ggtgtgaggg agagcaggac aagagactgc attgctacgc tagctggcgc  120
aattccagcg gcaccatcga gctggtgaag aagggctgtt ggctggacga gttcaactgt  180
```

```
tacgatagac aggagtgcgt ggccaccgag gagaatcctc aggtgtattt ttgctgttgc  240
gagggcaact tctgcaatga gaggttcacc cacctgccag aggctggagg accagaggtg  300
acctatgagc cacctccaac aggaggagga acccatacat gtccaccttg cccagctcca  360
gagctgctgg gaggcccttc cgtgttcctg tttccaccca agccaaagga caccctgatg  420
atctctagga ccccagaggt gacatgcgtg gtggtggacg tgtcccacga ggaccccgag  480
gtgaagttta actggtacgt ggatggcgtg gaggtgcata atgctaagac aaagccaagg  540
gaggagcagt acaactccac ctatcgggtg gtgagcgtgc tgacagtgct gcaccaggat  600
tggctgaacg gcaaggagta taagtgtaag gtgagcaata aggctctgcc tgccccaatc  660
gagaagacca tctctaaggc taagggccag cccagagagc ctcaggtgta cacactgcct  720
ccatcccgcg aggagatgac caagaaccag gtgagcctga catgcctggt gaagggcttc  780
tatcccagcg acatcgccgt ggagtgggag tctaatggcc agcctgagaa caattacaag  840
accacacccc ctgtgctgga cagcgatggc tctttctttc tgtattctaa gctgaccgtg  900
gataagtccc ggtggcagca gggcaacgtg ttttcttgtt ccgtgatgca tgaggccctg  960
cacaatcatt acacacagaa gagcctgtct ctgtcccctg gcaag                 1005

SEQ ID NO: 261          moltype = DNA  length = 1005
FEATURE                 Location/Qualifiers
source                  1..1005
                        mol_type = other DNA
                        organism = synthetic construct
SEQUENCE: 261
gagaccaggg agtgtatcta ctataacgcc aattgggagc tggagaggac aaaccagtcc  60
ggactggagc ggtgtgaggg agagcaggac aagagactgc attgctacgc tagctggcgc  120
aattccagcg gcaccatcga gctggtgaag aagggctgtt ggctggacga tgagaactgt  180
tacgatagac aggagtgcgt ggccaccgag gagaatcctc aggtgtattt ttgctgttgc  240
gagggcaact tctgcaatga gaggttcacc cacctgccag aggctggagg accagaggtg  300
acctatgagc cacctccaac aggaggagga acccatacat gtccaccttg cccagctcca  360
gagctgctgg gaggcccttc cgtgttcctg tttccaccca agccaaagga caccctgatg  420
atctctagga ccccagaggt gacatgcgtg gtggtggacg tgtcccacga ggaccccgag  480
gtgaagttta actggtacgt ggatggcgtg gaggtgcata atgctaagac aaagccaagg  540
gaggagcagt acaactccac ctatcgggtg gtgagcgtgc tgacagtgct gcaccaggat  600
tggctgaacg gcaaggagta taagtgtaag gtgagcaata aggctctgcc tgccccaatc  660
gagaagacca tctctaaggc taagggccag cccagagagc ctcaggtgta cacactgcct  720
ccatcccgcg aggagatgac caagaaccag gtgagcctga catgcctggt gaagggcttc  780
tatcccagcg acatcgccgt ggagtgggag tctaatggcc agcctgagaa caattacaag  840
accacacccc ctgtgctgga cagcgatggc tctttctttc tgtattctaa gctgaccgtg  900
gataagtccc ggtggcagca gggcaacgtg ttttcttgtt ccgtgatgca tgaggccctg  960
cacaatcatt acacacagaa gagcctgtct ctgtcccctg gcaag                 1005

SEQ ID NO: 262          moltype = DNA  length = 1005
FEATURE                 Location/Qualifiers
source                  1..1005
                        mol_type = other DNA
                        organism = synthetic construct
SEQUENCE: 262
gagaccaggg agtgtatcta ctataacgcc aattgggagc tggagaggac aaaccagtcc  60
ggactggagc ggtgtgaggg agagtacgac aagagactgc attgctacgc tagctggcgc  120
aattccagcg gcaccatcga gctggtgaag aagggctgtt ggctggacga tttcaactgt  180
tacgatagac aggagtgcgt ggccaccgag gagaatcctc aggtgtattt ttgctgttgc  240
gagggcaact tctgcaatga gaggttcacc cacctgccag aggctggagg accagaggtg  300
acctatgagc cacctccaac aggaggagga acccatacat gtccaccttg cccagctcca  360
gagctgctgg gaggcccttc cgtgttcctg tttccaccca agccaaagga caccctgatg  420
atctctagga ccccagaggt gacatgcgtg gtggtggacg tgtcccacga ggaccccgag  480
gtgaagttta actggtacgt ggatggcgtg gaggtgcata atgctaagac aaagccaagg  540
gaggagcagt acaactccac ctatcgggtg gtgagcgtgc tgacagtgct gcaccaggat  600
tggctgaacg gcaaggagta taagtgtaag gtgagcaata aggctctgcc tgccccaatc  660
gagaagacca tctctaaggc taagggccag cccagagagc ctcaggtgta cacactgcct  720
ccatcccgcg aggagatgac caagaaccag gtgagcctga catgcctggt gaagggcttc  780
tatcccagcg acatcgccgt ggagtgggag tctaatggcc agcctgagaa caattacaag  840
accacacccc ctgtgctgga cagcgatggc tctttctttc tgtattctaa gctgaccgtg  900
gataagtccc ggtggcagca gggcaacgtg ttttcttgtt ccgtgatgca tgaggccctg  960
cacaatcatt acacacagaa gagcctgtct ctgtcccctg gcaag                 1005

SEQ ID NO: 263          moltype = DNA  length = 1005
FEATURE                 Location/Qualifiers
source                  1..1005
                        mol_type = other DNA
                        organism = synthetic construct
SEQUENCE: 263
gagaccaggg agtgtatcta ctataacgcc aattgggagc tggagaggac aaaccagtcc  60
ggactggagc ggtgtgaggg agagcagcag aagagactgc attgctacgc tagctggcgc  120
aattccagcg gcaccatcga gctggtgaag aagggctgtt ggctggacga tttcaactgt  180
tacgatagac aggagtgcgt ggccaccgag gagaatcctc aggtgtattt ttgctgttgc  240
gagggcaact tctgcaatga gaggttcacc cacctgccag aggctggagg accagaggtg  300
acctatgagc cacctccaac aggaggagga acccatacat gtccaccttg cccagctcca  360
gagctgctgg gaggcccttc cgtgttcctg tttccaccca agccaaagga caccctgatg  420
atctctagga ccccagaggt gacatgcgtg gtggtggacg tgtcccacga ggaccccgag  480
gtgaagttta actggtacgt ggatggcgtg gaggtgcata atgctaagac aaagccaagg  540
gaggagcagt acaactccac ctatcgggtg gtgagcgtgc tgacagtgct gcaccaggat  600
```

```
tggctgaacg gcaaggagta taagtgtaag gtgagcaata aggctctgcc tgccccaatc  660
gagaagacca tctctaaggc taagggccag cccagagagc ctcaggtgta cacactgcct  720
ccatcccgcg aggagatgac caagaaccag gtgagcctga catgcctggt gaagggcttc  780
tatcccagcg acatcgccgt ggagtgggag tctaatggcc agcctgagaa caattacaag  840
accacacccc ctgtgctgga cagcgatggc tctttctttc tgtattctaa gctgaccgtg  900
gataagtccc ggtggcagca gggcaacgtg ttttcttgtt ccgtgatgca tgaggccctg  960
cacaatcatt acacacagaa gagcctgtct ctgtcccctg gcaag                 1005

SEQ ID NO: 264          moltype = DNA  length = 1005
FEATURE                 Location/Qualifiers
source                  1..1005
                        mol_type = other DNA
                        organism = synthetic construct
SEQUENCE: 264
gagaccaggg agtgtatcta ctataacgcc aattgggagc tggagaggac aaaccagtcc  60
ggactggagc ggtgtgaggg agagcaggac tacagactgc attgctacgc tagctggcgc  120
aattccagcg gcaccatcga gctggtgaag aagggctgtt ggctggacga tttcaactgt  180
tacgatagac aggagtgcgt ggccaccgag gagaatcctc aggtgtattt ttgctgttgc  240
gagggcaact tctgcaatga gaggttcacc cacctgccag aggctggagg accagaggtg  300
acctatgagc cacctccaac aggaggagga acccatacat gtccaccttg cccagctcca  360
gagctgctgg gaggcccttc cgtgttcctg tttccaccca agccaaagga caccctgatg  420
atctctagga ccccagaggt gacatgcgtg gtggtggacg tgtcccacga ggaccccgag  480
gtgaagttta actggtacgt ggatggcgtg gaggtgcata atgctaagac aaagccaagg  540
gaggagcagt acaactccac ctatcgggtg gtgagcgtgc tgacagtgct gcaccaggat  600
tggctgaacg gcaaggagta taagtgtaag gtgagcaata aggctctgcc tgccccaatc  660
gagaagacca tctctaaggc taagggccag cccagagagc ctcaggtgta cacactgcct  720
ccatcccgcg aggagatgac caagaaccag gtgagcctga catgcctggt gaagggcttc  780
tatcccagcg acatcgccgt ggagtgggag tctaatggcc agcctgagaa caattacaag  840
accacacccc ctgtgctgga cagcgatggc tctttctttc tgtattctaa gctgaccgtg  900
gataagtccc ggtggcagca gggcaacgtg ttttcttgtt ccgtgatgca tgaggccctg  960
cacaatcatt acacacagaa gagcctgtct ctgtcccctg gcaag                 1005

SEQ ID NO: 265          moltype = DNA  length = 1005
FEATURE                 Location/Qualifiers
source                  1..1005
                        mol_type = other DNA
                        organism = synthetic construct
SEQUENCE: 265
gagaccaggg agtgtatcta ctataacgcc aattgggagc tggagaggac aaaccagtcc  60
ggactggagc ggtgtgaggg agagcaggac aagagactgc attgctacgc taggtggcgc  120
aattccagcg gcaccatcga gctggtgaag aagggctgtt ggctggacga tttcaactgt  180
tacgatagac aggagtgcgt ggccaccgag gagaatcctc aggtgtattt ttgctgttgc  240
gagggcaact tctgcaatga gaggttcacc cacctgccag aggctggagg accagaggtg  300
acctatgagc cacctccaac aggaggagga acccatacat gtccaccttg cccagctcca  360
gagctgctgg gaggcccttc cgtgttcctg tttccaccca agccaaagga caccctgatg  420
atctctagga ccccagaggt gacatgcgtg gtggtggacg tgtcccacga ggaccccgag  480
gtgaagttta actggtacgt ggatggcgtg gaggtgcata atgctaagac aaagccaagg  540
gaggagcagt acaactccac ctatcgggtg gtgagcgtgc tgacagtgct gcaccaggat  600
tggctgaacg gcaaggagta taagtgtaag gtgagcaata aggctctgcc tgccccaatc  660
gagaagacca tctctaaggc taagggccag cccagagagc ctcaggtgta cacactgcct  720
ccatcccgcg aggagatgac caagaaccag gtgagcctga catgcctggt gaagggcttc  780
tatcccagcg acatcgccgt ggagtgggag tctaatggcc agcctgagaa caattacaag  840
accacacccc ctgtgctgga cagcgatggc tctttctttc tgtattctaa gctgaccgtg  900
gataagtccc ggtggcagca gggcaacgtg ttttcttgtt ccgtgatgca tgaggccctg  960
cacaatcatt acacacagaa gagcctgtct ctgtcccctg gcaag                 1005

SEQ ID NO: 266          moltype = DNA  length = 1005
FEATURE                 Location/Qualifiers
source                  1..1005
                        mol_type = other DNA
                        organism = synthetic construct
SEQUENCE: 266
gagaccaggg agtgtatcta ctataacgcc aattgggagc tggagaggac aaaccagtcc  60
ggactggagc ggtgtgaggg agagcaggac aagagactgc attgctacgc tagctggcgc  120
aattccagcg gcaccatcga gctggtgaag aagggctgtt ggctggacga tttcaactgt  180
tacgatagac aggagtgcgt ggccaccgag gagaatcctc agcagtattt ttgctgttgc  240
gagggcaact tctgcaatga gaggttcacc cacctgccag aggctggagg accagaggtg  300
acctatgagc cacctccaac aggaggagga acccatacat gtccaccttg cccagctcca  360
gagctgctgg gaggcccttc cgtgttcctg tttccaccca agccaaagga caccctgatg  420
atctctagga ccccagaggt gacatgcgtg gtggtggacg tgtcccacga ggaccccgag  480
gtgaagttta actggtacgt ggatggcgtg gaggtgcata atgctaagac aaagccaagg  540
gaggagcagt acaactccac ctatcgggtg gtgagcgtgc tgacagtgct gcaccaggat  600
tggctgaacg gcaaggagta taagtgtaag gtgagcaata aggctctgcc tgccccaatc  660
gagaagacca tctctaaggc taagggccag cccagagagc ctcaggtgta cacactgcct  720
ccatcccgcg aggagatgac caagaaccag gtgagcctga catgcctggt gaagggcttc  780
tatcccagcg acatcgccgt ggagtgggag tctaatggcc agcctgagaa caattacaag  840
accacacccc ctgtgctgga cagcgatggc tctttctttc tgtattctaa gctgaccgtg  900
gataagtccc ggtggcagca gggcaacgtg ttttcttgtt ccgtgatgca tgaggccctg  960
cacaatcatt acacacagaa gagcctgtct ctgtcccctg gcaag                 1005
```

```
SEQ ID NO: 267          moltype = DNA  length = 1005
FEATURE                 Location/Qualifiers
source                  1..1005
                        mol_type = other DNA
                        organism = synthetic construct
SEQUENCE: 267
gagaccaggg agtgtatcta ctataacgcc aattgggagc tggagaggac aaaccagtcc  60
ggactggagc ggtgtgaggg agagcaggac aagagactgc attgctacgc tagctggcgc  120
aattccagcg gcaccatcga gctggtgaag aagggctgtt ggctggacga tttcaactgt  180
tacgatagac aggagtgcgt ggccaccgag gagaatcctc aggtgtatga ctgctgttgc  240
gagggcaact tctgcaatga gaggttcacc cacctgccag aggctggagg accagaggtg  300
acctatgagc cacctccaac aggaggagga acccatacat gtccaccttg cccagctcca  360
gagctgctgg gaggcccttc cgtgttcctg tttccaccca agccaaagga caccctgatg  420
atctctagga ccccagaggt gacatgcgtg gtggtggacg tgtcccacga ggaccccgag  480
gtgaagttta actggtacgt ggatggcgtg gaggtgcata atgctaagac aaagccaagg  540
gaggagcagt acaactccac ctatcgggtg gtgagcgtgc tgacagtgct gcaccaggat  600
tggctgaacg gcaaggagta taagtgtaag gtgagcaata aggctctgcc tgccccaatc  660
gagaagacca tctctaaggc taagggccag cccagagagc ctcaggtgta cacactgcct  720
ccatcccgcg aggagatgac caagaaccag gtgagcctga catgcctggt gaagggcttc  780
tatcccagcg acatcgccgt ggagtgggag tctaatggcc agcctgagaa caattacaag  840
accacacccc ctgtgctgga cagcgatggc tctttctttc tgtattctaa gctgaccgtg  900
gataagtccc ggtggcagca gggcaacgtg ttttcttgtt ccgtgatgca tgaggccctg  960
cacaatcatt acacacagaa gagcctgtct ctgtcccctg gcaag                1005

SEQ ID NO: 268          moltype = DNA  length = 1035
FEATURE                 Location/Qualifiers
source                  1..1035
                        mol_type = other DNA
                        organism = synthetic construct
SEQUENCE: 268
gagaccaggg agtgtatcta ctataacgcc aattgggagc tggagaggac aaaccagtcc  60
ggactggagc ggtgtgaggg cgagcaggac aagagactgc attgctacgc tagctggcgc  120
aattccagcg gcaccatcga gctggtgaag aagggctgtt ggctggacga tgagaactgt  180
tacgatagac aggagtgcgt ggccaccgag gagaatcctc aggtgtattt ttgctgttgc  240
gagggcaact tctgcaatga gaggttcacc cacctgccag aggctggagg accagaggtg  300
acctatgagc cacctccaac aggaggagga ggctctggag gaggaggctc cggaggagga  360
ggaacccata catgtccacc ttgcccagct ccagagctgc tgggaggccc ttccgtgttc  420
ctgtttccac ccaagccaaa ggacaccctg atgatctcta ggaccccaga ggtgacatgc  480
gtggtggtgg acgtgtccca cgaggacccc gaggtgaagt ttaactggta cgtggatggc  540
gtggaggtgc ataatgctaa gacaaagcca agggaggagc agtacaactc cacctatcgg  600
gtggtgagcg tgctgacagt gctgcaccag gattggctga acggcaagga gtataagtgt  660
aaggtgagca ataaggctct gcctgcccca atcgagaaga ccatctctaa ggctaagggc  720
cagcccagag agcctcaggt gtacacactg cctccatccc gcgacgagct gaccaagaac  780
caggtgagcc tgacatgcct ggtgaagggc ttctatccca gcgacatcgc cgtggagtgg  840
gagtctaatg gccagcctga gaacaattac aagaccacac cccctgtgct ggacagcgat  900
ggctctttct ttctgtattc taagctgacc gtggataagt cccggtggca gcagggcaac  960
gtgttttctt gttccgtgat gcatgaggcc ctgcacaatc attacacaca gaagagcctg  1020
tctctgtccc ctggc                                                  1035

SEQ ID NO: 269          moltype = DNA  length = 1002
FEATURE                 Location/Qualifiers
source                  1..1002
                        mol_type = other DNA
                        organism = synthetic construct
SEQUENCE: 269
gagaccaggg agtgtatcta ctataacgcc aattgggagc tggagaggac aaaccagtcc  60
ggactggagc ggtgtgaggg agagcaggac aagagactgc attgctacgc tagctggcgc  120
aattccagcg gcaccatcga gctggtgaag aagggctgtt ggctggacga tgagaactgt  180
tacgatagac aggagtgcgt ggccaccgag gagaatcctc aggtgtattt ttgctgttgc  240
gagggcaact tctgcaatga gaggttcacc cacctgccag aggctggagg accagaggtg  300
acctatgagc cacctccaac aggaggagga acccatacat gtccaccttg cccagctcca  360
gagctgctgg gaggcccttc cgtgttcctg tttccaccca agccaaagga caccctgatg  420
atctctagga ccccagaggt gacatgcgtg gtggtggacg tgtcccacga ggaccccgag  480
gtgaagttta actggtacgt ggatggcgtg gaggtgcata atgctaagac aaagccaagg  540
gaggagcagt acaactccac ctatcgggtg gtgagcgtgc tgacagtgct gcaccaggat  600
tggctgaacg gcaaggagta taagtgtaag gtgagcaata aggctctgcc tgccccaatc  660
gagaagacca tctctaaggc taagggccag cccagagagc ctcaggtgta cacactgcct  720
ccatcccgcg acgagctgac caagaaccag gtgagcctga catgcctggt gaagggcttc  780
tatcccagcg acatcgccgt ggagtgggag tctaatggcc agcctgagaa caattacaag  840
accacacccc ctgtgctgga cagcgatggc tctttctttc tgtattctaa gctgaccgtg  900
gataagtccc ggtggcagca gggcaacgtg ttttcttgtt ccgtgatgca tgaggccctg  960
cacaatcatt acacacagaa gagcctgtct ctgtcccctg gc                   1002

SEQ ID NO: 270          moltype = DNA  length = 1002
FEATURE                 Location/Qualifiers
source                  1..1002
                        mol_type = other DNA
                        organism = synthetic construct
```

```
SEQUENCE: 270
gagaccaggg agtgtatcta ctataacgcc aattgggagc tggagaggac aaaccagtcc  60
ggactggagc ggtgtgaggg agagcaggac aagagactgc attgctacgc tagctggcgc  120
aattccagcg gcaccatcga gctggtgaag aagggctgtt ggctggacga tgagaactgt  180
tacgatagac aggagtgcgt ggccaccgag gagaatcctc aggtgtattt ttgctgttgc  240
gagggcaact tctgcaatga gaggttcacc cacctgccag aggctggagg accagaggtg  300
acctatgagc cacctccaac aggaggagga acccatacat gtccaccttg cccagctcca  360
gagctgctgg gaggcccttc cgtgttcctg tttccaccca agccaaagga caccctgtac  420
atctctagga ccccagaggt gacatgcgtg gtggtggacg tgtcccacga ggaccccgag  480
gtgaagttta actggtacgt ggatggcgtg gaggtgcata atgctaagac aaagccaagg  540
gaggagcagt acaactccac ctatcgggtg gtgagcgtgc tgacagtgct gcaccaggat  600
tggctgaacg gcaaggagta taagtgtaag gtgagcaata aggctctgcc tgccccaatc  660
gagaagacca tctctaaggc taagggccag cccagagagc ctcaggtgta cacactgcct  720
ccatcccgcg acgagctgac caagaaccag gtgagcctga catgcctggt gaagggcttc  780
tatcccagcg acatcgccgt ggagtgggag tctaatggcc agcctgagaa caattacaag  840
accacacccc ctgtgctgga cagcgatggc tctttctttc tgtattctaa gctgaccgtg  900
gataagtccc ggtggcagca gggcaacgtg ttttcttgtt ccgtgatgca tgaggccctg  960
cacaatcatt acacacagaa gagcctgtct ctgtcccctg gc                      1002

SEQ ID NO: 271          moltype = DNA  length = 1002
FEATURE                 Location/Qualifiers
source                  1..1002
                        mol_type = other DNA
                        organism = synthetic construct
SEQUENCE: 271
gagaccaggg agtgtatcta ctataacgcc aattgggagc tggagaggac aaaccagtcc  60
ggactggagc ggtgtgaggg agagcaggac aagagactgc attgctacgc tagctggcgc  120
aattccagcg gcaccatcga gctggtgaag aagggctgtt ggctggacga tgagaactgt  180
tacgatagac aggagtgcgt ggccaccgag gagaatcctc aggtgtattt ttgctgttgc  240
gagggcaact tctgcaatga gaggttcacc cacctgccag aggctggagg accagaggtg  300
acctatgagc cacctccaac aggaggagga acccatacat gtccaccttg cccagctcca  360
gagctgctgg gaggcccttc cgtgttcctg tttccaccca agccaaagga caccctgtac  420
atcaccaggg agccagaggt gacatgcgtg gtggtggacg tgtcccacga ggaccccgag  480
gtgaagttta actggtacgt ggatggcgtg gaggtgcata atgctaagac aaagccaagg  540
gaggagcagt acaactccac ctatcgggtg gtgagcgtgc tgacagtgct gcaccaggat  600
tggctgaacg gcaaggagta taagtgtaag gtgagcaata aggctctgcc tgccccaatc  660
gagaagacca tctctaaggc taagggccag cccagagagc ctcaggtgta cacactgcct  720
ccatcccgcg acgagctgac caagaaccag gtgagcctga catgcctggt gaagggcttc  780
tatcccagcg acatcgccgt ggagtgggag tctaatggcc agcctgagaa caattacaag  840
accacacccc ctgtgctgga cagcgatggc tctttctttc tgtattctaa gctgaccgtg  900
gataagtccc ggtggcagca gggcaacgtg ttttcttgtt ccgtgatgca tgaggccctg  960
cacaatcatt acacacagaa gagcctgtct ctgtcccctg gc                      1002

SEQ ID NO: 272          moltype = DNA  length = 1050
FEATURE                 Location/Qualifiers
source                  1..1050
                        mol_type = other DNA
                        organism = synthetic construct
SEQUENCE: 272
gagaccaggg agtgtatcta ctataacgcc aattgggagc tggagaggac aaaccagtcc  60
ggactggagc ggtgtgaggg agagcaggac aagagactgc attgctacgc tagctggcgc  120
aattccagcg gcaccatcga gctggtgaag aagggctgtt ggctggacga tgagaactgt  180
tacgatagac aggagtgcgt ggccaccgag gagaatcctc aggtgtattt ttgctgttgc  240
gagggcaact tctgcaatga gaggttcacc cacctgccag aggctggagg accagaggtg  300
acctatgagc cacctccaac aggaggagga ggctccggtg gcggcggcag cggcggcggc  360
ggctctggcg gcggcggcac ccatacatgt ccaccttgcc cagctccaga gctgctggga  420
ggcccttccg tgttcctgtt tccacccaag ccaaaggaca ccctgatgat ctctaggacc  480
ccagaggtga catgcgtggt ggtggacgtg tcccacgagg accccgaggt gaagtttaac  540
tggtacgtgg atggcgtgga ggtgcataat gctaagacaa agccaaggga ggagcagtac  600
aactccacct atcgggtggt gagcgtgctg acagtgctgc accaggattg gctgaacggc  660
aaggagtata agtgtaaggt gagcaataag gctctgcctg ccccaatcga gaagaccatc  720
tctaaggcta agggccagcc cagagagcct caggtgtaca cactgcctcc atcccgcgac  780
gagctgacca agaaccaggt gagcctgaca tgcctggtga agggcttcta tcccagcgac  840
atcgccgtgg agtgggagtc taatggccag cctgagaaca attacaagac cacacccccct  900
gtgctggaca gcgatggctc tttctttctg tattctaagc tgaccgtgga taagtcccgg  960
tggcagcagg gcaacgtgtt ttcttgttcc gtgatgcatg aggccctgca caatcattac  1020
acacagaaga gcctgtctct gtcccctggc                                    1050

SEQ ID NO: 273          moltype = DNA  length = 1110
FEATURE                 Location/Qualifiers
source                  1..1110
                        mol_type = other DNA
                        organism = synthetic construct
SEQUENCE: 273
gagaccaggg agtgtatcta ctataacgcc aattgggagc tggagaggac aaaccagtcc  60
ggactggagc ggtgtgaggg agagcaggac aagagactgc attgctacgc tagctggcgc  120
aattccagcg gcaccatcga gctggtgaag aagggctgtt ggctggacga tgagaactgt  180
tacgatagac aggagtgcgt ggccaccgag gagaatcctc aggtgtattt ttgctgttgc  240
gagggcaact tctgcaatga gaggttcacc cacctgccag aggctggagg accagaggtg  300
```

-continued

```
acctatgagc cacctccaac aggaggagga ggctccggtg gcggcggcag cggcggcggc  360
ggctctggcg gcggcggctc cggtggtggt ggcagcggtg gtggtggctc tggtggtggc  420
ggctccggtg gtggcggcac ccatacatgt ccaccttgcc cagctccaga gctgctggga  480
ggcccttccg tgttcctgtt tccacccaag ccaaaggaca ccctgatgat ctctaggacc  540
ccagaggtga catgcgtggt ggtggacgtg tcccacgagg accccgaggt gaagtttaac  600
tggtacgtgg atggcgtgga ggtgcataat gctaagacaa agccaaggga ggagcagtac  660
aactccacct atcgggtggt gagcgtgctg acagtgctgc accaggattg gctgaacggc  720
aaggagtata agtgtaaggt gagcaataag gctctgcctg ccccaatcga gaagaccatc  780
tctaaggcta agggccagcc cagagagcct caggtgtaca cactgcctcc atcccgcgac  840
gagctgacca agaaccaggt gagcctgaca tgcctggtga agggcttcta tcccagcgac  900
atcgccgtgg agtgggagtc taatggccag cctgagaaca attacaagac cacacccccct  960
gtgctggaca gcgatggctc tttctttctg tattctaagc tgaccgtgga taagtcccgg  1020
tggcagcagg gcaacgtgtt ttcttgttcc gtgatgcatg aggccctgca caatcattac  1080
acacagaaga gcctgtctct gtcccctggc                                 1110
```

```
SEQ ID NO: 274          moltype = DNA  length = 1035
FEATURE                 Location/Qualifiers
source                  1..1035
                        mol_type = other DNA
                        organism = synthetic construct
SEQUENCE: 274
gagaccaggg agtgtatcta ctataacgcc aattgggagc tggagaggac aaaccagtcc  60
ggactggagc ggtgtgaggg agagcaggac aagagactgc attgctacgc tagctggcgc  120
aattccagcg gcaccatcga gctggtgaag aagggctgtt ggctggacga tgagaactgt  180
tacgatagac aggagtgcgt ggccaccgag gagaatcctc aggtgtattt ttgctgttgc  240
gagggcaact tctgcaatga gaggttcacc cacctgccag aggctggagg accagaggtg  300
acctatgagc cacctccaac aggaggagga ggctccggtg gcggcggcag cggcggcggc  360
ggcccatgcc cccccttgcaa gtgtcctgct ccaaacctgc tgggaggacc tagcgtgttc  420
atctttccac ccaagatcaa ggacgtgctg atgatctccc tgagccctat cgtgacctgc  480
gtggtggtgg acgtgtctga ggacgatcca gatgtgcaga tctcctggtt cgtgaacaat  540
gtggaggtgc acaccgccca gacccagaca catagggagg attacaattc cacactgcgg  600
gtggtgtccg ccctgcctat ccagcaccag gactggatgt ctggcaagga gtttaagtgc  660
aaggtgaaca ataaggatct gcccgcccct atcgagagga ccatcagcaa gccaaagggc  720
tctgtgagag ctccccaggt gtatgtgctg cctccacccg aggaggagat gaccaagaag  780
caggtgaccc tgacatgtat ggtgacagac ttcatgccag aggatatcta cgtggagtgg  840
accaacaatg gcaagacaga gctgaactat aagaataccg agcccgtgct ggacagcgat  900
ggctcttact ttatgtattc caagctgaga gtggagaaga agaactgggt ggagcgcaat  960
tcttactcct gcagcgtggt gcacgagggc ctgcataacc accataccac aaagtctttc  1020
tccaggacac caggc                                                 1035
```

```
SEQ ID NO: 275          moltype = DNA  length = 1050
FEATURE                 Location/Qualifiers
source                  1..1050
                        mol_type = other DNA
                        organism = synthetic construct
SEQUENCE: 275
gagaccaggg agtgtatcta ctataacgcc aattgggagc tggagaggac aaaccagtcc  60
ggactggagc ggtgtgaggg agagcaggac aagagactgc attgctacgc tagctggcgc  120
aattccagcg gcaccatcga gctggtgaag aagggctgtt ggctggacga tgagaactgt  180
tacgatagac aggagtgcgt ggccaccgag gagaatcctc aggtgtattt ttgctgttgc  240
gagggcaact tctgcaatga gaggttcacc cacctgccag aggctggagg accagaggtg  300
acctatgagc cacctccaac aggaggagga ggctccggtg gcggcggcag cggcggcggc  360
ggctctggcg gcggcggccc atgccccccct tgcaagtgtc ctgctccaaa cctgctggga  420
ggacctagcg tgttcatctt tccacccaag atcaaggacg tgctgatgat ctccctgagc  480
cctatcgtga cctgcgtggt ggtggacgtg tctgaggacg atccagatgt gcagatctcc  540
tggttcgtga acaatgtgga ggtgcacacc gcccagaccc agacacatag ggaggattac  600
aattccacac tgcgggtggt gtccgccctg cctatccagc accaggactg gatgtctggc  660
aaggagttta agtgcaaggt gaacaataag gatctgcccg cccctatcga gaggaccatc  720
agcaagccaa agggctctgt gagagctccc caggtgtatg tgctgcctcc acccgaggag  780
gagatgacca agaagcaggt gaccctgaca tgtatggtga cagacttcat gccagaggat  840
atctacgtgg agtggaccaa caatggcaag acagagctga actataagaa taccgagccc  900
gtgctggaca gcgatggctc ttactttatg tattccaagc tgagagtgga gaagaagaac  960
tgggtggagc gcaattctta ctcctgcagc gtggtgcacg agggcctgca taaccaccat  1020
accacaaagt ctttctccag gacaccaggc                                 1050
```

```
SEQ ID NO: 276          moltype = DNA  length = 1110
FEATURE                 Location/Qualifiers
source                  1..1110
                        mol_type = other DNA
                        organism = synthetic construct
SEQUENCE: 276
gagaccaggg agtgtatcta ctataacgcc aattgggagc tggagaggac aaaccagtcc  60
ggactggagc ggtgtgaggg agagcaggac aagagactgc attgctacgc tagctggcgc  120
aattccagcg gcaccatcga gctggtgaag aagggctgtt ggctggacga tgagaactgt  180
tacgatagac aggagtgcgt ggccaccgag gagaatcctc aggtgtattt ttgctgttgc  240
gagggcaact tctgcaatga gaggttcacc cacctgccag aggctggagg accagaggtg  300
acctatgagc cacctccaac aggaggagga ggctccggtg gcggcggcag cggcggcggc  360
ggctctggcg gcggcggctc cggtggtggt ggcagcggtg gcggcggctc tggaggagga  420
ggctccggcg gaggaggacc atgccccccct tgcaagtgtc ctgctccaaa cctgctggga  480
```

```
ggacctagcg tgttcatctt tccacccaag atcaaggacg tgctgatgat ctccctgagc  540
cctatcgtga cctgcgtggt ggtggacgtg tctgaggacg atccagatgt gcagatctcc  600
tggttcgtga acaatgtgga ggtgcacacc gcccagaccc agacacatag ggaggattac  660
aattccacac tgcgggtggt gtccgccctg cctatccagc accaggactg gatgtctggc  720
aaggagttta agtgcaaggt gaacaataag gatctgcccg cccctatcga gaggaccatc  780
agcaagccaa agggctctgt gagagctccc caggtgtatg tgctgcctcc acccgaggag  840
gagatgacca agaagcaggt gaccctgaca tgtatggtga cagacttcat gccagaggat  900
atctacgtgg agtggaccaa caatggcaag acagagctga actataagaa taccgagccc  960
gtgctggaca gcgatggctc ttactttatg tattccaagc tgagagtgga gaagaagaac  1020
tgggtggagc gcaattctta ctcctgcagc gtggtgcacg agggcctgca taaccaccat  1080
accacaaagt ctttctccag gacaccaggc                                   1110

SEQ ID NO: 277         moltype = DNA  length = 1002
FEATURE                Location/Qualifiers
source                 1..1002
                       mol_type = other DNA
                       organism = synthetic construct
SEQUENCE: 277
gagaccaggg agtgtatcta ctataacgcc aattgggagc tggagaggac aaaccagtcc  60
ggactggagc ggtgtgaggg agagcaggac aagagactgc attgctacgc tagctggcgc  120
aattccagcg gcaccatcga gctggtgaag aagggctgtt ggctggacga tgagaactgt  180
tacgatagac aggagtgcgt ggccaccgag gagaatcctc aggtgtattt ttgctgttgc  240
gagggcaact tctgcaatga gaggttcacc cacctgccag aggctggagg accagaggtg  300
acctatgagc caccacctac cggaggagga ccatgcccac catgcaagtg tccagctcct  360
aacctgctgg gaggaccatc cgtgttcatc tttcctccaa agatcaagga cgtgctgatg  420
atctccctga gccccatcgt gacatgcgtg gtggtggacg tgagcgagga cgatcctgat  480
gtgcagatct cttggttcgt gaacaatgtg gaggtgcaca ccgcccagac ccagacacat  540
agggaggatt acaattctac actgcgggtg gtgtccgctc tgcccatcca gcaccaggac  600
tggatgagcg gcaaggagtt taagtgcaag gtgaacaata aggatctgcc agcccccatc  660
gagaggacca tctccaagcc taagggcagc gtgagagctc cacaggtgta tgtgctgccc  720
cctccagagg aggagatgac caagaagcag gtgaccctga catgtatggt gacagacttc  780
atgcctgagg atatctacgt ggagtggacc aacaatggca agacagagct gaactataag  840
aataccgagc cagtgctgga cagcgatggc tcttacttta tgtattctaa gctgagagtg  900
gagaagaaga actgggtgga gcgcaattct tactcctgca gcgtggtgca cgagggcctg  960
cataaccacc ataccacaaa gtctttctcc aggacacccg gc                     1002

SEQ ID NO: 278         moltype = DNA  length = 1002
FEATURE                Location/Qualifiers
source                 1..1002
                       mol_type = other DNA
                       organism = synthetic construct
SEQUENCE: 278
gagaccaggg agtgtatcta ctataacgcc aattgggagc tggagaggac aaaccagtcc  60
ggactggagc ggtgtgaggg agagcaggac aagagactgc attgctacgc tagctggcgc  120
aattccagcg gcaccatcga gctggtgaag aagggctgtt ggctggacga tgacaactgt  180
tacgatagac aggagtgcgt ggccaccgag gagaatcctc aggtgtattt ttgctgttgc  240
gagggcaact tctgcaatga gaggttcacc cacctgccag aggctggagg accagaggtg  300
acctatgagc cacctccaac aggaggagga acccatacat gtccaccttg cccagctcca  360
gagctgctgg gaggcccttc cgtgttcctg tttccaccca agccaaagga caccctgatg  420
atctctagga ccccagaggt gacatgcgtg gtggtggacg tgtcccacga ggacccccgag  480
gtgaagttta actggtacgt ggatggcgtg gaggtgcata atgctaagac aaagccaagg  540
gaggagcagt acaactccac ctatcgggtg gtgagcgtgc tgacagtgct gcaccaggat  600
tggctgaacg gcaaggagta taagtgtaag gtgagcaata aggctctgcc tgccccaatc  660
gagaagacca tctctaaggc taagggccag cccagagagc ctcaggtgta cacactgcct  720
ccatcccgcg aggagatgac caagaaccag gtgagcctga catgcctggt gaagggcttc  780
tatcccagcg acatcgccgt ggagtgggag tctaatggcc agcctgagaa caattacaag  840
accacacccc ctgtgctgga cagcgatggc tctttctttc tgtattctaa gctgaccgtg  900
gataagtccc ggtggcagca gggcaacgtg ttttcttgtt ccgtgatgca tgaggccctg  960
cacaatcatt acacacagaa gagcctgtct ctgtcccctg gc                     1002

SEQ ID NO: 279         moltype = DNA  length = 1002
FEATURE                Location/Qualifiers
source                 1..1002
                       mol_type = other DNA
                       organism = synthetic construct
SEQUENCE: 279
gagaccaggg agtgtatcta ctataacgcc aattgggagc tggagaggac aaaccagtcc  60
ggactggagc ggtgtgaggg agagcaggac aagagactgc attgctacgc tagctggcgc  120
aattccagcg gcaccatcga gctggtgaag aagggctgtt ggctggacga tgacaactgt  180
tacgatagac aggagtgcgt ggccaccgag gagaatcctc aggtgtattt ttgctgttgc  240
gagggcaact tctgcaatga gaggttcacc cacctgccag aggctggagg accagaggtg  300
acctatgagc cacctccaac aggaggagga acccatacat gtccaccttg cccagctcca  360
gagctgctgg gaggcccttc cgtgttcctg tttccaccca agccaaagga caccctgatg  420
atctctagga ccccagaggt gacatgcgtg gtggtggacg tgtcccacga ggacccccgag  480
gtgaagttta actggtacgt ggatggcgtg gaggtgcata atgctaagac aaagccaagg  540
gaggagcagt acaactccac ctatcgggtg gtgagcgtgc tgacagtgct gcaccaggat  600
tggctgaacg gcaaggagta taagtgtaag gtgagcaata aggctctgcc tgccccaatc  660
gagaagacca tctctaaggc taagggccag cccagagagc ctcaggtgta cacactgcct  720
ccatcccgcg acgagctgac caagaaccag gtgagcctga catgcctggt gaagggcttc  780
```

```
tatcccagcg acatcgccgt ggagtgggag tctaatggcc agcctgagaa caattacaag  840
accacacccc ctgtgctgga cagcgatggc tctttctttc tgtattctaa gctgaccgtg  900
gataagtccc ggtggcagca gggcaacgtg ttttcttgtt ccgtgatgca tgaggccctg  960
cacaatcatt acacacagaa gagcctgtct ctgtcccctg gc                    1002

SEQ ID NO: 280          moltype = DNA  length = 1002
FEATURE                 Location/Qualifiers
source                  1..1002
                        mol_type = other DNA
                        organism = synthetic construct
SEQUENCE: 280
gagaccaggg agtgtatcta ctataacgcc aattgggagc tggagaggac aaaccagtcc  60
ggactggagc ggtgtgaggg agagcaggac aagagactgc attgctacgc tagctggcgc  120
aattccagcg gcaccatcga gctggtgaag aagggctgtt ggctggacga tgacaactgt  180
tacgatagac aggagtgcgt ggccaccgag gagaatcctc aggtgtattt ttgctgttgc  240
gagggcaact tctgcaatga gaggttcacc cacctgccag aggctggagg accagaggtg  300
acctatgagc caccacctac cggaggagga ccatgcccac catgcaagtg tccagctcct  360
aacctgctgg gaggaccatc cgtgttcatc tttcctccaa agatcaagga cgtgctgatg  420
atctccctga gccccatcgt gacatgcgtg gtggtggacg tgagcgagga cgatcctgat  480
gtgcagatct cttggttcgt gaacaatgtg gaggtgcaca ccgcccagac ccagacacat  540
agggaggatt acaattctac actgcgggtg gtgtccgctc tgcccatcca gcaccaggac  600
tggatgagcg gcaaggagtt taagtgcaag gtgaacaata aggatctgcc agccccaatc  660
gagaggacca tctccaagcc taagggcagc gtgagagctc cacaggtgta tgtgctgccc  720
cctccagagg aggagatgac caagaagcag gtgaccctga catgtatggt gacagacttc  780
atgcctgagg atatctacgt ggagtggacc aacaatggca agacagagct gaactataag  840
aataccgagc cagtgctgga cagcgatggc tcttacttta tgtattctaa gctgagagtg  900
gagaagaaga actgggtgga gcgcaattct tactcctgca gcgtggtgca cgagggcctg  960
cataaccacc ataccacaaa gtctttctcc aggacacccg gc                    1002

SEQ ID NO: 281          moltype = DNA  length = 1035
FEATURE                 Location/Qualifiers
source                  1..1035
                        mol_type = other DNA
                        organism = synthetic construct
SEQUENCE: 281
gagaccaggg agtgtatcta ctataacgcc aattgggagc tggagaggac aaaccagtcc  60
ggactggagc ggtgtgaggg cgagcaggac aagagactgc attgctacgc tagctggcgc  120
aattccagcg gcaccatcga gctggtgaag aagggctgtt ggctggacga tgacaactgt  180
tacgatagac aggagtgcgt ggccaccgag gagaatcctc aggtgtattt ttgctgttgc  240
gagggcaact tctgcaatga gaggttcacc cacctgccag aggctggagg accagaggtg  300
acctatgagc cacctccaac aggaggagga ggctctggag gaggaggctc cggaggagga  360
ggaacccata catgtccacc ttgcccagct ccagagctgc tgggaggccc ttccgtgttc  420
ctgtttccac ccaagccaaa ggacaccctg atgatctcta ggaccccaga ggtgacatgc  480
gtggtggtgg acgtgtccca cgaggacccc gaggtgaagt ttaactggta cgtggatggc  540
gtggaggtgc ataatgctaa gacaaagcca agggaggagc agtacaactc cacctatcgg  600
gtggtgagcg tgctgacagt gctgcaccag gattggctga acggcaagga gtataagtgt  660
aaggtgagca ataaggctct gcctgcccca atcgagaaga ccatctctaa ggctaagggc  720
cagcccagag agcctcaggt gtacacactg cctccatccc gcgaggagat gaccaagaac  780
caggtgagcc tgacatgcct ggtgaagggc ttctatccca gcgacatcgc cgtggagtgg  840
gagtctaatg gccagcctga gaacaattac aagaccacac cccctgtgct ggacagcgat  900
ggctctttct ttctgtattc taagctgacc gtggataagt cccggtggca gcagggcaac  960
gtgttttctt gttccgtgat gcatgaggcc ctgcacaatc attacacaca gaagagcctg  1020
tctctgtccc ctggc                                                  1035

SEQ ID NO: 282          moltype = DNA  length = 1035
FEATURE                 Location/Qualifiers
source                  1..1035
                        mol_type = other DNA
                        organism = synthetic construct
SEQUENCE: 282
gagaccaggg agtgtatcta ctataacgcc aattgggagc tggagaggac aaaccagtcc  60
ggactggagc ggtgtgaggg cgagcaggac aagagactgc attgctacgc tagctggcgc  120
aattccagcg gcaccatcga gctggtgaag aagggctgtt ggctggacga tgacaactgt  180
tacgatagac aggagtgcgt ggccaccgag gagaatcctc aggtgtattt ttgctgttgc  240
gagggcaact tctgcaatga gaggttcacc cacctgccag aggctggagg accagaggtg  300
acctatgagc cacctccaac aggaggagga ggctctggag gaggaggctc cggaggagga  360
ggaacccata catgtccacc ttgcccagct ccagagctgc tgggaggccc ttccgtgttc  420
ctgtttccac ccaagccaaa ggacaccctg atgatctcta ggaccccaga ggtgacatgc  480
gtggtggtgg acgtgtccca cgaggacccc gaggtgaagt ttaactggta cgtggatggc  540
gtggaggtgc ataatgctaa gacaaagcca agggaggagc agtacaactc cacctatcgg  600
gtggtgagcg tgctgacagt gctgcaccag gattggctga acggcaagga gtataagtgt  660
aaggtgagca ataaggctct gcctgcccca atcgagaaga ccatctctaa ggctaagggc  720
cagcccagag agcctcaggt gtacacactg cctccatccc gcgacgagct gaccaagaac  780
caggtgagcc tgacatgcct ggtgaagggc ttctatccca gcgacatcgc cgtggagtgg  840
gagtctaatg gccagcctga gaacaattac aagaccacac cccctgtgct ggacagcgat  900
ggctctttct ttctgtattc taagctgacc gtggataagt cccggtggca gcagggcaac  960
gtgttttctt gttccgtgat gcatgaggcc ctgcacaatc attacacaca gaagagcctg  1020
tctctgtccc ctggc                                                  1035
```

```
SEQ ID NO: 283          moltype = DNA  length = 1110
FEATURE                 Location/Qualifiers
source                  1..1110
                        mol_type = other DNA
                        organism = synthetic construct
SEQUENCE: 283
gagaccaggg agtgtatcta ctataacgcc aattgggagc tggagaggac aaaccagtcc  60
ggactggagc ggtgtgaggg agagcaggac aagagactgc attgctacgc tagctggcgc  120
aattccagcg gcaccatcga gctggtgaag aagggctgtt ggctggacga tgacaactgt  180
tacgatagac aggagtgcgt ggccaccgag gagaatcctc aggtgtattt ttgctgttgc  240
gagggcaact tctgcaatga gaggttcacc cacctgccag aggctggagg accagaggtg  300
acctatgagc cacctccaac aggaggagga ggctccggtg gcggcggcag cggcggcggc  360
ggctctggcg gcggcggctc cggtggtggt ggcagcggtg gtggtggctc tggtggtggc  420
ggctccggtg gtggcggcac ccatacatgt ccaccttgcc cagctccaga gctgctggga  480
ggcccttccg tgttcctgtt tccacccaag ccaaaggaca ccctgatgat ctctaggacc  540
ccagaggtga catgcgtggt ggtggacgtg tcccacgagg accccgaggt gaagtttaac  600
tggtacgtgg atggcgtgga ggtgcataat gctaagacaa agccaaggga ggagcagtac  660
aactccacct atcgggtggt gagcgtgctg acagtgctgc accaggattg gctgaacggc  720
aaggagtata agtgtaaggt gagcaataag gctctgcctg ccccaatcga gaagaccatc  780
tctaaggcta agggccagcc cagagagcct caggtgtaca cactgcctcc atcccgcgac  840
gagctgacca agaaccaggt gagcctgaca tgcctggtga agggcttcta tcccagcgac  900
atcgccgtgg agtgggagtc taatggccag cctgagaaca attacaagac cacacccccct  960
gtgctggaca gcgatggctc tttctttctg tattctaagc tgaccgtgga taagtcccgg  1020
tggcagcagg gcaacgtgtt ttcttgttcc gtgatgcatg aggccctgca caatcattac  1080
acacagaaga gcctgtctct gtcccctggc                                  1110

SEQ ID NO: 284          moltype = DNA  length = 1110
FEATURE                 Location/Qualifiers
source                  1..1110
                        mol_type = other DNA
                        organism = synthetic construct
SEQUENCE: 284
gagaccaggg agtgtatcta ctataacgcc aattgggagc tggagaggac aaaccagtcc  60
ggactggagc ggtgtgaggg agagcaggac aagagactgc attgctacgc tagctggcgc  120
aattccagcg gcaccatcga gctggtgaag aagggctgtt ggctggacga tgacaactgt  180
tacgatagac aggagtgcgt ggccaccgag gagaatcctc aggtgtattt ttgctgttgc  240
gagggcaact tctgcaatga gaggttcacc cacctgccag aggctggagg accagaggtg  300
acctatgagc cacctccaac aggaggagga ggctccggtg gcggcggcag cggcggcggc  360
ggctctggcg gcggcggctc cggtggtggt ggcagcggtg gcggcggctc tggaggagga  420
ggctccggcg gaggaggacc atgccccct tgcaagtgtc ctgctccaaa cctgctggga  480
ggacctagcg tgttcatctt tccacccaag atcaaggacg tgctgatgat ctccctgagc  540
cctatcgtga cctgcgtggt ggtggacgtg tctgaggacg atccagatgt gcagatctcc  600
tggttcgtga acaatgtgga ggtgcacacc gcccagaccc agacacatag ggaggattac  660
aattccacac tgcgggtggt gtccgccctg cctatccagc accaggactg gatgtctggc  720
aaggagttta agtgcaaggt gaacaataag gatctgcccg cccctatcga gaggaccatc  780
agcaagccaa agggctctgt gagagctccc caggtgtatg tgctgcctcc acccgaggag  840
gagatgacca agaagcaggt gaccctgaca tgtatggtga cagacttcat gccagaggat  900
atctacgtgg agtggaccaa caatggcaag acagagctga actataagaa taccgagccc  960
gtgctggaca gcgatggctc ttactttatg tattccaagc tgagagtgga gaagaagaac  1020
tgggtggagc gcaattctta ctcctgcagc gtggtgcacg agggcctgca taaccaccat  1080
accacaaagt ctttctccag gacaccaggc                                  1110

SEQ ID NO: 285          moltype = DNA  length = 1002
FEATURE                 Location/Qualifiers
source                  1..1002
                        mol_type = other DNA
                        organism = synthetic construct
SEQUENCE: 285
gagaccaggg agtgtatcta ctataacgcc aattgggagc tggagaggac aaaccagtcc  60
ggactggagc ggtgtgaggg agagcaggac aagagactgc attgctacgc tagctggcgc  120
aattccagcg gcaccatcga gctggtgaag aagggctgtt ggctggacga ttacaactgt  180
tacgatagac aggagtgcgt ggccaccgag gagaatcctc aggtgtattt ttgctgttgc  240
gagggcaact tctgcaatga gaggttcacc cacctgccag aggctggagg accagaggtg  300
acctatgagc cacctccaac aggaggagga acccatacat gtccaccttg cccagctcca  360
gagctgctgg gaggcccttc cgtgttcctg tttccaccca agccaaagga caccctgatg  420
atctctagga ccccagaggt gacatgcgtg gtggtggacg tgtcccacga ggaccccgag  480
gtgaagttta actggtacgt ggatggcgtg gaggtgcata atgctaagac aaagccaagg  540
gaggagcagt acaactccac ctatcgggtg gtgagcgtgc tgacagtgct gcaccaggat  600
tggctgaacg gcaaggagta taagtgtaag gtgagcaata aggctctgcc tgccccaatc  660
gagaagacca tctctaaggc taagggccag cccagagagc ctcaggtgta cacactgcct  720
ccatcccgcg aggagatgac caagaaccag gtgagcctga catgcctggt gaagggcttc  780
tatcccagcg acatcgccgt ggagtgggag tctaatggcc agcctgagaa caattacaag  840
accacacccc ctgtgctgga cagcgatggc tctttctttc tgtattctaa gctgaccgtg  900
gataagtccc ggtggcagca gggcaacgtg ttttcttgtt ccgtgatgca tgaggccctg  960
cacaatcatt acacacagaa gagcctgtct ctgtcccctg gc                    1002

SEQ ID NO: 286          moltype = DNA  length = 1002
FEATURE                 Location/Qualifiers
source                  1..1002
```

```
                        mol_type = other DNA
                        organism = synthetic construct
SEQUENCE: 286
gagaccaggg agtgtatcta ctataacgcc aattgggagc tggagaggac aaaccagtcc  60
ggactggagc ggtgtgaggg agagcaggac aagagactgc attgctacgc tagctggcgc  120
aattccagcg gcaccatcga gctggtgaag aagggctgtt ggctggacga ttacaactgt  180
tacgatagac aggagtgcgt ggccaccgag gagaatcctc aggtgtattt ttgctgttgc  240
gagggcaact tctgcaatga gaggttcacc cacctgccag aggctggagg accagaggtg  300
acctatgagc cacctccaac aggaggagga acccatacat gtccaccttg cccagctcca  360
gagctgctgg gaggcccttc cgtgttcctg tttccaccca agccaaagga caccctgatg  420
atctctagga ccccagaggt gacatgcgtg gtggtggacg tgtcccacga ggaccccgag  480
gtgaagttta actggtacgt ggatggcgtg gaggtgcata atgctaagac aaagccaagg  540
gaggagcagt acaactccac ctatcgggtg gtgagcgtgc tgacagtgct gcaccaggat  600
tggctgaacg gcaaggagta taagtgtaag gtgagcaata aggctctgcc tgccccaatc  660
gagaagacca tctctaaggc taagggccag cccagagagc ctcaggtgta cacactgcct  720
ccatcccgcg acgagctgac caagaaccag gtgagcctga catgcctggt gaagggcttc  780
tatcccagcg acatcgccgt ggagtgggag tctaatggcc agcctgagaa caattacaag  840
accacacccc ctgtgctgga cagcgatggc tctttctttc tgtattctaa gctgaccgtg  900
gataagtccc ggtggcagca gggcaacgtg ttttcttgtt ccgtgatgca tgaggccctg  960
cacaatcatt acacacagaa gagcctgtct ctgtcccctg gc                     1002

SEQ ID NO: 287          moltype = DNA  length = 1002
FEATURE                 Location/Qualifiers
source                  1..1002
                        mol_type = other DNA
                        organism = synthetic construct
SEQUENCE: 287
gagaccaggg agtgtatcta ctataacgcc aattgggagc tggagaggac aaaccagtcc  60
ggactggagc ggtgtgaggg agagcaggac aagagactgc attgctacgc tagctggcgc  120
aattccagcg gcaccatcga gctggtgaag aagggctgtt ggctggacga ttacaactgt  180
tacgatagac aggagtgcgt ggccaccgag gagaatcctc aggtgtattt ttgctgttgc  240
gagggcaact tctgcaatga gaggttcacc cacctgccag aggctggagg accagaggtg  300
acctatgagc caccacctac cggaggagga ccatgcccac catgcaagtg tccagctcct  360
aacctgctgg gaggaccatc cgtgttcatc tttcctccaa agatcaagga cgtgctgatg  420
atctccctga gccccatcgt gacatgcgtg gtggtggacg tgagcgagga cgatcctgat  480
gtgcagatct cttggttcgt gaacaatgtg gaggtgcaca ccgcccagac ccagacacat  540
agggaggatt acaattctac actgcgggtg gtgtccgctc tgcccatcca gcaccaggac  600
tggatgagcg gcaaggagtt taagtgcaag gtgaacaata aggatctgcc agcccccatc  660
gagaggacca tctccaagcc taagggcagc gtgagagctc cacaggtgta tgtgctgccc  720
cctccagagg aggagatgac caagaagcag gtgaccctga catgtatggt gacagacttc  780
atgcctgagg atatctacgt ggagtggacc aacaatggca agacagagct gaactataag  840
aataccgagc cagtgctgga cagcgatggc tcttacttta tgtattctaa gctgagagtg  900
gagaagaaga actgggtgga gcgcaattct tactcctgca gcgtggtgca cgagggcctg  960
cataaccacc ataccacaaa gtctttctcc aggacacccg gc                     1002

SEQ ID NO: 288          moltype = DNA  length = 1035
FEATURE                 Location/Qualifiers
source                  1..1035
                        mol_type = other DNA
                        organism = synthetic construct
SEQUENCE: 288
gagaccaggg agtgtatcta ctataacgcc aattgggagc tggagaggac aaaccagtcc  60
ggactggagc ggtgtgaggg cgagcaggac aagagactgc attgctacgc tagctggcgc  120
aattccagcg gcaccatcga gctggtgaag aagggctgtt ggctggacga ttacaactgt  180
tacgatagac aggagtgcgt ggccaccgag gagaatcctc aggtgtattt ttgctgttgc  240
gagggcaact tctgcaatga gaggttcacc cacctgccag aggctggagg accagaggtg  300
acctatgagc cacctccaac aggaggagga ggctctggag gaggaggctc cggaggagga  360
ggaacccata catgtccacc ttgcccagct ccagagctgc tgggaggccc ttccgtgttc  420
ctgtttccac ccaagccaaa ggacaccctg atgatctcta ggaccccaga ggtgacatgc  480
gtggtggtgg acgtgtccca cgaggacccc gaggtgaagt ttaactggta cgtggatggc  540
gtggaggtgc ataatgctaa gacaaagcca agggaggagc agtacaactc cacctatcgg  600
gtggtgagcg tgctgacagt gctgcaccag gattggctga acggcaagga gtataagtgt  660
aaggtgagca ataaggctct gcctgcccca atcgagaaga ccatctctaa ggctaagggc  720
cagcccagag agcctcaggt gtacacactg cctccatccc gcgaggagat gaccaagaac  780
caggtgagcc tgacatgcct ggtgaagggc ttctatccca gcgacatcgc cgtggagtgg  840
gagtctaatg gccagcctga gaacaattac aagaccacac cccctgtgct ggacagcgat  900
ggctctttct ttctgtattc taagctgacc gtggataagt cccggtggca gcagggcaac  960
gtgttttctt gttccgtgat gcatgaggcc ctgcacaatc attacacaca gaagagcctg  1020
tctctgtccc ctggc                                                   1035

SEQ ID NO: 289          moltype = DNA  length = 1035
FEATURE                 Location/Qualifiers
source                  1..1035
                        mol_type = other DNA
                        organism = synthetic construct
SEQUENCE: 289
gagaccaggg agtgtatcta ctataacgcc aattgggagc tggagaggac aaaccagtcc  60
ggactggagc ggtgtgaggg cgagcaggac aagagactgc attgctacgc tagctggcgc  120
aattccagcg gcaccatcga gctggtgaag aagggctgtt ggctggacga ttacaactgt  180
```

```
tacgatagac aggagtgcgt ggccaccgag gagaatcctc aggtgtattt ttgctgttgc  240
gagggcaact tctgcaatga gaggttcacc cacctgccag aggctggagg accagaggtg  300
acctatgagc cacctccaac aggaggagga ggctctggag gaggaggctc cggaggagga  360
ggaacccata catgtccacc ttgcccagct ccagagctgc tgggaggccc ttccgtgttc  420
ctgtttccac ccaagccaaa ggacaccctg atgatctcta ggaccccaga ggtgacatgc  480
gtggtggtgg acgtgtccca cgaggacccc gaggtgaagt ttaactggta cgtggatggc  540
gtggaggtgc ataatgctaa gacaaagcca agggaggagc agtacaactc cacctatcgg  600
gtggtgagcg tgctgacagt gctgcaccag gattggctga acggcaagga gtataagtgt  660
aaggtgagca ataaggctct gcctgcccca atcgagaaga ccatctctaa ggctaagggc  720
cagcccagag agcctcaggt gtacacactg cctccatccc gcgacgagct gaccaagaac  780
caggtgagcc tgacatgcct ggtgaagggc ttctatccca gcgacatcgc cgtggagtgg  840
gagtctaatg gccagcctga gaacaattac aagaccacac cccctgtgct ggacagcgat  900
ggctctttct ttctgtattc taagctgacc gtggataagt cccggtggca gcagggcaac  960
gtgtttcctt gttccgtgat gcatgaggcc ctgcacaatc attacacaca gaagagcctg  1020
tctctgtccc ctggc                                                   1035

SEQ ID NO: 290          moltype = DNA  length = 1110
FEATURE                 Location/Qualifiers
source                  1..1110
                        mol_type = other DNA
                        organism = synthetic construct
SEQUENCE: 290
gagaccaggg agtgtatcta ctataacgcc aattgggagc tggagaggac aaaccagtcc  60
ggactggagc ggtgtgaggg agagcaggac aagagactgc attgctacgc tagctggcgc  120
aattccagcg gcaccatcga gctggtgaag aagggctgtt ggctggacga ttacaactgt  180
tacgatagac aggagtgcgt ggccaccgag gagaatcctc aggtgtattt ttgctgttgc  240
gagggcaact tctgcaatga gaggttcacc cacctgccag aggctggagg accagaggtg  300
acctatgagc cacctccaac aggaggagga ggctccggtg gcggcggcag cggcggcggc  360
ggctctggcg gcggcggctc cggtggtggt ggcagcggtg gtggtggctc tggtggtggc  420
ggctccggtg gtggcggcac ccatacatgt ccaccttgcc cagctccaga gctgctggga  480
ggcccttccg tgttcctgtt tccacccaag ccaaaggaca ccctgatgat ctctaggacc  540
ccagaggtga catgcgtggt ggtggacgtg tcccacgagg accccgaggt gaagtttaac  600
tggtacgtgg atggcgtgga ggtgcataat gctaagacaa agccaaggga ggagcagtac  660
aactccacct atcgggtggt gagcgtgctg acagtgctgc accaggattg gctgaacggc  720
aaggagtata agtgtaaggt gagcaataag gctctgcctg ccccaatcga gaagaccatc  780
tctaaggcta agggccagcc cagagagcct caggtgtaca cactgcctcc atcccgcgac  840
gagctgacca agaaccaggt gagcctgaca tgcctggtga agggcttcta tcccagcgac  900
atcgccgtgg agtgggagtc taatggccag cctgagaaca attacaagac cacacccct  960
gtgctggaca gcgatggctc tttctttctg tattctaagc tgaccgtgga taagtcccgg  1020
tggcagcagg gcaacgtgtt ttcttgttcc gtgatgcatg aggccctgca caatcattac  1080
acacagaaga gcctgtctct gtcccctggc                                   1110

SEQ ID NO: 291          moltype = DNA  length = 1110
FEATURE                 Location/Qualifiers
source                  1..1110
                        mol_type = other DNA
                        organism = synthetic construct
SEQUENCE: 291
gagaccaggg agtgtatcta ctataacgcc aattgggagc tggagaggac aaaccagtcc  60
ggactggagc ggtgtgaggg agagcaggac aagagactgc attgctacgc tagctggcgc  120
aattccagcg gcaccatcga gctggtgaag aagggctgtt ggctggacga ttacaactgt  180
tacgatagac aggagtgcgt ggccaccgag gagaatcctc aggtgtattt ttgctgttgc  240
gagggcaact tctgcaatga gaggttcacc cacctgccag aggctggagg accagaggtg  300
acctatgagc cacctccaac aggaggagga ggctccggtg gcggcggcag cggcggcggc  360
ggctctggcg gcggcggctc cggtggtggt ggcagcggtg gcggcggctc tggaggagga  420
ggctccggcg gaggaggacc atgccccct tgcaagtgtc ctgctccaaa cctgctggga  480
ggacctagcg tgttcatctt tccacccaag atcaaggacg tgctgatgat ctccctgagc  540
cctatcgtga cctgcgtggt ggtggacgtg tctgaggacg atccagatgt gcagatctcc  600
tggttcgtga acaatgtgga ggtgcacacc gcccagaccc agacacatag ggaggattac  660
aattccacac tgcgggtggt gtccgccctg cctatccagc accaggactg gatgtctggc  720
aaggagttta agtgcaaggt gaacaataag gatctgcccg cccctatcga gaggaccatc  780
agcaagccaa agggctctgt gagagctccc caggtgtatg tgctgcctcc acccgaggag  840
gagatgacca agaagcaggt gaccctgaca tgtatggtga cagacttcat gccagaggat  900
atctacgtgg agtggaccaa caatggcaag acagagctga actataagaa taccgagccc  960
gtgctggaca gcgatggctc ttactttatg tattccaagc tgagagtgga gaagaagaac  1020
tgggtggagc gcaattctta ctcctgcagc gtggtgcacg agggcctgca taaccaccat  1080
accacaaagt ctttctccag gacaccaggc                                   1110

SEQ ID NO: 292          moltype = DNA  length = 1002
FEATURE                 Location/Qualifiers
source                  1..1002
                        mol_type = other DNA
                        organism = synthetic construct
SEQUENCE: 292
gagaccaggg agtgtatcta ctataacgcc aattgggagc tggagaggac aaaccagtcc  60
ggactggagc ggtgtgaggg agagcaggac aagagactgc attgctacgc tagctggcgc  120
aattccagcg gcaccatcga gctggtgaag aagggctgtt ggctggacga taagaactgt  180
tacgatagac aggagtgcgt ggccaccgag gagaatcctc aggtgtattt ttgctgttgc  240
gagggcaact tctgcaatga gaggttcacc cacctgccag aggctggagg accagaggtg  300
```

-continued

```
acctatgagc cacctccaac aggaggagga acccatacat gtccaccttg cccagctcca  360
gagctgctgg gaggcccttc cgtgttcctg tttccaccca agccaaagga caccctgatg  420
atctctagga ccccagaggt gacatgcgtg gtggtggacg tgtcccacga ggaccccgag  480
gtgaagttta actggtacgt ggatggcgtg gaggtgcata atgctaagac aaagccaagg  540
gaggagcagt acaactccac ctatcgggtg gtgagcgtgc tgacagtgct gcaccaggat  600
tggctgaacg gcaaggagta taagtgtaag gtgagcaata aggctctgcc tgccccaatc  660
gagaagacca tctctaaggc taagggccag cccagagagc ctcaggtgta cacactgcct  720
ccatcccgcg aggagatgac caagaaccag gtgagcctga catgcctggt gaagggcttc  780
tatcccagcg acatcgccgt ggagtgggag tctaatggcc agcctgagaa caattacaag  840
accacacccc ctgtgctgga cagcgatggc tctttcttc tgtattctaa gctgaccgtg  900
gataagtccc ggtggcagca gggcaacgtg ttttcttgtt ccgtgatgca tgaggccctg  960
cacaatcatt acacacagaa gagcctgtct ctgtcccctg gc                    1002

SEQ ID NO: 293          moltype = DNA  length = 1002
FEATURE                 Location/Qualifiers
source                  1..1002
                        mol_type = other DNA
                        organism = synthetic construct
SEQUENCE: 293
gagaccaggg agtgtatcta ctataacgcc aattgggagc tggagaggac aaaccagtcc  60
ggactggagc ggtgtgaggg agagcaggac aagagactgc attgctacgc tagctggcgc  120
aattccagcg gcaccatcga gctggtgaag aagggctgtt ggctggacga taagaactgt  180
tacgatagac aggagtgcgt ggccaccgag gagaatcctc aggtgtattt ttgctgttgc  240
gagggcaact tctgcaatga gaggttcacc cacctgccag aggctggagg accagaggtg  300
acctatgagc cacctccaac aggaggagga acccatacat gtccaccttg cccagctcca  360
gagctgctgg gaggcccttc cgtgttcctg tttccaccca agccaaagga caccctgatg  420
atctctagga ccccagaggt gacatgcgtg gtggtggacg tgtcccacga ggaccccgag  480
gtgaagttta actggtacgt ggatggcgtg gaggtgcata atgctaagac aaagccaagg  540
gaggagcagt acaactccac ctatcgggtg gtgagcgtgc tgacagtgct gcaccaggat  600
tggctgaacg gcaaggagta taagtgtaag gtgagcaata aggctctgcc tgccccaatc  660
gagaagacca tctctaaggc taagggccag cccagagagc ctcaggtgta cacactgcct  720
ccatcccgcg acgagctgac caagaaccag gtgagcctga catgcctggt gaagggcttc  780
tatcccagcg acatcgccgt ggagtgggag tctaatggcc agcctgagaa caattacaag  840
accacacccc ctgtgctgga cagcgatggc tctttcttc tgtattctaa gctgaccgtg  900
gataagtccc ggtggcagca gggcaacgtg ttttcttgtt ccgtgatgca tgaggccctg  960
cacaatcatt acacacagaa gagcctgtct ctgtcccctg gc                    1002

SEQ ID NO: 294          moltype = DNA  length = 1002
FEATURE                 Location/Qualifiers
source                  1..1002
                        mol_type = other DNA
                        organism = synthetic construct
SEQUENCE: 294
gagaccaggg agtgtatcta ctataacgcc aattgggagc tggagaggac aaaccagtcc  60
ggactggagc ggtgtgaggg agagcaggac aagagactgc attgctacgc tagctggcgc  120
aattccagcg gcaccatcga gctggtgaag aagggctgtt ggctggacga taagaactgt  180
tacgatagac aggagtgcgt ggccaccgag gagaatcctc aggtgtattt ttgctgttgc  240
gagggcaact tctgcaatga gaggttcacc cacctgccag aggctggagg accagaggtg  300
acctatgagc caccacctac cggaggagga ccatgcccac catgcaagtg tccagctcct  360
aacctgctgg gaggaccatc cgtgttcatc tttcctccaa agatcaagga cgtgctgatg  420
atctccctga gccccatcgt gacatgcgtg gtggtggacg tgagcgagga cgatcctgat  480
gtgcagatct cttggttcgt gaacaatgtg gaggtgcaca ccgcccagac ccagacacat  540
agggaggatt acaattctac actgcgggtg gtgtccgctc tgcccatcca gcaccaggac  600
tggatgagcg gcaaggagtt taagtgcaag gtgaacaata aggatctgcc agcccccatc  660
gagaggacca tctccaagcc taagggcagc gtgagagctc cacaggtgta tgtgctgccc  720
cctccagagg aggagatgac caagaagcag gtgaccctga catgtatggt gacagacttc  780
atgcctgagg atatctacgt ggagtggacc aacaatggca agacagagct gaactataag  840
aataccgagc cagtgctgga cagcgatggc tcttacttta tgtattctaa gctgagagtg  900
gagaagaaga actgggtgga gcgcaattct tactcctgca gcgtggtgca cgagggcctg  960
cataaccacc ataccacaaa gtctttctcc aggacacccg gc                    1002

SEQ ID NO: 295          moltype = DNA  length = 1035
FEATURE                 Location/Qualifiers
source                  1..1035
                        mol_type = other DNA
                        organism = synthetic construct
SEQUENCE: 295
gagaccaggg agtgtatcta ctataacgcc aattgggagc tggagaggac aaaccagtcc  60
ggactggagc ggtgtgaggg cgagcaggac aagagactgc attgctacgc tagctggcgc  120
aattccagcg gcaccatcga gctggtgaag aagggctgtt ggctggacga taagaactgt  180
tacgatagac aggagtgcgt ggccaccgag gagaatcctc aggtgtattt ttgctgttgc  240
gagggcaact tctgcaatga gaggttcacc cacctgccag aggctggagg accagaggtg  300
acctatgagc cacctccaac aggaggagga ggctctggag gaggaggctc cggaggagga  360
ggaacccata catgtccacc ttgcccagct ccagagctgc tgggaggccc ttccgtgttc  420
ctgtttccac ccaagccaaa ggacaccctg atgatctcta ggaccccaga ggtgacatgc  480
gtggtggtgg acgtgtccca cgaggacccc gaggtgaagt ttaactggta cgtggatggc  540
gtggaggtgc ataatgctaa gacaaagcca agggaggagc agtacaactc cacctatcgg  600
gtggtgagcg tgctgacagt gctgcaccag gattggctga acggcaagga gtataagtgt  660
aaggtgagca ataaggctct gcctgcccca atcgagaaga ccatctctaa ggctaagggc  720
```

-continued

```
cagcccagag agcctcaggt gtacacactg cctccatccc gcgaggagat gaccaagaac  780
caggtgagcc tgacatgcct ggtgaagggc ttctatccca gcgacatcgc cgtggagtgg  840
gagtctaatg gccagcctga gaacaattac aagaccacac cccctgtgct ggacagcgat  900
ggctctttct ttctgtattc taagctgacc gtggataagt cccggtggca gcagggcaac  960
gtgttttctt gttccgtgat gcatgaggcc ctgcacaatc attacacaca gaagagcctg  1020
tctctgtccc ctggc                                                   1035

SEQ ID NO: 296         moltype = DNA  length = 1035
FEATURE                Location/Qualifiers
source                 1..1035
                       mol_type = other DNA
                       organism = synthetic construct
SEQUENCE: 296
gagaccaggg agtgtatcta ctataacgcc aattgggagc tggagaggac aaaccagtcc  60
ggactggagc ggtgtgaggg cgagcaggac aagagactgc attgctacgc tagctggcgc  120
aattccagcg gcaccatcga gctggtgaag aagggctgtt ggctggacga taagaactgt  180
tacgatagac aggagtgcgt ggccaccgag gagaatcctc aggtgtattt ttgctgttgc  240
gagggcaact tctgcaatga gaggttcacc cacctgccag aggctggagg accagaggtg  300
acctatgagc cacctccaac aggaggagga ggctctggag gaggaggctc cggaggagga  360
ggaacccata catgtccacc ttgcccagct ccagagctgc tgggaggccc ttccgtgttc  420
ctgtttccac ccaagccaaa ggacaccctg atgatctcta ggaccccaga ggtgacatgc  480
gtggtggtgg acgtgtccca cgaggacccc gaggtgaagt ttaactggta cgtggatggc  540
gtggaggtgc ataatgctaa gacaaagcca agggaggagc agtacaactc cacctatcgg  600
gtggtgagcg tgctgacagt gctgcaccag gattggctga acggcaagga gtataagtgt  660
aaggtgagca ataaggctct gcctgcccca atcgagaaga ccatctctaa ggctaagggc  720
cagcccagag agcctcaggt gtacacactg cctccatccc gcgacgagct gaccaagaac  780
caggtgagcc tgacatgcct ggtgaagggc ttctatccca gcgacatcgc cgtggagtgg  840
gagtctaatg gccagcctga gaacaattac aagaccacac cccctgtgct ggacagcgat  900
ggctctttct ttctgtattc taagctgacc gtggataagt cccggtggca gcagggcaac  960
gtgttttctt gttccgtgat gcatgaggcc ctgcacaatc attacacaca gaagagcctg  1020
tctctgtccc ctggc                                                   1035

SEQ ID NO: 297         moltype = DNA  length = 1110
FEATURE                Location/Qualifiers
source                 1..1110
                       mol_type = other DNA
                       organism = synthetic construct
SEQUENCE: 297
gagaccaggg agtgtatcta ctataacgcc aattgggagc tggagaggac aaaccagtcc  60
ggactggagc ggtgtgaggg agagcaggac aagagactgc attgctacgc tagctggcgc  120
aattccagcg gcaccatcga gctggtgaag aagggctgtt ggctggacga taagaactgt  180
tacgatagac aggagtgcgt ggccaccgag gagaatcctc aggtgtattt ttgctgttgc  240
gagggcaact tctgcaatga gaggttcacc cacctgccag aggctggagg accagaggtg  300
acctatgagc cacctccaac aggaggagga ggctccggtg gcggcggcag cggcggcggc  360
ggctctggcg gcggcggctc cggtggtggt ggcagcggtg gtggtggctc tggtggtggc  420
ggctccggtg gtggcggcac ccatacatgt ccaccttgcc cagctccaga gctgctggga  480
ggcccttccg tgttcctgtt tccacccaag ccaaaggaca ccctgatgat ctctaggacc  540
ccagaggtga catgcgtggt ggtggacgtg tcccacgagg accccgaggt gaagtttaac  600
tggtacgtgg atggcgtgga ggtgcataat gctaagacaa agccaaggga ggagcagtac  660
aactccacct atcgggtggt gagcgtgctg acagtgctgc accaggattg gctgaacggc  720
aaggagtata agtgtaaggt gagcaataag gctctgcctg ccccaatcga gaagaccatc  780
tctaaggcta agggccagcc cagagagcct caggtgtaca cactgcctcc atcccgcgac  840
gagctgacca agaaccaggt gagcctgaca tgcctggtga agggcttcta tcccagcgac  900
atcgccgtgg agtgggagtc taatggccag cctgagaaca attacaagac cacacccccct  960
gtgctggaca gcgatggctc tttctttctg tattctaagc tgaccgtgga taagtcccgg  1020
tggcagcagg gcaacgtgtt ttcttgttcc gtgatgcatg aggccctgca caatcattac  1080
acacagaaga gcctgtctct gtcccctggc                                   1110

SEQ ID NO: 298         moltype = DNA  length = 1110
FEATURE                Location/Qualifiers
source                 1..1110
                       mol_type = other DNA
                       organism = synthetic construct
SEQUENCE: 298
gagaccaggg agtgtatcta ctataacgcc aattgggagc tggagaggac aaaccagtcc  60
ggactggagc ggtgtgaggg agagcaggac aagagactgc attgctacgc tagctggcgc  120
aattccagcg gcaccatcga gctggtgaag aagggctgtt ggctggacga taagaactgt  180
tacgatagac aggagtgcgt ggccaccgag gagaatcctc aggtgtattt ttgctgttgc  240
gagggcaact tctgcaatga gaggttcacc cacctgccag aggctggagg accagaggtg  300
acctatgagc cacctccaac aggaggagga ggctccggtg gcggcggcag cggcggcggc  360
ggctctggcg gcggcggctc cggtggtggt ggcagcggtg gcggcggctc tggaggagga  420
ggctccggcg gaggaggacc atgcccccct tgcaagtgtc ctgctccaaa cctgctggga  480
ggacctagcg tgttcatctt tccacccaag atcaaggacg tgctgatgat ctccctgagc  540
cctatcgtga cctgcgtggt ggtggacgtg tctgaggacg atccagatgt gcagatctcc  600
tggttcgtga acaatgtgga ggtgcacacc gcccagaccc agacacatag ggaggattac  660
aattccacac tgcgggtggt gtccgccctg cctatccagc accaggactg gatgtctggc  720
aaggagttta agtgcaaggt gaacaataag gatctgcccg cccctatcga gaggaccatc  780
agcaagccaa agggctctgt gagagctccc caggtgtatg tgctgcctcc acccgaggag  840
gagatgacca agaagcaggt gaccctgaca tgtatggtga cagacttcat gccagaggat  900
```

-continued

```
atctacgtgg agtggaccaa caatggcaag acagagctga actataagaa taccgagccc  960
gtgctggaca gcgatggctc ttactttatg tattccaagc tgagagtgga gaagaagaac  1020
tgggtggagc gcaattctta ctcctgcagc gtggtgcacg agggcctgca taaccaccat  1080
accacaaagt ctttctccag gacaccaggc                                   1110

SEQ ID NO: 299          moltype = DNA  length = 1002
FEATURE                 Location/Qualifiers
source                  1..1002
                        mol_type = other DNA
                        organism = synthetic construct
SEQUENCE: 299
gagaccaggg agtgtatcta ctataacgcc aattgggagc tggagaggac aaaccagtcc  60
ggactggagc ggtgtgaggg agagcaggac aagagactgc attgctacgc tagctggcgc  120
aattccagcg gcaccatcga gctggtgaag aagggctgtt ggctggacga tcagaactgt  180
tacgatagac aggagtgcgt ggccaccgag gagaatcctc aggtgtattt ttgctgttgc  240
gagggcaact tctgcaatga gaggttcacc cacctgccag aggctggagg accagaggtg  300
acctatgagc cacctccaac aggaggagga acccatacat gtccaccttg cccagctcca  360
gagctgctgg gaggcccttc cgtgttcctg tttccaccca agccaaagga caccctgatg  420
atctctagga ccccagaggt gacatgcgtg gtggtggacg tgtcccacga ggaccccgag  480
gtgaagttta actggtacgt ggatggcgtg gaggtgcata atgctaagac aaagccaagg  540
gaggagcagt acaactccac ctatcgggtg gtgagcgtgc tgacagtgct gcaccaggat  600
tggctgaacg gcaaggagta taagtgtaag gtgagcaata aggctctgcc tgccccaatc  660
gagaagacca tctctaaggc taagggccag cccagagagc ctcaggtgta cacactgcct  720
ccatcccgcg aggagatgac caagaaccag gtgagcctga catgcctggt gaagggcttc  780
tatcccagcg acatcgccgt ggagtgggag tctaatggcc agcctgagaa caattacaag  840
accacacccc ctgtgctgga cagcgatggc tctttctttc tgtattctaa gctgaccgtg  900
gataagtccc ggtggcagca gggcaacgtg ttttcttgtt ccgtgatgca tgaggccctg  960
cacaatcatt acacacagaa gagcctgtct ctgtcccctg gc                     1002

SEQ ID NO: 300          moltype = DNA  length = 1002
FEATURE                 Location/Qualifiers
source                  1..1002
                        mol_type = other DNA
                        organism = synthetic construct
SEQUENCE: 300
gagaccaggg agtgtatcta ctataacgcc aattgggagc tggagaggac aaaccagtcc  60
ggactggagc ggtgtgaggg agagcaggac aagagactgc attgctacgc tagctggcgc  120
aattccagcg gcaccatcga gctggtgaag aagggctgtt ggctggacga tcagaactgt  180
tacgatagac aggagtgcgt ggccaccgag gagaatcctc aggtgtattt ttgctgttgc  240
gagggcaact tctgcaatga gaggttcacc cacctgccag aggctggagg accagaggtg  300
acctatgagc cacctccaac aggaggagga acccatacat gtccaccttg cccagctcca  360
gagctgctgg gaggcccttc cgtgttcctg tttccaccca agccaaagga caccctgatg  420
atctctagga ccccagaggt gacatgcgtg gtggtggacg tgtcccacga ggaccccgag  480
gtgaagttta actggtacgt ggatggcgtg gaggtgcata atgctaagac aaagccaagg  540
gaggagcagt acaactccac ctatcgggtg gtgagcgtgc tgacagtgct gcaccaggat  600
tggctgaacg gcaaggagta taagtgtaag gtgagcaata aggctctgcc tgccccaatc  660
gagaagacca tctctaaggc taagggccag cccagagagc ctcaggtgta cacactgcct  720
ccatcccgcg acgagctgac caagaaccag gtgagcctga catgcctggt gaagggcttc  780
tatcccagcg acatcgccgt ggagtgggag tctaatggcc agcctgagaa caattacaag  840
accacacccc ctgtgctgga cagcgatggc tctttctttc tgtattctaa gctgaccgtg  900
gataagtccc ggtggcagca gggcaacgtg ttttcttgtt ccgtgatgca tgaggccctg  960
cacaatcatt acacacagaa gagcctgtct ctgtcccctg gc                     1002

SEQ ID NO: 301          moltype = DNA  length = 1002
FEATURE                 Location/Qualifiers
source                  1..1002
                        mol_type = other DNA
                        organism = synthetic construct
SEQUENCE: 301
gagaccaggg agtgtatcta ctataacgcc aattgggagc tggagaggac aaaccagtcc  60
ggactggagc ggtgtgaggg agagcaggac aagagactgc attgctacgc tagctggcgc  120
aattccagcg gcaccatcga gctggtgaag aagggctgtt ggctggacga tcagaactgt  180
tacgatagac aggagtgcgt ggccaccgag gagaatcctc aggtgtattt ttgctgttgc  240
gagggcaact tctgcaatga gaggttcacc cacctgccag aggctggagg accagaggtg  300
acctatgagc caccacctac cggaggagga ccatgcccac catgcaagtg tccagctcct  360
aacctgctgg gaggaccatc cgtgttcatc tttcctccaa agatcaagga cgtgctgatg  420
atctccctga gccccatcgt gacatgcgtg gtggtggacg tgagcgagga cgatcctgat  480
gtgcagatct cttggttcgt gaacaatgtg gaggtgcaca ccgcccagac ccagacacat  540
agggaggatt acaattctac actgcgggtg gtgtccgctc tgcccatcca gcaccaggac  600
tggatgagcg gcaaggagtt taagtgcaag gtgaacaata aggatctgcc agcccccatc  660
gagaggacca tctccaagcc taagggcagc gtgagagctc cacaggtgta tgtgctgccc  720
cctccagagg aggagatgac caagaagcag gtgaccctga catgtatggt gacagacttc  780
atgcctgagg atatctacgt ggagtggacc aacaatggca agacagagct gaactataag  840
aataccgagc cagtgctgga cagcgatggc tcttacttta tgtattctaa gctgagagtg  900
gagaagaaga actgggtgga gcgcaattct tactcctgca gcgtggtgca cgagggcctg  960
cataaccacc ataccacaaa gtctttctcc aggacacccg gc                     1002

SEQ ID NO: 302          moltype = DNA  length = 1035
FEATURE                 Location/Qualifiers
```

```
source                 1..1035
                       mol_type = other DNA
                       organism = synthetic construct
SEQUENCE: 302
gagaccaggg agtgtatcta ctataacgcc aattgggagc tggagaggac aaaccagtcc  60
ggactggagc ggtgtgaggg cgagcaggac aagagactgc attgctacgc tagctggcgc  120
aattccagcg gcaccatcga gctggtgaag aagggctgtt ggctggacga tcagaactgt  180
tacgatagac aggagtgcgt ggccaccgag gagaatcctc aggtgtattt ttgctgttgc  240
gagggcaact tctgcaatga gaggttcacc cacctgccag aggctggagg accagaggtg  300
acctatgagc cacctccaac aggaggagga ggctctggag gaggaggctc cggaggagga  360
ggaacccata catgtccacc ttgcccagct ccagagctgc tgggaggccc ttccgtgttc  420
ctgtttccac ccaagccaaa ggacaccctg atgatctcta ggaccccaga ggtgacatgc  480
gtggtggtgg acgtgtccca cgaggacccc gaggtgaagt ttaactggta cgtggatggc  540
gtggaggtgc ataatgctaa gacaaagcca agggaggagc agtacaactc cacctatcgg  600
gtggtgagcg tgctgacagt gctgcaccag gattggctga acggcaagga gtataagtgt  660
aaggtgagca ataaggctct gcctgcccca atcgagaaga ccatctctaa ggctaagggc  720
cagcccagag agcctcaggt gtacacactg cctccatccc gcgaggagat gaccaagaac  780
caggtgagcc tgacatgcct ggtgaagggc ttctatccca gcgacatcgc cgtggagtgg  840
gagtctaatg gccagcctga gaacaattac aagaccacac cccctgtgct ggacagcgat  900
ggctctttct ttctgtattc taagctgacc gtggataagt cccggtggca gcagggcaac  960
gtgttttctt gttccgtgat gcatgaggcc ctgcacaatc attacacaca gaagagcctg  1020
tctctgtccc ctggc                                                   1035

SEQ ID NO: 303         moltype = DNA  length = 1035
FEATURE                Location/Qualifiers
source                 1..1035
                       mol_type = other DNA
                       organism = synthetic construct
SEQUENCE: 303
gagaccaggg agtgtatcta ctataacgcc aattgggagc tggagaggac aaaccagtcc  60
ggactggagc ggtgtgaggg cgagcaggac aagagactgc attgctacgc tagctggcgc  120
aattccagcg gcaccatcga gctggtgaag aagggctgtt ggctggacga tcagaactgt  180
tacgatagac aggagtgcgt ggccaccgag gagaatcctc aggtgtattt ttgctgttgc  240
gagggcaact tctgcaatga gaggttcacc cacctgccag aggctggagg accagaggtg  300
acctatgagc cacctccaac aggaggagga ggctctggag gaggaggctc cggaggagga  360
ggaacccata catgtccacc ttgcccagct ccagagctgc tgggaggccc ttccgtgttc  420
ctgtttccac ccaagccaaa ggacaccctg atgatctcta ggaccccaga ggtgacatgc  480
gtggtggtgg acgtgtccca cgaggacccc gaggtgaagt ttaactggta cgtggatggc  540
gtggaggtgc ataatgctaa gacaaagcca agggaggagc agtacaactc cacctatcgg  600
gtggtgagcg tgctgacagt gctgcaccag gattggctga acggcaagga gtataagtgt  660
aaggtgagca ataaggctct gcctgcccca atcgagaaga ccatctctaa ggctaagggc  720
cagcccagag agcctcaggt gtacacactg cctccatccc gcgacgagct gaccaagaac  780
caggtgagcc tgacatgcct ggtgaagggc ttctatccca gcgacatcgc cgtggagtgg  840
gagtctaatg gccagcctga gaacaattac aagaccacac cccctgtgct ggacagcgat  900
ggctctttct ttctgtattc taagctgacc gtggataagt cccggtggca gcagggcaac  960
gtgttttctt gttccgtgat gcatgaggcc ctgcacaatc attacacaca gaagagcctg  1020
tctctgtccc ctggc                                                   1035

SEQ ID NO: 304         moltype = DNA  length = 1110
FEATURE                Location/Qualifiers
source                 1..1110
                       mol_type = other DNA
                       organism = synthetic construct
SEQUENCE: 304
gagaccaggg agtgtatcta ctataacgcc aattgggagc tggagaggac aaaccagtcc  60
ggactggagc ggtgtgaggg agagcaggac aagagactgc attgctacgc tagctggcgc  120
aattccagcg gcaccatcga gctggtgaag aagggctgtt ggctggacga tcagaactgt  180
tacgatagac aggagtgcgt ggccaccgag gagaatcctc aggtgtattt ttgctgttgc  240
gagggcaact tctgcaatga gaggttcacc cacctgccag aggctggagg accagaggtg  300
acctatgagc cacctccaac aggaggagga ggctccggtg gcggcggcag cggcggcggc  360
ggctctggcg gcggcggctc cggtggtggt ggcagcggtg gtggtggctc tggtggtggc  420
ggctccggtg gtggcggcac ccatacatgt ccaccttgcc cagctccaga gctgctggga  480
ggcccttccg tgttcctgtt tccacccaag ccaaaggaca ccctgatgat ctctaggacc  540
ccagaggtga catgcgtggt ggtggacgtg tcccacgagg accccgaggt gaagtttaac  600
tggtacgtgg atggcgtgga ggtgcataat gctaagacaa agccaaggga ggagcagtac  660
aactccacct atcgggtggt gagcgtgctg acagtgctgc accaggattg gctgaacggc  720
aaggagtata agtgtaaggt gagcaataag gctctgcctg ccccaatcga gaagaccatc  780
tctaaggcta agggccagcc cagagagcct caggtgtaca cactgcctcc atcccgcgac  840
gagctgacca agaaccaggt gagcctgaca tgcctggtga agggcttcta tcccagcgac  900
atcgccgtgg agtgggagtc taatggccag cctgagaaca attacaagac cacaccccct  960
gtgctggaca gcgatggctc tttctttctg tattctaagc tgaccgtgga taagtcccgg  1020
tggcagcagg gcaacgtgtt ttcttgttcc gtgatgcatg aggccctgca caatcattac  1080
acacagaaga gcctgtctct gtcccctggc                                   1110

SEQ ID NO: 305         moltype = DNA  length = 1110
FEATURE                Location/Qualifiers
source                 1..1110
                       mol_type = other DNA
                       organism = synthetic construct
```

SEQUENCE: 305
gagaccaggg agtgtatcta ctataacgcc aattgggagc tggagaggac aaaccagtcc 60
ggactggagc ggtgtgaggg agagcaggac aagagactgc attgctacgc tagctggcgc 120
aattccagcg gcaccatcga gctggtgaag aagggctgtt ggctggacga tcagaactgt 180
tacgatagac aggagtgcgt ggccaccgag gagaatcctc aggtgtattt ttgctgttgc 240
gagggcaact tctgcaatga gaggttcacc cacctgccag aggctggagg accagaggtg 300
acctatgagc cacctccaac aggaggagga ggctccggtg gcggcggcag cggcggcggc 360
ggctctggcg gcggcggctc cggtggtggt ggcagcggtg gcggcggctc tggaggagga 420
ggctccggcg gaggaggacc atgcccccct tgcaagtgtc ctgctccaaa cctgctggga 480
ggacctagcg tgttcatctt tccacccaag atcaaggacg tgctgatgat ctccctgagc 540
cctatcgtga cctgcgtggt ggtggacgtg tctgaggacg atccagatgt gcagatctcc 600
tggttcgtga acaatgtgga ggtgcacacc gcccagaccc agacacatag ggaggattac 660
aattccacac tgcgggtggt gtccgccctg cctatccagc accaggactg gatgtctggc 720
aaggagttta agtgcaaggt gaacaataag gatctgcccg cccctatcga gaggaccatc 780
agcaagccaa agggctctgt gagagctccc caggtgtatg tgctgcctcc acccgaggag 840
gagatgacca agaagcaggt gaccctgaca tgtatggtga cagacttcat gccagaggat 900
atctacgtgg agtggaccaa caatggcaag acagagctga actataagaa taccgagccc 960
gtgctggaca gcgatggctc ttactttatg tattccaagc tgagagtgga gaagaagaac 1020
tgggtggagc gcaattctta ctcctgcagc gtggtgcacg agggcctgca taaccaccat 1080
accacaaagt ctttctccag gacaccaggc 1110

SEQ ID NO: 306 moltype = DNA length = 1002
FEATURE Location/Qualifiers
source 1..1002
mol_type = other DNA
organism = synthetic construct
SEQUENCE: 306
gagaccaggg agtgtatcta ctataacgcc aattgggagc tggagaggac aaaccagtcc 60
ggactggagc ggtgtgaggg agagcaggac aagagactgc attgctacgc tagctggcgc 120
aattccagcg gcaccatcga gctggtgaag aagggctgtt ggctggacga ttggaactgt 180
tacgatagac aggagtgcgt ggccaccgag gagaatcctc aggtgtattt ttgctgttgc 240
gagggcaact tctgcaatga gaggttcacc cacctgccag aggctggagg accagaggtg 300
acctatgagc cacctccaac aggaggagga acccatacat gtccaccttg cccagctcca 360
gagctgctgg gaggcccttc cgtgttcctg tttccaccca agccaaagga caccctgatg 420
atctctagga ccccagaggt gacatgcgtg gtggtggacg tgtcccacga ggaccccgag 480
gtgaagttta actggtacgt ggatggcgtg gaggtgcata atgctaagac aaagccaagg 540
gaggagcagt acaactccac ctatcgggtg gtgagcgtgc tgacagtgct gcaccaggat 600
tggctgaacg gcaaggagta taagtgtaag gtgagcaata aggctctgcc tgccccaatc 660
gagaagacca tctctaaggc taagggccag cccagagagc ctcaggtgta cacactgcct 720
ccatcccgcg aggagatgac caagaaccag gtgagcctga catgcctggt gaagggcttc 780
tatcccagcg acatcgccgt ggagtgggag tctaatggcc agcctgagaa caattacaag 840
accacacccc ctgtgctgga cagcgatggc tctttctttc tgtattctaa gctgaccgtg 900
gataagtccc ggtggcagca gggcaacgtg ttttcttgtt ccgtgatgca tgaggccctg 960
cacaatcatt acacacagaa gagcctgtct ctgtcccctg gc 1002

SEQ ID NO: 307 moltype = DNA length = 1002
FEATURE Location/Qualifiers
source 1..1002
mol_type = other DNA
organism = synthetic construct
SEQUENCE: 307
gagaccaggg agtgtatcta ctataacgcc aattgggagc tggagaggac aaaccagtcc 60
ggactggagc ggtgtgaggg agagcaggac aagagactgc attgctacgc tagctggcgc 120
aattccagcg gcaccatcga gctggtgaag aagggctgtt ggctggacga ttggaactgt 180
tacgatagac aggagtgcgt ggccaccgag gagaatcctc aggtgtattt ttgctgttgc 240
gagggcaact tctgcaatga gaggttcacc cacctgccag aggctggagg accagaggtg 300
acctatgagc cacctccaac aggaggagga acccatacat gtccaccttg cccagctcca 360
gagctgctgg gaggcccttc cgtgttcctg tttccaccca agccaaagga caccctgatg 420
atctctagga ccccagaggt gacatgcgtg gtggtggacg tgtcccacga ggaccccgag 480
gtgaagttta actggtacgt ggatggcgtg gaggtgcata atgctaagac aaagccaagg 540
gaggagcagt acaactccac ctatcgggtg gtgagcgtgc tgacagtgct gcaccaggat 600
tggctgaacg gcaaggagta taagtgtaag gtgagcaata aggctctgcc tgccccaatc 660
gagaagacca tctctaaggc taagggccag cccagagagc ctcaggtgta cacactgcct 720
ccatcccgcg acgagctgac caagaaccag gtgagcctga catgcctggt gaagggcttc 780
tatcccagcg acatcgccgt ggagtgggag tctaatggcc agcctgagaa caattacaag 840
accacacccc ctgtgctgga cagcgatggc tctttctttc tgtattctaa gctgaccgtg 900
gataagtccc ggtggcagca gggcaacgtg ttttcttgtt ccgtgatgca tgaggccctg 960
cacaatcatt acacacagaa gagcctgtct ctgtcccctg gc 1002

SEQ ID NO: 308 moltype = DNA length = 1002
FEATURE Location/Qualifiers
source 1..1002
mol_type = other DNA
organism = synthetic construct
SEQUENCE: 308
gagaccaggg agtgtatcta ctataacgcc aattgggagc tggagaggac aaaccagtcc 60
ggactggagc ggtgtgaggg agagcaggac aagagactgc attgctacgc tagctggcgc 120
aattccagcg gcaccatcga gctggtgaag aagggctgtt ggctggacga ttggaactgt 180
tacgatagac aggagtgcgt ggccaccgag gagaatcctc aggtgtattt ttgctgttgc 240

-continued

```
gagggcaact tctgcaatga gaggttcacc cacctgccag aggctggagg accagaggtg  300
acctatgagc caccacctac cggaggagga ccatgcccac catgcaagtg tccagctcct  360
aacctgctgg gaggaccatc cgtgttcatc tttcctccaa agatcaagga cgtgctgatg  420
atctccctga gccccatcgt gacatgcgtg gtggtggacg tgagcgagga cgatcctgat  480
gtgcagatct cttggttcgt gaacaatgtg gaggtgcaca ccgcccagac ccagacacat  540
agggaggatt acaattctac actgcgggtg gtgtccgctc tgcccatcca gcaccaggac  600
tggatgagcg gcaaggagtt taagtgcaag gtgaacaata aggatctgcc agccccccatc  660
gagaggacca tctccaagcc taagggcagc gtgagagctc cacaggtgta tgtgctgccc  720
cctccagagg aggagatgac caagaagcag gtgaccctga catgtatggt gacagacttc  780
atgcctgagg atatctacgt ggagtggacc aacaatggca agacagagct gaactataag  840
aataccgagc cagtgctgga cagcgatggc tcttacttta tgtattctaa gctgagagtg  900
gagaagaaga actgggtgga gcgcaattct tactcctgca gcgtggtgca cgagggcctg  960
cataaccacc ataccacaaa gtctttctcc aggacacccg gc                   1002

SEQ ID NO: 309         moltype = DNA  length = 1035
FEATURE                Location/Qualifiers
source                 1..1035
                       mol_type = other DNA
                       organism = synthetic construct
SEQUENCE: 309
gagaccaggg agtgtatcta ctataacgcc aattgggagc tggagaggac aaaccagtcc  60
ggactggagc ggtgtgaggg cgagcaggac aagagactgc attgctacgc tagctggcgc  120
aattccagcg gcaccatcga gctggtgaag aagggctgtt ggctggacga ttggaactgt  180
tacgatagac aggagtgcgt ggccaccgag gagaatcctc aggtgtattt ttgctgttgc  240
gagggcaact tctgcaatga gaggttcacc cacctgccag aggctggagg accagaggtg  300
acctatgagc cacctccaac aggaggagga ggctctggag gaggaggctc cggaggagga  360
ggaacccata catgtccacc ttgcccagct ccagagctgc tgggaggccc ttccgtgttc  420
ctgtttccac ccaagccaaa ggacaccctg atgatctcta ggaccccaga ggtgacatgc  480
gtggtggtgg acgtgtccca cgaggacccc gaggtgaagt ttaactggta cgtggatggc  540
gtggaggtgc ataatgctaa gacaaagcca agggaggagc agtacaactc cacctatcgg  600
gtggtgagcg tgctgacagt gctgcaccag gattggctga acggcaagga gtataagtgt  660
aaggtgagca ataaggctct gcctgcccca atcgagaaga ccatctctaa ggctaagggc  720
cagcccagag agcctcaggt gtacacactg cctccatccc gcgaggagat gaccaagaac  780
caggtgagcc tgacatgcct ggtgaagggc ttctatccca gcgacatcgc cgtggagtgg  840
gagtctaatg gccagcctga gaacaattac aagaccacac cccctgtgct ggacagcgat  900
ggctctttct ttctgtattc taagctgacc gtggataagt cccggtggca gcagggcaac  960
gtgttttctt gttccgtgat gcatgaggcc ctgcacaatc attacacaca gaagagcctg  1020
tctctgtccc ctggc                                                  1035

SEQ ID NO: 310         moltype = DNA  length = 1035
FEATURE                Location/Qualifiers
source                 1..1035
                       mol_type = other DNA
                       organism = synthetic construct
SEQUENCE: 310
gagaccaggg agtgtatcta ctataacgcc aattgggagc tggagaggac aaaccagtcc  60
ggactggagc ggtgtgaggg cgagcaggac aagagactgc attgctacgc tagctggcgc  120
aattccagcg gcaccatcga gctggtgaag aagggctgtt ggctggacga ttggaactgt  180
tacgatagac aggagtgcgt ggccaccgag gagaatcctc aggtgtattt ttgctgttgc  240
gagggcaact tctgcaatga gaggttcacc cacctgccag aggctggagg accagaggtg  300
acctatgagc cacctccaac aggaggagga ggctctggag gaggaggctc cggaggagga  360
ggaacccata catgtccacc ttgcccagct ccagagctgc tgggaggccc ttccgtgttc  420
ctgtttccac ccaagccaaa ggacaccctg atgatctcta ggaccccaga ggtgacatgc  480
gtggtggtgg acgtgtccca cgaggacccc gaggtgaagt ttaactggta cgtggatggc  540
gtggaggtgc ataatgctaa gacaaagcca agggaggagc agtacaactc cacctatcgg  600
gtggtgagcg tgctgacagt gctgcaccag gattggctga acggcaagga gtataagtgt  660
aaggtgagca ataaggctct gcctgcccca atcgagaaga ccatctctaa ggctaagggc  720
cagcccagag agcctcaggt gtacacactg cctccatccc gcgacgagct gaccaagaac  780
caggtgagcc tgacatgcct ggtgaagggc ttctatccca gcgacatcgc cgtggagtgg  840
gagtctaatg gccagcctga gaacaattac aagaccacac cccctgtgct ggacagcgat  900
ggctctttct ttctgtattc taagctgacc gtggataagt cccggtggca gcagggcaac  960
gtgttttctt gttccgtgat gcatgaggcc ctgcacaatc attacacaca gaagagcctg  1020
tctctgtccc ctggc                                                  1035

SEQ ID NO: 311         moltype = DNA  length = 1110
FEATURE                Location/Qualifiers
source                 1..1110
                       mol_type = other DNA
                       organism = synthetic construct
SEQUENCE: 311
gagaccaggg agtgtatcta ctataacgcc aattgggagc tggagaggac aaaccagtcc  60
ggactggagc ggtgtgaggg agagcaggac aagagactgc attgctacgc tagctggcgc  120
aattccagcg gcaccatcga gctggtgaag aagggctgtt ggctggacga ttggaactgt  180
tacgatagac aggagtgcgt ggccaccgag gagaatcctc aggtgtattt ttgctgttgc  240
gagggcaact tctgcaatga gaggttcacc cacctgccag aggctggagg accagaggtg  300
acctatgagc cacctccaac aggaggagga ggctccggtg gcggcggcag cggcggcggc  360
ggctctggcg gcggcggctc cggtggtggt ggcagcggtg gtggtggctc tggtggtggc  420
ggctccggtg gtggcggcac ccatacatgt ccaccttgcc cagctccaga gctgctggga  480
ggcccttccg tgttcctgtt tccacccaag ccaaaggaca ccctgatgat ctctaggacc  540
```

-continued

```
ccagaggtga catgcgtggt ggtggacgtg tcccacgagg accccgaggt gaagtttaac  600
tggtacgtgg atggcgtgga ggtgcataat gctaagacaa agccaaggga ggagcagtac  660
aactccacct atcgggtggt gagcgtgctg acagtgctgc accaggattg gctgaacggc  720
aaggagtata agtgtaaggt gagcaataag gctctgcctg ccccaatcga gaagaccatc  780
tctaaggcta agggccagcc cagagagcct caggtgtaca cactgcctcc atcccgcgac  840
gagctgacca agaaccaggt gagcctgaca tgcctggtga agggcttcta tcccagcgac  900
atcgccgtgg agtgggagtc taatggccag cctgagaaca attacaagac cacacccccct  960
gtgctggaca gcgatggctc tttctttctg tattctaagc tgaccgtgga taagtcccgg  1020
tggcagcagg gcaacgtgtt ttcttgttcc gtgatgcatg aggccctgca caatcattac  1080
acacagaaga gcctgtctct gtcccctggc                                   1110

SEQ ID NO: 312          moltype = DNA  length = 1110
FEATURE                 Location/Qualifiers
source                  1..1110
                        mol_type = other DNA
                        organism = synthetic construct
SEQUENCE: 312
gagaccaggg agtgtatcta ctataacgcc aattgggagc tggagaggac aaaccagtcc  60
ggactggagc ggtgtgaggg agagcaggac aagagactgc attgctacgc tagctggcgc  120
aattccagcg gcaccatcga gctggtgaag aagggctgtt ggctggacga ttggaactgt  180
tacgatagac aggagtgcgt ggccaccgag gagaatcctc aggtgtattt ttgctgttgc  240
gagggcaact tctgcaatga gaggttcacc cacctgccag aggctggagg accagaggtg  300
acctatgagc cacctccaac aggaggagga ggctccggtg gcggcggcag cggcggcggc  360
ggctctggcg gcggcggctc cggtggtggt ggcagcggtg gcggcggctc tggaggagga  420
ggctccggcg gaggaggacc atgcccccct tgcaagtgtc ctgctccaaa cctgctggga  480
ggacctagcg tgttcatctt tccacccaag atcaaggacg tgctgatgat ctccctgagc  540
cctatcgtga cctgcgtggt ggtggacgtg tctgaggacg atccagatgt gcagatctcc  600
tggttcgtga acaatgtgga ggtgcacacc gcccagaccc agacacatag ggaggattac  660
aattccacac tgcgggtggt gtccgccctg cctatccagc accaggactg gatgtctggc  720
aaggagttta agtgcaaggt gaacaataag gatctgcccg cccctatcga gaggaccatc  780
agcaagccaa agggctctgt gagagctccc caggtgtatg tgctgcctcc acccgaggag  840
gagatgacca agaagcaggt gaccctgaca tgtatggtga cagacttcat gccagaggat  900
atctacgtgg agtggaccaa caatggcaag acagagctga actataagaa taccgagccc  960
gtgctggaca gcgatggctc ttactttatg tattccaagc tgagagtgga gaagaagaac  1020
tgggtggagc gcaattctta ctcctgcagc gtggtgcacg agggcctgca taaccaccat  1080
accacaaagt ctttctccag gacaccaggc                                   1110

SEQ ID NO: 313          moltype = DNA  length = 1035
FEATURE                 Location/Qualifiers
source                  1..1035
                        mol_type = other DNA
                        organism = synthetic construct
SEQUENCE: 313
gagaccaggg agtgtatcta ctataacgcc aattgggagc tggagaggac aaaccagtcc  60
ggactggagc ggtgtgagga cgagcaggac aagagactgc attgctacgc tagctggcgc  120
aattccagcg gcaccatcga gctggtgaag aagggctgtt ggctggacga tttcaactgt  180
tacgatagac aggagtgcgt ggccaccgag gagaatcctc aggtgtattt ttgctgttgc  240
gagggcaact tctgcaatga gaggttcacc cacctgccag aggctggagg accagaggtg  300
acctatgagc cacctccaac aggaggagga ggctctggag gaggaggctc cggaggagga  360
ggaacccata catgtccacc ttgcccagct ccagagctgc tgggaggccc ttccgtgttc  420
ctgtttccac ccaagccaaa ggacaccctg atgatctcta ggaccccaga ggtgacatgc  480
gtggtggtgg acgtgtccca cgaggacccc gaggtgaagt ttaactggta cgtggatggc  540
gtggaggtgc ataatgctaa gacaaagcca agggaggagc agtacaactc cacctatcgg  600
gtggtgagcg tgctgacagt gctgcaccag gattggctga acggcaagga gtataagtgt  660
aaggtgagca ataaggctct gcctgcccca atcgagaaga ccatctctaa ggctaagggc  720
cagcccagag agcctcaggt gtacacactg cctccatccc gcgacgagct gaccaagaac  780
caggtgagcc tgacatgcct ggtgaagggc ttctatccca gcgacatcgc cgtggagtgg  840
gagtctaatg gccagcctga gaacaattac aagaccacac cccctgtgct ggacagcgat  900
ggctctttct ttctgtattc taagctgacc gtggataagt cccggtggca gcagggcaac  960
gtgttttctt gttccgtgat gcatgaggcc ctgcacaatc attacacaca gaagagcctg  1020
tctctgtccc ctggc                                                   1035

SEQ ID NO: 314          moltype = DNA  length = 1011
FEATURE                 Location/Qualifiers
source                  1..1011
                        mol_type = other DNA
                        organism = synthetic construct
SEQUENCE: 314
gagaccaggg agtgtatcta ctataacgcc aattgggagc tggagaggac aaaccagtcc  60
ggactggagc ggtgtgaggg cgagcaggac aagagactgc attgctacgc tagctggcgc  120
aattccagcg gcaccatcga gctggtgaag aagggctgtt ggctggacga taagaactgt  180
tacgatagac aggagtgcgt ggccaccgag gagaatcctc aggtgtattt ttgctgttgc  240
gagggcaact tctgcaatga gaggttcacc cacctgccag aggctggagg accagaggtg  300
acctatgagc cacctccaac aggaggagga ggctctggaa cccatacatg tccaccttgc  360
ccagctccag agctgctggg aggcccttcc gtgttcctgt ttccacccaa gccaaaggac  420
accctgatga tctctaggac cccagaggtg acatgcgtgg tggtggacgt gtcccacgag  480
gaccccgagg tgaagtttaa ctggtacgtg gatggcgtgg aggtgcataa tgctaagaca  540
aagccaaggg aggagcagta caactccacc tatcgggtgg tgagcgtgct gacagtgctg  600
caccaggatt ggctgaacgg caaggagtat aagtgtaagg tgagcaataa ggctctgcct  660
```

```
gccccaatcg agaagaccat ctctaaggct aagggccagc ccagagagcc tcaggtgtac  720
acactgcctc catcccgcga cgagctgacc aagaaccagg tgagcctgac atgcctggtg  780
aagggcttct atcccagcga catcgccgtg gagtgggagt ctaatggcca gcctgagaac  840
aattacaaga ccacaccccc tgtgctggac agcgatggct ctttctttct gtattctaag  900
ctgaccgtgg ataagtcccg gtggcagcag ggcaacgtgt tttcttgttc cgtgatgcat  960
gaggccctgc acaatcatta cacacagaag agcctgtctc tgtcccctgg c           1011

SEQ ID NO: 315         moltype = DNA  length = 1023
FEATURE                Location/Qualifiers
source                 1..1023
                       mol_type = other DNA
                       organism = synthetic construct
SEQUENCE: 315
gagaccaggg agtgtatcta ctataacgcc aattgggagc tggagaggac aaaccagtcc  60
ggactggagc ggtgtgaggg cgagcaggac aagagactgc attgctacgc tagctggcgc  120
aattccagcg gcaccatcga gctggtgaag aagggctgtt ggctggacga taagaactgt  180
tacgatagac aggagtgcgt ggccaccgag gagaatcctc aggtgtattt ttgctgttgc  240
gagggcaact tctgcaatga gaggttcacc cacctgccag aggctggagg accagaggtg  300
acctatgagc cacctccaac aggaggagga ggctctggag gaggaggctc cacccataca  360
tgtccacctt gcccagctcc agagctgctg ggaggccctt ccgtgttcct gtttccaccc  420
aagccaaagg acaccctgat gatctctagg accccagagg tgacatgcgt ggtggtggac  480
gtgtcccacg aggaccccga ggtgaagttt aactggtacg tggatggcgt ggaggtgcat  540
aatgctaaga caaagccaag ggaggagcag tacaactcca cctatcgggt ggtgagcgtg  600
ctgacagtgc tgcaccagga ttggctgaac ggcaaggagt ataagtgtaa ggtgagcaat  660
aaggctctgc ctgccccaat cgagaagacc atctctaagg ctaagggcca gcccagagag  720
cctcaggtgt acacactgcc tccatcccgc gacgagctga ccaagaacca ggtgagcctg  780
acatgcctgg tgaagggctt ctatcccagc gacatcgccg tggagtggga gtctaatggc  840
cagcctgaga acaattacaa gaccacaccc cctgtgctgg acagcgatgg ctctttcttt  900
ctgtattcta agctgaccgt ggataagtcc cggtggcagc agggcaacgt gttttcttgt  960
tccgtgatgc atgaggccct gcacaatcat tacacacaga agagcctgtc tctgtcccct  1020
ggc                                                               1023

SEQ ID NO: 316         moltype = DNA  length = 1050
FEATURE                Location/Qualifiers
source                 1..1050
                       mol_type = other DNA
                       organism = synthetic construct
SEQUENCE: 316
gagaccaggg agtgtatcta ctataacgcc aattgggagc tggagaggac aaaccagtcc  60
ggactggagc ggtgtgaggg cgagcaggac aagagactgc attgctacgc tagctggcgc  120
aattccagcg gcaccatcga gctggtgaag aagggctgtt ggctggacga taagaactgt  180
tacgatagac aggagtgcgt ggccaccgag gagaatcctc aggtgtattt ttgctgttgc  240
gagggcaact tctgcaatga gaggttcacc cacctgccag aggctggagg accagaggtg  300
acctatgagc cacctccaac aggaggaggc ggctccggcg gcggaggctc tggaggagga  360
ggctccggag gaggaggaac ccatacatgt ccaccttgcc cagctccaga gctgctggga  420
ggcccttccg tgttcctgtt tccacccaag ccaaaggaca ccctgatgat ctctaggacc  480
ccagaggtga catgcgtggt ggtggacgtg tcccacgagg accccgaggt gaagtttaac  540
tggtacgtgg atggcgtgga ggtgcataat gctaagacaa agccaaggga ggagcagtac  600
aactccacct atcgggtggt gagcgtgctg acagtgctgc accaggattg gctgaacggc  660
aaggagtata agtgtaaggt gagcaataag gctctgcctg ccccaatcga gaagaccatc  720
tctaaggcta agggccagcc cagagagcct caggtgtaca cactgcctcc atcccgcgac  780
gagctgacca agaaccaggt gagcctgaca tgcctggtga agggcttcta tcccagcgac  840
atcgccgtgg agtgggagtc taatggccag cctgagaaca attacaagac cacaccccct  900
gtgctggaca gcgatggctc tttctttctg tattctaagc tgaccgtgga taagtcccgg  960
tggcagcagg gcaacgtgtt ttcttgttcc gtgatgcatg aggccctgca caatcattac  1020
acacagaaga gcctgtctct gtcccctggc                                  1050

SEQ ID NO: 317         moltype = DNA  length = 1110
FEATURE                Location/Qualifiers
source                 1..1110
                       mol_type = other DNA
                       organism = synthetic construct
SEQUENCE: 317
gagaccaggg agtgtatcta ctataacgcc aattgggagc tggagaggac aaaccagtcc  60
ggactggagc ggtgtgaggg cgagcaggac aagagactgc attgctacgc tagctggcgc  120
aattccagcg gcaccatcga gctggtgaag aagggctgtt ggctggacga taagaactgt  180
tacgatagac aggagtgcgt ggccaccgag gagaatcctc aggtgtattt ttgctgttgc  240
gagggcaact tctgcaatga gaggttcacc cacctgccag aggctggagg accagaggtg  300
acctatgagc cacctccaac aggaggaggc ggctccggcg gcggcggctc cggcggcggc  360
ggctccggcg gcggcggctc cggcggcggc ggctccggcg gcggaggctc tggaggagga  420
ggctccggag gaggaggaac ccatacatgt ccaccttgcc cagctccaga gctgctggga  480
ggcccttccg tgttcctgtt tccacccaag ccaaaggaca ccctgatgat ctctaggacc  540
ccagaggtga catgcgtggt ggtggacgtg tcccacgagg accccgaggt gaagtttaac  600
tggtacgtgg atggcgtgga ggtgcataat gctaagacaa agccaaggga ggagcagtac  660
aactccacct atcgggtggt gagcgtgctg acagtgctgc accaggattg gctgaacggc  720
aaggagtata agtgtaaggt gagcaataag gctctgcctg ccccaatcga gaagaccatc  780
tctaaggcta agggccagcc cagagagcct caggtgtaca cactgcctcc atcccgcgac  840
gagctgacca agaaccaggt gagcctgaca tgcctggtga agggcttcta tcccagcgac  900
atcgccgtgg agtgggagtc taatggccag cctgagaaca attacaagac cacaccccct  960
```

-continued

```
gtgctggaca gcgatggctc tttctttctg tattctaagc tgaccgtgga taagtcccgg  1020
tggcagcagg gcaacgtgtt ttcttgttcc gtgatgcatg aggccctgca caatcattac  1080
acacagaaga gcctgtctct gtcccctggc                                   1110

SEQ ID NO: 318         moltype = DNA  length = 1011
FEATURE                Location/Qualifiers
source                 1..1011
                       mol_type = other DNA
                       organism = synthetic construct
SEQUENCE: 318
gagaccaggg agtgtatcta ctataacgcc aattgggagc tggagaggac aaaccagtcc  60
ggactggagc ggtgtgaggg agagcaggac aagagactgc attgctacgc tagctggcgc  120
aattccagcg gcaccatcga gctggtgaag aagggctgtt ggctggacga tgagaactgt  180
tacgatagac aggagtgcgt ggccaccgag gagaatcctc aggtgtattt ttgctgttgc  240
gagggcaact tctgcaatga gaggttcacc cacctgccag aggctggagg accagaggtg  300
acctatgagc cacctccaac aggaggaggc ggctccggaa cccatacatg tccaccttgc  360
ccagctccag agctgctggg aggcccttcc gtgttcctgt ttccacccaa gccaaaggac  420
accctgatga tctctaggac cccagaggtg acatgcgtgg tggtggacgt gtcccacgag  480
gaccccgagg tgaagtttaa ctggtacgtg gatggcgtgg aggtgcataa tgctaagaca  540
aagccaaggg aggagcagta caactccacc tatcgggtgg tgagcgtgct gacagtgctg  600
caccaggatt ggctgaacgg caaggagtat aagtgtaagg tgagcaataa ggctctgcct  660
gccccaatcg agaagaccat ctctaaggct aagggccagc ccagagagcc tcaggtgtac  720
acactgcctc catcccgcga cgagctgacc aagaaccagg tgagcctgac atgcctggtg  780
aagggcttct atcccagcga catcgccgtg gagtgggagt ctaatggcca gcctgagaac  840
aattacaaga ccacaccccc tgtgctggac agcgatggct ctttctttct gtattctaag  900
ctgaccgtgg ataagtcccg gtggcagcag ggcaacgtgt tttcttgttc cgtgatgcat  960
gaggccctgc acaatcatta cacacagaag agcctgtctc tgtcccctgg c           1011

SEQ ID NO: 319         moltype = DNA  length = 1023
FEATURE                Location/Qualifiers
source                 1..1023
                       mol_type = other DNA
                       organism = synthetic construct
SEQUENCE: 319
gagaccaggg agtgtatcta ctataacgcc aattgggagc tggagaggac aaaccagtcc  60
ggactggagc ggtgtgaggg agagcaggac aagagactgc attgctacgc tagctggcgc  120
aattccagcg gcaccatcga gctggtgaag aagggctgtt ggctggacga tgagaactgt  180
tacgatagac aggagtgcgt ggccaccgag gagaatcctc aggtgtattt ttgctgttgc  240
gagggcaact tctgcaatga gaggttcacc cacctgccag aggctggagg accagaggtg  300
acctatgagc cacctccaac aggaggaggc ggctccggag gcggcggctc cacccataca  360
tgtccacctt gcccagctcc agagctgctg ggaggccctt ccgtgttcct gtttccaccc  420
aagccaaagg acaccctgat gatctctagg accccagagg tgacatgcgt ggtggtggac  480
gtgtcccacg aggaccccga ggtgaagttt aactggtacg tggatggcgt ggaggtgcat  540
aatgctaaga caaagccaag ggaggagcag tacaactcca cctatcgggt ggtgagcgtg  600
ctgacagtgc tgcaccagga ttggctgaac ggcaaggagt ataagtgtaa ggtgagcaat  660
aaggctctgc ctgccccaat cgagaagacc atctctaagg ctaagggcca gcccagagag  720
cctcaggtgt acacactgcc tccatcccgc gacgagctga ccaagaacca ggtgagcctg  780
acatgcctgg tgaagggctt ctatcccagc gacatcgccg tggagtggga gtctaatggc  840
cagcctgaga acaattacaa gaccacaccc cctgtgctgg acagcgatgg ctctttcttt  900
ctgtattcta agctgaccgt ggataagtcc cggtggcagc agggcaacgt gttttcttgt  960
tccgtgatgc atgaggccct gcacaatcat tacacacaga agagcctgtc tctgtcccct  1020
ggc                                                                1023

SEQ ID NO: 320         moltype = DNA  length = 1044
FEATURE                Location/Qualifiers
source                 1..1044
                       mol_type = other DNA
                       organism = synthetic construct
SEQUENCE: 320
gagaccaggg agtgtatcta ctataacgcc aattgggagc tggagaggac aaaccagtcc  60
ggactggagc ggtgtgaggg cgagcaggac aagagactgc attgctacgc tagctggcgc  120
aattccagcg gcaccatcga gctggtgaag aagggctgtt ggctggacga tgagaactgt  180
tacgatagac aggagtgcgt ggccaccgag gagaatcctc aggtgtattt ttgctgttgc  240
gagggcaact tctgcaatga gaggttcacc cacctgccag aggctggagg accagaggtg  300
acctatgagc cacctcccac cgccccaaca ggaggaggag gctctggagg aggaggctcc  360
ggaggaggag gaacccatac atgtccacct tgcccagctc cagagctgct gggaggccct  420
tccgtgttcc tgtttccacc caagccaaag gacaccctga tgatctctag gaccccagag  480
gtgacatgcg tggtggtgga cgtgtcccac gaggaccccg aggtgaagtt taactggtac  540
gtggatggcg tggaggtgca taatgctaag acaaagccaa gggaggagca gtacaactcc  600
acctatcggg tggtgagcgt gctgacagtg ctgcaccagg attggctgaa cggcaaggag  660
tataagtgta aggtgagcaa taaggctctg cctgccccaa tcgagaagac catctctaag  720
gctaagggcc agcccagaga gcctcaggtg tacacactgc ctccatcccg cgacgagctg  780
accaagaacc aggtgagcct gacatgcctg gtgaagggct tctatcccag cgacatcgcc  840
gtggagtggg agtctaatgg ccagcctgag aacaattaca agaccacacc ccctgtgctg  900
gacagcgatg gctctttctt tctgtattct aagctgaccg tggataagtc ccggtggcag  960
cagggcaacg tgttttcttg ttccgtgatg catgaggccc tgcacaatca ttacacacag  1020
aagagcctgt ctctgtcccc tggc                                         1044

SEQ ID NO: 321         moltype = DNA  length = 1035
```

-continued

```
FEATURE                Location/Qualifiers
source                 1..1035
                       mol_type = other DNA
                       organism = synthetic construct
SEQUENCE: 321
gagaccaggg agtgtatcta ctataacgcc aattgggagc tggagaggac aaaccagtcc  60
ggactggagc ggtgtgaggg cgagcaggac aagagactgc attgctacgc tagctggcgc  120
aattccagcg gcaccatcga gctggtgaag aagggctgtt ggctggacga taacaactgt  180
tacgatagac aggagtgcgt ggccaccgag gagaatcctc aggtgtattt ttgctgttgc  240
gagggcaact tctgcaatga gaggttcacc cacctgccag aggctggagg accagaggtg  300
acctatgagc cacctccaac aggaggagga ggctctggag gaggaggctc cggaggagga  360
ggaacccata catgtccacc ttgcccagct ccagagctgc tgggaggccc ttccgtgttc  420
ctgtttccac ccaagccaaa ggacaccctg atgatctcta ggaccccaga ggtgacatgc  480
gtggtggtgg acgtgtccca cgaggacccc gaggtgaagt ttaactggta cgtggatggc  540
gtggaggtgc ataatgctaa gacaaagcca agggaggagc agtacaactc cacctatcgg  600
gtggtgagcg tgctgacagt gctgcaccag gattggctga acggcaagga gtataagtgt  660
aaggtgagca ataaggctct gcctgcccca atcgagaaga ccatctctaa ggctaagggc  720
cagcccagag agcctcaggt gtacacactg cctccatccc gcgacgagct gaccaagaac  780
caggtgagcc tgacatgcct ggtgaagggc ttctatccca gcgacatcgc cgtggagtgg  840
gagtctaatg gccagcctga gaacaattac aagaccacac cccctgtgct ggacagcgat  900
ggctctttct ttctgtattc taagctgacc gtggataagt cccggtggca gcagggcaac  960
gtgttttctt gttccgtgat gcatgaggcc ctgcacaatc attacacaca gaagagcctg  1020
tctctgtccc ctggc                                                   1035

SEQ ID NO: 322         moltype = DNA  length = 1035
FEATURE                Location/Qualifiers
source                 1..1035
                       mol_type = other DNA
                       organism = synthetic construct
SEQUENCE: 322
gagaccaggg agtgtatcta ctataacgcc aattgggagc tggagaggac aaaccagtcc  60
ggactggagc ggtgtgaggg cgagcaggac aagagactgc attgctacgc tagctggcgc  120
aattccagcg gcaccatcga gctggtgaag aagggctgtt ggctggacga taggaactgt  180
tacgatagac aggagtgcgt ggccaccgag gagaatcctc aggtgtattt ttgctgttgc  240
gagggcaact tctgcaatga gaggttcacc cacctgccag aggctggagg accagaggtg  300
acctatgagc cacctccaac aggaggagga ggctctggag gaggaggctc cggaggagga  360
ggaacccata catgtccacc ttgcccagct ccagagctgc tgggaggccc ttccgtgttc  420
ctgtttccac ccaagccaaa ggacaccctg atgatctcta ggaccccaga ggtgacatgc  480
gtggtggtgg acgtgtccca cgaggacccc gaggtgaagt ttaactggta cgtggatggc  540
gtggaggtgc ataatgctaa gacaaagcca agggaggagc agtacaactc cacctatcgg  600
gtggtgagcg tgctgacagt gctgcaccag gattggctga acggcaagga gtataagtgt  660
aaggtgagca ataaggctct gcctgcccca atcgagaaga ccatctctaa ggctaagggc  720
cagcccagag agcctcaggt gtacacactg cctccatccc gcgacgagct gaccaagaac  780
caggtgagcc tgacatgcct ggtgaagggc ttctatccca gcgacatcgc cgtggagtgg  840
gagtctaatg gccagcctga gaacaattac aagaccacac cccctgtgct ggacagcgat  900
ggctctttct ttctgtattc taagctgacc gtggataagt cccggtggca gcagggcaac  960
gtgttttctt gttccgtgat gcatgaggcc ctgcacaatc attacacaca gaagagcctg  1020
tctctgtccc ctggc                                                   1035

SEQ ID NO: 323         moltype = DNA  length = 1035
FEATURE                Location/Qualifiers
source                 1..1035
                       mol_type = other DNA
                       organism = synthetic construct
SEQUENCE: 323
gagaccaggg agtgtatcta ctataacgcc aattgggagc tggagaggac aaaccagtcc  60
ggactggagc ggtgtgaggg cgagcaggac aagagactgc attgctacgc tagctggcgc  120
aattccagcg gcaccatcga gctggtgaag aagggctgtt ggctggacga tcacaactgt  180
tacgatagac aggagtgcgt ggccaccgag gagaatcctc aggtgtattt ttgctgttgc  240
gagggcaact tctgcaatga gaggttcacc cacctgccag aggctggagg accagaggtg  300
acctatgagc cacctccaac aggaggagga ggctctggag gaggaggctc cggaggagga  360
ggaacccata catgtccacc ttgcccagct ccagagctgc tgggaggccc ttccgtgttc  420
ctgtttccac ccaagccaaa ggacaccctg atgatctcta ggaccccaga ggtgacatgc  480
gtggtggtgg acgtgtccca cgaggacccc gaggtgaagt ttaactggta cgtggatggc  540
gtggaggtgc ataatgctaa gacaaagcca agggaggagc agtacaactc cacctatcgg  600
gtggtgagcg tgctgacagt gctgcaccag gattggctga acggcaagga gtataagtgt  660
aaggtgagca ataaggctct gcctgcccca atcgagaaga ccatctctaa ggctaagggc  720
cagcccagag agcctcaggt gtacacactg cctccatccc gcgacgagct gaccaagaac  780
caggtgagcc tgacatgcct ggtgaagggc ttctatccca gcgacatcgc cgtggagtgg  840
gagtctaatg gccagcctga gaacaattac aagaccacac cccctgtgct ggacagcgat  900
ggctctttct ttctgtattc taagctgacc gtggataagt cccggtggca gcagggcaac  960
gtgttttctt gttccgtgat gcatgaggcc ctgcacaatc attacacaca gaagagcctg  1020
tctctgtccc ctggc                                                   1035

SEQ ID NO: 324         moltype = DNA  length = 1011
FEATURE                Location/Qualifiers
source                 1..1011
                       mol_type = other DNA
                       organism = synthetic construct
```

```
SEQUENCE: 324
gagaccaggg agtgtatcta ctataacgcc aattgggagc tggagaggac aaaccagtcc  60
ggactggagc ggtgtgaggg cgagcaggac aagagactgc attgctacgc tagctggcgc  120
aattccagcg gcaccatcga gctggtgaag aagggctgtt ggctggacga tcagaactgt  180
tacgatagac aggagtgcgt ggccaccgag gagaatcctc aggtgtattt ttgctgttgc  240
gagggcaact tctgcaatga gaggttcacc cacctgccag aggctggagg accagaggtg  300
acctatgagc cacctccaac aggaggagga ggctctggaa cccatacatg tccaccttgc  360
ccagctccag agctgctggg aggcccttcc gtgttcctgt ttccacccaa gccaaaggac  420
accctgatga tctctaggac ccccagaggtg acatgcgtgg tggtggacgt gtcccacgag  480
gaccccgagg tgaagtttaa ctggtacgtg gatggcgtgg aggtgcataa tgctaagaca  540
aagccaaggg aggagcagta caactccacc tatcgggtgg tgagcgtgct gacagtgctg  600
caccaggatt ggctgaacgg caaggagtat aagtgtaagg tgagcaataa ggctctgcct  660
gccccaatcg agaagaccat ctctaaggct aagggccagc ccagagagcc tcaggtgtac  720
acactgcctc catcccgcga cgagctgacc aagaaccagg tgagcctgac atgcctggtg  780
aagggcttct atcccagcga catcgccgtg gagtgggagt ctaatggcca gcctgagaac  840
aattacaaga ccacaccccc tgtgctggac agcgatggct ctttctttct gtattctaag  900
ctgaccgtgg ataagtcccg gtggcagcag ggcaacgtgt tttcttgttc cgtgatgcat  960
gaggccctgc acaatcatta cacacagaag agcctgtctc tgtcccctgg c           1011

SEQ ID NO: 325          moltype = DNA  length = 1023
FEATURE                 Location/Qualifiers
source                  1..1023
                        mol_type = other DNA
                        organism = synthetic construct
SEQUENCE: 325
gagaccaggg agtgtatcta ctataacgcc aattgggagc tggagaggac aaaccagtcc  60
ggactggagc ggtgtgaggg cgagcaggac aagagactgc attgctacgc tagctggcgc  120
aattccagcg gcaccatcga gctggtgaag aagggctgtt ggctggacga tcagaactgt  180
tacgatagac aggagtgcgt ggccaccgag gagaatcctc aggtgtattt ttgctgttgc  240
gagggcaact tctgcaatga gaggttcacc cacctgccag aggctggagg accagaggtg  300
acctatgagc cacctccaac aggaggagga ggctctggag gaggaggctc cacccataca  360
tgtccacctt gcccagctcc agagctgctg ggaggccctt ccgtgttcct gtttccaccc  420
aagccaaagg acaccctgat gatctctagg accccagagg tgacatgcgt ggtggtggac  480
gtgtcccacg aggaccccga ggtgaagttt aactggtacg tggatggcgt ggaggtgcat  540
aatgctaaga caaagccaag ggaggagcag tacaactcca cctatcgggt ggtgagcgtg  600
ctgacagtgc tgcaccagga ttggctgaac ggcaaggagt ataagtgtaa ggtgagcaat  660
aaggctctgc ctgccccaat cgagaagacc atctctaagg ctaagggcca gcccagagag  720
cctcaggtgt acacactgcc tccatcccgc gacgagctga ccaagaacca ggtgagcctg  780
acatgcctgg tgaagggctt ctatcccagc gacatcgccg tggagtggga gtctaatggc  840
cagcctgaga acaattacaa gaccacaccc cctgtgctgg acagcgatgg ctctttcttt  900
ctgtattcta agctgaccgt ggataagtcc cggtggcagc agggcaacgt gttttcttgt  960
tccgtgatgc atgaggccct gcacaatcat tacacacaga agagcctgtc tctgtcccct  1020
ggc                                                               1023

SEQ ID NO: 326          moltype = DNA  length = 1050
FEATURE                 Location/Qualifiers
source                  1..1050
                        mol_type = other DNA
                        organism = synthetic construct
SEQUENCE: 326
gagaccaggg agtgtatcta ctataacgcc aattgggagc tggagaggac aaaccagtcc  60
ggactggagc ggtgtgaggg agagcaggac aagagactgc attgctacgc tagctggcgc  120
aattccagcg gcaccatcga gctggtgaag aagggctgtt ggctggacga tcagaactgt  180
tacgatagac aggagtgcgt ggccaccgag gagaatcctc aggtgtattt ttgctgttgc  240
gagggcaact tctgcaatga gaggttcacc cacctgccag aggctggagg accagaggtg  300
acctatgagc cacctccaac aggaggagga ggctccggtg gcggcggcag cggcggcggc  360
ggctctggcg gcggcggcac ccatacatgt ccaccttgcc cagctccaga gctgctggga  420
ggcccttccg tgttcctgtt tccacccaag ccaaaggaca ccctgatgat ctctaggacc  480
ccagaggtga catgcgtggt ggtggacgtg tcccacgagg accccgaggt gaagtttaac  540
tggtacgtgg atggcgtgga ggtgcataat gctaagacaa agccaaggga ggagcagtac  600
aactccacct atcgggtggt gagcgtgctg acagtgctgc accaggattg gctgaacggc  660
aaggagtata agtgtaaggt gagcaataag gctctgcctg ccccaatcga gaagaccatc  720
tctaaggcta agggccagcc cagagagcct caggtgtaca cactgcctcc atcccgcgac  780
gagctgacca agaaccaggt gagcctgaca tgcctggtga agggcttcta tcccagcgac  840
atcgccgtgg agtgggagtc taatggccag cctgagaaca attacaagac cacaccccct  900
gtgctggaca gcgatggctc tttctttctg tattctaagc tgaccgtgga taagtcccgg  960
tggcagcagg gcaacgtgtt ttcttgttcc gtgatgcatg aggccctgca caatcattac  1020
acacagaaga gcctgtctct gtcccctggc                                  1050

SEQ ID NO: 327          moltype = DNA  length = 1002
FEATURE                 Location/Qualifiers
source                  1..1002
                        mol_type = other DNA
                        organism = synthetic construct
SEQUENCE: 327
gagaccaggg agtgtatcta ctataacgcc aattgggagc tggagaggac aaaccagtcc  60
ggactggagc ggtgtgaggg agagcaggac aagagactgc attgctacgc tagctggcgc  120
aattccagcg gcaccatcga gctggtgaag aagggctgtt ggctggacga ggagaactgt  180
tacgatagac aggagtgcgt ggccaccgag gagaatcctc aggtgtattt ttgctgttgc  240
```

```
gagggcaact tctgcaatga gaggttcacc cacctgccag aggctggagg accagaggtg  300
acctatgagc cacctccaac aggaggagga acccatacat gtccaccttg cccagctcca  360
gagctgctgg gaggcccttc cgtgttcctg tttccaccca agccaaagga caccctgatg  420
atctctagga ccccagaggt gacatgcgtg gtggtggacg tgtcccacga ggaccccgag  480
gtgaagttta actggtacgt ggatggcgtg gaggtgcata atgctaagac aaagccaagg  540
gaggagcagt acaactccac ctatcgggtg gtgagcgtgc tgacagtgct gcaccaggat  600
tggctgaacg gcaaggagta taagtgtaag gtgagcaata aggctctgcc tgccccaatc  660
gagaagacca tctctaaggc taagggccag cccagagagc ctcaggtgta cacactgcct  720
ccatcccgcg acgagctgac caagaaccag gtgagcctga catgcctggt gaagggcttc  780
tatcccagcg acatcgccgt ggagtgggag tctaatggcc agcctgagaa caattacaag  840
accacacccc ctgtgctgga cagcgatggc tctttctttc tgtattctaa gctgaccgtg  900
gataagtccc ggtggcagca gggcaacgtg ttttcttgtt ccgtgatgca tgaggccctg  960
cacaatcatt acacacagaa gagcctgtct ctgtcccctg gc                     1002
```

```
SEQ ID NO: 328          moltype = DNA  length = 1035
FEATURE                 Location/Qualifiers
source                  1..1035
                        mol_type = other DNA
                        organism = synthetic construct
SEQUENCE: 328
gagaccaggg agtgtatcta ctataacgcc aattgggagc tggagaggac aaaccagtcc  60
ggactggagc ggtgtgaggg cgagtacgac aagagactgc attgctacgc tagctggcgc  120
aattccagcg gcaccatcga gctggtgaag aagggctgtt ggctggacga tgagaactgt  180
tacgatagac aggagtgcgt ggccaccgag gagaatcctc aggtgtattt ttgctgttgc  240
gagggcaact tctgcaatga gaggttcacc cacctgccag aggctggagg accagaggtg  300
acctatgagc cacctccaac aggaggagga ggctctggag gaggaggctc cggaggagga  360
ggaacccata catgtccacc ttgcccagct ccagagctgc tgggaggccc ttccgtgttc  420
ctgtttccac ccaagccaaa ggacaccctg atgatctcta ggaccccaga ggtgacatgc  480
gtggtggtgg acgtgtccca cgaggacccc gaggtgaagt ttaactggta cgtggatggc  540
gtggaggtgc ataatgctaa gacaaagcca agggaggagc agtacaactc cacctatcgg  600
gtggtgagcg tgctgacagt gctgcaccag gattggctga acggcaagga gtataagtgt  660
aaggtgagca ataaggctct gcctgcccca atcgagaaga ccatctctaa ggctaagggc  720
cagcccagag agcctcaggt gtacacactg cctccatccc gcgacgagct gaccaagaac  780
caggtgagcc tgacatgcct ggtgaagggc ttctatccca gcgacatcgc cgtggagtgg  840
gagtctaatg gccagcctga gaacaattac aagaccacac cccctgtgct ggacagcgat  900
ggctctttct ttctgtattc taagctgacc gtggataagt cccggtggca gcagggcaac  960
gtgttttctt gttccgtgat gcatgaggcc ctgcacaatc attacacaca gaagagcctg  1020
tctctgtccc ctggc                                                   1035
```

```
SEQ ID NO: 329          moltype = DNA  length = 1035
FEATURE                 Location/Qualifiers
source                  1..1035
                        mol_type = other DNA
                        organism = synthetic construct
SEQUENCE: 329
gagaccaggg agtgtatcta ctataacgcc aattgggagc tggagaggac aaaccagtcc  60
ggactggagc ggtgtgaggg cgagcagcag aagagactgc attgctacgc tagctggcgc  120
aattccagcg gcaccatcga gctggtgaag aagggctgtt ggctggacga tgagaactgt  180
tacgatagac aggagtgcgt ggccaccgag gagaatcctc aggtgtattt ttgctgttgc  240
gagggcaact tctgcaatga gaggttcacc cacctgccag aggctggagg accagaggtg  300
acctatgagc cacctccaac aggaggagga ggctctggag gaggaggctc cggaggagga  360
ggaacccata catgtccacc ttgcccagct ccagagctgc tgggaggccc ttccgtgttc  420
ctgtttccac ccaagccaaa ggacaccctg atgatctcta ggaccccaga ggtgacatgc  480
gtggtggtgg acgtgtccca cgaggacccc gaggtgaagt ttaactggta cgtggatggc  540
gtggaggtgc ataatgctaa gacaaagcca agggaggagc agtacaactc cacctatcgg  600
gtggtgagcg tgctgacagt gctgcaccag gattggctga acggcaagga gtataagtgt  660
aaggtgagca ataaggctct gcctgcccca atcgagaaga ccatctctaa ggctaagggc  720
cagcccagag agcctcaggt gtacacactg cctccatccc gcgacgagct gaccaagaac  780
caggtgagcc tgacatgcct ggtgaagggc ttctatccca gcgacatcgc cgtggagtgg  840
gagtctaatg gccagcctga gaacaattac aagaccacac cccctgtgct ggacagcgat  900
ggctctttct ttctgtattc taagctgacc gtggataagt cccggtggca gcagggcaac  960
gtgttttctt gttccgtgat gcatgaggcc ctgcacaatc attacacaca gaagagcctg  1020
tctctgtccc ctggc                                                   1035
```

```
SEQ ID NO: 330          moltype = DNA  length = 1002
FEATURE                 Location/Qualifiers
source                  1..1002
                        mol_type = other DNA
                        organism = synthetic construct
SEQUENCE: 330
gagaccaggg agtgtatcta ctataacgcc aattgggagc tggagaggac aaaccagtcc  60
ggactggagc ggtgtgagga cgagcaggac aagagactgc attgctacgc tagctggcgc  120
aattccagcg gcaccatcga gctggtgaag aagggctgtt ggctggacga tgagaactgt  180
tacgatagac aggagtgcgt ggccaccgag gagaatcctc aggtgtattt ttgctgttgc  240
gagggcaact tctgcaatga gaggttcacc cacctgccag aggctggagg accagaggtg  300
acctatgagc cacctccaac aggaggagga acccatacat gtccaccttg cccagctcca  360
gagctgctgg gaggcccttc cgtgttcctg tttccaccca agccaaagga caccctgatg  420
atctctagga ccccagaggt gacatgcgtg gtggtggacg tgtcccacga ggaccccgag  480
gtgaagttta actggtacgt ggatggcgtg gaggtgcata atgctaagac aaagccaagg  540
```

-continued

```
gaggagcagt acaactccac ctatcgggtg gtgagcgtgc tgacagtgct gcaccaggat  600
tggctgaacg gcaaggagta taagtgtaag gtgagcaata aggctctgcc tgccccaatc  660
gagaagacca tctctaaggc taagggccag cccagagagc ctcaggtgta cacactgcct  720
ccatcccgcg aggagatgac caagaaccag gtgagcctga catgcctggt gaagggcttc  780
tatcccagcg acatcgccgt ggagtgggag tctaatggcc agcctgagaa caattacaag  840
accacacccc ctgtgctgga cagcgatggc tctttctttc tgtattctaa gctgaccgtg  900
gataagtccc ggtggcagca gggcaacgtg ttttcttgtt ccgtgatgca tgaggccctg  960
cacaatcatt acacacagaa gagcctgtct ctgtccctg gc                     1002

SEQ ID NO: 331         moltype = AA  length = 107
FEATURE                Location/Qualifiers
source                 1..107
                       mol_type = protein
                       organism = synthetic construct
SEQUENCE: 331
ETRECIYYNA NWELERTNQS GLERCEGEQQ KRLHCYASWR NSSGTIELVK KGCWLDDENC  60
YDRQECVATE ENPQVYFCCC EGNFCNERFT HLPEAGGPEV TYEPPPT                107

SEQ ID NO: 332         moltype = AA  length = 107
FEATURE                Location/Qualifiers
source                 1..107
                       mol_type = protein
                       organism = synthetic construct
SEQUENCE: 332
ETRECIYYNA NWELERTNQS GLERCEDEQD KRLHCYASWR NSSGTIELVK KGCWLDDENC  60
YDRQECVATE ENPQVYFCCC EGNFCNERFT HLPEAGGPEV TYEPPPT                107

SEQ ID NO: 333         moltype = AA  length = 345
FEATURE                Location/Qualifiers
source                 1..345
                       mol_type = protein
                       organism = synthetic construct
SEQUENCE: 333
ETRECIYYNA NWELERTNQS GLERCEGEQD KRLHCYASWR NSSGTIELVK KGCWLDEFNC  60
YDRQECVATE ENPQVYFCCC EGNFCNERFT HLPEAGGPEV TYEPPPTGGG GSGGGGSGGG  120
GTHTCPPCPA PELLGGPSVF LFPPKPKDTL MISRTPEVTC VVVDVSHEDP EVKFNWYVDG  180
VEVHNAKTKP REEQYNSTYR VVSVLTVLHQ DWLNGKEYKC KVSNKALPAP IEKTISKAKG  240
QPREPQVYTL PPSRDELTKN QVSLTCLVKG FYPSDIAVEW ESNGQPENNY KTTPPVLDSD  300
GSFFLYSKLT VDKSRWQQGN VFSCSVMHEA LHNHYTQKSL SLSPG                  345

SEQ ID NO: 334         moltype = DNA  length = 1035
FEATURE                Location/Qualifiers
source                 1..1035
                       mol_type = other DNA
                       organism = synthetic construct
SEQUENCE: 334
gagaccaggg agtgtatcta ctataacgcc aattgggagc tggagaggac aaaccagtcc  60
ggactggagc ggtgtgaggg cgagcaggac aagagactgc attgctacgc tagctggcgc  120
aattccagcg gcaccatcga gctggtgaag aagggctgtt ggctggacga gttcaactgt  180
tacgatagac aggagtgcgt ggccaccgag gagaatcctc aggtgtattt ttgctgttgc  240
gagggcaact tctgcaatga gaggttcacc cacctgccag aggctggagg accagaggtg  300
acctatgagc cacctccaac aggaggagga ggctctggag gaggaggctc cggaggagga  360
ggaacccata catgtccacc ttgcccagct ccagagctgc tgggaggccc ttccgtgttc  420
ctgtttccac ccaagccaaa ggacaccctg atgatctcta ggaccccaga ggtgacatgc  480
gtggtggtgg acgtgtccca cgaggacccc gaggtgaagt ttaactggta cgtggatggc  540
gtggaggtgc ataatgctaa gacaaagcca agggaggagc agtacaactc cacctatcgg  600
gtggtgagcg tgctgacagt gctgcaccag gattggctga acggcaagga gtataagtgt  660
aaggtgagca ataaggctct gcctgcccca atcgagaaga ccatctctaa ggctaagggc  720
cagcccagag agcctcaggt gtacacactg cctccatccc gcgacgagct gaccaagaac  780
caggtgagcc tgacatgcct ggtgaagggc ttctatccca gcgacatcgc cgtggagtgg  840
gagtctaatg gccagcctga gaacaattac aagaccacac cccctgtgct ggacagcgat  900
ggctctttct ttctgtattc taagctgacc gtggataagt cccggtggca gcagggcaac  960
gtgttttctt gttccgtgat gcatgaggcc ctgcacaatc attacacaca gaagagcctg  1020
tctctgtccc ctggc                                                   1035

SEQ ID NO: 335         moltype = AA  length = 5
FEATURE                Location/Qualifiers
source                 1..5
                       mol_type = protein
                       organism = synthetic construct
SEQUENCE: 335
GGGAG                                                              5

SEQ ID NO: 336         moltype = AA  length = 6
FEATURE                Location/Qualifiers
source                 1..6
                       mol_type = protein
                       organism = synthetic construct
SEQUENCE: 336
```

-continued

```
GGGAGG                                                        6

SEQ ID NO: 337         moltype = AA  length = 7
FEATURE                Location/Qualifiers
source                 1..7
                       mol_type = protein
                       organism = synthetic construct
SEQUENCE: 337
GGGAGGG                                                       7

SEQ ID NO: 338         moltype = AA  length = 224
FEATURE                Location/Qualifiers
source                 1..224
                       mol_type = protein
                       organism = synthetic construct
SEQUENCE: 338
THTCPPCPAP ELLGGPSVFL FPPKPKDTLY ISRTPEVTCV VVDVSHEDPE VKFNWYVDGV  60
EVHNAKTKPR EEQYNSTYRV VSVLTVLHQD WLNGKEYKCK VSNKALPAPI EKTISKAKGQ  120
PREPQVYTLP PSREEMTKNQ VSLTCLVKGF YPSDIAVEWE SNGQPENNYK TTPPVLDSDG  180
SFFLYSKLTV DKSRWQQGNV FSCSVMHEAL HNHYTQKSLS LSPG                  224

SEQ ID NO: 339         moltype = AA  length = 345
FEATURE                Location/Qualifiers
source                 1..345
                       mol_type = protein
                       organism = synthetic construct
SEQUENCE: 339
ETRECIYYNA NWELERTNQS GLERCEGEQD YRLHCYASWR NSSGTIELVK KGCWLDDFNC  60
YDRQECVATE ENPQVYFCCC EGNFCNERFT HLPEAGGPEV TYEPPPTGGG GSGGGGSGGG  120
GTHTCPPCPA PELLGGPSVF LFPPKPKDTL MISRTPEVTC VVVDVSHEDP EVKFNWYVDG  180
VEVHNAKTKP REEQYNSTYR VVSVLTVLHQ DWLNGKEYKC KVSNKALPAP IEKTISKAKG  240
QPREPQVYTL PPSREEMTKN QVSLTCLVKG FYPSDIAVEW ESNGQPENNY KTTPPVLDSD  300
GSFFLYSKLT VDKSRWQQGN VFSCSVMHEA LHNHYTQKSL SLSPG                  345

SEQ ID NO: 340         moltype = AA  length = 345
FEATURE                Location/Qualifiers
source                 1..345
                       mol_type = protein
                       organism = synthetic construct
SEQUENCE: 340
ETRECIYYNA NWELERTNQS GLERCEGEQD KRLHCYASWR NSSGTIELVK KGCWLDDFNC  60
YDRQECVATE ENPQQYFCCC EGNFCNERFT HLPEAGGPEV TYEPPPTGGG GSGGGGSGGG  120
GTHTCPPCPA PELLGGPSVF LFPPKPKDTL MISRTPEVTC VVVDVSHEDP EVKFNWYVDG  180
VEVHNAKTKP REEQYNSTYR VVSVLTVLHQ DWLNGKEYKC KVSNKALPAP IEKTISKAKG  240
QPREPQVYTL PPSREEMTKN QVSLTCLVKG FYPSDIAVEW ESNGQPENNY KTTPPVLDSD  300
GSFFLYSKLT VDKSRWQQGN VFSCSVMHEA LHNHYTQKSL SLSPG                  345

SEQ ID NO: 341         moltype = AA  length = 343
FEATURE                Location/Qualifiers
source                 1..343
                       mol_type = protein
                       organism = synthetic construct
SEQUENCE: 341
ILGRSETQEC LFFNANWEKD RTNQTGVEPC YGDKDKRRHC FATWKNISGS IEIVKQGCWL  60
DDINCYDRTD CVEKKDSPEV YFCCCEGNMC NEKFSYFPEM EVTQPTSNPV TPKPPTGGGP  120
CPPCKCPAPN LLGGPSVFIF PPKIKDVLMI SLSPIVTCVV VDVSEDDPDV QISWFVNNVE  180
VHTAQTQTHR EDYNSTLRVV SALPIQHQDW MSGKEFKCKV NNKDLPAPIE RTISKPKGSV  240
RAPQVYVLPP PEEEMTKKQV TLTCMVTDFM PEDIYVEWTN NGKTELNYKN TEPVLDSDGS  300
YFMYSKLRVE KKNWVERNSY SCSVVHEGLH NHHTTKSFSR TPG                    343

SEQ ID NO: 342         moltype = DNA  length = 1035
FEATURE                Location/Qualifiers
source                 1..1035
                       mol_type = other DNA
                       organism = synthetic construct
SEQUENCE: 342
gagaccaggg agtgtatcta ctataacgcc aattgggagc tggagaggac aaaccagtcc  60
ggactggagc ggtgtgaggg cgagcaggac tacagactgc attgctacgc tagctggcgc  120
aattccagcg gcaccatcga gctggtgaag aagggctgtt ggctggacga tttcaactgt  180
tacgatagac aggagtgcgt ggccaccgag gagaatcctc aggtgtattt ttgctgttgc  240
gagggcaact tctgcaatga gaggttcacc cacctgccag aggctggagg accagaggtg  300
acctatgagc cacctccaac aggaggagga ggctctggag gaggaggctc cggaggagga  360
ggaacccata catgtccacc ttgcccagct ccagagctgc tgggaggccc ttccgtgttc  420
ctgtttccac ccaagccaaa ggacaccctg atgatctcta ggaccccaga ggtgacatgc  480
gtggtggtgg acgtgtccca cgaggacccc gaggtgaagt ttaactggta cgtggatggc  540
gtggaggtgc ataatgctaa gacaaagcca agggaggagc agtacaactc cacctatcgg  600
gtggtgagcg tgctgacagt gctgcaccag gattggctga acggcaagga gtataagtgt  660
aaggtgagca ataaggctct gcctgcccca atcgagaaga ccatctctaa ggctaagggc  720
cagcccagag agcctcaggt gtacacactg cctccatccc gcgacgagct gaccaagaac  780
```

-continued

```
caggtgagcc tgacatgcct ggtgaagggc ttctatccca gcgacatcgc cgtggagtgg  840
gagtctaatg gccagcctga gaacaattac aagaccacac cccctgtgct ggacagcgat  900
ggctctttct ttctgtattc taagctgacc gtggataagt cccggtggca gcagggcaac  960
gtgttttctt gttccgtgat gcatgaggcc ctgcacaatc attacacaca gaagagcctg  1020
tctctgtccc ctggc                                                   1035

SEQ ID NO: 343          moltype = DNA  length = 1035
FEATURE                 Location/Qualifiers
source                  1..1035
                        mol_type = other DNA
                        organism = synthetic construct
SEQUENCE: 343
gagaccaggg agtgtatcta ctataacgcc aattgggagc tggagaggac aaaccagtcc  60
ggactggagc ggtgtgaggg cgagcaggac aagagactgc attgctacgc tagctggcgc  120
aattccagcg gcaccatcga gctggtgaag aagggctgtt ggctggacga tttcaactgt  180
tacgatagac aggagtgcgt ggccaccgag gagaatcctc agcagtattt ttgctgttgc  240
gagggcaact tctgcaatga gaggttcacc cacctgccag aggctggagg accagaggtg  300
acctatgagc cacctccaac aggaggagga ggctctggag gaggaggctc cggaggagga  360
ggaacccata catgtccacc ttgcccagct ccagagctgc tgggaggccc ttccgtgttc  420
ctgtttccac ccaagccaaa ggacaccctg atgatctcta ggaccccaga ggtgacatgc  480
gtggtggtgg acgtgtccca cgaggacccc gaggtgaagt ttaactggta cgtggatggc  540
gtggaggtgc ataatgctaa gacaaagcca agggaggagc agtacaactc cacctatcgg  600
gtggtgagcg tgctgacagt gctgcaccag gattggctga acggcaagga gtataagtgt  660
aaggtgagca ataaggctct gcctgcccca atcgagaaga ccatctctaa ggctaagggc  720
cagcccagag agcctcaggt gtacacactg cctccatccc gcgacgagct gaccaagaac  780
caggtgagcc tgacatgcct ggtgaagggc ttctatccca gcgacatcgc cgtggagtgg  840
gagtctaatg gccagcctga gaacaattac aagaccacac cccctgtgct ggacagcgat  900
ggctctttct ttctgtattc taagctgacc gtggataagt cccggtggca gcagggcaac  960
gtgttttctt gttccgtgat gcatgaggcc ctgcacaatc attacacaca gaagagcctg  1020
tctctgtccc ctggc                                                   1035

SEQ ID NO: 344          moltype = DNA  length = 1029
FEATURE                 Location/Qualifiers
source                  1..1029
                        mol_type = other DNA
                        organism = synthetic construct
SEQUENCE: 344
atcctgggcc gcagcgagac acaggagtgt ctgttcttta acgccaattg ggagaaggat  60
aggaccaacc agacaggcgt ggagccatgt tatggcgaca aggataagag gcggcattgc  120
ttcgctacct ggaagaacat ctccggcagc atcgagatcg tgaagcaggg ctgttggctg  180
gacgatatca attgttacga ccggacagat tgcgtggaga agaaggactc tcccgaggtg  240
tatttttgct gttgcgaggg caacatgtgc aatgagaagt tctcttactt tcccgagatg  300
gaggtgaccc agcctacatc caatccagtg accccaaagc cacctacagg aggaggacca  360
tgcccaccat gcaagtgtcc agctcctaac ctgctgggag gaccatccgt gttcatcttt  420
cctccaaaga tcaaggacgt gctgatgatc tccctgagcc ccatcgtgac atgcgtggtg  480
gtggacgtga gcgaggacga tcctgatgtg cagatctctt ggttcgtgaa caatgtggag  540
gtgcacaccg cccagaccca gacacatagg gaggattaca attctacact gcgggtggtg  600
tccgctctgc ccatccagca ccaggactgg atgagcggca aggagtttaa gtgcaaggtg  660
aacaataagg atctgccagc ccccatcgag aggaccatct ccaagcctaa gggcagcgtg  720
agagctccac aggtgtatgt gctgccccct ccagaggagg agatgaccaa gaagcaggtg  780
accctgacat gtatggtgac agacttcatg cctgaggata tctacgtgga gtggaccaac  840
aatggcaaga cagagctgaa ctataagaat accgagccag tgctggacag cgatggctct  900
tactttatgt attctaagct gagagtggag aagaagaact gggtggagcg caattcttac  960
tcctgcagcg tggtgcacga gggcctgcat aaccaccata ccacaaagtc tttctccagg  1020
acacccggc                                                          1029

SEQ ID NO: 345          moltype = AA  length = 50
FEATURE                 Location/Qualifiers
source                  1..50
                        mol_type = protein
                        organism = synthetic construct
REPEAT                  1..5
                        note = single repeat of (GGGGS)n where n=2-10
VARIANT                 6..50
                        note = up to 8 copies of (GGGGS) can be deleted
SEQUENCE: 345
GGGGSGGGGS GGGGSGGGGS GGGGSGGGGS GGGGSGGGGS GGGGSGGGGS             50
```

ACTIVIN RECEPTOR TYPE IIB VARIANTS AND USES THEREOF

CROSS-REFERENCE TO RELATED APPLICATIONS

The present application is a US non-provisional application claiming the benefit of priority from U.S. Provisional Application No. 63/304,478, filed Jan. 28, 2022; U.S. Provisional Application No. 63/397,773, filed Aug. 12, 2022; U.S. Provisional Application No. 63/416,852, filed Oct. 17, 2022; and U.S. Provisional Application No. 63/420,999, filed Oct. 31, 2022, the contents of each of which are incorporated herein by reference in their entireties.

REFERENCE TO AN ELECTRONIC SEQUENCE LISTING

The content of the electronic sequence listing (35PH_002_04US_Sub_SeqList_ST26.xml; Size: 418,894 bytes; and Date of Creation: Sep. 19, 2023) is herein incorporated by reference in its entirety.

FIELD

The present disclosure relates to polypeptides that include an Activin receptor type IIB (ActRIIB) ectodomain (ECD) variant and uses thereof for binding and neutralizing TGFβ superfamily ligands, particularly for the treatment of diseases and conditions associated with TGFβ superfamily signaling such as pulmonary hypertension, fibrosis, muscle weakness and atrophy, metabolic disorders and cardiometabolic disease, bone damage, and low red blood cell levels.

BACKGROUND

The transforming growth factor beta (TGFβ) superfamily includes 35 ligands that regulate several physiological processes, including cell proliferation, migration and differentiation, muscle growth, vascular homeostasis, and osteogenesis. Perturbation of their levels and/or signaling pathways gives rise to significant pathological effects. For instance, TGFβ and activin ligands have been implicated in the pathogenesis of multiple human disorders and play critical pathogenic roles in many diseases. Examples of TGFβ-superfamily associated disorders include pulmonary hypertension (including pulmonary arterial hypertension), hematologic malignancies, solid tumors, bone marrow failure states, muscle weakness, and a wide variety of disorders characterized by uncontrolled fibrosis such as pulmonary, liver, renal and cardiac fibrosis, and systemic sclerosis (SSc; also called scleroderma) (Nanthakumar, D. B. et al., 2015; Meng, X.-M. et al., 2016). There remains a need in the art for therapeutics effective in the treatment of TGFβ-superfamily associated disorders.

SUMMARY

There are provided herein activin receptor type IIB (ActRIIB)-ectodomain (ECD) based traps having a tailored ligand specificity profile for binding and neutralization of TGFβ superfamily ligands, and pharmaceutical compositions and methods of use thereof in the treatment of diseases and conditions associated with or mediated by TGFβ superfamily signaling.

ActRIIB-ECD traps provided herein comprise an ActRIIB-ECD variant fused to an Fc domain monomer that can function to assemble two polypeptides together. ActRIIB-ECD variants provided herein have been designed to tailor ligand specificity, in order to maximize therapeutic efficacy in certain disease indications while minimizing adverse effects. The ActRIIB-ECD variants provided herein are constructed by introducing novel amino acid substitutions into the ActRIIB-ECD, with the goal of preventing or reducing disruption of endogenous BMP-9 signaling, while maintaining and/or increasing neutralization of other TGFβ superfamily ligands such as activin A, activin B, GDF-8, and/or GDF-11. Without wishing to be limited by theory, the goal of sparing BMP-9 signaling is based on the finding that BMP-9 is important for the maintenance of vascular quiescence and homeostasis (Desroches-Castan, A. et al., 2022). Wild type ActRIIB binds to BMP-9; therefore, ActRIIB-ECD-based traps have the potential to disrupt vascular homeostasis which may result in bleeding concerns. In support of this concept, telangiectasias, epistaxis and gingival bleeding were observed in clinical studies of a non-mutated ActRIIB-ECD trap (called ACE-031) (Campbell, C. et al., 2017). It was suggested that these vascular effects may have resulted from inhibition of the BMP-9 pathway.

The preferred ActRIIB-ECD variants provided herein exhibit: (1) similar or improved binding to activin A, activin B, GDF-8, GDF-11, and/or BMP-10 compared to wild type ActRIIB, which allows them to compete with endogenous activin receptors for ligand binding and reduce or inhibit endogenous ligand-stimulated receptor signaling; and (2) reduced or removed binding to BMP-9 compared to wild type ActRIIB, which allows homeostatic BMP-9 signaling to be maintained. These variants can be used to treat diseases and conditions in which activin receptor signaling is elevated, such as pulmonary hypertension (PH) (e.g., PAH, venous PH, hypoxic PH, thromboembolic PH, or miscellaneous PH), metabolic disease, bone disease, muscle disease, fibrosis, and/or low red blood cell levels (e.g., anemia). The variants can for example lead to a reduction in the symptoms or progression of PH (e.g., PAH, venous PH, hypoxic PH, thromboembolic PH, or miscellaneous PH), a reduction in bone resorption or osteoclast activity, an increase in bone formation or bone mineral density, an increase in muscle mass or strength, a reduction in fibrosis (e.g., reduced fibrosis or a slowing or stopping of the progression of fibrosis), and/or an increase in red blood cell levels (e.g., an increase in hemoglobin levels, hematocrit, or red blood cell counts).

In some embodiments, the present disclosure provides a polypeptide comprising: (a) an Activin receptor type IIB (ActRIIB) ectodomain (ECD) variant; (b) a peptide linker comprising at least 10 amino acids; and (c) an Fc domain monomer. In some embodiments, the ActRIIB ECD comprises one or more amino acid substitutions at a position selected from G27, Q29, D30, K31, S38, D57, F58, V75, and F77 relative to the human wild type ActRIIB-ECD of SEQ ID NO: 2.

In some embodiments, the ActRIIB ECD comprises the amino acid substitution G27D. In some embodiments, the ActRIIB ECD comprises an amino acid sequence that is at least 95%, 96%, 97%, 98%, or 99% identical to SEQ ID NO: 20. In some embodiments, the ActRIIB ECD comprises the amino acid substitution Q29Y. In some embodiments, the ActRIIB ECD comprises an amino acid sequence that is at least 95%, 96%, 97%, 98%, or 99% identical to SEQ ID NO: 14. In some embodiments, the ActRIIB ECD comprises the amino acid substitution D30Q. In some embodiments, the ActRIIB ECD comprises an amino acid sequence that is at least 95%, 96%, 97%, 98%, or 99% identical to SEQ ID NO:

15. In some embodiments, the ActRIIB ECD comprises the amino acid substitution K31Y. In some embodiments, the ActRIIB ECD comprises an amino acid sequence that is at least 95%, 96%, 97%, 98%, or 99% identical to SEQ ID NO: 16. In some embodiments, the ActRIIB ECD comprises the amino acid substitution S38R. In some embodiments, the ActRIIB ECD comprises an amino acid sequence that is at least 95%, 96%, 97%, 98%, or 99% identical to SEQ ID NO: 17. In some embodiments, the ActRIIB ECD comprises the amino acid substitution D57E. In some embodiments, the ActRIIB ECD comprises an amino acid sequence that is at least 95%, 96%, 97%, 98%, or 99% identical to SEQ ID NO: 4.

In some embodiments, the ActRIIB ECD comprises an amino acid substitution at position F58 selected from F58D, F58E, F58Y, F58K, F58Q, F58N, F58R, F58H, and F58W. In some embodiments, the ActRIIB ECD comprises the amino acid substitution F58D. In some embodiments, the ActRIIB ECD comprises an amino acid sequence that is at least 95%, 96%, 97%, 98%, or 99% identical to SEQ ID NO: 6. In some embodiments, the ActRIIB-ECD variant comprises the amino acid substitution F58E. In some embodiments, the ActRIIB ECD comprises an amino acid sequence that is at least 95%, 96%, 97%, 98%, or 99% identical to SEQ ID NO: 5. In some embodiments, the variant comprises amino acid substitution F58Y. In some embodiments, the ActRIIB ECD comprises an amino acid sequence that is at least 95%, 96%, 97%, 98%, or 99% identical to SEQ ID NO: 7. In some embodiments, the ActRIIB ECD comprises amino acid substitution F58K. In some embodiments, ActRIIB ECD comprises an amino acid sequence that is at least 95%, 96%, 97%, 98%, or 99% identical to SEQ ID NO: 8. In some embodiments, the variant comprises amino acid substitution F58Q. In some embodiments, the ActRIIB ECD comprises an amino acid sequence that is at least 95%, 96%, 97%, 98%, or 99% identical to SEQ ID NO: 9. In some embodiments, the variant comprises amino acid substitution F58W. In some embodiments, the ActRIIB ECD comprises an amino acid sequence that is at least 95%, 96%, 97%, 98%, or 99% identical to SEQ ID NO: 10. In some embodiments, the variant comprises the amino acid substitution F58N. In some embodiments, the ActRIIB ECD comprises an amino acid sequence that is at least 95%, 96%, 97%, 98%, or 99% identical to SEQ ID NO: 11. In some embodiments, the variant comprises the amino acid substitution F58H. In some embodiments, the ActRIIB ECD comprises an amino acid sequence that is at least 95%, 96%, 97%, 98%, or 99% identical to SEQ ID NO: 13. In some embodiments, the variant comprises the amino acid substitution F58R. In some embodiments, the ActRIIB ECD comprises an amino acid sequence that is at least 95%, 96%, 97%, 98%, or 99% identical to SEQ ID NO: 12.

In some embodiments, the ActRIIB ECD comprises the amino acid substitution V75Q. In some embodiments, the ActRIIB ECD comprises an amino acid sequence that is at least 95%, 96%, 97%, 98%, or 99% identical to SEQ ID NO: 18. In some embodiments, the ActRIIB ECD comprises the amino acid substitution F77D. In some embodiments, the ActRIIB ECD comprises an amino acid sequence that is at least 95%, 96%, 97%, 98%, or 99% identical to SEQ ID NO: 19.

In some embodiments, the ActRIIB-ECD variant further comprises one or more additional amino acid substitutions. In some embodiments, the ActRIIB-ECD variant further comprises the following amino acids at the N terminus: GRGEA (SEQ ID NO: 23). In some embodiments, the ActRIIB-ECD variant further comprises a 3-amino acid extension of alanine-proline-threonine (APT) at the C-terminus.

In some embodiments, the polypeptide comprises the following structure, from N- to C-terminus: ActRIIB-ECD-peptide linker-Fc domain monomer.

In some embodiments, the Fc domain monomer is an IgG1, IgG2, IgG3 or IgG4 isotype. In some embodiments, the Fc domain monomer is a human Fc domain monomer or a murine Fc domain monomer. In some embodiments, the Fc domain monomer is engineered to reduce aggregation or to modulate stability of a dimer of the polypeptide. In some embodiments, the Fc domain monomer comprises the amino acid substitutions of M252Y, S254T, and T256E (YTE). In some embodiments, the Fc domain monomer comprises the M252Y amino acid substitution. In some embodiments, the Fc domain monomer includes a D at position 356 and an L at position 358 (DL). In some embodiments, the Fc domain monomer includes an E at position 356 and an M at position 358 (EM). In some embodiments, the Fc domain monomer further comprises a Lysine residue (K) at the C terminus.

In some embodiments, the Fc domain monomer comprises an amino acid sequence that is at least 85%, at least 90%, at least 95%, at least 96%, at least 97%, at least 98%, or at least 99% identical to any one of SEQ ID NOs: 134-173 and 338. In some embodiments, the Fc domain monomer comprises or consists of an amino acid sequence selected from any one of SEQ ID NOs: 134-173 and 338. In some embodiments, the Fc domain monomer: (a) is an IgG1 isotype and comprises or consists of the amino acid sequence set forth in SEQ ID NO: 135 or SEQ ID NO: 134; or (b) is an IgG2 isotype and comprises or consists of the amino acid sequence set forth in SEQ ID NO: 157. In some embodiments, the Fc domain monomer forms a dimer.

In some embodiments, the peptide linker is Glycine-rich. In some embodiments, the peptide linker is between 10 and 40 amino acids long. In some embodiments, the linker is at least 10 amino acids long, at least 14 amino acids long, at least 19 amino acids long, or at least 39 amino acids long. In some embodiments, the linker is 10 amino acids long, 14 amino acids long, 19 amino acids long, or 39 amino acids long. In some embodiments, the linker is 14 amino acids long. In some embodiments, the peptide linker comprises the amino acid sequence set forth in any one of SEQ ID NOs: 34, 54, 59, or 63.

In some embodiments, the ActRIIB-ECD comprises an amino acid sequence that is at least 95%, 96%, 97%, 98%, or 99% identical to any one of SEQ ID NOs: 4-22, 331, 332, and 24-33. In some embodiments, the ActRIIB-ECD comprises or consists of an amino acid sequence selected from any one of SEQ ID NOs: 4-22, 331, 332, and 24-33. In some embodiments, the ActRIIB-ECD comprises or consists of the amino acid sequence of SEQ ID NO: 5, or a sequence at least 95%, at least 96%, at least 97%, at least 98%, or at least 99% identical thereto. In some embodiments, the ActRIIB-ECD comprises or consists of the amino acid sequence of SEQ ID NO: 8 or a sequence at least 95%, at least 96%, at least 97%, at least 98%, or at least 99% identical thereto. In some embodiments, the ActRIIB-ECD comprises or consists of the amino acid sequence of SEQ ID NO: 9 or a sequence at least 95%, at least 96%, at least 97%, at least 98%, or at least 99% identical thereto.

In some embodiments, the polypeptide comprises an amino acid sequence that is at least 95%, 96%, 97%, 98%, or 99% identical to an amino acid sequence selected from SEQ ID NOs: 174-254, 333, and 339-341. In some embodiments, the polypeptide comprises or consists of an amino acid sequence selected from SEQ ID NOs: 174-254, 333, and 339-341. In some embodiments, the polypeptide comprises an amino acid sequence that is at least 95%, 96%, 97%, 98%, or 99% identical to an amino acid sequence selected from SEQ ID NOs: 186, 190-194, 232-233, and 247-248. In some embodiments, the polypeptide comprises or consists of an amino acid sequence selected from SEQ ID NOs: 186, 190-194, 232-233, and 247-248. In some embodiments, the polypeptide comprises or consists of the amino acid sequence of SEQ ID NO: 186, or an amino acid sequence that is at least 95%, 96%, 97%, 98%, or 99% identical thereto. In some embodiments, the polypeptide comprises an amino acid sequence that is at least 95%, 96%, 97%, 98%, or 99% identical to an amino acid sequence selected from SEQ ID NOs: 213-216, and 242-244. In some embodiments, the polypeptide comprises or consists of an amino acid sequence selected from SEQ ID NOs: 213-216, and 242-244. In some embodiments, the polypeptide comprises an amino acid sequence that is at least 95%, 96%, 97%, 98%, or 99% identical to an amino acid sequence selected from SEQ ID NOs: 220-223, 253, and 254. In some embodiments, the polypeptide comprises or consists of an amino acid sequence selected from SEQ ID NOs: 220-223, 253, and 254.

In some embodiments, the polypeptide further comprises an albumin-binding domain, a fibronectin domain, or a human serum albumin domain fused to the N- or C-terminus of the ActRIIB-ECD via a linker. In some embodiments, the polypeptide further comprises a signal peptide of SEQ ID NO: 1 at the N-terminus of the ActRIIB-ECD. In some embodiments, the polypeptide is conjugated with a targeting agent, a therapeutic moiety, a detectable moiety, or a diagnostic moiety.

In some embodiments, the targeting agent, the therapeutic moiety, the detectable moiety, or the diagnostic moiety comprises an antibody or antigen binding fragment thereof, a binding agent having affinity for another member of the TGFβ superfamily or for another therapeutic target, a radiotherapy agent, an imaging agent, a fluorescent moiety, a cytotoxic agent, an anti-mitotic drug, a nanoparticle-based carrier, a polymer-conjugated drug, a nanocarrier, an imaging agent, a stabilizing agent, a drug, a nanocarrier, or a dendrimer.

In some embodiments, the polypeptide forms a dimer comprising a first and a second polypeptide linked by at least one disulfide bond between the Fc domain monomer of the first polypeptide and the Fc domain monomer of the second polypeptide.

In some embodiments, the present disclosure provides a TGFβ superfamily ligand binding agent comprising a first polypeptide described herein and a second polypeptide described herein, wherein the first and second polypeptides are linked by at least one disulfide bond between the Fc domain monomer of the first polypeptide and the Fc domain monomer of the second polypeptide. In some embodiments, the first polypeptide and the second polypeptide comprise or consist of an amino acid sequence selected from SEQ ID NOs: 174-254, 333, and 339-341, or an amino acid sequence that is at least 95%, 96%, 97%, 98%, or 99% identical thereto.

In some embodiments, the first polypeptide and the second polypeptide comprise or consist of an amino acid sequence selected from SEQ ID NOs: 186, 190-194, 232-233, and 247-248, or an amino acid sequence that is at least 95%, 96%, 97%, 98%, or 99% identical thereto. In some embodiments, the first polypeptide and the second polypeptide comprise or consist of SEQ ID NOs: 186, or an amino acid sequence that is at least 95%, 96%, 97%, 98%, or 99% identical thereto. In some embodiments, the first polypeptide and the second polypeptide comprise or consist of an amino acid sequence selected from SEQ ID NOs: 213-216, and 242-244, or an amino acid sequence that is at least 95%, 96%, 97%, 98%, or 99% identical thereto. In some embodiments, the first polypeptide and the second polypeptide comprise or consist of an amino acid sequence selected from SEQ ID NOs: 220-223, 253, and 254, or an amino acid sequence that is at least 95%, 96%, 97%, 98%, or 99% identical thereto.

In some embodiments, the polypeptide or binding agent binds to human activin A, activin B, GDF-8, GDF-11, and/or bone morphogenetic protein (BMP)-10, and has reduced binding to human BMP-9 relative to the binding of a human wild type ActRIIB-ECD to human BMP-9. In some embodiments, the polypeptide or binding agent does not substantially bind to human BMP-9. In some embodiments, the polypeptide or binding agent inhibits signaling of one or more of human activin A, activin B, GDF-8, GDF-11, and BMP-10. In some embodiments, the polypeptide or binding agent does not inhibit human BMP-9 signaling.

In some embodiments, the inhibition potency of the polypeptide or binding agent for human BMP-9 signaling is about 100-fold, about 200-fold, or about 300-fold less compared to the inhibition potency of human wild type ActRIIB-ECD for human BMP-9 signaling. In some embodiments, the inhibition potency of the polypeptide or binding agent for one or more of human activin A, activin B, GDF-8, GDF-11, and BMP-10 is substantially the same as, or is increased compared to the inhibition potency of human wild type ActRIIB-ECD for the same respective ligand(s). In some embodiments, the inhibition potency of the polypeptide or binding agent for one or more of human activin A, activin B, GDF-8, GDF-11, and BMP-10 is increased by about 2-fold, about 3-fold, about 4-fold, or about 5-fold, or more compared to the inhibition potency of the human wild type ActRIIB-ECD for the same respective ligand(s).

In some embodiments, the present disclosure provides a nucleic acid molecule encoding a polypeptide described herein. In some embodiments, the nucleic acid sequence is at least at least 95%, at least 96%, at least 97%, at least 98%, or at least 99% identical to any one of SEQ ID NOs: 256-330, 334, or 342-344. In some embodiments, the nucleic acid molecule comprises or consists of the nucleic acid sequence of any one of SEQ ID NOs: 256-330, 334, or 342-344. In some embodiments, the nucleic acid further comprises the sequence set forth in SEQ ID NO: 255 at the 5' end of the nucleic acid molecule.

In some embodiments, the present disclosure provides a vector comprising a nucleic acid described herein. In some embodiments, the present disclosure provides a host cell comprising a nucleic acid molecule or vector described herein, wherein the nucleic acid molecule or the vector is expressed in the host cell.

In some embodiments, the present disclosure provides a method of preparing a polypeptide described herein comprising: (a) providing a host cell comprising a nucleic acid molecule or vector described herein, and (b) culturing the host cell under conditions allowing expression of the polypeptide; and (c) recovering the expressed polypeptide from the culture.

In some embodiments, the present disclosure provides a pharmaceutical composition comprising a polypeptide or binding agent described herein and a pharmaceutically acceptable carrier, diluent or excipient. In some embodiments, the composition is formulated for administration by injection or infusion. In some embodiments, the composition is formulated for intravenous, subcutaneous, intraperitoneal, or intramuscular administration.

In some embodiments, the polypeptide or binding agent does not cause a vascular complication in a subject and/or does not increase vascular permeability or leakage in a subject. In some embodiments, the polypeptide or binding agent does not increase red blood cell mass, does not increase hemoglobin, does not cause thrombocytopenia, and/or does not cause a hematological complication in a subject.

In some embodiments, the present disclosure provides a kit comprising a polypeptide or binding agent described herein, or a pharmaceutical composition described herein and, optionally, directions for use.

In some embodiments, the present disclosure provides a method of treating or preventing a disease or condition associated with TGFβ-superfamily ligand signaling in a subject in need thereof, the method comprising administering a polypeptide, binding agent, or pharmaceutical composition described herein to the subject. In some embodiments, the subject is a human. In some embodiments, the TGFβ-superfamily ligand is one or more of activin A, activin B, GDF-8, GDF-11, and BMP-10.

In some embodiments, the present disclosure provides a method of treating or preventing a disease or condition associated with or mediated by activin A, activin B, GDF-8, GDF-11, and/or BMP-10 in a subject, the method comprising administering a polypeptide, binding agent, or pharmaceutical composition described herein to the subject. In some embodiments, the disease or condition is characterized by overexpression or overactivation of activin A and/or activin B and/or GDF-8 and/or GDF-11.

In some embodiments, the disease or condition is selected from pulmonary hypertension (PH), fibrosis, muscle weakness or atrophy, metabolic disorders, cardiometabolic disease, bone damage, and low red blood cell levels.

In some embodiments, the PH is pulmonary arterial hypertension (PAH). In some embodiments, the PAH is idiopathic PAH, heritable PAH, or PAH associated with an infection, a congenital heart abnormality, portal hypertension, pulmonary veno-occlusive disease, pulmonary capillary hemangiomatosis, a connective tissue disorder, chronic obstructive pulmonary disease, an autoimmune disorder (e.g., scleroderma or lupus), or drug use (e.g., use of cocaine or methamphetamine).

In some embodiments, the fibrosis is pulmonary fibrosis, idiopathic pulmonary fibrosis, renal fibrosis, liver fibrosis, lung fibrosis, kidney fibrosis, bone marrow fibrosis, systemic sclerosis, skin fibrosis, heart fibrosis, myelofibrosis, corneal fibrosis, mediastinal fibrosis, retroperitoneal fibrosis, osteoarticular fibrosis, arthrofibrosis, tissue fibrosis, a fibroproliferative disorder or a connective tissue disorder.

In some embodiments, the muscle weakness or atrophy disease or condition is Duchenne muscular dystrophy (DMD), facioscapulohumeral muscular dystrophy (FSHD), inclusion body myositis (IBM), amyotrophic lateral sclerosis (ALS), sarcopenia, or cancer cachexia.

In some embodiments, the metabolic disorder is obesity, Type 1 diabetes, Type 2 diabetes, or pre-diabetes.

In some embodiments, the cardiometabolic disease or condition is heart failure with a reduced ejection fraction (HFrEF) or heart failure with preserved ejection fraction (HFpEF).

In some embodiments, the bone damage comprises bone demineralization, osteoporosis (e.g., primary or secondary), osteopenia, osteopetrosis, bone fracture, bone cancer or cancer metastasis-related bone loss, Paget's disease, renal osteodystrophy, treatment-related bone loss, diet-related bone loss, bone loss associated with the treatment of obesity, low gravity-related bone loss, or immobility-related bone loss.

In some embodiments, the low blood cell level disease or condition is anemia or blood loss.

In some embodiments, the present disclosure provides a method of reducing or inhibiting activin A, activin B, GDF-8, GDF-11 and/or BMP10 signaling in a subject in need thereof without substantially reducing or inhibiting BMP9 signaling in the subject, the method comprising administering a polypeptide, binding agent, or pharmaceutical composition described herein to the subject. In some embodiments, the subject is a mammal. In some embodiments, the mammal is a human.

In some embodiments, the method does not: cause a vascular complication in a subject; increase vascular permeability or leakage in a subject; increase red blood cell mass; increase hemoglobin; cause thrombocytopenia; and/or cause a hematological complication in a subject.

Further scope, applicability and advantages of the present technology will become apparent from the non-restrictive detailed description given hereinafter. It should be understood, however, that this detailed description, while indicating exemplary embodiments of the technology, is given by way of example only, with reference to the accompanying drawings.

BRIEF DESCRIPTION OF THE DRAWINGS

For a better understanding of the technology and to show more clearly how it may be carried into effect, reference will now be made by way of example to the accompanying drawings, which illustrate aspects and features according to non-limiting embodiments of the present technology.

FIG. 2A shows results for activin A, FIG. 2B shows results for activin B, FIG. 2C shows results for GDF-8, and FIG. 2D shows results for GDF-11. Error bars indicate standard error of the mean (SEM). The dashed line represents baseline activity.

FIG. 3A shows results for BMP-9 and FIG. 3B shows results for BMP-10. Error bars indicate standard error of the mean (SEM).

FIG. 4A shows results for P120 and P121, FIG. 4B shows results for P122, P123, and P125, FIG. 4C shows results for P126 and P127, and FIG. 4D shows results for P622 and P624, as indicated. Error bars indicate standard error of the mean (SEM).

FIG. 5A shows results for P120 and P121, FIG. 5B shows results for P122, P123, and P125, FIG. 5C shows results for P126 and P127, and FIG. 5D shows results for P622 and P624, as indicated. Error bars indicate standard error of the mean (SEM).

FIG. 6A shows results for P120, and P121, FIG. 6B shows results for P122, P123, and P125, FIG. 6C shows results for P126 and P127, and FIG. 6D shows results for P622 and P624, as indicated. Error bars indicate standard error of the mean (SEM).

FIG. 7A shows results for P120, and P121, FIG. 7B shows results for P122, P123, and P125, FIG. 7C shows results for P126 and P127, and FIG. 7D shows results for P622 and P624, as indicated. Error bars indicate standard error of the mean (SEM).

FIG. 8A shows results for P120 and P121, FIG. 8B shows results for P122, P123, and P125, FIG. 8C shows results for P126 and P127, and FIG. 8D shows results for P622 and P624, as indicated. Error bars indicate standard error of the mean (SEM).

FIG. 9A shows results for P120 and P121, FIG. 9B shows results for P122, P123, and P125, FIG. 9C shows results for P126 and P127, and FIG. 9D shows results for P622 and P624, as indicated. Error bars indicate standard error of the mean (SEM).

FIGS. 10A-10F show exemplary test proteins for which increased linker length improved potency for all or a subset of ligands. FIGS. 10G-10J show exemplary test proteins for which increased linker length decreased potency for a subset of ligands. FIGS. 10K-10L show exemplary test proteins for which increased linker length did not affect potency on any of the ligands tested.

FIG. 11A shows results for P757, P758, P759, P761, and P762, FIG. 11B shows results for P694, P715, P718, P719, and P720, FIG. 11C shows results for P119, P441, and P124, and FIG. 11D shows results for P687, P1213, P1215, and P1217, as indicated. Error bars indicate standard error of the mean (SEM).

FIG. 12A shows results for P757, P758, P759, P761, and P762, FIG. 12B shows results for P694, P715, P718, P719, and P720, FIG. 12C shows results for P119, P441, and P124, and FIG. 12D shows results for P687, as indicated. Error bars indicate standard error of the mean (SEM).

FIG. 13A shows results for P757, P758, P759, P761, and P762, FIG. 13B shows results for P694, P715, P718, P719, and P720, FIG. 13C shows results for P119, P441, and P124, and FIG. 13D shows results for P687, P1213, P1215, and P1217, as indicated. Error bars indicate standard error of the mean (SEM).

FIG. 14A shows results for P757, P758, P759, P761, and P762, FIG. 14B shows results for P694, P715, P718, P719, and P720, FIG. 14C shows results for P119, P441, and P124, and FIG. 14D shows results for P687, as indicated. Error bars indicate standard error of the mean (SEM).

FIG. 15A shows results for P757, P758, P759, P761, and P762, FIG. 15B shows results for P694, P715, P718, P719, and P720, FIG. 15C shows results for P119, P441, and P124, and FIG. 15D shows results for P687, P1213, P1215, and P1217, as indicated. Error bars indicate standard error of the mean (SEM).

FIG. 16A shows results for P757, P758, P759, P761, and P762, FIG. 16B shows results for P694, P715, P718, P719, and P720, FIG. 16C shows results for P119, P441, and P124, and FIG. 16D shows results for P687, as indicated. Error bars indicate standard error of the mean (SEM).

FIG. 17A shows the average concentration of agents in mouse serum following a single intraperitoneal injection of P121 or P75 at 10 mg/kg and 50 mg/kg, and FIG. 17B shows exposure vs. dose level of P622 or P75 at 1 mg/kg, 3 mg/kg, 10 mg/kg, 25 mg/kg, and 50 mg/kg in mouse serum.

FIG. 19A shows results for gastrocnemius, FIG. 19B shows results for quadriceps, FIG. 19C shows results for pectoralis, and FIG. 19D shows results for triceps. Data are presented as a percent increase compared to vehicle at the end of the study; left- and right-side muscles were averaged for each mouse. FIG. 19E shows results for Mss51 expression levels and FIG. 19F shows results for Igf2 expression levels in quadriceps muscle were assessed. Tissues were snap-frozen after collection, and <30 mg of tissue was lysed using sonication (5 cycles of 10 seconds, with 5 seconds rest on ice). RNA was extracted using a RNeasy fibrous tissue kit (Qiagen #74704) following the manufacturer's instructions. RNA was reverse transcribed, and gene expression was assessed by qPCR as per manufacturer's instructions (Qiagen). Actb and Gapdh were used as housekeeping genes. Error bars indicate standard error of the mean (SEM). Results were analyzed by one-way ANOVA followed by post-hoc Bonferroni-corrected multiple comparison test; *p<0.05, p<0.01, *p<0.001, ***p<0.0001.

FIG. 21A-FIG. 21C shows results from P622 treatment. FIG. 21D-FIG. 21F shows results from P624 treatment. Parameters assessed were (FIG. 21A and FIG. 21D) red blood cell (RBC) count, (FIG. 21B and FIG. 21E) hemoglobin levels, and (FIG. 21C and FIG. 21F) hematocrit. Error bars indicate standard error of the mean (SEM). Results were analyzed by two-way ANOVA followed by post-hoc Bonferroni-corrected multiple comparison test.

(FIG. 25A-FIG. 25B) Pathology evaluation on stained sections was performed on each animal by characterizing 30 blood vessels in the peripheral region and between 10-50 m in external diameter as non-muscularized, partially muscularized, or fully muscularized. (FIG. 25L-FIG. 25O) RV samples from 3 animals per group (naïve, MCT+Vehicle, MCT+P670 16 mg/kg, and MCT+P671 16 mg/kg) were analyzed by RNA-sequencing. (FIG. 25L-FIG. 25M) Expression level heatmaps for all differentially expressed genes (DEGs) between Naive and MCT samples (FIG. 25L) and for DEGs belonging to KEGG pathways of interest in this disease model (FIG. 25M). Values are centered to the mean expression levels of the naïve animals. (FIG. 25N-FIG. 25O) Number of DEGs using the naïve group (FIG. 25N) or MCT group (FIG. 25O) as reference.

(FIG. 26A) activin A (n=5), (FIG. 26B) GDF-8 (n=5), (FIG. 26C) GDF-11 (n=6), and (FIG. 26D) activin AB (n=1). On day 3 (~24 h later), cells were harvested, and RNA was collected for RT-qPCR analyses. ACTA2 and CTGF mRNA levels were assessed relative to GAPDH, a housekeeping gene. Error bars indicate standard error of the mean (SEM). Results were analyzed by one-way ANOVA followed by post-hoc Bonferroni-corrected multiple comparison test.

(FIG. 27A) activin A+GDF-8 (n=3), and (FIG. 27B) activin A+GDF-11 (n=3). On day 3 (~24 h later), cells were harvested, and RNA was collected for RT-qPCR analyses. ACTA2 (FIG. 27A and FIG. 27D), CTGF (FIG. 27B and FIG. 27E), and INHBA (FIG. 27C and FIG. 27F) mRNA levels were assessed relative to GAPDH, a housekeeping gene. Error bars indicate standard error of the mean (SEM). Results were analyzed by one-way ANOVA followed by post-hoc Bonferroni-corrected multiple comparison test.

(FIG. 28A) GDF-8+GDF-11 (n=3), and (FIG. 28B) Activin B+GDF-8 (n=2). On day 3 (~24 h later), cells were harvested, and RNA was collected for RT-qPCR analyses. ACTA2 (FIG. 28A and FIG. 28D), CTGF (FIG. 28B and FIG. 28E), and INHBA (FIG. 28C and FIG. 28F) mRNA levels were assessed relative to GAPDH, a housekeeping gene. Error bars indicate standard error of the mean (SEM). Results were analyzed by one-way ANOVA followed by post-hoc Bonferroni-corrected multiple comparison test.

(FIG. 29A) Phosphorylated SMAD2 (pSMAD2) and (FIG. 29B) pSMAD3 were assessed by immunohistology. Error bars indicate standard error of the mean (SEM). Results were analyzed by one-way ANOVA followed by post-hoc Bonferroni-corrected multiple comparison test. (FIG. 29C) Displays representative pSMAD3 images from certain exemplary agents.

(FIG. 30A) Inhba, (FIG. 30B) Gdfl1, and (FIG. 30C) Serpine1 mRNA levels were assessed relative to Rpl13a, Rpl19, Gusb, and Gapdh, which are housekeeping genes. Error bars indicate standard error of the mean (SEM). Results were analyzed by one-way ANOVA followed by post-hoc Bonferroni-corrected multiple comparison test.

(FIG. 31A) Body weights at day 21, normalized to the vehicle group. (FIG. 31B-FIG. 31C) Gastrocnemius and tibialis anterior weights were normalized to the vehicle group, and plotted as a function of dose. (FIG. 31D) FSH levels were assessed in plasma at day 21 (MPTMAG-49K, Millipore Sigma). (FIG. 31E) FSHβ (Fshb) gene expression levels were assessed in pituitary glands. Pituitary gland was snap-frozen and lysed using the gentleMACS™ Octo Dissociator (Miltenyi Biotech). RNA was extracted and reverse transcribed, and gene expression was assessed by qPCR as per manufacturer's instructions (Qiagen). Actb and Gapdh were used as housekeeping genes. Error bars indicate standard error of the mean (SEM). Results were analyzed by one-way ANOVA followed by post-hoc Bonferroni-corrected multiple comparison test. *$p<0.05$, $p<0.01$, *$p<0.001$, ***$p<0.0001$.

DETAILED DESCRIPTION

Overview

Figure 1B:
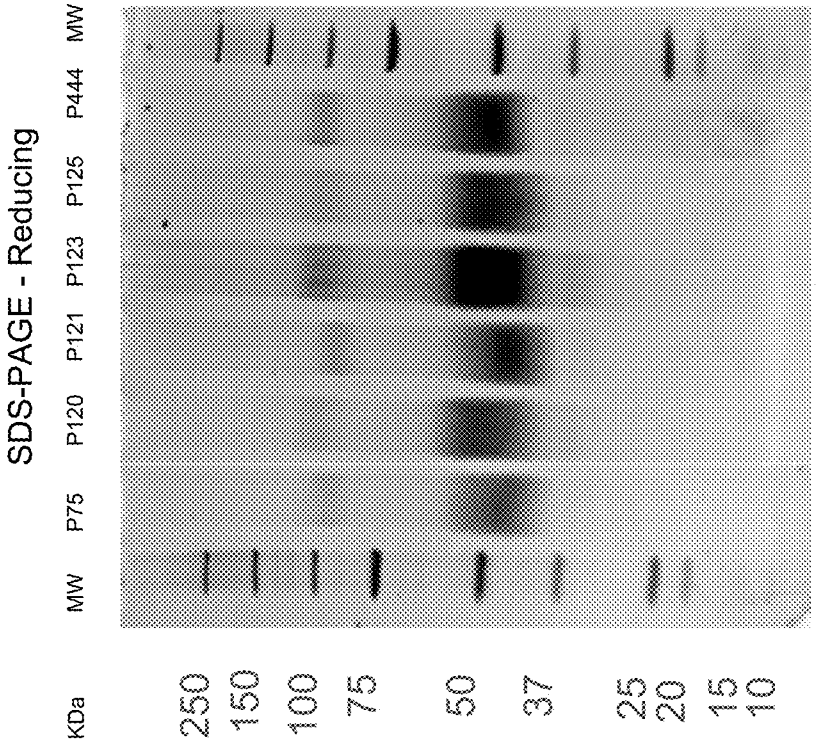
FIG. 1A-FIG. 1B show polyacrylamide gel electrophoresis analysis under (FIG. 1A) non-reducing and (FIG. 1B) reducing conditions of representative ActRIIB-ECD polypeptide constructs. After expression and purification, 1 μg of each protein was loaded on the gel, as indicated: P75: Protein 75; P120: Protein 120; P121: Protein 121; P123: Protein 123; P125: Protein 125; P444: Protein 444. "NR": non-reducing conditions; "R": reducing conditions.

Activin type II receptors are single transmembrane domain receptors that modulate signals for ligands in the TGFβ superfamily. There exist two types of activin type II receptors: ActRIIA and ActRIIB. Examples of ligands in the TGFβ superfamily include activin (e.g., activin A and activin B), inhibin, growth differentiation factors (GDFs) (e.g., GDF-8, also known as myostatin and GDF-11), and bone morphogenetic proteins (BMPs) (e.g., BMP-9, BMP-10). Activity of TGFβ superfamily ligands has been implicated in a variety of diseases and disorders including pulmonary hypertension (PH), fibrosis, muscular diseases (including muscular dystrophy), metabolic disorders (including Type II diabetes), bone diseases, and anemia.

One approach to developing therapeutic agents that inhibit TGFβ superfamily ligand function has been to use soluble decoy receptors (also termed receptor ectodomain (ECD)-based ligand traps) to bind and sequester ligands, thereby blocking access to the cell surface receptors. In general, receptor ECD-based traps are a class of therapeutic agents that are able to selectively sequester ligands, and that can be optimized using protein-engineering approaches. For example, polypeptide fusions based on a TGFβ receptor ectodomain that binds or "traps" the TGFβ 1 and/or TGFβ2 and/or TGFβ3 ligand isoforms have been used to inhibit TGFβ signaling (see for example, WO01/83525; WO2005/028517; WO2008/113185; WO2008/157367; WO2010/0031168; WO2010/099219; WO2012/071649; WO2012/142515; WO2013/000234; WO2018/158727; U.S. Pat. No. 5,693,607; US2005/0203022; US2007/0244042; U.S. Pat. Nos. 8,318,135; 8,658,135; 8,815,247; US2015/0225483; US2015/0056199; and WO2017/037634).

In the endothelium and vasculature of the lung, bone morphogenetic proteins (BMPs) can induce anti-proliferative effects in smooth muscle cells (SMCs) and survival of endothelial cells (ECs), while activins and growth differentiation factors (GDFs) can induce opposing effects, i.e., pro-proliferative effects in SMCs and apoptosis of ECs (Yung, L. M. et al., 2020; Ryanto, G. R. T. et al., 2021). Under physiological conditions, these ligands act in concert to maintain homeostasis. However, in certain disease conditions such as PAH these pathways become unbalanced. For example, nearly ~80% of familial and ~20% of idiopathic cases of PAH are caused by mutations in the bone morphogenetic protein (BMP) type 2 receptor (BMPR2) (Austin, E. D. and Loyd, J. E., 2007; Quarck, R. and Perros, F., 2017). This results in an imbalance between activin/GDF and BMP signaling pathways (Ryanto, G. R. T. et al., 2021). It is desirable therefore to provide a receptor ectodomain-based trap that can neutralize certain ligands and not others, in order to rebalance the pathways and to re-establish vascular homeostasis.

Some ECD-based traps comprise amino acid mutations in the ectodomain portion of the compound in order to alter binding to one or more TGFβ superfamily ligands. See e.g., WO 2021/158675; WO 2022/150590; WO 2021/158675; WO 2022/072882; WO 2021/189019; and WO 2021/189010. Although point mutations in the ActRIIB ECD have been described in the context of other trap-based agents, the present disclosure highlights the effects of these mutations when combined with long peptide linkers. Specifically, the data in the present application demonstrate that certain mutations in the ActRIIB ECD have unpredictable effects on TGFβ superfamily ligand binding when combined with long peptide linkers (i.e., 10 or more amino acids).

The present application therefore provides TGFβ superfamily ligand binding agents that demonstrate improved ligand binding profiles and therapeutic efficacy. The combination of point mutations in the ActRIIB ECD with the long linkers described herein provides a platform by which the beneficial ligand binding profiles of these point mutations can be further enhanced by combination with linkers of a particular length. These platform compounds are useful in the treatment of various diseases and disorders driven by TGFβ superfamily ligands including pulmonary hypertension, muscular diseases, metabolic disorders, bone diseases, anemia, and fibrosis.

The present technology is explained in greater detail below. This description is not intended to be a detailed catalog of all the different ways in which the technology may be implemented, or all the features that may be added to the instant technology. For examples, features illustrated with respect to one embodiment may be incorporated into other embodiments, and features illustrated with respect to a particular embodiment may be deleted from that embodiment. In addition, numerous variations and additions to the various embodiments suggested herein will be apparent to those skilled in the art in light of the instant disclosure, which variations and additions do not depart from the present technology. Hence, the following description is intended to illustrate some particular embodiments of the technology, and not to exhaustively specify all permutations, combinations and variations thereof.

Definitions

In order to provide a clear and consistent understanding of the terms used in the present specification, a number of definitions are provided below. Moreover, unless defined otherwise, all technical and scientific terms as used herein have the same meaning as commonly understood to one of ordinary skill in the art to which this invention pertains.

The use of the terms "a" and "an" and "the" when used in conjunction with the term "comprising" in the claims and/or the specification may mean "one", but it is also consistent with the meaning of "one or more", "at least one", and "one or more than one". Similarly, the term "another" may mean at least a second or more. These terms are to be construed to cover both the singular and the plural, unless otherwise indicated herein or clearly contradicted by context.

As used herein, the terms "comprising" (and any form of comprising, such as "comprise" and "comprises"), "having" (and any form of having, such as "have" and "has"), "including" (and any form of including, such as "include" and "includes") or "containing" (and any form of containing, such as "contain" and "contains"), are inclusive or open-ended and do not exclude additional, unrecited elements or process steps. The term "consisting of" is to be construed as close-ended.

The term "about" is used to indicate that a value or quantity refers to the actual given value and also the approximation of such given value that would reasonably be inferred based on the ordinary skill in the art, including equivalents and approximations due to the experimental and/or measurement conditions for such given value. For example, the term "about" in the context of a given value or range refers to a value or range that is within 20%, preferably within 15%, more preferably within 10%, more preferably within 9%, more preferably within 8%, more preferably within 7%, more preferably within 6%, and more preferably within 5% of the given value or range.

The expression "and/or" where used herein is to be taken as specific disclosure of each of the specified features or components with or without the other. For example, "A and/or B" is to be taken as specific disclosure of each of (i) A, (ii) B, and (iii) A and B, just as if each is set out individually herein. Unless specifically stated or obvious from context, as used herein the term "or" is understood to be inclusive and covers both "or" and "and". For example, an embodiment of "a composition comprising A or B" would typically present an aspect with a composition comprising both A and B. "Or" should, however, be construed to exclude those aspects presented that cannot be combined without contradiction (e.g., a composition pH that is between 9 and 10 or between 7 and 8).

It is to be understood herein that terms such as "from 1 to 20" include any individual values comprised within and including 1 and 20. Therefore, the term "from 1 to 20" includes 1, 2, 3, 4, 5, 6, 7, 8, 9, 10, 11, 12, 13, 14, 15, 16, 17, 18, 19 and/or 20. Terms such as "from 1 to 20" also include any individual sub-ranges comprised within and including from 1 to 20. The term "from 1 to 20" therefore also includes sub-ranges such as "from 1 to 9", "from 2 to 9", "from 3 to 5", from 5 to 9", "from 5 to 20", "from 8 to 20" etc. The same applies for similar expressions such as and not limited to "from 1 to 19", "from 1 to 18", "from 1 to 10", "from 1 to 9", "from 5 to 15", etc.

It is to be understood herein that terms such as "from about 15 to about 35" include any individual values comprised within and including 15 and 35. Therefore, terms such as "from about 15 to about 35" include any number between and including 15 and 35 such as 15, 16, 17, 18, 19, 20, 21, 22, 23, 24, 25, 26, 27, 28, 29, 30, 31, 32, 33, 34 and/or 35. Terms such as "from about 15 to about 35" also include any individual sub-ranges comprised within and including from 15 to 35, "from about 16 to about 34", "from about 16 to about 24", from about 24 to about 34" and the like. The term "about" in the context of the number of amino acids means that the specified number of amino acids is specifically encompassed and allows a variation of +/−2 in the number of amino acid residues. As such, the terms such as "from about 15 to about 35" also includes "from 13 to 37", "from 13 to 35", "from 17 to 37", from 17 to 35", etc. The same applies for similar expressions such as and not limited to "from about 16 to about 34", "from about 16 to about 24", from about 24 to about 34" and the like.

It is to be understood herein that terms such as "at least 80% identical" include any individual values comprised within and including from 80% to 100% and including 80%, 81%, 82%, 83%, 84%, 85%, 86%, 87%, 88%, 89%, 90%, 91%, 92%, 93%, 94%, 95%, 96%, 97%, 98%, 99% and 100%. The term "at least 80% identical" also includes any individual sub-ranges comprised within and including from 80% to 100%, such as for example, "from 85% to 99%", "from 97% to 100%", "from 90% to 100%", etc. The same applies for similar expressions such as, and not limited to, expressions such as "at least 70% identical", "at least 90% identical", and the like.

As used herein, the term "IC50" refers to the half maximal inhibitory concentration (i.e., the concentration of a substance that is required for 50% inhibition in vitro). It is a measure of the potency or effectiveness of a substance in inhibiting a specific biological or biochemical function. IC50 values are typically expressed as molar concentration. The IC50 of an inhibitor can be determined by constructing a dose-response curve and examining the effect of different concentrations of inhibitor on the specific biological or biochemical function in question.

As used herein, the term "inhibition potency" refers to effectiveness of a substance in inhibiting a specific biological or biochemical function such as, without limitation, binding between a protein receptor and its ligand, or activation of a cell receptor by its ligand. In some embodiments, potency of inhibition is determined by measuring the IC50 of an inhibitor for a particular ligand or substrate. In that case, relative inhibition potency for different inhibitors and/or ligands may be assessed by comparing IC50 values. For example, a relative inhibition potency of 3:1 means the ratio of IC50 values for two substances being compared is 3:1, wherein the first substance has a lower inhibition potency (i.e., a greater IC50) than the second substance. A relative inhibition potency of 1:3 means the ratio of IC50 values for two substances being compared is 1:3, wherein the first substance has a greater inhibition potency (i.e., a lower IC50) than the second substance. As the IC50 of an inhibitor can vary depending on the assay conditions, relative inhibition potency for different inhibitors and/or ligands is generally determined by comparing IC50 values obtained under the same assay conditions. The terms "inhibition potency", "inhibitory potency", "potency of inhibition" and "neutralization potency" are used interchangeably herein.

As used herein, the term "substantially the same" in reference to relative inhibition potency means that two proteins have a relative inhibition potency that is about the same, e.g., no more than about 2-fold different (+/−2-fold) under the same experimental conditions, e.g., the ratio of IC50 values for the two proteins is about 2:1, 1:2, or 1:1.

As used herein, the term "functionally equivalent" refers to variant sequences that have the same or substantially the same biological activity or function as the original sequence from which it is derived, e.g., no significant change in physiological, chemical, physiochemical or functional properties compared to the original sequence. The term "substantially identical" refers to sequences that are functionally equivalent to the original or reference sequence and have a high degree of sequence identity thereto. Generally, a substantially identical sequence is at least about 80%, at least about 85%, at least about 90%, at least about 95%, at least about 96%, at least about 97%, at least about 98%, or at least about 99% identical to the original or reference sequence and has the same function. In some cases when referring to nucleic acid sequences, a substantially identical sequence hybridizes to the original sequence under high stringency conditions, for example at salt and temperature conditions substantially equivalent to 0.5×SSC to about 5×SSC and 65° C. for both hybridization and wash.

The term "dimeric" refers to the presence of two polypeptides as described herein in a TGFβ superfamily ligand binding agent (also referred to herein as a "binding agent"). "Homodimeric" means the two polypeptides have the same amino acid sequence, whereas "heterodimeric" means the two polypeptides have different amino acid sequences.

The term "divalent" refers to the presence of two TGFβ R superfamily ligand binding regions (e.g., the ectodomains) in a TGFβ superfamily ligand binding agent.

As used herein, a "recombinant polypeptide" is a polypeptide made through the use of recombinant DNA technology or genetic engineering. In the context of the present disclosure, recombinant polypeptides are often referred to as "polypeptide constructs" or simply as "polypeptides".

Proteins (including fragments thereof, preferably biologically active fragments, and peptides, usually having less than 30 amino acids) comprise two or more amino acids coupled to each other via a covalent peptide bond (resulting in a chain of amino acids). The term "polypeptide" as used herein describes a group of molecules, which usually consist of more than 10 amino acids. The terms "polypeptide", "polypeptide chain" and "chain" are used interchangeably herein. Polypeptides may further form multimers such as dimers, trimers, and higher oligomers, i.e., consisting of more than one polypeptide molecule. Polypeptide molecules forming such dimers, trimers etc. may be identical or non-identical. The corresponding higher order structures of such multimers are, consequently, termed homo- or heterodimers, homo- or heterotrimers etc. An example for a heteromultimer is an antibody molecule, which, in its naturally occurring form, consists of two identical light polypeptide chains and two identical heavy polypeptide chains. The terms "peptide", "polypeptide" and "protein" also refer to naturally modified peptides/polypeptides/proteins wherein the modification is effected, e.g. by post-translational modifications like glycosylation, acetylation, phosphorylation and the like. A "peptide", "polypeptide" or "protein" when referred to herein may also be chemically modified such as pegylated. Such modifications are well known in the art and described herein.

As used herein, the terms "(specifically) binds to", (specifically) recognizes", "specific for", "is (specifically) directed to", and "(specifically) reacts with" mean that a polypeptide interacts or specifically interacts with a given target(s), such as a specific member(s) of the TGFβ superfamily of ligands. Specific binding is believed to be effected by specific motifs in the amino acid sequence of a polypeptide. Thus, binding is achieved as a result of their primary, secondary and/or tertiary structure as well as the result of secondary modifications of said structures. The specific interaction of the target-interaction-site with its specific target may result in a simple binding of said site to the target. Moreover, the specific interaction of the target-interaction-site with its specific target may alternatively or additionally result in the initiation of a signal, e.g. due to the induction of a change of the conformation of the target, an oligomerization of the target, etc., or may block the target from performing another activity, such as binding to an endogenous receptor.

Generally, binding is considered specific when the binding affinity is about 10-12 to 10-9 M, 10-12 to 10-19 M, 10-11 to 10-9 M, or of about 10-11 to 10-9 M. Whether a polypeptide or binding agent specifically reacts with or binds to a target can be tested readily by, inter alia, comparing the reaction of the polypeptide or binding agent with a target with the reaction of the polypeptide or binding agent with other proteins. In some embodiments, a polypeptide or binding agent of the disclosure does not substantially bind to TGFβ superfamily ligands other than the desired ligands, e.g., does not substantially bind to BMP-9.

As used herein, the term "does not substantially bind" or "is not capable of binding" means that a polypeptide or binding agent of the present disclosure does not demonstrate detectable binding to a given target, e.g., does not show reactivity of more than 30%, not more than 20%, not more than 10%, or not more than 9%, 8%, 7%, 6%, 5% or 3% with the given target.

As used herein, the term "selectively binds" is used to mean that a polypeptide binds to a target site that is not shared with other proteins. In general, a selective binding agent will not cross-react with other proteins and exclusively binds to the designated target protein(s). In the context of the present disclosure, "selective for activin A and GDF-8" means that a polypeptide or binding agent binds or neutralizes the activin A and GDF-8 ligands exclusively, without substantially binding or neutralizing other TGFβ superfamily ligands such as, e.g., BMP-9.

"Half-life" means the time where 50% of an administered drug is eliminated through biological processes, e.g., metabolism, excretion, etc.

"Hepatic first-pass metabolism" refers to the propensity of a drug to be metabolized upon first contact with the liver, i.e., during its first pass through the liver.

"Volume of distribution" refers to the degree of retention of a drug throughout the various compartments of the body, such as, e.g., intracellular and extracellular spaces, tissues and organs, etc. and the distribution of the drug within these compartments.

"Degree of blood serum binding" refers to the propensity of a drug to interact with and bind to blood serum proteins, such as albumin, leading to a reduction or loss of biological activity of the drug.

The term "amino acid" or "amino acid residue" typically refers to an amino acid having its art recognized definition such as an amino acid selected from the group consisting of: alanine (Ala or A); arginine (Arg or R); asparagine (Asn or N); aspartic acid (Asp or D); cysteine (Cys or C); glutamine (Gln or Q); glutamic acid (Glu or E); glycine (Gly or G); histidine (His or H); isoleucine (He or I): leucine (Leu or L); lysine (Lys or K); methionine (Met or M); phenylalanine (Phe or F); pro line (Pro or P); serine (Ser or S); threonine (Thr or T); tryptophan (Trp or W); tyrosine (Tyr or Y); and valine (Val or V), although modified, synthetic, or rare amino acids may be used as desired. Generally, amino acids can be grouped as having a nonpolar side chain (e.g., Ala, Cys, He, Leu, Met, Phe, Pro, Val); a negatively charged side chain (e.g., Asp, Glu); a positively charged sidechain (e.g., Arg, His, Lys); or an uncharged polar side chain (e.g., Asn, Cys, Gin, Gly, His, Met, Phe, Ser, Thr, Trp, and Tyr).

In a similar manner, "percent (%) nucleic acid sequence identity" with respect to the nucleic acid sequence of the polypeptides or binding agents identified herein is defined as the percentage of nucleotide residues in a candidate sequence that are identical with the nucleotide residues in the coding sequence of the polypeptides or binding agents. A specific method utilizes the BLASTN module of WU-BLAST-2 set to the default parameters, with overlap span and overlap fraction set to 1 and 0.125, respectively.

TGFβ Superfamily Ligand Binding Agents

Figure 36:
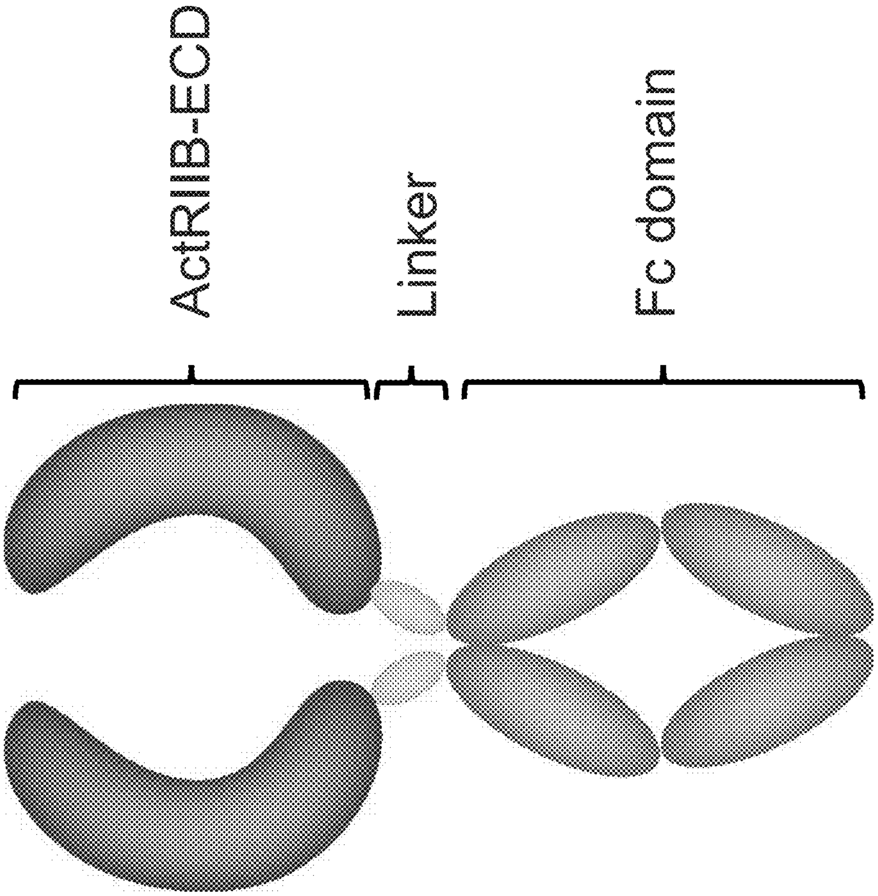
FIG. 36 provides an exemplary schematic of binding agents described herein.

In some embodiments, the present disclosure provides TGFβ superfamily ligand binding agents comprising an ActRIIB-ECD region, a linker region, and an Fc domain (also referred to herein as "binding agents" or "TGFβ ligand binding agents"). The individual components of the binding agents described herein are described in further detail in the following sections. In general, however, the binding agents described herein are dimeric proteins comprising two polypeptides each comprising an ActRIIB-ECD, a peptide linker, and an Fc domain monomer. The two polypeptides assemble via the Fc domain monomers to form the dimeric binding agents described herein. See schematic in FIG. 36. When assembled, the Fc domain monomers in each of the polypeptides form a dimeric Fc domain at one terminus and a divalent ActRIIB-ECD region at the other terminus. Binding agents of the present disclosure can bind to one or more ligand selected from activin A, activin B, GDF-8, GDF-11, and BMP-10 and inhibit signaling of the one or more ligand through their respective receptors, without substantially binding to BMP-9 and/or inhibiting BMP-9 signaling through its receptor. Binding agents may also have further biological activities or functions such as binding to other ligands or targets and the like, as further described herein.

In some embodiments, the binding agents of the present disclosure include two polypeptide chains that are associated via an Fc domain monomer of an antibody or via a constant CH2 domain, a constant CH3 domain and/or via a combination of CH2 and CH3. The constant region of the antibody may be from a human IgG1, IgG2, IgG3 or IgG4 antibody, or substantially identical thereto. The association of both polypeptide chains generally occurs during expression and secretion of the protein, e.g. in mammalian cells. The Fc domain monomer generally comprises a CH2, a CH3, or a CH2 and a CH3 from an antibody heavy chain that is of human origin and typically provides for disulfide crosslinking between single chain polypeptides. In an embodiment, the Fc domain monomer provides for at least one disulfide link between single chain polypeptides. In another embodiment, the Fc domain monomer provides for at least two disulfide links between single chain polypeptides. In some cases, the antibody heavy chain also provides for Protein A-based isolation of the dimeric polypeptide, e.g. after production in host cells.

As noted above, certain TGFβ superfamily ligand binding agents and point mutations in the ECD are described in the art. See e.g., WO 2021/158675; WO 2022/150590; WO 2021/158675; WO 2022/072882; WO 2021/189019; and WO 2021/189010. Although point mutations in the ActRIIB ECD have been described in the context of other TGFβ superfamily ligand binding agents, the effects of these mutations in the context of these previously described agents do not predict the effects of these same mutations in the context of the binding agents described herein. Specifically, the data in the present application demonstrates that certain mutations in the ActRIIB have unpredictable effects on TGFβ superfamily ligand binding when combined with peptide linkers of variable lengths.

For example, P121, P622, P624, P666, and P667 each have the F58E mutation in the ActRIIB-ECD. P121 and P624 have a 3aa linker connecting the ActRIIB ECD and the Fc domain, P622 has a 14aa linker connecting the ActRIIB ECD and the Fc domain, P666 has a 19aa linker connecting the ActRIIB ECD and the Fc domain, and P667 has a 39aa linker connecting the ActRIIB ECD and the Fc domain. As shown in Table 9 below, combination of the F58E mutation with the longer linkers (14aa and above) increased the inhibition potency of the P622, P666, and P667 binding agents for Activin A and Activin B compared to the same mutation in combination with a short (3aa) linker. Inhibition potency for GDF-8 and GDF-11 remained similar between short linker and long linker binding agents comprising the F58E mutation. See FIGS. 10C and 10D. The F58E mutation in combination with a longer linker (14aa) also demonstrated superior therapeutic effects in a rat model of PAH (See Example 5).

Similarly, introduction of the D57E mutation in the ActRIIB-ECD increased the inhibition potency of fusion proteins when combined with a long linker (14aa). For example, P759 has a 14aa linker connecting the ActRIIB ECD and the Fc domain and P120 has a 3aa linker connecting the ActRIIB ECD and the Fc domain. Each of P759 and P120 comprise the D57E mutation in the ActRIIB-ECD. As shown in Table 9 and FIG. 10E and FIG. 10F, P759 demonstrated an increased inhibition potency for each of Activin A, Activin B, GDF-8, and GDF-11, compared to the same mutation in combination with a short (3aa) linker (P120).

In contrast, introduction of the K31Y or G27D mutation had completely different effects when combined with short and long linkers. Each of the P124 and P761 binding agents comprise the K31Y mutation. Each of the P758 and P119 binding agents comprise the G27D mutation. Combination of either the K31Y or G27D mutation with the longer linkers (14aa and above) decreased the inhibition potency of the P124 and P758 binding agents for Activin A, Activin B, GDF-8, and GDF-11 compared to the same mutation in combination with a short (3aa) linker (P119 and P761). See FIG. 10G-10J.

Figure 10A:
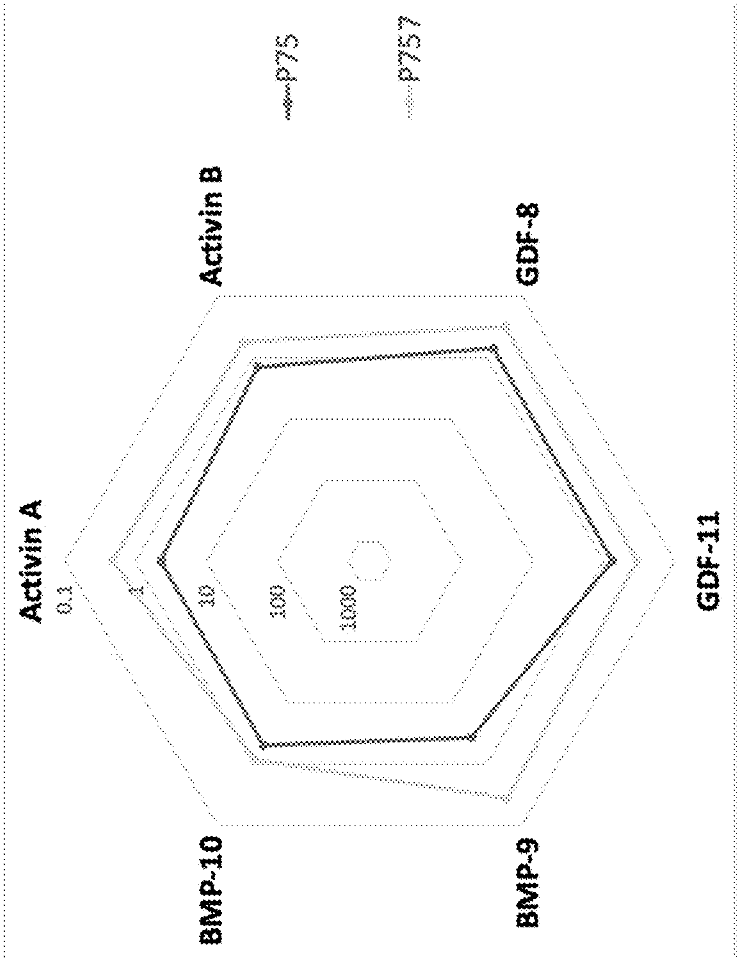
FIG. 10A, FIG. 10C, FIG. 10E, FIG. 10G, FIG. 10I and FIG. 10K show comparative charts in which IC50 values for neutralization of TGFβ superfamily ligands (activin A, activin B, GDF-8, GDF-11, BMP-9, and BMP-10) are displayed for exemplary test proteins, as indicated. Points at the center of the chart indicate low neutralization potency for a given cytokine (high IC50 value), whereas points at the edge of the chart indicate high neutralization potency for a given cytokine (low IC50 value).

Further still, introduction of the V75Q mutation also demonstrated unpredictable effects when combined with short and long linkers. Each of the P762 and P126 binding agents comprise the V75Q mutation. However, in contrast to the F58E, K31Y, and G27D mutations described above, combination of the V75Q mutation with different linker lengths had no effect on the inhibition potencies for any of Activin A, Activin B, GDF-8, GDF-11, or BMP-9. Inhibition potencies for each ligand remained similar between short and long linker agents comprising the V75Q mutation. See FIG. 10K and FIG. 10L.

As such, the efficacy of a particular binding agent described herein is determined not only by the mutations comprised in the extracellular ligand binding domain, but also by the length of the linker used. As outlined above, the combination of point mutations in the ActRIIB ECD and the length of the linker connecting the ActRIIB ECD to the Fc domain has unpredictable effects on binding to and inhibition of TGFβ superfamily ligands.

Additional ECD-based traps have been evaluated clinically, e.g., luspatercept and sotatercept. Luspatercept (also known as ACE-536, REBLOZYL®) is a soluble fusion protein composed of a modified form of the extracellular domain of the activin receptor type IIB (ActRIIB) linked to the Fc portion of human IgG1. Luspatercept inhibits several endogenous TGFβ superfamily ligands, thereby diminishing Smad2/3 signaling. It is used for the treatment of anemia in beta thalassemia and myelodysplastic syndromes. For a description of luspatercept and other related fusion proteins, see for example U.S. Pat. Nos. 7,842,663; 8,058,229; 8,216,997; 8,252,900; 8,343,933; 8,361,957; 8,703,927; 9,138,459; 9,399,669; 9,439,945; 9,932,379; 10,131,700; 10,259,861; 10,689,427; and 10,829,532.

Sotatercept (also known as ACE-011) is a soluble decoy receptor that is composed of the extracellular domain of the activin receptor type IIA (ActRIIA) linked to the Fc portion of human IgG1, and that is able to bind and neutralize activins and GDFs. Sotatercept has been evaluated in healthy volunteers, and in patients with conditions characterized by dysfunctional TGF-β superfamily signaling including hematologic disorders, bone loss, chemotherapy-induced anemia, multiple myeloma, myelodysplastic syndromes, β-thalassemia, and end-stage kidney disease (Raftopoulos, H. et al., 2016; Abdulkadyrov, K. M. et al., 2014; Ruckle, J. et al. 2009; Komrokji, R. et al., 2018; Cappellini, M. D. et al., 2019; Coyne, D. W. et al., 2019; Sherman, M. L. et al., 2013). Most recently, sotatercept has been evaluated for the treatment of pulmonary arterial hypertension (PAH).

By acting as a ligand trap for activins and GDFs, sotatercept may correct the imbalance between the growth-promoting activin/growth differentiation factor pathway and the growth-inhibiting BMP pathway that occurs in PAH. In a Phase 2 trial in PAH patients, sotatercept was shown to reduce pulmonary vascular resistance (Humbert, M. et al., 2021). Additional PH trials, including a Phase 3 trial, are ongoing or planned. For a description of sotatercept and other related fusion proteins, see for example U.S. Pat. Nos. 7,612,041; 7,709,605; 7,951,771; 7,988,973; 8,007,809; 8,629,109; 8,895,016; and 9,163,075. However, in some clinical studies of sotatercept, vascular and hematologic side effects have been found to be dose limiting, restricting the potential therapeutic efficacy. For example, a multiple ascending dose study in healthy, postmenopausal women planned to evaluate four doses of 0.1, 0.3, 1 mg/kg and 2 mg/kg but was terminated early at the 1 mg/kg level as increases in hemoglobin, hematocrit and red blood cell counts were found to be dose limiting (Sherman, M. L. et al., 2013). In a Phase 2 clinical trial in PAH patients, thrombocytopenia and an increased hemoglobin level were the most common hematologic adverse events, with 17% of patients who received a dose of 0.7 mg/kg experiencing an adverse event of increased hemoglobin (Humbert, M. et al., 2021). Such vascular and hematologic side effects are dose-limiting as they may not allow for administration of dosages required for maximal efficacy, restricting the potential to achieve maximum therapeutic effect (Humbert, M. et al., 2021). In contrast, the binding agents provided herein (e.g., P622 and P624) do not induce hematological effects in non-human primates, suggesting that these agents may have a broader therapeutic window than sotatercept.

In some embodiments, binding agents of the present disclosure comprise homodimers, i.e., dimers of a polypeptide having the sequence set forth in any one of SEQ ID NOs: 174-254, 333, or 339-341, or a sequence at least 90%, at least 95%, at least 96%, at least 97%, at least 98%, or at least 99% identical thereto, or a functionally equivalent variant thereof. In other embodiments, binding agents comprise heterodimers, i.e., dimers of two different polypeptides, at least one of the polypeptides having the sequence set forth in any one of SEQ ID NOs: 174-254, 333, or 339-341, or a sequence at least 90%, at least 95%, at least 96%, at least 97%, at least 98%, or at least 99% identical thereto, or a functionally equivalent variant thereof.

In some embodiments, the binding agents of the present disclosure comprise a dimer of a polypeptide comprising an ActRIIB-ECD comprising an F58E mutation and a long peptide linker. In some embodiments, the peptide linker is, or is at least, 10 amino acids in length. In some embodiments, the peptide linker is, or is at least, 14 amino acids in length. In some embodiments, the peptide linker is, or is at least, 19 amino acids in length. In some embodiments, the peptide linker is, or is at least, 39 amino acids in length. In some embodiments, the binding agents of the present disclosure comprise a dimer of a polypeptide comprising or consisting of an amino acid sequence selected from SEQ ID NOs: 186, 190-194, 232-233, and 247-248, or a sequence that is at least 90%, at least 95%, at least 96%, at least 97%, at least 98%, or at least 99% identical thereto, or a functionally equivalent variant thereof.

In some embodiments, the binding agents of the present disclosure comprise a dimer of a polypeptide comprising or consisting of SEQ ID NO: 186, or a sequence that is at least 90%, at least 95%, at least 96%, at least 97%, at least 98%, or at least 99% identical thereto, or a functionally equivalent variant thereof. In some embodiments, the binding agents of the present disclosure comprise a dimer of a polypeptide comprising or consisting of SEQ ID NO: 190, or a sequence that is at least 90%, at least 95%, at least 96%, at least 97%, at least 98%, or at least 99% identical thereto, or a functionally equivalent variant thereof. In some embodiments, the binding agents of the present disclosure comprise a dimer of a polypeptide comprising or consisting of SEQ ID NO: 191, or a sequence that is at least 90%, at least 95%, at least 96%, at least 97%, at least 98%, or at least 99% identical thereto, or a functionally equivalent variant thereof. In some embodiments, the binding agents of the present disclosure comprise a dimer of a polypeptide comprising or consisting of SEQ ID NO: 192, or a sequence that is at least 90%, at least 95%, at least 96%, at least 97%, at least 98%, or at least 99% identical thereto, or a functionally equivalent variant thereof. In some embodiments, the binding agents of the present disclosure comprise a dimer of a polypeptide comprising or consisting of SEQ ID NO: 193, or a sequence that is at least 90%, at least 95%, at least 96%, at least 97%, at least 98%, or at least 99% identical thereto, or a functionally equivalent variant thereof. In some embodiments, the binding agents of the present disclosure comprise a dimer of a polypeptide comprising or consisting of SEQ ID NO: 194, or a sequence that is at least 90%, at least 95%, at least 96%, at least 97%, at least 98%, or at least 99% identical thereto, or a functionally equivalent variant thereof. In some embodiments, the binding agents of the present disclosure comprise a dimer of a polypeptide comprising or consisting of SEQ ID NO: 232, or a sequence that is at least 90%, at least 95%, at least 96%, at least 97%, at least 98%, or at least 99% identical thereto, or a functionally equivalent variant thereof. In some embodiments, the binding agents of the present disclosure comprise a dimer of a polypeptide comprising or consisting of SEQ ID NO: 233, or a sequence that is at least 90%, at least 95%, at least 96%, at least 97%, at least 98%, or at least 99% identical thereto, or a functionally equivalent variant thereof. In some embodiments, the binding agents of the present disclosure comprise a dimer of a polypeptide comprising or consisting of SEQ ID NO: 247, or a sequence that is at least 90%, at least 95%, at least 96%, at least 97%, at least 98%, or at least 99% identical thereto, or a functionally equivalent variant thereof. In some embodiments, the binding agents of the present disclosure comprise a dimer of a polypeptide comprising or consisting of SEQ ID NO: 248, or a sequence that is at least 90%, at least 95%, at least 96%, at least 97%, at least 98%, or at least 99% identical thereto, or a functionally equivalent variant thereof.

In some embodiments, the binding agents of the present disclosure comprise a dimer of a polypeptide comprising an ActRIIB-ECD comprising an F58K mutation and a long peptide linker. In some embodiments, the peptide linker is, or is at least, 10 amino acids in length. In some embodiments, the peptide linker is, or is at least, 14 amino acids in length. In some embodiments, the peptide linker is, or is at least, 19 amino acids in length. In some embodiments, the peptide linker is, or is at least, 39 amino acids in length. In some embodiments, the binding agents of the present disclosure comprise a dimer of a polypeptide comprising or consisting of an amino acid sequence selected from SEQ ID NOs: 213-216 or 242-244, or a sequence that is at least 90%, at least 95%, at least 96%, at least 97%, at least 98%, or at least 99% identical thereto, or a functionally equivalent variant thereof.

In some embodiments, the binding agents of the present disclosure comprise a dimer of a polypeptide comprising or consisting of SEQ ID NO: 213, or a sequence that is at least 90%, at least 95%, at least 96%, at least 97%, at least 98%, or at least 99% identical thereto, or a functionally equivalent variant thereof. In some embodiments, the binding agents of the present disclosure comprise a dimer of a polypeptide comprising or consisting of SEQ ID NO: 214, or a sequence that is at least 90%, at least 95%, at least 96%, at least 97%, at least 98%, or at least 99% identical thereto, or a functionally equivalent variant thereof. In some embodiments, the binding agents of the present disclosure comprise a dimer of a polypeptide comprising or consisting of SEQ ID NO: 215, or a sequence that is at least 90%, at least 95%, at least 96%, at least 97%, at least 98%, or at least 99% identical thereto, or a functionally equivalent variant thereof. In some embodiments, the binding agents of the present disclosure comprise a dimer of a polypeptide comprising or consisting of SEQ ID NO: 216, or a sequence that is at least 90%, at least 95%, at least 96%, at least 97%, at least 98%, or at least 99% identical thereto, or a functionally equivalent variant thereof. In some embodiments, the binding agents of the present disclosure comprise a dimer of a polypeptide comprising or consisting of SEQ ID NO: 242, or a sequence that is at least 90%, at least 95%, at least 96%, at least 97%, at least 98%, or at least 99% identical thereto, or a functionally equivalent variant thereof. In some embodiments, the binding agents of the present disclosure comprise a dimer of a polypeptide comprising or consisting of SEQ ID NO: 243, or a sequence that is at least 90%, at least 95%, at least 96%, at least 97%, at least 98%, or at least 99% identical thereto, or a functionally equivalent variant thereof. In some embodiments, the binding agents of the present disclosure comprise a dimer of a polypeptide comprising or consisting of SEQ ID NO: 244, or a sequence that is at least 90%, at least 95%, at least 96%, at least 97%, at least 98%, or at least 99% identical thereto, or a functionally equivalent variant thereof.

In some embodiments, the binding agents of the present disclosure comprise a dimer of a polypeptide comprising an ActRIIB-ECD comprising an F58Q mutation and a long peptide linker. In some embodiments, the peptide linker is, or is at least, 10 amino acids in length. In some embodiments, the peptide linker is, or is at least, 14 amino acids in length. In some embodiments, the peptide linker is, or is at least, 19 amino acids in length. In some embodiments, the peptide linker is, or is at least, 39 amino acids in length. In some embodiments, the binding agents of the present disclosure comprise a dimer of a polypeptide comprising or consisting of an amino acid sequence selected from SEQ ID NOs: 220-223, 253, and 254, or a sequence that is at least 90%, at least 95%, at least 96%, at least 97%, at least 98%, or at least 99% identical thereto, or a functionally equivalent variant thereof.

In some embodiments, the binding agents of the present disclosure comprise a dimer of a polypeptide comprising or consisting of SEQ ID NO: 220, or a sequence that is at least 90%, at least 95%, at least 96%, at least 97%, at least 98%, or at least 99% identical thereto, or a functionally equivalent variant thereof. In some embodiments, the binding agents of the present disclosure comprise a dimer of a polypeptide comprising or consisting of SEQ ID NO: 221, or a sequence that is at least 90%, at least 95%, at least 96%, at least 97%, at least 98%, or at least 99% identical thereto, or a functionally equivalent variant thereof. In some embodiments, the binding agents of the present disclosure comprise a dimer of a polypeptide comprising or consisting of SEQ ID NO: 222, or a sequence that is at least 90%, at least 95%, at least 96%, at least 97%, at least 98%, or at least 99% identical thereto, or a functionally equivalent variant thereof. In some embodiments, the binding agents of the present disclosure comprise a dimer of a polypeptide comprising or consisting of SEQ ID NO: 223, or a sequence that is at least 90%, at least 95%, at least 96%, at least 97%, at least 98%, or at least 99% identical thereto, or a functionally equivalent variant thereof. In some embodiments, the binding agents of the present disclosure comprise a dimer of a polypeptide comprising or consisting of SEQ ID NO: 253, or a sequence that is at least 90%, at least 95%, at least 96%, at least 97%, at least 98%, or at least 99% identical thereto, or a functionally equivalent variant thereof. In some embodiments, the binding agents of the present disclosure comprise a dimer of a polypeptide comprising or consisting of SEQ ID NO: 254, or a sequence that is at least 90%, at least 95%, at least 96%, at least 97%, at least 98%, or at least 99% identical thereto, or a functionally equivalent variant thereof.

Activin Receptor Type IIB Ectodomain Variants

As used herein, the term "Activin receptor type IIB ectodomain variants" or "ActRIIB-ECD variants" refers to a polypeptide comprising the soluble, extracellular portion of the single transmembrane receptor, ActRIIB, that has at least one amino acid substitution relative to a wild type extracellular ActRIIB. The sequence of the wild type human ActRIIB-ECD is shown in SEQ ID NO: 2 (Table 1). Unless otherwise noted, indicated positions for amino acid substitutions are numbered according to the amino acid sequence of SEQ ID NO: 2. For the purposes of this disclosure, the "human wild type ActRIIB-ECD" refers to SEQ ID NO: 2.

In some embodiments, the ActRIIB-ECD variant comprises one or more amino acid substitutions at a position selected from G27, Q29, D30, K31, S38, D57, F58, V75, and F77. In some embodiments, the ActRIIB-ECD variant polypeptide comprises one or more amino acid substitutions selected from G27D, Q29Y, D30Q, K31Y, S38R, D57E, F58E, F58D, F58Y, F58K, F58Q, F58W, F58N, F58R, F58H, V75Q, and F77D. In some embodiments, the ActRIIB-ECD variant comprises one or more amino acid substitutions selected from F58E, F58D, F58Y, F58K, F58Q, F58W, F58N, F58R, and F58H. In some embodiments, the ActRIIB-ECD variant comprises one or more amino acid substitutions selected from F58E, F58K, and F58Q. In some embodiments, the ActRIIB-ECD variant comprises an amino acid substitution of F58E. In some embodiments, the ActRIIB-ECD variant comprises an amino acid substitution of F58K. In some embodiments, the ActRIIB-ECD variant comprises an amino acid substitution of F58Q. Other amino acid substitutions in the ActRIIB-ECD are known in the art (e.g., WO 2021/158675; WO 2022/150590; WO 2021/158675; WO 2022/072882; WO 2021/189019; and WO 2021/189010, each of which are incorporated herein by reference). These additional mutations can be used in combination with the linkers described herein, and incorporated into the binding agents described herein, to alter ligand binding properties of the ActRIIB-ECD.

In some embodiments, the ActRIIB-ECD variant comprises the amino acid sequence set forth in any one of SEQ ID NOs: 4-22, 331, 332, or 24-33. In some embodiments, an ActRIIB-ECD variant comprises at least 85% (e.g., at least 85%, at least 87%, at least 90%, at least 92%, at least 95%, at least 96%, at least 97%, at least 98%, at least 99%, or greater) amino acid sequence identity to the sequence of a wild type human ActRIIB-ECD. In some embodiments, an ActRIIB-ECD variant may have at least 85% (e.g., at least 85%, at least 87%, at least 90%, at least 92%, at least 95%, at least 96%, at least 97%, at least 98%, at least 99%, or greater) amino acid sequence identity to the sequence set forth in SEQ ID NO: 2.

In some embodiments, the amino acid sequence of the ActRIIB-ECD variant comprises at least 95%, at least 96%, at least 97%, at least 98%, or at least 99% sequence identity to any one of SEQ ID NOs: 4-22, 331, 332, or 24-33. In some embodiments, the ActRIIB-ECD variant comprises an amino acid substitution at position F58 and comprises an amino acid sequence that is at least 95%, at least 96%, at least 97%, at least 98%, or at least 99% sequence identity to any one of SEQ ID NOs: 5-13. In some embodiments, the ActRIIB-ECD variant comprises an amino acid substitution at position F58 and comprises or consists of an amino acid sequence selected from SEQ ID NOs: 5-13. In some embodiments, the ActRIIB-ECD variant comprises an amino acid substitution at position F58 and comprises or consists of the amino acid sequence of SEQ ID NO: 5. In some embodiments, the ActRIIB-ECD variant comprises an amino acid substitution at position F58 and comprises or consists of the amino acid sequence of SEQ ID NO: 6. In some embodiments, the ActRIIB-ECD variant comprises an amino acid substitution at position F58 and comprises or consists of the amino acid sequence of SEQ ID NO: 7. In some embodiments, the ActRIIB-ECD variant comprises an amino acid substitution at position F58 and comprises or consists of the amino acid sequence of SEQ ID NO: 8. In some embodiments, the ActRIIB-ECD variant comprises an amino acid substitution at position F58 and comprises or consists of the amino acid sequence of SEQ ID NO: 9. In some embodiments, the ActRIIB-ECD variant comprises an amino acid substitution at position F58 and comprises or consists of the amino acid sequence of SEQ ID NO: 10. In some embodiments, the ActRIIB-ECD variant comprises an amino acid substitution at position F58 and comprises or consists of the amino acid sequence of SEQ ID NO: 11. In some embodiments, the ActRIIB-ECD variant comprises an amino acid substitution at position F58 and comprises or consists of the amino acid sequence of SEQ ID NO: 12. In some embodiments, the ActRIIB-ECD variant comprises an amino acid substitution at position F58 and comprises or consists of the amino acid sequence of SEQ ID NO: 13.

In some embodiments, the ActRIIB-ECD variant comprises an amino acid substitution at position D57 and comprises an amino acid sequence that is at least 95%, at least 96%, at least 97%, at least 98%, or at least 99% sequence identity to SEQ ID NOs: 4. In some embodiments, the ActRIIB-ECD variant comprises an amino acid substitution at position D57 and comprises or consists of SEQ ID NO: 4.

Exemplary ActRIIB ECDs are provided in Table 1. Amino acid substitutions are indicated by bold and enlarged text.

TABLE 1

Exemplary ActRIIB and ActRIIB variant ECDs

| ECD | AA Sequence | SEQ ID |
|---|---|---|
| WT ActRIIB-ECD | ETRECIYYNANWELERTNQSGLERCEGEQDKRLHCYASWRNS<br>SGTIELVKKGCWLDDFNCYDRQECVATEENPQVYFCCCEGNF<br>CNERFTHLPEAGGPEVTYEPPPT | 2 |
| WT ActRIIA-ECD | ILGRSETQECLFFNANWEKDRTNQTGVEPCYGDKDKRRHCFA<br>TWKNISGSIEIVKQGCWLDDINCYDRTDCVEKKDSPEVYFCC<br>CEGNMCNEKFSYFPEMEVTQPTSNPVTPKPPT | 3 |
| ActRIIB-ECD (D57E) | ETRECIYYNANWELERTNQSGLERCEGEQDKRLHCYASWRNS<br>SGTIELVKKGCWLD**E**FNCYDRQECVATEENPQVYFCCCEGNF<br>CNERFTHLPEAGGPEVTYEPPPT | 4 |
| ActRIIB-ECD (F58E) | ETRECIYYNANWELERTNQSGLERCEGEQDKRLHCYASWRNS<br>SGTIELVKKGCWLDD**E**NCYDRQECVATEENPQVYFCCCEGNF<br>CNERFTHLPEAGGPEVTYEPPPT | 5 |
| ActRIIB-ECD (F58D) | ETRECIYYNANWELERTNQSGLERCEGEQDKRLHCYASWRNS<br>SGTIELVKKGCWLDD**D**NCYDRQECVATEENPQVYFCCCEGNF<br>CNERFTHLPEAGGPEVTYEPPPT | 6 |
| ActRIIB-ECD (F58Y) | ETRECIYYNANWELERTNQSGLERCEGEQDKRLHCYASWRNS<br>SGTIELVKKGCWLDD**Y**NCYDRQECVATEENPQVYFCCCEGNF<br>CNERFTHLPEAGGPEVTYEPPPT | 7 |
| ActRIIB-ECD (F58K) | ETRECIYYNANWELERTNQSGLERCEGEQDKRLHCYASWRNS<br>SGTIELVKKGCWLDD**K**NCYDRQECVATEENPQVYFCCCEGNF<br>CNERFTHLPEAGGPEVTYEPPPT | 8 |
| ActRIIB-ECD (F58Q) | ETRECIYYNANWELERTNQSGLERCEGEQDKRLHCYASWRNS<br>SGTIELVKKGCWLDD**Q**NCYDRQECVATEENPQVYFCCCEGNF<br>CNERFTHLPEAGGPEVTYEPPPT | 9 |
| ActRIIB-ECD (F58W) | ETRECIYYNANWELERTNQSGLERCEGEQDKRLHCYASWRNS<br>SGTIELVKKGCWLDD**W**NCYDRQECVATEENPQVYFCCCEGNF<br>CNERFTHLPEAGGPEVTYEPPPT | 10 |
| ActRIIB-ECD (F58N) | ETRECIYYNANWELERTNQSGLERCEGEQDKRLHCYASWRNS<br>SGTIELVKKGCWLDD**N**NCYDRQECVATEENPQVYFCCCEGNF<br>CNERFTHLPEAGGPEVTYEPPPT | 11 |
| ActRIIB-ECD (F58R) | ETRECIYYNANWELERTNQSGLERCEGEQDKRLHCYASWRNS<br>SGTIELVKKGCWLDD**R**NCYDRQECVATEENPQVYFCCCEGNF<br>CNERFTHLPEAGGPEVTYEPPPT | 12 |
| ActRIIB-ECD (F58H) | ETRECIYYNANWELERTNQSGLERCEGEQDKRLHCYASWRNS<br>SGTIELVKKGCWLDD**H**NCYDRQECVATEENPQVYFCCCEGNF<br>CNERFTHLPEAGGPEVTYEPPPT | 13 |
| ActRIIB-ECD (Q29Y) | ETRECIYYNANWELERTNQSGLERCEGE**Y**DKRLHCYASWRNS<br>SGTIELVKKGCWLDDFNCYDRQECVATEENPQVYFCCCEGNF<br>CNERFTHLPEAGGPEVTYEPPPT | 14 |
| ActRIIB-ECD (D30Q) | ETRECIYYNANWELERTNQSGLERCEGEQ**Q**KRLHCYASWRNS<br>SGTIELVKKGCWLDDFNCYDRQECVATEENPQVYFCCCEGNF<br>CNERFTHLPEAGGPEVTYEPPPT | 15 |
| ActRIIB-ECD (K31Y) | ETRECIYYNANWELERTNQSGLERCEGEQD**Y**RLHCYASWRNS<br>SGTIELVKKGCWLDDFNCYDRQECVATEENPQVYFCCCEGNF<br>CNERFTHLPEAGGPEVTYEPPPT | 16 |
| ActRIIB-ECD (S38R) | ETRECIYYNANWELERTNQSGLERCEGEQDKRLHCYA**R**WRNS<br>SGTIELVKKGCWLDDFNCYDRQECVATEENPQVYFCCCEGNF<br>CNERFTHLPEAGGPEVTYEPPPT | 17 |
| ActRIIB-ECD (V75Q) | ETRECIYYNANWELERTNQSGLERCEGEQDKRLHCYASWRNS<br>SGTIELVKKGCWLDDFNCYDRQECVATEENPQ**Q**YFCCCEGNF<br>CNERFTHLPEAGGPEVTYEPPPT | 18 |

TABLE 1-continued

| Exemplary ActRIIB and ActRIIB variant ECDs | | |
|---|---|---|
| ECD | AA Sequence | SEQ ID |
| ActRIIB-ECD (F77D) | ETRECIYYNANWELERTNQSGLERCEGEQDKRLHCYASWRNS SGTIELVKKGCWLDDFNCYDRQECVATEENPQVY**D**CCCEGNF CNERFTHLPEAGGPEVTYEPPPT | 19 |
| ActRIIB-ECD (G27D) | ETRECIYYNANWELERTNQSGLERCE**D**EQDKRLHCYASWRNS SGTIELVKKGCWLDDFNCYDRQECVATEENPQVYFCCCEGNF CNERFTHLPEAGGPEVTYEPPPT | 20 |
| ActRIIB-ECD (D57E + F58E) | ETRECIYYNANWELERTNQSGLERCEGEQDKRLHCYASWRNS SGTIELVKKGCWLD**EE**NCYDRQECVATEENPQVYFCCCEGNF CNERFTHLPEAGGPEVTYEPPPT | 21 |
| ActRIIB-ECD (Q29Y F58E) | ETRECIYYNANWELERTNQSGLERCEGE**Y**DKRLHCYASWRNS SGTIELVKKGCWLDD**E**NCYDRQECVATEENPQVYFCCCEGNF CNERFTHLPEAGGPEVTYEPPPT | 22 |
| ActRIIB-ECD (D30Q + F58E) | ETRECIYYNANWELERTNQSGLERCEGEQ**Q**KRLHCYASWRNS SGTIELVKKGCWLDD**E**NCYDRQECVATEENPQVYFCCCEGNF CNERFTHLPEAGGPEVTYEPPPT | 331 |
| ActRIIB-ECD (G27D + F58E) | ETRECIYYNANWELERTNQSGLERCE**D**EQDKRLHCYASWRNS SGTIELVKKGCWLDD**E**NCYDRQECVATEENPQVYFCCCEGNF CNERFTHLPEAGGPEVTYEPPPT | 332 |

In some embodiments, an AcIRIIB-ECD variant of the disclosure further includes an extension of up to 5 amino acids at the N-terminus. In some embodiments, the ActRIIB-ECD variant of the disclosure further includes an extension of 5 amino acids at the N-terminus, e.g., of GRGEA (SEQ ID NO: 23). In some embodiments, the ActRIIB-ECD variant of the disclosure further includes an extension at the N-terminus of 4 amino acids, 3 amino acids, 2 amino acids, or 1 amino acid, for example and without limitation, RGEA, GEA, EA, or A. Exemplary ActRIIB ECDs with N-terminal extensions are provided in Table 2. The N-terminal extension amino acids are indicated in bold and italicized text. Amino acid substitutions are indicated in bold and enlarged text.

TABLE 2

| ActRIIB-ECDs with N-terminal extensions | | |
|---|---|---|
| ECD | AA Sequence | SEQ ID |
| wild type ActRIIB-ECD with N-terminal extension | ***GRGEA***ETRECIYYNANWELERTNQSGLERCEGEQDKRL HCYASWRNSSGTIELVKKGCWLDDFNCYDRQECVATEE NPQVYFCCCEGNFCNERFTHLPEAGGPEVTYEPPPT | 24 |
| wild type ActRIIB-ECD with N-terminal extension | ***RGEA***ETRECIYYNANWELERTNQSGLERCEGEQDKRLH CYASWRNSSGTIELVKKGCWLDDFNCYDRQECVATEEN PQVYFCCCEGNFCNERFTHLPEAGGPEVTYEPPPT | 25 |
| wild type ActRIIB-ECD with N-terminal extension | ***GEA***ETRECIYYNANWELERTNQSGLERCEGEQDKRLHC YASWRNSSGTIELVKKGCWLDDFNCYDRQECVATEENP QVYFCCCEGNFCNERFTHLPEAGGPEVTYEPPPT | 26 |
| wild type ActRIIB-ECD with N-terminal extension | ***EA***ETRECIYYNANWELERTNQSGLERCEGEQDKRLHCY ASWRNSSGTIELVKKGCWLDDFNCYDRQECVATEENPQ VYFCCCEGNFCNERFTHLPEAGGPEVTYEPPPT | 27 |
| wild type ActRIIB-ECD with N-terminal extension | ***A***ETRECIYYNANWELERTNQSGLERCEGEQDKRLHCYA SWRNSSGTIELVKKGCWLDDFNCYDRQECVATEENPQV YFCCCEGNFCNERFTHLPEAGGPEVTYEPPPT | 28 |
| ActRIIB-ECD F58E variant with N-terminal extension | ***GRGEA***ETRECIYYNANWELERTNQSGLERCEGEQDKRL HCYASWRNSSGTIELVKKGCWLDD**E**NCYDRQECVATEE NPQVYFCCCEGNFCNERFTHLPEAGGPEVTYEPPPT | 29 |
| ActRIIB-ECD F58E variant with N-terminal extension | ***RGEA***ETRECIYYNANWELERTNQSGLERCEGEQDKRLH CYASWRNSSGTIELVKKGCWLDD**E**NCYDRQECVATEEN PQVYFCCCEGNFCNERFTHLPEAGGPEVTYEPPPT | 30 |
| ActRIIB-ECD F58E variant with N-terminal extension | ***GEA***ETRECIYYNANWELERTNQSGLERCEGEQDKRLHC YASWRNSSGTIELVKKGCWLDD**E**NCYDRQECVATEENP QVYFCCCEGNFCNERFTHLPEAGGPEVTYEPPPT | 31 |

TABLE 2-continued

ActRIIB-ECDs with N-terminal extensions

| ECD | AA Sequence | SEQ ID |
|---|---|---|
| ActRIIB-ECD F58E variant with N-terminal extension | ***EA***ETRECIYYNANWELERTNQSGLERCEGEQDKRLHCYASWRNSSGTIELVKKGCWLDD**E**NCYDRQECVATEENPQVYFCCCEGNFCNERFTHLPEAGGPEVTYEPPPT | 32 |
| ActRIIB-ECD F58E variant with N-terminal extension | ***A***ETRECIYYNANWELERTNQSGLERCEGEQDKRLHCYASWRNSSGTIELVKKGCWLDD**E**NCYDRQECVATEENPQVYFCCCEGNFCNERFTHLPEAGGPEVTYEPPPT | 33 |

Figure 10B:
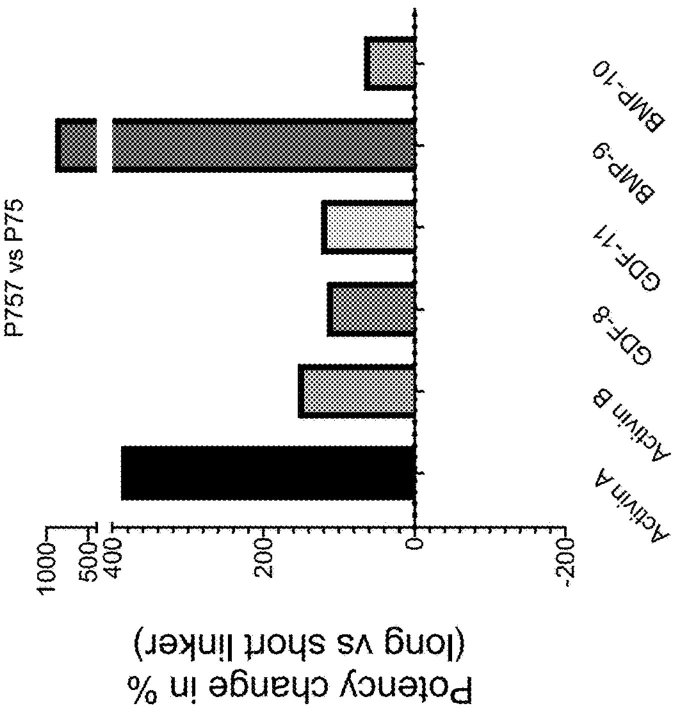
FIG. 10B, FIG. 10D, FIG. 10F, FIG. 10H, FIG. 10J and FIG. 10L show histograms indicating the relative gain or loss of potency (in %) between the long and short linker for each pair of exemplary test proteins.

In some embodiments, the ActRIIB-ECD variants of the present disclosure further comprise an extension of alanine-proline-threonine (APT) at the C-terminus. As shown in FIG. 10O-10P, the addition of the C-terminal extension APT to the ActRIIB-ECD does not affect inhibition potency. As such, in some embodiments, any one of SEQ ID NOs: 2-22, 331, 332, and 24-33 can further comprise an extension of APT at the C-terminus.

ActRIIB-ECD variants of the disclosure have been designed to maximize therapeutic efficacy in certain disease indications while minimizing adverse effects, specifically to prevent or reduce disruption of endogenous BMP-9 signaling, while maintaining and/or increasing neutralization potency for other TGFβ superfamily ligands such as activin A, activin B, GDF-8, GDF-11, and/or BMP-10. ActRIIB-ECD variants of the disclosure exhibit: (1) similar or improved binding to activin A, activin B, GDF-8, GDF-11, and/or BMP-10 compared to wild type ActRIIB-ECD, which allows them to compete with endogenous receptors for ligand binding and reduce or inhibit endogenous receptor signaling; and (2) reduced or removed binding to BMP-9 compared to wild type ActRIIB-ECD, which allows them to avoid toxicity associated with inhibition of BMP-9 signaling. These variants can be used to treat a wide range of diseases and conditions in which activin receptor signaling is elevated, such as pulmonary hypertension (PH) (e.g., PAH, venous PH, hypoxic PH, thromboembolic PH, or miscellaneous PH), metabolic disorders and cardiometabolic disease (e.g., obesity, Type 1 diabetes, Type 2 diabetes, pre-diabetes, heart failure), bone disease (e.g., diseases or conditions involving bone damage), muscle disease, fibrosis, and low red blood cell levels (e.g., anemia, blood loss), as further described herein. The variants can, for example and without limitation, lead to a reduction in the symptoms or progression of PH (e.g., PAH, venous PH, hypoxic PH, thromboembolic PH, or miscellaneous PH), a reduction in bone resorption or osteoclast activity, an increase in bone formation or bone mineral density, an increase in muscle mass or strength, a reduction in fibrosis (e.g., reduced fibrosis or a slowing or stopping of the progression of fibrosis), and/or an increase in red blood cell levels (e.g., an increase in hemoglobin levels, hematocrit, or red blood cell counts, e.g., an increase in red blood cell production), as described further herein.

In some embodiments, ActRIIB-ECD variants of the disclosure bind to one or more ligand selected from activin A, activin B, GDF-8, GDF-11, and BMP-10 and inhibit signaling of the one or more ligand through their respective receptors, without substantially binding to BMP-9 and/or inhibiting BMP-9 signaling through its receptor.

In some embodiments, the inhibition potency of an ActRIIB-ECD variant of the disclosure for human BMP-9 signaling is reduced by about 100-fold compared to the inhibition potency of the human wild type ActRIIB-ECD for human BMP-9 signaling.

In some embodiments, the inhibition potency of ActRIIB-ECD variant of the disclosure for the one or more ligand selected from activin A, activin B, GDF-8, GDF-11, and BMP-10 is increased or is substantially the same as the inhibition potency of the human wild type ActRIIB-ECD for the same one or more ligand.

In some embodiments, the ActRIIB-ECD variant of the disclosure has greater inhibition potency for activin A and lower inhibition potency for BMP-9 compared to the human wild type ActRIIB-ECD.

In some embodiments, the ActRIIB-ECD variant of the disclosure does not cause a vascular complication in a subject.

In some embodiments, the ActRIIB-ECD variant of the disclosure does not increase vascular permeability or leakage in a subject.

Consequently, in accordance with the disclosure there are provided herein novel polypeptides comprising an Activin receptor type IIB (ActRIIB) ectodomain (ECD) variant, the variant having one or more amino acid substitution relative to the sequence of the human wild type ActRIIB-ECD, having a tailored TGFβ superfamily ligand specificity in order to maximize therapeutic efficacy while minimizing adverse effects, specifically with the goal of preventing or reducing disruption of endogenous BMP-9 signaling, while maintaining and/or increasing neutralization potency for other TGFβ superfamily ligands such as activin A, activin B, GDF-8, GDF-11, and/or BMP-10.

Polypeptides Comprising ActRIIB ECD Variants

In some embodiments, the present disclosure provides polypeptides comprising an ActRIIB ECD variant fused, via a linker, to an Fc domain monomer. In some embodiments, the polypeptides comprise, from N-terminus to C-terminus, an ActRIIB ECD variant-peptide linker-Fc domain monomer. The polypeptides comprising ActRIIB ECDs can dimerize via cysteine bonds between Fc domain monomers to form the TGFβ superfamily ligand binding agents described herein.

Linkers

In some embodiments, the ActRIIB ECD variants described herein are fused to a heterologous domain by way of a linker. In some embodiments, the heterologous domain increases stability of the polypeptide. In some embodiments, the heterologous domain is selected from the group consisting of an Fc domain monomer (e.g., a wild-type Fc domain monomer, an Fc domain monomer with one or more amino acid substitutions), an albumin-binding peptide, a fibronectin domain, or a human serum albumin domain.

As used herein, the terms "peptide linker" and "linker" are used interchangeably to refer to a short stretch of amino acids used to connect two functional domains together in a polypeptide chain. For example, in some embodiments of the polypeptides or binding agents of the disclosure, the ActRIIB-ECD variant and the Fc domain monomer are linked together on a polypeptide chain via one or more peptide linkers. Peptide linkers can also be used to attach other domains or modules or regions (such as half-life extending domains) to the polypeptides or binding agents of the disclosure. The term "long linker" as used herein refers to a linker that is at least 10 amino acids in length (i.e., 10, 11, 12, 13, 14, 15, 16, 17, 18, 19, 20 or more amino acids in length). The term "short linker" as used herein refers to a linker that is less than 10 amino acids in length (i.e., 9, 8, 7, 6, 5, 4, 3, 2, or 1 amino acids in length)

Suitable peptide linkers are known in the art, and include, for example, peptide linkers containing flexible amino acid residues such as glycine, alanine, and serine. In some embodiments, a linker can contain motifs, e.g., multiple or repeating motifs, of GA, GS, GG, GGA, GGS, GGG, GGGA (SEQ ID NO: 92), GGGS (SEQ ID NO: 91), GGGG (SEQ ID NO: 69), GGGGA (SEQ ID NO: 90), GGGGS (SEQ ID NO: 68), GGGGG (SEQ ID NO: 89), GGAG (SEQ ID NO: 88), GGSG (SEQ ID NO: 87), AGGG (SEQ ID NO: 86), or SGGG (SEQ ID NO: 76).

In some embodiments, a linker can contain 2 to 12 amino acids including motifs of GA or GS, e.g., GA, GS, GAGA (SEQ ID NO: 103), GSGS (SEQ ID NO: 95), GAGAGA (SEQ ID NO: 96), GSGSGS (SEQ ID NO: 97), GAGAGAGA (SEQ ID NO: 98), GSGSGSGS (SEQ ID NO: 99), GAGAGAGAGA (SEQ ID NO: 100), GSGSGSGSGS (SEQ ID NO: 101), GAGAGAGAGAGA (SEQ ID NO: 102), and GSGSGSGSGSGS (SEQ ID NO: 104). In some embodiments, a linker can contain 3 to 12 amino acids including motifs of GGA or GGS, e.g., GGA, GGS, GGAGGA (SEQ ID NO: 105), GGSGGS (SEQ ID NO: 106), GGAGGAGGA (SEQ ID NO: 107), GGSGGSGGS (SEQ ID NO: 108), GGAGGAGGAGGA (SEQ ID NO: 109), and GGSGGSGGSGGS (SEQ ID NO: 110). In some embodiments, a linker can contain 4 to 12 amino acids including motifs of GGAG (SEQ ID NO: 111), GGSG (SEQ ID NO: 112), GGAGGGAG (SEQ ID NO: 113), GGSGGGSG (SEQ ID NO: 114), GGAGGGAGGGAG (SEQ ID NO: 115), and GGSGGGSGGGSG (SEQ ID NO: 116). In some embodiments, a linker can contain motifs of GGGGA (SEQ ID NO: 90) or GGGGS (SEQ ID NO: 68), e.g, GGGGAGGGGAGGGGA (SEQ ID NO: 117) and GGGGSGGGGSGGGGS (SEQ ID NO: 58). In some embodiments, an amino acid linker between an ActRIIB-ECD variant and a heterologous domain (e.g., an Fc domain monomer (e.g., a wild-type Fc domain monomer, an Fc domain monomer with one or more amino acid substitutions), an albumin-binding peptide, a fibronectin domain, or a human serum albumin domain) may be GGG, GGGA (SEQ ID NO: 92), GGGG (SEQ ID NO: 69), GGGAG (SEQ ID NO: 335), GGGAGG (SEQ ID NO: 336), or GGGAGGG (SEQ ID NO: 337).

In the event that a linker is used, the linker is generally of a length and sequence sufficient to ensure that each of the domains can, independently from one another, retain their differential binding specificities and/or functions. In some embodiments, peptide linkers which furthermore do not promote any secondary structures are selected. The linkage of said domains to each other can be provided, e.g., by genetic engineering, as described herein. Methods for preparing fused and operatively linked polypeptide constructs and expressing them in mammalian cells or bacteria are well-known in the art (e.g., WO 99/54440 or Sambrook et al., Molecular Cloning: A Laboratory Manual, Cold Spring Harbor Laboratory Press, Cold Spring Harbor, N.Y., 2001).

In some embodiments, the linker comprises various permutations of amino acid sequences containing Gly and Ser. In some embodiments, the linkers are glycine and serine rich linkers. In some embodiments, the linker may be rich in glycine (e.g, 2-10, 2-5, 2-4, 2-3 glycine residues) or glycine and proline residues and may, for example, contain a single sequence of threonine/serine and glycines or repeating sequences of threonine/serine and/or glycines, e.g., GGG, GGGG (SEQ ID NO: 69), GGGS (SEQ ID NO: 91), TGGGG (SEQ ID NO: 74), SGGGG (SEQ ID NO: 75), TGGG (SEQ ID NO: 73), or SGGG (SEQ ID NO: 76) singlets, or repeats. Other near neutral amino acids, such as, but not limited to, Thr, Asn, Pro and Ala, may also be used in the linker sequence.

In some embodiments, the linker is 10 amino acids in length. In some embodiments, the linker is greater than 10 amino acids in length. In some embodiments, the linker has a length of at least 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, or 50 amino acids. In some embodiments, the linker is less than 40, 35, 30, 25, 22 or 20 amino acids. In some embodiments, the linker is 10-50, 10-40, 10-30, 10-25, 10-21, 10-15, 10-14, 12-14, 15-25, 17-22, 20, or 21 amino acids in length. In some embodiments, the linker is 14-40, 14-39, 14-35, 14-30, 14-25, or 14-20 amino acids in length. In some embodiments, the linker is at least 10 amino acids in length. In some embodiments, the linker is at least 14 amino acids in length. In some embodiments, the linker is at least 19 amino acids in length. In some embodiments, the linker is at least 39 amino acids in length. In some embodiments, the linker is 14 amino acids in length. In some embodiments, the linker is 19 amino acids in length. In some embodiments, the linker is 39 amino acids in length. In some embodiments, the linker is 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, or 50 amino acids in length. In further embodiments, the linkers have a length of at least 12, 14, 15, 20, 21, 25, 30, 35, 40, 45 or 50 amino acids.

In some embodiments, the linker comprises SEQ ID NO: 59. In some embodiments, the linker comprises SEQ ID NO: 54. In some embodiments, the linker comprises SEQ ID NO: 34. In some embodiments, the linker comprises SEQ ID NO: 63.

In some embodiments, the linker consists of SEQ ID NO: 59. In some embodiments, the linker consists of SEQ ID NO: 54. In some embodiments, the linker consists of SEQ ID NO: 34. In some embodiments, the linker consists of SEQ ID NO: 63.

In some embodiments, the linker comprises or consists of the sequence set forth in any one of SEQ ID NOs: 34-133 and 335-337.

In some embodiments, linkers are Glycine-rich, often Glycine/Serine-rich, peptides of up to 40 amino acids, or from 1 to 40 amino acids, from 2 to 39 amino acids, from 3 to 39 amino acids, from 3 to 14 amino acids, from 3 to 19 amino acids, from 5 to 25 amino acids, from 5 to 20 amino acids, from 5 to 15 amino acids, or from 15 to 25 amino acids. In some embodiments, peptide linkers comprise only a relatively small number of amino acid residues, e.g., 39 amino acids or less, 19 amino acids or less, 14 amino acids or less, 5 amino acids or less, or 3 amino acids of less. In certain embodiments, Gly-rich linkers are used. In one embodiment, a peptide linker may consist of the single amino acid Glycine (Gly). In another embodiment, a peptide linker comprises or consists of the amino acid sequence Gly-Gly-Gly-Gly-Ser (SEQ ID NO: 68), i.e. Gly4Ser (SEQ ID NO: 68), or polymers thereof, i.e. (Gly4Ser)n (SEQ ID NO: 345), where n is an integer of 1 or greater, or n is from 1 to 8 (e.g. 1, 2, 3, 4, 5, 6, 7, or 8).

In some embodiments, the linker comprises the amino acid sequence GlyGlyGlyGlySer (GGGGS) (SEQ ID NO: 68), or repetitions thereof (GGGGS)n (SEQ ID NO: 345), where n>2. In particular embodiments n>3, or n=3-10. In some embodiments, n>4, or n=4-10. In some embodiments, n is not greater than 4 in a (GGGGS)n (SEQ ID NO: 345) linker. In some embodiments, n=4-10, 4-9, 4-8, 4-7, 4-6, 4-5, 5-8, 5-7, or 5-6. In some embodiments, n=3, 4, 5, 6, or 7. In some embodiments, n=4. In some embodiments, a linker comprising a (GGGGS)n (SEQ ID NO: 345) sequence also comprises an N-terminal threonine.

In some embodiments, a linker can also contain amino acids other than glycine, alanine, and serine, e.g., AAAL (SEQ ID NO: 118), AAAK (SEQ ID NO: 119), AAAR (SEQ ID NO: 120), EGKSSGSGSESKST (SEQ ID NO: 121), GSAGSAAGSGEF (SEQ ID NO: 122), AEAAAKEAAAKA (SEQ ID NO: 123), KESGSVSSEQLAQFRSLD (SEQ ID NO: 124), GENLYFQSGG (SEQ ID NO: 125), SACYCELS (SEQ ID NO: 126), RSIAT (SEQ ID NO: 127), RPACKIPNDLKQKVMNH (SEQ ID NO: 128), GGSAGGSGSGSSGGSSGASGTGTAGGTGSGSGTGSG (SEQ ID NO: 129), AAANSSIDLISVPVDSR (SEQ ID NO: 130), or GGSGGGSEGGGSEGGGSEGGGSEGGGSEGGGS GGGS (SEQ ID NO: 131). In some embodiments, a linker can contain motifs, e.g., multiple or repeating motifs, of EAAAK (SEQ ID NO: 132). In some embodiments, a linker can contain motifs, e.g., multiple or repeating motifs, of praline-rich sequences such as (XP)n, in which X may be any amino acid (e.g., A, K, or E) and n is from 1-5, and PAPAP (SEQ ID NO: 133).

The length of the peptide linker and the amino acids used can be adjusted depending on the two proteins involved and the degree of flexibility desired in the final protein fusion polypeptide. The length of the linker can be adjusted to ensure proper protein folding and avoid aggregate formation.

Non-limiting examples of linkers are depicted in Table 3. It should be understood that the linkers are not meant to be particularly limited and any suitable linker may be used, as long as the desired functions (binding, neutralization, etc.) of the polypeptide or binding agent are provided.

TABLE 3

Exemplary linker sequences

| SEQ ID | Linker sequence |
|---|---|
| 34 | GGGGSGGGGSGGGGSGGGGSGGGGSGGGGSGGGGSGGGG |
| 35 | GGGGSGGGGSGGGGSGGGGSGGGGSGGGGSGGGGSGGG |
| 36 | GGGGSGGGGSGGGGSGGGGSGGGGSGGGGSGGGGSGG |
| 37 | GGGGSGGGGSGGGGSGGGGSGGGGSGGGGSGGGGSG |
| 38 | GGGGSGGGGSGGGGSGGGGSGGGGSGGGGSGGGGS |
| 39 | GGGGSGGGGSGGGGSGGGGSGGGGSGGGGSGGGG |

TABLE 3-continued

Exemplary linker sequences

| SEQ ID | Linker sequence |
|---|---|
| 40 | GGGGSGGGGSGGGGSGGGGSGGGGSGGGGSGGG |
| 41 | GGGGSGGGGSGGGGSGGGGSGGGGSGGGGSGG |
| 42 | GGGGSGGGGSGGGGSGGGGSGGGGSGGGGSG |
| 43 | GGGGSGGGGSGGGGSGGGGSGGGGSGGGGS |
| 44 | GGGGSGGGGSGGGGSGGGGSGGGGSGGGG |
| 45 | GGGGSGGGGSGGGGSGGGGSGGGGSGGG |
| 46 | GGGGSGGGGSGGGGSGGGGSGGGGSGG |
| 47 | GGGGSGGGGSGGGGSGGGGSGGGGSG |
| 48 | GGGGSGGGGSGGGGSGGGGSGGGGS |
| 49 | GGGGSGGGGSGGGGSGGGGSGGGG |
| 50 | GGGGSGGGGSGGGGSGGGGSGGG |
| 51 | GGGGSGGGGSGGGGSGGGGSGG |
| 52 | GGGGSGGGGSGGGGSGGGGSG |
| 53 | GGGGSGGGGSGGGGSGGGGS |
| 54 | GGGGSGGGGSGGGGSGGGG |
| 55 | GGGGSGGGGSGGGGSGGG |
| 56 | GGGGSGGGGSGGGGSGG |
| 57 | GGGGSGGGGSGGGGSG |
| 58 | GGGGSGGGGSGGGGS |
| 59 | GGGGSGGGGSGGGG |
| 60 | GGGGSGGGGSGGG |
| 61 | GGGGSGGGGSGG |
| 62 | GGGGSGGGGSG |
| 63 | GGGGSGGGGS |
| 64 | GGGGSGGGG |
| 65 | GGGGSGGG |
| 66 | GGGGSGG |
| 67 | GGGGSG |
| 68 | GGGGS |
| 69 | GGGG |
| NA | GGG |
| NA | GG |
| 72 | GGGGSGGGGSGGGGSGGGGSGGGGSGGGGSGGGGSGGGGS |
| 73 | TGGG |
| 74 | TGGGG |
| 75 | SGGGG |
| 76 | SGGG |
| 77 | TGGGGSGGGGS |

TABLE 3-continued

Exemplary linker sequences

| SEQ ID | Linker sequence |
|---|---|
| 78 | TGGGGSGGGGSGGGGS |
| 79 | TGGGGSGGGGSGGGGSGGGGS |
| 80 | TGGGGSGGGGSGGGGSGGGGSGGGGS |
| 81 | TGGGGSGGGGSGGGGSGGGGSGGGGSGGGGS |
| 82 | TGGGGSGGGGSGGGGSGGGGSGGGGSGGGGSGGGGS |
| 83 | TGGGPKSCDK |
| NA | GA |
| NA | GS |
| 86 | AGGG |
| 87 | GGSG |
| 88 | GGAG |
| 89 | GGGGG |
| 90 | GGGGA |
| 91 | GGGS |
| 92 | GGGA |
| NA | GGS |
| NA | GGA |
| 95 | GSGS |
| 96 | GAGAGA |
| 97 | GSGSGS |
| 98 | GAGAGAGA |
| 99 | GSGSGSGS |
| 100 | GAGAGAGAGA |
| 101 | GSGSGSGSGS |
| 102 | GAGAGAGAGAGA |
| 103 | GAGA |
| 104 | GSGSGSGSGSGS |
| 105 | GGAGGA |
| 106 | GGSGGS |
| 107 | GGAGGAGGA |
| 108 | GGSGGSGGS |
| 109 | GGAGGAGGAGGA |
| 110 | GGSGGSGGSGGS |
| 111 | GGAG |
| 112 | GGSG |
| 113 | GGAGGGAG |
| 114 | GGSGGGSG |
| 115 | GGAGGGAGGGAG |

TABLE 3-continued

Exemplary linker sequences

| SEQ ID | Linker sequence |
|---|---|
| 116 | GGSGGGSGGGSG |
| 117 | GGGGAGGGGAGGGGA |
| 118 | AAAL |
| 119 | AAAK |
| 120 | AAAR |
| 121 | EGKSSGSGSESKST |
| 122 | GSAGSAAGSGEF |
| 123 | AEAAAKEAAAKA |
| 124 | KESGSVSSEQLAQFRSLD |
| 125 | GENLYFQSGG |
| 126 | SACYCELS |
| 127 | RSIAT |
| 128 | RPACKIPNDLKQKVMNH |
| 129 | GGSAGGSGSGSSGGSSGASGTGTAGGTGSGSGTGSG |
| 130 | AAANSSIDLISVPVDSR |
| 131 | GGSGGGSEGGGSEGGGSEGGGSEGGGSEGGGSGGGS |
| 132 | EAAAK |
| 133 | PAPAP |
| 335 | GGGAG |
| 336 | GGGAGG |
| 337 | GGGAGGG |

In some embodiments, the ActRIIB ECD variant polypeptide or binding agent of the disclosure comprises one or more linkers having the sequence set forth in any one of SEQ ID NOs: 59, 54, 34, or 63. In some embodiments, the ActRIIB ECD variant polypeptide or binding agent comprises a Glycine-rich linker at the C-terminus of the ActRIIB ECD variant polypeptide that is 2, 3, 6, 10, 14, 19, or 39 amino acids long. In some embodiments, the ActRIIB ECD variant polypeptide or binding agent of the disclosure comprises a linker of SEQ ID NO: 59 at the C-terminus of the ActRIIB ECD variant polypeptide. In some embodiments, the ActRIIB ECD variant polypeptide or binding agent of the disclosure comprises a linker of SEQ ID NO: 54 at the C-terminus of the ActRIIB ECD variant polypeptide. In some embodiments, the ActRIIB ECD variant polypeptide or binding agent of the disclosure comprises a linker of SEQ ID NO: 34 at the C-terminus of the ActRIIB ECD variant polypeptide. In some embodiments, the ActRIIB ECD variant polypeptide or binding agent of the disclosure comprises a linker of SEQ ID NO: 63 at the C-terminus of the ActRIIB ECD variant polypeptide.

Fc Domain Monomers and Fc Domains

In some embodiments, the present disclosure provides polypeptides comprising an ActRIIB-ECD variant described herein fused, via linker, to an Fc domain monomer. In some embodiments, the ActRIIB-ECD variant is fused at the C-terminus, via a linker, to the N-terminus of the Fc domain monomer.

As used herein, "Fc domain monomer" describes the single chain protein that, when associated with another Fc domain monomer, forms a functional Fc domain. The association of two Fc domain monomers creates one Fc domain. As used herein, "Fc domain" describes the minimum region (in the context of a larger polypeptide) or smallest protein folded structure (in the context of an isolated protein) that can bind to or be bound by an Fc receptor (FcR). When two Fc domain monomers associate, the resulting Fc domain has Fc receptor binding activity. Thus, an Fc domain is a dimeric structure that can bind an Fc receptor. Unless otherwise noted, all references herein to a "variant Fc domain" are to be understood as referring to a dimeric Fc domain, in which each Fc domain monomer comprises the referenced mutation.

It will be understood that Fc domain as used herein includes the polypeptides comprising the constant region of an antibody excluding the first constant region immunoglobulin domain. Thus, Fc refers to the last two constant region immunoglobulin domains (CH2, CH3) of IgG and optionally the flexible hinge N-terminal to these domains. Although the boundaries of the Fc domain monomer may vary, the human IgG heavy chain Fe domain monomer is usually defined to comprise residues C226 or P230 to its carboxyl-terminus. Unless otherwise noted, all references to amino acid positions in Fc domains and Fc domain monomers are according to the EU index as set forth in Kabat (1991, NIH Publication 91-3242, National Technical Information Service, Springfield, Va.). Fc may refer to this region in isolation, or this region in the context of a polypeptide construct. It is noted that polymorphisms have been observed at a number of Fc positions, including but not limited to Kabat 270, 272, 312, 315, 356, and 358, and thus slight differences between the sequences provided herein and sequences in the art may exist. The Fc domain monomer included in the polypeptides or binding agents of the present disclosure may be an IgG1, IgG2, IgG3, or IgG4 domain.

In exemplary embodiments, the polypeptides of the disclosure comprise one or more constant region of an antibody, e.g., the second constant domain (CH2) and/or the third constant domain (CH3) of an antibody heavy chain, or an Fc domain monomer of an antibody heavy chain. The antibody may be, for example and without limitation, an IgG antibody such as an IgG1, IgG2, IgG3 or IgG4 antibody. In particular embodiments, the antibody is a human antibody, e.g., the Fc domain monomer comprises a constant region of the heavy chain of a human IgG1, IgG2, IgG3 or IgG4. In some embodiments, the Fc domain monomer has at least 85%, at least 90%, at least 95%, at least 96%, at least 97%, at least 98%, or at least 99% sequence identity with a human IgG1, IgG2, IgG3 or IgG4 constant region. In a particular embodiment, the Fc domain monomer comprises or consists of an Fc domain monomer of a human IgG1 antibody. In another particular embodiment, the Fc domain monomer comprises or consists of an Fc domain monomer of a human IgG2 antibody. In another particular embodiment, the Fc domain monomer comprises or consists of an Fc domain monomer of a human IgG4 antibody. Exemplary Fc domain sequences (including both wild type sequences, polymorphisms thereof, and variant sequences) are provided in Table 4.

TABLE 4

Exemplary Fc domain sequences

| Isotype | AA Sequence | SEQ ID |
|---|---|---|
| IgG1 - EEM polymorph ("IgG1-EM") | THTCPPCPAPELLGGPSVFLFPPKPKDTLMISRTPEVTCVVVDV SHEDPEVKFNWYVDGVEVHNAKTKPREEQYNSTYRVVSVLTVLH QDWLNGKEYKCKVSNKALPAPIEKTISKAKGQPREPQVYTLPPS REEMTKNQVSLTCLVKGFYPSDIAVEWESNGQPENNYKTTPPVL DSDGSFFLYSKLTVDKSRWQQGNVFSCSVMHEALHNHYTQKSLS LSPG | 134 |
| IgG1 - DEL polymorph ("IgG1 -DL") | THTCPPCPAPELLGGPSVFLFPPKPKDTLMISRTPEVTCVVVDV SHEDPEVKFNWYVDGVEVHNAKTKPREEQYNSTYRVVSVLTVLH QDWLNGKEYKCKVSNKALPAPIEKTISKAKGQPREPQVYTLPPS RDELTKNQVSLTCLVKGFYPSDIAVEWESNGQPENNYKTTPPVL DSDGSFFLYSKLTVDKSRWQQGNVFSCSVMHEALHNHYTQKSLS LSPG | 135 |
| IgG1 - YTE-EM | THTCPPCPAPELLGGPSVFLFPPKPKDTLYITREPEVTCVVVDV SHEDPEVKFNWYVDGVEVHNAKTKPREEQYNSTYRVVSVLTVLH QDWLNGKEYKCKVSNKALPAPIEKTISKAKGQPREPQVYTLPPS REEMTKNQVSLTCLVKGFYPSDIAVEWESNGQPENNYKTTPPVL DSDGSFFLYSKLTVDKSRWQQGNVFSCSVMHEALHNHYTQKSLS LSPG | 136 |
| IgG1 - YTE-DL | THTCPPCPAPELLGGPSVFLFPPKPKDTLYITREPEVTCVVVDV SHEDPEVKFNWYVDGVEVHNAKTKPREEQYNSTYRVVSVLTVLH QDWLNGKEYKCKVSNKALPAPIEKTISKAKGQPREPQVYTLPPS RDELTKNQVSLTCLVKGFYPSDIAVEWESNGQPENNYKTTPPVL DSDGSFFLYSKLTVDKSRWQQGNVFSCSVMHEALHNHYTQKSLS LSPG | 137 |
| IgG1 - Y-DL | THTCPPCPAPELLGGPSVFLFPPKPKDTLYISRTPEVTCVVVDV SHEDPEVKFNWYVDGVEVHNAKTKPREEQYNSTYRVVSVLTVLH QDWLNGKEYKCKVSNKALPAPIEKTISKAKGQPREPQVYTLPPS RDELTKNQVSLTCLVKGFYPSDIAVEWESNGQPENNYKTTPPVL DSDGSFFLYSKLTVDKSRWQQGNVFSCSVMHEALHNHYTQKSLS LSPG | 138 |

TABLE 4-continued

| Exemplary Fc domain sequences | | |
|---|---|---|
| Isotype | AA Sequence | SEQ ID |
| IgG1 - Y-EM | THTCPPCPAPELLGGPSVFLFPPKPKDTLYISRTPEVTCVVVDV SHEDPEVKFNWYVDGVEVHNAKTKPREEQYNSTYRVVSVLTVLH QDWLNGKEYKCKVSNKALPAPIEKTISKAKGQPREPQVYTLPPS REEMTKNQVSLTCLVKGFYPSDIAVEWESNGQPENNYKTTPPVL DSDGSFFLYSKLTVDKSRWQQGNVFSCSVMHEALHNHYTQKSLS LSPG | 338 |
| IgG1 - DL | APELLGGPSVFLFPPKPKDTLMISRTPEVTCVVVDVSHEDPEVK FNWYVDGVEVHNAKTKPREEQYNSTYRVVSVLTVLHQDWLNGKE YKCKVSNKALPAPIEKTISKAKGQPREPQVYTLPPSRDELTKNQ VSLTCLVKGFYPSDIAVEWESNGQPENNYKTTPPVLDSDGSFFL YSKLTVDKSRWQQGNVFSCSVMHEALHNHYTQKSLSLSPGK | 139 |
| IgG1 - DL | APELLGGPSVFLFPPKPKDTLMISRTPEVTCVVVDVSHEDPEVK FNWYVDGVEVHNAKTKPREEQYNSTYRVVSVLTVLHQDWLNGKE YKCKVSNKALPAPIEKTISKAKGQPREPQVYTLPPSRDELTKNQ VSLTCLVKGFYPSDIAVEWESNGQPENNYKTTPPVLDSDGSFFL YSKLTVDKSRWQQGNVFSCSVMHEALHNHYTQKSLSLSPG | 140 |
| IgG1 - DL | PPCPAPELLGGPSVFLFPPKPKDTLMISRTPEVTCVVVDVSHED PEVKFNWYVDGVEVHNAKTKPREEQYNSTYRVVSVLTVLHQDWL NGKEYKCKVSNKALPAPIEKTISKAKGQPREPQVYTLPPSRDEL TKNQVSLTCLVKGFYPSDIAVEWESNGQPENNYKTTPPVLDSDG SFFLYSKLTVDKSRWQQGNVFSCSVMHEALHNHYTQKSLSLSPG | 141 |
| IgG1 - DL | DKTHTCPPCPAPELLGGPSVFLFPPKPKDTLMISRTPEVTCVVV DVSHEDPEVKFNWYVDGVEVHNAKTKPREEQYNSTYRVVSVLTV LHQDWLNGKEYKCKVSNKALPAPIEKTISKAKGQPREPQVYTLP PSRDELTKNQVSLTCLVKGFYPSDIAVEWESNGQPENNYKTTPP VLDSDGSFFLYSKLTVDKSRWQQGNVFSCSVMHEALHNHYTQKS LSLSPG | 142 |
| IgG1 - DL | EPKSSDKTHTCPPCPAPELLGGPSVFLFPPKPKDTLMISRTPEV TCVVVDVSHEDPEVKFNWYVDGVEVHNAKTKPREEQYNSTYRVV SVLTVLHQDWLNGKEYKCKVSNKALPAPIEKTISKAKGQPREPQ VYTLPPSRDELTKNQVSLTCLVKGFYPSDIAVEWESNGQPENNY KTTPPVLDSDGSFFLYSKLTVDKSRWQQGNVFSCSVMHEALHNH YTQKSLSLSPG | 143 |
| IgG1 - DL | EPKSSDKTHTSPPSPAPELLGGPSVFLFPPKPKDTLMISRTPEV TCVVVDVSHEDPEVKFNWYVDGVEVHNAKTKPREEQYNSTYRVV SVLTVLHQDWLNGKEYKCKVSNKALPAPIEKTISKAKGQPREPQ VYTLPPSRDELTKNQVSLTCLVKGFYPSDIAVEWESNGQPENNY KTTPPVLDSDGSFFLYSKLTVDKSRWQQGNVFSCSVMHEALHNH YTQKSLSLSPG | 144 |
| IgG1 - EM | THTCPPCPAPELLGGPSVFLFPPKPKDTLYISRTPEVTCVVVDV SHEDPEVKFNWYVDGVEVHNAKTKPREEQYNSTYRVVSVLTVLH QDWLNGKEYKCKVSNKALPAPIEKTISKAKGQPREPQVYTLPPS REEMTKNQVSLTCLVKGFYPSDIAVEWESNGQPENNYKTTPPVL DSDGSFFLYSKLTVDKSRWQQGNVFSCSVMHEALHNHYTQKSLS LSPG | 145 |
| IgG1 - DL | THTCPPCPAPELLGGPSVFLFPPKPKDTLMISRTPEVTCVVVDV SHEDPEVKFNWYVDGVEVHNAKTKPREEQYNSTYRVVSVLTVLH QDWLNGKEYKCKVSNKALPVPIEKTISKAKGQPREPQVYTLPPS RDELTKNQVSLTCLVKGFYPSDIAVEWESNGQPENNYKTTPPVL DSDGSFFLYSKLTVDKSRWQQGNVFSCSVMHEALHNHYTQKSLS LSPG | 146 |
| IgG1 - EM | THTCPPCPAPELLGGPSVFLFPPKPKDTLMISRTPEVTCVVVDV SHEDPEVKFNWYVDGVEVHNAKTKPREEQYNSTYRVVSVLTVLH QDWLNGKEYKCKVSNKALPVPIEKTISKAKGQPREPQVYTLPPS REEMTKNQVSLTCLVKGFYPSDIAVEWESNGQPENNYKTTPPVL DSDGSFFLYSKLTVDKSRWQQGNVFSCSVMHEALHNHYTQKSLS LSPG | 147 |
| IgG2 | APPVAGPSVFLFPPKPKDTLMISRTPEVTCVVVDVSHEDPEVQF NWYVDGVEVHNAKTKPREEQFNSTFRVVSVLTVVHQDWLNGKEY KCKVSNKGLPAPIEKTISKTKGQPREPQVYTLPPSREEMTKNQV SLTCLVKGFYPSDISVEWESNGQPENNYKTTPPMLDSDGSFFLY SKLTVDKSRWQQGNVFSCSVMHEALHNHYTQKSLSLSPGK | 148 |
| IgG2 | VECPPCPAPPVAGPSVFLFPPKPKDTLMISRTPEVTCVVVDVSH EDPEVQFNWYVDGVEVHNAKTKPREEQFNSTFRVVSVLTVVHQD WLNGKEYKCKVSNKGLPAPIEKTISKTKGQPREPQVYTLPPSRE | 149 |

TABLE 4-continued

| Exemplary Fc domain sequences | | |
|---|---|---|
| Isotype | AA Sequence | SEQ ID |
| | EMTKNQVSLTCLVKGFYPSDIAVEWESNGQPENNYKTTPPMLDSDGSFFLYSKLTVDKSRWQQGNVFSCSVMHEALHNHYTQKSLSLSPGK | |
| IgG2 | ERKCCVECPPCPAPPVAGPSVFLFPPKPKDTLMISRTPEVTCVVVDVSHEDPEVQFNWYVDGVEVHNAKTKPREEQFNSTFRVVSVLTVVHQDWLNGKEYKCKVSNKGLPAPIEKTISKTKGQPREPQVYTLPPSREEMTKNQVSLTCLVKGFYPSDISVEWESNGQPENNYKTTPPMLDSDGSFFLYSKLTVDKSRWQQGNVFSCSVMHEALHNHYTQKSLSLSPGK | 150 |
| IgG2 | ERKSSVECPPCPAPPVAGPSVFLFPPKPKDTLMISRTPEVTCVVVDVSHEDPEVQFNWYVDGVEVHNAKTKPREEQFNSTFRVVSVLTVVHQDWLNGKEYKCKVSNKGLPAPIEKTISKTKGQPREPQVYTLPPSREEMTKNQVSLTCLVKGFYPSDISVEWESNGQPENNYKTTPPMLDSDGSFFLYSKLTVDKSRWQQGNVFSCSVMHEALHNHYTQKSLSLSPG | 151 |
| IgG2 | ERKSSVESPPCPAPPVAGPSVFLFPPKPKDTLMISRTPEVTCVVVDVSHEDPEVQFNWYVDGVEVHNAKTKPREEQFNSTFRVVSVLTVVHQDWLNGKEYKCKVSNKGLPAPIEKTISKTKGQPREPQVYTLPPSREEMTKNQVSLTCLVKGFYPSDISVEWESNGQPENNYKTTPPMLDSDGSFFLYSKLTVDKSRWQQGNVFSCSVMHEALHNHYTQKSLSLSPG | 152 |
| IgG2 | ERKSSVESPPSPAPPVAGPSVFLFPPKPKDTLMISRTPEVTCVVVDVSHEDPEVQFNWYVDGVEVHNAKTKPREEQFNSTFRVVSVLTVVHQDWLNGKEYKCKVSNKGLPAPIEKTISKTKGQPREPQVYTLPPSREEMTKNQVSLTCLVKGFYPSDISVEWESNGQPENNYKTTPPMLDSDGSFFLYSKLTVDKSRWQQGNVFSCSVMHEALHNHYTQKSLSLSPG | 153 |
| IgG2 | APPVAGPSVFLFPPKPKDTLMISRTPEVTCVVVDVSHEDPEVQFNWYVDGVEVHNAKTKPREEQFNSTFRVVSVLTVVHQDWLNGKEYKCKVSNKGLPAPIEKTISKTKGQPREPQVYTLPPSREEMTKNQVSLTCLVKGFYPSDISVEWESNGQPENNYKTTPPMLDSDGSFFLYSKLTVDKSRWQQGNVFSCSVMHEALHNHYTQKSLSLSPG | 154 |
| IgG2 | PPCPAPPVAGPSVFLFPPKPKDTLMISRTPEVTCVVVDVSHEDPEVQFNWYVDGVEVHNAKTKPREEQFNSTFRVVSVLTVVHQDWLNGKEYKCKVSNKGLPAPIEKTISKTKGQPREPQVYTLPPSREEMTKNQVSLTCLVKGFYPSDISVEWESNGQPENNYKTTPPMLDSDGSFFLYSKLTVDKSRWQQGNVFSCSVMHEALHNHYTQKSLSLSPG | 155 |
| IgG2 | VECPPCPAPPVAGPSVFLFPPKPKDTLMISRTPEVTCVVVDVSHEDPEVQFNWYVDGVEVHNAKTKPREEQFNSTFRVVSVLTVVHQDWLNGKEYKCKVSNKGLPAPIEKTISKTKGQPREPQVYTLPPSREEMTKNQVSLTCLVKGFYPSDISVEWESNGQPENNYKTTPPMLDSDGSFFLYSKLTVDKSRWQQGNVFSCSVMHEALHNHYTQKSLSLSPG | 156 |
| IgG2 | PCPPCKCPAPNLLGGPSVFIFPPKIKDVLMISLSPIVTCVVVDVSEDDPDVQISWFVNNVEVHTAQTQTHREDYNSTLRVVSALPIQHQDWMSGKEFKCKVNNKDLPAPIERTISKPKGSVRAPQVYVLPPPEEEMTKKQVTLTCMVTDFMPEDIYVEWTNNGKTELNYKNTEPVLDSDGSYFMYSKLRVEKKNWVERNSYSCSVVHEGLHNHHTTKSFSRTPG | 157 |
| IgG3 | APELLGGPSVFLFPPKPKDTLMISRTPEVTCVVVDVSHEDPEVQFKWYVDGVEVHNAKTKPREEQYNSTFRVVSVLTVLHQDWLNGKEYKCKVSNKALPAPIEKTISKTKGQPREPQVYTLPPSREEMTKNQVSLTCLVKGFYPSDIAVEWESSGQPENNYNTTPPMLDSDGSFFLYSKLTVDKSRWQQGNIFSCSVMHEALHNRFTQKSLSLSPGK | 158 |
| IgG3 | APELLGGPSVFLFPPKPKDTLMISRTPEVTCVVVDVSHEDPEVQFKWYVDGVEVHNAKTKPREEQYNSTFRVVSVLTVLHQDWLNGKEYKCKVSNKALPAPIEKTISKTKGQPREPQVYTLPPSREEMTKNQVSLTCLVKGFYPSDIAVEWESSGQPENNYNTTPPMLDSDGSFFLYSKLTVDKSRWQQGNIFSCSVMHEALHNRFTQKSLSLSPG | 159 |
| IgG3 | PRCPAPELLGGPSVFLFPPKPKDTLMISRTPEVTCVVVDVSHEDPEVQFKWYVDGVEVHNAKTKPREEQYNSTFRVVSVLTVLHQDWLNGKEYKCKVSNKALPAPIEKTISKTKGQPREPQVYTLPPSREEMTKNQVSLTCLVKGFYPSDIAVEWESSGQPENNYNTTPPMLDSDGSFFLYSKLTVDKSRWQQGNIFSCSVMHEALHNRFTQKSLSLSPG | 160 |

TABLE 4-continued

Exemplary Fc domain sequences

| Isotype | AA Sequence | SEQ ID |
|---|---|---|
| IgG3 | DTPPPCPRCPAPELLGGPSVFLFPPKPKDTLMISRTPEVTCVVV DVSHEDPEVQFKWYVDGVEVHNAKTKPREEQYNSTFRVVSVLTV LHQDWLNGKEYKCKVSNKALPAPIEKTISKTKGQPREPQVYTLP PSREEMTKNQVSLTCLVKGFYPSDIAVEWESSGQPENNYNTTPP MLDSDGSFFLYSKLTVDKSRWQQGNIFSCSVMHEALHNRFTQKS LSLSPG | 161 |
| IgG3 | EPKSSDTPPPCPRCPAPELLGGPSVFLFPPKPKDTLMISRTPEV TCVVVDVSHEDPEVQFKWYVDGVEVHNAKTKPREEQYNSTFRVV SVLTVLHQDWLNGKEYKCKVSNKALPAPIEKTISKTKGQPREPQ VYTLPPSREEMTKNQVSLTCLVKGFYPSDIAVEWESSGQPENNY NTTPPMLDSDGSFFLYSKLTVDKSRWQQGNIFSCSVMHEALHNR FTQKSLSLSPG | 162 |
| IgG3 | EPKSSDTPPPSPRCPAPELLGGPSVFLFPPKPKDTLMISRTPEV TCVVVDVSHEDPEVQFKWYVDGVEVHNAKTKPREEQYNSTFRVV SVLTVLHQDWLNGKEYKCKVSNKALPAPIEKTISKTKGQPREPQ VYTLPPSREEMTKNQVSLTCLVKGFYPSDIAVEWESSGQPENNY NTTPPMLDSDGSFFLYSKLTVDKSRWQQGNIFSCSVMHEALHNR FTQKSLSLSPG | 163 |
| IgG3 | EPKSSDTPPPSPRSPAPELLGGPSVFLFPPKPKDTLMISRTPEV TCVVVDVSHEDPEVQFKWYVDGVEVHNAKTKPREEQYNSTFRVV SVLTVLHQDWLNGKEYKCKVSNKALPAPIEKTISKTKGQPREPQ VYTLPPSREEMTKNQVSLTCLVKGFYPSDIAVEWESSGQPENNY NTTPPMLDSDGSFFLYSKLTVDKSRWQQGNIFSCSVMHEALHNR FTQKSLSLSPG | 164 |
| IgG4 | APEFLGGPSVFLFPPKPKDTLMISRTPEVTCVVVDVSQEDPEVQ FNWYVDGVEVHNAKTKPREEQFNSTYRVVSVLTVLHQDWLNGKE YKCKVSNKGLPSSIEKTISKAKGQPREPQVYTLPPSQEEMTKNQ VSLTCLVKGFYPSDIAVEWESNGQPENNYKTTPPVLDSDGSFFL YSRLTVDKSRWQEGNVFSCSVMHEALHNHYTQKSLSLSLGK | 165 |
| IgG4 | GPPCPPCPAPEFLGGPSVFLFPPKPKDTLMISRTPEVTCVVVDV SQEDPEVQFNWYVDGVEVHNAKTKPREEQFNSTYRVVSVLTVLH QDWLNGKEYKCKVSNKGLPSSIEKTISKAKGQPREPQVYTLPPS QEEMTKNQVSLTCLVKGFYPSDIAVEWESNGQPENNYKTTPPVL DSDGSFFLYSRLTVDKSRWQEGNVFSCSVMHEALHNHYTQKSLS LSLG | 166 |
| IgG4 | APEFLGGPSVFLFPPKPKDTLMISRTPEVTCVVVDVSQEDPEVQ FNWYVDGVEVHNAKTKPREEQFNSTYRVVSVLTVLHQDWLNGKE YKCKVSNKGLPSSIEKTISKAKGQPREPQVYTLPPSQEEMTKNQ VSLTCLVKGFYPSDIAVEWESNGQPENNYKTTPPVLDSDGSFFL YSRLTVDKSRWQEGNVFSCSVMHEALHNHYTQKSLSLSLG | 167 |
| IgG4 | PSCPAPEFLGGPSVFLFPPKPKDTLMISRTPEVTCVVVDVSQED PEVQFNWYVDGVEVHNAKTKPREEQFNSTYRVVSVLTVLHQDWL NGKEYKCKVSNKGLPSSIEKTISKAKGQPREPQVYTLPPSQEEM TKNQVSLTCLVKGFYPSDIAVEWESNGQPENNYKTTPPVLDSDG SFFLYSRLTVDKSRWQEGNVFSCSVMHEALHNHYTQKSLSLSLG | 168 |
| IgG4 | ESKYGPPCPSCPAPEFLGGPSVFLFPPKPKDTLMISRTPEVTCV VVDVSQEDPEVQFNWYVDGVEVHNAKTKPREEQFNSTYRVVSVL TVLHQDWLNGKEYKCKVSNKGLPSSIEKTISKAKGQPREPQVYT LPPSQEEMTKNQVSLTCLVKGFYPSDIAVEWESNGQPENNYKTT PPVLDSDGSFFLYSRLTVDKSRWQEGNVFSCSVMHEALHNHYTQ KSLSLSLG | 169 |
| IgG4 | ESKYGPPCPPCPAPEFLGGPSVFLFPPKPKDTLMISRTPEVTCV VVDVSQEDPEVQFNWYVDGVEVHNAKTKPREEQFNSTYRVVSVL TVLHQDWLNGKEYKCKVSNKGLPSSIEKTISKAKGQPREPQVYT LPPSQEEMTKNQVSLTCLVKGFYPSDIAVEWESNGQPENNYKTT PPVLDSDGSFFLYSRLTVDKSRWQEGNVFSCSVMHEALHNHYTQ KSLSLSLG | 170 |
| IgG4 | ESKYGPPCPPCPAPEFLGGPSVFLFPPKPKDTLMISRTPEVTCV VVDVSQEDPEVQFNWYVDGVEVHNAKTKPREEQFNSTYRVVSVL TVLHQDWLNGKEYKCKVSNKGLPSSIEKTISKAKGQPREPQVYT LPPSQEEMTKNQVSLTCLVKGFYPSDIAVEWESNGQPENNYKTT PPVLDSDGSFFLYSKLTVDKSRWQEGNVFSCSVMHEALHNHYTQ KSLSLSLG | 171 |
| IgG4 | ESKYGPPSPSCPAPEFLGGPSVFLFPPKPKDTLMISRTPEVTCV VVDVSQEDPEVQFNWYVDGVEVHNAKTKPREEQFNSTYRVVSVL | 172 |

TABLE 4-continued

| Exemplary Fc domain sequences | | |
|---|---|---|
| Isotype | AA Sequence | SEQ ID |
| | TVLHQDWLNGKEYKCKVSNKGLPSSIEKTISKAKGQPREPQVYT LPPSQEEMTKNQVSLTCLVKGFYPSDIAVEWESNGQPENNYKTT PPVLDSDGSFFLYSRLTVDKSRWQEGNVFSCSVMHEALHNHYTQ KSLSLSLG | |
| IgG4 | ESKYGPPSPSSPAPEFLGGPSVFLFPPKPKDTLMISRTPEVTCV VVDVSQEDPEVQFNWYVDGVEVHNAKTKPREEQFNSTYRVVSVL TVLHQDWLNGKEYKCKVSNKGLPSSIEKTISKAKGQPREPQVYT LPPSQEEMTKNQVSLTCLVKGFYPSDIAVEWESNGQPENNYKTT PPVLDSDGSFFLYSRLTVDKSRWQEGNVFSCSVMHEALHNHYTQ KSLSLSLG | 173 |

In general, AcIRIIB-ECD polypeptides are organized such that the Fc domain monomer is linked at its N-terminus to the C-terminus of the ActRIIB-ECD variant, so that for each ActRIIB-ECD polypeptide, the orientation of the construct is, from N-terminus to C-terminus, a single chain of (ActRIIB-ECD variant)-(linker)-(Fc domain monomer). However, the orientation of constructs is not particularly limited, and other orientations are contemplated. For example, in some embodiments the Fc domain monomer may be linked at its C-terminus to the N-terminus of the ActRIIB-ECD variant.

In an exemplary embodiment, the Fc domain monomer allows assembly of two or more polypeptide chains in a covalent manner, for example by disulfide linking between cysteine residues. In this way the Fc domain monomer acts as a dimerization domain, allowing assembly of two ActRIIB-ECD polypeptide chains to form a dimer. In accordance with the present disclosure, such dimers generally comprise two polypeptides, each polypeptide including an ActIIRB-ECD variant linked to the Fc domain monomer as described herein, thereby forming a divalent TGFβ superfamily ligand binding agent. The binding agents described herein therefore comprise two ActIIRB-ECD variants, a linker domain, and an Fc domain.

The Fc domain monomer generally comprises one or more cysteine residue for crosslinking of a first polypeptide with a second polypeptide in a homodimeric construct. For example, the Fc domain monomer may include at least two cysteine residues for forming a disulfide bridge between two polypeptides, thereby forming a dimer. In some embodiments of the present technology, the Fc domain monomer comprises or consists of the sequence set forth in any one of SEQ ID NOs: 134-173 and 338, or a sequence at least 90%, at least 95%, at least 96%, at least 97%, at least 98%, or at least 99% identical thereto. In a particular embodiment, the Fc domain monomer comprises or consists of the amino acid sequence set forth in SEQ ID NO: 134. In a particular embodiment, the Fc domain monomer comprises or consists of the amino acid sequence set forth in SEQ ID NO: 135. In a particular embodiment, the Fc domain monomer comprises or consists of the amino acid sequence set forth in SEQ ID NO: 137. In a particular embodiment, the Fc domain monomer comprises or consists of the amino acid sequence set forth in SEQ ID NO: 138. In a particular embodiment, the Fc domain monomer comprises or consists of the amino acid sequence set forth in SEQ ID NO: 157.

In some embodiments, the present disclosure provides binding agents comprising a variant Fc domain, i.e., a non-naturally occurring Fc domain, for example an Fc domain comprising one or more non-naturally occurring amino acid residue, substitution, addition, deletion, etc.

In some embodiments of the technology, the Fc domain is a variant Fc domain that forms a variant Fc domain with a desirable property, such as increased half-life, on the polypeptide or binding agent compared to naturally occurring (wild-type) Fc sequences. As used herein, a "variant Fc domain" refers to a non-naturally occurring Fc domain, for example an Fc domain comprising one or more non-naturally occurring amino acid residues, one or more amino acid substitutions relative to a wild-type human constant domain, or one or more amino acid deletion, addition and/or modification.

There are many known polymorphs for the IgG1 Fc domain, including the "DEL" polymorph and the "EEM" polymorph. The DEL polymorph comprises the amino acids D-E-L at positions 356, 357, and 358, respectively (also referred to herein as "Fc-DL", e.g., SEQ ID NO: 135). The EEM polymorph comprises the amino acids E-E-M at positions 356, 357, and 358, respectively (also referred to herein as "Fc-EM", e.g., SEQ ID NO: 134). Two binding agents that are otherwise identical except for the presence of a DEL Fc domain or an EEM Fc domain are expected to demonstrate similar properties in terms of ligand binding and therapeutic efficacy. In some embodiments of the technology, the Fc domain is a DEL Fc domain ("DL"). In some embodiments of the technology, the Fc domain is an EEM Fc domain ("EM"). Other polymorphs may also be used, e.g., IgG1 polymorphs of SEQ ID NOs: 134-135 and 139-147, IgG2 polymorphs of SEQ ID NOs: 148-157, IgG3 polymorphs of SEQ ID NOs: 158-164, and IgG4 polymorphs of SEQ ID NOs: 165-173.

In some embodiments, a variant Fc domain formed by two variant Fc domain monomers has altered binding properties for an Fc receptor such as FcRn, relative to a comparable molecule (e.g., a protein having the same amino acid sequence except having a wild type Fc domain monomer). The serum half-life of proteins comprising Fc domains may be increased by increasing the binding affinity of the Fc domain for FcRn. In one embodiment, the Fc domain variant has enhanced serum half-life relative to a comparable molecule. In a particular embodiment, the Fc domain variant comprises at least one amino acid substitution at one or more positions selected from the group consisting of M252Y, S254T and T256 (referred to herein as "YTE"; e.g., SEQ ID NO: 137). In another embodiment, the Fc domain variant comprises a Y at position 252 (e.g., SEQ ID NO: 138, referred to herein as "Fc-Y"). In another embodiment, the Fc domain variant comprises a T at position 254. In another embodiment, the Fc domain variant comprises an E at position 256.

Consequently, in some embodiments of the present technology, the ActRIIB-ECD polypeptide comprises a variant Fc domain monomer that forms an Fc domain with increased in vivo half-life relative to a comparable molecule. In some such embodiments, the Fc domain monomer of the ActRIIB-ECD polypeptide comprises at least one substitution of an amino acid residue selected from the group consisting of: residue 252, 254, and 256.

In some embodiments, an ActRIIB-ECD polypeptide comprises a variant Fc domain monomer comprising at least one amino acid substitution selected from the group consisting of M252Y, S254T, and T256E. In such embodiments, the variant Fc domain monomer may further comprise one or more additional amino acid substitution(s) such as, without limitation, E356D and M358L.

In some embodiments, an ActRIIB-ECD polypeptide comprises a variant Fc domain monomer comprising the following amino acid substitutions: M252Y, S254T, and T256E, referred to herein as "FcYTE" or "YTE". In some embodiments, the FcYTE domain monomer is a DEL polymorph (referred to herein as YTE-DL, e.g., SEQ ID NO: 137). In some embodiments, the FcYTE domain monomer is an EEM polymorph (referred to herein as YTE-EM, e.g., SEQ ID NO: 136).

In some embodiments, an ActRIIB-ECD polypeptide comprises a variant Fc domain monomer comprising the following amino acid substitutions: M252Y, referred to herein as "FcY". In some embodiments, the FcY domain monomer is a DEL polymorph (referred to herein as Y-DL, e.g., SEQ ID NO: 138). In some embodiments, the FcY domain monomer is an EEM polymorph (referred to herein as Y-EM, e.g., SEQ ID NO: 338).

In some embodiments, an ActRIIB-ECD polypeptide comprises an Fc domain monomer comprising a Lysine residue (K) at the C-terminus.

In some embodiments, a variant Fc domain (e.g., an Fc domain formed by two variant Fc domain monomers) for use in the ActRIIB-ECD polypeptides of the disclosure comprises one or more amino acid substitution that reduces aggregation and/or increases stability and/or increases half-life of the ActRIIB-ECD polypeptide compared to naturally occurring Fc sequences. In some embodiments, the Fc domain is selected to provide one or more effector function such as antibody dependent cellular cytotoxicity (ADCC), complement activation (complement dependent cytotoxicity or CDC), opsonization, and the like. In an embodiment, a variant Fc domain has enhanced binding to an Fc receptor relative to a comparable molecule. In a specific embodiment, a variant Fc domain has enhanced binding to the neonatal Fc receptor FcRn. In another embodiment, the variant Fc domain and/or the polypeptide or binding agent containing the variant Fc domain has a binding affinity for FcRn that is at least 2 fold, or at least 3 fold, or at least 5 fold, or at least 7 fold, or at least 10 fold, or at least 20 fold, or at least 30 fold, or at least 40 fold, or at least 50 fold, or at least 60 fold, or at least 70 fold, or at least 80 fold, or at least 90 fold, or at least 100 fold, or at least 200 fold greater than that of a comparable molecule. The serum half-life of proteins comprising Fc domain may be increased by increasing the binding affinity of the Fc domain monomer for FcRn. Consequently, in one embodiment the polypeptide or binding agent comprising the variant Fc domain has an enhanced serum half-life relative to a comparable molecule.

Examples for means to extend serum half-life of the polypeptides and binding agents of the disclosure include peptides, proteins or domains of proteins, which are fused or otherwise attached to the polypeptides and binding agents. The group of peptides, proteins or protein domains includes peptides binding to other proteins with preferred pharmacokinetic profile in the human body such as serum albumin (see WO 2009/127691). An alternative concept of such half-life extending peptides includes peptides binding to the neonatal Fc receptor (FcRn, see WO 2007/098420), which can also be used in the polypeptides and binding agents of the present disclosure. The concept of attaching larger domains of proteins or complete proteins includes e.g. the fusion of human serum albumin, variants or mutants of human serum albumin (see WO 2011/051489, WO 2012/059486, WO 2012/150319, WO 2013/135896, WO 2014/072481, WO 2013/075066) or domains thereof as well as the fusion of constant region of immunoglobulins (Fc domains) and variants thereof, as described herein. Such variants of Fc domains may be optimized/modified in order to allow the desired pairing of dimers or multimers, to abolish Fc receptor binding (e.g., the Fcg receptor), to enhance binding to FcRn, or for other reasons. A further concept known in the art to extend the half-life of small protein compounds in the human body is the pegylation of those compounds such as the polypeptide or binding agent of the present disclosure.

In one embodiment, the present disclosure provides binding agents, wherein the Fc domain comprises a non-naturally occurring amino acid residue at one or more positions selected from the group consisting of 234, 235, 236, 237, 238, 239, 240, 241, 243, 244, 245, 247, 251, 252, 254, 255, 256, 262, 263, 264, 265, 266, 267, 268, 269, 279, 280, 284, 292, 296, 297, 298, 299, 305, 313, 316, 325, 326, 327, 328, 329, 330, 332, 333, 334, 339, 341, 343, 370, 373, 378, 392, 416, 419, 421, 440 and 443 as numbered by the EU index as set forth in Kabat. Optionally, the Fc domain may comprise a non-naturally occurring amino acid residue at additional and/or alternative positions known to one skilled in the art (see, e.g., U.S. Pat. Nos. 5,624,821; 6,277,375; 6,737,056; PCT Patent Publications WO 01/58957; WO 02/06919; WO 04/016750; WO 04/029207; WO 04/035752; WO 04/074455; WO 04/099249; WO 04/063351; WO 05/070963; WO 05/040217, WO 05/092925 and WO 06/020114). In a specific embodiment, the present disclosure provides an Fc variant protein composition, wherein the Fc domain comprises at least one amino acid substitution selected from the group consisting of 234D, 234E, 234N, 234Q, 234T, 234H, 234Y, 2341, 234V, 234F, 235A, 235D, 235R. 235W, 235P, 235S, 235N, 235Q, 235T, 235H, 235Y, 2351, 235V, 235F, 236E, 239D, 239E, 239N, 239Q, 239F, 239T, 239H, 239Y, 2401, 240A, 240T, 240M, 241W, 241 L, 241Y, 241E, 241R. 243W, 243L 243Y, 243R, 243Q, 244H, 245A, 247L, 247V, 247G, 251F, 252Y, 254T, 255L, 256E, 256M, 2621, 262A, 262T, 262E, 2631, 263A, 263T, 263M, 264L, 2641, 264W, 264T, 264R, 264F, 264M, 264Y, 264E, 265G, 265N, 265Q, 265Y, 265F, 265V, 2651, 265L, 265H, 265T, 2661, 266A, 266T, 266M, 267Q, 267L, 268E, 269H, 269Y, 269F, 269R, 270E, 280A, 284M, 292P, 292L, 296E, 296Q, 296D, 296N, 296S, 296T, 296L, 2961, 296H, 269G, 297S, 297D, 297E, 298H, 298I, 298T, 298F, 2991, 299L, 299A, 299S, 299V, 299H, 299F, 299E, 3051, 313F, 316D, 325Q, 325L, 3251, 325D, 325E, 325A, 325T, 325V, 325H, 327G, 327W, 327N, 327L, 328S, 328M, 328D, 328E, 328N, 328Q, 328F, 328I, 328V, 328T, 328H, 328A, 329F, 329H, 329Q, 330K, 330G, 330T, 330C, 330L, 330Y, 330V, 3301, 330F, 330R, 330H, 332D, 332S, 332W, 332F, 332E, 332N, 332Q, 332T, 332H, 332Y, 332A, 339T, 370E, 370N, 378D, 392T, 396L, 416G, 419H, 421K, 440Y and 434W as numbered by the EU index as set forth in Kabat. Optionally, the Fc domain may comprise additional and/or alternative amino acid substitutions known to one skilled in the art (see, e.g., U.S. Pat. Nos. 5,624,821; 6,277,375; 6,737,056; PCT Patent Publications WO 01/58957; WO 02/06919; WO 04/016750; WO 04/029207; WO 04/035752 and WO 05/040217).

Additional Domains

It is envisaged that the ActRIIB-ECD polypeptide and/or binding agent of the disclosure may have, in addition to its function to bind to the target TGFβ superfamily ligand(s) as specified, a further binding specificity or a further function. In some embodiments of the present technology, a ActRIIB-ECD polypeptide or binding agent may be conjugated with a targeting agent, a therapeutic moiety, a detectable moiety and/or a diagnostic moiety. In some embodiments, a polypeptide may possess a further function such as a fully functional Fc constant domain mediating antibody-dependent cellular cytotoxicity through recruitment of effector cells like NK cells, by providing a label (fluorescent etc.), by providing a therapeutic agent such as a toxin or radionuclide, and/or by providing means to enhance serum half-life, etc.

In some embodiments, the ActRIIB-ECD polypeptides described herein comprise an ActRIIB-ECD, a linker, an Fc domain monomer, and one or more additional domains. In some embodiments, the one or more additional domains is selected from a fibronectin domain, a human serum albumin domain, As used herein, the term "fibronectin domain" refers to a high molecular weight glycoprotein of the extracellular matrix, or a fragment thereof, that binds to, e.g., membrane-spanning receptor proteins such as integrins and extracellular matrix components such as collagens and fibrins. In some embodiments, a fibronectin domain is a fibronectin type III domain having amino acids 610-702 of the sequence of UniProt ID NO: P02751. In other embodiments, a fibronectin domain is an adnectin protein.

In some embodiments, a polypeptide or binding agent of the disclosure includes an ActRIIB-ECD variant fused to one or more fibronectin domain. Binding to fibronectin domains can improve the pharmacokinetics of protein pharmaceuticals. A fibronectin domain is a high molecular weight glycoprotein of the extracellular matrix, or a fragment thereof, that binds to, e.g., membrane-spanning receptor proteins such as integrins and extracellular matrix components such as collagens and fibrins. In some embodiments of the present invention, a fibronectin domain is joined to the N- or C-terminus (e.g., C-terminus) of an ActRIIB-ECD variant described herein (e.g., an ActRIIB-ECD variant having the amino acid sequence set forth in any one of SEQ ID NOs: 4-22, 331-332, and 24-33) to increase the serum half-life of the ActRIIB-ECD variant. A fibronectin domain can be joined, either directly or through a linker, to the N- or C-terminus of an ActRIIB-ECD variant, or a polypeptide thereof, or a binding agent thereof. In some embodiments, a polypeptide or binding agent of the disclosure may be fused to the N- or C-terminus of a fibronectin domain, e.g., through conventional genetic or chemical means, e.g., chemical conjugation. If desired, a linker (e.g., a spacer) can be inserted between the ActRIIB-ECD variant and the fibronectin domain. Without being bound by theory, it is expected that in some embodiments inclusion of a fibronectin domain in an ActRIIB-ECD variant described herein may lead to prolonged retention of the therapeutic protein through its binding to integrins and extracellular matrix components such as collagens and fibrins.

As one example, fibronectin domains that can be used in the methods and compositions and polypeptides of the disclosure are generally known in the art. In one embodiment, the fibronectin domain is a fibronectin type III domain having amino acids 610-702 of the sequence of UniProt ID NO: P02751. In another embodiment, the fibronectin domain is an adnectin protein.

As used herein, the term "human serum albumin" refers to the albumin protein present in human blood plasma. Human serum albumin is the most abundant protein in the blood. It constitutes about half of the blood serum protein. In some embodiments, a human serum albumin has the sequence of UniProt ID NO: P02768.

In some embodiments, an ActRIIB variant or a polypeptide or a binding agent described herein may be fused to serum albumin. Binding to serum albumins can improve the pharmacokinetics of protein pharmaceuticals. Serum albumin is a globular protein that is the most abundant blood protein in mammals. Serum albumin is produced in the liver and constitutes about half of the blood serum proteins. It is monomeric and soluble in the blood. Some of the most crucial functions of serum albumin include transporting hormones, fatty acids, and other proteins in the body, buffering pH, and maintaining osmotic pressure needed for proper distribution of bodily fluids between blood vessels and body tissues. In some embodiments, serum albumin is human serum albumin. In some embodiments, a human serum albumin is joined to the N- or C-terminus (e.g., C-terminus) of an ActRIIB-ECD variant described herein (e.g., an ActRIIB-ECD variant having the amino acid sequence set forth in any one of SEQ ID NOs: 4-22, 331-332 and 24-33) to increase the serum half-life of the ActRIIB-ECD variant. A human serum albumin can be joined, either directly or through a linker, to the N- or C-terminus of an ActRIIB-ECD variant.

As one example, serum albumins that can be used in the polypeptides and methods and compositions described herein are generally known in the art. In one embodiment, the serum albumin includes the sequence of UniProt ID NO: P02768. In some embodiments, a polypeptide or binding agent of the disclosure may be fused to the N- or C-terminus of a human serum albumin, e.g., through conventional genetic or chemical means, e.g., chemical conjugation. If desired, a linker (e.g., a spacer) can be inserted between the ActRIIB-ECD variant and the human serum albumin. Without being bound by theory, it is expected that in some embodiments inclusion of a human serum albumin in an ActRIIB-ECD variant described herein may lead to prolonged retention of the therapeutic protein.

In some embodiments, a polypeptide or binding agent of the disclosure further includes a moiety (e.g., Fc domain monomer, a wild-type Fc domain, an Fc domain with amino acid substitutions (e.g., one or more substitutions that reduce dimerization, an albumin-binding peptide, a fibronectin domain, or a human serum albumin), which may be fused to the N- or C-terminus (e.g., C-terminus) of the ActRIIB-ECD variant, the polypeptide, or the binding agent by way of a linker or other covalent bonds. A polypeptide including an ActRIIB-ECD variant fused to an Fc domain monomer may form a dimer (e.g., homodimer or heterodimer) through the interaction between two Fc domain monomers, which combine to form an Fc domain in the dimer. Furthermore, in some embodiments, a polypeptide or binding agent described herein has a serum half-life of at least 7 days in humans.

Exemplary TGFβ Superfamily Binding Agents

The overall structures of exemplary binding agents described herein are provided in Table 5. The amino acid sequences of each binding agent are provided in Table 6.

TABLE 5

Structure of exemplary binding agents

| Binding agent | ActRII ECD | Linker | Fc domain | SEQ ID |
|---|---|---|---|---|
| P75 | WT hActRIIB (SEQ ID: 2) | 3aa (GGG) | IgG1 FcDL (SEQ ID: 135) | 174 |
| P757 | WT hActRIIB (SEQ ID: 2) | 14aa (SEQ ID: 59) | IgG1 FcDL (SEQ ID: 135) | 175 |
| P444 | WT hActRIIA (SEQ ID: 3) | 3aa (GGG) | IgG1 FcEM (SEQ ID: 147) | 176 |
| P119 | hActRIIB - G27D (SEQ ID: 20) | 3aa (GGG) | IgG1 FcEM (SEQ ID: 134) | 177 |
| P120 | hActRIIB - D57E (SEQ ID: 4) | 3aa (GGG) | IgG1 FcEM (SEQ ID: 134) | 178 |
| P121 | hActRIIB - F58E (SEQ ID: 5) | 3aa (GGG) | IgG1 FcEM (SEQ ID: 134) | 179 |
| P122 | hActRIIB - Q29Y (SEQ ID: 14) | 3aa (GGG) | IgG1 FcEM (SEQ ID: 134) | 180 |
| P123 | hActRIIB - D30Q (SEQ ID: 15) | 3aa (GGG) | IgG1 FcEM (SEQ ID: 134) | 181 |
| P124 | hActRIIB -K31Y (SEQ ID: 16) | 3aa (GGG) | IgG1 FcEM (SEQ ID: 134) | 182 |
| P125 | hActRIIB - S38R (SEQ ID: 17) | 3aa (GGG) | IgG1 FcEM (SEQ ID: 134) | 183 |
| P126 | hActRIIB - V75Q (SEQ ID: 18) | 3aa (GGG) | IgG1 FcEM (SEQ ID: 134) | 184 |
| P127 | hActRIIB - F77D (SEQ ID: 19) | 3aa (GGG) | IgG1 FcEM (SEQ ID: 134) | 185 |
| P622 | hActRIIB - F58E (SEQ ID: 5) | 14aa (SEQ ID: 59) | IgG1 FcDL (SEQ ID: 135) | 186 |
| P624 | hActRIIB - F58E (SEQ ID: 5) | 3aa (GGG) | IgG1 FcDL (SEQ ID: 135) | 187 |
| P625 | hActRIIB - F58E (SEQ ID: 5) | 3aa (GGG) | IgG1 FcY-DL (SEQ ID: 138) | 188 |
| P626 | hActRIIB - F58E (SEQ ID: 5) | 3aa (GGG) | IgG1 FcYTE-DL (SEQ ID: 137) | 189 |
| P666 | hActRIIB - F58E (SEQ ID: 5) | 19aa (SEQ ID: 54) | IgG1 FcDL (SEQ ID: 135) | 190 |
| P667 | hActRIIB - F58E (SEQ ID: 5) | 39aa (SEQ ID: 34) | IgG1 FcDL (SEQ ID: 135) | 191 |
| P671 | hActRIIB - F58E (SEQ ID: 5) | 14aa (SEQ ID: 59) | IgG2 (SEQ ID: 157) | 192 |
| P672 | hActRIIB - F58E (SEQ ID: 5) | 19aa (SEQ ID: 54) | IgG2 (SEQ ID: 157) | 193 |
| P673 | hActRIIB - F58E (SEQ ID: 5) | 39aa (SEQ ID: 34) | IgG2 (SEQ ID: 157) | 194 |
| P674 | hActRIIB - F58E (SEQ ID: 5) | 3aa (GGG) | IgG2 (SEQ ID: 157) | 195 |
| P683 | hActRIIB - F58D (SEQ ID: 6) | 3aa (GGG) | IgG1 FcEM (SEQ ID: 134) | 196 |
| P684 | hActRIIB - F58D (SEQ ID: 6) | 3aa (GGG) | IgG1 FcDL (SEQ ID: 135) | 197 |
| P685 | hActRIIB - F58D (SEQ ID: 6) | 3aa (GGG) | IgG2 (SEQ ID: 157) | 198 |
| P686 | hActRIIB - F58D (SEQ ID: 6) | 14aa (SEQ ID: 59) | IgG1 FcEM (SEQ ID: 134) | 199 |
| P687 | hActRIIB - F58D (SEQ ID: 6) | 14aa (SEQ ID: 59) | IgG1 FcDL (SEQ ID: 135) | 200 |
| P688 | hActRIIB - F58D (SEQ ID: 6) | 39aa (SEQ ID: 34) | IgG1 FcDL (SEQ ID: 135) | 201 |
| P689 | hActRIIB - F58D (SEQ ID: 6) | 39aa (SEQ ID: 34) | IgG2 (SEQ ID: 157) | 202 |
| P690 | hActRIIB - F58Y (SEQ ID: 7) | 3aa (GGG) | IgG1 FcEM (SEQ ID: 134) | 203 |
| P691 | hActRIIB - F58Y (SEQ ID: 7) | 3aa (GGG) | IgG1 FcDL (SEQ ID: 135) | 204 |
| P692 | hActRIIB - F58Y (SEQ ID: 7) | 3aa (GGG) | IgG2 (SEQ ID: 125) | 205 |
| P693 | hActRIIB - F58Y (SEQ ID: 7) | 14aa (SEQ ID: 59) | IgG1 FcEM (SEQ ID: 134) | 206 |
| P694 | hActRIIB - F58Y (SEQ ID: 7) | 14aa (SEQ ID: 59) | IgG1 FcDL (SEQ ID: 135) | 207 |
| P695 | hActRIIB - F58Y (SEQ ID: 7) | 39aa (SEQ ID: 34) | IgG1 FcDL (SEQ ID: 135) | 208 |
| P696 | hActRIIB - F58Y (SEQ ID: 7) | 39aa (SEQ ID: 34) | IgG2 (SEQ ID: 157) | 209 |
| P697 | hActRIIB - F58K (SEQ ID: 8) | 3aa (GGG) | IgG1 FcEM (SEQ ID: 134) | 210 |

TABLE 5-continued

Structure of exemplary binding agents

| Binding agent | ActRII ECD | Linker | Fc domain | SEQ ID |
|---|---|---|---|---|
| P698 | hActRIIB - F58K (SEQ ID: 8) | 3aa (GGG) | IgG1 FcDL (SEQ ID: 135) | 211 |
| P699 | hActRIIB - F58K (SEQ ID: 8) | 3aa (GGG) | IgG2 (SEQ ID: 157) | 212 |
| P700 | hActRIIB - F58K (SEQ ID: 8) | 14aa (SEQ ID: 59) | IgG1 FcEM (SEQ ID: 134) | 213 |
| P701 | hActRIIB - F58K (SEQ ID: 8) | 14aa (SEQ ID: 59) | IgG1 FcDL (SEQ ID: 135) | 214 |
| P702 | hActRIIB - F58K (SEQ ID: 8) | 39aa (SEQ ID: 34) | IgG1 FcDL (SEQ ID: 135) | 215 |
| P703 | hActRIIB - F58K (SEQ ID: 8) | 39aa (SEQ ID: 34) | IgG2 (SEQ ID: 157) | 216 |
| P704 | hActRIIB - F58Q (SEQ ID: 9) | 3aa (GGG) | IgG1 FcEM (SEQ ID: 134) | 217 |
| P705 | hActRIIB - F58Q (SEQ ID: 9) | 3aa (GGG) | IgG1 FcDL (SEQ ID: 135) | 218 |
| P706 | hActRIIB - F58Q (SEQ ID: 9) | 3aa (GGG) | IgG2 (SEQ ID: 157) | 219 |
| P707 | hActRIIB - F58Q (SEQ ID: 9) | 14aa (SEQ ID: 59) | IgG1 FcEM (SEQ ID: 134) | 220 |
| P708 | hActRIIB - F58Q (SEQ ID: 9) | 14aa (SEQ ID: 59) | IgG1 FcDL (SEQ ID: 135) | 221 |
| P709 | hActRIIB - F58Q (SEQ ID: 9) | 39aa (SEQ ID: 34) | IgG1 FcDL (SEQ ID: 135) | 222 |
| P710 | hActRIIB - F58Q (SEQ ID: 9) | 39aa (SEQ ID: 34) | IgG2 (SEQ ID: 157) | 223 |
| P711 | hActRIIB - F58W (SEQ ID: 10) | 3aa (GGG) | IgG1 FcEM (SEQ ID: 134) | 224 |
| P712 | hActRIIB - F58W (SEQ ID: 10) | 3aa (GGG) | IgG1 FcDL (SEQ ID: 135) | 225 |
| P713 | hActRIIB - F58W (SEQ ID: 10) | 3aa (GGG) | IgG2 (SEQ ID: 157) | 226 |
| P714 | hActRIIB - F58W (SEQ ID: 10) | 14aa (SEQ ID: 59) | IgG1 FcEM (SEQ ID: 134) | 227 |
| P715 | hActRIIB - F58W (SEQ ID: 10) | 14aa (SEQ ID: 59) | IgG1 FcDL (SEQ ID: 135) | 228 |
| P716 | hActRIIB - F58W (SEQ ID: 10) | 39aa (SEQ ID: 34) | IgG1 FcDL (SEQ ID: 135) | 229 |
| P717 | hActRIIB - F58W (SEQ ID: 10) | 39aa (SEQ ID: 34) | IgG2 (SEQ ID: 157) | 230 |
| P758 | hActRIIB - G27D (SEQ ID: 20) | 14aa (SEQ ID: 59) | IgG1 FcDL (SEQ ID: 135) | 240 |
| P1153 | hActRIIB - F58K (SEQ ID: 8) | 6aa (SEQ ID: 67) | IgG1 FcDL (SEQ ID: 135) | 241 |
| P1154 | hActRIIB - F58K (SEQ ID: 8) | 10aa (SEQ ID: 63) | IgG1 FcDL (SEQ ID: 135) | 242 |
| P1155 | hActRIIB - F58K (SEQ ID: 8) | 19aa (SEQ ID: 54) | IgG1 FcDL (SEQ ID: 135) | 243 |
| P1156 | hActRIIB - F58K (SEQ ID: 8) | 39aa (SEQ ID: 34) | IgG1 FcDL (SEQ ID: 135) | 244 |
| P1163 | hActRIIB - F58E (SEQ ID: 5) | 6aa (SEQ ID: 67) | IgG1 FcDL (SEQ ID: 135) | 246 |
| P1164 | hActRIIB - F58E (SEQ ID: 5) | 10aa (SEQ ID: 63) | IgG1 FcDL (SEQ ID: 135) | 247 |
| P1168 | hActRIIB - F58E + C-term APT | 14aa (SEQ ID: 59) | IgG1 FcDL (SEQ ID: 135) | 248 |
| P1213 | hActRIIB - F58N (SEQ ID: 11) | 14aa (SEQ ID: 59) | IgG1 FcDL (SEQ ID: 135) | 249 |
| P1215 | hActRIIB - F58R (SEQ ID: 12) | 14aa (SEQ ID: 59) | IgG1 FcDL (SEQ ID: 135) | 250 |
| P1217 | hActRIIB - F58H (SEQ ID: 13) | 14aa (SEQ ID: 59) | IgG1 FcDL (SEQ ID: 135) | 251 |
| P1218 | hActRIIB - F58Q (SEQ ID: 9) | 6aa (SEQ ID: 67) | IgG1 FcDL (SEQ ID: 135) | 252 |
| P1219 | hActRIIB - F58Q (SEQ ID: 9) | 10aa (SEQ ID: 63) | IgG1 FcDL (SEQ ID: 135) | 253 |
| P1220 | hActRIIB - F58Q (SEQ ID: 9) | 19aa (SEQ ID: 54) | IgG1 FcDL (SEQ ID: 135) | 254 |
| P718 | hActRIIB - D57E + F58E (SEQ ID: 21) | 3aa (GGG) | IgG1 FcDL (SEQ ID: 135) | 231 |
| P719 | hActRIIB - Q29Y + F58E (SEQ ID: 22) | 14aa (SEQ ID: 59) | IgG1 FcDL (SEQ ID: 135) | 232 |

TABLE 5-continued

| Structure of exemplary binding agents | | | | |
|---|---|---|---|---|
| Binding agent | ActRII ECD | Linker | Fc domain | SEQ ID |
| P720 | hActRIIB - D30Q + F58E (SEQ ID: 331) | 14aa (SEQ ID: 59) | IgG1 FcDL (SEQ ID: 135) | 233 |
| P441 | hActRIIB - G27D + F58E (SEQ ID: 332) | 3aa (GGG) | IgG1 FcEM (SEQ ID: 134) | 235 |
| P759 | hActRIIB - D57E (SEQ ID: 4) | 14aa (SEQ ID: 59) | IgG1 FcDL (SEQ ID: 135 | 333 |
| P761 | hActRIIB - K31Y (SEQ ID: 16) | 14aa (SEQ ID: 59) | IgG1 FcDL (SEQ ID: 135) | 339 |
| P762 | hActRIIB - V75Q (SEQ ID: 18) | 14aa (SEQ ID: 59) | IgG1 FcDL (SEQ ID: 135) | 340 |
| P670 | WT hActRIIA (SEQ ID: 3) | 3aa (GGG) | IgG2 (SEQ ID: 157) | 341 |

TABLE 6

| Exemplary binding agent amino acid sequences | | |
|---|---|---|
| Agent | AA Sequence | SEQ ID |
| P75 | ETRECIYYNANWELERTNQSGLERCEGEQDKRLHCYASWRNSSGTIEL<br>VKKGCWLDDFNCYDRQECVATEENPQVYFCCCEGNFCNERFTHLPEAG<br>GPEVTYEPPPT***GGG***THTCPPCPAPELLGGPSVFLFPPKPKDTLMISRT<br>PEVTCVVVDVSHEDPEVKFNWYVDGVEVHNAKTKPREEQYNSTYRVVS<br>VLTVLHQDWLNGKEYKCKVSNKALPAPIEKTISKAKGQPREPQVYTLP<br>PSRDELTKNQVSLTCLVKGFYPSDIAVEWESNGQPENNYKTTPPVLDS<br>DGSFFLYSKLTVDKSRWQQGNVFSCSVMHEALHNHYTQKSLSLSPG | 174 |
| P757 | ETRECIYYNANWELERTNQSGLERCEGEQDKRLHCYASWRNSSGTIEL<br>VKKGCWLDDFNCYDRQECVATEENPQVYFCCCEGNFCNERFTHLPEAG<br>GPEVTYEPPPT***GGGGSGGGGSGGGG***THTCPPCPAPELLGGPSVFLFPP<br>KPKDTLMISRTPEVTCVVVDVSHEDPEVKFNWYVDGVEVHNAKTKPRE<br>EQYNSTYRVVSVLTVLHQDWLNGKEYKCKVSNKALPAPIEKTISKAKG<br>QPREPQVYTLPPSRDELTKNQVSLTCLVKGFYPSDIAVEWESNGQPEN<br>NYKTTPPVLDSDGSFFLYSKLTVDKSRWQQGNVFSCSVMHEALHNHYT<br>QKSLSLSPG | 175 |
| P444 | ILGRSETQECLFFNANWEKDRTNQTGVEPCYGDKDKRRHCFATWKNIS<br>GSIEIVKQGCWLDDINCYDRTDCVEKKDSPEVYFCCCEGNMCNEKFSY<br>FPEMEVTQPTSNPVTPKPPT***GGG***THTCPPCPAPELLGGPSVFLFPPKP<br>KDTLMISRTPEVTCVVVDVSHEDPEVKFNWYVDGVEVHNAKTKPREEQ<br>YNSTYRVVSVLTVLHQDWLNGKEYKCKVSNKALPVPIEKTISKAKGQP<br>REPQVYTLPPSREEMTKNQVSLTCLVKGFYPSDIAVEWESNGQPENNY<br>KTTPPVLDSDGSFFLYSKLTVDKSRWQQGNVFSCSVMHEALHNHYTQK<br>SLSLSPG | 176 |
| P119 | ETRECIYYNANWELERTNQSGLERCEDEQDKRLHCYASWRNSSGTIEL<br>VKKGCWLDDFNCYDRQECVATEENPQVYFCCCEGNFCNERFTHLPEAG<br>GPEVTYEPPPT***GGG***THTCPPCPAPELLGGPSVFLFPPKPKDTLMISRT<br>PEVTCVVVDVSHEDPEVKFNWYVDGVEVHNAKTKPREEQYNSTYRVVS<br>VLTVLHQDWLNGKEYKCKVSNKALPAPIEKTISKAKGQPREPQVYTLP<br>PSREEMTKNQVSLTCLVKGFYPSDIAVEWESNGQPENNYKTTPPVLDS<br>DGSFFLYSKLTVDKSRWQQGNVFSCSVMHEALHNHYTQKSLSLSPG | 177 |
| P120 | ETRECIYYNANWELERTNQSGLERCEGEQDKRLHCYASWRNSSGTIEL<br>VKKGCWLDEFNCYDRQECVATEENPQVYFCCCEGNFCNERFTHLPEAG<br>GPEVTYEPPPT***GGG***THTCPPCPAPELLGGPSVFLFPPKPKDTLMISRT<br>PEVTCVVVDVSHEDPEVKFNWYVDGVEVHNAKTKPREEQYNSTYRVVS<br>VLTVLHQDWLNGKEYKCKVSNKALPAPIEKTISKAKGQPREPQVYTLP<br>PSREEMTKNQVSLTCLVKGFYPSDIAVEWESNGQPENNYKTTPPVLDS<br>DGSFFLYSKLTVDKSRWQQGNVFSCSVMHEALHNHYTQKSLSLSPG | 178 |
| P121 | ETRECIYYNANWELERTNQSGLERCEGEQDKRLHCYASWRNSSGTIEL<br>VKKGCWLDDENCYDRQECVATEENPQVYFCCCEGNFCNERFTHLPEAG<br>GPEVTYEPPPT***GGG***THTCPPCPAPELLGGPSVFLFPPKPKDTLMISRT<br>PEVTCVVVDVSHEDPEVKFNWYVDGVEVHNAKTKPREEQYNSTYRVVS<br>VLTVLHQDWLNGKEYKCKVSNKALPAPIEKTISKAKGQPREPQVYTLP<br>PSREEMTKNQVSLTCLVKGFYPSDIAVEWESNGQPENNYKTTPPVLDS<br>DGSFFLYSKLTVDKSRWQQGNVFSCSVMHEALHNHYTQKSLSLSPG | 179 |

TABLE 6-continued

| Agent | AA Sequence | SEQ ID |
|---|---|---|
| | Exemplary binding agent amino acid sequences | |
| P122 | ETRECIYYNANWELERTNQSGLERCEGEYDKRLHCYASWRNSSGTIEL<br>VKKGCWLDDFNCYDRQECVATEENPQVYFCCCEGNFCNERFTHLPEAG<br>GPEVTYEPPPT***GGG***THTCPPCPAPELLGGPSVFLFPPKPKDTLMISRT<br>PEVTCVVVDVSHEDPEVKFNWYVDGVEVHNAKTKPREEQYNSTYRVVS<br>VLTVLHQDWLNGKEYKCKVSNKALPAPIEKTISKAKGQPREPQVYTLP<br>PSREEMTKNQVSLTCLVKGFYPSDIAVEWESNGQPENNYKTTPPVLDS<br>DGSFFLYSKLTVDKSRWQQGNVFSCSVMHEALHNHYTQKSLSLSPG | 180 |
| P123 | ETRECIYYNANWELERTNQSGLERCEGEQQKRLHCYASWRNSSGTIEL<br>VKKGCWLDDFNCYDRQECVATEENPQVYFCCCEGNFCNERFTHLPEAG<br>GPEVTYEPPPT***GGG***THTCPPCPAPELLGGPSVFLFPPKPKDTLMISRT<br>PEVTCVVVDVSHEDPEVKFNWYVDGVEVHNAKTKPREEQYNSTYRVVS<br>VLTVLHQDWLNGKEYKCKVSNKALPAPIEKTISKAKGQPREPQVYTLP<br>PSREEMTKNQVSLTCLVKGFYPSDIAVEWESNGQPENNYKTTPPVLDS<br>DGSFFLYSKLTVDKSRWQQGNVFSCSVMHEALHNHYTQKSLSLSPG | 181 |
| P124 | ETRECIYYNANWELERTNQSGLERCEGEQDYRLHCYASWRNSSGTIEL<br>VKKGCWLDDFNCYDRQECVATEENPQVYFCCCEGNFCNERFTHLPEAG<br>GPEVTYEPPPT***GGG***THTCPPCPAPELLGGPSVFLFPPKPKDTLMISRT<br>PEVTCVVVDVSHEDPEVKFNWYVDGVEVHNAKTKPREEQYNSTYRVVS<br>VLTVLHQDWLNGKEYKCKVSNKALPAPIEKTISKAKGQPREPQVYTLP<br>PSREEMTKNQVSLTCLVKGFYPSDIAVEWESNGQPENNYKTTPPVLDS<br>DGSFFLYSKLTVDKSRWQQGNVFSCSVMHEALHNHYTQKSLSLSPG | 182 |
| P125 | ETRECIYYNANWELERTNQSGLERCEGEQDKRLHCYARWRNSSGTIEL<br>VKKGCWLDDFNCYDRQECVATEENPQVYFCCCEGNFCNERFTHLPEAG<br>GPEVTYEPPPT***GGG***THTCPPCPAPELLGGPSVFLFPPKPKDTLMISRT<br>PEVTCVVVDVSHEDPEVKFNWYVDGVEVHNAKTKPREEQYNSTYRVVS<br>VLTVLHQDWLNGKEYKCKVSNKALPAPIEKTISKAKGQPREPQVYTLP<br>PSREEMTKNQVSLTCLVKGFYPSDIAVEWESNGQPENNYKTTPPVLDS<br>DGSFFLYSKLTVDKSRWQQGNVFSCSVMHEALHNHYTQKSLSLSPG | 183 |
| P126 | ETRECIYYNANWELERTNQSGLERCEGEQDKRLHCYASWRNSSGTIEL<br>VKKGCWLDDFNCYDRQECVATEENPQQYFCCCEGNFCNERFTHLPEAG<br>GPEVTYEPPPT***GGG***THTCPPCPAPELLGGPSVFLFPPKPKDTLMISRT<br>PEVTCVVVDVSHEDPEVKFNWYVDGVEVHNAKTKPREEQYNSTYRVVS<br>VLTVLHQDWLNGKEYKCKVSNKALPAPIEKTISKAKGQPREPQVYTLP<br>PSREEMTKNQVSLTCLVKGFYPSDIAVEWESNGQPENNYKTTPPVLDS<br>DGSFFLYSKLTVDKSRWQQGNVFSCSVMHEALHNHYTQKSLSLSPG | 184 |
| P127 | ETRECIYYNANWELERTNQSGLERCEGEQDKRLHCYASWRNSSGTIEL<br>VKKGCWLDDFNCYDRQECVATEENPQVYDCCCEGNFCNERFTHLPEAG<br>GPEVTYEPPPT***GGG***THTCPPCPAPELLGGPSVFLFPPKPKDTLMISRT<br>PEVTCVVVDVSHEDPEVKFNWYVDGVEVHNAKTKPREEQYNSTYRVVS<br>VLTVLHQDWLNGKEYKCKVSNKALPAPIEKTISKAKGQPREPQVYTLP<br>PSREEMTKNQVSLTCLVKGFYPSDIAVEWESNGQPENNYKTTPPVLDS<br>DGSFFLYSKLTVDKSRWQQGNVFSCSVMHEALHNHYTQKSLSLSPG | 185 |
| P622 | ETRECIYYNANWELERTNQSGLERCEGEQDKRLHCYASWRNSSGTIEL<br>VKKGCWLDDENCYDRQECVATEENPQVYFCCCEGNFCNERFTHLPEAG<br>GPEVTYEPPPT***GGGGSGGGGSGGGG***TH THTCPPCPAPELLGGPSVFLFPP<br>KPKDTLMISRTPEVTCVVVDVSHEDPEVKFNWYVDGVEVHNAKTKPRE<br>EQYNSTYRVVSVLTVLHQDWLNGKEYKCKVSNKALPAPIEKTISKAKG<br>QPREPQVYTLPPSRDELTKNQVSLTCLVKGFYPSDIAVEWESNGQPEN<br>NYKTTPPVLDSDGSFFLYSKLTVDKSRWQQGNVFSCSVMHEALHNHYT<br>QKSLSLSPG | 186 |
| P624 | ETRECIYYNANWELERTNQSGLERCEGEQDKRLHCYASWRNSSGTIEL<br>VKKGCWLDDENCYDRQECVATEENPQVYFCCCEGNFCNERFTHLPEAG<br>GPEVTYEPPPT***GGG***THTCPPCPAPELLGGPSVFLFPPKPKDTLMISRT<br>PEVTCVVVDVSHEDPEVKFNWYVDGVEVHNAKTKPREEQYNSTYRVVS<br>VLTVLHQDWLNGKEYKCKVSNKALPAPIEKTISKAKGQPREPQVYTLP<br>PSRDELTKNQVSLTCLVKGFYPSDIAVEWESNGQPENNYKTTPPVLDS<br>DGSFFLYSKLTVDKSRWQQGNVFSCSVMHEALHNHYTQKSLSLSPG | 187 |
| P625 | ETRECIYYNANWELERTNQSGLERCEGEQDKRLHCYASWRNSSGTIEL<br>VKKGCWLDDENCYDRQECVATEENPQVYFCCCEGNFCNERFTHLPEAG<br>GPEVTYEPPPT***GGG***THTCPPCPAPELLGGPSVFLFPPKPKDTLYISRT<br>PEVTCVVVDVSHEDPEVKFNWYVDGVEVHNAKTKPREEQYNSTYRVVS<br>VLTVLHQDWLNGKEYKCKVSNKALPAPIEKTISKAKGQPREPQVYTLP<br>PSRDELTKNQVSLTCLVKGFYPSDIAVEWESNGQPENNYKTTPPVLDS<br>DGSFFLYSKLTVDKSRWQQGNVFSCSVMHEALHNHYTQKSLSLSPG | 188 |
| P626 | ETRECIYYNANWELERTNQSGLERCEGEQDKRLHCYASWRNSSGTIEL<br>VKKGCWLDDENCYDRQECVATEENPQVYFCCCEGNFCNERFTHLPEAG<br>GPEVTYEPPPT***GGG***THTCPPCPAPELLGGPSVFLFPPKPKDTLYITRE | 189 |

TABLE 6-continued

Exemplary binding agent amino acid sequences

| Agent | AA Sequence | SEQ ID |
|---|---|---|
| | PEVTCVVVDVSHEDPEVKFNWYVDGVEVHNAKTKPREEQYNSTYRVVS VLTVLHQDWLNGKEYKCKVSNKALPAPIEKTISKAKGQPREPQVYTLP PSRDELTKNQVSLTCLVKGFYPSDIAVEWESNGQPENNYKTTPPVLDS DGSFFLYSKLTVDKSRWQQGNVFSCSVMHEALHNHYTQKSLSLSPG | |
| P666 | ETRECIYYNANWELERTNQSGLERCEGEQDKRLHCYASWRNSSGTIEL VKKGCWLDDENCYDRQECVATEENPQVYFCCCEGNFCNERFTHLPEAG GPEVTYEPPP***GGGGSGGGGSGGGGSGGGG*** THTCPPCPAPELLGGPSV FLFPPKPKDTLMISRTPEVTCVVVDVSHEDPEVKFNWYVDGVEVHNAK TKPREEQYNSTYRVVSVLTVLHQDWLNGKEYKCKVSNKALPAPIEKTI SKAKGQPREPQVYTLPPSRDELTKNQVSLTCLVKGFYPSDIAVEWESN GQPENNYKTTPPVLDSDGSFFLYSKLTVDKSRWQQGNVFSCSVMHEAL HNHYTQKSLSLSPG | 190 |
| P667 | ETRECIYYNANWELERTNQSGLERCEGEQDKRLHCYASWRNSSGTIEL VKKGCWLDDENCYDRQECVATEENPQVYFCCCEGNFCNERFTHLPEAG GPEVTYEPPP***GGGGSGGGGSGGGGSGGGGSGGGGSGGGGSGGGGSGG GG*** THTCPPCPAPELLGGPSVFLFPPKPKDTLMISRTPEVTCVVVDVSH EDPEVKFNWYVDGVEVHNAKTKPREEQYNSTYRVVSVLTVLHQDWLNG KEYKCKVSNKALPAPIEKTISKAKGQPREPQVYTLPPSRDELTKNQVS LTCLVKGFYPSDIAVEWESNGQPENNYKTTPPVLDSDGSFFLYSKLTV DKSRWQQGNVFSCSVMHEALHNHYTQKSLSLSPG | 191 |
| P671 | ETRECIYYNANWELERTNQSGLERCEGEQDKRLHCYASWRNSSGTIEL VKKGCWLDDENCYDRQECVATEENPQVYFCCCEGNFCNERFTHLPEAG GPEVTYEPPP***GGGGSGGGGSGGGG*** PCPPCKCPAPNLLGGPSVFIFPP KIKDVLMISLSPIVTCVVVDVSEDDPDVQISWFVNNVEVHTAQTQTHR EDYNSTLRVVSALPIQHQDWMSGKEFKCKVNNKDLPAPIERTISKPKG SVRAPQVYVLPPPEEEMTKKQVTLTCMVTDFMPEDIYVEWTNNGKTEL NYKNTEPVLDSDGSYFMYSKLRVEKKNWVERNSYSCSVVHEGLHNHHT TKSFSRTPG | 192 |
| P672 | VKKGCWLDDENCYDRQECVATEENPQVYFCCCEGNFCNERFTHLPEAG GPEVTYEPPP***GGGGSGGGGSGGGGSGGGG*** PCPPCKCPAPNLLGGPSV FIFPPKIKDVLMISLSPIVTCVVVDVSEDDPDVQISWFVNNVEVHTAQ TQTHREDYNSTLRVVSALPIQHQDWMSGKEFKCKVNNKDLPAPIERTI SKPKGSVRAPQVYVLPPPEEEMTKKQVTLTCMVTDFMPEDIYVEWTNN GKTELNYKNTEPVLDSDGSYFMYSKLRVEKKNWVERNSYSCSVVHEGL HNHHTTKSFSRTPG | 193 |
| P673 | ETRECIYYNANWELERTNQSGLERCEGEQDKRLHCYASWRNSSGTIEL VKKGCWLDDENCYDRQECVATEENPQVYFCCCEGNFCNERFTHLPEAG GPEVTYEPPP***GGGGSGGGGSGGGGSGGGGSGGGGSGGGGSGGGGSGG GG*** PCPPCKCPAPNLLGGPSVFIFPPKIKDVLMISLSPIVTCVVVDVSE DDPDVQISWFVNNVEVHTAQTQTHREDYNSTLRVVSALPIQHQDWMSG KEFKCKVNNKDLPAPIERTISKPKGSVRAPQVYVLPPPEEEMTKKQVT LTCMVTDFMPEDIYVEWTNNGKTELNYKNTEPVLDSDGSYFMYSKLRV EKKNWVERNSYSCSVVHEGLHNHHTTKSFSRTPG | 194 |
| P674 | ETRECIYYNANWELERTNQSGLERCEGEQDKRLHCYASWRNSSGTIEL VKKGCWLDDENCYDRQECVATEENPQVYFCCCEGNFCNERFTHLPEAG GPEVTYEPPP***GGG*** PCPPCKCPAPNLLGGPSVFIFPPKIKDVLMISLS PIVTCVVVDVSEDDPDVQISWFVNNVEVHTAQTQTHREDYNSTLRVVS ALPIQHQDWMSGKEFKCKVNNKDLPAPIERTISKPKGSVRAPQVYVLP PPEEEMTKKQVTLTCMVTDFMPEDIYVEWTNNGKTELNYKNTEPVLDS DGSYFMYSKLRVEKKNWVERNSYSCSVVHEGLHNHHTTKSFSRTPG | 195 |
| P683 | ETRECIYYNANWELERTNQSGLERCEGEQDKRLHCYASWRNSSGTIEL VKKGCWLDDDNCYDRQECVATEENPQVYFCCCEGNFCNERFTHLPEAG GPEVTYEPPP***GGG*** THTCPPCPAPELLGGPSVFLFPPKPKDTLMISRT PEVTCVVVDVSHEDPEVKFNWYVDGVEVHNAKTKPREEQYNSTYRVVS VLTVLHQDWLNGKEYKCKVSNKALPAPIEKTISKAKGQPREPQVYTLP PSREEMTKNQVSLTCLVKGFYPSDIAVEWESNGQPENNYKTTPPVLDS DGSFFLYSKLTVDKSRWQQGNVFSCSVMHEALHNHYTQKSLSLSPG | 196 |
| P684 | ETRECIYYNANWELERTNQSGLERCEGEQDKRLHCYASWRNSSGTIEL VKKGCWLDDDNCYDRQECVATEENPQVYFCCCEGNFCNERFTHLPEAG GPEVTYEPPP***GGG*** THTCPPCPAPELLGGPSVFLFPPKPKDTLMISRT PEVTCVVVDVSHEDPEVKFNWYVDGVEVHNAKTKPREEQYNSTYRVVS VLTVLHQDWLNGKEYKCKVSNKALPAPIEKTISKAKGQPREPQVYTLP PSRDELTKNQVSLTCLVKGFYPSDIAVEWESNGQPENNYKTTPPVLDS DGSFFLYSKLTVDKSRWQQGNVFSCSVMHEALHNHYTQKSLSLSPG | 197 |

TABLE 6-continued

Exemplary binding agent amino acid sequences

| Agent | AA Sequence | SEQ ID |
|---|---|---|
| P685 | ETRECIYYNANWELERTNQSGLERCEGEQDKRLHCYASWRNSSGTIEL<br>VKKGCWLDDDNCYDRQECVATEENPQVYFCCCEGNFCNERFTHLPEAG<br>GPEVTYEPPPT*GGG* PCPPCKCPAPNLLGGPSVFIFPPKIKDVLMISLS<br>PIVTCVVVDVSEDDPDVQISWFVNNVEVHTAQTQTHREDYNSTLRVVS<br>ALPIQHQDWMSGKEFKCKVNNKDLPAPIERTISKPKGSVRAPQVYVLP<br>PPEEEMTKKQVTLTCMVTDFMPEDIYVEWTNNGKTELNYKNTEPVLDS<br>DGSYFMYSKLRVEKKNWVERNSYSCSVVHEGLHNHHTTKSFSRTPG | 198 |
| P686 | ETRECIYYNANWELERTNQSGLERCEGEQDKRLHCYASWRNSSGTIEL<br>VKKGCWLDDDNCYDRQECVATEENPQVYFCCCEGNFCNERFTHLPEAG<br>GPEVTYEPPPT*GGGGSGGGGSGGGG* THTCPPCPAPELLGGPSVFLFPP<br>KPKDTLMISRTPEVTCVVVDVSHEDPEVKFNWYVDGVEVHNAKTKPRE<br>EQYNSTYRVVSVLTVLHQDWLNGKEYKCKVSNKALPAPIEKTISKAKG<br>QPREPQVYTLPPSREEMTKNQVSLTCLVKGFYPSDIAVEWESNGQPEN<br>NYKTTPPVLDSDGSFFLYSKLTVDKSRWQQGNVFSCSVMHEALHNHYT<br>QKSLSLSPG | 199 |
| P687 | ETRECIYYNANWELERTNQSGLERCEGEQDKRLHCYASWRNSSGTIEL<br>VKKGCWLDDDNCYDRQECVATEENPQVYFCCCEGNFCNERFTHLPEAG<br>GPEVTYEPPPT*GGGGSGGGGSGGGG* THTCPPCPAPELLGGPSVFLFPP<br>KPKDTLMISRTPEVTCVVVDVSHEDPEVKFNWYVDGVEVHNAKTKPRE<br>EQYNSTYRVVSVLTVLHQDWLNGKEYKCKVSNKALPAPIEKTISKAKG<br>QPREPQVYTLPPSRDELTKNQVSLTCLVKGFYPSDIAVEWESNGQPEN<br>NYKTTPPVLDSDGSFFLYSKLTVDKSRWQQGNVFSCSVMHEALHNHYT<br>QKSLSLSPG | 200 |
| P688 | ETRECIYYNANWELERTNQSGLERCEGEQDKRLHCYASWRNSSGTIEL<br>VKKGCWLDDDNCYDRQECVATEENPQVYFCCCEGNFCNERFTHLPEAG<br>GPEVTYEPPPT*GGGGSGGGGSGGGGSGGGGSGGGGSGGGGSGGGGSGG*<br>*GG*T THTCPPCPAPELLGGPSVFLFPPKPKDTLMISRTPEVTCVVVDVSH<br>EDPEVKFNWYVDGVEVHNAKTKPREEQYNSTYRVVSVLTVLHQDWLNG<br>KEYKCKVSNKALPAPIEKTISKAKGQPREPQVYTLPPSRDELTKNQVS<br>LTCLVKGFYPSDIAVEWESNGQPENNYKTTPPVLDSDGSFFLYSKLTV<br>DKSRWQQGNVFSCSVMHEALHNHYTQKSLSLSPG | 201 |
| P689 | ETRECIYYNANWELERTNQSGLERCEGEQDKRLHCYASWRNSSGTIEL<br>VKKGCWLDDDNCYDRQECVATEENPQVYFCCCEGNFCNERFTHLPEAG<br>GPEVTYEPPPT*GGGGSGGGGSGGGGSGGGGSGGGGSGGGGSGGGGSGG*<br>*GG*PCPPCKCPAPNLLGGPSVFIFPPKIKDVLMISLSPIVTCVVVDVSE<br>DDPDVQISWFVNNVEVHTAQTQTHREDYNSTLRVVSALPIQHQDWMSG<br>KEFKCKVNNKDLPAPIERTISKPKGSVRAPQVYVLPPPEEEMTKKQVT<br>LTCMVTDFMPEDIYVEWTNNGKTELNYKNTEPVLDSDGSYFMYSKLRV<br>EKKNWVERNSYSCSVVHEGLHNHHTTKSFSRTPG | 202 |
| P690 | ETRECIYYNANWELERTNQSGLERCEGEQDKRLHCYASWRNSSGTIEL<br>VKKGCWLDDYNCYDRQECVATEENPQVYFCCCEGNFCNERFTHLPEAG<br>GPEVTYEPPPT*GGG*THTCPPCPAPELLGGPSVFLFPPKPKDTLMISRT<br>PEVTCVVVDVSHEDPEVKFNWYVDGVEVHNAKTKPREEQYNSTYRVVS<br>VLTVLHQDWLNGKEYKCKVSNKALPAPIEKTISKAKGQPREPQVYTLP<br>PSREEMTKNQVSLTCLVKGFYPSDIAVEWESNGQPENNYKTTPPVLDS<br>DGSFFLYSKLTVDKSRWQQGNVFSCSVMHEALHNHYTQKSLSLSPG | 203 |
| P691 | ETRECIYYNANWELERTNQSGLERCEGEQDKRLHCYASWRNSSGTIEL<br>VKKGCWLDDYNCYDRQECVATEENPQVYFCCCEGNFCNERFTHLPEAG<br>GPEVTYEPPPT*GGG*THTCPPCPAPELLGGPSVFLFPPKPKDTLMISRT<br>PEVTCVVVDVSHEDPEVKFNWYVDGVEVHNAKTKPREEQYNSTYRVVS<br>VLTVLHQDWLNGKEYKCKVSNKALPAPIEKTISKAKGQPREPQVYTLP<br>PSRDELTKNQVSLTCLVKGFYPSDIAVEWESNGQPENNYKTTPPVLDS<br>DGSFFLYSKLTVDKSRWQQGNVFSCSVMHEALHNHYTQKSLSLSPG | 204 |
| P692 | ETRECIYYNANWELERTNQSGLERCEGEQDKRLHCYASWRNSSGTIEL<br>VKKGCWLDDYNCYDRQECVATEENPQVYFCCCEGNFCNERFTHLPEAG<br>GPEVTYEPPPT*GGG*PCPPCKCPAPNLLGGPSVFIFPPKIKDVLMISLS<br>PIVTCVVVDVSEDDPDVQISWFVNNVEVHTAQTQTHREDYNSTLRVVS<br>ALPIQHQDWMSGKEFKCKVNNKDLPAPIERTISKPKGSVRAPQVYVLP<br>PPEEEMTKKQVTLTCMVTDFMPEDIYVEWTNNGKTELNYKNTEPVLDS<br>DGSYFMYSKLRVEKKNWVERNSYSCSVVHEGLHNHHTTKSFSRTPG | 205 |
| P693 | ETRECIYYNANWELERTNQSGLERCEGEQDKRLHCYASWRNSSGTIEL<br>VKKGCWLDDYNCYDRQECVATEENPQVYFCCCEGNFCNERFTHLPEAG<br>GPEVTYEPPPT*GGGGSGGGGSGGGG*THTCPPCPAPELLGGPSVFLFPP<br>KPKDTLMISRTPEVTCVVVDVSHEDPEVKFNWYVDGVEVHNAKTKPRE<br>EQYNSTYRVVSVLTVLHQDWLNGKEYKCKVSNKALPAPIEKTISKAKG<br>QPREPQVYTLPPSREEMTKNQVSLTCLVKGFYPSDIAVEWESNGQPEN | 206 |

TABLE 6-continued

Exemplary binding agent amino acid sequences

| Agent | AA Sequence | SEQ ID |
| --- | --- | --- |
| | NYKTTPPVLDSDGSFFLYSKLTVDKSRWQQGNVFSCSVMHEALHNHYT<br>QKSLSLSPG | |
| P694 | ETRECIYYNANWELERTNQSGLERCEGEQDKRLHCYASWRNSSGTIEL<br>VKKGCWLDDYNCYDRQECVATEENPQVYFCCCEGNFCNERFTHLPEAG<br>GPEVTYEPPPT***GGGGSGGGGSGGGG***THTCPPCPAPELLGGPSVFLFPP<br>KPKDTLMISRTPEVTCVVVDVSHEDPEVKFNWYVDGVEVHNAKTKPRE<br>EQYNSTYRVVSVLTVLHQDWLNGKEYKCKVSNKALPAPIEKTISKAKG<br>QPREPQVYTLPPSRDELTKNQVSLTCLVKGFYPSDIAVEWESNGQPEN<br>NYKTTPPVLDSDGSFFLYSKLTVDKSRWQQGNVFSCSVMHEALHNHYT<br>QKSLSLSPG | 207 |
| P695 | ETRECIYYNANWELERTNQSGLERCEGEQDKRLHCYASWRNSSGTIEL<br>VKKGCWLDDYNCYDRQECVATEENPQVYFCCCEGNFCNERFTHLPEAG<br>GPEVTYEPPPT***GGGGSGGGGSGGGGSGGGGSGGGGSGGGGSGGGGSGG***<br>***GG***THTCPPCPAPELLGGPSVFLFPPKPKDTLMISRTPEVTCVVVDVSH<br>EDPEVKFNWYVDGVEVHNAKTKPREEQYNSTYRVVSVLTVLHQDWLNG<br>KEYKCKVSNKALPAPIEKTISKAKGQPREPQVYTLPPSRDELTKNQVS<br>LTCLVKGFYPSDIAVEWESNGQPENNYKTTPPVLDSDGSFFLYSKLTV<br>DKSRWQQGNVFSCSVMHEALHNHYTQKSLSLSPG | 208 |
| P696 | ETRECIYYNANWELERTNQSGLERCEGEQDKRLHCYASWRNSSGTIEL<br>VKKGCWLDDYNCYDRQECVATEENPQVYFCCCEGNFCNERFTHLPEAG<br>GPEVTYEPPPT***GGGGSGGGGSGGGGSGGGGSGGGGSGGGGSGGGGSGG***<br>***GG***PCPPCKCPAPNLLGGPSVFIFPPKIKDVLMISLSPIVTCVVVDVSE<br>DDPDVQISWFVNNVEVHTAQTQTHREDYNSTLRVVSALPIQHQDWMSG<br>KEFKCKVNNKDLPAPIERTISKPKGSVRAPQVYVLPPPEEEMTKKQVT<br>LTCMVTDFMPEDIYVEWTNNGKTELNYKNTEPVLDSDGSYFMYSKLRV<br>EKKNWVERNSYSCSVVHEGLHNHHTTKSFSRTPG | 209 |
| P697 | ETRECIYYNANWELERTNQSGLERCEGEQDKRLHCYASWRNSSGTIEL<br>VKKGCWLDDKNCYDRQECVATEENPQVYFCCCEGNFCNERFTHLPEAG<br>GPEVTYEPPPT***GGG***THTCPPCPAPELLGGPSVFLFPPKPKDTLMISRT<br>PEVTCVVVDVSHEDPEVKFNWYVDGVEVHNAKTKPREEQYNSTYRVVS<br>VLTVLHQDWLNGKEYKCKVSNKALPAPIEKTISKAKGQPREPQVYTLP<br>PSREEMTKNQVSLTCLVKGFYPSDIAVEWESNGQPENNYKTTPPVLDS<br>DGSFFLYSKLTVDKSRWQQGNVFSCSVMHEALHNHYTQKSLSLSPG | 210 |
| P698 | ETRECIYYNANWELERTNQSGLERCEGEQDKRLHCYASWRNSSGTIEL<br>VKKGCWLDDKNCYDRQECVATEENPQVYFCCCEGNFCNERFTHLPEAG<br>GPEVTYEPPPT***GGG***THTCPPCPAPELLGGPSVFLFPPKPKDTLMISRT<br>PEVTCVVVDVSHEDPEVKFNWYVDGVEVHNAKTKPREEQYNSTYRVVS<br>VLTVLHQDWLNGKEYKCKVSNKALPAPIEKTISKAKGQPREPQVYTLP<br>PSRDELTKNQVSLTCLVKGFYPSDIAVEWESNGQPENNYKTTPPVLDS<br>DGSFFLYSKLTVDKSRWQQGNVFSCSVMHEALHNHYTQKSLSLSPG | 211 |
| P699 | ETRECIYYNANWELERTNQSGLERCEGEQDKRLHCYASWRNSSGTIEL<br>VKKGCWLDDKNCYDRQECVATEENPQVYFCCCEGNFCNERFTHLPEAG<br>GPEVTYEPPPT***GGG***PCPPCKCPAPNLLGGPSVFIFPPKIKDVLMISLS<br>PIVTCVVVDVSEDDPDVQISWFVNNVEVHTAQTQTHREDYNSTLRVVS<br>ALPIQHQDWMSGKEFKCKVNNKDLPAPIERTISKPKGSVRAPQVYVLP<br>PPEEEMTKKQVTLTCMVTDFMPEDIYVEWTNNGKTELNYKNTEPVLDS<br>DGSYFMYSKLRVEKKNWVERNSYSCSVVHEGLHNHHTTKSFSRTPG | 212 |
| P700 | ETRECIYYNANWELERTNQSGLERCEGEQDKRLHCYASWRNSSGTIEL<br>VKKGCWLDDKNCYDRQECVATEENPQVYFCCCEGNFCNERFTHLPEAG<br>GPEVTYEPPPT***GGGGSGGGGSGGGG***THTCPPCPAPELLGGPSVFLFPP<br>KPKDTLMISRTPEVTCVVVDVSHEDPEVKFNWYVDGVEVHNAKTKPRE<br>EQYNSTYRVVSVLTVLHQDWLNGKEYKCKVSNKALPAPIEKTISKAKG<br>QPREPQVYTLPPSREEMTKNQVSLTCLVKGFYPSDIAVEWESNGQPEN<br>NYKTTPPVLDSDGSFFLYSKLTVDKSRWQQGNVFSCSVMHEALHNHYT<br>QKSLSLSPG | 213 |
| P701 | ETRECIYYNANWELERTNQSGLERCEGEQDKRLHCYASWRNSSGTIEL<br>VKKGCWLDDKNCYDRQECVATEENPQVYFCCCEGNFCNERFTHLPEAG<br>GPEVTYEPPPT***GGGGSGGGGSGGGG***THTCPPCPAPELLGGPSVFLFPP<br>KPKDTLMISRTPEVTCVVVDVSHEDPEVKFNWYVDGVEVHNAKTKPRE<br>EQYNSTYRVVSVLTVLHQDWLNGKEYKCKVSNKALPAPIEKTISKAKG<br>QPREPQVYTLPPSRDELTKNQVSLTCLVKGFYPSDIAVEWESNGQPEN<br>NYKTTPPVLDSDGSFFLYSKLTVDKSRWQQGNVFSCSVMHEALHNHYT<br>QKSLSLSPG | 214 |
| P702 | ETRECIYYNANWELERTNQSGLERCEGEQDKRLHCYASWRNSSGTIEL<br>VKKGCWLDDKNCYDRQECVATEENPQVYFCCCEGNFCNERFTHLPEAG<br>GPEVTYEPPPT***GGGGSGGGGSGGGGSGGGGSGGGGSGGGGSGGGGSGG***<br>***GG***THTCPPCPAPELLGGPSVFLFPPKPKDTLMISRTPEVTCVVVDVSH | 215 |

TABLE 6-continued

Exemplary binding agent amino acid sequences

| Agent | AA Sequence | SEQ ID |
|---|---|---|
| | EDPEVKFNWYVDGVEVHNAKTKPREEQYNSTYRVVSVLTVLHQDWLNG<br>KEYKCKVSNKALPAPIEKTISKAKGQPREPQVYTLPPSRDELTKNQVS<br>LTCLVKGFYPSDIAVEWESNGQPENNYKTTPPVLDSDGSFFLYSKLTV<br>DKSRWQQGNVFSCSVMHEALHNHYTQKSLSLSPG | |
| P703 | ETRECIYYNANWELERTNQSGLERCEGEQDKRLHCYASWRNSSGTIEL<br>VKKGCWLDDKNCYDRQECVATEENPQVYFCCCEGNFCNERFTHLPEAG<br>GPEVTYEPPPT***GGGGSGGGGSGGGGSGGGGSGGGGSGGGGSGGGGSGG***<br>***GG***PCPPCKCPAPNLLGGPSVFIFPPKIKDVLMISLSPIVTCVVVDVSE<br>DDPDVQISWFVNNVEVHTAQTQTHREDYNSTLRVVSALPIQHQDWMSG<br>KEFKCKVNNKDLPAPIERTISKPKGSVRAPQVYVLPPPEEEMTKKQVT<br>LTCMVTDFMPEDIYVEWTNNGKTELNYKNTEPVLDSDGSYFMYSKLRV<br>EKKNWVERNSYSCSVVHEGLHNHHTTKSFSRTPG | 216 |
| P704 | ETRECIYYNANWELERTNQSGLERCEGEQDKRLHCYASWRNSSGTIEL<br>VKKGCWLDDQNCYDRQECVATEENPQVYFCCCEGNFCNERFTHLPEAG<br>GPEVTYEPPPT***GGG***T HTCPPCPAPELLGGPSVFLFPPKPKDTLMISRT<br>PEVTCVVVDVSHEDPEVKFNWYVDGVEVHNAKTKPREEQYNSTYRVVS<br>VLTVLHQDWLNGKEYKCKVSNKALPAPIEKTISKAKGQPREPQVYTLP<br>PSREEMTKNQVSLTCLVKGFYPSDIAVEWESNGQPENNYKTTPPVLDS<br>DGSFFLYSKLTVDKSRWQQGNVFSCSVMHEALHNHYTQKSLSLSPG | 217 |
| P705 | ETRECIYYNANWELERTNQSGLERCEGEQDKRLHCYASWRNSSGTIEL<br>VKKGCWLDDQNCYDRQECVATEENPQVYFCCCEGNFCNERFTHLPEAG<br>GPEVTYEPPPT***GGG***THTCPPCPAPELLGGPSVFLFPPKPKDTLMISRT<br>PEVTCVVVDVSHEDPEVKFNWYVDGVEVHNAKTKPREEQYNSTYRVVS<br>VLTVLHQDWLNGKEYKCKVSNKALPAPIEKTISKAKGQPREPQVYTLP<br>PSRDELTKNQVSLTCLVKGFYPSDIAVEWESNGQPENNYKTTPPVLDS<br>DGSFFLYSKLTVDKSRWQQGNVFSCSVMHEALHNHYTQKSLSLSPG | 218 |
| P706 | ETRECIYYNANWELERTNQSGLERCEGEQDKRLHCYASWRNSSGTIEL<br>VKKGCWLDDQNCYDRQECVATEENPQVYFCCCEGNFCNERFTHLPEAG<br>GPEVTYEPPPT***GGG***PCPPCKCPAPNLLGGPSVFIFPPKIKDVLMISLS<br>PIVTCVVVDVSEDDPDVQISWFVNNVEVHTAQTQTHREDYNSTLRVVS<br>ALPIQHQDWMSGKEFKCKVNNKDLPAPIERTISKPKGSVRAPQVYVLP<br>PPEEEMTKKQVTLTCMVTDFMPEDIYVEWTNNGKTELNYKNTEPVLDS<br>DGSYFMYSKLRVEKKNWVERNSYSCSVVHEGLHNHHTTKSFSRTPG | 219 |
| P707 | ETRECIYYNANWELERTNQSGLERCEGEQDKRLHCYASWRNSSGTIEL<br>VKKGCWLDDQNCYDRQECVATEENPQVYFCCCEGNFCNERFTHLPEAG<br>GPEVTYEPPPT***GGGGSGGGGSGGGG***T THTCPPCPAPELLGGPSVFLFPP<br>KPKDTLMISRTPEVTCVVVDVSHEDPEVKFNWYVDGVEVHNAKTKPRE<br>EQYNSTYRVVSVLTVLHQDWLNGKEYKCKVSNKALPAPIEKTISKAKG<br>QPREPQVYTLPPSREEMTKNQVSLTCLVKGFYPSDIAVEWESNGQPEN<br>NYKTTPPVLDSDGSFFLYSKLTVDKSRWQQGNVFSCSVMHEALHNHYT<br>QKSLSLSPG | 220 |
| P708 | ETRECIYYNANWELERTNQSGLERCEGEQDKRLHCYASWRNSSGTIEL<br>VKKGCWLDDQNCYDRQECVATEENPQVYFCCCEGNFCNERFTHLPEAG<br>GPEVTYEPPPT***GGGGSGGGGSGGGG*** THTCPPCPAPELLGGPSVFLFPP<br>KPKDTLMISRTPEVTCVVVDVSHEDPEVKFNWYVDGVEVHNAKTKPRE<br>EQYNSTYRVVSVLTVLHQDWLNGKEYKCKVSNKALPAPIEKTISKAKG<br>QPREPQVYTLPPSRDELTKNQVSLTCLVKGFYPSDIAVEWESNGQPEN<br>NYKTTPPVLDSDGSFFLYSKLTVDKSRWQQGNVFSCSVMHEALHNHYT<br>QKSLSLSPG | 221 |
| P709 | ETRECIYYNANWELERTNQSGLERCEGEQDKRLHCYASWRNSSGTIEL<br>VKKGCWLDDQNCYDRQECVATEENPQVYFCCCEGNFCNERFTHLPEAG<br>GPEVTYEPPPT***GGGGSGGGGSGGGGSGGGGSGGGGSGGGGSGGGGSGG***<br>***GG***T THTCPPCPAPELLGGPSVFLFPPKPKDTLMISRTPEVTCVVVDVSH<br>EDPEVKFNWYVDGVEVHNAKTKPREEQYNSTYRVVSVLTVLHQDWLNG<br>KEYKCKVSNKALPAPIEKTISKAKGQPREPQVYTLPPSRDELTKNQVS<br>LTCLVKGFYPSDIAVEWESNGQPENNYKTTPPVLDSDGSFFLYSKLTV<br>DKSRWQQGNVFSCSVMHEALHNHYTQKSLSLSPG | 222 |
| P710 | ETRECIYYNANWELERTNQSGLERCEGEQDKRLHCYASWRNSSGTIEL<br>VKKGCWLDDQNCYDRQECVATEENPQVYFCCCEGNFCNERFTHLPEAG<br>GPEVTYEPPPT***GGGGSGGGGSGGGGSGGGGSGGGGSGGGGSGGGGSGG***<br>***GG***P PCPPCKCPAPNLLGGPSVFIFPPKIKDVLMISLSPIVTCVVVDVSE<br>DDPDVQISWFVNNVEVHTAQTQTHREDYNSTLRVVSALPIQHQDWMSG<br>KEFKCKVNNKDLPAPIERTISKPKGSVRAPQVYVLPPPEEEMTKKQVT<br>LTCMVTDFMPEDIYVEWTNNGKTELNYKNTEPVLDSDGSYFMYSKLRV<br>EKKNWVERNSYSCSVVHEGLHNHHTTKSFSRTPG | 223 |

TABLE 6-continued

Exemplary binding agent amino acid sequences

| Agent | AA Sequence | SEQ ID |
|---|---|---|
| P711 | ETRECIYYNANWELERTNQSGLERCEGEQDKRLHCYASWRNSSGTIEL<br>VKKGCWLDDWNCYDRQECVATEENPQVYFCCCEGNFCNERFTHLPEAG<br>GPEVTYEPPPT***GGG*** THTCPPCPAPELLGGPSVFLFPPKPKDTLMISRT<br>PEVTCVVVDVSHEDPEVKFNWYVDGVEVHNAKTKPREEQYNSTYRVVS<br>VLTVLHQDWLNGKEYKCKVSNKALPAPIEKTISKAKGQPREPQVYTLP<br>PSREEMTKNQVSLTCLVKGFYPSDIAVEWESNGQPENNYKTTPPVLDS<br>DGSFFLYSKLTVDKSRWQQGNVFSCSVMHEALHNHYTQKSLSLSPG | 224 |
| P712 | ETRECIYYNANWELERTNQSGLERCEGEQDKRLHCYASWRNSSGTIEL<br>VKKGCWLDDWNCYDRQECVATEENPQVYFCCCEGNFCNERFTHLPEAG<br>GPEVTYEPPPT***GGG*** THTCPPCPAPELLGGPSVFLFPPKPKDTLMISRT<br>PEVTCVVVDVSHEDPEVKFNWYVDGVEVHNAKTKPREEQYNSTYRVVS<br>VLTVLHQDWLNGKEYKCKVSNKALPAPIEKTISKAKGQPREPQVYTLP<br>PSRDELTKNQVSLTCLVKGFYPSDIAVEWESNGQPENNYKTTPPVLDS<br>DGSFFLYSKLTVDKSRWQQGNVFSCSVMHEALHNHYTQKSLSLSPG | 225 |
| P713 | ETRECIYYNANWELERTNQSGLERCEGEQDKRLHCYASWRNSSGTIEL<br>VKKGCWLDDWNCYDRQECVATEENPQVYFCCCEGNFCNERFTHLPEAG<br>GPEVTYEPPPT***GGG*** PCPPCKCPAPNLLGGPSVFIFPPKIKDVLMISLS<br>PIVTCVVVDVSEDDPDVQISWFVNNVEVHTAQTQTHREDYNSTLRVVS<br>ALPIQHQDWMSGKEFKCKVNNKDLPAPIERTISKPKGSVRAPQVYVLP<br>PPEEEMTKKQVTLTCMVTDFMPEDIYVEWTNNGKTELNYKNTEPVLDS<br>DGSYFMYSKLRVEKKNWVERNSYSCSVVHEGLHNHHTTKSFSRTPG | 226 |
| P714 | ETRECIYYNANWELERTNQSGLERCEGEQDKRLHCYASWRNSSGTIEL<br>VKKGCWLDDWNCYDRQECVATEENPQVYFCCCEGNFCNERFTHLPEAG<br>GPEVTYEPPPT***GGGGSGGGGSGGGG***T THTCPPCPAPELLGGPSVFLFPP<br>KPKDTLMISRTPEVTCVVVDVSHEDPEVKFNWYVDGVEVHNAKTKPRE<br>EQYNSTYRVVSVLTVLHQDWLNGKEYKCKVSNKALPAPIEKTISKAKG<br>QPREPQVYTLPPSREEMTKNQVSLTCLVKGFYPSDIAVEWESNGQPEN<br>NYKTTPPVLDSDGSFFLYSKLTVDKSRWQQGNVFSCSVMHEALHNHYT<br>QKSLSLSPG | 227 |
| P715 | ETRECIYYNANWELERTNQSGLERCEGEQDKRLHCYASWRNSSGTIEL<br>VKKGCWLDDWNCYDRQECVATEENPQVYFCCCEGNFCNERFTHLPEAG<br>GPEVTYEPPPT***GGGGSGGGGSGGGG***T THTCPPCPAPELLGGPSVFLFPP<br>KPKDTLMISRTPEVTCVVVDVSHEDPEVKFNWYVDGVEVHNAKTKPRE<br>EQYNSTYRVVSVLTVLHQDWLNGKEYKCKVSNKALPAPIEKTISKAKG<br>QPREPQVYTLPPSRDELTKNQVSLTCLVKGFYPSDIAVEWESNGQPEN<br>NYKTTPPVLDSDGSFFLYSKLTVDKSRWQQGNVFSCSVMHEALHNHYT<br>QKSLSLSPG | 228 |
| P716 | ETRECIYYNANWELERTNQSGLERCEGEQDKRLHCYASWRNSSGTIEL<br>VKKGCWLDDWNCYDRQECVATEENPQVYFCCCEGNFCNERFTHLPEAG<br>GPEVTYEPPPT***GGGGSGGGGSGGGGSGGGGSGGGGSGGGGSGGGGSGG***<br>***GG***T THTCPPCPAPELLGGPSVFLFPPKPKDTLMISRTPEVTCVVVDVSH<br>EDPEVKFNWYVDGVEVHNAKTKPREEQYNSTYRVVSVLTVLHQDWLNG<br>KEYKCKVSNKALPAPIEKTISKAKGQPREPQVYTLPPSRDELTKNQVS<br>LTCLVKGFYPSDIAVEWESNGQPENNYKTTPPVLDSDGSFFLYSKLTV<br>DKSRWQQGNVFSCSVMHEALHNHYTQKSLSLSPG | 229 |
| P717 | ETRECIYYNANWELERTNQSGLERCEGEQDKRLHCYASWRNSSGTIEL<br>VKKGCWLDDWNCYDRQECVATEENPQVYFCCCEGNFCNERFTHLPEAG<br>GPEVTYEPPPT***GGGGSGGGGSGGGGSGGGGSGGGGSGGGGSGGGGSGG***<br>***GG***P PCPPCKCPAPNLLGGPSVFIFPPKIKDVLMISLSPIVTCVVVDVSE<br>DDPDVQISWFVNNVEVHTAQTQTHREDYNSTLRVVSALPIQHQDWMSG<br>KEFKCKVNNKDLPAPIERTISKPKGSVRAPQVYVLPPPEEEMTKKQVT<br>LTCMVTDFMPEDIYVEWTNNGKTELNYKNTEPVLDSDGSYFMYSKLRV<br>EKKNWVERNSYSCSVVHEGLHNHHTTKSFSRTPG | 230 |
| P718 | ETRECIYYNANWELERTNQSGLERCEGEQDKRLHCYASWRNSSGTIEL<br>VKKGCWLDEENCYDRQECVATEENPQVYFCCCEGNFCNERFTHLPEAG<br>GPEVTYEPPPT***GGG***T HTCPPCPAPELLGGPSVFLFPPKPKDTLMISRT<br>PEVTCVVVDVSHEDPEVKFNWYVDGVEVHNAKTKPREEQYNSTYRVVS<br>VLTVLHQDWLNGKEYKCKVSNKALPAPIEKTISKAKGQPREPQVYTLP<br>PSRDELTKNQVSLTCLVKGFYPSDIAVEWESNGQPENNYKTTPPVLDS<br>DGSFFLYSKLTVDKSRWQQGNVFSCSVMHEALHNHYTQKSLSLSPG | 231 |
| P719 | ETRECIYYNANWELERTNQSGLERCEGEYDKRLHCYASWRNSSGTIEL<br>VKKGCWLDDENCYDRQECVATEENPQVYFCCCEGNFCNERFTHLPEAG<br>GPEVTYEPPPT***GGGGSGGGGSGGGG*** THTCPPCPAPELLGGPSVFLFPP<br>KPKDTLMISRTPEVTCVVVDVSHEDPEVKFNWYVDGVEVHNAKTKPRE<br>EQYNSTYRVVSVLTVLHQDWLNGKEYKCKVSNKALPAPIEKTISKAKG | 232 |

TABLE 6-continued

Exemplary binding agent amino acid sequences

| Agent | AA Sequence | SEQ ID |
|---|---|---|
| | QPREPQVYTLPPSRDELTKNQVSLTCLVKGFYPSDIAVEWESNGQPEN<br>NYKTTPPVLDSDGSFFLYSKLTVDKSRWQQGNVFSCSVMHEALHNHYT<br>QKSLSLSPG | |
| P720 | ETRECIYYNANWELERTNQSGLERCEGEQQKRLHCYASWRNSSGTIEL<br>VKKGCWLDDENCYDRQECVATEENPQVYFCCCEGNFCNERFTHLPEAG<br>GPEVTYEPPPT***GGGGSGGGGSGGGG*** THTCPPCPAPELLGGPSVFLFPP<br>KPKDTLMISRTPEVTCVVVDVSHEDPEVKFNWYVDGVEVHNAKTKPRE<br>EQYNSTYRVVSVLTVLHQDWLNGKEYKCKVSNKALPAPIEKTISKAKG<br>QPREPQVYTLPPSRDELTKNQVSLTCLVKGFYPSDIAVEWESNGQPEN<br>NYKTTPPVLDSDGSFFLYSKLTVDKSRWQQGNVFSCSVMHEALHNHYT<br>QKSLSLSPG | 233 |
| P441 | ETRECIYYNANWELERTNQSGLERCEDEQDKRLHCYASWRNSSGTIEL<br>VKKGCWLDDENCYDRQECVATEENPQVYFCCCEGNFCNERFTHLPEAG<br>GPEVTYEPPPT***GGG***THTCPPCPAPELLGGPSVFLFPPKPKDTLMISRT<br>PEVTCVVVDVSHEDPEVKFNWYVDGVEVHNAKTKPREEQYNSTYRVVS<br>VLTVLHQDWLNGKEYKCKVSNKALPAPIEKTISKAKGQPREPQVYTLP<br>PSREEMTKNQVSLTCLVKGFYPSDIAVEWESNGQPENNYKTTPPVLDS<br>DGSFFLYSKLTVDKSRWQQGNVFSCSVMHEALHNHYTQKSLSLSPG | 234 |
| P622 w/<br>N term<br>extension | **GRGEA**ETRECIYYNANWELERTNQSGLERCEGEQDKRLHCYASWRNSS<br>GTIELVKKGCWLDDENCYDRQECVATEENPQVYFCCCEGNFCNERFTH<br>LPEAGGPEVTYEPPPT***GGGGSGGGGSGGGG***T HTCPPCPAPELLGGPSV<br>FLFPPKPKDTLMISRTPEVTCVVVDVSHEDPEVKFNWYVDGVEVHNAK<br>TKPREEQYNSTYRVVSVLTVLHQDWLNGKEYKCKVSNKALPAPIEKTI<br>SKAKGQPREPQVYTLPPSRDELTKNQVSLTCLVKGFYPSDIAVEWESN<br>GQPENNYKTTPPVLDSDGSFFLYSKLTVDKSRWQQGNVFSCSVMHEAL<br>HNHYTQKSLSLSPG | 235 |
| P622 w/<br>N term<br>extension | **RGEA**ETRECIYYNANWELERTNQSGLERCEGEQDKRLHCYASWRNSSG<br>TIELVKKGCWLDDENCYDRQECVATEENPQVYFCCCEGNFCNERFTHL<br>PEAGGPEVTYEPPPT***GGGGSGGGGSGGGG***T HTCPPCPAPELLGGPSVF<br>LFPPKPKDTLMISRTPEVTCVVVDVSHEDPEVKFNWYVDGVEVHNAKT<br>KPREEQYNSTYRVVSVLTVLHQDWLNGKEYKCKVSNKALPAPIEKTIS<br>KAKGQPREPQVYTLPPSRDELTKNQVSLTCLVKGFYPSDIAVEWESNG<br>QPENNYKTTPPVLDSDGSFFLYSKLTVDKSRWQQGNVFSCSVMHEALH<br>NHYTQKSLSLSPG | 236 |
| P622 w/<br>N term<br>extension | **GEA**ETRECIYYNANWELERTNQSGLERCEGEQDKRLHCYASWRNSSGT<br>IELVKKGCWLDDENCYDRQECVATEENPQVYFCCCEGNFCNERFTHLP<br>EAGGPEVTYEPPPT***GGGGSGGGGSGGGG***T HTCPPCPAPELLGGPSVFL<br>FPPKPKDTLMISRTPEVTCVVVDVSHEDPEVKFNWYVDGVEVHNAKTK<br>PREEQYNSTYRVVSVLTVLHQDWLNGKEYKCKVSNKALPAPIEKTISK<br>AKGQPREPQVYTLPPSRDELTKNQVSLTCLVKGFYPSDIAVEWESNGQ<br>PENNYKTTPPVLDSDGSFFLYSKLTVDKSRWQQGNVFSCSVMHEALHN<br>HYTQKSLSLSPG | 237 |
| P622 w/<br>N term<br>extension | **EA**ETRECIYYNANWELERTNQSGLERCEGEQDKRLHCYASWRNSSGTI<br>ELVKKGCWLDDENCYDRQECVATEENPQVYFCCCEGNFCNERFTHLPE<br>AGGPEVTYEPPPT***GGGGSGGGGSGGGG***T HTCPPCPAPELLGGPSVFLF<br>PPKPKDTLMISRTPEVTCVVVDVSHEDPEVKFNWYVDGVEVHNAKTKP<br>REEQYNSTYRVVSVLTVLHQDWLNGKEYKCKVSNKALPAPIEKTISKA<br>KGQPREPQVYTLPPSRDELTKNQVSLTCLVKGFYPSDIAVEWESNGQP<br>ENNYKTTPPVLDSDGSFFLYSKLTVDKSRWQQGNVFSCSVMHEALHNH<br>YTQKSLSLSPG | 238 |
| P622 w/<br>N term<br>extension | **A**ETRECIYYNANWELERTNQSGLERCEGEQDKRLHCYASWRNSSGTIE<br>LVKKGCWLDDENCYDRQECVATEENPQVYFCCCEGNFCNERFTHLPEA<br>GGPEVTYEPPPT***GGGGSGGGGSGGGG***T HTCPPCPAPELLGGPSVFLFP<br>PKPKDTLMISRTPEVTCVVVDVSHEDPEVKFNWYVDGVEVHNAKTKPR<br>EEQYNSTYRVVSVLTVLHQDWLNGKEYKCKVSNKALPAPIEKTISKAK<br>GQPREPQVYTLPPSRDELTKNQVSLTCLVKGFYPSDIAVEWESNGQPE<br>NNYKTTPPVLDSDGSFFLYSKLTVDKSRWQQGNVFSCSVMHEALHNHY<br>TQKSLSLSPG | 239 |
| P758 | ETRECIYYNANWELERTNQSGLERCEDEQDKRLHCYASWRNSSGTIEL<br>VKKGCWLDDFNCYDRQECVATEENPQVYFCCCEGNFCNERFTHLPEAG<br>GPEVTYEPPPT***GGGGSGGGGSGGGG***T HTCPPCPAPELLGGPSVFLFPP<br>KPKDTLMISRTPEVTCVVVDVSHEDPEVKFNWYVDGVEVHNAKTKPRE<br>EQYNSTYRVVSVLTVLHQDWLNGKEYKCKVSNKALPAPIEKTISKAKG<br>QPREPQVYTLPPSRDELTKNQVSLTCLVKGFYPSDIAVEWESNGQPEN<br>NYKTTPPVLDSDGSFFLYSKLTVDKSRWQQGNVFSCSVMHEALHNHYT<br>QKSLSLSPG | 240 |

TABLE 6-continued

| Exemplary binding agent amino acid sequences | | |
|---|---|---|
| Agent | AA Sequence | SEQ ID |
| P1153 | ETRECIYYNANWELERTNQSGLERCEGEQDKRLHCYASWRNSSGTIEL<br>VKKGCWLDDKNCYDRQECVATEENPQVYFCCCEGNFCNERFTHLPEAG<br>GPEVTYEPPPT***GGGGSG*** THTCPPCPAPELLGGPSVFLFPPKPKDTLMI<br>SRTPEVTCVVVDVSHEDPEVKFNWYVDGVEVHNAKTKPREEQYNSTYR<br>VVSVLTVLHQDWLNGKEYKCKVSNKALPAPIEKTISKAKGQPREPQVY<br>TLPPSRDELTKNQVSLTCLVKGFYPSDIAVEWESNGQPENNYKTTPPV<br>LDSDGSFFLYSKLTVDKSRWQQGNVFSCSVMHEALHNHYTQKSLSLSP<br>G | 241 |
| P1154 | ETRECIYYNANWELERTNQSGLERCEGEQDKRLHCYASWRNSSGTIEL<br>VKKGCWLDDKNCYDRQECVATEENPQVYFCCCEGNFCNERFTHLPEAG<br>GPEVTYEPPPT***GGGGSGGGGS***T THTCPPCPAPELLGGPSVFLFPPKPKD<br>TLMISRTPEVTCVVVDVSHEDPEVKFNWYVDGVEVHNAKTKPREEQYN<br>STYRVVSVLTVLHQDWLNGKEYKCKVSNKALPAPIEKTISKAKGQPRE<br>PQVYTLPPSRDELTKNQVSLTCLVKGFYPSDIAVEWESNGQPENNYKT<br>TPPVLDSDGSFFLYSKLTVDKSRWQQGNVFSCSVMHEALHNHYTQKSL<br>SLSPG | 242 |
| P1155 | ETRECIYYNANWELERTNQSGLERCEGEQDKRLHCYASWRNSSGTIEL<br>VKKGCWLDDKNCYDRQECVATEENPQVYFCCCEGNFCNERFTHLPEAG<br>GPEVTYEPPPT***GGGGSGGGGSGGGGSGGGG***T THTCPPCPAPELLGGPSV<br>FLFPPKPKDTLMISRTPEVTCVVVDVSHEDPEVKFNWYVDGVEVHNAK<br>TKPREEQYNSTYRVVSVLTVLHQDWLNGKEYKCKVSNKALPAPIEKTI<br>SKAKGQPREPQVYTLPPSRDELTKNQVSLTCLVKGFYPSDIAVEWESN<br>GQPENNYKTTPPVLDSDGSFFLYSKLTVDKSRWQQGNVFSCSVMHEAL<br>HNHYTQKSLSLSPG | 243 |
| P1156 | ETRECIYYNANWELERTNQSGLERCEGEQDKRLHCYASWRNSSGTIEL<br>VKKGCWLDDKNCYDRQECVATEENPQVYFCCCEGNFCNERFTHLPEAG<br>GPEVTYEPPPT***GGGGSGGGGSGGGGSGGGGSGGGGSGGGGSGGGGSGG***<br>***GG*** THTCPPCPAPELLGGPSVFLFPPKPKDTLMISRTPEVTCVVVDVSH<br>EDPEVKFNWYVDGVEVHNAKTKPREEQYNSTYRVVSVLTVLHQDWLNG<br>KEYKCKVSNKALPAPIEKTISKAKGQPREPQVYTLPPSRDELTKNQVS<br>LTCLVKGFYPSDIAVEWESNGQPENNYKTTPPVLDSDGSFFLYSKLTV<br>DKSRWQQGNVFSCSVMHEALHNHYTQKSLSLSPG | 244 |
| P1163 | ETRECIYYNANWELERTNQSGLERCEGEQDKRLHCYASWRNSSGTIEL<br>VKKGCWLDDENCYDRQECVATEENPQVYFCCCEGNFCNERFTHLPEAG<br>GPEVTYEPPPT***GGGGSG*** THTCPPCPAPELLGGPSVFLFPPKPKDTLMI<br>SRTPEVTCVVVDVSHEDPEVKFNWYVDGVEVHNAKTKPREEQYNSTYR<br>VVSVLTVLHQDWLNGKEYKCKVSNKALPAPIEKTISKAKGQPREPQVY<br>TLPPSRDELTKNQVSLTCLVKGFYPSDIAVEWESNGQPENNYKTTPPV<br>LDSDGSFFLYSKLTVDKSRWQQGNVFSCSVMHEALHNHYTQKSLSLSP<br>G | 246 |
| P1164 | ETRECIYYNANWELERTNQSGLERCEGEQDKRLHCYASWRNSSGTIEL<br>VKKGCWLDDENCYDRQECVATEENPQVYFCCCEGNFCNERFTHLPEAG<br>GPEVTYEPPPT***GGGGSGGGGS***T THTCPPCPAPELLGGPSVFLFPPKPKD<br>TLMISRTPEVTCVVVDVSHEDPEVKFNWYVDGVEVHNAKTKPREEQYN<br>STYRVVSVLTVLHQDWLNGKEYKCKVSNKALPAPIEKTISKAKGQPRE<br>PQVYTLPPSRDELTKNQVSLTCLVKGFYPSDIAVEWESNGQPENNYKT<br>TPPVLDSDGSFFLYSKLTVDKSRWQQGNVFSCSVMHEALHNHYTQKSL<br>SLSPG | 247 |
| P1168 | ETRECIYYNANWELERTNQSGLERCEGEQDKRLHCYASWRNSSGTIEL<br>VKKGCWLDDENCYDRQECVATEENPQVYFCCCEGNFCNERFTHLPEAG<br>GPEVTYEPPPT**APT*****GGGGSGGGGSGGGG*** THTCPPCPAPELLGGPSVFL<br>FPPKPKDTLMISRTPEVTCVVVDVSHEDPEVKFNWYVDGVEVHNAKTK<br>PREEQYNSTYRVVSVLTVLHQDWLNGKEYKCKVSNKALPAPIEKTISK<br>AKGQPREPQVYTLPPSRDELTKNQVSLTCLVKGFYPSDIAVEWESNGQ<br>PENNYKTTPPVLDSDGSFFLYSKLTVDKSRWQQGNVFSCSVMHEALHN<br>HYTQKSLSLSPG | 248 |
| P1213 | ETRECIYYNANWELERTNQSGLERCEGEQDKRLHCYASWRNSSGTIEL<br>VKKGCWLDDNNCYDRQECVATEENPQVYFCCCEGNFCNERFTHLPEAG<br>GPEVTYEPPPT***GGGGSGGGGSGGGG*** THTCPPCPAPELLGGPSVFLFPP<br>KPKDTLMISRTPEVTCVVVDVSHEDPEVKFNWYVDGVEVHNAKTKPRE<br>EQYNSTYRVVSVLTVLHQDWLNGKEYKCKVSNKALPAPIEKTISKAKG<br>QPREPQVYTLPPSRDELTKNQVSLTCLVKGFYPSDIAVEWESNGQPEN<br>NYKTTPPVLDSDGSFFLYSKLTVDKSRWQQGNVFSCSVMHEALHNHYT<br>QKSLSLSPG | 249 |
| P1215 | ETRECIYYNANWELERTNQSGLERCEGEQDKRLHCYASWRNSSGTIEL<br>VKKGCWLDDRNCYDRQECVATEENPQVYFCCCEGNFCNERFTHLPEAG | 250 |

TABLE 6-continued

| Exemplary binding agent amino acid sequences | | |
|---|---|---|
| Agent | AA Sequence | SEQ ID |
| | GPEVTYEPPPT*GGGGSGGGGSGGGG* THTCPPCPAPELLGGPSVFLFPP<br>KPKDTLMISRTPEVTCVVVDVSHEDPEVKFNWYVDGVEVHNAKTKPRE<br>EQYNSTYRVVSVLTVLHQDWLNGKEYKCKVSNKALPAPIEKTISKAKG<br>QPREPQVYTLPPSRDELTKNQVSLTCLVKGFYPSDIAVEWESNGQPEN<br>NYKTTPPVLDSDGSFFLYSKLTVDKSRWQQGNVFSCSVMHEALHNHYT<br>QKSLSLSPG | |
| P1217 | ETRECIYYNANWELERTNQSGLERCEGEQDKRLHCYASWRNSSGTIEL<br>VKKGCWLDDHNCYDRQECVATEENPQVYFCCCEGNFCNERFTHLPEAG<br>GPEVTYEPPPT*GGGGSGGGGSGGGG* THTCPPCPAPELLGGPSVFLFPP<br>KPKDTLMISRTPEVTCVVVDVSHEDPEVKFNWYVDGVEVHNAKTKPRE<br>EQYNSTYRVVSVLTVLHQDWLNGKEYKCKVSNKALPAPIEKTISKAKG<br>QPREPQVYTLPPSRDELTKNQVSLTCLVKGFYPSDIAVEWESNGQPEN<br>NYKTTPPVLDSDGSFFLYSKLTVDKSRWQQGNVFSCSVMHEALHNHYT<br>QKSLSLSPG | 251 |
| P1218 | ETRECIYYNANWELERTNQSGLERCEGEQDKRLHCYASWRNSSGTIEL<br>VKKGCWLDDQNCYDRQECVATEENPQVYFCCCEGNFCNERFTHLPEAG<br>GPEVTYEPPPT*GGGGSG* THTCPPCPAPELLGGPSVFLFPPKPKDTLMI<br>SRTPEVTCVVVDVSHEDPEVKFNWYVDGVEVHNAKTKPREEQYNSTYR<br>VVSVLTVLHQDWLNGKEYKCKVSNKALPAPIEKTISKAKGQPREPQVY<br>TLPPSRDELTKNQVSLTCLVKGFYPSDIAVEWESNGQPENNYKTTPPV<br>LDSDGSFFLYSKLTVDKSRWQQGNVFSCSVMHEALHNHYTQKSLSLSP<br>G | 252 |
| P1219 | ETRECIYYNANWELERTNOSGLERCEGEQDKRLHCYASWRNSSGTIEL<br>VKKGCWLDDQNCYDRQECVATEENPQVYFCCCEGNFCNERFTHLPEAG<br>GPEVTYEPPPT THTCPPCPAPELLGGPSVFLFPPKPKD<br>TLMISRTPEVTCVVVDVSHEDPEVKFNWYVDGVEVHNAKTKPREEQYN<br>STYRVVSVLTVLHQDWLNGKEYKCKVSNKALPAPIEKTISKAKGQPRE<br>PQVYTLPPSRDELTKNQVSLTCLVKGFYPSDIAVEWESNGQPENNYKT<br>TPPVLDSDGSFFLYSKLTVDKSRWQQGNVFSCSVMHEALHNHYTQKSL<br>SLSPG | 253 |
| P1220 | ETRECIYYNANWELERTNQSGLERCEGEQDKRLHCYASWRNSSGTIEL<br>VKKGCWLDDQNCYDRQECVATEENPQVYFCCCEGNFCNERFTHLPEAG<br>GPEVTYEPPPT*GGGGSGGGGSGGGGSGGGG* THTCPPCPAPELLGGPSV<br>FLFPPKPKDTLMISRTPEVTCVVVDVSHEDPEVKFNWYVDGVEVHNAK<br>TKPREEQYNSTYRVVSVLTVLHQDWLNGKEYKCKVSNKALPAPIEKTI<br>SKAKGQPREPQVYTLPPSRDELTKNQVSLTCLVKGFYPSDIAVEWESN<br>GQPENNYKTTPPVLDSDGSFFLYSKLTVDKSRWQQGNVFSCSVMHEAL<br>HNHYTQKSLSLSPG | 254 |
| P759 | ETRECIYYNANWELERTNQSGLERCEGEQDKRLHCYASWRNSSGTIEL<br>VKKGCWLDEFNCYDRQECVATEENPQVYFCCCEGNFCNERFTHLPEAG<br>GPEVTYEPPPT*GGGGSGGGGSGGGG*T THTCPPCPAPELLGGPSVFLFPP<br>KPKDTLMISRTPEVTCVVVDVSHEDPEVKFNWYVDGVEVHNAKTKPRE<br>EQYNSTYRVVSVLTVLHQDWLNGKEYKCKVSNKALPAPIEKTISKAKG<br>QPREPQVYTLPPSRDELTKNQVSLTCLVKGFYPSDIAVEWESNGQPEN<br>NYKTTPPVLDSDGSFFLYSKLTVDKSRWQQGNVFSCSVMHEALHNHYT<br>QKSLSLSPG | 333 |
| P761 | ETRECIYYNANWELERTNQSGLERCEGEQDYRLHCYASWRNSSGTIEL<br>VKKGCWLDDFNCYDRQECVATEENPQVYFCCCEGNFCNERFTHLPEAG<br>GPEVTYEPPPT*GGGGSGGGGSGGGG* THTCPPCPAPELLGGPSVFLFPP<br>KPKDTLMISRTPEVTCVVVDVSHEDPEVKFNWYVDGVEVHNAKTKPRE<br>EQYNSTYRVVSVLTVLHQDWLNGKEYKCKVSNKALPAPIEKTISKAKG<br>QPREPQVYTLPPSREEMTKNQVSLTCLVKGFYPSDIAVEWESNGQPEN<br>NYKTTPPVLDSDGSFFLYSKLTVDKSRWQQGNVFSCSVMHEALHNHYT<br>QKSLSLSPG | 339 |
| P762 | ETRECIYYNANWELERTNQSGLERCEGEQDKRLHCYASWRNSSGTIEL<br>VKKGCWLDDFNCYDRQECVATEENPQQYFCCCEGNFCNERFTHLPEAG<br>GPEVTYEPPPT*GGGGSGGGGSGGGG* THTCPPCPAPELLGGPSVFLFPP<br>KPKDTLMISRTPEVTCVVVDVSHEDPEVKFNWYVDGVEVHNAKTKPRE<br>EQYNSTYRVVSVLTVLHQDWLNGKEYKCKVSNKALPAPIEKTISKAKG<br>QPREPQVYTLPPSREEMTKNQVSLTCLVKGFYPSDIAVEWESNGQPEN<br>NYKTTPPVLDSDGSFFLYSKLTVDKSRWQQGNVFSCSVMHEALHNHYT<br>QKSLSLSPG | 340 |
| P670 | ILGRSETQECLFFNANWEKDRTNQTGVEPCYGDKDKRRHCFATWKNIS<br>GSIEIVKQGCWLDDINCYDRTDCVEKKDSPEVYFCCCEGNMCNEKFSY<br>FPEMEVTQPTSNPVTPKPPT*GGG*P PCPPCKCPAPNLLGGPSVFIFPPKI<br>KDVLMISLSPIVTCVVVDVSEDDPDVQISWFVNNVEVHTAQTQTHRED<br>YNSTLRVVSALPIQHQDWMSGKEFKCKVNNKDLPAPIERTISKPKGSV | 341 |

TABLE 6-continued

Exemplary binding agent amino acid sequences

| Agent | AA Sequence | SEQ ID |
|---|---|---|
| | RAPQVYVLPPPEEEMTKKQVTLTCMVTDFMPEDIYVEWTNNGKTELNY KNTEPVLDSDGSYFMYSKLRVEKKNWVERNSYSCSVVHEGLHNHHTTK SFSRTPG | |

*Bold and italicized text indicates the linker sequence; Bold text indicates the N-terminal extension amino acids In some embodiments, the binding agent comprises, from N-terminus to C-terminus, an ActRIIB ECD, a peptide linker, and an Fc domain. In some embodiments, the ActRIIB ECD comprises one or more amino acid substitutions. In some embodiments, the one or more amino acid substitutions are substitutions at a position selected from G27, Q29, D30, K31, S38, D57, F58, V75, and F77, wherein the amino acid numbering is based on SEQ ID NO: 2. In some embodiments, the amino acid substitution at position G27 is G27D. In some embodiments, the amino acid substitution at position Q29 is Q29Y. In some embodiments, the amino acid substitution at position D30 is D30Q. In some embodiments, the amino acid substitution at position K31 is K31Y. In some embodiments, the amino acid substitution at position S38 is S38R. In some embodiments, the amino acid substitution at position D57 is D57E. In some embodiments, the amino acid substitution at position F58 is selected from F58D, F58E, F58K, F58Q, F58W, F58N, F58R, F58H, and F58Y. In some embodiments, the amino acid substitution at position F58 is F58E. In some embodiments, the amino acid substitution at position F58 is F58K. In some embodiments, the amino acid substitution at position F58 is F58Q. In some embodiments, the amino acid substitution at position V75 is V75Q. In some embodiments, the amino acid substitution at position F77 is F77D.

In some embodiments the TGFβ superfamily ligand binding agent is a homodimeric polypeptide, wherein each polypeptide chain comprises from N-terminus to C-terminus, an ActRIIB ECD comprising the amino acid substitution of G27D, a peptide linker that is 3aa in length, and an IgG1 Fc domain monomer. In some embodiments, the TGFβ superfamily ligand binding agent is a homodimeric polypeptide, wherein each polypeptide chain comprises from N-terminus to C-terminus, an ActRIIB ECD comprising an amino acid sequence that is at least 95%, 96%, 97%, 98%, or 99% identical to SEQ ID NO: 20, a peptide linker that is 3aa in length, and an IgG1 FcEM Fc domain monomer. In some embodiments, the TGFβ superfamily ligand binding agent is a homodimeric polypeptide, wherein each polypeptide chain comprises from N-terminus to C-terminus, an ActRIIB ECD comprising or consisting of the amino acid sequence of SEQ ID NO: 20, a peptide linker that is 3aa in length, and an IgG1 FcEM Fc domain monomer. In some embodiments, the TGFβ superfamily ligand binding agent is a homodimeric polypeptide, wherein each polypeptide chain comprises an amino acid sequence that is at least 95%, 96%, 97%, 98%, or 99% identical to SEQ ID NO: 177 (P119). In some embodiments the TGFβ superfamily ligand binding agent is a homodimeric polypeptide, wherein each polypeptide chain comprises or consists of the amino acid sequence of SEQ ID NO: 177 (P119).

In some embodiments the TGFβ superfamily ligand binding agent is a homodimeric polypeptide, wherein each polypeptide chain comprises from N-terminus to C-terminus, an ActRIIB ECD comprising the amino acid substitution of D57E, a peptide linker that is 3aa in length, and an IgG1 Fc domain monomer. In some embodiments the TGFβ superfamily ligand binding agent is a homodimeric polypeptide, wherein each polypeptide chain comprises from N-terminus to C-terminus, an ActRIIB ECD comprising an amino acid sequence that is at least 95%, 96%, 97%, 98%, or 99% identical to SEQ ID NO: 4, a peptide linker that is 3aa in length, and an IgG1 FcEM Fc domain monomer. In some embodiments the TGFβ superfamily ligand binding agent is a homodimeric polypeptide, wherein each polypeptide chain comprises from N-terminus to C-terminus, an ActRIIB ECD comprising or consisting of the amino acid sequence of SEQ ID NO: 4, a peptide linker that is 3aa in length, and an IgG1 FcEM Fc domain monomer. In some embodiments the TGFβ superfamily ligand binding agent is a homodimeric polypeptide, wherein each polypeptide chain comprises an amino acid sequence that is at least 95%, 96%, 97%, 98%, or 99% identical to SEQ ID NO: 178 (P120). In some embodiments the TGFβ superfamily ligand binding agent is a homodimeric polypeptide, wherein each polypeptide chain comprises or consists of the amino acid sequence of SEQ ID NO: 178 (P120).

In some embodiments, the TGFβ superfamily ligand binding agent is a homodimeric polypeptide, wherein each polypeptide chain comprises from N-terminus to C-terminus, an ActRIIB ECD comprising the amino acid substitution of F58E, a peptide linker that is 3aa in length, and an IgG1 Fc domain monomer. In some embodiments, the TGFβ superfamily ligand binding agent is a homodimeric polypeptide, wherein each polypeptide chain comprises from N-terminus to C-terminus, an ActRIIB ECD comprising an amino acid sequence that is at least 95%, 96%, 97%, 98%, or 99% identical to SEQ ID NO: 5, a peptide linker that is 3aa in length, and an IgG1 FcEM Fc domain monomer. In some embodiments, the TGFβ superfamily ligand binding agent is a homodimeric polypeptide, wherein each polypeptide chain comprises from N-terminus to C-terminus, an ActRIIB ECD comprising or consisting of the amino acid sequence of SEQ ID NO: 5, a peptide linker that is 3aa in length, and an IgG1 FcEM Fc domain monomer. In some embodiments the TGFβ superfamily ligand binding agent is a homodimeric polypeptide, wherein each polypeptide chain comprises an amino acid sequence that is at least 95%, 96%, 97%, 98%, or 99% identical to SEQ ID NO: 179 (P121). In some embodiments the TGFβ superfamily ligand binding agent is a homodimeric polypeptide, wherein each polypeptide chain comprises or consists of the amino acid sequence of SEQ ID NO: 179 (P121).

In some embodiments, the TGFβ superfamily ligand binding agent is a homodimeric polypeptide, wherein each polypeptide chain comprises from N-terminus to C-terminus, an ActRIIB ECD comprising the amino acid substitution of Q29Y, a peptide linker that is 3aa in length, and an IgG1 Fc domain monomer. In some embodiments, the TGFβ superfamily ligand binding agent is a homodimeric polypeptide, wherein each polypeptide chain comprises from N-terminus to C-terminus, an ActRIIB ECD comprising an amino acid sequence that is at least 95%, 96%, 97%, 98%, or 99% identical to SEQ ID NO: 14, a peptide linker that is 3aa in length, and an IgG1 FcEM Fc domain monomer. In some embodiments, the TGFβ superfamily ligand binding agent is a homodimeric polypeptide, wherein each polypeptide chain comprises from N-terminus to C-terminus, an ActRIIB ECD comprising or consisting of the amino acid sequence of SEQ ID NO: 14, a peptide linker that is 3aa in length, and an IgG1 FcEM Fc domain monomer. In some embodiments the TGFβ superfamily ligand binding agent is a homodimeric polypeptide, wherein each polypeptide chain comprises an amino acid sequence that is at least 95%, 96%, 97%, 98%, or 99% identical to SEQ ID NO: 180 (P122). In some embodiments the TGFβ superfamily ligand binding agent is a homodimeric polypeptide, wherein each polypeptide chain comprises or consists of the amino acid sequence of SEQ ID NO: 180 (P122).

In some embodiments, the TGFβ superfamily ligand binding agent is a homodimeric polypeptide, wherein each polypeptide chain comprises from N-terminus to C-terminus, an ActRIIB ECD comprising the amino acid substitution of D30Q, a peptide linker that is 3aa in length, and an IgG1 Fc domain monomer. In some embodiments, the TGFβ superfamily ligand binding agent is a homodimeric polypeptide, wherein each polypeptide chain comprises from N-terminus to C-terminus, an ActRIIB ECD comprising an amino acid sequence that is at least 95%, 96%, 97%, 98%, or 99% identical to SEQ ID NO: 15, a peptide linker that is 3aa in length, and an IgG1 FcEM Fc domain monomer. In some embodiments, the TGFβ superfamily ligand binding agent is a homodimeric polypeptide, wherein each polypeptide chain comprises from N-terminus to C-terminus, an ActRIIB ECD comprising or consisting of the amino acid sequence of SEQ ID NO: 15, a peptide linker that is 3aa in length, and an IgG1 FcEM Fc domain monomer. In some embodiments the TGFβ superfamily ligand binding agent is a homodimeric polypeptide, wherein each polypeptide chain comprises an amino acid sequence that is at least 95%, 96%, 97%, 98%, or 99% identical to SEQ ID NO: 181 (P123). In some embodiments the TGFβ superfamily ligand binding agent is a homodimeric polypeptide, wherein each polypeptide chain comprises or consists of the amino acid sequence of SEQ ID NO: 181 (P123).

In some embodiments, the TGFβ superfamily ligand binding agent is a homodimeric polypeptide, wherein each polypeptide chain comprises from N-terminus to C-terminus, an ActRIIB ECD comprising the amino acid substitution of K31Y, a peptide linker that is 3aa in length, and an IgG1 Fc domain monomer. In some embodiments, the TGFβ superfamily ligand binding agent is a homodimeric polypeptide, wherein each polypeptide chain comprises from N-terminus to C-terminus, an ActRIIB ECD comprising an amino acid sequence that is at least 95%, 96%, 97%, 98%, or 99% identical to SEQ ID NO: 16, a peptide linker that is 3aa in length, and an IgG1 FcEM Fc domain monomer. In some embodiments, the TGFβ superfamily ligand binding agent is a homodimeric polypeptide, wherein each polypeptide chain comprises from N-terminus to C-terminus, an ActRIIB ECD comprising or consisting of the amino acid sequence of SEQ ID NO: 16, a peptide linker that is 3aa in length, and an IgG1 FcEM Fc domain monomer. In some embodiments the TGFβ superfamily ligand binding agent is a homodimeric polypeptide, wherein each polypeptide chain comprises an amino acid sequence that is at least 95%, 96%, 97%, 98%, or 99% identical to SEQ ID NO: 182 (P124). In some embodiments the TGFβ superfamily ligand binding agent is a homodimeric polypeptide, wherein each polypeptide chain comprises or consists of the amino acid sequence of SEQ ID NO: 182 (P124).

In some embodiments, the TGFβ superfamily ligand binding agent is a homodimeric polypeptide, wherein each polypeptide chain comprises from N-terminus to C-terminus, an ActRIIB ECD comprising the amino acid substitution of S38R, a peptide linker that is 3aa in length, and an IgG1 Fc domain monomer. In some embodiments, the TGFβ superfamily ligand binding agent is a homodimeric polypeptide, wherein each polypeptide chain comprises from N-terminus to C-terminus, an ActRIIB ECD comprising an amino acid sequence that it at least 95%, 96%, 97%, 98%, or 99% identical to SEQ ID NO: 17, a peptide linker that is 3aa in length, and an IgG1 FcEM Fc domain monomer. In some embodiments, the TGFβ superfamily ligand binding agent is a homodimeric polypeptide, wherein each polypeptide chain comprises from N-terminus to C-terminus, an ActRIIB ECD comprising or consisting of the amino acid sequence of SEQ ID NO: 17, a peptide linker that is 3aa in length, and an IgG1 FcEM Fc domain monomer. In some embodiments the TGFβ superfamily ligand binding agent is a homodimeric polypeptide, wherein each polypeptide chain comprises an amino acid sequence that is at least 95%, 96%, 97%, 98%, or 99% identical to SEQ ID NO: 183 (P125). In some embodiments the TGFβ superfamily ligand binding agent is a homodimeric polypeptide, wherein each polypeptide chain comprises or consists of the amino acid sequence of SEQ ID NO: 183 (P125).

In some embodiments, the TGFβ superfamily ligand binding agent is a homodimeric polypeptide, wherein each polypeptide chain comprises from N-terminus to C-terminus, an ActRIIB ECD comprising the amino acid substitution of V75Q, a peptide linker that is 3aa in length, and an IgG1 Fc domain monomer. In some embodiments, the TGFβ superfamily ligand binding agent is a homodimeric polypeptide, wherein each polypeptide chain comprises from N-terminus to C-terminus, an ActRIIB ECD comprising an amino acid sequence that is at least 95%, 96%, 97%, 98%, or 99% identical to SEQ ID NO: 18, a peptide linker that is 3aa in length, and an IgG1 FcEM Fc domain monomer. In some embodiments, the TGFβ superfamily ligand binding agent is a homodimeric polypeptide, wherein each polypeptide chain comprises from N-terminus to C-terminus, an ActRIIB ECD comprising or consisting of the amino acid sequence of SEQ ID NO: 18, a peptide linker that is 3aa in length, and an IgG1 FcEM Fc domain monomer. In some embodiments the TGFβ superfamily ligand binding agent is a homodimeric polypeptide, wherein each polypeptide chain comprises an amino acid sequence that is at least 95%, 96%, 97%, 98%, or 99% identical to SEQ ID NO: 184 (P126). In some embodiments the TGFβ superfamily ligand binding agent is a homodimeric polypeptide, wherein each polypeptide chain comprises or consists of the amino acid sequence of SEQ ID NO: 184 (P126).

In some embodiments, the TGFβ superfamily ligand binding agent is a homodimeric polypeptide, wherein each polypeptide chain comprises from N-terminus to C-terminus, an ActRIIB ECD comprising the amino acid substitution of F77D, a peptide linker that is 3aa in length, and an IgG1 Fc domain monomer. In some embodiments, the TGFβ superfamily ligand binding agent is a homodimeric polypeptide, wherein each polypeptide chain comprises from N-terminus to C-terminus, an ActRIIB ECD comprising an amino acid sequence that is at least 95%, 96%, 97%, 98%, or 99% identical to the amino acid sequence of SEQ ID NO: 19, a peptide linker that is 3aa in length, and an IgG1 FcEM Fc domain monomer. In some embodiments, the TGFβ superfamily ligand binding agent is a homodimeric polypeptide, wherein each polypeptide chain comprises from N-terminus to C-terminus, an ActRIIB ECD comprising or consisting of the amino acid sequence of SEQ ID NO: 19, a peptide linker that is 3aa in length, and an IgG1 FcEM Fc domain monomer. In some embodiments the TGFβ superfamily ligand binding agent is a homodimeric polypeptide, wherein each polypeptide chain comprises an amino acid sequence that is at least 95%, 96%, 97%, 98%, or 99% identical to SEQ ID NO: 185 (P127). In some embodiments the TGFβ superfamily ligand binding agent is a homodimeric polypeptide, wherein each polypeptide chain comprises or consists of the amino acid sequence of SEQ ID NO: 185 (P127).

In some embodiments, the TGFβ superfamily ligand binding agent is a homodimeric polypeptide, wherein each polypeptide chain comprises from N-terminus to C-terminus, an ActRIIB ECD comprising the amino acid substitution of F58E, a peptide linker that is 14aa in length, and an IgG1 Fc domain monomer. In some embodiments, the TGFβ superfamily ligand binding agent is a homodimeric polypeptide, wherein each polypeptide chain comprises from N-terminus to C-terminus, an ActRIIB ECD comprising an amino acid sequence that is at least 95%, 96%, 97%, 98%, or 99% identical to the amino acid sequence of SEQ ID NO: 5, a peptide linker that is 14aa in length, and an IgG1 FcDL Fc domain monomer. In some embodiments, the TGFβ superfamily ligand binding agent is a homodimeric polypeptide, wherein each polypeptide chain comprises from N-terminus to C-terminus, an ActRIIB ECD comprising or consisting of the amino acid sequence of SEQ ID NO: 5, a peptide linker that is 14aa in length, and an IgG1 FcDL Fc domain monomer. In some embodiments the TGFβ superfamily ligand binding agent is a homodimeric polypeptide, wherein each polypeptide chain comprises an amino acid sequence that is at least 95%, 96%, 97%, 98%, or 99% identical to SEQ ID NO: 186 (P622). In some embodiments the TGFβ superfamily ligand binding agent is a homodimeric polypeptide, wherein each polypeptide chain comprises or consists of the amino acid sequence of SEQ ID NO: 186 (P622).

In some embodiments, the TGFβ superfamily ligand binding agent is a homodimeric polypeptide, wherein each polypeptide chain comprises from N-terminus to C-terminus, an ActRIIB ECD comprising the amino acid substitution of F58E, a peptide linker that is 3aa in length, and an IgG1 Fc domain monomer. In some embodiments, the TGFβ superfamily ligand binding agent is a homodimeric polypeptide, wherein each polypeptide chain comprises from N-terminus to C-terminus, an ActRIIB ECD comprising an amino acid sequence that is at least 95%, 96%, 97%, 98%, or 99% identical to the amino acid sequence of SEQ ID NO: 5, a peptide linker that is 3aa in length, and an IgG1 FcDL Fc domain monomer. In some embodiments, the TGFβ superfamily ligand binding agent is a homodimeric polypeptide, wherein each polypeptide chain comprises from N-terminus to C-terminus, an ActRIIB ECD comprising or consisting of the amino acid sequence of SEQ ID NO: 5, a peptide linker that is 3aa in length, and an IgG1 FcDL Fc domain monomer. In some embodiments the TGFβ superfamily ligand binding agent is a homodimeric polypeptide, wherein each polypeptide chain comprises an amino acid sequence that is at least 95%, 96%, 97%, 98%, or 99% identical to SEQ ID NO: 187 (P624). In some embodiments the TGFβ superfamily ligand binding agent is a homodimeric polypeptide, wherein each polypeptide chain comprises or consists of the amino acid sequence of SEQ ID NO: 187 (P624).

In some embodiments, the TGFβ superfamily ligand binding agent is a homodimeric polypeptide, wherein each polypeptide chain comprises from N-terminus to C-terminus, an ActRIIB ECD comprising the amino acid substitution of F58E, a peptide linker that is 3aa in length, and an IgG1 Fc domain monomer. In some embodiments, the TGFβ superfamily ligand binding agent is a homodimeric polypeptide, wherein each polypeptide chain comprises from N-terminus to C-terminus, an ActRIIB ECD comprising an amino acid sequence that is at least 95%, 96%, 97%, 98%, or 99% identical to the amino acid sequence of SEQ ID NO: 5, a peptide linker that is 3aa in length, and an IgG1 FcY-DL Fc domain monomer. In some embodiments, the TGFβ superfamily ligand binding agent is a homodimeric polypeptide, wherein each polypeptide chain comprises from N-terminus to C-terminus, an ActRIIB ECD comprising or consisting of the amino acid sequence of SEQ ID NO: 5, a peptide linker that is 3aa in length, and an IgG1 FcY-DL Fc domain monomer. In some embodiments the TGFβ superfamily ligand binding agent is a homodimeric polypeptide, wherein each polypeptide chain comprises an amino acid sequence that is at least 95%, 96%, 97%, 98%, or 99% identical to SEQ ID NO: 188 (P625). In some embodiments the TGFβ superfamily ligand binding agent is a homodimeric polypeptide, wherein each polypeptide chain comprises or consists of the amino acid sequence of SEQ ID NO: 188 (P625).

In some embodiments, the TGFβ superfamily ligand binding agent is a homodimeric polypeptide, wherein each polypeptide chain comprises from N-terminus to C-terminus, an ActRIIB ECD comprising the amino acid substitution of F58E, a peptide linker that is 3aa in length, and an IgG1 Fc domain monomer. In some embodiments, the TGFβ superfamily ligand binding agent is a homodimeric polypeptide, wherein each polypeptide chain comprises from N-terminus to C-terminus, an ActRIIB ECD comprising an amino acid sequence that is at least 95%, 96%, 97%, 98%, or 99% identical to SEQ ID NO: 5, a peptide linker that is 3aa in length, and an IgG1 FcYTE-DL Fc domain monomer. In some embodiments, the TGFβ superfamily ligand binding agent is a homodimeric polypeptide, wherein each polypeptide chain comprises from N-terminus to C-terminus, an ActRIIB ECD comprising or consisting of the amino acid sequence of SEQ ID NO: 5, a peptide linker that is 3aa in length, and an IgG1 FcYTE-DL Fc domain monomer. In some embodiments the TGFβ superfamily ligand binding agent is a homodimeric polypeptide, wherein each polypeptide chain comprises an amino acid sequence that is at least 95%, 96%, 97%, 98%, or 99% identical to SEQ ID NO: 189 (P626). In some embodiments the TGFβ superfamily ligand binding agent is a homodimeric polypeptide, wherein each polypeptide chain comprises or consists of the amino acid sequence of SEQ ID NO: 189 (P626).

In some embodiments, the TGFβ superfamily ligand binding agent is a homodimeric polypeptide, wherein each polypeptide chain comprises from N-terminus to C-terminus, an ActRIIB ECD comprising the amino acid substitution of F58E, a peptide linker that is 19aa in length, and an IgG1 Fc domain monomer. In some embodiments, the TGFβ superfamily ligand binding agent is a homodimeric polypeptide, wherein each polypeptide chain comprises from N-terminus to C-terminus, an ActRIIB ECD comprising an amino acid sequence that is at least 95%, 96%, 97%, 98%, or 99% identical to SEQ ID NO: 5, a peptide linker that is 19aa in length, and an IgG1 Fc-DL Fc domain monomer. In some embodiments, the TGFβ superfamily ligand binding agent is a homodimeric polypeptide, wherein each polypeptide chain comprises from N-terminus to C-terminus, an ActRIIB ECD comprising or consisting of the amino acid sequence of SEQ ID NO: 5, a peptide linker that is 19aa in length, and an IgG1 Fc-DL Fc domain monomer. In some embodiments the TGFβ superfamily ligand binding agent is a homodimeric polypeptide, wherein each polypeptide chain comprises an amino acid sequence that is at least 95%, 96%, 97%, 98%, or 99% identical to SEQ ID NO: 190 (P666). In some embodiments the TGFβ superfamily ligand binding agent is a homodimeric polypeptide, wherein each polypeptide chain comprises or consists of the amino acid sequence of SEQ ID NO: 190 (P666).

In some embodiments, the TGFβ superfamily ligand binding agent is a homodimeric polypeptide, wherein each polypeptide chain comprises from N-terminus to C-terminus, an ActRIIB ECD comprising the amino acid substitution of F58E, a peptide linker that is 39aa in length, and an IgG1 Fc domain monomer. In some embodiments, the TGFβ superfamily ligand binding agent is a homodimeric polypeptide, wherein each polypeptide chain comprises from N-terminus to C-terminus, an ActRIIB ECD comprising an amino acid sequence that is at least 95%, 96%, 97%, 98%, or 99% identical to SEQ ID NO: 5, a peptide linker that is 39aa in length, and an IgG1 Fc-DL Fc domain monomer. In some embodiments, the TGFβ superfamily ligand binding agent is a homodimeric polypeptide, wherein each polypeptide chain comprises from N-terminus to C-terminus, an ActRIIB ECD comprising or consisting of the amino acid sequence of SEQ ID NO: 5, a peptide linker that is 39aa in length, and an IgG1 Fc-DL Fc domain monomer. In some embodiments the TGFβ superfamily ligand binding agent is a homodimeric polypeptide, wherein each polypeptide chain comprises an amino acid sequence that is at least 95%, 96%, 97%, 98%, or 99% identical to SEQ ID NO: 191 (P667). In some embodiments the TGFβ superfamily ligand binding agent is a homodimeric polypeptide, wherein each polypeptide chain comprises or consists of the amino acid sequence of SEQ ID NO: 191 (P667).

In some embodiments, the TGFβ superfamily ligand binding agent is a homodimeric polypeptide, wherein each polypeptide chain comprises from N-terminus to C-terminus, an ActRIIB ECD comprising the amino acid substitution of F58E, a peptide linker that is 14aa in length, and an IgG2 Fc domain monomer. In some embodiments, the TGFβ superfamily ligand binding agent is a homodimeric polypeptide, wherein each polypeptide chain comprises from N-terminus to C-terminus, an ActRIIB ECD comprising an amino acid sequence that is at least 95%, 96%, 97%, 98%, or 99% identical to SEQ ID NO: 5, a peptide linker that is 14aa in length, and an IgG2 Fc domain monomer of SEQ ID NO: 157. In some embodiments, the TGFβ superfamily ligand binding agent is a homodimeric polypeptide, wherein each polypeptide chain comprises from N-terminus to C-terminus, an ActRIIB ECD comprising or consisting of the amino acid sequence of SEQ ID NO: 5, a peptide linker that is 14aa in length, and an IgG2 Fc domain monomer of SEQ ID NO: 157. In some embodiments the TGFβ superfamily ligand binding agent is a homodimeric polypeptide, wherein each polypeptide chain comprises an amino acid sequence that is at least 95%, 96%, 97%, 98%, or 99% identical to SEQ ID NO: 192 (P671). In some embodiments the TGFβ superfamily ligand binding agent is a homodimeric polypeptide, wherein each polypeptide chain comprises or consists of the amino acid sequence of SEQ ID NO: 192 (P671).

In some embodiments, the TGFβ superfamily ligand binding agent is a homodimeric polypeptide, wherein each polypeptide chain comprises from N-terminus to C-terminus, an ActRIIB ECD comprising the amino acid substitution of F58E, a peptide linker that is 19aa in length, and an IgG2 Fc domain monomer. In some embodiments, the TGFβ superfamily ligand binding agent is a homodimeric polypeptide, wherein each polypeptide chain comprises from N-terminus to C-terminus, an ActRIIB ECD comprising an amino acid sequence that is at least 95%, 96%, 97%, 98%, or 99% identical to SEQ ID NO: 5, a peptide linker that is 19aa in length, and an IgG2 Fc domain monomer of SEQ ID NO: 157. In some embodiments, the TGFβ superfamily ligand binding agent is a homodimeric polypeptide, wherein each polypeptide chain comprises from N-terminus to C-terminus, an ActRIIB ECD comprising or consisting of the amino acid sequence of SEQ ID NO: 5, a peptide linker that is 19aa in length, and an IgG2 Fc domain monomer of SEQ ID NO: 157. In some embodiments the TGFβ superfamily ligand binding agent is a homodimeric polypeptide, wherein each polypeptide chain comprises an amino acid sequence that is at least 95%, 96%, 97%, 98%, or 99% identical to SEQ ID NO: 193 (P672). In some embodiments the TGFβ superfamily ligand binding agent is a homodimeric polypeptide, wherein each polypeptide chain comprises or consists of the amino acid sequence of SEQ ID NO: 193 (P672).

In some embodiments, the TGFβ superfamily ligand binding agent is a homodimeric polypeptide, wherein each polypeptide chain comprises from N-terminus to C-terminus, an ActRIIB ECD comprising the amino acid substitution of F58E, a peptide linker that is 39aa in length, and an IgG2 Fc domain monomer. In some embodiments, the TGFβ superfamily ligand binding agent is a homodimeric polypeptide, wherein each polypeptide chain comprises from N-terminus to C-terminus, an ActRIIB ECD comprising an amino acid sequence that is at least 95%, 96%, 97%, 98%, or 99% identical to SEQ ID NO: 5, a peptide linker that is 39aa in length, and an IgG2 Fc domain monomer of SEQ ID NO: 157. In some embodiments, the TGFβ superfamily ligand binding agent is a homodimeric polypeptide, wherein each polypeptide chain comprises from N-terminus to C-terminus, an ActRIIB ECD comprising or consisting of the amino acid sequence of SEQ ID NO: 5, a peptide linker that is 39aa in length, and an IgG2 Fc domain monomer of SEQ ID NO: 157. In some embodiments the TGFβ superfamily ligand binding agent is a homodimeric polypeptide, wherein each polypeptide chain comprises an amino acid sequence that is at least 95%, 96%, 97%, 98%, or 99% identical to SEQ ID NO: 194 (P673). In some embodiments the TGFβ superfamily ligand binding agent is a homodimeric polypeptide, wherein each polypeptide chain comprises or consists of the amino acid sequence of SEQ ID NO: 194 (P673).

In some embodiments, the TGFβ superfamily ligand binding agent is a homodimeric polypeptide, wherein each polypeptide chain comprises from N-terminus to C-terminus, an ActRIIB ECD comprising the amino acid substitution of F58E, a peptide linker that is 3aa in length, and an IgG2 Fc domain monomer. In some embodiments, the TGFβ superfamily ligand binding agent is a homodimeric polypeptide, wherein each polypeptide chain comprises from N-terminus to C-terminus, an ActRIIB ECD comprising an amino acid sequence that is at least 95%, 96%, 97%, 98%, or 99% identical to SEQ ID NO: 5, a peptide linker that is 3aa in length, and an IgG2 Fc domain monomer of SEQ ID NO: 157. In some embodiments, the TGFβ superfamily ligand binding agent is a homodimeric polypeptide, wherein each polypeptide chain comprises from N-terminus to C-terminus, an ActRIIB ECD comprising or consisting of the amino acid sequence of SEQ ID NO: 5, a peptide linker that is 3aa in length, and an IgG2 Fc domain monomer of SEQ ID NO: 157. In some embodiments the TGFβ superfamily ligand binding agent is a homodimeric polypeptide, wherein each polypeptide chain comprises an amino acid sequence that is at least 95%, 96%, 97%, 98%, or 99% identical to SEQ ID NO: 195 (P674). In some embodiments the TGFβ superfamily ligand binding agent is a homodimeric polypeptide, wherein each polypeptide chain comprises or consists of the amino acid sequence of SEQ ID NO: 195 (P674).

In some embodiments, the TGFβ superfamily ligand binding agent is a homodimeric polypeptide, wherein each polypeptide chain comprises from N-terminus to C-terminus, an ActRIIB ECD comprising the amino acid substitution of F58D, a peptide linker that is 3aa in length, and an IgG1 Fc domain monomer. In some embodiments, the TGFβ superfamily ligand binding agent is a homodimeric polypeptide, wherein each polypeptide chain comprises from N-terminus to C-terminus, an ActRIIB ECD comprising an amino acid sequence that is at least 95%, 96%, 97%, 98%, or 99% identical to SEQ ID NO: 6, a peptide linker that is 3aa in length, and an IgG1 Fc-EM Fc domain monomer. In some embodiments, the TGFβ superfamily ligand binding agent is a homodimeric polypeptide, wherein each polypeptide chain comprises from N-terminus to C-terminus, an ActRIIB ECD comprising or consisting of the amino acid sequence of SEQ ID NO: 6, a peptide linker that is 3aa in length, and an IgG1 Fc-EM Fc domain monomer. In some embodiments the TGFβ superfamily ligand binding agent is a homodimeric polypeptide, wherein each polypeptide chain comprises an amino acid sequence that is at least 95%, 96%, 97%, 98%, or 99% identical to SEQ ID NO: 196 (P683). In some embodiments the TGFβ superfamily ligand binding agent is a homodimeric polypeptide, wherein each polypeptide chain comprises or consists of the amino acid sequence of SEQ ID NO: 196 (P683).

In some embodiments, the TGFβ superfamily ligand binding agent is a homodimeric polypeptide, wherein each polypeptide chain comprises from N-terminus to C-terminus, an ActRIIB ECD comprising the amino acid substitution of F58D, a peptide linker that is 3aa in length, and an IgG1 Fc domain monomer. In some embodiments, the TGFβ superfamily ligand binding agent is a homodimeric polypeptide, wherein each polypeptide chain comprises from N-terminus to C-terminus, an ActRIIB ECD comprising an amino acid sequence that is at least 95%, 96%, 97%, 98%, or 99% identical to SEQ ID NO: 6, a peptide linker that is 3aa in length, and an IgG1 Fc-DL Fc domain monomer. In some embodiments, the TGFβ superfamily ligand binding agent is a homodimeric polypeptide, wherein each polypeptide chain comprises from N-terminus to C-terminus, an ActRIIB ECD comprising or consisting of the amino acid sequence of SEQ ID NO: 6, a peptide linker that is 3aa in length, and an IgG1 Fc-DL Fc domain monomer. In some embodiments the TGFβ superfamily ligand binding agent is a homodimeric polypeptide, wherein each polypeptide chain comprises an amino acid sequence that is at least 95%, 96%, 97%, 98%, or 99% identical to SEQ ID NO: 197 (P684). In some embodiments the TGFβ superfamily ligand binding agent is a homodimeric polypeptide, wherein each polypeptide chain comprises or consists of the amino acid sequence of SEQ ID NO: 197 (P684).

In some embodiments, the TGFβ superfamily ligand binding agent is a homodimeric polypeptide, wherein each polypeptide chain comprises from N-terminus to C-terminus, an ActRIIB ECD comprising the amino acid substitution of F58D, a peptide linker that is 3aa in length, and an IgG2 Fc domain monomer. In some embodiments, the TGFβ superfamily ligand binding agent is a homodimeric polypeptide, wherein each polypeptide chain comprises from N-terminus to C-terminus, an ActRIIB ECD comprising an amino acid sequence that is at least 95%, 96%, 97%, 98%, or 99% identical to SEQ ID NO: 6, a peptide linker that is 3aa in length, and an IgG2 Fc domain monomer of SEQ ID NO: 157. In some embodiments, the TGFβ superfamily ligand binding agent is a homodimeric polypeptide, wherein each polypeptide chain comprises from N-terminus to C-terminus, an ActRIIB ECD comprising or consisting of the amino acid sequence of SEQ ID NO: 6, a peptide linker that is 3aa in length, and an IgG2 Fc domain monomer of SEQ ID NO: 157. In some embodiments the TGFβ superfamily ligand binding agent is a homodimeric polypeptide, wherein each polypeptide chain comprises an amino acid sequence that is at least 95%, 96%, 97%, 98%, or 99% identical to SEQ ID NO: 198 (P685). In some embodiments the TGFβ superfamily ligand binding agent is a homodimeric polypeptide, wherein each polypeptide chain comprises or consists of the amino acid sequence of SEQ ID NO: 198 (P685).

In some embodiments, the TGFβ superfamily ligand binding agent is a homodimeric polypeptide, wherein each polypeptide chain comprises from N-terminus to C-terminus, an ActRIIB ECD comprising the amino acid substitution of F58D, a peptide linker that is 14aa in length, and an IgG1 Fc domain monomer. In some embodiments, the TGFβ superfamily ligand binding agent is a homodimeric polypeptide, wherein each polypeptide chain comprises from N-terminus to C-terminus, an ActRIIB ECD comprising an amino acid sequence that is at least 95%, 96%, 97%, 98%, or 99% identical to SEQ ID NO: 6, a peptide linker that is 14aa in length, and an IgG1 Fc-EM Fc domain monomer. In some embodiments, the TGFβ superfamily ligand binding agent is a homodimeric polypeptide, wherein each polypeptide chain comprises from N-terminus to C-terminus, an ActRIIB ECD comprising or consisting of the amino acid sequence of SEQ ID NO: 6, a peptide linker that is 14aa in length, and an IgG1 Fc-EM Fc domain monomer. In some embodiments the TGFβ superfamily ligand binding agent is a homodimeric polypeptide, wherein each polypeptide chain comprises an amino acid sequence that is at least 95%, 96%, 97%, 98%, or 99% identical to SEQ ID NO: 199 (P686). In some embodiments the TGFβ superfamily ligand binding agent is a homodimeric polypeptide, wherein each polypeptide chain comprises or consists of the amino acid sequence of SEQ ID NO: 199 (P686).

In some embodiments, the TGFβ superfamily ligand binding agent is a homodimeric polypeptide, wherein each polypeptide chain comprises from N-terminus to C-terminus, an ActRIIB ECD comprising the amino acid substitution of F58D, a peptide linker that is 14aa in length, and an IgG1 Fc domain monomer. In some embodiments, the TGFβ superfamily ligand binding agent is a homodimeric polypeptide, wherein each polypeptide chain comprises from N-terminus to C-terminus, an ActRIIB ECD comprising an amino acid sequence that is at least 95%, 96%, 97%, 98%, or 99% identical to SEQ ID NO: 6, a peptide linker that is 14aa in length, and an IgG1 Fc-DL Fc domain monomer. In some embodiments, the TGFβ superfamily ligand binding agent is a homodimeric polypeptide, wherein each polypeptide chain comprises from N-terminus to C-terminus, an ActRIIB ECD comprising or consisting of the amino acid sequence of SEQ ID NO: 6, a peptide linker that is 14aa in length, and an IgG1 Fc-DL Fe domain monomer. In some embodiments the TGFβ superfamily ligand binding agent is a homodimeric polypeptide, wherein each polypeptide chain comprises an amino acid sequence that is at least 95%, 96%, 97%, 98%, or 99% identical to SEQ ID NO: 200 (P687). In some embodiments the TGFβ superfamily ligand binding agent is a homodimeric polypeptide, wherein each polypeptide chain comprises or consists of the amino acid sequence of SEQ ID NO: 200 (P687).

In some embodiments, the TGFβ superfamily ligand binding agent is a homodimeric polypeptide, wherein each polypeptide chain comprises from N-terminus to C-terminus, an ActRIIB ECD comprising the amino acid substitution of F58D, a peptide linker that is 39aa in length, and an IgG1 Fc domain monomer. In some embodiments, the TGFβ superfamily ligand binding agent is a homodimeric polypeptide, wherein each polypeptide chain comprises from N-terminus to C-terminus, an ActRIIB ECD comprising an amino acid sequence that is at least 95%, 96%, 97%, 98%, or 99% identical to SEQ ID NO: 6, a peptide linker that is 39aa in length, and an IgG1 Fc-DL Fc domain monomer. In some embodiments, the TGFβ superfamily ligand binding agent is a homodimeric polypeptide, wherein each polypeptide chain comprises from N-terminus to C-terminus, an ActRIIB ECD comprising or consisting of the amino acid sequence of SEQ ID NO: 6, a peptide linker that is 39aa in length, and an IgG1 Fc-DL Fc domain monomer. In some embodiments the TGFβ superfamily ligand binding agent is a homodimeric polypeptide, wherein each polypeptide chain comprises an amino acid sequence that is at least 95%, 96%, 97%, 98%, or 99% identical to SEQ ID NO: 201 (P688). In some embodiments the TGFβ superfamily ligand binding agent is a homodimeric polypeptide, wherein each polypeptide chain comprises or consists of the amino acid sequence of SEQ ID NO: 201 (P688).

In some embodiments, the TGFβ superfamily ligand binding agent is a homodimeric polypeptide, wherein each polypeptide chain comprises from N-terminus to C-terminus, an ActRIIB ECD comprising the amino acid substitution of F58D, a peptide linker that is 39aa in length, and an IgG2 Fc domain monomer. In some embodiments, the TGFβ superfamily ligand binding agent is a homodimeric polypeptide, wherein each polypeptide chain comprises from N-terminus to C-terminus, an ActRIIB ECD comprising an amino acid sequence that is at least 95%, 96%, 97%, 98%, or 99% identical to SEQ ID NO: 6, a peptide linker that is 39aa in length, and an IgG2 Fc domain monomer of SEQ ID NO: 157. In some embodiments, the TGFβ superfamily ligand binding agent is a homodimeric polypeptide, wherein each polypeptide chain comprises from N-terminus to C-terminus, an ActRIIB ECD comprising or consisting of the amino acid sequence of SEQ ID NO: 6, a peptide linker that is 39aa in length, and an IgG2 Fc domain monomer of SEQ ID NO: 157. In some embodiments the TGFβ superfamily ligand binding agent is a homodimeric polypeptide, wherein each polypeptide chain comprises an amino acid sequence that is at least 95%, 96%, 97%, 98%, or 99% identical to SEQ ID NO: 202 (P689). In some embodiments the TGFβ superfamily ligand binding agent is a homodimeric polypeptide, wherein each polypeptide chain comprises or consists of the amino acid sequence of SEQ ID NO: 202 (P689).

In some embodiments, the TGFβ superfamily ligand binding agent is a homodimeric polypeptide, wherein each polypeptide chain comprises from N-terminus to C-terminus, an ActRIIB ECD comprising the amino acid substitution of F58Y, a peptide linker that is 3aa in length, and an IgG1 Fc domain monomer. In some embodiments, the TGFβ superfamily ligand binding agent is a homodimeric polypeptide, wherein each polypeptide chain comprises from N-terminus to C-terminus, an ActRIIB ECD comprising an amino acid sequence that is at least 95%, 96%, 97%, 98%, or 99% identical to SEQ ID NO: 7, a peptide linker that is 3aa in length, and an IgG1 Fc-EM Fc domain monomer. In some embodiments, the TGFβ superfamily ligand binding agent is a homodimeric polypeptide, wherein each polypeptide chain comprises from N-terminus to C-terminus, an ActRIIB ECD comprising or consisting of the amino acid sequence of SEQ ID NO: 7, a peptide linker that is 3aa in length, and an IgG1 Fc-EM Fc domain monomer. In some embodiments the TGFβ superfamily ligand binding agent is a homodimeric polypeptide, wherein each polypeptide chain comprises an amino acid sequence that is at least 95%, 96%, 97%, 98%, or 99% identical to SEQ ID NO: 203 (P690). In some embodiments the TGFβ superfamily ligand binding agent is a homodimeric polypeptide, wherein each polypeptide chain comprises or consists of the amino acid sequence of SEQ ID NO: 203 (P690).

In some embodiments, the TGFβ superfamily ligand binding agent is a homodimeric polypeptide, wherein each polypeptide chain comprises from N-terminus to C-terminus, an ActRIIB ECD comprising the amino acid substitution of F58Y, a peptide linker that is 3aa in length, and an IgG1 Fc domain monomer. In some embodiments, the TGFβ superfamily ligand binding agent is a homodimeric polypeptide, wherein each polypeptide chain comprises from N-terminus to C-terminus, an ActRIIB ECD comprising an amino acid sequence that is at least 95%, 96%, 97%, 98%, or 99% identical to SEQ ID NO: 7, a peptide linker that is 3aa in length, and an IgG1 Fc-DL Fc domain monomer. In some embodiments, the TGFβ superfamily ligand binding agent is a homodimeric polypeptide, wherein each polypeptide chain comprises from N-terminus to C-terminus, an ActRIIB ECD comprising or consisting of the amino acid sequence of SEQ ID NO: 7, a peptide linker that is 3aa in length, and an IgG1 Fc-DL Fc domain monomer. In some embodiments the TGFβ superfamily ligand binding agent is a homodimeric polypeptide, wherein each polypeptide chain comprises an amino acid sequence that is at least 95%, 96%, 97%, 98%, or 99% identical to SEQ ID NO: 204 (P691). In some embodiments the TGFβ superfamily ligand binding agent is a homodimeric polypeptide, wherein each polypeptide chain comprises or consists of the amino acid sequence of SEQ ID NO: 204 (P691).

In some embodiments, the TGFβ superfamily ligand binding agent is a homodimeric polypeptide, wherein each polypeptide chain comprises from N-terminus to C-terminus, an ActRIIB ECD comprising the amino acid substitution of F58Y, a peptide linker that is 3aa in length, and an IgG2 Fc domain monomer. In some embodiments, the TGFβ superfamily ligand binding agent is a homodimeric polypeptide, wherein each polypeptide chain comprises from N-terminus to C-terminus, an ActRIIB ECD comprising an amino acid sequence that is at least 95%, 96%, 97%, 98%, or 99% identical to SEQ ID NO: 7, a peptide linker that is 3aa in length, and an IgG2 Fc domain monomer of SEQ ID NO: 157. In some embodiments, the TGFβ superfamily ligand binding agent is a homodimeric polypeptide, wherein each polypeptide chain comprises from N-terminus to C-terminus, an ActRIIB ECD comprising or consisting of the amino acid sequence of SEQ ID NO: 7, a peptide linker that is 3aa in length, and an IgG2 Fc domain monomer of SEQ ID NO: 157. In some embodiments the TGFβ superfamily ligand binding agent is a homodimeric polypeptide, wherein each polypeptide chain comprises an amino acid sequence that is at least 95%, 96%, 97%, 98%, or 99% identical to SEQ ID NO: 205 (P692). In some embodiments the TGFβ superfamily ligand binding agent is a homodimeric polypeptide, wherein each polypeptide chain comprises or consists of the amino acid sequence of SEQ ID NO: 205 (P692).

In some embodiments, the TGFβ superfamily ligand binding agent is a homodimeric polypeptide, wherein each polypeptide chain comprises from N-terminus to C-terminus, an ActRIIB ECD comprising the amino acid substitution of F58Y, a peptide linker that is 14aa in length, and an IgG1 Fc domain monomer. In some embodiments, the TGFβ superfamily ligand binding agent is a homodimeric polypeptide, wherein each polypeptide chain comprises from N-terminus to C-terminus, an ActRIIB ECD comprising an amino acid sequence that is at least 95%, 96%, 97%, 98%, or 99% identical to SEQ ID NO: 7, a peptide linker that is 14aa in length, and an IgG1 Fc-EM Fc domain monomer. In some embodiments, the TGFβ superfamily ligand binding agent is a homodimeric polypeptide, wherein each polypeptide chain comprises from N-terminus to C-terminus, an ActRIIB ECD comprising or consisting of the amino acid sequence of SEQ ID NO: 7, a peptide linker that is 14aa in length, and an IgG1 Fc-EM Fc domain monomer. In some embodiments the TGFβ superfamily ligand binding agent is a homodimeric polypeptide, wherein each polypeptide chain comprises an amino acid sequence that is at least 95%, 96%, 97%, 98%, or 99% identical to SEQ ID NO: 206 (P693). In some embodiments the TGFβ superfamily ligand binding agent is a homodimeric polypeptide, wherein each polypeptide chain comprises or consists of the amino acid sequence of SEQ ID NO: 206 (P693).

In some embodiments, the TGFβ superfamily ligand binding agent is a homodimeric polypeptide, wherein each polypeptide chain comprises from N-terminus to C-terminus, an ActRIIB ECD comprising the amino acid substitution of F58Y, a peptide linker that is 14aa in length, and an IgG1 Fc domain monomer. In some embodiments, the TGFβ superfamily ligand binding agent is a homodimeric polypeptide, wherein each polypeptide chain comprises from N-terminus to C-terminus, an ActRIIB ECD comprising an amino acid sequence that is at least 95%, 96%, 97%, 98%, or 99% identical to SEQ ID NO: 7, a peptide linker that is 14aa in length, and an IgG1 Fc-DL Fc domain monomer. In some embodiments, the TGFβ superfamily ligand binding agent is a homodimeric polypeptide, wherein each polypeptide chain comprises from N-terminus to C-terminus, an ActRIIB ECD comprising or consisting of the amino acid sequence of SEQ ID NO: 7, a peptide linker that is 14aa in length, and an IgG1 Fc-DL Fc domain monomer. In some embodiments the TGFβ superfamily ligand binding agent is a homodimeric polypeptide, wherein each polypeptide chain comprises an amino acid sequence that is at least 95%, 96%, 97%, 98%, or 99% identical to SEQ ID NO: 207 (P694). In some embodiments the TGFβ superfamily ligand binding agent is a homodimeric polypeptide, wherein each polypeptide chain comprises or consists of the amino acid sequence of SEQ ID NO: 207 (P694).

In some embodiments, the TGFβ superfamily ligand binding agent is a homodimeric polypeptide, wherein each polypeptide chain comprises from N-terminus to C-terminus, an ActRIIB ECD comprising the amino acid substitution of F58Y, a peptide linker that is 39aa in length, and an IgG1 Fc domain monomer. In some embodiments, the TGFβ superfamily ligand binding agent is a homodimeric polypeptide, wherein each polypeptide chain comprises from N-terminus to C-terminus, an ActRIIB ECD comprising an amino acid sequence that is at least 95%, 96%, 97%, 98%, or 99% identical to SEQ ID NO: 7, a peptide linker that is 39aa in length, and an IgG1 Fc-DL Fc domain monomer. In some embodiments, the TGFβ superfamily ligand binding agent is a homodimeric polypeptide, wherein each polypeptide chain comprises from N-terminus to C-terminus, an ActRIIB ECD comprising or consisting of the amino acid sequence of SEQ ID NO: 7, a peptide linker that is 39aa in length, and an IgG1 Fc-DL Fc domain monomer. In some embodiments the TGFβ superfamily ligand binding agent is a homodimeric polypeptide, wherein each polypeptide chain comprises an amino acid sequence that is at least 95%, 96%, 97%, 98%, or 99% identical to SEQ ID NO: 208 (P695). In some embodiments the TGFβ superfamily ligand binding agent is a homodimeric polypeptide, wherein each polypeptide chain comprises or consists of the amino acid sequence of SEQ ID NO: 208 (P695).

In some embodiments, the TGFβ superfamily ligand binding agent is a homodimeric polypeptide, wherein each polypeptide chain comprises from N-terminus to C-terminus, an ActRIIB ECD comprising the amino acid substitution of F58Y, a peptide linker that is 39aa in length, and an IgG2 Fc domain monomer. In some embodiments, the TGFβ superfamily ligand binding agent is a homodimeric polypeptide, wherein each polypeptide chain comprises from N-terminus to C-terminus, an ActRIIB ECD comprising an amino acid sequence that is at least 95%, 96%, 97%, 98%, or 99% identical to SEQ ID NO: 7, a peptide linker that is 39aa in length, and an IgG2 Fc domain monomer of SEQ ID NO: 157. In some embodiments, the TGFβ superfamily ligand binding agent is a homodimeric polypeptide, wherein each polypeptide chain comprises from N-terminus to C-terminus, an ActRIIB ECD comprising or consisting of the amino acid sequence of SEQ ID NO: 7, a peptide linker that is 39aa in length, and an IgG2 Fc domain monomer of SEQ ID NO: 157. In some embodiments the TGFβ superfamily ligand binding agent is a homodimeric polypeptide, wherein each polypeptide chain comprises an amino acid sequence that is at least 95%, 96%, 97%, 98%, or 99% identical to SEQ ID NO: 209 (P696). In some embodiments the TGFβ superfamily ligand binding agent is a homodimeric polypeptide, wherein each polypeptide chain comprises or consists of the amino acid sequence of SEQ ID NO: 209 (P696).

In some embodiments, the TGFβ superfamily ligand binding agent is a homodimeric polypeptide, wherein each polypeptide chain comprises from N-terminus to C-terminus, an ActRIIB ECD comprising the amino acid substitution of F58K, a peptide linker that is 3aa in length, and an IgG1 Fc domain monomer. In some embodiments, the TGFβ superfamily ligand binding agent is a homodimeric polypeptide, wherein each polypeptide chain comprises from N-terminus to C-terminus, an ActRIIB ECD comprising an amino acid sequence that is at least 95%, 96%, 97%, 98%, or 99% identical to SEQ ID NO: 8, a peptide linker that is 3aa in length, and an IgG1 Fc-EM Fc domain monomer. In some embodiments, the TGFβ superfamily ligand binding agent is a homodimeric polypeptide, wherein each polypeptide chain comprises from N-terminus to C-terminus, an ActRIIB ECD comprising or consisting of the amino acid sequence of SEQ ID NO: 8, a peptide linker that is 3aa in length, and an IgG1 Fc-EM Fc domain monomer. In some embodiments the TGFβ superfamily ligand binding agent is a homodimeric polypeptide, wherein each polypeptide chain comprises an amino acid sequence that is at least 95%, 96%, 97%, 98%, or 99% identical to SEQ ID NO: 210 (P697). In some embodiments the TGFβ superfamily ligand binding agent is a homodimeric polypeptide, wherein each polypeptide chain comprises or consists of the amino acid sequence of SEQ ID NO: 210 (P697).

In some embodiments, the TGFβ superfamily ligand binding agent is a homodimeric polypeptide, wherein each polypeptide chain comprises from N-terminus to C-terminus, an ActRIIB ECD comprising the amino acid substitution of F58K, a peptide linker that is 3aa in length, and an IgG1 Fc domain monomer. In some embodiments, the TGFβ superfamily ligand binding agent is a homodimeric polypeptide, wherein each polypeptide chain comprises from N-terminus to C-terminus, an ActRIIB ECD comprising an amino acid sequence that is at least 95%, 96%, 97%, 98%, or 99% identical to SEQ ID NO: 8, a peptide linker that is 3aa in length, and an IgG1 Fc-DL Fc domain monomer. In some embodiments, the TGFβ superfamily ligand binding agent is a homodimeric polypeptide, wherein each polypeptide chain comprises from N-terminus to C-terminus, an ActRIIB ECD comprising or consisting of the amino acid sequence of SEQ ID NO: 8, a peptide linker that is 3aa in length, and an IgG1 Fc-DL Fc domain monomer. In some embodiments the TGFβ superfamily ligand binding agent is a homodimeric polypeptide, wherein each polypeptide chain comprises an amino acid sequence that is at least 95%, 96%, 97%, 98%, or 99% identical to SEQ ID NO: 211 (P698). In some embodiments the TGFβ superfamily ligand binding agent is a homodimeric polypeptide, wherein each polypeptide chain comprises or consists of the amino acid sequence of SEQ ID NO: 211 (P698).

In some embodiments, the TGFβ superfamily ligand binding agent is a homodimeric polypeptide, wherein each polypeptide chain comprises from N-terminus to C-terminus, an ActRIIB ECD comprising the amino acid substitution of F58K, a peptide linker that is 3aa in length, and an IgG2 Fc domain monomer. In some embodiments, the TGFβ superfamily ligand binding agent is a homodimeric polypeptide, wherein each polypeptide chain comprises from N-terminus to C-terminus, an ActRIIB ECD comprising an amino acid sequence that is at least 95%, 96%, 97%, 98%, or 99% identical to SEQ ID NO: 8, a peptide linker that is 3aa in length, and an IgG2 Fc domain monomer of SEQ ID NO: 157. In some embodiments, the TGFβ superfamily ligand binding agent is a homodimeric polypeptide, wherein each polypeptide chain comprises from N-terminus to C-terminus, an ActRIIB ECD comprising or consisting of the amino acid sequence of SEQ ID NO: 8, a peptide linker that is 3aa in length, and an IgG2 Fc domain monomer of SEQ ID NO: 157. In some embodiments the TGFβ superfamily ligand binding agent is a homodimeric polypeptide, wherein each polypeptide chain comprises an amino acid sequence that is at least 95%, 96%, 97%, 98%, or 99% identical to SEQ ID NO: 212 (P699). In some embodiments the TGFβ superfamily ligand binding agent is a homodimeric polypeptide, wherein each polypeptide chain comprises or consists of the amino acid sequence of SEQ ID NO: 212 (P699).

In some embodiments, the TGFβ superfamily ligand binding agent is a homodimeric polypeptide, wherein each polypeptide chain comprises from N-terminus to C-terminus, an ActRIIB ECD comprising the amino acid substitution of F58K, a peptide linker that is 14aa in length, and an IgG1 Fc domain monomer. In some embodiments, the TGFβ superfamily ligand binding agent is a homodimeric polypeptide, wherein each polypeptide chain comprises from N-terminus to C-terminus, an ActRIIB ECD comprising an amino acid sequence that is at least 95%, 96%, 97%, 98%, or 99% identical to SEQ ID NO: 8, a peptide linker that is 14aa in length, and an IgG1 Fc-EM Fc domain monomer. In some embodiments, the TGFβ superfamily ligand binding agent is a homodimeric polypeptide, wherein each polypeptide chain comprises from N-terminus to C-terminus, an ActRIIB ECD comprising or consisting of the amino acid sequence of SEQ ID NO: 8, a peptide linker that is 14aa in length, and an IgG1 Fc-EM Fc domain monomer. In some embodiments the TGFβ superfamily ligand binding agent is a homodimeric polypeptide, wherein each polypeptide chain comprises an amino acid sequence that is at least 95%, 96%, 97%, 98%, or 99% identical to SEQ ID NO: 213 (P700). In some embodiments the TGFβ superfamily ligand binding agent is a homodimeric polypeptide, wherein each polypeptide chain comprises or consists of the amino acid sequence of SEQ ID NO: 213 (P700).

In some embodiments, the TGFβ superfamily ligand binding agent is a homodimeric polypeptide, wherein each polypeptide chain comprises from N-terminus to C-terminus, an ActRIIB ECD comprising the amino acid substitution of F58K, a peptide linker that is 14aa in length, and an IgG1 Fc domain monomer. In some embodiments, the TGFβ superfamily ligand binding agent is a homodimeric polypeptide, wherein each polypeptide chain comprises from N-terminus to C-terminus, an ActRIIB ECD comprising an amino acid sequence that is at least 95%, 96%, 97%, 98%, or 99% identical to SEQ ID NO: 8, a peptide linker that is 14aa in length, and an IgG1 Fc-DL Fc domain monomer. In some embodiments, the TGFβ superfamily ligand binding agent is a homodimeric polypeptide, wherein each polypeptide chain comprises from N-terminus to C-terminus, an ActRIIB ECD comprising or consisting of the amino acid sequence of SEQ ID NO: 8, a peptide linker that is 14aa in length, and an IgG1 Fc-DL Fc domain monomer. In some embodiments the TGFβ superfamily ligand binding agent is a homodimeric polypeptide, wherein each polypeptide chain comprises an amino acid sequence that is at least 95%, 96%, 97%, 98%, or 99% identical to SEQ ID NO: 214 (P701). In some embodiments the TGFβ superfamily ligand binding agent is a homodimeric polypeptide, wherein each polypeptide chain comprises or consists of the amino acid sequence of SEQ ID NO: 214 (P701).

In some embodiments, the TGFβ superfamily ligand binding agent is a homodimeric polypeptide, wherein each polypeptide chain comprises from N-terminus to C-terminus, an ActRIIB ECD comprising the amino acid substitution of F58K, a peptide linker that is 39aa in length, and an IgG1 Fc domain monomer. In some embodiments, the TGFβ superfamily ligand binding agent is a homodimeric polypeptide, wherein each polypeptide chain comprises from N-terminus to C-terminus, an ActRIIB ECD comprising an amino acid sequence that is at least 95%, 96%, 97%, 98%, or 99% identical to SEQ ID NO: 8, a peptide linker that is 39aa in length, and an IgG1 Fc-DL Fc domain monomer. In some embodiments, the TGFβ superfamily ligand binding agent is a homodimeric polypeptide, wherein each polypeptide chain comprises from N-terminus to C-terminus, an ActRIIB ECD comprising or consisting of the amino acid sequence of SEQ ID NO: 8, a peptide linker that is 39aa in length, and an IgG1 Fc-DL Fc domain monomer. In some embodiments the TGFβ superfamily ligand binding agent is a homodimeric polypeptide, wherein each polypeptide chain comprises an amino acid sequence that is at least 95%, 96%, 97%, 98%, or 99% identical to SEQ ID NO: 215 (P702). In some embodiments the TGFβ superfamily ligand binding agent is a homodimeric polypeptide, wherein each polypeptide chain comprises or consists of the amino acid sequence of SEQ ID NO: 215 (P702).

In some embodiments, the TGFβ superfamily ligand binding agent is a homodimeric polypeptide, wherein each polypeptide chain comprises from N-terminus to C-terminus, an ActRIIB ECD comprising the amino acid substitution of F58K, a peptide linker that is 39aa in length, and an IgG2 Fc domain. In some embodiments, the TGFβ superfamily ligand binding agent is a homodimeric polypeptide, wherein each polypeptide chain comprises from N-terminus to C-terminus, an ActRIIB ECD comprising an amino acid sequence that is at least 95%, 96%, 97%, 98%, or 99% identical to SEQ ID NO: 8, a peptide linker that is 39aa in length, and an IgG2 Fc domain monomer of SEQ ID NO: 157. In some embodiments, the TGFβ superfamily ligand binding agent is a homodimeric polypeptide, wherein each polypeptide chain comprises from N-terminus to C-terminus, an ActRIIB ECD comprising or consisting of the amino acid sequence of SEQ ID NO: 8, a peptide linker that is 39aa in length, and an IgG2 Fc domain monomer of SEQ ID NO: 157. In some embodiments the TGFβ superfamily ligand binding agent is a homodimeric polypeptide, wherein each polypeptide chain comprises an amino acid sequence that is at least 95%, 96%, 97%, 98%, or 99% identical to SEQ ID NO: 216 (P703). In some embodiments the TGFβ superfamily ligand binding agent is a homodimeric polypeptide, wherein each polypeptide chain comprises or consists of the amino acid sequence of SEQ ID NO: 216 (P703).

In some embodiments, the TGFβ superfamily ligand binding agent is a homodimeric polypeptide, wherein each polypeptide chain comprises from N-terminus to C-terminus, an ActRIIB ECD comprising the amino acid substitution of F58Q, a peptide linker that is 3aa in length, and an IgG1 Fc domain monomer. In some embodiments, the TGFβ superfamily ligand binding agent is a homodimeric polypeptide, wherein each polypeptide chain comprises from N-terminus to C-terminus, an ActRIIB ECD comprising an amino acid sequence that is at least 95%, 96%, 97%, 98%, or 99% identical to SEQ ID NO: 9, a peptide linker that is 3aa in length, and an IgG1 Fc-EM Fc domain monomer. In some embodiments, the TGFβ superfamily ligand binding agent is a homodimeric polypeptide, wherein each polypeptide chain comprises from N-terminus to C-terminus, an ActRIIB ECD comprising or consisting of the amino acid sequence of SEQ ID NO: 9, a peptide linker that is 3aa in length, and an IgG1 Fc-EM Fc domain monomer. In some embodiments the TGFβ superfamily ligand binding agent is a homodimeric polypeptide, wherein each polypeptide chain comprises an amino acid sequence that is at least 95%, 96%, 97%, 98%, or 99% identical to SEQ ID NO: 217 (P704). In some embodiments the TGFβ superfamily ligand binding agent is a homodimeric polypeptide, wherein each polypeptide chain comprises or consists of the amino acid sequence of SEQ ID NO: 217 (P704).

In some embodiments, the TGFβ superfamily ligand binding agent is a homodimeric polypeptide, wherein each polypeptide chain comprises from N-terminus to C-terminus, an ActRIIB ECD comprising the amino acid substitution of F58Q, a peptide linker that is 3aa in length, and an IgG1 Fc domain monomer. In some embodiments, the TGFβ superfamily ligand binding agent is a homodimeric polypeptide, wherein each polypeptide chain comprises from N-terminus to C-terminus, an ActRIIB ECD comprising an amino acid sequence that is at least 95%, 96%, 97%, 98%, or 99% identical to SEQ ID NO: 9, a peptide linker that is 3aa in length, and an IgG1 Fc-DL Fc domain monomer. In some embodiments, the TGFβ superfamily ligand binding agent is a homodimeric polypeptide, wherein each polypeptide chain comprises from N-terminus to C-terminus, an ActRIIB ECD comprising or consisting of the amino acid sequence of SEQ ID NO: 9, a peptide linker that is 3aa in length, and an IgG1 Fc-DL Fc domain monomer. In some embodiments the TGFβ superfamily ligand binding agent is a homodimeric polypeptide, wherein each polypeptide chain comprises an amino acid sequence that is at least 95%, 96%, 97%, 98%, or 99% identical to SEQ ID NO: 218 (P705). In some embodiments the TGFβ superfamily ligand binding agent is a homodimeric polypeptide, wherein each polypeptide chain comprises or consists of the amino acid sequence of SEQ ID NO: 218 (P705).

In some embodiments, the TGFβ superfamily ligand binding agent is a homodimeric polypeptide, wherein each polypeptide chain comprises from N-terminus to C-terminus, an ActRIIB ECD comprising the amino acid substitution of F58Q, a peptide linker that is 3aa in length, and an IgG2 Fc domain monomer. In some embodiments, the TGFβ superfamily ligand binding agent is a homodimeric polypeptide, wherein each polypeptide chain comprises from N-terminus to C-terminus, an ActRIIB ECD comprising an amino acid sequence that is at least 95%, 96%, 97%, 98%, or 99% identical to SEQ ID NO: 9, a peptide linker that is 3aa in length, and an IgG2 Fc domain monomer of SEQ ID NO: 157. In some embodiments, the TGFβ superfamily ligand binding agent is a homodimeric polypeptide, wherein each polypeptide chain comprises from N-terminus to C-terminus, an ActRIIB ECD comprising or consisting of the amino acid sequence of SEQ ID NO: 9, a peptide linker that is 3aa in length, and an IgG2 Fc domain monomer of SEQ ID NO: 157. In some embodiments the TGFβ superfamily ligand binding agent is a homodimeric polypeptide, wherein each polypeptide chain comprises an amino acid sequence that is at least 95%, 96%, 97%, 98%, or 99% identical to SEQ ID NO: 219 (P706). In some embodiments the TGFβ superfamily ligand binding agent is a homodimeric polypeptide, wherein each polypeptide chain comprises or consists of the amino acid sequence of SEQ ID NO: 219 (P706).

In some embodiments, the TGFβ superfamily ligand binding agent is a homodimeric polypeptide, wherein each polypeptide chain comprises from N-terminus to C-terminus, an ActRIIB ECD comprising the amino acid substitution of F58Q, a peptide linker that is 14aa in length, and an IgG1 Fc domain monomer. In some embodiments, the TGFβ superfamily ligand binding agent is a homodimeric polypeptide, wherein each polypeptide chain comprises from N-terminus to C-terminus, an ActRIIB ECD comprising an amino acid sequence that is at least 95%, 96%, 97%, 98%, or 99% identical to SEQ ID NO: 9, a peptide linker that is 14aa in length, and an IgG1 Fc-EM Fc domain monomer. In some embodiments, the TGFβ superfamily ligand binding agent is a homodimeric polypeptide, wherein each polypeptide chain comprises from N-terminus to C-terminus, an ActRIIB ECD comprising or consisting of the amino acid sequence of SEQ ID NO: 9, a peptide linker that is 14aa in length, and an IgG1 Fc-EM Fc domain monomer. In some embodiments the TGFβ superfamily ligand binding agent is a homodimeric polypeptide, wherein each polypeptide chain comprises an amino acid sequence that is at least 95%, 96%, 97%, 98%, or 99% identical to SEQ ID NO: 220 (P707). In some embodiments the TGFβ superfamily ligand binding agent is a homodimeric polypeptide, wherein each polypeptide chain comprises or consists of the amino acid sequence of SEQ ID NO: 220 (P707).

In some embodiments, the TGFβ superfamily ligand binding agent is a homodimeric polypeptide, wherein each polypeptide chain comprises from N-terminus to C-terminus, an ActRIIB ECD comprising the amino acid substitution of F58Q, a peptide linker that is 14aa in length, and an IgG1 Fc domain monomer. In some embodiments, the TGFβ superfamily ligand binding agent is a homodimeric polypeptide, wherein each polypeptide chain comprises from N-terminus to C-terminus, an ActRIIB ECD comprising an amino acid sequence that is at least 95%, 96%, 97%, 98%, or 99% identical to SEQ ID NO: 9, a peptide linker that is 14aa in length, and an IgG1 Fc-DL Fc domain monomer. In some embodiments, the TGFβ superfamily ligand binding agent is a homodimeric polypeptide, wherein each polypeptide chain comprises from N-terminus to C-terminus, an ActRIIB ECD comprising or consisting of the amino acid sequence of SEQ ID NO: 9, a peptide linker that is 14aa in length, and an IgG1 Fc-DL Fc domain monomer. In some embodiments the TGFβ superfamily ligand binding agent is a homodimeric polypeptide, wherein each polypeptide chain comprises an amino acid sequence that is at least 95%, 96%, 97%, 98%, or 99% identical to SEQ ID NO: 221 (P708). In some embodiments the TGFβ superfamily ligand binding agent is a homodimeric polypeptide, wherein each polypeptide chain comprises or consists of the amino acid sequence of SEQ ID NO: 221 (P708).

In some embodiments, the TGFβ superfamily ligand binding agent is a homodimeric polypeptide, wherein each polypeptide chain comprises from N-terminus to C-terminus, an ActRIIB ECD comprising the amino acid substitution of F58Q, a peptide linker that is 39aa in length, and an IgG1 Fc domain monomer. In some embodiments, the TGFβ superfamily ligand binding agent is a homodimeric polypeptide, wherein each polypeptide chain comprises from N-terminus to C-terminus, an ActRIIB ECD comprising an amino acid sequence that is at least 95%, 96%, 97%, 98%, or 99% identical to SEQ ID NO: 9, a peptide linker that is 39aa in length, and an IgG1 Fc-DL Fc domain monomer. In some embodiments, the TGFβ superfamily ligand binding agent is a homodimeric polypeptide, wherein each polypeptide chain comprises from N-terminus to C-terminus, an ActRIIB ECD comprising or consisting of the amino acid sequence of SEQ ID NO: 9, a peptide linker that is 39aa in length, and an IgG1 Fc-DL Fe domain monomer. In some embodiments the TGFβ superfamily ligand binding agent is a homodimeric polypeptide, wherein each polypeptide chain comprises an amino acid sequence that is at least 95%, 96%, 97%, 98%, or 99% identical to SEQ ID NO: 222 (P709). In some embodiments the TGFβ superfamily ligand binding agent is a homodimeric polypeptide, wherein each polypeptide chain comprises or consists of the amino acid sequence of SEQ ID NO: 222 (P709).

In some embodiments, the TGFβ superfamily ligand binding agent is a homodimeric polypeptide, wherein each polypeptide chain comprises from N-terminus to C-terminus, an ActRIIB ECD comprising the amino acid substitution of F58Q, a peptide linker that is 39aa in length, and an IgG2 Fc domain monomer. In some embodiments, the TGFβ superfamily ligand binding agent is a homodimeric polypeptide, wherein each polypeptide chain comprises from N-terminus to C-terminus, an ActRIIB ECD comprising an amino acid sequence that is at least 95%, 96%, 97%, 98%, or 99% identical to SEQ ID NO: 9, a peptide linker that is 39aa in length, and an IgG2 Fc domain monomer of SEQ ID NO: 157. In some embodiments, the TGFβ superfamily ligand binding agent is a homodimeric polypeptide, wherein each polypeptide chain comprises from N-terminus to C-terminus, an ActRIIB ECD comprising or consisting of the amino acid sequence of SEQ ID NO: 9, a peptide linker that is 39aa in length, and an IgG2 Fc domain monomer of SEQ ID NO: 157. In some embodiments the TGFβ superfamily ligand binding agent is a homodimeric polypeptide, wherein each polypeptide chain comprises an amino acid sequence that is at least 95%, 96%, 97%, 98%, or 99% identical to SEQ ID NO: 223 (P710). In some embodiments the TGFβ superfamily ligand binding agent is a homodimeric polypeptide, wherein each polypeptide chain comprises or consists of the amino acid sequence of SEQ ID NO: 223 (P710).

In some embodiments, the TGFβ superfamily ligand binding agent is a homodimeric polypeptide, wherein each polypeptide chain comprises from N-terminus to C-terminus, an ActRIIB ECD comprising the amino acid substitution of F58W, a peptide linker that is 3aa in length, and an IgG1 Fc domain monomer. In some embodiments, the TGFβ superfamily ligand binding agent is a homodimeric polypeptide, wherein each polypeptide chain comprises from N-terminus to C-terminus, an ActRIIB ECD comprising an amino acid sequence that is at least 95%, 96%, 97%, 98%, or 99% identical to SEQ ID NO: 10, a peptide linker that is 3aa in length, and an IgG1 Fc-EM Fc domain monomer. In some embodiments, the TGFβ superfamily ligand binding agent is a homodimeric polypeptide, wherein each polypeptide chain comprises from N-terminus to C-terminus, an ActRIIB ECD comprising or consisting of the amino acid sequence of SEQ ID NO: 10, a peptide linker that is 3aa in length, and an IgG1 Fc-EM Fc domain monomer. In some embodiments the TGFβ superfamily ligand binding agent is a homodimeric polypeptide, wherein each polypeptide chain comprises an amino acid sequence that is at least 95%, 96%, 97%, 98%, or 99% identical to SEQ ID NO: 224 (P711). In some embodiments the TGFβ superfamily ligand binding agent is a homodimeric polypeptide, wherein each polypeptide chain comprises or consists of the amino acid sequence of SEQ ID NO: 224 (P711).

In some embodiments, the TGFβ superfamily ligand binding agent is a homodimeric polypeptide, wherein each polypeptide chain comprises from N-terminus to C-terminus, an ActRIIB ECD comprising the amino acid substitution of F58W, a peptide linker that is 3aa in length, and an IgG1 Fc domain monomer. In some embodiments, the TGFβ superfamily ligand binding agent is a homodimeric polypeptide, wherein each polypeptide chain comprises from N-terminus to C-terminus, an ActRIIB ECD comprising an amino acid sequence that is at least 95%, 96%, 97%, 98%, or 99% identical to SEQ ID NO: 10, a peptide linker that is 3aa in length, and an IgG1 Fc-DL Fc domain monomer. In some embodiments, the TGFβ superfamily ligand binding agent is a homodimeric polypeptide, wherein each polypeptide chain comprises from N-terminus to C-terminus, an ActRIIB ECD comprising or consisting of the amino acid sequence of SEQ ID NO: 10, a peptide linker that is 3aa in length, and an IgG1 Fc-DL Fc domain monomer. In some embodiments the TGFβ superfamily ligand binding agent is a homodimeric polypeptide, wherein each polypeptide chain comprises an amino acid sequence that is at least 95%, 96%, 97%, 98%, or 99% identical to SEQ ID NO: 225 (P712). In some embodiments the TGFβ superfamily ligand binding agent is a homodimeric polypeptide, wherein each polypeptide chain comprises or consists of the amino acid sequence of SEQ ID NO: 225 (P712).

In some embodiments, the TGFβ superfamily ligand binding agent is a homodimeric polypeptide, wherein each polypeptide chain comprises from N-terminus to C-terminus, an ActRIIB ECD comprising the amino acid substitution of F58W, a peptide linker that is 3aa in length, and an IgG2 Fc domain monomer. In some embodiments, the TGFβ superfamily ligand binding agent is a homodimeric polypeptide, wherein each polypeptide chain comprises from N-terminus to C-terminus, an ActRIIB ECD comprising an amino acid sequence that is at least 95%, 96%, 97%, 98%, or 99% identical to SEQ ID NO: 10, a peptide linker that is 3aa in length, and an IgG2 Fc domain monomer of SEQ ID NO: 157. In some embodiments, the TGFβ superfamily ligand binding agent is a homodimeric polypeptide, wherein each polypeptide chain comprises from N-terminus to C-terminus, an ActRIIB ECD comprising or consisting of the amino acid sequence of SEQ ID NO: 10, a peptide linker that is 3aa in length, and an IgG2 Fc domain monomer of SEQ ID NO: 157. In some embodiments the TGFβ superfamily ligand binding agent is a homodimeric polypeptide, wherein each polypeptide chain comprises an amino acid sequence that is at least 95%, 96%, 97%, 98%, or 99% identical to SEQ ID NO: 226 (P713). In some embodiments the TGFβ superfamily ligand binding agent is a homodimeric polypeptide, wherein each polypeptide chain comprises or consists of the amino acid sequence of SEQ ID NO: 226 (P713).

In some embodiments, the TGFβ superfamily ligand binding agent is a homodimeric polypeptide, wherein each polypeptide chain comprises from N-terminus to C-terminus, an ActRIIB ECD comprising the amino acid substitution of F58W, a peptide linker that is 14aa in length, and an IgG1 Fc domain monomer. In some embodiments, the TGFβ superfamily ligand binding agent is a homodimeric polypeptide, wherein each polypeptide chain comprises from N-terminus to C-terminus, an ActRIIB ECD comprising an amino acid sequence that is at least 95%, 96%, 97%, 98%, or 99% identical to SEQ ID NO: 10, a peptide linker that is 14aa in length, and an IgG1 Fc-EM Fc domain monomer. In some embodiments, the TGFβ superfamily ligand binding agent is a homodimeric polypeptide, wherein each polypeptide chain comprises from N-terminus to C-terminus, an ActRIIB ECD comprising or consisting of the amino acid sequence of SEQ ID NO: 10, a peptide linker that is 14aa in length, and an IgG1 Fc-EM Fc domain monomer. In some embodiments the TGFβ superfamily ligand binding agent is a homodimeric polypeptide, wherein each polypeptide chain comprises an amino acid sequence that is at least 95%, 96%, 97%, 98%, or 99% identical to SEQ ID NO: 227 (P714). In some embodiments the TGFβ superfamily ligand binding agent is a homodimeric polypeptide, wherein each polypeptide chain comprises or consists of the amino acid sequence of SEQ ID NO: 227 (P714).

In some embodiments, the TGFβ superfamily ligand binding agent is a homodimeric polypeptide, wherein each polypeptide chain comprises from N-terminus to C-terminus, an ActRIIB ECD comprising the amino acid substitution of F58W, a peptide linker that is 14aa in length, and an IgG1 Fc domain monomer. In some embodiments, the TGFβ superfamily ligand binding agent is a homodimeric polypeptide, wherein each polypeptide chain comprises from N-terminus to C-terminus, an ActRIIB ECD comprising an amino acid sequence that is at least 95%, 96%, 97%, 98%, or 99% identical to SEQ ID NO: 10, a peptide linker that is 14aa in length, and an IgG1 Fc-DL Fc domain monomer. In some embodiments, the TGFβ superfamily ligand binding agent is a homodimeric polypeptide, wherein each polypeptide chain comprises from N-terminus to C-terminus, an ActRIIB ECD comprising or consisting of the amino acid sequence of SEQ ID NO: 10, a peptide linker that is 14aa in length, and an IgG1 Fc-DL Fc domain monomer. In some embodiments the TGFβ superfamily ligand binding agent is a homodimeric polypeptide, wherein each polypeptide chain comprises an amino acid sequence that is at least 95%, 96%, 97%, 98%, or 99% identical to SEQ ID NO: 228 (P715). In some embodiments the TGFβ superfamily ligand binding agent is a homodimeric polypeptide, wherein each polypeptide chain comprises or consists of the amino acid sequence of SEQ ID NO: 228 (P715).

In some embodiments, the TGFβ superfamily ligand binding agent is a homodimeric polypeptide, wherein each polypeptide chain comprises from N-terminus to C-terminus, an ActRIIB ECD comprising the amino acid substitution of F58W, a peptide linker that is 39aa in length, and an IgG1 Fc domain monomer. In some embodiments, the TGFβ superfamily ligand binding agent is a homodimeric polypeptide, wherein each polypeptide chain comprises from N-terminus to C-terminus, an ActRIIB ECD comprising an amino acid sequence that is at least 95%, 96%, 97%, 98%, or 99% identical to SEQ ID NO: 10, a peptide linker that is 39aa in length, and an IgG1 Fc-DL Fc domain monomer. In some embodiments, the TGFβ superfamily ligand binding agent is a homodimeric polypeptide, wherein each polypeptide chain comprises from N-terminus to C-terminus, an ActRIIB ECD comprising or consisting of the amino acid sequence of SEQ ID NO: 10, a peptide linker that is 39aa in length, and an IgG1 Fc-DL Fc domain monomer. In some embodiments the TGFβ superfamily ligand binding agent is a homodimeric polypeptide, wherein each polypeptide chain comprises an amino acid sequence that is at least 95%, 96%, 97%, 98%, or 99% identical to SEQ ID NO: 229 (P716). In some embodiments the TGFβ superfamily ligand binding agent is a homodimeric polypeptide, wherein each polypeptide chain comprises or consists of the amino acid sequence of SEQ ID NO: 229 (P716).

In some embodiments, the TGFβ superfamily ligand binding agent is a homodimeric polypeptide, wherein each polypeptide chain comprises from N-terminus to C-terminus, an ActRIIB ECD comprising the amino acid substitution of F58W, a peptide linker that is 39aa in length, and an IgG2 Fc domain monomer. In some embodiments, the TGFβ superfamily ligand binding agent is a homodimeric polypeptide, wherein each polypeptide chain comprises from N-terminus to C-terminus, an ActRIIB ECD comprising an amino acid sequence that is at least 95%, 96%, 97%, 98%, or 99% identical to SEQ ID NO: 10, a peptide linker that is 39aa in length, and an IgG2 Fc domain monomer of SEQ ID NO: 157. In some embodiments, the TGFβ superfamily ligand binding agent is a homodimeric polypeptide, wherein each polypeptide chain comprises from N-terminus to C-terminus, an ActRIIB ECD comprising or consisting of the amino acid sequence of SEQ ID NO: 10, a peptide linker that is 39aa in length, and an IgG2 Fc domain monomer of SEQ ID NO: 157. In some embodiments the TGFβ superfamily ligand binding agent is a homodimeric polypeptide, wherein each polypeptide chain comprises an amino acid sequence that is at least 95%, 96%, 97%, 98%, or 99% identical to SEQ ID NO: 230 (P717). In some embodiments the TGFβ superfamily ligand binding agent is a homodimeric polypeptide, wherein each polypeptide chain comprises or consists of the amino acid sequence of SEQ ID NO: 230 (P717).

In some embodiments, the TGFβ superfamily ligand binding agent is a homodimeric polypeptide, wherein each polypeptide chain comprises from N-terminus to C-terminus, an ActRIIB ECD comprising the amino acid substitution of G27D, a peptide linker that is 14aa in length, and an IgG1 Fc domain monomer. In some embodiments, the TGFβ superfamily ligand binding agent is a homodimeric polypeptide, wherein each polypeptide chain comprises from N-terminus to C-terminus, an ActRIIB ECD comprising an amino acid sequence that is at least 95%, 96%, 97%, 98%, or 99% identical to SEQ ID NO: 20, a peptide linker that is 14aa in length, and an IgG1 FcDL Fc domain monomer. In some embodiments, the TGFβ superfamily ligand binding agent is a homodimeric polypeptide, wherein each polypeptide chain comprises from N-terminus to C-terminus, an ActRIIB ECD comprising or consisting of the amino acid sequence of SEQ ID NO: 10, a peptide linker that is 14aa in length, and an IgG1 FcDL Fc domain monomer. In some embodiments the TGFβ superfamily ligand binding agent is a homodimeric polypeptide, wherein each polypeptide chain comprises an amino acid sequence that is at least 95%, 96%, 97%, 98%, or 99% identical to SEQ ID NO: 240 (P758). In some embodiments the TGFβ superfamily ligand binding agent is a homodimeric polypeptide, wherein each polypeptide chain comprises or consists of the amino acid sequence of SEQ ID NO: 240 (P758).

In some embodiments, the TGFβ superfamily ligand binding agent is a homodimeric polypeptide, wherein each polypeptide chain comprises from N-terminus to C-terminus, an ActRIIB ECD comprising the amino acid substitution of F58K, a peptide linker that is 6aa in length, and an IgG1 Fc domain monomer. In some embodiments, the TGFβ superfamily ligand binding agent is a homodimeric polypeptide, wherein each polypeptide chain comprises from N-terminus to C-terminus, an ActRIIB ECD comprising an amino acid sequence that is at least 95%, 96%, 97%, 98%, or 99% identical to SEQ ID NO: 8, a peptide linker that is 6aa in length, and an IgG1 FcDL Fc domain monomer. In some embodiments, the TGFβ superfamily ligand binding agent is a homodimeric polypeptide, wherein each polypeptide chain comprises from N-terminus to C-terminus, an ActRIIB ECD comprising or consisting of the amino acid sequence of SEQ ID NO: 8, a peptide linker that is 6aa in length, and an IgG1 FcDL Fc domain monomer. In some embodiments the TGFβ superfamily ligand binding agent is a homodimeric polypeptide, wherein each polypeptide chain comprises an amino acid sequence that is at least 95%, 96%, 97%, 98%, or 99% identical to SEQ ID NO: 241 (P1153). In some embodiments the TGFβ superfamily ligand binding agent is a homodimeric polypeptide, wherein each polypeptide chain comprises or consists of the amino acid sequence of SEQ ID NO: 241 (P1153).

In some embodiments, the TGFβ superfamily ligand binding agent is a homodimeric polypeptide, wherein each polypeptide chain comprises from N-terminus to C-terminus, an ActRIIB ECD comprising the amino acid substitution of F58K, a peptide linker that is 10aa in length, and an IgG1 Fc domain monomer. In some embodiments, the TGFβ superfamily ligand binding agent is a homodimeric polypeptide, wherein each polypeptide chain comprises from N-terminus to C-terminus, an ActRIIB ECD comprising an amino acid sequence that is at least 95%, 96%, 97%, 98%, or 99% identical to SEQ ID NO: 8, a peptide linker that is 10aa in length, and an IgG1 FcDL Fc domain monomer. In some embodiments, the TGFβ superfamily ligand binding agent is a homodimeric polypeptide, wherein each polypeptide chain comprises from N-terminus to C-terminus, an ActRIIB ECD comprising or consisting of the amino acid sequence of SEQ ID NO: 8, a peptide linker that is 10aa in length, and an IgG1 FcDL Fc domain monomer. In some embodiments the TGFβ superfamily ligand binding agent is a homodimeric polypeptide, wherein each polypeptide chain comprises an amino acid sequence that is at least 95%, 96%, 97%, 98%, or 99% identical to SEQ ID NO: 242 (P1154). In some embodiments the TGFβ superfamily ligand binding agent is a homodimeric polypeptide, wherein each polypeptide chain comprises or consists of the amino acid sequence of SEQ ID NO: 242 (P1154).

In some embodiments, the TGFβ superfamily ligand binding agent is a homodimeric polypeptide, wherein each polypeptide chain comprises from N-terminus to C-terminus, an ActRIIB ECD comprising the amino acid substitution of F58K, a peptide linker that is 19aa in length, and an IgG1 Fc domain monomer. In some embodiments, the TGFβ superfamily ligand binding agent is a homodimeric polypeptide, wherein each polypeptide chain comprises from N-terminus to C-terminus, an ActRIIB ECD comprising an amino acid sequence that is at least 95%, 96%, 97%, 98%, or 99% identical to SEQ ID NO: 8, a peptide linker that is 19aa in length, and an IgG1 FcDL Fc domain monomer. In some embodiments, the TGFβ superfamily ligand binding agent is a homodimeric polypeptide, wherein each polypeptide chain comprises from N-terminus to C-terminus, an ActRIIB ECD comprising or consisting of the amino acid sequence of SEQ ID NO: 8, a peptide linker that is 19aa in length, and an IgG1 FcDL Fc domain monomer. In some embodiments the TGFβ superfamily ligand binding agent is a homodimeric polypeptide, wherein each polypeptide chain comprises an amino acid sequence that is at least 95%, 96%, 97%, 98%, or 99% identical to SEQ ID NO: 243 (P1155). In some embodiments the TGFβ superfamily ligand binding agent is a homodimeric polypeptide, wherein each polypeptide chain comprises or consists of the amino acid sequence of SEQ ID NO: 243 (P1155).

In some embodiments, the TGFβ superfamily ligand binding agent is a homodimeric polypeptide, wherein each polypeptide chain comprises from N-terminus to C-terminus, an ActRIIB ECD comprising the amino acid substitution of F58K, a peptide linker that is 39aa in length, and an IgG1 Fc domain monomer. In some embodiments, the TGFβ superfamily ligand binding agent is a homodimeric polypeptide, wherein each polypeptide chain comprises from N-terminus to C-terminus, an ActRIIB ECD comprising an amino acid sequence that is at least 95%, 96%, 97%, 98%, or 99% identical to SEQ ID NO: 8, a peptide linker that is 39aa in length, and an IgG1 FcDL Fc domain monomer. In some embodiments, the TGFβ superfamily ligand binding agent is a homodimeric polypeptide, wherein each polypeptide chain comprises from N-terminus to C-terminus, an ActRIIB ECD comprising or consisting of the amino acid sequence of SEQ ID NO: 8, a peptide linker that is 39aa in length, and an IgG1 FcDL Fc domain monomer. In some embodiments the TGFβ superfamily ligand binding agent is a homodimeric polypeptide, wherein each polypeptide chain comprises an amino acid sequence that is at least 95%, 96%, 97%, 98%, or 99% identical to SEQ ID NO: 244 (P1156). In some embodiments the TGFβ superfamily ligand binding agent is a homodimeric polypeptide, wherein each polypeptide chain comprises or consists of the amino acid sequence of SEQ ID NO: 244 (P1156).

In some embodiments, the TGFβ superfamily ligand binding agent is a homodimeric polypeptide, wherein each polypeptide chain comprises from N-terminus to C-terminus, an ActRIIB ECD comprising the amino acid substitution of F58E, a peptide linker that is 6aa in length, and an IgG1 Fc domain monomer. In some embodiments, the TGFβ superfamily ligand binding agent is a homodimeric polypeptide, wherein each polypeptide chain comprises from N-terminus to C-terminus, an ActRIIB ECD comprising an amino acid sequence that is at least 95%, 96%, 97%, 98%, or 99% identical to SEQ ID NO: 5, a peptide linker that is 6aa in length, and an IgG1 FcDL Fc domain monomer. In some embodiments, the TGFβ superfamily ligand binding agent is a homodimeric polypeptide, wherein each polypeptide chain comprises from N-terminus to C-terminus, an ActRIIB ECD comprising or consisting of the amino acid sequence of SEQ ID NO: 5, a peptide linker that is 6aa in length, and an IgG1 FcDL Fc domain monomer. In some embodiments the TGFβ superfamily ligand binding agent is a homodimeric polypeptide, wherein each polypeptide chain comprises an amino acid sequence that is at least 95%, 96%, 97%, 98%, or 99% identical to SEQ ID NO: 246 (P1163). In some embodiments the TGFβ superfamily ligand binding agent is a homodimeric polypeptide, wherein each polypeptide chain comprises or consists of the amino acid sequence of SEQ ID NO: 246 (P1163).

In some embodiments, the TGFβ superfamily ligand binding agent is a homodimeric polypeptide, wherein each polypeptide chain comprises from N-terminus to C-terminus, an ActRIIB ECD comprising the amino acid substitution of F58E, a peptide linker that is 10aa in length, and an IgG1 Fc domain monomer. In some embodiments, the TGFβ superfamily ligand binding agent is a homodimeric polypeptide, wherein each polypeptide chain comprises from N-terminus to C-terminus, an ActRIIB ECD comprising an amino acid sequence that is at least 95%, 96%, 97%, 98%, or 99% identical to SEQ ID NO: 5, a peptide linker that is 10aa in length, and an IgG1 FcDL Fc domain monomer. In some embodiments, the TGFβ superfamily ligand binding agent is a homodimeric polypeptide, wherein each polypeptide chain comprises from N-terminus to C-terminus, an ActRIIB ECD comprising or consisting of the amino acid sequence of SEQ ID NO: 5, a peptide linker that is 10aa in length, and an IgG1 FcDL Fc domain monomer. In some embodiments the TGFβ superfamily ligand binding agent is a homodimeric polypeptide, wherein each polypeptide chain comprises an amino acid sequence that is at least 95%, 96%, 97%, 98%, or 99% identical to SEQ ID NO: 247 (P1164). In some embodiments the TGFβ superfamily ligand binding agent is a homodimeric polypeptide, wherein each polypeptide chain comprises or consists of the amino acid sequence of SEQ ID NO: 247 (P1164).

In some embodiments, the TGFβ superfamily ligand binding agent is a homodimeric polypeptide, wherein each polypeptide chain comprises from N-terminus to C-terminus, an ActRIIB ECD comprising the amino acid substitution of F58E and a C-terminal APT sequence, a peptide linker that is 14aa in length, and an IgG1 Fc domain monomer. In some embodiments, the TGFβ superfamily ligand binding agent is a homodimeric polypeptide, wherein each polypeptide chain comprises from N-terminus to C-terminus, an ActRIIB ECD comprising an amino acid sequence that is at least 95%, 96%, 97%, 98%, or 99% identical to SEQ ID NO: 5 and a C-terminal APT sequence, a peptide linker that is 14aa in length, and an IgG1 FcDL Fc domain monomer. In some embodiments, the TGFβ superfamily ligand binding agent is a homodimeric polypeptide, wherein each polypeptide chain comprises from N-terminus to C-terminus, an ActRIIB ECD comprising or consisting of the amino acid sequence of SEQ ID NO: 5 and a C-terminal APT sequence, a peptide linker that is 14aa in length, and an IgG1 FcDL Fc domain monomer. In some embodiments the TGFβ superfamily ligand binding agent is a homodimeric polypeptide, wherein each polypeptide chain comprises an amino acid sequence that is at least 95%, 96%, 97%, 98%, or 99% identical to SEQ ID NO: 248 (P1168). In some embodiments the TGFβ superfamily ligand binding agent is a homodimeric polypeptide, wherein each polypeptide chain comprises or consists of the amino acid sequence of SEQ ID NO: 248 (P1168).

In some embodiments, the TGFβ superfamily ligand binding agent is a homodimeric polypeptide, wherein each polypeptide chain comprises from N-terminus to C-terminus, an ActRIIB ECD comprising the amino acid substitution of F58N, a peptide linker that is 14aa in length, and an IgG1 Fc domain monomer. In some embodiments, the TGFβ superfamily ligand binding agent is a homodimeric polypeptide, wherein each polypeptide chain comprises from N-terminus to C-terminus, an ActRIIB ECD comprising an amino acid sequence that is at least 95%, 96%, 97%, 98%, or 99% identical to SEQ ID NO: 11, a peptide linker that is 14aa in length, and an IgG1 FcDL Fc domain monomer. In some embodiments, the TGFβ superfamily ligand binding agent is a homodimeric polypeptide, wherein each polypeptide chain comprises from N-terminus to C-terminus, an ActRIIB ECD comprising or consisting of the amino acid sequence of SEQ ID NO: 11, a peptide linker that is 14aa in length, and an IgG1 FcDL Fc domain monomer. In some embodiments the TGFβ superfamily ligand binding agent is a homodimeric polypeptide, wherein each polypeptide chain comprises an amino acid sequence that is at least 95%, 96%, 97%, 98%, or 99% identical to SEQ ID NO: 249 (P1213). In some embodiments the TGFβ superfamily ligand binding agent is a homodimeric polypeptide, wherein each polypeptide chain comprises or consists of the amino acid sequence of SEQ ID NO: 249 (P1213).

In some embodiments, the TGFβ superfamily ligand binding agent is a homodimeric polypeptide, wherein each polypeptide chain comprises from N-terminus to C-terminus, an ActRIIB ECD comprising the amino acid substitution of F58R, a peptide linker that is 14aa in length, and an IgG1 Fc domain monomer. In some embodiments, the TGFβ superfamily ligand binding agent is a homodimeric polypeptide, wherein each polypeptide chain comprises from N-terminus to C-terminus, an ActRIIB ECD comprising an amino acid sequence that is at least 95%, 96%, 97%, 98%, or 99% identical to SEQ ID NO: 12, a peptide linker that is 14aa in length, and an IgG1 FcDL Fc domain monomer. In some embodiments, the TGFβ superfamily ligand binding agent is a homodimeric polypeptide, wherein each polypeptide chain comprises from N-terminus to C-terminus, an ActRIIB ECD comprising or consisting of the amino acid sequence of SEQ ID NO: 12, a peptide linker that is 14aa in length, and an IgG1 FcDL Fc domain monomer. In some embodiments the TGFβ superfamily ligand binding agent is a homodimeric polypeptide, wherein each polypeptide chain comprises an amino acid sequence that is at least 95%, 96%, 97%, 98%, or 99% identical to SEQ ID NO: 250 (P1215). In some embodiments the TGFβ superfamily ligand binding agent is a homodimeric polypeptide, wherein each polypeptide chain comprises or consists of the amino acid sequence of SEQ ID NO: 250 (P1215).

In some embodiments, the TGFβ superfamily ligand binding agent is a homodimeric polypeptide, wherein each polypeptide chain comprises from N-terminus to C-terminus, an ActRIIB ECD comprising the amino acid substitution of F58H, a peptide linker that is 14aa in length, and an IgG1 Fc domain monomer. In some embodiments, the TGFβ superfamily ligand binding agent is a homodimeric polypeptide, wherein each polypeptide chain comprises from N-terminus to C-terminus, an ActRIIB ECD comprising an amino acid sequence that is at least 95%, 96%, 97%, 98%, or 99% identical to SEQ ID NO: 13, a peptide linker that is 14aa in length, and an IgG1 FcDL Fc domain monomer. In some embodiments, the TGFβ superfamily ligand binding agent is a homodimeric polypeptide, wherein each polypeptide chain comprises from N-terminus to C-terminus, an ActRIIB ECD comprising or consisting of the amino acid sequence of SEQ ID NO: 13, a peptide linker that is 14aa in length, and an IgG1 FcDL Fc domain monomer. In some embodiments the TGFβ superfamily ligand binding agent is a homodimeric polypeptide, wherein each polypeptide chain comprises an amino acid sequence that is at least 95%, 96%, 97%, 98%, or 99% identical to SEQ ID NO: 251 (P1217). In some embodiments the TGFβ superfamily ligand binding agent is a homodimeric polypeptide, wherein each polypeptide chain comprises or consists of the amino acid sequence of SEQ ID NO: 251 (P1217).

In some embodiments, the TGFβ superfamily ligand binding agent is a homodimeric polypeptide, wherein each polypeptide chain comprises from N-terminus to C-terminus, an ActRIIB ECD comprising the amino acid substitution of F58Q, a peptide linker that is 6aa in length, and an IgG1 Fc domain monomer. In some embodiments, the TGFβ superfamily ligand binding agent is a homodimeric polypeptide, wherein each polypeptide chain comprises from N-terminus to C-terminus, an ActRIIB ECD comprising an amino acid sequence that is at least 95%, 96%, 97%, 98%, or 99% identical to SEQ ID NO: 9, a peptide linker that is 6aa in length, and an IgG1 FcDL Fc domain monomer. In some embodiments, the TGFβ superfamily ligand binding agent is a homodimeric polypeptide, wherein each polypeptide chain comprises from N-terminus to C-terminus, an ActRIIB ECD comprising or consisting of the amino acid sequence of SEQ ID NO: 9, a peptide linker that is 6aa in length, and an IgG1 FcDL Fc domain monomer. In some embodiments the TGFβ superfamily ligand binding agent is a homodimeric polypeptide, wherein each polypeptide chain comprises an amino acid sequence that is at least 95%, 96%, 97%, 98%, or 99% identical to SEQ ID NO: 252 (P1218). In some embodiments the TGFβ superfamily ligand binding agent is a homodimeric polypeptide, wherein each polypeptide chain comprises or consists of the amino acid sequence of SEQ ID NO: 252 (P1218).

In some embodiments, the TGFβ superfamily ligand binding agent is a homodimeric polypeptide, wherein each polypeptide chain comprises from N-terminus to C-terminus, an ActRIIB ECD comprising the amino acid substitution of F58Q, a peptide linker that is 10aa in length, and an IgG1 Fc domain monomer. In some embodiments, the TGFβ superfamily ligand binding agent is a homodimeric polypeptide, wherein each polypeptide chain comprises from N-terminus to C-terminus, an ActRIIB ECD comprising an amino acid sequence that is at least 95%, 96%, 97%, 98%, or 99% identical to SEQ ID NO: 9, a peptide linker that is 10aa in length, and an IgG1 FcDL Fc domain monomer. In some embodiments, the TGFβ superfamily ligand binding agent is a homodimeric polypeptide, wherein each polypeptide chain comprises from N-terminus to C-terminus, an ActRIIB ECD comprising or consisting of the amino acid sequence of SEQ ID NO: 9, a peptide linker that is 10aa in length, and an IgG1 FcDL Fc domain monomer. In some embodiments the TGFβ superfamily ligand binding agent is a homodimeric polypeptide, wherein each polypeptide chain comprises an amino acid sequence that is at least 95%, 96%, 97%, 98%, or 99% identical to SEQ ID NO: 253 (P1219). In some embodiments the TGFβ superfamily ligand binding agent is a homodimeric polypeptide, wherein each polypeptide chain comprises or consists of the amino acid sequence of SEQ ID NO: 253 (P1219).

In some embodiments, the TGFβ superfamily ligand binding agent is a homodimeric polypeptide, wherein each polypeptide chain comprises from N-terminus to C-terminus, an ActRIIB ECD comprising the amino acid substitution of F58Q, a peptide linker that is 19aa in length, and an IgG1 Fc domain monomer. In some embodiments, the TGFβ superfamily ligand binding agent is a homodimeric polypeptide, wherein each polypeptide chain comprises from N-terminus to C-terminus, an ActRIIB ECD comprising an amino acid sequence that is at least 95%, 96%, 97%, 98%, or 99% identical to SEQ ID NO: 9, a peptide linker that is 19aa in length, and an IgG1 FcDL Fc domain monomer. In some embodiments, the TGFβ superfamily ligand binding agent is a homodimeric polypeptide, wherein each polypeptide chain comprises from N-terminus to C-terminus, an ActRIIB ECD comprising or consisting of the amino acid sequence of SEQ ID NO: 9, a peptide linker that is 19aa in length, and an IgG1 FcDL Fc domain monomer. In some embodiments the TGFβ superfamily ligand binding agent is a homodimeric polypeptide, wherein each polypeptide chain comprises an amino acid sequence that is at least 95%, 96%, 97%, 98%, or 99% identical to SEQ ID NO: 254 (P1220). In some embodiments the TGFβ superfamily ligand binding agent is a homodimeric polypeptide, wherein each polypeptide chain comprises or consists of the amino acid sequence of SEQ ID NO: 254 (P1220).

In some embodiments, the TGFβ superfamily ligand binding agent is a homodimeric polypeptide, wherein each polypeptide chain comprises from N-terminus to C-terminus, an ActRIIB ECD comprising the amino acid substitutions of D57E and F58E, a peptide linker that is 3aa in length, and an IgG1 Fc domain monomer. In some embodiments, the TGFβ superfamily ligand binding agent is a homodimeric polypeptide, wherein each polypeptide chain comprises from N-terminus to C-terminus, an ActRIIB ECD comprising an amino acid sequence that is at least 95%, 96%, 97%, 98%, or 99% identical to SEQ ID NO: 21, a peptide linker that is 3aa in length, and an IgG1 Fc-DL Fc domain monomer. In some embodiments, the TGFβ superfamily ligand binding agent is a homodimeric polypeptide, wherein each polypeptide chain comprises from N-terminus to C-terminus, an ActRIIB ECD comprising or consisting of the amino acid sequence of SEQ ID NO: 21, a peptide linker that is 3aa in length, and an IgG1 Fc-DL Fc domain monomer. In some embodiments the TGFβ superfamily ligand binding agent is a homodimeric polypeptide, wherein each polypeptide chain comprises an amino acid sequence that is at least 95%, 96%, 97%, 98%, or 99% identical to SEQ ID NO: 231 (P718). In some embodiments the TGFβ superfamily ligand binding agent is a homodimeric polypeptide, wherein each polypeptide chain comprises or consists of the amino acid sequence of SEQ ID NO: 231 (P718).

In some embodiments, the TGFβ superfamily ligand binding agent is a homodimeric polypeptide, wherein each polypeptide chain comprises from N-terminus to C-terminus, an ActRIIB ECD comprising the amino acid substitutions of Q29Y and F58E, a peptide linker that is 14aa in length, and an IgG1 Fc domain monomer. In some embodiments, the TGFβ superfamily ligand binding agent is a homodimeric polypeptide, wherein each polypeptide chain comprises from N-terminus to C-terminus, an ActRIIB ECD comprising an amino acid sequence that is at least 95%, 96%, 97%, 98%, or 99% identical to SEQ ID NO: 22, a peptide linker that is 14aa in length, and an IgG1 Fc-DL Fc domain monomer. In some embodiments, the TGFβ superfamily ligand binding agent is a homodimeric polypeptide, wherein each polypeptide chain comprises from N-terminus to C-terminus, an ActRIIB ECD comprising or consisting of the amino acid sequence of SEQ ID NO: 22, a peptide linker that is 14aa in length, and an IgG1 Fc-DL Fc domain monomer. In some embodiments the TGFβ superfamily ligand binding agent is a homodimeric polypeptide, wherein each polypeptide chain comprises an amino acid sequence that is at least 95%, 96%, 97%, 98%, or 99% identical to SEQ ID NO: 232 (P719). In some embodiments the TGFβ superfamily ligand binding agent is a homodimeric polypeptide, wherein each polypeptide chain comprises or consists of the amino acid sequence of SEQ ID NO: 232 (P719).

In some embodiments, the TGFβ superfamily ligand binding agent is a homodimeric polypeptide, wherein each polypeptide chain comprises from N-terminus to C-terminus, an ActRIIB ECD comprising the amino acid substitutions of D30Q and F58E, a peptide linker that is 14aa in length, and an IgG1 Fc domain monomer. In some embodiments, the TGFβ superfamily ligand binding agent is a homodimeric polypeptide, wherein each polypeptide chain comprises from N-terminus to C-terminus, an ActRIIB ECD comprising an amino acid sequence that is at least 95%, 96%, 97%, 98%, or 99% identical to SEQ ID NO: 331, a peptide linker that is 14aa in length, and an IgG1 Fc-DL Fc domain monomer. In some embodiments, the TGFβ superfamily ligand binding agent is a homodimeric polypeptide, wherein each polypeptide chain comprises from N-terminus to C-terminus, an ActRIIB ECD comprising or consisting of the amino acid sequence of SEQ ID NO: 331, a peptide linker that is 14aa in length, and an IgG1 Fc-DL Fc domain monomer. In some embodiments the TGFβ superfamily ligand binding agent is a homodimeric polypeptide, wherein each polypeptide chain comprises an amino acid sequence that is at least 95%, 96%, 97%, 98%, or 99% identical to SEQ ID NO: 233 (P720). In some embodiments the TGFβ superfamily ligand binding agent is a homodimeric polypeptide, wherein each polypeptide chain comprises or consists of the amino acid sequence of SEQ ID NO: 233 (P720).

In some embodiments, the TGFβ superfamily ligand binding agent is a homodimeric polypeptide, wherein each polypeptide chain comprises from N-terminus to C-terminus, an ActRIIB ECD comprising the amino acid substitutions of G27D and F58E, a peptide linker that is 3aa in length, and an IgG1 Fc domain monomer. In some embodiments, the TGFβ superfamily ligand binding agent is a homodimeric polypeptide, wherein each polypeptide chain comprises from N-terminus to C-terminus, an ActRIIB ECD comprising an amino acid sequence that is at least 95%, 96%, 97%, 98%, or 99% identical to SEQ ID NO: 332, a peptide linker that is 3aa in length, and an IgG1 Fc-DL Fc domain monomer. In some embodiments, the TGFβ superfamily ligand binding agent is a homodimeric polypeptide, wherein each polypeptide chain comprises from N-terminus to C-terminus, an ActRIIB ECD comprising or consisting of the amino acid sequence of SEQ ID NO: 332, a peptide linker that is 3aa in length, and an IgG1 Fc-DL Fc domain monomer. In some embodiments the TGFβ superfamily ligand binding agent is a homodimeric polypeptide, wherein each polypeptide chain comprises an amino acid sequence that is at least 95%, 96%, 97%, 98%, or 99% identical to SEQ ID NO: 235 (P441). In some embodiments the TGFβ superfamily ligand binding agent is a homodimeric polypeptide, wherein each polypeptide chain comprises or consists of the amino acid sequence of SEQ ID NO: 235 (P441).

In some embodiments, the TGFβ superfamily ligand binding agent is a homodimeric polypeptide, wherein each polypeptide chain comprises from N-terminus to C-terminus, an ActRIIB ECD comprising the amino acid substitution D57E, a peptide linker that is 14aa in length, and an IgG1 Fc domain monomer. In some embodiments, the TGFβ superfamily ligand binding agent is a homodimeric polypeptide, wherein each polypeptide chain comprises from N-terminus to C-terminus, an ActRIIB ECD comprising an amino acid sequence that is at least 95%, 96%, 97%, 98%, or 99% identical to SEQ ID NO: 4, a peptide linker that is 14aa in length, and an IgG1 Fc-DL Fc domain monomer. In some embodiments, the TGFβ superfamily ligand binding agent is a homodimeric polypeptide, wherein each polypeptide chain comprises from N-terminus to C-terminus, an ActRIIB ECD comprising or consisting of the amino acid sequence of SEQ ID NO: 4, a peptide linker that is 14aa in length, and an IgG1 Fc-DL Fc domain monomer. In some embodiments the TGFβ superfamily ligand binding agent is a homodimeric polypeptide, wherein each polypeptide chain comprises an amino acid sequence that is at least 95%, 96%, 97%, 98%, or 99% identical to SEQ ID NO: 333 (P759). In some embodiments the TGFβ superfamily ligand binding agent is a homodimeric polypeptide, wherein each polypeptide chain comprises or consists of the amino acid sequence of SEQ ID NO: 333 (P759).

In some embodiments, the TGFβ superfamily ligand binding agent is a homodimeric polypeptide, wherein each polypeptide chain comprises from N-terminus to C-terminus, an ActRIIB ECD comprising the amino acid substitution K31Y, a peptide linker that is 14aa in length, and an IgG1 Fc domain monomer. In some embodiments, the TGFβ superfamily ligand binding agent is a homodimeric polypeptide, wherein each polypeptide chain comprises from N-terminus to C-terminus, an ActRIIB ECD comprising an amino acid sequence that is at least 95%, 96%, 97%, 98%, or 99% identical to SEQ ID NO: 16, a peptide linker that is 14aa in length, and an IgG1 Fc-DL Fc domain monomer. In some embodiments, the TGFβ superfamily ligand binding agent is a homodimeric polypeptide, wherein each polypeptide chain comprises from N-terminus to C-terminus, an ActRIIB ECD comprising or consisting of the amino acid sequence of SEQ ID NO: 16, a peptide linker that is 14aa in length, and an IgG1 Fc-DL Fc domain monomer. In some embodiments the TGFβ superfamily ligand binding agent is a homodimeric polypeptide, wherein each polypeptide chain comprises an amino acid sequence that is at least 95%, 96%, 97%, 98%, or 99% identical to SEQ ID NO: 339 (P761). In some embodiments the TGFβ superfamily ligand binding agent is a homodimeric polypeptide, wherein each polypeptide chain comprises or consists of the amino acid sequence of SEQ ID NO: 339 (P761).

In some embodiments, the TGFβ superfamily ligand binding agent is a homodimeric polypeptide, wherein each polypeptide chain comprises from N-terminus to C-terminus, an ActRIIB ECD comprising the amino acid substitution V75Q, a peptide linker that is 14aa in length, and an IgG1 Fc domain monomer. In some embodiments, the TGFβ superfamily ligand binding agent is a homodimeric polypeptide, wherein each polypeptide chain comprises from N-terminus to C-terminus, an ActRIIB ECD comprising an amino acid sequence that is at least 95%, 96%, 97%, 98%, or 99% identical to SEQ ID NO: 18, a peptide linker that is 14aa in length, and an IgG1 Fc-DL Fc domain monomer. In some embodiments, the TGFβ superfamily ligand binding agent is a homodimeric polypeptide, wherein each polypeptide chain comprises from N-terminus to C-terminus, an ActRIIB ECD comprising or consisting of the amino acid sequence of SEQ ID NO: 18, a peptide linker that is 14aa in length, and an IgG1 Fc-DL Fe domain monomer. In some embodiments the TGFβ superfamily ligand binding agent is a homodimeric polypeptide, wherein each polypeptide chain comprises an amino acid sequence that is at least 95%, 96%, 97%, 98%, or 99% identical to SEQ ID NO: 340 (P762). In some embodiments the TGFβ superfamily ligand binding agent is a homodimeric polypeptide, wherein each polypeptide chain comprises or consists of the amino acid sequence of SEQ ID NO: 340 (P762).

In some embodiments, the polypeptides or binding agents of the disclosure are "isolated" or "substantially pure".

"Isolated" or "substantially pure", when used to describe the polypeptides or binding agents disclosed herein, means a polypeptide or binding agent that has been identified, separated and/or recovered from a component of its production environment. Preferably, the polypeptide or binding agent is free or substantially free of association with all other components from its production environment. Contaminant components of its production environment, such as that resulting from recombinant transfected cells, are materials that would typically interfere with diagnostic or therapeutic uses for the polypeptide, and may include enzymes, hormones, and other proteinaceous or non-proteinaceous solutes. The polypeptides or binding agents may, e.g., constitute at least about 5%, or at least about 50% by weight of the total protein in a given sample. It is understood that the isolated protein may constitute from 5% to 99.9% by weight of the total protein content, depending on the circumstances. The polypeptide or binding agent may be made at a significantly higher concentration through the use of an inducible promoter or high expression promoter, such that it is made at increased concentration levels. The definition includes the production of a polypeptide or binding agent in a wide variety of organisms and/or host cells that are known in the art. In preferred embodiments, the polypeptide or binding agent will be purified (1) to a degree sufficient to obtain at least 15 residues of N-terminal or internal amino acid sequence by use of a spinning cup sequenator, or (2) to homogeneity by SDS-PAGE under non-reducing or reducing conditions using Coomassie blue or, preferably, silver stain. Ordinarily, however, an isolated polypeptide or binding agent will be prepared by at least one purification step, such as, for example and without limitation, affinity and/or ion-exchange chromatography, e.g., binding to a Protein A column.

In some embodiments, polypeptides and binding agents of the present disclosure are characterized, for example, by one or more of the following: a particularly high affinity for one or more of activin A, activin B, GDF-8, GDF-11 and BMP-10; high neutralization potency (low IC50 values) for one or more of activin A, activin B, GDF-8, GDF-11 and BMP-10; a particularly low or undetectable affinity for BMP-9; low or not detectable neutralization potency (high IC50 value) for BMP-9; high thermostability; high plasma stability; long or extended half-life, low turbidity; high protein homogeneity; and/or high manufacturability.

The biological activity of a polypeptide or binding agent, or pharmaceutical composition thereof, of the disclosure can be determined for instance by cellular neutralization assays, binding assays, competition assays and the like. "Efficacy" or "in vivo efficacy" as used herein refers to the response to therapy using a polypeptide or binding agent or pharmaceutical composition of the disclosure. The success or in vivo efficacy of the therapy using a polypeptide or binding agent or pharmaceutical composition of the disclosure refers to the effectiveness of the a polypeptide or binding agent or composition for its intended purpose, e.g., the ability of the a polypeptide or binding agent or composition to cause its desired effect, i.e. treatment, amelioration, or prevention of a TGFβ superfamily-associated disease or disorder as defined herein. The in vivo efficacy may be monitored by established standard methods for the respective disease entities. In addition, various disease specific clinical chemistry parameters and other established standard methods may be used.

Another major challenge in the development of drugs such as a pharmaceutical composition of the disclosure is the predictable modulation of pharmacokinetic properties. To this end, a pharmacokinetic profile of the drug candidate, i.e., a profile of the pharmacokinetic parameters that affect the ability of a particular drug to treat a given condition, can be established. Pharmacokinetic parameters of the drug influencing the ability of a drug for treating a certain disease entity include, but are not limited to: half-life, volume of distribution, hepatic first-pass metabolism and the degree of blood serum binding. The efficacy of a given drug agent can be influenced by each of the parameters mentioned above.

Pharmacokinetic parameters also include bioavailability, lag time (Tlag), Tmax, absorption rates, more onset and/or Cmax for a given amount of drug administered. "Bioavailability" means the amount of a drug in the blood compartment. "Lag time" means the time delay between the administration of the drug and its detection and measurability in blood or plasma. "Tmax" is the time after which maximal blood concentration of the drug is reached, and "Cmax" is the blood concentration maximally obtained with a given drug. The time to reach a blood or tissue concentration of the drug which is required for its biological effect is influenced by all parameters.

In some embodiments, the polypeptide or binding agent of the present disclosure has a half-life of about 3 days or longer, about 5 days or longer, about 1 week or longer, about 2 weeks or longer, about 3 weeks or longer, about 4 weeks or longer, about 5 weeks or longer, about 6 weeks or longer, or about two months or longer.

In some embodiments, the polypeptides or binding agents of the present disclosure may show a favorable thermostability with aggregation temperatures of about 45° C. or higher, about 45 to about 50° C., about 52-about 54° C., about 56 to about 60° C., or about 60° C. or higher. The thermostability parameter can be determined in terms of polypeptide aggregation temperature as follows: Protein solution at a test concentration (e.g., 100 μg/ml, 250 μg/ml) is transferred into a single use cuvette and placed in a Dynamic Light Scattering (DLS) device. The sample is heated from 40° C. to 70° C. at a heating rate of 0.5° C./min with constant acquisition of the measured radius. Increase of radius indicating melting of the protein and aggregation is used to calculate the aggregation temperature of the polypeptide. Other methods known in the art may be used.

In an embodiment the polypeptide or binding agent according to the disclosure is stable at 2-8° C. for at least 1 month, 2 months, or 3 months. In an embodiment the polypeptide or binding agent according to the disclosure is stable at 25-40° C. for at least 4 weeks. In an embodiment the polypeptide or binding agent according to the disclosure is stable after undergoing 3 Freeze/Thaw cycles. In an embodiment the polypeptide or binding agent according to the disclosure is stable at −20° C. for 1 month, 2 month, 3 months or longer.

Alternatively, temperature melting curves can be determined by Differential Scanning Calorimetry (DSC) to determine intrinsic biophysical protein stabilities of the polypeptides or binding agents. These experiments may be performed using a MicroCal LLC (Northampton, Mass., U.S.A) VP-DSC device. The energy uptake of a sample containing a polypeptide or binding agent is recorded from 20° C. to 90° C. compared to a sample containing only the formulation buffer. For recording of the respective melting curve, the overall sample temperature is increased stepwise. At each temperature T energy uptake of the sample and the formulation buffer reference is recorded. The difference in energy uptake Cp (kcal/mole/° C.) of the sample minus the reference is plotted against the respective temperature. The melting temperature is defined as the temperature at the first maximum of energy uptake.

In a further embodiment the polypeptides or binding agents according to the disclosure are stable at acidic pH. The more tolerant the polypeptide or binding agent behaves at unphysiologic pH such as pH 5.5 (a pH which is required to run e.g. a cation exchange chromatography), the higher is the recovery of the polypeptide or binding agent eluted from an ion exchange column relative to the total amount of loaded protein. Recovery of the polypeptides or binding agents from an ion (e.g., cation) exchange column at pH 5.5 may be 50% or more, 60% or more, 65% or more, 70% or more, 72% or more, 74% or more, 76% or more, 78% or more, 80% or more, 90% or more, 95% or more, or 99% or more.

Amino Acid Sequence Modifications

Amino acid sequence modifications of the polypeptides and binding agents described herein are contemplated. For example, it may be desirable to improve the binding affinity, effector functions, half-life and/or other biological properties of the polypeptide or binding agent. Amino acid sequence modification/variants of the polypeptides and binding agents are generally prepared by introducing appropriate nucleotide changes into the encoding nucleic acid, or by peptide synthesis. All of the below described amino acid sequence modifications should result in a polypeptide or binding agent which still retains the desired biological activity (e.g., binding to one or more of activin A, activin B, GDF-8, GDF-11, and BMP-10, without substantial binding to BMP-9) of the unmodified parental molecule.

As used herein, the term "functionally equivalent" refers to modified sequences that have the same or substantially the same biological activity or function as the original sequence from which it is derived, e.g., no significant change in physiological, chemical, physico-chemical or functional properties compared to the original sequence. The term "substantially identical" refers to sequences that are functionally equivalent to the original or reference sequence and have a high degree of sequence identity thereto. Generally, a substantially identical sequence is at least about 90%, at least about 95%, at least about 96%, at least about 97%, at least about 98%, or at least about 99% identical to the original or reference sequence and has the same function. In some cases when referring to nucleic acid sequences, a substantially identical sequence hybridizes to the original sequence under high stringency conditions, for example at salt and temperature conditions substantially equivalent to 0.5×SSC to about 5×SSC and 65° C. for both hybridization and wash. In general, modified sequences that are substantially identical or functionally equivalent to sequences provided in accordance with the present disclosure are meant to be encompassed.

Amino acid modifications include, for example, deletions from, and/or insertions into, and/or substitutions of, residues within the amino acid sequences of the polypeptides or binding agents. Any combination of deletion, insertion, and substitution is made to arrive at the final construct, provided that the final construct possesses the desired characteristics. The amino acid changes also may alter post-translational processes of the polypeptides or binding agents, such as changing the number or position of glycosylation sites. In a particular embodiment, one or more amino acid is changed to alter a glycosylation site.

For example, 1, 2, 3, 4, 5, or 6 amino acids may be inserted or deleted in a polypeptide or binding agent. Preferably, amino acid sequence insertions include amino- and/or carboxyl-terminal fusions ranging in length from 1, 2, 3, 4, 5, 6, 7, 8, 9 or 10 residues to polypeptides containing a hundred or more residues, as well as intra-sequence insertions of single or multiple amino acid residues. An insertional variant of the polypeptides or binding agents of the disclosure includes fusion to the N-terminus or to the C-terminus of the polypeptides or binding agents of an enzyme or fusion to a polypeptide which increases the serum half-life of the polypeptides or binding agents.

It is envisioned that modifications of the polypeptides or binding agents described herein are also encompassed. Modifications encompassed by the present disclosure include those having a variation in the amino acid sequence of the polypeptides or binding agents. Modifications of the polypeptides or binding agents include, for example, those having similar or improved binding affinity, avidity, ligand specificity, potency of inhibition, stability, manufacturability, half-life, and/or reduced aggregation in comparison with the polypeptides or binding agents disclosed herein.

One site of interest for substitutional mutagenesis includes the Fc domain monomer, as described hereinabove. Exemplary embodiments of modified polypeptides or binding agents of the present disclosure may comprise those having a modified IgG1, IgG2, IgG3, or IgG4 constant region or a portion thereof. In an embodiment, the polypeptides or binding agents comprise an IgG1 constant region (modified or unmodified). In an embodiment, the polypeptides or binding agents comprise an IgG2 constant region (modified or unmodified). In an embodiment, the polypeptides or binding agents comprise an IgG3 constant region (modified or unmodified). In an embodiment, the polypeptides or binding agents comprise an IgG4 constant region (modified or unmodified).

Modifications encompassed by the present disclosure include those which may comprise an insertion, a deletion or an amino acid substitution (conservative or non-conservative). These modifications may have at least one amino acid residue in its amino acid sequence removed and a different residue inserted in its place. It should be understood that variation may occur in multiple regions of the polypeptides or binding agents, as long as the desired binding or biological activity is maintained.

It is known in the art that modifications and variants may be generated by substitutional mutagenesis and retain the biological activity (i.e., functional equivalence) of the polypeptides of the present disclosure. These modifications or variants have at least one amino acid residue in the amino acid sequence removed and a different residue inserted in its place, e.g., one or more conservative amino acid substitution. In general, a conservative amino acid substitution is the substitution of an amino acid residue for another amino acid residue with similar chemical properties (e.g., size, charge, or polarity).

Generally, the degree of similarity and identity between variant polypeptide chains is determined herein using the Blast2 sequence program (Tatusova, T. A. and Madden, T. L., 1999) using default settings, i.e., blastp program, BLOSUM62 matrix (open gap 11 and extension gap penalty 1; gapx dropoff 50, expect 10.0, word size 3) and activated filters.

However, the level of identity may also be determined over the entire length of a given sequence. Percent identity will therefore be indicative of amino acids which are identical in comparison with the original peptide and which may occupy the same or similar position. Percent similarity will be indicative of amino acids which are identical and those which are replaced with conservative amino acid substitution in comparison with the original peptide at the same or similar position.

In some embodiments, modifications of the polypeptides or binding agents of the present disclosure therefore comprise amino acid sequences which have at least 90%, at least 91%, at least 92%, at least 93%, at least 94%, at least 95%, at least 96%, at least 97%, at least 98%, or at least 99% sequence identity with an original sequence or a portion of an original sequence.

In some embodiments, substitutions are conservative substitutions. However, any substitution (including non-conservative substitution) is envisaged as long as the polypeptides or binding agents retain their capability to bind and/or inhibit the desired TGFβ superfamily ligands, without substantially binding or inhibiting BMP-9.

Generally, the nucleic acid sequence homology, similarity, or identity between the nucleotide sequences encoding polypeptides or binding agents of the disclosure and the nucleotide sequences depicted herein are at least 60%, and more typically with preferably increasing homologies or identities of at least 65%, 70%, 75%, 80%, 81%, 82%, 83%, 84%, 85%, 86%, 87%, 88%, 89%, 90%, 91%, 92%, 93%, 94%, 95%, 96%, 97%, 98%, or 99%, and almost 100%.

Nucleic Acids and Production of Polypeptides and Binding Agents

The disclosure further provides a polynucleotide encoding an ActRIIB-ECD polypeptide provided herein. In some embodiments, the polynucleotide comprises a nucleic acid sequence that is at least 80%, 85%, 90%, 95%, 96%, 97%, 98%, or 99% identical to one of SEQ ID NOs: 256-330, 334, or 342-344. In some embodiments, the polynucleotide comprises or consists of any one of SEQ ID NOs: 256-330, 334, or 342-344.

A polynucleotide is a biopolymer composed of nucleotide monomers covalently bonded in a chain. DNA (such as cDNA) and RNA (such as mRNA) are examples of polynucleotides with distinct biological function. Nucleotides are organic molecules that serve as the monomers or subunits of nucleic acid molecules like DNA or RNA. The nucleic acid molecule or polynucleotide can be double stranded or single stranded, linear or circular. In some embodiments, the nucleic acid molecule or polynucleotide is comprised in a vector. In some embodiments, the vector is comprised in a host cell. The host cell is, e.g. after transformation or transfection with the vector or the polynucleotide of the disclosure, capable of expressing the polypeptide or binding agent. For that purpose the polynucleotide or nucleic acid molecule is usually operatively linked with control sequences.

Furthermore, the disclosure provides a vector comprising a polynucleotide/nucleic acid molecule coding for a polypeptide or binding agent provided herein.

A vector is a nucleic acid molecule used as a vehicle to transfer (foreign) genetic material into a cell. The term "vector" encompasses—but is not restricted to—plasmids, viruses, cosmids and artificial chromosomes. In general, engineered vectors comprise an origin of replication, a multicloning site and a selectable marker. The vector itself is generally a nucleotide sequence, commonly a DNA sequence, that comprises an insert (transgene) and a larger sequence that serves as the "backbone" of the vector. Modern vectors may encompass additional features besides the transgene insert and a backbone: promoter, genetic marker, antibiotic resistance, reporter gene, targeting sequence, protein purification tag. Vectors called expression vectors (expression constructs) specifically are for the expression of the transgene in the target cell, and generally have control sequences.

The term "control sequences" refers to DNA sequences necessary for the expression of an operably linked coding sequence in a particular host organism. The control sequences that are suitable for prokaryotes, for example, include a promoter, optionally an operator sequence, and a ribosome binding site. Eukaryotic cells are known to utilize promoters, polyadenylation signals, and enhancers.

A nucleic acid is "operably linked" when it is placed into a functional relationship with another nucleic acid sequence. For example, DNA for a presequence or secretory leader (signal sequence) is operably linked to DNA for a polypeptide if it is expressed as a preprotein that participates in the secretion of the polypeptide; a promoter or enhancer is operably linked to a coding sequence if it affects the transcription of the sequence; or a ribosome binding site is operably linked to a coding sequence if it is positioned so as to facilitate translation. Generally, "operably linked" means that the DNA sequences being linked are contiguous, and, in the case of a secretory leader, contiguous and in reading phase. However, enhancers do not have to be contiguous. Linking is accomplished by ligation at convenient restriction sites. If such sites do not exist, the synthetic oligonucleotide adaptors or linkers are used in accordance with conventional practice.

"Transfection" is the process of deliberately introducing nucleic acid molecules or polynucleotides (including vectors) into target cells. The term is mostly used for non-viral methods in eukaryotic cells. Transduction is often used to describe virus-mediated transfer of nucleic acid molecules or polynucleotides. Transfection of animal cells typically involves opening transient pores or "holes" in the cell membrane, to allow the uptake of material. Transfection can be carried out using calcium phosphate, by electroporation, by cell squeezing or by mixing a cationic lipid with the material to produce liposomes, which fuse with the cell membrane and deposit their cargo inside.

The term "transformation" is used to describe non-viral transfer of nucleic acid molecules or polynucleotides (including vectors) into bacteria, and also into non-animal eukaryotic cells, including plant cells. Transformation is hence the genetic alteration of a bacterial or non-animal eukaryotic cell resulting from the direct uptake through the cell membrane(s) from its surroundings and subsequent incorporation of exogenous genetic material (nucleic acid molecules). Transformation can be effected by artificial means. For transformation to happen, cells or bacteria must be in a state of competence, which might occur as a time-limited response to environmental conditions such as starvation and cell density.

Moreover, the disclosure provides a host cell transformed or transfected with the polynucleotide/nucleic acid molecule or with the vector of the technology.

As used herein, the terms "host cell" and "recipient cell" are intended to include any individual cell or cell culture that can be or has/have been recipients of vectors, exogenous nucleic acid molecules, and polynucleotides encoding the polypeptide or binding agent of the present disclosure; and/or recipients of the polypeptide or binding agent itself. The introduction of the respective material into the cell is carried out by way of transformation, transfection and the like. The term "host cell" is also intended to include progeny or potential progeny of a single cell. Because certain modifications may occur in succeeding generations due to either natural, accidental, or deliberate mutation or due to environmental influences, such progeny may not, in fact, be completely identical (in morphology or in genomic or total DNA complement) to the parent cell but is still included within the scope of the term as used herein. Suitable host cells include prokaryotic or eukaryotic cells, and also include but are not limited to bacteria, yeast cells, fungi cells, plant cells, and animal cells such as insect cells and mammalian cells, e.g., murine, rat, macaque or human.

The polypeptide or binding agent of the disclosure can be produced in bacteria. After expression, the polypeptide or binding agent is isolated from the *E. coli* cell paste in a soluble fraction and can be purified through, e.g., affinity chromatography and/or size exclusion. Final purification can be carried out similar to the process for purifying protein expressed e.g., in CHO cells.

In addition to prokaryotes, eukaryotic microbes such as filamentous fungi or yeast are suitable cloning or expression hosts for the polypeptide or binding agent. *Saccharomyces cerevisiae*, or common baker's yeast, is the most commonly used among lower eukaryotic host microorganisms. However, a number of other genera, species, and strains are commonly available and useful herein, such as *Schizosaccharomyces pombe, Kluyveromyces* hosts such as *K. lactis, K. fragilis* (ATCC 12424), *K. bulgaricus* (ATCC 16045), K. wickeramii (ATCC 24178), *K. waltii* (ATCC 56500), *K. drosophilarum* (ATCC 36906), *K. thermotolerans*, and *K. marxianus; yarrowia* (EP 402 226); *Pichia pastoris* (EP 183 070); *Candida; Trichoderma* reesia (EP 244 234); *Neurospora crassa; Schwanniomyces* such as *Schwanniomyces occidentalis*; and filamentous fungi such as *Neurospora, Penicillium, Tolypocladium*, and *Aspergillus* hosts such as *A. nidulans* and *A. niger.*

Suitable host cells for the expression of glycosylated polypeptide or binding agent of the disclosure are derived from multicellular organisms. Examples of invertebrate cells include plant and insect cells. Numerous baculoviral strains and variants and corresponding permissive insect host cells from hosts such as *Spodoptera frugiperda* (caterpillar), *Aedes aegypti* (mosquito), *Aedes albopictus* (mosquito), *Drosophila melanogaster* (fruit fly), and *Bombyx* mon have been identified. A variety of viral strains for transfection are publicly available, e.g., the L-1 variant of *Autographa californica* NPV and the Bm-5 strain of *Bombyx mori* NPV, and such viruses may be used as the virus herein according to the present disclosure, particularly for transfection of *Spodoptera frugiperda* cells.

Plant cell cultures of cotton, corn, potato, soybean, *petunia*, tomato, *Arabidopsis* and tobacco can also be used as hosts. Cloning and expression vectors useful in the production of proteins in plant cell culture are known to those of skill in the art. See, e.g., Hiatt et al., Nature (1989) 342: 76-78, Owen et al. (1992) Bio/Technology 10: 790-794, Artsaenko et al. (1995) The Plant J 8: 745-750, and Fecker et al. (1996) Plant Mol Biol 32: 979-986.

However, interest has been greatest in vertebrate cells, and propagation of vertebrate cells in culture (tissue culture) has become a routine procedure. Examples of useful mammalian host cell lines are monkey kidney CV1 line transformed by SV40 (COS-7, ATCC CRL 1651); human embryonic kidney line (293 or 293 cells subcloned for growth in suspension culture, Graham et al., 1977); baby hamster kidney cells (BHK, ATCC CCL 10); Chinese hamster ovary cells/-DHFR (CHO, Urlaub et al., 1980); mouse sertoli cells (TM4, Mather, 1980); monkey kidney cells (CVI ATCC CCL 70); African green monkey kidney cells (VERO-76, ATCC CRL1587); human cervical carcinoma cells (HELA, ATCC CCL 2); canine kidney cells (MDCK, ATCC CCL 34); buffalo rat liver cells (BRL 3A, ATCC CRL 1442); human lung cells (W138, ATCC CCL 75); human liver cells (Hep G2,1413 8065); mouse mammary tumor (MMT 060562, ATCC CCL5 1); TRI cells (Mather et al., Annals N. Y Acad. Sci. (1982) 383: 44-68); MRC 5 cells; FS4 cells; and a human hepatoma line (Hep G2).

In a further embodiment the disclosure provides a process for the production of a polypeptide or binding agent, said process comprising culturing a host cell under conditions allowing the expression of the polypeptide or binding agent and recovering the produced polypeptide or binding agent from the culture.

As used herein, the term "culturing" refers to the in vitro maintenance, differentiation, growth, proliferation and/or propagation of cells under suitable conditions in a medium. The term "expression" includes any step involved in the production of a polypeptide or binding agent of the disclosure including, but not limited to, transcription, post-transcriptional modification, translation, post-translational modification, and secretion.

When using recombinant techniques, the polypeptide or binding agent can be produced intracellularly, in the periplasmic space, or directly secreted into the medium. If the polypeptide or binding agent is produced intracellularly, as a first step, the particulate debris, either host cells or lysed fragments, are removed, for example, by centrifugation or ultrafiltration. Carter et al., Bio/Technology 10: 163-167 (1992) describe a procedure for isolating antibodies which are secreted to the periplasmic space of *E. coli*. Briefly, cell paste is thawed in the presence of sodium acetate (pH 3.5), EDTA, and phenylmethylsulfonylfluoride (PMSF) over about 30 min. Cell debris can be removed by centrifugation. Where the antibody is secreted into the medium, supernatants from such expression systems are generally first concentrated using a commercially available protein concentration filter, for example, an Amicon or Millipore Pellicon ultrafiltration unit. A protease inhibitor such as PMSF may be included in any of the foregoing steps to inhibit proteolysis and antibiotics may be included to prevent the growth of adventitious contaminants.

The polypeptide or binding agent of the disclosure prepared from the host cells can be recovered or purified using, for example, hydroxylapatite chromatography, gel electrophoresis, dialysis, and affinity chromatography. Other techniques for protein purification such as fractionation on an ion-exchange column, ethanol precipitation, Reverse Phase HPLC, chromatography on silica, chromatography on heparin SEPHAROSE™, chromatography on an anion or cation exchange resin (such as a polyaspartic acid column), chromato-focusing, SDS-PAGE, and ammonium sulfate precipitation are also available depending on the antibody to be recovered. Where the polypeptide or binding agent of the disclosure comprises a CH3 domain, the Bakerbond ABX resin (J. T. Baker, Phillipsburg, N.J.) may be useful for purification.

Affinity chromatography is a common purification technique. The matrix to which the affinity ligand is attached is most often agarose, but other matrices are available. Mechanically stable matrices such as controlled pore glass or poly (styrenedivinyl) benzene allow for faster flow rates and shorter processing times than can be achieved with agarose.

The polypeptide or binding agent disclosed herein may be made by a variety of methods familiar to those skilled in the art, including by recombinant DNA methods.

In order to express the polypeptides or binding agents, nucleotide sequences able to encode the polypeptide chain described herein may be inserted into an expression vector, i.e., a vector that contains the elements for transcriptional and translational control of the inserted coding sequence in a particular host. These elements may include regulatory sequences, such as enhancers, constitutive and inducible promoters, and 5' and 3' un-translated regions. Methods that are well known to those skilled in the art may be used to construct such expression vectors. These methods include in vitro recombinant DNA techniques, synthetic techniques, in vivo genetic recombination and the like.

A variety of expression vector and host cell systems known to those of skill in the art may be used to express the polypeptide chains described herein. These include, but are not limited to, microorganisms such as bacteria transformed with recombinant bacteriophage, plasmid, or cosmid DNA expression vectors; yeast transformed with yeast expression vectors; insect cell systems infected with baculovirus vectors; plant cell systems transformed with viral or bacterial expression vectors; and animal cell systems. For long-term production of recombinant proteins in mammalian systems, stable expression in mammalian cell lines may be used. For example, nucleotide sequences able to encode any one of the polypeptide chains described herein may be transformed into cell lines using expression vectors that may contain viral origins of replication and/or endogenous expression elements and a selectable or visible marker gene on the same or on a separate vector. The present disclosure is not to be limited by the vector or host cell employed. In certain embodiments disclosed herein, nucleic acids able to encode polypeptide chains described herein may be ligated into expression vectors. In the event that the binding agent is composed of distinct polypeptide chains (i.e., the first polypeptide and the second polypeptide are not identical), each of such polypeptide chain may be ligated into separate vectors or into the same vector. In accordance with the present disclosure, the polypeptide chains of the binding agent may be encoded by a single vector or by separate vectors (e.g., a vector set). Cells are transformed with the desired vector or vector sets.

Alternatively, the polypeptide chains may be expressed from an in vitro transcription system or a coupled in vitro transcription/translation system respectively or any such cell-free system.

Host cells comprising nucleotide sequences may be cultured under conditions for the transcription of the corresponding RNA (mRNA, etc.) and/or the expression and secretion of the polypeptide(s) from cell culture. In an exemplary embodiment, expression vectors containing nucleotide sequences able to encode the polypeptide chains described herein may be designed to contain signal sequences that direct secretion of the polypeptide through a prokaryotic or eukaryotic cell membrane.

Due to the inherent degeneracy of the genetic code, DNA sequences that encode the same, substantially the same or a functionally equivalent amino acid sequence may be produced and used. The nucleotide sequences of the present disclosure may be engineered using methods generally known in the art in order to alter the nucleotide sequences for a variety of purposes including, but not limited to, modification of the cloning, processing, and/or expression of the gene product. DNA shuffling by random fragmentation and PCR reassembly of gene fragments and synthetic oligonucleotides may be used to engineer the nucleotide sequences. For example, oligonucleotide-mediated site-directed mutagenesis may be used to introduce mutations that create new restriction sites, alter glycosylation patterns, change codon preference, produce splice variants, and so forth. Codon-optimized nucleic acids encoding the polypeptide chains described herein are encompassed by the present disclosure.

In addition, a host cell strain may be chosen for its ability to modulate expression of the inserted sequences or to process the expressed polypeptide in the desired fashion. Different host cells that have specific cellular machinery and characteristic mechanisms for post-translational activities (e.g., CHO, HeLa, MDCK, HEK293, and W138) are available commercially and from the American Type Culture Collection (ATCC) and may be chosen to ensure the correct modification and processing of the expressed polypeptide.

Those of skill in the art will also readily recognize that the nucleic acid and polypeptide sequences may be synthesized, in whole or in part, using chemical or enzymatic methods well known in the art. For example, peptide synthesis may be performed using various solid-phase techniques and machines such as the ABI 431A Peptide synthesizer (PE Biosystems) may be used to automate synthesis. If desired, the amino acid sequence may be altered during synthesis and/or combined with sequences from other proteins to produce a variant protein.

Pharmaceutical Compositions

Pharmaceutical compositions comprising the polypeptides or TGFβ superfamily ligand binding agents disclosed herein are provided by the present disclosure. The pharmaceutical composition generally comprises the polypeptide or binding agent disclosed herein and a pharmaceutically acceptable carrier.

The preparation of pharmaceutical compositions can be carried out as known in the art (see, for example, Remington: The Science and Practice of Pharmacy, 20th Edition, 2000). For example, a therapeutic compound and/or composition, together with one or more solid or liquid pharmaceutical carrier substances and/or additives (or auxiliary substances) and, if desired, in combination with other pharmaceutically active compounds having therapeutic or prophylactic action, are brought into a suitable administration form or dosage form which can then be used as a pharmaceutical in human or veterinary medicine. Pharmaceutical preparations can also contain additives, of which many are known in the art, for example fillers, disintegrants, binders, lubricants, wetting agents, stabilizers, emulsifiers, dispersants, preservatives, sweeteners, colorants, flavorings, aromatizers, thickeners, diluents, buffer substances, solvents, solubilizers, agents for achieving a depot effect, salts for altering the osmotic pressure, coating agents or antioxidants.

The term “pharmaceutical composition” means a composition comprising a polypeptide or binding agent as described herein and at least one component comprising pharmaceutically acceptable carriers, diluents, adjuvants, excipients, or vehicles, such as preserving agents, fillers, disintegrating agents, wetting agents, emulsifying agents, suspending agents, sweetening agents, flavoring agents, perfuming agents, antibacterial agents, antifungal agents, lubricating agents and dispensing agents, depending on the nature of the mode of administration and dosage forms.

The term “pharmaceutically acceptable carrier” is used to mean any carrier, diluent, adjuvant, excipient, or vehicle, as described herein or as known in the art. Examples of suspending agents include ethoxylated isostearyl alcohols, polyoxyethylene sorbitol and sorbitan esters, microcrystalline cellulose, aluminum metahydroxide, bentonite, agar-agar and tragacanth, or mixtures of these substances. Prevention of the action of microorganisms can be ensured by various antibacterial and antifungal agents, for example, parabens, chlorobutanol, phenol, sorbic acid, and the like. It may also be desirable to include isotonic agents, for example sugars, sodium chloride, and the like. Prolonged absorption of the injectable pharmaceutical form can be brought about by the use of agents delaying absorption, for example, aluminum monosterate and gelatin. Non-limiting examples of suitable carriers, diluents, solvents, or vehicles include water, salt solutions, phosphate buffered saline (PBS), gelatins, oils, alcohols, polyols, suitable mixtures thereof, vegetable oils (such as olive oil), and injectable organic esters such as ethyl oleate. Non-limiting examples of excipients include lactose, milk sugar, sodium citrate, calcium carbonate, and dicalcium phosphate. Non-limiting examples of disintegrating agents include starch, alginic acids, and certain complex silicates. Non-limiting examples of lubricants include magnesium stearate, sodium lauryl sulphate, talc, as well as high molecular weight polyethylene glycols.

The term "pharmaceutically acceptable" means it is, within the scope of sound medical judgment, suitable for use in contact with the cells of a subject, e.g., humans and animals, without undue toxicity, irritation, allergic response, and the like, and are commensurate with a reasonable benefit/risk ratio.

As used herein "pharmaceutically acceptable carrier" or "pharmaceutical carrier" are known in the art and include, but are not limited to, 0.01-0.1 M or 0.05 M phosphate buffer or 0.8% saline. Additionally, such pharmaceutically acceptable carriers may be aqueous or non-aqueous solutions, suspensions, and emulsions. Examples of non-aqueous solvents are propylene glycol, polyethylene glycol, vegetable oils such as olive oil, and injectable organic esters such as ethyl oleate. Aqueous carriers include water, alcoholic/aqueous solutions, emulsions or suspensions, including saline and buffered media. Parenteral vehicles include sodium chloride solution, Ringer's dextrose, dextrose and sodium chloride, lactated Ringer's or fixed oils. Intravenous vehicles include fluid and nutrient replenishers, electrolyte replenishers such as those based on Ringer's dextrose, and the like. Preservatives and other additives may also be present, such as, for example, antimicrobials, antioxidants, collating agents, inert gases and the like.

A pharmaceutically acceptable carrier may include any and all solvents, dispersion media, coatings, antibacterial and antifungal agents, isotonic and absorption delaying agents, and the like that are physiologically compatible. In one embodiment, the carrier is suitable for parenteral administration. The carrier may be suitable for intravenous, intraperitoneal, subcutaneous or intramuscular administration. Alternatively, the carrier may be suitable for sublingual or oral administration. In other embodiments, the carrier is suitable for topical administration or for administration via inhalation. Pharmaceutically acceptable carriers include sterile aqueous solutions or dispersions and sterile powders for the extemporaneous preparation of sterile injectable solutions or dispersion. The use of such media and agents for pharmaceutically active substances is well known in the art. Except insofar as any conventional media or agent is incompatible with the active compound, use thereof in the pharmaceutical compositions provided herein is contemplated. Supplementary active compounds can also be incorporated into the compositions. For example, a pharmaceutical composition provided herein may further comprise at least one additional therapeutic agent, as discussed further below.

The pharmaceutical compositions described herein may be administered by any number of routes including, but not limited to, oral, intravenous, intramuscular, intra-arterial, intramedullary, intrathecal, intraventricular, transdermal, subcutaneous, intraperitoneal, intranasal, enteral, topical, sublingual, or rectal means.

In some embodiments, a pharmaceutical composition provided herein can be administered orally, for example in the form of pills, tablets, lacquered tablets, sugar-coated tablets, granules, hard and soft gelatin capsules, aqueous, alcoholic or oily solutions, syrups, emulsions or suspensions, or rectally, for example in the form of suppositories.

In other embodiments, a pharmaceutical composition provided herein can be administered parenterally, for example subcutaneously, intramuscularly or intravenously in the form of solutions for injection or infusion. Other suitable administration forms are, for example, percutaneous or topical administration, for example in the form of ointments, creams, tinctures, sprays or transdermal therapeutic systems, or the inhalative administration in the form of nasal sprays or aerosol mixtures, or, for example, microcapsules, implants or wafers.

Pharmaceutical compositions typically must be sterile and stable under the conditions of manufacture and storage. A composition can be formulated as a solution, microemulsion, liposome, or other ordered structure suitable to high drug concentration. The carrier can be a solvent or dispersion medium containing, for example, water, ethanol, polyol (for example, glycerol, propylene glycol, and liquid polyethylene glycol, and the like), and suitable mixtures thereof. The proper fluidity can be maintained, for example, by the use of a coating such as lecithin, by the maintenance of the required particle size in the case of dispersion and by the use of surfactants. In many cases, it will be preferable to include isotonic agents, for example, sugars, polyalcohols such as mannitol, sorbitol, or sodium chloride in the composition. Prolonged absorption of injectable compositions can be brought about by including in the composition an agent which delays absorption, for example, monostearate salts and gelatin. Moreover, a compound can be administered in a time release formulation, for example in a composition which includes a slow release polymer. The compound can be prepared with carriers that will protect against rapid release, such as a controlled release formulation, including implants and microencapsulated delivery systems. Biodegradable, biocompatible polymers can be used, such as ethylene vinyl acetate, polyanhydrides, polyglycolic acid, collagen, polyorthoesters, polylactic acid and polylactic, polyglycolic copolymers (PLG).

Many methods for the preparation of such formulations are generally known to those skilled in the art. Sterile injectable solutions can be prepared by incorporating an active compound, such as a polypeptide or binding agent provided herein, in the required amount in an appropriate solvent with one or a combination of ingredients enumerated above, as required, followed by filtered sterilization. Generally, dispersions are prepared by incorporating the active compound into a sterile vehicle that contains a basic dispersion medium and the required other ingredients from those enumerated above. In the case of sterile powders for the preparation of sterile injectable solutions, common methods of preparation are vacuum drying and freeze-drying which yields a powder of the active ingredient plus any additional desired ingredient from a previously sterile-filtered solution thereof. Compounds may also be formulated with one or more additional compounds that enhance their solubility.

In some embodiments, a pharmaceutical composition of the disclosure comprises a sterile injectable solution. In some embodiments, the sterile injectable solution comprises a sterile powder which is reconstituted with an acceptable solution, e.g., water.

It is often advantageous to formulate compositions (such as parenteral compositions) in dosage unit form for ease of administration and uniformity of dosage. The term "unit dosage form" refers to a physically discrete unit suitable as unitary dosages for human subjects and other animals, each unit containing a predetermined quantity of active material calculated to produce the desired therapeutic effect, in association with a suitable pharmaceutical carrier. The specification for the dosage unit forms of the invention may vary and are dictated by and directly dependent on (a) the unique characteristics of the therapeutic compound and the particular therapeutic effect to be achieved, and (b) the limitations inherent in the art of compounding such a therapeutic compound for the prevention or treatment of a TGFβ-superfamily associated disease or condition. Dosages are discussed further below.

The dosage regimen will be determined by the attending physician and clinical factors. As is well known in the medical arts, dosages for any one patient depend upon many factors, including the patient's size, body surface area, age, the particular compound to be administered, sex, time and route of administration, general health, and other drugs being administered concurrently.

For any compound, the therapeutically effective dose may be estimated initially either in cell culture assays or in animal models such as mice, rats, rabbits, dogs, or pigs. An animal model may also be used to determine the concentration range and route of administration. Such information may then be used to determine useful doses and routes for administration in humans. These techniques are well known to one skilled in the art and a therapeutically effective dose refers to that amount of active ingredient that ameliorates the symptoms or condition. Therapeutic efficacy and toxicity may be determined by standard pharmaceutical procedures in cell cultures or with experimental animals, such as by calculating and contrasting the ED50 (the dose therapeutically effective in 50% of the population) and LD50 (the dose lethal to 50% of the population). Any of the pharmaceutical compositions described herein may be applied to any subject in need of therapy, including, but not limited to, mammals such as dogs, cats, cows, horses, rabbits, monkeys, and especially humans.

The terms "effective dose", "effective dosage" and "effective amount" are used interchangeably to refer to an amount sufficient to achieve or at least partially achieve the desired effect. The term "therapeutically effective" dose or amount is defined as an amount sufficient to treat or to ameliorate or at least partially arrest the disease and its complications in a patient already suffering from the disease. A therapeutically effective amount of a polypeptide or binding agent or pharmaceutical composition of the disclosure generally results in a decrease in severity of disease symptoms, an increase in frequency or duration of disease symptom-free periods or a prevention of impairment or disability due to the disease affliction. In some embodiments, a therapeutically effective amount is an amount or dose of a polypeptide or binding agent or composition that prevents or treats a TGFβ superfamily-associated disease or disorder in a subject, as described herein. In some embodiments, an effective amount is an amount or dose of a polypeptide or binding agent or composition that inhibits one or more of activin A, activin B, GDF-8, GDF-11, and BMP-10 in a subject, as described herein.

Amounts or doses effective for this use will depend on the disorder to be treated (the indication), the delivered polypeptide or binding agent, the therapeutic context and objectives, the severity of the disease, prior therapy, the patient's clinical history and response to the therapeutic agent, the route of administration, the size (body weight, body surface or organ size) and/or condition (the age and general health) of the patient, and the general state of the patient's own immune system. The proper dose can be adjusted according to the judgment of the attending physician such that it can be administered to the patient once or over a series of administrations, and in order to obtain the optimal therapeutic effect.

A typical dosage may range from about 0.1 μg/kg to up to about 30 mg/kg or more, depending on the factors mentioned above. In specific embodiments, the dosage may range from 1.0 μg/kg up to about 20 mg/kg, optionally from 10 μg/kg up to about 10 mg/kg or from 100 μg/kg up to about 5 mg/kg. Dosages are discussed further below.

Methods of Use

Formulations described herein are useful as pharmaceutical compositions in the treatment, amelioration and/or prevention of a disease/disorder as described herein in a subject in need thereof. The term "treatment" refers to both therapeutic treatment and prophylactic or preventative measures. Treatment includes the application or administration of the formulation to the body, an isolated tissue, or cell from a patient who has a disease/disorder, a symptom of a disease/disorder, or a predisposition toward a disease/disorder, with the purpose to cure, heal, alleviate, relieve, alter, remedy, ameliorate, improve, or affect the disease, the symptom of the disease, or the predisposition toward the disease.

The term "amelioration" as used herein refers to any improvement of the disease state of a patient having a disease/disorder as specified herein below, by the administration of a polypeptide or binding agent or pharmaceutical composition according to the disclosure to a subject. For example, the term "amelioration" means to decrease, suppress, attenuate, diminish, arrest, or stabilize the development or progression of a disease. Such an improvement may also be seen as a slowing or stopping of the progression of disease/disorder of the patient. The term "prevention" as used herein means the avoidance of the occurrence or re-occurrence of a patient having a disease/disorder as specified herein below, by the administration of polypeptide or binding agent or pharmaceutical composition according to the disclosure to a subject in need thereof.

The term "disease or condition" (or "disease/condition") refers to any pathological medical condition that would benefit from treatment with the polypeptide or binding agent or the pharmaceutic composition described herein. This includes chronic and acute diseases or conditions including those pathological conditions that predispose the mammal to the disease/disorder in question. In some embodiments, the polypeptide or binding agent of the disclosure and compositions thereof are useful in the prevention, treatment or amelioration of a TGFβ superfamily associated disease or condition. As such, there are provided methods for prevention or treatment of a TGFβ superfamily associated disease or condition in a subject, the methods comprising administering a therapeutically effective amount of the polypeptide or binding agent or pharmaceutical composition described herein. Polypeptides and binding agents are generally administered in the form of a pharmaceutical composition. A subject may be in need of such treatment, i.e., having, suspected of having, or at risk of having a disease or condition associated with TGFβ superfamily signaling or mediated by one or more member of the TGFβ superfamily, as described herein.

The term "inhibition" or "inhibiting" is used herein to refer generally to reducing, slowing, restricting, delaying, suppressing, blocking, neutralizing, hindering, or preventing a process, such as without limitation reducing or slowing progression, growth, or spread of a disease or condition.

In some embodiments of the present disclosure, "treating" refers to neutralizing the biologic activity of excess activin A, activin B, GDF-8, GDF-11, and/or BMP-10. It may be determined by suitable clinical variables of improvement; by pathologic evaluation of the effects on a disease or condition; by a direct inhibition of activin A, activin B, GDF-8, GDF-11, and/or BMP-10 signaling (without substantially inhibiting BMP-9); or by another measure suitable for the disease or condition being treated.

In some embodiments, improvement is determined by comparing clinical variables to measurements made before treatment, or alternatively to typical values measured in healthy adults. In some embodiments, treatment or prevention are within the context of the present disclosure if there is a measurable difference between the performances of subjects treated using the polypeptides, binding agents, compositions and methods provided herein as compared to members of a placebo group, historical control, or between subsequent tests given to the same subject.

The term "subject" includes living organisms with a TGFβ superfamily associated disease or condition, or who are susceptible to or at risk thereof. Examples of subjects include mammals, e.g., humans, monkeys, cows, rabbits, sheep, goats, pigs, dogs, cats, rats, mice, and transgenic species thereof. The term "subject" generally includes animals susceptible to states characterized by TGFβ superfamily associated diseases or conditions such as pulmonary hypertension, fibrosis, muscle weakness and atrophy, metabolic disorders and/or cardiometabolic disease, bone damage, or low red blood cell levels, e.g., mammals, e.g., primates, e.g., humans. The animal can also be an animal model for a disorder, e.g., a mouse model, a xenograft recipient, and the like. In certain embodiments, the subject is a human.

There are no particular limitations on the dose of the polypeptide or binding agent for use in the compositions and methods of the disclosure. Exemplary doses include milligram or microgram amounts of the polypeptide or binding agent per kilogram of subject or sample weight (e.g., about 50 micrograms per kilogram to about 500 milligrams per kilogram, about 1 milligram per kilogram to about 100 milligrams per kilogram, about 1 milligram per kilogram to about 50 milligram per kilogram, about 1 milligram per kilogram to about 10 milligrams per kilogram, or about 3 milligrams per kilogram to about 5 milligrams per kilogram). Additional exemplary doses include doses of about 5 to about 500 mg, about 25 to about 300 mg, about 25 to about 200 mg, about 50 to about 150 mg, or about 50, about 100, about 150 mg, about 200 mg or about 250 mg, and, for example, daily or twice daily, or lower or higher amounts.

In some embodiments, the dose range for adult humans is generally from 0.005 mg to 10 g/day. Polypeptide or binding agent and compositions thereof may be provided in Unit dosage form, e.g., in a unit which is effective at such dosage or as a multiple of the same, for instance, units containing 5 mg to 500 mg, usually around 10 mg to 200 mg. A dosage unit can include from, for example, 1 to 30 mg, 1 to 40 mg, 1 to 100 mg, 1 to 300 mg, 1 to 500 mg, 2 to 500 mg, 3 to 100 mg, 5 to 20 mg, 5 to 100 mg (e.g. 1 mg, 2 mg, 3 mg, 4 mg, 5 mg, 6 mg, 7 mg, 8 mg, 9 mg, 10 mg, 11 mg, 12 mg, 13 mg, 14 mg, 15 mg, 16 mg, 17 mg, 18 mg, 19 mg, 20 mg, 25 mg, 30 mg, 35 mg, 40 mg, 45 mg, 50 mg, 55 mg, 60 mg, 65 mg, 70 mg, 75 mg, 80 mg, 85 mg, 90 mg, 95 mg, 100 mg, 150 mg, 200 mg, 250 mg, 300 mg, 350 mg, 400 mg, 450 mg, or 500 mg) of a polypeptide or binding agent or composition described herein.

It should be understood that the effective amount of a polypeptide or binding agent for therapeutic treatment of a disease or condition varies depending upon the manner of administration, the age, body weight, and general health of the subject. Ultimately, the attending physician or veterinarian decides the appropriate amount and dosage regimen. It should be understood that the dosage or amount of a polypeptide or binding agent used, alone or in combination with one or more active compounds to be administered, depends on the individual case and is, as is customary, to be adapted to the individual circumstances to achieve an optimum effect. Dosing and administration regimens are within the purview of the skilled artisan, and appropriate doses depend upon a number of factors within the knowledge of the ordinarily skilled physician, veterinarian, or researcher (e.g., see Wells et al. eds., Pharmacotherapy Handbook, 2nd Edition, Appleton and Lange, Stamford, Conn. (2000); PDR Pharmacopoeia, Tarascon Pocket Pharmacopoeia 2000, Deluxe Edition, Tarascon Publishing, Loma Linda, Calif. (2000)). For example, dosing and administration regimens depend on the nature and the severity of the disease or condition to be treated, and also on the sex, age, weight and individual responsiveness of the human or animal to be treated, on the efficacy and duration of action of the compounds used, on whether the therapy is acute or chronic or prophylactic, and/or on whether other active compounds are administered in addition to the therapeutic molecule(s).

Administration of polypeptides or binding agents or compositions provided herein can be carried out using known procedures, at dosages and for periods of time effective to achieve the desired purpose. Dosage regimens can be adjusted to provide the optimum therapeutic response. For example, several divided doses may be administered daily, weekly, biweekly, or monthly, or the dose may be proportionally reduced as indicated by the exigencies of the therapeutic situation. In some embodiments, a polypeptide or binding agent or composition is administered at a therapeutically effective dosage sufficient to prevent or treat a TGFβ superfamily associated disease or condition, e.g., pulmonary hypertension, fibrosis, muscle weakness and atrophy, metabolic disorders and/or cardiometabolic disease, bone damage, and/or low red blood cell levels, in a subject.

In some embodiments, in accordance with the methods of the present disclosure, one or more symptom of development or progression of a TGFβ superfamily associated disease or condition is reduced by at least 5%, e.g., at least 10%, at least 15%, at least 20%, at least 25%, at least 30%, at least 35%, at least 40%, at least 45%, at least 50%, at least 55%, at least 60%, at least 65%, at least 70%, at least 75%, at least 80%, at least 85%, at least 90%, at least 95%, or 100% in a subject.

In some embodiments of methods provided herein, the polypeptide or binding agent is administered in combination with one or more additional therapy or therapeutic agent. The additional therapy or therapeutic agent can be administered before, after or simultaneously with the administration of the polypeptide or binding agent or composition described herein. In some embodiments, the additional therapy or therapeutic agent is formulated together with the polypeptide or binding agent in the same composition. In other embodiments, the additional therapy or therapeutic agent is administered separately. Examples of additional therapies and therapeutic agents include, without limitation, an anti-fibrotic agent; an anti-cancer agent; an anti-inflammatory agent; an anti-obesity agent; an anti-diabetes agent; another TGF□ superfamily ligand binding agent or inhibitor, such as an antibody, antibody fragment, antigen-binding fragment, soluble TGFβ superfamily ligand trap, and the like; another agent that binds or inhibits one or more additional target, and the like.

Alternatively, in some embodiments, the polypeptide or binding agent may be conjugated with a detectable moiety or a diagnostic moiety that is useful for tracking the polypeptide or binding agent or cells or tissues expressing TGFβ superfamily ligands and/or another target. In some such embodiments, there are provided methods of diagnosis of a TGFβ superfamily associated disease or condition comprising administering to a subject a polypeptide or binding agent of the present disclosure conjugated with a detectable moiety or a diagnostic moiety, and detecting the polypeptide or binding agent such that a disease or disorder associated with TGFβ superfamily signaling (e.g., overexpression of activin A, activin B, GDF-8, GDF-11, or BMP-10) is diagnosed.

TGFβ Superfamily Associated Diseases and Conditions

The polypeptide or binding agent described herein, and pharmaceutical compositions thereof, are useful for prevention or treatment of TGFβ superfamily associated diseases and conditions. As such, there are provided methods for prevention or treatment of a disease or condition associated with TGFβ-superfamily ligand signaling in a subject, the methods comprising administering a therapeutically effective amount of the polypeptide, binding agent, or pharmaceutical composition described herein. Polypeptides and binding agents are generally administered in the form of a pharmaceutical composition. A subject may be in need of such treatment, i.e., having, suspected of having, or at risk of developing a disease or condition associated with TGFβ superfamily signaling, as described herein.

As used herein, the term "TGFβ-superfamily ligand signaling associated disease or condition" refers to diseases and conditions that may be ameliorated through inhibition of one or more TGFβ superfamily ligand, particularly activin A, activin B, GDF-8, GDF-11, and/or BMP-10 activity. TGFβ-superfamily associated diseases or conditions include, without limitation, diseases and conditions associated with over-expression or over-activation of TGFβ superfamily ligands, particularly activin A, activin B, GDF-8, GDF-11, and/or BMP-10. In some embodiments, a TGFβ-superfamily associated disease or condition is mediated by activin A and/or activin B. In one embodiment, the disease or condition to be treated is mediated by activin A. In one embodiment, the disease or condition to be treated is mediated by activin B. In one embodiment, the disease or condition to be treated is mediated by GDF-8. In one embodiment, the disease or condition to be treated is mediated by GDF-11. In one embodiment, the disease or condition to be treated is mediated by BMP-10. In another embodiment, the disease or condition to be treated is mediated by a combination of activin A, activin B, GDF-8, and GDF-11.

Examples of TGFβ-superfamily associated diseases or conditions that may be prevented or treated in accordance with the present disclosure include, without limitation: pulmonary hypertension, fibrosis, muscle weakness and atrophy, metabolic disorders and/or cardiometabolic disease, bone damage, and/or low red blood cell levels, as well as vascular diseases and vasculopathies.

Pulmonary Hypertension

In some embodiments, an ActRIIB-ECD polypeptide described herein or TGFβ superfamily ligand binding agent comprising the same is used for treatment or prevention of pulmonary hypertension (PH). For example, a polypeptide or binding agent described herein may be used to treat, prevent or reduce the progression rate and/or severity of a variety of conditions including, but not limited to, pulmonary vascular remodeling, pulmonary fibrosis, and right ventricular hypertrophy, or of one or more PH-associated complications, e.g., to reduce right ventricular systolic pressure in a subject in need thereof.

Pulmonary hypertension is a disease characterized by pulmonary vascular remodeling which results in high pulmonary artery pressure. An imbalance between the growth-promoting activin/growth differentiation factor pathway and the growth-inhibiting BMP pathway promotes the vascular remodeling observed in this disease. For example, elevated activin A has been observed in clinical and experimental pulmonary hypertension. Myostatin and activins are known to play a role in the regulation of skeletal muscle growth. For example, mice without myostatin show a large increase in skeletal muscle mass. Myostatin has also been implicated in promoting fibrosis. For example, mice without myostatin show a reduction in muscle fibrosis. Mice overexpressing activin A also exhibit increased fibrosis. In addition, activins are expressed abundantly in bone tissues and regulate bone formation by controlling both osteoblast and osteoclast functions. Activin has been reported to be upregulated in bone disease. Myostatin is also implicated in bone homeostasis through increasing osteogenesis and inhibiting osteoblast activity. Methods that reduce or inhibit activin and/or GDF signaling could therefore be useful in the treatment of diseases and conditions such as pulmonary hypertension (e.g., PAH, venous PH, hypoxic PH, thromboembolic PH, or miscellaneous PH), muscle atrophy or weakness, fibrosis, bone damage, or low red blood cell levels (e.g., anemia).

PH can be categorized into five major types: arterial (PAH), venous (PH secondary to left-sided heart disease), hypoxic (PH caused by lung disease), thromboembolic (PH caused by chronic arterial obstruction, e.g., blood clots), or miscellaneous (PH with unclear or multifactorial mechanisms), also known as WHO groups 1-V. PAH features increased pressure in blood vessels of the lungs caused by obstruction in, or narrowing of, small blood vessels due to remodeling. This leads to increased resistance to blood flow through the lungs which forces the right side of the heart to work harder, which may lead to heart failure. PAH can be idiopathic, heritable, or may be related to drug use, infection, liver cirrhosis, congenital heart abnormalities, or connective tissue/autoimmune disorders (e.g., scleroderma or lupus). Treatments for PH include vasodilators, anticoagulants, and supplemental oxygen, but these treatments manage disease symptoms rather than targeting the biological mechanisms that cause the disease.

Pulmonary hypertension (PH) is a disease characterized by high blood pressure in lung vasculature, including pulmonary arteries, pulmonary veins, and pulmonary capillaries. In general, PH is defined as a mean pulmonary arterial (PA) pressure ≥25 mm Hg at rest or ≥30 mm Hg with exercise (Hill et al., 2009). The main PH symptom is difficulty in breathing or shortness of breath, and other symptoms include fatigue, dizziness, fainting, peripheral edema (swelling in foot, legs or ankles), bluish lips and skin, chest pain, angina pectoris, light-headedness during exercise, non-productive cough, racing pulse and palpitations. PH can be a severe disease causing heart failure, which is one of the most common causes of death in people who have pulmonary hypertension. Postoperative pulmonary hypertension may complicate many types of surgeries or procedures, and present a challenge associated with a high mortality.

PH may be grouped based on different manifestations of the disease sharing similarities in pathophysiologic mechanisms, clinical presentation, and therapeutic approaches (Simonneau et al., 2009). Clinical classification of PH was first proposed in 1973, and a recent updated clinical classification was endorsed by the World Health Organization (WHO) in 2008. According to the updated PH clinical classification, there are five main groups of PH: pulmonary arterial hypertension (PAH), characterized by a PA wedge pressure ≤15 mm Hg; PH owing to a left heart disease (also known as pulmonary venous hypertension or congestive heart failure), characterized by a PA wedge pressure >15 mm Hg; PH owing to lung diseases and/or hypoxia; chronic thromboemboli PH; and PH with unclear or multifactorial etiologies (Simonneau et al., 2009; Hill et al., 2009). PAH is further classified into idiopathic PAH (IPAH), a sporadic disease in which there is neither a family history of PAH nor an identified risk factor; heritable PAH; PAH induced by drugs and toxins; PAH associated with connective tissue diseases, HIV infection, portal hypertension, congenital heart diseases, schistosomiasis, and chronic hemolytic anemia; and persistent PH of newborns (Simonneau et al., 2009). Diagnosis of various types of PH requires a series of tests.

In general, PH treatment depends on the cause or classification of the PH. Where PH is caused by a known medicine or medical condition, it is known as a secondary PH, and its treatment is usually directed at the underlying disease. Treatment of pulmonary venous hypertension generally involves optimizing left ventricular function by administering diuretics, beta blockers, and ACE inhibitors, or repairing or replacing a mitral valve or aortic valve. PAH therapies include pulmonary vasodilators, digoxin, diuretics, anticoagulants, and oxygen therapy. Pulmonary vasodilators target different pathways, including prostacyclin pathway (e.g., prostacyclins, including intravenous epoprostenol, subcutaneous or intravenous treprostinil, and inhaled iloprost), nitric oxide pathway (e.g., phosphodiesterase-5 inhibitors, including sildenafil and tadalafil), and endotheline-1 pathway (e.g., endothelin receptor antagonists, including oral bosentan and oral ambrisentan) (Humbert, M., 2009; Hill et al., 2009). However, currently available therapies provide no cure for PH, and they do not directly treat the underlying vascular remodeling and muscularization of blood vessels observed in many PH patients.

In some embodiments, the present disclosure relates to methods of treating PH comprising administering to a subject in need thereof an effective amount of an ActRIIB-ECD polypeptide described herein or TGFβ superfamily ligand binding agent comprising the same. In some embodiments, the disclosure relates to methods of preventing PH comprising administering to a patient in need thereof an effective amount of an ActRIIB-ECD polypeptide described herein or TGFβ superfamily ligand binding agent comprising the same. In some embodiments, the disclosure relates to methods of reducing the progression rate of PH comprising administering to a patient in need thereof comprising administering an effective amount of an ActRIIB-ECD polypeptide described herein or TGFβ superfamily ligand binding agent comprising the same.

In some embodiments, the disclosure provides for a method of treating an interstitial lung disease, comprising administering to a subject in need thereof an effective amount of an ActRIIB-ECD polypeptide described herein or TGFβ superfamily ligand binding agent comprising the same, wherein the an ActRIIB-ECD polypeptide described herein or TGFβ superfamily ligand binding agent comprising the same inhibits one or more of activin A, activin B, GDF-8, GDF-11, and BMP-10. In some embodiments, one or more additional TGFβ superfamily ligands such as, without limitation, GDF-3, BMP-6, BMP-15, ALK-4, ALK-5, and ALK-7, may also be inhibited.

In some embodiments, the disclosure provides for a method of treating, preventing, or reducing the progression rate and/or severity of one or more complications of an interstitial lung disease, comprising administering to a patient in need thereof an effective amount of an ActRIIB-ECD polypeptide described herein or TGFβ superfamily ligand binding agent comprising the same, wherein the polypeptide or binding agent inhibits one or more of activin A, activin B, GDF-8, GDF-11, and BMP-10. In some embodiments, the interstitial lung disease is idiopathic pulmonary fibrosis. In some embodiments, the disclosure relates to methods of reducing the severity of PH comprising administering to a patient in need thereof an effective amount of an ActRIIB-ECD polypeptide described herein or TGFβ superfamily ligand binding agent comprising the same. In certain aspects, the disclosure relates to methods of treating one or more complications (e.g., smooth muscle and/or endothelial cell proliferation in the pulmonary artery, angiogenesis in the pulmonary artery, dyspnea, chest pain, pulmonary vascular remodeling, right ventricular hypertrophy, and pulmonary fibrosis) of pulmonary hypertension comprising administering to a patient in need thereof an effective amount of a polypeptide or binding agent described herein.

In certain embodiments, the disclosure relates to methods of preventing one or more complication of PH (e.g., smooth muscle and/or endothelial cell proliferation in the pulmonary artery, angiogenesis in the pulmonary artery, dyspnea, chest pain, pulmonary vascular remodeling, right ventricular hypertrophy, and pulmonary fibrosis) comprising administering to a patient in need thereof an effective amount of an ActRIIB-ECD polypeptide described herein or TGFβ superfamily ligand binding agent comprising the same. In certain embodiments, the disclosure relates to methods of reducing the progression rate of one or more complication of PH (e.g., smooth muscle and/or endothelial cell proliferation in the pulmonary artery, angiogenesis in the pulmonary artery, dyspnea, chest pain, pulmonary vascular remodeling, right ventricular hypertrophy, and pulmonary fibrosis) comprising administering to a patient in need thereof an effective amount of a polypeptide or binding agent described herein. In certain aspects, the disclosure relates to methods of reducing the severity of one or more complication of pulmonary hypertension (e.g., smooth muscle and/or endothelial cell proliferation in the pulmonary artery, angiogenesis in the pulmonary artery, dyspnea, chest pain, pulmonary vascular remodeling, right ventricular hypertrophy, and pulmonary fibrosis) comprising administering to a patient in need thereof an effective amount of an ActRIIB-ECD polypeptide described herein or TGFβ superfamily ligand binding agent comprising the same.

In certain preferred embodiments, methods described herein relate to a subject having pulmonary arterial hypertension (PAH). In some embodiments, methods described herein relate to a subject having a resting pulmonary arterial pressure (PAP) of at least 25 mm Hg (e.g., at least 25, at least 30, at least 35, at least 40, at least 45, or at least 50 mm Hg). In some embodiments, the methods described herein reduce PAP in a subject having pulmonary hypertension. For example, the method may reduce PAP by at least 3 mmHg (e.g., at least 3, at least 5, at least 7, at least 10, at least 12, at least 15, at least 20, or at least 25 mm Hg) in a subject having pulmonary hypertension. In some embodiments, the methods described herein reduce pulmonary vascular resistance in a subject having pulmonary hypertension.

In some embodiments, the methods described herein increase pulmonary capillary wedge pressure in a subject having pulmonary hypertension. In some embodiments, the methods described herein increase left ventricular end-diastolic pressure in a subject having pulmonary hypertension. In some embodiments, the methods described herein increase (improve) exercise capacity (ability, tolerance) in a subject having pulmonary hypertension. For example, the method may increase 6-minute walk distance in a subject having pulmonary hypertension, optionally increasing 6-minute walk distance by at least 10 meters (e.g., at least 10, at least 20, at least 30, at least 40, at least 50, at least 60, at least 70, at least 80, at least 90, at least 100 or more meters). In addition, the method may reduce the subject's Borg dyspnea index (BDI), which optionally may be assessed after a 6-minute walk test. In some embodiments, the method reduces the subject's Borg dyspnea index (BDI) by at least 0.5 index points (e.g., at least 0.5, 1, 1.5, 2, 2.5, 3, 3.5, 4, 4.5, 5, 5.5, 6, 6.5, 7, 7.5, 8, 8.5, 9, 9.5, or 10 index points). In some embodiments, the methods described herein relate to a subject having Class I, Class II, Class III, or Class IV pulmonary hypertension as recognized by the World Health Organization. In some embodiments, the methods described herein relate to delaying clinical progression (worsening) of pulmonary hypertension (e.g., progression as measured by the World Health Organization standard). In some embodiments, the method prevents or delays pulmonary hypertension Class progression (e.g., prevents or delays progression from Class I to Class II, Class II to Class III, or Class III to Class IV pulmonary hypertension as recognized by the World Health Organization). In some embodiments, the method promotes or increases pulmonary hypertension Class regression (e.g., promotes or increases regression from Class IV to Class III, Class III to Class II, or Class II to Class I pulmonary hypertension as recognized by the World Health Organization).

In some embodiments, the subject is further administered one or more supportive therapies or active agents for treating pulmonary hypertension in addition to the one or more polypeptide or binding agent of the disclosure. For example, the subject also may be administered one or more supportive therapies or active agents selected from the group consisting of: prostacyclin and derivatives thereof (e.g., epoprostenol, treprostinil, and iloprost); prostacyclin receptor agonists (e.g., selexipag); endothelin receptor antagonists (e.g., thelin, ambrisentan, macitentan, and bosentan); calcium channel blockers (e.g., amlodipine, diltiazem, and nifedipine; anticoagulants (e.g., warfarin); diuretics; oxygen therapy; atrial septostomy; pulmonary thromboendarterectomy; phosphodiesterase type 5 inhibitors (e.g., sildenafil and tadalafil); activators of soluble guanylate cyclase (e.g., cinaciguat and riociguat); ASK-1 inhibitors (e.g., CIIA; SCH79797; GS-4997; MSC2032964A; 3H-naphtho[1,2,3-de]quiniline-2,7-diones, NQDI-1; 2-thioxo-thiazolidines, 5-bromo-3-(4-oxo-2-thioxo-thiazolidine-5-ylidene)-1,3-dihydro-indol-2-one-); NF-κB antagonists (e.g., dh404, CDDO-epoxide; 2.2-difluoropropionamide; C28 imidazole (CDDO-Im); 2-cyano-3,12-dioxoolean-1,9-dien-28-oic acid (CDDO); 3-Acetyloleanolic Acid; 3-Triflouroacetyloleanolic Acid; 28-Methyl-3-acetyloleanane; 28-Methyl-3-trifluoroacetyloleanane; 28-Methyloxyoleanolic Acid; SZCO14; SCZ015; SZC017; PEGylated derivatives of oleanolic acid; 3-O-(beta-D-glucopyranosyl) oleanolic acid; 3-O-[beta-D-glucopyranosyl-(1→3)-beta-D-glucopyranosyl]oleanolic acid; 3-O-[beta-D-glucopyranosyl-(1→2)-beta-D-glucopyranosyl]oleanolic acid; 3-O-[beta-D-glucopyranosyl-(1→3)-beta-D-glucopyranosyl]oleanolic acid 28-O-beta-D-glucopyranosyl ester; 3-O-[beta-D-glucopyranosyl-(1→2)-beta-D-glucopyranosyl]oleanolic acid 28-O-beta-D-glucopyranosyl ester; 3-O-[a-L-rhamnopyranosyl-(1→3)-beta-D-glucuronopyranosyl]oleanolic acid; 3-O-[alpha-L-rhamnopyranosyl-(1→3)-beta-D-glucuronopyranosyl-] oleanolic acid 28-O-beta-D-glucopyranosyl ester; 28-O-β-D-glucopyranosyl-oleanolic acid; 3-O-β-D-glucopyranosyl (1→3)-β-D-glucopyranosiduronic acid (CS1); oleanolic acid 3-O-β-D-glucopyranosyl (1→3)-β-D-glucopyranosiduronic acid (CS2); methyl 3,11-dioxoolean-12-en-28-olate (DIOXOL); ZCVI4-2; Benzyl 3-dehydroxy-1,2,5-oxadiazolo[3',4':2,3]oleanolate) lung and/or heart transplantation.

In some embodiments, the subject may also be administered a BMP-9 polypeptide. In some embodiments the BMP-9 polypeptide is a mature BMP-9 polypeptide. In some embodiments, the BMP-9 polypeptide comprises a BMP-9 prodomain polypeptide. In some embodiments, the BMP-9 polypeptide is administered in a pharmaceutical preparation, which optionally may comprise a BMP-9 prodomain polypeptide. In such BMP-9 pharmaceutical preparations comprising a BMP-9 prodomain polypeptide, the BMP-9 polypeptide may be noncovalently associated with the BMP-9 prodomain polypeptide. In some embodiments, BMP-9 pharmaceutical preparations are substantially free, or do not comprise, of BMP9 prodomain polypeptide. In some embodiments, the subject may also be administered oleanolic acid or a derivative thereof.

Fibrosis

In some embodiments, a polypeptide or binding agent described herein is used for treatment or prevention of fibrosis. For example, an ActRIIB-ECD polypeptide described herein or TGFβ superfamily ligand binding agent comprising the same may be used to treat, prevent or reduce the progression rate and/or severity of a variety of conditions including, but not limited to, fibrotic disease of tissues and/or organs, fibrotic scarring, and fibroproliferative disorders, in a subject in need thereof. Non-limiting examples of fibrotic diseases or conditions include pulmonary fibrosis (e.g., idiopathic pulmonary fibrosis), renal fibrosis, liver fibrosis (e.g., hepatic cirrhosis), systemic sclerosis, scleroderma, skin fibrosis, heart fibrosis, bone marrow fibrosis, ocular fibrosis, and myelofibrosis. In one particular embodiment, systemic sclerosis (SSc) is treated or prevented. In another particular embodiment, scleroderma is treated or prevented. In another particular embodiment, myelofibrosis (MF) is treated or prevented.

Fibrosis is the formation of excess connective tissue in an organ or tissue. The connective tissue, which can form in response to damage (e.g., injury) or as part of an immune response (e.g., an inflammatory response), can disrupt the structure and function of the organ or tissue in which it forms, leading to an increase in tissue stiffness. Fibrosis can occur in many organs and tissues within the body, including the lung (e.g., pulmonary fibrosis, cystic fibrosis), liver (e.g., cirrhosis), heart (e.g., endomyocardial fibrosis or fibrosis after myocardial infarction), brain (e.g., glial scar formation), skin (e.g., formation of keloids), kidney (e.g., renal fibrosis), and eye (e.g., corneal fibrosis), among others; and is known to be associated with certain medical treatments (e.g., chemotherapy, radiation therapy, and surgery). However, there are limited treatment options currently available for subjects with fibrosis, and most available treatments are focused on improving quality of life or temporarily slowing disease progression.

Other exemplary embodiments of fibrosis that may be prevented or treated include, for example and without limitation: interstitial lung disease; human fibrotic lung disease (e.g., obliterative bronchiolitis, idiopathic pulmonary fibrosis, pulmonary fibrosis from a known etiology, tumor stroma in lung disease, systemic sclerosis affecting lungs, Hermansky-Pudlak syndrome, coal worker's pneumoconiosis, asbestosis, silicosis, chronic pulmonary hypertension); AIDS-associated treatable types of fibrosis, including lung fibrosis, cystic fibrosis, liver fibrosis, heart fibrosis, mediastinal fibrosis, retroperitoneal cavity fibrosis, bone marrow fibrosis, skin fibrosis; scleroderma; and systemic sclerosis. Specific forms of fibrosis that can be treated or prevented include those that affect any organ or tissue or cell of the body, such as human tenon's fibroblasts, kidney, lung, intestine, liver, heart, bone marrow, genitalia, skin and eye. These diseases include, but are not limited to, cystic fibrosis, systemic sclerosis, chronic obstructive pulmonary disease (COPD), Dupuytren's contracture, glomerulonephritis, liver fibrosis, post-infarction cardiac fibrosis, restenosis, ocular surgery-induced fibrosis, and scarring. Genetic disorders of connective tissue can also be treated, and include but are not limited to, Marfan syndrome (MFS) and Osteogenesis imperfecta.

In some embodiments, an ActRIIB-ECD polypeptide described herein or TGFβ superfamily ligand binding agent comprising the same is used for inhibiting differentiation of fibroblasts into myofibroblasts.

In some embodiments, an ActRIIB-ECD polypeptide described herein or TGFβ superfamily ligand binding agent comprising the same is used for treatment or prevention of a fibroproliferative disorder. Fibroproliferative disorders are characterized by proliferation of fibroblasts plus the corresponding overexpression of extracellular matrix such as fibronectin, laminin and collagen.

In some embodiments, the disclosure provides for a method of decreasing or preventing fibrosis in a subject in need thereof by administering to the subject a therapeutically effective amount of an ActRIIB-ECD polypeptide described herein or TGFβ superfamily ligand binding agent comprising the same or a pharmaceutical composition described herein.

In some embodiments, the disclosure provides for a method of slowing or inhibiting the progression of fibrosis in a subject in need thereof by administering to the subject a therapeutically effective amount of an ActRIIB-ECD polypeptide described herein or TGFβ superfamily ligand binding agent comprising the same or a pharmaceutical composition described herein.

In some embodiments, the disclosure provides for a method of reducing the risk of developing fibrosis in a subject in need thereof by administering to the subject a therapeutically effective amount of an ActRIIB-ECD polypeptide described herein or TGFβ superfamily ligand binding agent comprising the same described herein or a pharmaceutical composition described herein.

In some embodiments, the disclosure provides for a method of treating a subject having or at risk of developing fibrosis by administering to the subject a therapeutically effective amount of a polypeptide or binding agent described herein or a pharmaceutical composition described herein.

In some embodiments, the fibrosis is chemotherapeutic drug-induced fibrosis, radiation-induced fibrosis, pulmonary fibrosis, hepatic fibrosis, renal fibrosis (e.g., fibrosis related to chronic kidney disease), corneal fibrosis, heart fibrosis, bone marrow fibrosis, mediastinal fibrosis, retropertinoneal fibrosis, arthrofibrosis, osteoarticular fibrosis, tissue fibrosis, a tumor stroma, a desmoplastic tumor, a surgical adhesion, a hypertrophic scar, or a keloid.

In some embodiments, the fibrosis is fibrosis associated with wounds, burns, hepatitis B or C infection, fatty liver disease, *Schistosoma* infection, kidney disease (e.g., chronic kidney disease), heart disease, macular degeneration, Crohn's disease, retinal or vitreal retinopathy, systemic or local scleroderma, atherosclerosis, or restenosis. In some embodiments, the fibrosis results from chronic kidney disease. In some embodiments, the disease or condition is chemotherapeutic drug-induced fibrosis, radiation-induced fibrosis, pulmonary fibrosis, hepatic fibrosis, renal fibrosis (e.g., fibrosis related to chronic kidney disease), corneal fibrosis, heart fibrosis, bone marrow fibrosis, mediastinal fibrosis, retroperitoneal fibrosis, arthrofibrosis, osteoarticular fibrosis, tissue fibrosis, a tumor stroma, a desmoplastic tumor, a surgical adhesion, a hypertrophic scar, or a keloid. In some embodiments, the disease or condition is fibrosis associated with wounds, burns, hepatitis B or C infection, fatty liver disease, *Schistosoma* infection, kidney disease (e.g., chronic kidney disease), heart disease, macular degeneration, Crohn's disease, retinal or vitreal retinopathy, systemic or local scleroderma, atherosclerosis, or restenosis. In some embodiments, the fibrosis results from chronic kidney disease.

In some embodiments, the tissue fibrosis is fibrosis affecting a tissue selected from the group consisting of muscle tissue, skin epidermis, skin dermis, tendon, cartilage, pancreatic tissue, uterine tissue, neural tissue, heart tissue, testis, ovary, adrenal gland, artery, vein, colon, small intestine, large intestine, biliary tract, and gut.

In some embodiments, the disclosure provides for a method of improving the function of a fibrotic tissue or organ. In some embodiments, the disclosure provides for a method of slowing or inhibiting the progression of fibrosis. In some embodiments, the disclosure provides for a method of reducing one or more symptom of fibrosis, for example reducing the frequency or severity of one or more symptom of fibrosis.

In some embodiments, the disclosure provides for a method of treating a subject having or at risk of developing a fibrotic disease comprising administering to a subject in need thereof an effective amount of a polypeptide or binding agent or pharmaceutical composition described herein. In some such embodiments, activin A, activin B, GDF-8, GDF-11, and/or BMP-10 signaling is inhibited in the subject. For example, in some embodiments the disclosure relates to methods of reducing or inhibiting the binding of activin A, activin B, GDF-8, GDF-11, and/or BMP-10 to their endogenous receptors in a subject having or at risk of developing a disease or condition involving fibrosis, the method comprising administering to a subject in need thereof an effective amount of an ActRIIB-ECD polypeptide described herein or TGFβ superfamily ligand binding agent comprising the same or pharmaceutical composition described herein.

In some embodiments, in accordance with the methods of the present disclosure, fibrotic symptoms are reduced in a subject. For example, the polypeptide or binding agent or composition may reduce fibrosis, fibrotic scarring, or skin thickening in a subject by at least 5%, e.g., at least 10%, at least 15%, at least 20%, at least 25%, at least 30%, at least 35%, at least 40%, at least 45%, at least 50%, at least 55%, at least 60%, at least 65%, at least 70%, at least 75%, at least 80%, at least 85%, at least 90%, at least 95%, or 100%.

In some embodiments, in accordance with the methods of the present disclosure, the differentiation of fibroblasts into myofibroblasts is inhibited in a subject, e.g., by at least 5%, e.g., at least 10%, at least 15%, at least 20%, at least 25%, at least 30%, at least 35%, at least 40%, at least 45%, at least 50%, at least 55%, at least 60%, at least 65%, at least 70%, at least 75%, at least 80%, at least 85%, at least 90%, at least 95%, or 100%.

In some embodiments, in accordance with the methods of the present disclosure, tumor growth and/or metastasis is inhibited in a subject, e.g., by at least 5%, e.g., at least 10%, at least 15%, at least 20%, at least 25%, at least 30%, at least 35%, at least 40%, at least 45%, at least 50%, at least 55%, at least 60%, at least 65%, at least 70%, at least 75%, at least 80%, at least 85%, at least 90%, at least 95%, or 100%.

In some embodiments, in accordance with the methods of the present disclosure, hematopoietic colony formation and/or hematopoiesis in bone marrow hematopoietic stem or progenitor cells (HSPCs) is increased in the bone marrow of a subject, e.g., by at least 5%, e.g., at least 10%, at least 15%, at least 20%, at least 25%, at least 30%, at least 35%, at least 40%, at least 45%, at least 50%, at least 55%, at least 60%, at least 65%, at least 70%, at least 75%, at least 80%, at least 85%, at least 90%, at least 95%, or 100%.

In some embodiments, in accordance with the methods of the present disclosure, a positive response in lung fibrosis is revealed as a consistent slowing in the rate of decline in lung function, as measured by forced vital capacity.

In some embodiments, in accordance with the methods of the present disclosure, a positive response for skin fibrosis associated with systemic sclerosis is determined by an improvement in the Modified Rodnan Skin Score (MRSS). For example, the MRSS may improve in a subject by at least 5%, e.g., at least 10%, at least 15%, at least 20%, at least 25%, at least 30%, at least 35%, at least 40%, at least 45%, at least 50%, at least 55%, at least 60%, at least 65%, at least 70%, at least 75%, at least 80%, at least 85%, at least 90%, at least 95%, or 100%.

Muscle Weakness and Atrophy

In some embodiments, an ActRIIB-ECD polypeptide described herein or TGFβ superfamily ligand binding agent comprising the same is used for treatment or prevention of diseases and conditions involving muscle disorders, such as without limitation, muscle weakness and atrophy. For example, an ActRIIB-ECD polypeptide described herein or TGFβ superfamily ligand binding agent comprising the same herein may be used to treat, prevent or reduce the progression rate and/or severity of a variety of conditions including, but not limited to, Duchenne muscular dystrophy (DMD), facioscapulohumeral muscular dystrophy (FSHD), inclusion body myositis (IBM), amyotrophic lateral sclerosis (ALS), sarcopenia, or cancer cachexia.

Duchenne muscular dystrophy (DMD), facioscapulohumeral muscular dystrophy (FSHD), inclusion body myositis (IBM), and amyotrophic lateral sclerosis (ALS) are examples of muscle diseases that involve weakness and atrophy of muscles and/or motor neurons that control voluntary muscle movements. DMD is caused by mutations in the X-linked dystrophin gene and characterized by progressive muscle degeneration and weakness in all skeletal muscles. FSHD particularly affects skeletal muscles of the face, shoulders, upper arms, and lower legs. IBM is an inflammatory muscle disease that mainly affects muscles of the thighs and muscles of the arms that control finger and wrist flexion. ALS is a motor neuron disease characterized by stiff muscles, muscle twitching, and muscle atrophy throughout the body due to the degeneration of the motor neurons. However, few treatment options are available for these devastating muscle diseases.

In some embodiments, the present disclosure relates to methods of treating DMD comprising administering to a subject in need thereof an effective amount of an ActRIIB-ECD polypeptide described herein or TGFβ superfamily ligand binding agent comprising the same. In some embodiments, the disclosure relates to methods of preventing FSHD comprising administering to a subject in need thereof an effective amount of an ActRIIB-ECD polypeptide described herein or TGFβ superfamily ligand binding agent comprising the same. In some embodiments, the disclosure relates to methods of treating IBM comprising administering to a patient in need thereof an effective amount of an ActRIIB-ECD polypeptide described herein or TGFβ superfamily ligand binding agent comprising the same. In some embodiments, the present disclosure relates to methods of treating ALS comprising administering to a subject in need thereof an effective amount of an ActRIIB-ECD polypeptide described herein or TGFβ superfamily ligand binding agent comprising the same. In some embodiments, the present disclosure relates to methods of treating sarcopenia comprising administering to a subject in need thereof an effective amount of an ActRIIB-ECD polypeptide described herein or TGFβ superfamily ligand binding agent comprising the same. In some embodiments, the present disclosure relates to methods of treating cancer cachexia comprising administering to a subject in need thereof an effective amount of an ActRIIB-ECD polypeptide described herein or TGFβ superfamily ligand binding agent comprising the same.

In some embodiments, the disclosure provides for a method of increasing muscle mass and/or strength in a subject in need thereof comprising administering to a subject in need thereof an effective amount of an ActRIIB-ECD polypeptide described herein or TGFβ superfamily ligand binding agent comprising the same.

In some embodiments, the disclosure provides for a method of increasing lean mass in a subject in need thereof comprising administering to a subject in need thereof an effective amount of an ActRIIB-ECD polypeptide described herein or TGFβ superfamily ligand binding agent comprising the same.

In some embodiments, the disclosure provides for a method of increasing muscle mass in a subject in need thereof comprising administering to a subject in need thereof an effective amount of an ActRIIB-ECD polypeptide described herein or TGFβ superfamily ligand binding agent comprising the same.

In some embodiments, the disclosure provides for a method of treating a subject having or at risk of developing a muscle disease comprising administering to a subject in need thereof an effective amount of an ActRIIB-ECD polypeptide described herein or TGFβ superfamily ligand binding agent comprising the same. In some embodiments, the muscle disease is DMD, FSHD, IBM, ALS, sarcopenia, or cancer cachexia. In some such embodiments, activin A, activin B, GDF-8, GDF-11, and/or BMP-10 signaling is inhibited in the subject. For example, in some embodiments the disclosure relates to methods of reducing or inhibiting the binding of activin A, activin B, GDF-8, GDF-11, and/or BMP-10 to their endogenous receptors in a subject having or at risk of developing a disease or condition involving weakness and atrophy of muscles, the method comprising administering to a subject in need thereof an effective amount of an ActRIIB-ECD polypeptide described herein or TGFβ superfamily ligand binding agent comprising the same.

In some embodiments, the present disclosure relates to methods of treating muscle disorders, such as muscle wasting due to disease or disuse, comprising administering to a subject in need thereof an effective amount of an ActRIIB-ECD polypeptide described herein or TGFβ superfamily ligand binding agent comprising the same. The muscle disorder may be a musculoskeletal disease or disorder, such as muscle atrophy. There are many causes of muscle atrophy, including as a result of treatment with a glucocorticoid such as cortisol, dexamethasone, betamethasone, prednisone, methylprednisolone, or prednisolone. The muscle atrophy can also be a result of denervation due to nerve trauma or a result of degenerative, metabolic, or inflammatory neuropathy (e.g., Guillian-Barre syndrome, peripheral neuropathy, or exposure to environmental toxins or drugs).

In addition, the muscle atrophy can be a result of myopathy, such as myotonia; a congenital myopathy, including nemalene myopathy, multi/minicore myopathy and myotubular (centronuclear) myopathy; mitochondrial myopathy; familial periodic paralysis; inflammatory myopathy; metabolic myopathy, such as caused by a glycogen or lipid storage disease; dermatomyositisis; polymyositis; inclusion body myositis; myositis ossificans; rhabdomyolysis and myoglobinurias.

The myopathy may be caused by a muscular dystrophy syndrome, such as Duchenne, Becker, myotonic, fascioscapulohumeral, Emery-Dreifuss, oculopharyngeal, scapulohumeral, limb girdle, Fukuyama, a congenital muscular dystrophy, or hereditary distal myopathy. The musculoskeletal disease can also be osteoporosis, a bone fracture, short stature, or dwarfism.

In addition, the muscle atrophy can be a result of an adult motor neuron disease, infantile spinal muscular atrophy, amyotrophic lateral sclerosis, juvenile spinal muscular atrophy, autoimmune motor neuropathy with multifocal conductor block, paralysis due to stroke or spinal cord injury, skeletal immobilization due to trauma, prolonged bed rest, voluntary inactivity, involuntary inactivity, metabolic stress or nutritional insufficiency, cancer, AIDS, fasting, a thyroid gland disorder, diabetes, benign congenital hypotonia, central core disease, burn injury, chronic obstructive pulmonary disease, liver diseases (examples such as fibrosis, cirrhosis), sepsis, renal failure, congestive heart failure, ageing, space travel or time spent in a zero gravity environment.

In addition, the muscle atrophy can be associated with metabolic disorders, including without limitation Type II Diabetes, Metabolic Syndrome, hyperglycemia, and obesity.

Metabolic Disorders and Cardiometabolic Disease

In some embodiments, a polypeptide or binding agent described herein is used for treatment or prevention of a metabolic disorder and/or a cardiometabolic disease. Non-limiting examples of metabolic disorders include Type 1 Diabetes, Type 2 Diabetes, diabetic complications (such as, for example, retinopathy, nephropathy or neuropathies, diabetic foot, ulcus, macroangiopathies), metabolic acidosis or ketosis, hyperglycemia, reactive hypoglycemia, hyperinsulinemia, glucose metabolism disorder, insulin resistance, metabolic syndrome, Dyslipidaemias, atherosclerosis and related diseases, obesity, pre-diabetes, hypertension, chronic heart failure, acute renal failure, edema, and hyperuricemia. Non-limiting examples of cardiometabolic diseases include heart attack, stroke, diabetes, insulin resistance, non-alcoholic fatty liver disease, chronic renal failure, heart failure and/or low ejection fraction, including heart failure with reduced ejection fraction (HFrEF) and heart failure with preserved ejection fraction (HFpEF).

Treatment of obesity or overweight condition and their related comorbidities, such as Type II Diabetes, dyslipidemia, hyperglycemia, cardiovascular disease, and other metabolic disorders, represent a substantial, unmet medical need. Obesity is a risk factor of overall mortality and is estimated to have caused 3.4 million deaths worldwide in 2010 (Lim et al 2012). Obesity, diabetes, high blood sugar and related conditions are high risk factors for serious or life-threatening complications such as heart disease, stroke, kidney problems, nerve damage, and eye disorders. In particular, cardiometabolic diseases such as stroke, heart attack, and heart and blood vessel diseases can be ameliorated by lowering blood sugar levels or achieving weight loss in patients with type 2 diabetes or obesity. Pharmacotherapeutics that can improve body composition, by changing the ratio of lean mass versus fat mass and thereby achieve weight loss or decrease of central adiposity, and improve patient glycemic status, are highly sought. There is also a need for therapies that address heart failure associated with left ventricular dysfunction, such as Heart Failure with preserved Ejection Fraction (HFpEF). HFpEF represents more than half of heart failure cases worldwide and therapies to address HFpEF and associated risk factors such as obesity are highly desired.

There is a need for pharmacotherapeutics that can improve body composition, by changing the ratio of lean mass versus fat mass and thereby achieve weight loss or decrease of central adiposity and improve patient glycemic status. It has been reported that muscle mass increases in myostatin knockout mice and in wild type mice where myostatin is sequestered by a soluble ActRIIB, and that this increase is associated with improved whole body insulin sensitivity and with resistance to diet-induced and genetic obesity (Guo et al, 2009, Akpan et al, 2009). Inhibition of ActRIIB with an antibody has been shown to reduce white adipose tissue in mice on a normal or high-fat diet, while increasing skeletal muscle mass (Fournier et al 2012).

In some embodiments, the disclosure provides for a method of treating a subject having a metabolic disorder comprising administering to a subject in need thereof an effective amount of an ActRIIB-ECD polypeptide described herein or TGFβ superfamily ligand binding agent comprising the same. For example, methods of treating Type 2 Diabetes, Metabolic Syndrome, hyperglycemia, and obesity are provided. In some embodiments therefore, there is provided a method of preventing or treating a metabolic disorder or condition such as, without limitation, Type 1 Diabetes, Type 2 Diabetes, diabetic complications (such as, for example, retinopathy, nephropathy or neuropathies, diabetic foot, ulcus, macroangiopathies), metabolic acidosis or ketosis, reactive hypoglycemia, hyperinsulinemia, glucose metabolism disorder, insulin resistance, metabolic syndrome, Dyslipidaemias, atherosclerosis and related diseases, obesity, pre-diabetes, hypertension, chronic heart failure, acute renal failure, edema, or hyperuricemia.

In some embodiments, the disclosure provides for a method of increasing lean mass in a subject having a metabolic disorder, comprising administering to a subject in need thereof an effective amount of an ActRIIB-ECD polypeptide described herein or TGFβ superfamily ligand binding agent comprising the same.

In some embodiments, the disclosure provides for a method of increasing muscle mass in a subject having a metabolic disorder, comprising administering to a subject in need thereof an effective amount of an ActRIIB-ECD polypeptide described herein or TGFβ superfamily ligand binding agent comprising the same.

In some embodiments, the disclosure provides for a method of decreasing white fat and/or increasing brown fat in a subject in need thereof, e.g., a subject having a metabolic disorder, comprising administering to a subject in need thereof an effective amount of an ActRIIB-ECD polypeptide described herein or TGFβ superfamily ligand binding agent comprising the same.

In some embodiments, the disclosure provides for a method of decreasing total body fat mass (FM) in a subject in need thereof, e.g., a subject having a metabolic disorder, comprising administering to a subject in need thereof an effective amount of an ActRIIB-ECD polypeptide described herein or TGFβ superfamily ligand binding agent comprising the same.

In some embodiments, the disclosure provides for a method of decreasing total body fat mass (FM) while at the same time increasing muscle mass in a subject in need thereof, e.g., a subject having a metabolic disorder, e.g., obesity, comprising administering to a subject in need thereof an effective amount of an ActRIIB-ECD polypeptide described herein or TGFβ superfamily ligand binding agent comprising the same.

In some embodiments, the disclosure provides for a method of improving insulin sensitivity in a subject in need thereof, e.g., a subject having a metabolic disorder, comprising administering to a subject in need thereof an effective amount of an ActRIIB-ECD polypeptide described herein or TGFβ superfamily ligand binding agent comprising the same.

In some embodiments, the disclosure provides for a method of increasing energy expenditure in a subject in need thereof, e.g., a subject having a metabolic disorder, comprising administering to a subject in need thereof an effective amount of an ActRIIB-ECD polypeptide described herein or TGFβ superfamily ligand binding agent comprising the same.

In some embodiments, the disclosure provides for a method of treating a subject having a cardiometabolic disease comprising administering to a subject in need thereof an effective amount of an ActRIIB-ECD polypeptide described herein or TGFβ superfamily ligand binding agent comprising the same. Non-limiting examples of cardiometabolic disease include heart attack, stroke, diabetes, insulin resistance, non-alcoholic fatty liver disease, and chronic renal failure. In some such embodiments, the disclosure provides for a method of reducing the risk of cardiovascular death in subjects with type 2 Diabetes and established cardiovascular disease. In some such embodiments, the disclosure provides for a method of reducing the risk of death and/or hospitalization in people with heart failure and/or low ejection fraction. In some such embodiments, the disclosure provides for a method of reducing the risk of death and/or hospitalization in people with heart failure with a reduced ejection fraction (HFrEF) or with heart failure with preserved ejection fraction (HFpEF). In some such embodiments, the disclosure provides for a method of reducing the risk of cardiovascular death and/or hospitalization for heart failure in adults. In some such embodiments, the disclosure provides for a method of reducing glucose levels in subjects with type 2 Diabetes. In some such embodiments, the disclosure provides for a method of treating or preventing metabolic disorders such as diabetes and/or improving glycemic control in a subject with moderate renal impairment or stage 3 chronic kidney disease.

In some embodiments, the disclosure provides for a method of improving body composition, e.g., for the treatment of central adiposity, obesity or overweight condition and related comorbidities, comprising administering to a subject in need thereof an effective amount of an ActRIIB-ECD polypeptide described herein or TGFβ superfamily ligand binding agent comprising the same.

In some embodiments, the disclosure provides for a method of treating Type II diabetes, e.g., by improving glycemic control or increasing insulin sensitivity, comprising administering to a subject in need thereof an effective amount of an ActRIIB-ECD polypeptide described herein or TGFβ superfamily ligand binding agent comprising the same.

In some embodiments, the disclosure provides for a method of improving body composition in a subject, wherein the improvement comprises an increase in lean mass and a decrease in fat mass, comprising administering to the subject an effective amount of a polypeptide or binding agent described herein. Body composition may be determined by, for example, body mass index (BMI), body shape index (ABSI), dual energy absorptiometry (DXA), magnetic resonance imaging (MM), and/or bioelectrical impedance techniques.

In some embodiments, the disclosure provides for a method of treating obesity or overweight disorder, e.g., by improving body composition whereby lean mass is increased and fat mass is reduced, comprising administering to a subject in need thereof an effective amount of an ActRIIB-ECD polypeptide described herein or TGFβ superfamily ligand binding agent comprising the same.

In some embodiments, the disclosure provides for a method of treating, preventing or reducing obesity or overweight condition related comorbidities, comprising administering to a subject in need thereof an effective amount of a polypeptide or binding agent described herein. "Obesity or overweight condition related comorbidities" refers to serious chronic disorders associated with obesity, including but not limited to type 2 diabetes or glucose intolerance, prediabetes, high triglycerides, physical impairment, osteoporosis, renal disease, obstructive sleep apnea, sexual hormones impairment, endocrine reproductive disorders such as polycystic ovary syndrome or male hypogonadism, osteoarthritis, gastrointestinal cancers, dyslipidaemia, hypertension, heart failure, coronary heart disease and stroke, gallstones, hypertension, and altered gonadal hormone profile. In some such embodiments, the disclosure provides a method of improving glycemic control, e.g., in a patient suffering from Type II Diabetes, e.g., by increasing insulin sensitivity.

Bone Damage

In some embodiments, a polypeptide or binding agent described herein is used for treatment or prevention of bone damage and associated conditions. For example, a polypeptide or binding agent described herein may be used to treat, prevent or reduce the progression rate and/or severity of a variety of diseases and conditions involving bone damage, including, but not limited to, primary osteoporosis, secondary osteoporosis, osteopenia, osteopetrosis, bone fracture, bone cancer or cancer metastasis-related bone loss, Paget's disease, renal osteodystrophy, treatment-related bone loss, diet-related bone loss, bone loss associated with the treatment of obesity, low gravity-related bone loss, or immobility.

Healthy bone undergoes a constant remodeling that involves both bone breakdown and bone growth. Bone growth is mediated by the osteoblast cell type whereas osteoclast cells resorb the bone. Pathology can occur when these systems fall out of balance either through downregulation of the anabolic program, upregulation of the catabolic system or a combination of both, resulting in a net bone loss. Controlling the balance in bone remodeling can therefore be useful for promoting the healing of damage to bone as well as the treatment of disorders, such as osteoporosis, associated with loss of bone mass and bone demineralization.

Bone damage can result from a range of root causes, including age- or cancer-related bone loss, genetic conditions, or adverse side effects of drug treatment. The World Health Organization estimates that osteoporosis alone affects 75 million people in the U.S., Europe and Japan, and is a significant risk factor in bone damage. In general, the whole of bone loss represents pathological states for which there are few effective treatments. Available treatments focus on immobilization, exercise and dietary modifications rather than agents that directly promote bone growth and increase bone density. With respect to osteoporosis, estrogen, calcitonin, osteocalcin with vitamin K, or high doses of dietary calcium are all used as therapeutic interventions. Other therapeutic approaches to osteoporosis include bisphosphonates, parathyroid hormone, parathyroid hormone related protein (PTHrP), calcimimetics, statins, anabolic steroids, lanthanum and strontium salts, and sodium fluoride, although these are often associated with undesirable side effects.

In some embodiments, a polypeptide or binding agent described herein is used to increase bone mass or bone mineral density in a subject having or at risk of developing a disease or condition involving bone damage.

In some embodiments, the disclosure provides a method of increasing bone mineral density in a subject in need thereof, comprising administering to the subject a therapeutically effective amount of an ActRIIB-ECD polypeptide described herein or TGFβ superfamily ligand binding agent comprising the same or pharmaceutical composition described herein.

In some embodiments, the disclosure provides a method of reducing bone resorption in a subject in need thereof, comprising administering to the subject a therapeutically effective amount of an ActRIIB-ECD polypeptide described herein or TGFβ superfamily ligand binding agent comprising the same or pharmaceutical composition described herein.

In some embodiments, the disclosure provides a method of increasing bone formation in a subject in need thereof, comprising administering to the subject a therapeutically effective amount of an ActRIIB-ECD polypeptide described herein or TGFβ superfamily ligand binding agent comprising the same or pharmaceutical composition described herein.

In some embodiments, the disclosure provides a method of increasing bone strength in a subject in need thereof, comprising administering to the subject a therapeutically effective amount of an ActRIIB-ECD polypeptide described herein or TGFβ superfamily ligand binding agent comprising the same or pharmaceutical composition described herein.

In some embodiments, the disclosure provides a method of reducing the risk of bone fracture in a subject in need thereof, comprising administering to the subject a therapeutically effective amount of an ActRIIB-ECD polypeptide described herein or TGFβ superfamily ligand binding agent comprising the same or pharmaceutical composition described herein.

In some embodiments, the disclosure provides a method of treating a subject having or at risk of developing bone disease, comprising administering to the subject a therapeutically effective amount of an ActRIIB-ECD polypeptide described herein or TGFβ superfamily ligand binding agent comprising the same or pharmaceutical composition described herein. Non-limiting examples of bone disease that may be treated in accordance with the present methods include primary osteoporosis, secondary osteoporosis, osteopenia, osteopetrosis, bone fracture, bone cancer or cancer metastasis related bone loss, Paget's disease, renal osteodystrophy, treatment-related bone loss, diet-related bone loss, bone loss associated with the treatment of obesity, low gravity-related bone loss, or immobility related bone loss. In some embodiments, the bone disease is osteoporosis. In some embodiments, the primary osteoporosis is age-related osteoporosis or hormone-related osteoporosis. In some embodiments of any of the above aspects, the secondary osteoporosis is immobilization-induced osteoporosis or glucocorticoid-induced osteoporosis. In some embodiments, the cancer is multiple myeloma. In some embodiments, the treatment-related bone loss occurs due to treatment with FGF-21, due to treatment with GLP-1, due to cancer therapy, e.g., chemotherapy or radiation, or due to treatment for obesity or Type-2 diabetes. In some embodiments, the diet-related bone loss is rickets, e.g., vitamin D deficiency. In some embodiments, the low gravity-related bone loss is lack of load-related bone loss. In some embodiments, the subject is at risk of bone fracture. In some embodiments, the polypeptide or binding agent described herein inhibits one or more of activin A, activin B, GDF-8, GDF-11, and BMP-10 in the subject, e.g., by reducing or inhibiting the binding of activin A, activin B, GDF-8, GDF-11, and/or BMP-10 to their receptors or inhibiting signaling through their receptors.

In some embodiments of methods of the disclosure, the method increases bone formation in the subject. In some embodiments of methods of the disclosure, the method decreases bone resorption in the subject. In some embodiments of methods of the disclosure, the method decreases bone loss in the subject. In some embodiments of methods of the disclosure, the method increases osteoblast activity or osteoblastogenesis in the subject. In some embodiments of methods of the disclosure, the method decreases osteoclast activity or decreases osteoclastogenesis in the subject. In some embodiments of methods of the disclosure, the method decreases the risk of bone fracture in the subject. In some embodiments of methods of the disclosure, the method increases bone strength in the subject. In some embodiments of methods of the disclosure, the bone is cortical bone. In some embodiments of methods of the disclosure, the bone is trabecular bone.

As used herein, the terms "bone mineral density (BMD)," "bone density," and "bone mass" refer to a measure of the amount of bone mineral (e.g., calcium) in bone tissue. BMD may be measured by well-established clinical techniques known to one of skill in the art (e.g., by single or dual-energy photon or X-ray absorptiometry). The concept of BMD relates to the mass of mineral per volume of bone, although clinically it is measured by proxy according to optical density per square centimeter of bone surface upon imaging. BMD measurement is used in clinical medicine as an indirect indicator of osteoporosis and fracture risk. In some embodiments, BMD test results are provided as a T-score, where the T-score represents the BMD of a subject compared to the ideal or peak bone mineral density of a healthy 30-year-old adult. A score of O indicates that the BMD is equal to the normal reference value for a healthy young adult. Differences between the measured BMD of subject and that of the reference value for a healthy young adult are measured in standard deviation units (SDs). Accordingly, a T-score of between +1 SD and −1 SD may indicate a normal BMD, a T-score of between −1 SD and −2.5 SD may indicate low bone mass (e.g., osteopenia), and a T-score lower than −2.5 SD may indicate osteoporosis or severe osteoporosis. In some embodiments of methods of the disclosure, a subject has low bone mass (e.g., a T-Score of between −1 SD and −2.5 SD). In some embodiments of methods of the disclosure, a subject has osteoporosis (e.g., a T-Score of less than −2.5 SD). In some embodiments of methods of the disclosure, the subject's BMD is increased by administration of a polypeptide or binding agent or pharmaceutical composition described herein. For example, treatment in accordance with the methods of the disclosure may increase the T-score of the subject, e.g., by 0.1 or more, 0.2 or more, 0.3 or more, 0.4 or more, 0.5 or more, 1.0 or more, or 2.0 or more.

In some embodiments, in bone marrow failure diseases including for example myelofibrosis, positive responses are revealed by improvements in anemia (for example, transfusion-independent patients exhibiting an increase in hemoglobin level, transfusion dependent patients become transfusion independent).

As used herein, the term "bone strength" refers to a measurement of bone that is determined by bone quality in addition to bone mineral density. Bone quality is influenced by bone geometry, microarchitecture, and the properties of constituent tissues. Bone strength can be used to assess the bone's risk of fracture.

As used herein, the term "bone disease" refers to a condition characterized by bone damage (e.g., decreased bone mineral density, decreased bone strength, and/or bone loss). Such diseases or conditions may be caused by an imbalance in osteoblast and/or osteoclast activity (e.g., increased bone resorption or reduced bone formation). Bone diseases include, without limitation, primary osteoporosis, secondary osteoporosis, osteopenia, osteopetrosis, bone fracture, bone cancer or cancer metastasis-related bone loss (e.g., bone loss associated with multiple myeloma), Paget's disease, renal osteodystrophy, treatment-related bone loss, diet-related bone loss, bone loss associated with the treatment of obesity, low gravity-related bone loss, and immobility-related bone loss.

As used herein, the terms "bone remodeling" or "bone metabolism" refer to the process for maintaining bone strength and ion homeostasis by replacing discrete parts of old bone with newly synthesized packets of proteinaceous matrix. Bone is resorbed by osteoclasts and is deposited by osteoblasts in a process called ossification. Osteocyte activity plays a key role in this process. Conditions that result in a decrease in bone mass, can either be caused by an increase in resorption, or a decrease in ossification. In a healthy individual, during childhood, bone formation exceeds resorption. As the aging process occurs, resorption exceeds formation. Bone resorption rates are also typically much higher in post-menopausal older women due to estrogen deficiency related to menopause.

As used herein, the terms "bone resorption" or "bone catabolic activity" refer to a process by which osteoclasts break down the tissue in bones and release the minerals, resulting in a transfer of the mineral (e.g., calcium) from bone tissue to the blood. Increased rates of bone resorption are associated with aging, including in post-menopausal women. High rates of bone resorption, or rates of bone resorption that exceed the rate of ossification, are associated with bone disorders, such as decreased bone mineral density, including osteopenia and osteoporosis, and can result in bone loss. In some embodiments of methods of the disclosure, bone resorption is decreased in the subject, e.g., bone loss is decreased in the subject, by administration of a polypeptide or binding agent or pharmaceutical composition described herein.

As used herein, the terms "bone formation," "ossification," " "osteogenesis," or "bone anabolic activity" refer to the process of forming new bone tissue by osteoblasts. Reduced rates of bone formation, or rates of bone formation that are exceeded by the rate of bone resorption, can result in bone loss. In some embodiments of methods of the disclosure, bone formation is increased in the subject, e.g., the amount or rate of bone formation or osteogenesis is increased in the subject, by administration of a polypeptide or binding agent or pharmaceutical composition described herein.

In some embodiments of methods of the disclosure, administration of a polypeptide or binding agent or pharmaceutical composition described herein acts to increase bone mineral density, increase bone formation, increase bone strength, reduce the risk of bone fracture, and/or reduce bone resorption in the subject, compared to measurements obtained prior to treatment or compared to measurements typically observed in untreated subjects.

Low Red Blood Cell Levels

In some embodiments, a polypeptide or binding agent described herein is used for treatment or prevention of a disease or condition associated with low red blood cell levels, such as anemia or blood loss. For example, a polypeptide or binding agent described herein may be used to treat, prevent or reduce the progression rate and/or severity of a variety of diseases and conditions involving low red blood cell levels, including, but not limited to, anemia or blood loss, e.g., by increasing red blood cell levels (for example by increasing hemoglobin levels, increasing red blood cell count, increasing hematocrit, or increasing red blood cell formation or production) in a subject in need thereof.

Anemia is a global health problem with health implications that affect both morbidity and mortality. In the United States alone, the prevalence of anemia nearly doubled from 2003 to 2012. Symptoms of anemia include fatigue, weakness, shortness of breath, heart palpitations, and reduced cognitive performance, and children, pregnant women, women of reproductive age, and the elderly have been found to have the highest risk of developing anemia. The most common form of anemia is iron deficiency anemia, but anemia can also be caused by chronic diseases, blood loss, and red blood cell destruction. While iron deficiency anemia can be treated with iron supplements, many other forms of anemia, such as aplastic anemia, anemia of chronic disease, and hemolytic anemia may require blood transfusions.

In some embodiments, the disclosure provides a method of treating low red blood cell levels in a subject in need thereof comprising administering to the subject an effective amount of an ActRIIB-ECD polypeptide described herein or TGFβ superfamily ligand binding agent comprising the same or pharmaceutical composition described herein.

In some embodiments, the disclosure provides a method of treating anemia in a subject in need thereof comprising administering to the subject an effective amount of an ActRIIB-ECD polypeptide described herein or TGFβ superfamily ligand binding agent comprising the same or pharmaceutical composition described herein.

In some embodiments, the disclosure provides a method of treating blood loss in a subject in need thereof comprising administering to the subject an effective amount of an ActRIIB-ECD polypeptide described herein or TGFβ superfamily ligand binding agent comprising the same or pharmaceutical composition described herein.

In some embodiments, the disclosure provides a method of increasing red blood cell levels in a subject in need thereof comprising administering to the subject an effective amount of an ActRIIB-ECD polypeptide described herein or TGFβ superfamily ligand binding agent comprising the same or pharmaceutical composition described herein.

In some embodiments, the disclosure provides a method of increasing hemoglobin levels in a subject in need thereof comprising administering to the subject an effective amount of a polypeptide or binding agent or pharmaceutical composition described herein.

In some embodiments, the disclosure provides a method of increasing red blood cell count in a subject in need thereof comprising administering to the subject an effective amount of an ActRIIB-ECD polypeptide described herein or TGFβ superfamily ligand binding agent comprising the same or pharmaceutical composition described herein.

In some embodiments, the disclosure provides a method of increasing hematocrit in a subject in need thereof comprising administering to the subject an effective amount of an ActRIIB-ECD polypeptide described herein or TGFβ superfamily ligand binding agent comprising the same or pharmaceutical composition described herein.

In some embodiments, the disclosure provides a method of increasing red blood cell formation in a subject in need thereof, comprising administering to the subject an effective amount of an ActRIIB-ECD polypeptide described herein or TGFβ superfamily ligand binding agent comprising the same or pharmaceutical composition described herein.

In some embodiments of methods of the disclosure, the subject may have or be at risk of developing anemia or blood loss. In some embodiments, the anemia is due to other diseases or conditions, such as chronic kidney disease, rheumatoid arthritis, cancer, or inflammatory diseases (e.g., Crohn's disease, SLE, or ulcerative colitis), or due to medical treatments, such as chemotherapy, radiation therapy, or surgery. In some embodiments, the polypeptide or binding agent described herein inhibits one or more of activin A, activin B, GDF-8, GDF-11, and BMP-10 in the subject, e.g., by reducing or inhibiting the binding of activin A, activin B, GDF-8, GDF-11, and/or BMP-10 to their receptors or inhibiting signaling through their receptors.

In some embodiments, the disclosure provides a method of increasing red blood cells (e.g., increasing hemoglobin levels, red blood cell count, or hematocrit) in a subject in need thereof, comprising administering to the subject a therapeutically effective amount of a polypeptide or binding agent or pharmaceutical composition described herein, wherein red blood cells are increased (e.g., hemoglobin levels, red blood cell count, or hematocrit are increased) compared to measurements obtained prior to treatment.

In some embodiments, the disclosure provides a method of increasing red blood cell levels in a subject who has or is at risk of developing anemia or blood loss. In some embodiments, the anemia or blood loss is associated with cancer, cancer treatment, renal disease or failure (e.g., chronic kidney disease or acute renal disease or failure), myelodysplastic syndrome, thalassemia, nutritional deficits, adverse reaction to medication, an inflammatory or autoimmune disease, splenomegaly, *porphyria*, vasculitis, hemolysis, bone marrow defects, bone marrow transplantation, diabetes, liver disease (e.g., acute liver disease or chronic liver disease), bleeding (e.g., acute or chronic bleeding), infection, hemoglobinopathy, drug use, alcohol abuse, advanced age, Churg-Strauss syndrome, Felty syndrome, graft versus host disease, hematopoietic stem cell transplantation, osteomyelofibrosis, pancytopenia, pure red-cell aplasia, purpura, Schoenlein Henoch, Shwachman syndrome (e.g., Shwachman-Diamond syndrome), contraindication to transfusion, surgery, trauma, a wound, an ulcer, urinary tract bleeding, digestive tract bleeding, frequent blood donation, or heavy menstrual bleeding.

In some embodiments of methods of the disclosure, the anemia is aplastic anemia, iron deficiency anemia, vitamin deficiency anemia, anemia of chronic disease, anemia associated with bone marrow disease, hemolytic anemia, sickle cell anemia, microcytic anemia, hypochromic anemia, sideroblastic anemia, Diamond Blackfan anemia, Fanconi's anemia, or refractory anemia with excess of blasts.

In some embodiments of methods of the disclosure, the subject in need of treatment is a subject who does not respond well to treatment with erythropoietin (EPO) or is susceptible to the adverse effects of EPO.

As used herein, the terms "increase red blood cell levels" and "promote red blood cell formation" refer to clinically observable metrics, such as hematocrit, red blood cell counts, and hemoglobin measurements, and are intended to be neutral as to the mechanism by which such changes occur. The term "low red blood cell levels" as used herein refers to red blood cell counts, hematocrit, and hemoglobin measurements that are below the range of values that is considered normal for the subject's age and gender.

As used herein, the terms "red blood cell formation" and "red blood cell production" refer to the generation of red blood cells, such as the process of erythropoiesis in which red blood cells are produced in the bone marrow.

As used herein, the term "anemia" refers to any abnormality in hemoglobin or red blood cells that leads to reduced oxygen levels in the blood. Anemia can be associated with abnormal production, processing, or performance of erythrocytes and/or hemoglobin. The term anemia refers to any reduction in the number of red blood cells and/or level of hemoglobin in blood relative to normal blood levels.

In some embodiments of methods of the disclosure, administration of a polypeptide or binding agent or pharmaceutical composition described herein acts to increase red blood cell formation, red blood cell count, hemoglobin levels, or hematocrit in the subject, e.g., compared to measurements obtained prior to treatment. In some embodiments of methods of the disclosure, administration of the polypeptide or binding agent of the disclosure reduces the subject's need for a blood transfusion.

In some embodiments, the disclosure provides a method of treating a vascular disease or vasculopathy in a subject in need thereof, comprising administering to the subject a therapeutically effective amount of an ActRIIB-ECD polypeptide described herein or TGFβ superfamily ligand binding agent comprising the same or pharmaceutical composition described herein. Non-limiting examples of vascular disease or vasculopathy include vasculitis, arteriosclerosis, aortic aneurysms and vascular calcification, which may present alone or in connection with other diseases such as, for example and without limitation, chronic kidney disease (CKD), diabetes, or rare disorders such as sickle cell anemia and Kawasaki disease.

Kits

In accordance with the present disclosure, polypeptides, TGFβ superfamily ligand binding agents and pharmaceutical compositions described herein may be assembled into kits or pharmaceutical systems for use in treating or preventing TGFβ superfamily-associated diseases or conditions. Kits or pharmaceutical systems may comprise a container (e.g., packaging, a box, a carton, a vial, etc.), having in close confinement therein one or more container, such as vials, tubes, ampoules, bottles, and the like, that contains the polypeptide, binding agent or pharmaceutical composition. Additional kit components may include acids, bases, buffering agents, inorganic salts, solvents, antioxidants, preservatives, or metal chelators. The additional kit components may be present as pure compositions, or as aqueous or organic solutions that incorporate one or more additional kit components. Any or all of the kit components optionally further comprise buffers. Kits may also include tools for administration, such as needles, syringes, and the like. The kit may be used according to the methods described herein and may include instructions for use in such methods. Kits may also include instructions for administration and use of the polypeptide, binding agent or pharmaceutical composition.

In some embodiments, a kit comprises one or more recipients (such as vials, ampoules, containers, syringes, bottles, bags) of any appropriate shape, size and material (preferably waterproof, e.g., plastic or glass) containing the polypeptide or binding agent or pharmaceutical composition of the present disclosure in an appropriate dosage for administration (as discussed above). The kit may additionally contain directions for use (e.g., in the form of a leaflet or instruction manual), means for administering the polypeptide or binding agent of the present disclosure such as a syringe, pump, infuser or the like, means for reconstituting the polypeptide or binding agent of the disclosure and/or means for diluting the polypeptide or binding agent of the disclosure.

The disclosure also provides kits for a single-dose administration unit. The kit of the disclosure may also contain a first recipient comprising a dried/lyophilized polypeptide or binding agent and a second recipient comprising an aqueous formulation. In certain embodiments, kits containing single-chambered and multi-chambered pre-filled syringes (e.g., liquid syringes and lyosyringes) are provided.

Further Numbered Embodiments

The present invention is also described, for example and without limitation, in the following numbered embodiments which are not to be construed as limiting the scope thereof in any manner.

Embodiment 1. A polypeptide comprising an Activin receptor type IIB (ActRIIB) ectodomain (ECD) variant, the variant having one or more amino acid substitution relative to the sequence of the human wild type ActRIIB-ECD, optionally wherein the variant comprises a substitution of F58 which is not F581.

Embodiment 2. The polypeptide of embodiment 1, wherein the variant has one amino acid substitution relative to the sequence of the human wild type ActRIIB-ECD, the one amino acid substitution being a substitution of F58 which is not F581.

Embodiment 3. The polypeptide of embodiment 1 or 2, wherein the variant comprises amino acid substitution F58D, F58E, F58Y, F58K, F58Q, F58N, F58R, F58H, or F58W.

Embodiment 4. The polypeptide of embodiment 3, wherein the variant comprises amino acid substitution F58D.

Embodiment 5. The polypeptide of embodiment 3, wherein the variant comprises amino acid substitution F58E.

Embodiment 6. The polypeptide of embodiment 3, wherein the variant comprises amino acid substitution F58Y.

Embodiment 7. The polypeptide of embodiment 3, wherein the variant comprises amino acid substitution F58K.

Embodiment 8. The polypeptide of embodiment 3, wherein the variant comprises amino acid substitution F58Q.

Embodiment 9. The polypeptide of embodiment 3, wherein the variant comprises amino acid substitution F58W; or, wherein the variant comprises amino acid substitution F58N; or, wherein the variant comprises amino acid substitution F58R; or, wherein the variant comprises amino acid substitution F58H.

Embodiment 10. The polypeptide of any one of embodiments 1 to 9, wherein the variant further comprises one or more additional amino acid substitution.

Embodiment 11. The polypeptide of any one of embodiments 1 to 10, wherein the human wild type ActRIIB-ECD has the sequence

```
                                                (SEQ ID NO: 2)
ETRECIYYNANWELERTNQSGLERCEGEQDKRLHCYASWRNSSGTIELVK

KGCWLDDFNCYDRQECVATEENPQVYFCCCEGNFCNERFTHLPEAGGPEV

TYEPPPT.
```

Embodiment 12. The polypeptide of embodiment 11, wherein the human wild type ActRIIB-ECD further comprises one or more additional amino acid.

Embodiment 13. The polypeptide of embodiment 12, wherein the human wild type ActRIIB-ECD further comprises the following amino acids at the N terminus: GRGEA (SEQ ID NO: 23).

Embodiment 14. The polypeptide of any one of embodiments 1 to 11, wherein the variant has the sequence set forth in SEQ ID NO: 5.

Embodiment 15. The polypeptide of any one of embodiments 1 to 11, wherein the variant has the sequence set forth in SEQ ID NO: 6.

Embodiment 16. The polypeptide of any one of embodiments 1 to 11, wherein the variant has the sequence set forth in SEQ ID NO: 7.

Embodiment 17. The polypeptide of any one of embodiments 1 to 11, wherein the variant has the sequence set forth in SEQ ID NO: 8.

Embodiment 18. The polypeptide of any one of embodiments 1 to 11, wherein the variant has the sequence set forth in SEQ ID NO: 9.

Embodiment 19. The polypeptide of any one of embodiments 1 to 11, wherein the variant has the sequence set forth in SEQ ID NO: 10.

Embodiment 19A. The polypeptide of any one of embodiments 1 to 11, wherein the variant has the sequence set forth in SEQ ID NO: 11.

Embodiment 19B. The polypeptide of any one of embodiments 1 to 11, wherein the variant has the sequence set forth in SEQ ID NO: 12.

Embodiment 19C. The polypeptide of any one of embodiments 1 to 11, wherein the variant has the sequence set forth in SEQ ID NO: 13.

Embodiment 20. The polypeptide of any one of embodiments 14 to 19C, wherein the variant further comprises one or more additional amino acid.

Embodiment 21. The polypeptide of embodiment 20, wherein the variant further comprises the following amino acids at the N terminus: GRGEA (SEQ ID NO: 23), and optionally wherein the variant further comprises the amino acids APT at the C-terminus.

Embodiment 22. The polypeptide of any one of embodiments 1 to 21, further comprising an Fc domain monomer fused to the C-terminus of the variant via a linker.

Embodiment 23. The polypeptide of embodiment 22, wherein the Fc domain monomer is an IgG1, IgG2, IgG3 or IgG4.

Embodiment 24. The polypeptide of embodiment 22 or 23, wherein the Fc domain monomer is a human Fc domain monomer.

Embodiment 25. The polypeptide of embodiment 22 or 23, wherein the Fc domain monomer is a mouse Fc domain monomer.

Embodiment 26. The polypeptide of any one of embodiments 22 to 25, wherein the Fc domain monomer is engineered to reduce aggregation or to modulate stability of a dimer of the polypeptide.

Embodiment 27. The polypeptide of any one of embodiments 22 to 26, wherein the Fc domain monomer has the following three mutations: M252Y/S254T/T256E (YTE).

Embodiment 28. The polypeptide of any one of embodiments 22 to 27, wherein the Fc domain monomer has a M252Y mutation.

Embodiment 29. The polypeptide of any one of embodiments 22 to 28, wherein the Fc domain monomer includes a D at position 356 and an L at position 358 (DL).

Embodiment 30. The polypeptide of any one of embodiments 22 to 28, wherein the Fc domain monomer includes an E at position 356 and an M at position 358 (EM).

Embodiment 31. The polypeptide of any one of embodiments 22 to 30, wherein the Fc domain monomer is IgG1.

Embodiment 32. The polypeptide of embodiment 31, wherein the Fc domain monomer includes a Lysine residue (K) at the C terminus.

Embodiment 33. The polypeptide of embodiment 31, wherein the Fc domain monomer has the amino acid sequence set forth in any one of SEQ ID NOs: 134-147 and 338, or a sequence at least 85%, at least 90%, at least 95%, at least 96%, at least 97%, at least 98%, or at least 99% identical thereto.

Embodiment 34. The polypeptide of any one of embodiments 31 to 33, wherein the Fe domain monomer comprises or consists of the amino acid sequence set forth in any one of SEQ ID NOs: 134-147 and 338.

Embodiment 35. The polypeptide of any one of embodiments 31 to 33, wherein the Fc domain monomer comprises or consists of the amino acid sequence set forth in any one of SEQ ID NOs: 134, 135, 137, 138 and 157.

Embodiment 36. The polypeptide of any one of embodiments 31 to 33, wherein the Fc domain monomer comprises or consists of the amino acid sequence set forth in SEQ ID NO: 135.

Embodiment 37. The polypeptide of any one of embodiments 33 to 36, wherein the Fc domain monomer further comprises a Lysine residue (K) at the C terminus.

Embodiment 38. The polypeptide of any one of embodiments 22 to 30, wherein the Fc domain monomer is IgG2.

Embodiment 39. The polypeptide of embodiment 38, wherein the Fc domain monomer has the amino acid sequence set forth in any one of SEQ ID NOs: 148-157, or a sequence at least 85%, at least 90%, at least 95%, at least 96%, at least 97%, at least 98%, or at least 99% identical thereto.

Embodiment 40. The polypeptide of any one of embodiments 10-17, wherein the Fc domain monomer comprises or consists of the amino acid sequence set forth in any one of SEQ ID NOs: 148-157.

Embodiment 41. The polypeptide of any one of embodiments 38 to 40, wherein the Fc domain monomer comprises or consists of the amino acid sequence set forth in SEQ ID NO: 157.

Embodiment 42. The polypeptide of any one of embodiments 22 to 30, wherein the Fc domain monomer has the amino acid sequence set forth in any one of SEQ ID NOs: 134-173 and 338, or a sequence at least 85%, at least 90%, at least 95%, at least 96%, at least 97%, at least 98%, or at least 99% identical thereto.

Embodiment 43. The polypeptide of any one of embodiments 22 to 30 and 42, wherein the Fc domain monomer comprises or consists of the amino acid sequence set forth in any one of SEQ ID NOs: 134-173 and 338.

Embodiment 44. The polypeptide of embodiment 42 or 43, wherein the Fc domain monomer further comprises a Lysine residue (K) at the C terminus.

Embodiment 45. The polypeptide of any one of embodiments 22 to 44, wherein the Fe domain monomer forms a dimer.

Embodiment 46. The polypeptide of any one of embodiments 22 to 45, wherein the linker is an amino acid spacer.

Embodiment 47. The polypeptide of any one of embodiments 22 to 46, wherein the linker is Glycine-rich.

Embodiment 48. The polypeptide of any one of embodiments 22 to 47, wherein the linker is from 2 to 40 amino acids long, or wherein the linker is from 10 to 40 amino acids long.

Embodiment 49. The polypeptide of embodiment 48, wherein the linker is from 3 to 39 amino acids long, or is from 3 to 14 amino acids long, or is from 10 to 39 amino acids long, or is from 10 to 14 amino acids long, or is 3 amino acids long, 10 amino acids long, 14 amino acids long, 19 amino acids long, or 39 amino acids long.

Embodiment 50. The polypeptide of embodiment 49, wherein the linker is 14 amino acids long; or, wherein the linker is at least 14 amino acids long.

Embodiment 51. The polypeptide of any one of embodiments 46 to 51, wherein the linker is 10 amino acids long; or, wherein the linker is at least 10 amino acids long.

Embodiment 52. The polypeptide of any one of embodiments 46 to 51, wherein the linker has the amino acid sequence set forth in SEQ ID NO:59, 54, 34, or 63.

Embodiment 53. The polypeptide of any one of embodiments 1 to 52, wherein the linker has the amino acid sequence $(Gly_4Ser)_n$ where n is an integer from 1 to 8.

Embodiment 54. The polypeptide of any one of embodiments 22 to 53, wherein the linker has the amino acid sequence set forth in any one of SEQ ID NOs: 34-133 and 335-337.

Embodiment 55. The polypeptide of any one of embodiments 22 to 54, wherein the linker has the amino acid sequence set forth in SEQ ID NO: 59.

Embodiment 56. The polypeptide of any one of embodiments 1 to 55, wherein the polypeptide comprises or consists of a polypeptide having the amino acid sequence set forth in any one of SEQ ID NOs: 174-254, 333, or 339-341, or a sequence at least 90%, at least 95%, at least 96%, at least 97%, at least 98%, or at least 99% identical thereto.

Embodiment 57. The polypeptide of embodiment 56, wherein the polypeptide comprises a polypeptide having the amino acid sequence set forth in SEQ ID NO: 186, or a sequence at least 90%, at least 95%, at least 96%, at least 97%, at least 98%, or at least 99% identical thereto.

Embodiment 58. The polypeptide of embodiment 56, wherein the polypeptide consists of a polypeptide having the amino acid sequence set forth in SEQ ID NO: 186, or a sequence at least 90%, at least 95%, at least 96%, at least 97%, at least 98%, or at least 99% identical thereto.

Embodiment 59. The polypeptide of embodiment 57, wherein the polypeptide comprises a polypeptide having the amino acid sequence set forth in SEQ ID NO: 186.

Embodiment 60. The polypeptide of embodiment 58 wherein the polypeptide consists of a polypeptide having the amino acid sequence set forth in SEQ ID NO: 186.

Embodiment 61. A polypeptide having the amino acid sequence set forth in SEQ ID NO: 186.

Embodiment 62. The polypeptide of embodiment 56, wherein the polypeptide comprises or consists of a polypeptide having the amino acid sequence set forth in any one of SEQ ID NOs: 174-254, 333, or 339-341.

Embodiment 63. The polypeptide of any one of embodiments 1 to 62, further comprising an albumin-binding domain fused to the N- or C-terminus of the polypeptide via a linker.

Embodiment 64. The polypeptide of any one of embodiments 1 to 63, further comprising a fibronectin domain fused to the N- or C-terminus of the polypeptide via a linker.

Embodiment 65. The polypeptide of any one of embodiments 1 to 64, further comprising a human serum albumin fused to the N- or C-terminus of the polypeptide via a linker.

Embodiment 66. The polypeptide of any one of embodiments 1 to 65, further comprising an amino acid sequence suitable for expression, detection and/or purification of the polypeptide.

Embodiment 67. The polypeptide of any one of embodiments 1 to 66, further comprising a signal peptide having the sequence set forth in SEQ ID NO: 1, or a sequence substantially identical thereto.

Embodiment 68. The polypeptide of any one of embodiments 1 to 67, wherein the polypeptide is conjugated with a targeting agent, a therapeutic moiety, a detectable moiety, or a diagnostic moiety.

Embodiment 69. The polypeptide of embodiment 68, wherein the targeting agent, the therapeutic moiety, the detectable moiety, or the diagnostic moiety comprises an antibody or antigen binding fragment thereof, a binding agent having affinity for another member of the TGFβ superfamily or for another therapeutic target, a radiotherapy agent, an imaging agent, a fluorescent moiety, a cytotoxic agent, an anti-mitotic drug, a nanoparticle-based carrier, a polymer-conjugated drug, a nanocarrier, an imaging agent, a stabilizing agent, a drug, a nanocarrier, or a dendrimer.

Embodiment 70. The polypeptide of any one of embodiments 1 to 69, wherein two or more polypeptides are covalently linked by at least one disulfide bridge between respective Fc domain monomers.

Embodiment 71. The polypeptide of any one of embodiments 1 to 70, wherein the polypeptide binds to human activin A, activin B, GDF-8, GDF-11, and/or bone morphogenetic protein (BMP)-10, and has reduced or weak binding to human BMP-9.

Embodiment 72. The polypeptide of embodiment 71, wherein the polypeptide does not substantially bind to human BMP-9.

Embodiment 73. The polypeptide of embodiment 71 or 72, wherein the polypeptide inhibits signaling of one or more of human activin A, activin B, GDF-8, GDF-11, and BMP-10 through their receptors.

Embodiment 74. The polypeptide of any one of embodiments 71 to 73, wherein the polypeptide does not substantially inhibit human BMP-9 signaling.

Embodiment 75. The polypeptide of any one of embodiments 1 to 74, wherein the inhibition potency of the polypeptide for human BMP-9 signaling is reduced by about 100-fold or more compared to the inhibition potency of human wild type ActRIIB-ECD for human BMP-9 signaling.

Embodiment 76. The polypeptide of embodiment 75, wherein the inhibition potency of the polypeptide for human BMP-9 signaling is reduced by about 200-fold, by about 300-fold, or more, compared to the inhibition potency of human wild type ActRIIB-ECD for human BMP-9 signaling.

Embodiment 77. The polypeptide of any one of embodiments 1 to 74, wherein the inhibition potency of the polypeptide for human BMP-9 signaling is reduced by about 100-fold or more compared to the inhibition potency of the polypeptide having the amino acid sequence set forth in SEQ ID NO: 174 for human BMP-9 signaling.

Embodiment 78. The polypeptide of embodiment 77, wherein the inhibition potency of the polypeptide for human BMP-9 signaling is reduced by about 200-fold, by about 300-fold, or more, compared to the inhibition potency of the polypeptide having the amino acid sequence set forth in SEQ ID NO: 174.

Embodiment 79. The polypeptide of any one of embodiments 1 to 78, wherein the polypeptide's inhibition potency for one or more of human activin A, activin B, GDF-8, GDF-11, and BMP-10 is the same or substantially the same as the inhibition potency of human wild type ActRIIB-ECD for the same respective ligand(s).

Embodiment 80. The polypeptide of any one of embodiments 1 to 78, wherein the polypeptide's inhibition potency for one or more of human activin A, activin B, GDF-8, GDF-11, and BMP-10 is the same or substantially the same as the inhibition potency of the polypeptide having the amino acid sequence set forth in SEQ ID NO: 174 for the same respective ligand(s).

Embodiment 81. The polypeptide of any one of embodiments 1 to 78, wherein the relative inhibition potency for one or more of human activin A, activin B, GDF-8, GDF-11, and BMP-10 is increased compared to the inhibition potency of human wild type ActRIIB-ECD for the same respective ligand(s).

Embodiment 82. The polypeptide of any one of embodiments 1 to 78, wherein the relative inhibition potency for one or more of human activin A, activin B, GDF-8, GDF-11, and BMP-10 is increased compared to the inhibition potency of the polypeptide having the amino acid sequence set forth in SEQ ID NO: 174 for the same respective ligand(s).

Embodiment 83. The polypeptide of embodiment 81 or 82, wherein the relative inhibition potency for one or more of human activin A, activin B, GDF-8, GDF-11, and BMP-10 is increased by about 2-fold or more, about 3-fold or more, about 4-fold or more, or about 5-fold or more, compared to the inhibition potency of the human wild type ActRIIB-ECD or the polypeptide having the amino acid sequence set forth in SEQ ID NO: 174 for the same respective ligand(s).

Embodiment 84. The polypeptide of any one of embodiments 1 to 78, wherein the polypeptide's inhibition potency for activin A is at least about 2-fold higher than that of the polypeptide having the amino acid sequence set forth in SEQ ID NO: 174, and the polypeptide's inhibition potency for BMP-9 is at least about 100-fold lower than that of the polypeptide having the amino acid sequence set forth in SEQ ID NO: 174.

Embodiment 85. The polypeptide of embodiment 84, wherein the polypeptide's inhibition potency for activin A is at least about 5-fold higher than that of the polypeptide having the amino acid sequence set forth in SEQ ID NO: 174, and the polypeptide's inhibition potency for BMP-9 is at least about 300-fold lower than that of the polypeptide having the amino acid sequence set forth in SEQ ID NO: 174.

Embodiment 86. A nucleic acid molecule encoding the polypeptide of any one of embodiments 1 to 85.

Embodiment 87. The nucleic acid molecule of embodiment 86, wherein the nucleic acid molecule encodes the polypeptide in a form that is secretable by a selected expression host.

Embodiment 88. A nucleic acid molecule encoding at least one polypeptide having the amino acid sequence set forth in any one of SEQ ID NOs: 174-254, 333, or 339-341, or a sequence substantially identical thereto.

Embodiment 89. A nucleic acid molecule encoding a polypeptide having the amino acid sequence set forth in SEQ ID NO: 186 or a sequence at least 90%, at least 95%, at least 96%, at least 97%, at least 98%, or at least 99% identical thereto.

Embodiment 90. A nucleic acid molecule encoding a polypeptide having the amino acid sequence set forth in SEQ ID NO: 186.

Embodiment 91. A nucleic acid molecule having the sequence set forth in any one of SEQ ID NOs: 256-330, 334, or 342-344, or a sequence substantially identical thereto.

Embodiment 92. A nucleic acid molecule having the sequence set forth in SEQ ID NO: 268, or a sequence substantially identical thereto, or a sequence at least 90%, at least 95%, at least 96%, at least 97%, at least 98%, or at least 99% identical thereto.

Embodiment 93. A nucleic acid molecule having the sequence set forth in SEQ ID NO: 268.

Embodiment 94. A nucleic acid molecule comprising the sequence set forth in SEQ ID NO: 268, or a sequence substantially identical thereto, or a sequence at least 90%, at least 95%, at least 96%, at least 97%, at least 98%, or at least 99% identical thereto.

Embodiment 95. A nucleic acid molecule comprising the sequence set forth in SEQ ID NO: 268.

Embodiment 96. The nucleic acid molecule of any one of embodiments 86 to 95, further comprising, at the 5' end, the sequence set forth in SEQ ID NO: 255, or a sequence substantially identical thereto.

Embodiment 97. A vector comprising the nucleic acid molecule of any one of embodiments 86 to 96.

Embodiment 98. A vector comprising a nucleic acid molecule comprising or consisting of the sequence set forth in SEQ ID NO: 268, or a sequence substantially identical thereto, or a sequence at least 90%, at least 95%, at least 96%, at least 97%, at least 98%, or at least 99% identical thereto.

Embodiment 99. A vector comprising a nucleic acid molecule comprising the sequence set forth in SEQ ID NO: 268.

Embodiment 100. A vector comprising a nucleic acid molecule consisting of the sequence set forth in SEQ ID NO: 268.

Embodiment 101. A cellular host comprising the nucleic acid molecule of any one of embodiments 86 to 96 or the vector of any one of embodiments 97 to 100, wherein the nucleic acid molecule or the vector is expressed in the cellular host.

Embodiment 102. A method of preparing the polypeptide of any one of embodiments 1 to 85, the method comprising: a) providing a host cell comprising the nucleic acid molecule of any one of embodiments 86 to 96 or the vector of any one of embodiments 97 to 100, and b) culturing the host cell under conditions allowing expression of the polypeptide; and c) recovering the expressed polypeptide from the culture.

Embodiment 103. A TGFβ superfamily ligand binding agent comprising: a first polypeptide as defined in any one of embodiments 1 to 85, and a second polypeptide as defined in any one of embodiments 1 to 85; wherein the first polypeptide and the second polypeptide are associated together through their respective Fc domain monomers.

Embodiment 104. The binding agent of embodiment 103, wherein the binding agent binds to one or more ligand selected from activin A, activin B, GDF-8, GDF-11, and BMP-10 and inhibits signaling of the one or more ligand through their respective receptors, wherein the binding agent does not substantially bind to BMP-9 or substantially inhibit BMP-9 signaling through its receptor.

Embodiment 105. The binding agent of embodiment 103 to 104, wherein the inhibition potency of the binding agent for human BMP-9 signaling is reduced by about 100-fold compared to the inhibition potency of a second binding agent comprising the human wild type ActRIIB-ECD for human BMP-9 signaling.

Embodiment 106. The binding agent of any one of embodiments 103 to 105, wherein the inhibition potency of the binding agent for the one or more ligand selected from activin A, activin B, GDF-8, GDF-11, and BMP-10 is substantially the same as the inhibition potency of the second binding agent for the same one or more ligand.

Embodiment 107. The binding agent of any one of embodiments 103 to 105, wherein the inhibition potency of the binding agent for the one or more ligand selected from activin A, activin B, GDF-8, GDF-11, and BMP-10 is increased compared to the inhibition potency of the second binding agent for the same one or more ligand.

Embodiment 108. The binding agent of any one of embodiments 103 to 105 and 107, wherein the binding agent has greater inhibition potency for activin A and lower inhibition potency for BMP-9 compared to the second binding agent comprising the human wild type ActRIIB-ECD.

Embodiment 109. The binding agent of embodiment 108, wherein the binding agent's inhibition potency for activin A is at least about 2-fold greater and the binding agent's inhibition potency for BMP-9 is at least about 100-fold lower than the inhibition potency of the second binding agent for activin A and BMP-9 respectively.

Embodiment 110. The binding agent of embodiment 109, wherein the binding agent's inhibition potency for activin A is at least about 5-fold greater and the binding agent's inhibition potency for BMP-9 is at least about 300-fold lower than the inhibition potency of the second binding agent for activin A and BMP-9 respectively.

Embodiment 111. The binding agent of embodiment 109, wherein the binding agent's inhibition potency for activin A is at least about 2-fold greater, at least about 3-fold greater, at least about 4-fold greater, or at least about 5-fold greater, and the binding agent's inhibition potency for BMP-9 is at least about 100-fold lower, at least about 200-fold lower, or at least about 300-fold lower, than the inhibition potency of the second binding agent for activin A and BMP-9 respectively.

Embodiment 112. The binding agent of any one of embodiments 103 to 111, wherein the binding agent is a homodimer of the polypeptide set forth in SEQ ID NO: 186, or a sequence at least 90%, at least 95%, at least 96%, at least 97%, at least 98%, or at least 99% identical thereto.

Embodiment 113. The binding agent of embodiment 112, wherein the binding agent is a homodimer of the polypeptide set forth in SEQ ID NO: 186.

Embodiment 114. The binding agent of any one of embodiments 105 to 113, wherein the second binding agent is a homodimer of the polypeptide set forth in SEQ ID NO: 186.

Embodiment 115. The binding agent of any one of embodiments 103 to 114, wherein the binding agent does not cause a vascular complication in a subject and/or does not increase vascular permeability or leakage in a subject.

Embodiment 116. The binding agent of any one of embodiments 103 to 115, wherein the binding agent does not increase red blood cell mass, does not increase hemoglobin, does not cause thrombocytopenia, and/or does not cause a hematological complication in a subject.

Embodiment 117. The binding agent of any one of embodiments 103 to 116, wherein the binding agent is a homodimer, the first polypeptide and the second polypeptide being the same or substantially the same.

Embodiment 118. The binding agent of embodiment 117, wherein the first polypeptide and the second polypeptide comprise or consist of the sequence set forth in any one of SEQ ID NOs: 174-254, 333, or 339-341, or a sequence at least 90%, at least 95%, at least 96%, at least 97%, at least 98%, or at least 99% identical thereto.

Embodiment 119. The binding agent of embodiment 118, wherein the first polypeptide and the second polypeptide comprise or consist of the sequence set forth in any one of SEQ ID NOs: 174-254, 333, or 339-341.

Embodiment 120. The binding agent of embodiment 117, wherein the first polypeptide and the second polypeptide comprise the sequence set forth in SEQ ID NO: 186, or a sequence at least 90%, at least 95%, at least 96%, at least 97%, at least 98%, or at least 99% identical thereto.

Embodiment 121. The binding agent of embodiment 117, wherein the first polypeptide and the second polypeptide consist of the sequence set forth in SEQ ID NO: 186, or a sequence at least 90%, at least 95%, at least 96%, at least 97%, at least 98%, or at least 99% identical thereto.

Embodiment 122. The binding agent of embodiment 120, wherein the first polypeptide and the second polypeptide comprise the sequence set forth in SEQ ID NO: 186.

Embodiment 123. The binding agent of embodiment 121, wherein the first polypeptide and the second polypeptide consist of the sequence set forth in SEQ ID NO: 186.

Embodiment 124. The binding agent of any one of embodiments 103 to 123, wherein the binding agent is a homodimer of a polypeptide having the sequence set forth in SEQ ID NO: 186, or a sequence at least 90%, at least 95%, at least 96%, at least 97%, at least 98%, or at least 99% identical thereto.

Embodiment 125. The binding agent of embodiment 124, wherein the binding agent is a homodimer of a polypeptide having the sequence set forth in SEQ ID NO: 186.

Embodiment 126. The binding agent of any one of embodiments 103 to 123, wherein the binding agent is a heterodimer, the first polypeptide and the second polypeptide comprising different amino acid sequences.

Embodiment 127. The binding agent of embodiment 126, wherein the first polypeptide comprises or consists of the sequence set forth in SEQ ID NO: 186, or a sequence at least 90%, at least 95%, at least 96%, at least 97%, at least 98%, or at least 99% identical thereto.

Embodiment 128. The binding agent of embodiment 127, wherein the first polypeptide comprises or consists of the sequence set forth in SEQ ID NO: 186.

Embodiment 129. A pharmaceutical composition comprising the polypeptide of any one of embodiments 1 to 85 or the binding agent of any one of embodiments 103 to 128 and a pharmaceutically acceptable carrier, diluent or excipient.

Embodiment 130. The pharmaceutical composition of embodiment 129, wherein the composition is formulated for administration by injection or infusion.

Embodiment 131. The pharmaceutical composition of embodiment 130, wherein the composition is formulated for intravenous, subcutaneous, intraperitoneal, or intramuscular administration.

Embodiment 132. A kit comprising the polypeptide of any one of embodiments 1 to 85 and a recipient, and, optionally, directions for use.

Embodiment 133. A method of manufacturing the polypeptide of any one of embodiments 1 to 85 or the binding agent of any one of embodiments 103 to 128, the method comprising expressing the first polypeptide and/or the second polypeptide in a cell.

Embodiment 134. The method of embodiment 133, further comprising culturing the cell and isolating and/or purifying the polypeptide or the binding agent expressed in the cell.

Embodiment 135. The method of embodiment 134, wherein the polypeptide and/or the binding agent is secreted by the cell, and the polypeptide and/or the binding agent is obtained from medium in which the cell is cultured.

Embodiment 136. A method of treating or preventing a disease or condition associated with TGFβ-superfamily ligand signaling in a subject in need thereof, the method comprising administering the polypeptide of any one of embodiments 1 to 85, the binding agent of any one of embodiments 103 to 128 or the pharmaceutical composition of any one of embodiments 129 to 131 to the subject, such that the disease or condition is treated or prevented in the subject.

Embodiment 137. The method of embodiment 136, wherein the subject is a mammal.

Embodiment 138. The method of embodiment 137, wherein the mammal is a human.

Embodiment 139. The method of any one of embodiments 136 to 138, wherein the subject has, or is suspected of having, a disease or condition mediated by one or more TGFβ-superfamily ligand.

Embodiment 140. The method of any one of embodiments 136 to 139, wherein the subject has, or is suspected of having, a disease or condition mediated by activin A, activin B, GDF-8, GDF-11, and/or BMP-10.

Embodiment 141. The method of any one of embodiments 136 to 140, wherein the TGFβ-superfamily ligand is one or more of activin A, activin B, GDF-8, GDF-11, and BMP-10.

Embodiment 142. A method of treating or preventing a disease or condition mediated by activin A, activin B, GDF-8, GDF-11, and/or BMP-10 in a subject, the method comprising administering the polypeptide of any one of embodiments 1 to 85, the binding agent of any one of embodiments 103 to 128 or the pharmaceutical composition of any one of embodiments 129 to 131 to the subject, such that the disease or condition mediated by activin A, activin B, GDF-8, GDF-11, and/or BMP-10 is treated or prevented in the subject.

Embodiment 143. The method of embodiment 142, wherein the disease is mediated by activin A.

Embodiment 144. The method of embodiment 142 or 143, wherein the disease is mediated by activin B.

Embodiment 145. The method of any one of embodiments 142 to 144, wherein the disease is mediated by GDF-8.

Embodiment 146. The method of any one of embodiments 142 to 145, wherein the disease is mediated by GDF-11.

Embodiment 147. The method of any one of embodiments 142 to 146, wherein the disease is mediated by BMP-10.

Embodiment 148. The method of any one of embodiments 142 to 147, wherein the disease or condition is characterized by overexpression or overactivation of activin A and/or activin B and/or GDF-8 and/or GDF-11.

Embodiment 149. The method of any one of embodiments 136 to 148, wherein the disease or condition is selected from pulmonary hypertension, fibrosis, muscle weakness or atrophy, metabolic disorders, cardiometabolic disease, bone damage, and low red blood cell levels.

Embodiment 150. The method of any one of embodiments 136 to 149, wherein the disease or condition is pulmonary hypertension (PH).

Embodiment 151. The method of embodiment 150, wherein the PH is arterial, venous, hypoxic, thromboembolic, or miscellaneous PH (also known as WHO groups 1-V).

Embodiment 152. The method of embodiment 150 or 151, wherein the PH is pulmonary arterial hypertension (PAH).

Embodiment 153. The method of embodiment 152, wherein the PAH is idiopathic PAH, heritable PAH, or PAH associated with an infection, a congenital heart abnormality, portal hypertension, pulmonary veno-occlusive disease, pulmonary capillary hemangiomatosis, a connective tissue disorder, chronic obstructive pulmonary disease, an autoimmune disorder (e.g., scleroderma or lupus), or drug use (e.g., use of cocaine or methamphetamine)

Embodiment 154. The method of any one of embodiments 136 to 149, wherein the disease or condition is fibrosis.

Embodiment 155. The method of embodiment 154, wherein the fibrosis is pulmonary fibrosis, idiopathic pulmonary fibrosis, renal fibrosis, liver fibrosis, lung fibrosis, kidney fibrosis, bone marrow fibrosis, systemic sclerosis, skin fibrosis, heart fibrosis, myelofibrosis, corneal fibrosis, mediastinal fibrosis, retroperitoneal fibrosis, osteoarticular fibrosis, arthrofibrosis, tissue fibrosis, a fibroproliferative disorder or a connective tissue disorder.

Embodiment 156. The method of any one of embodiments 136 to 149, wherein the disease or condition is muscle weakness or atrophy.

Embodiment 157. The method of embodiment 156, wherein the disease or condition is Duchenne muscular dystrophy (DMD), facioscapulohumeral muscular dystrophy (FSHD), inclusion body myositis (IBM), amyotrophic lateral sclerosis (ALS), sarcopenia, or cancer cachexia.

Embodiment 158. The method of any one of embodiments 136 to 149, wherein the disease or condition is a metabolic disorder.

Embodiment 159. The method of embodiment 158, wherein the metabolic disorder is obesity, Type 1 diabetes, Type 2 diabetes, or pre-diabetes.

Embodiment 160. The method of any one of embodiments 136 to 149, wherein the disease or condition is a cardiometabolic disease.

Embodiment 161. The method of embodiment 160, wherein the disease or condition is heart failure with a reduced ejection fraction (HFrEF) or heart failure with preserved ejection fraction (HFpEF).

Embodiment 162. The method of any one of embodiments 136 to 149, wherein the disease or condition is bone damage.

Embodiment 163. The method of embodiment 162, wherein the bone damage comprises bone demineralization, osteoporosis (e.g., primary or secondary), osteopenia, osteopetrosis, bone fracture, bone cancer or cancer metastasis-related bone loss, Paget's disease, renal osteodystrophy, treatment-related bone loss, diet-related bone loss, bone loss associated with the treatment of obesity, low gravity-related bone loss, or immobility-related bone loss.

Embodiment 164. The method of any one of embodiments 136 to 149, wherein the disease or condition is low red blood cell levels.

Embodiment 165. The method of embodiment 164, wherein the disease or condition is anemia or blood loss.

Embodiment 166. A method of increasing lean mass in a subject in need thereof, comprising administering to the subject a therapeutically effective amount of the polypeptide of any one of embodiments 1 to 85, the binding agent of any one of embodiments 103 to 128, or the pharmaceutical composition of any one of embodiments 129 to 131, such that lean mass is increased in the subject.

Embodiment 167. A method of increasing muscle mass in a subject in need thereof, comprising administering to the subject a therapeutically effective amount of the polypeptide of any one of embodiments 1 to 85, the binding agent of any one of embodiments 103 to 128, or the pharmaceutical composition of any one of embodiments 129 to 131, such that lean mass is increased in the subject.

Embodiment 168. The method of embodiment 167, wherein the subject has Duchenne muscular dystrophy, facioscapulohumeral muscular dystrophy, inclusion body myositis, amyotrophic lateral sclerosis, sarcopenia, or cancer cachexia.

Embodiment 169. A method of treating a subject having or at risk of developing Duchenne muscular dystrophy, facioscapulohumeral muscular dystrophy, inclusion body myositis, amyotrophic lateral sclerosis, sarcopenia, or cancer cachexia, comprising administering to the subject a therapeutically effective amount of the polypeptide of any one of embodiments 1 to 85 or the binding agent of any one of embodiments 103 to 128 or the pharmaceutical composition of any one of embodiments 129 to 131.

Embodiment 170. A method of increasing bone mineral density in a subject in need thereof, comprising administering to the subject a therapeutically effective amount of the polypeptide of any one of embodiments 1 to 85, the binding agent of any one of embodiments 103 to 128, or the pharmaceutical composition of any one of embodiments 129 to 131, such that bone mineral density is increased in the subject.

Embodiment 171. A method of reducing bone resorption in a subject in need thereof, comprising administering to the subject a therapeutically effective amount of the polypeptide of any one of embodiments 1 to 85, the binding agent of any one of embodiments 103 to 128, or the pharmaceutical composition of any one of embodiments 129 to 131, such that bone resorption is reduced in the subject.

Embodiment 172. A method of increasing bone formation in a subject in need thereof, comprising administering to the subject a therapeutically effective amount of the polypeptide of any one of embodiments 1 to 85, the binding agent of any one of embodiments 103 to 128, or the pharmaceutical composition of any one of embodiments 88 to 90, such that bone formation is increased in the subject.

Embodiment 173. A method of increasing bone strength in a subject in need thereof, comprising administering to the subject a therapeutically effective amount of the polypeptide of any one of embodiments 1 to 85, the binding agent of any one of embodiments 103 to 128, or the pharmaceutical composition of any one of embodiments 129 to 131, such that bone strength is increased in the subject.

Embodiment 174. A method of reducing the risk of bone fracture in a subject in need thereof, comprising administering to the subject a therapeutically effective amount of the polypeptide of any one of embodiments 1 to 85, the binding agent of any one of embodiments 103 to 128, or the pharmaceutical composition of any one of embodiments 129 to 131, such that the risk of bone fracture is reduced in the subject.

Embodiment 175. The method of any one of embodiments 170 to 174, wherein the subject has primary osteoporosis, secondary osteoporosis, osteopenia, osteopetrosis, bone fracture, bone cancer or cancer metastasis-related bone loss, multiple myeloma, Paget's disease, renal osteodystrophy, treatment-related bone loss, diet-related bone loss, bone loss associated with the treatment of obesity, low gravity-related bone loss, or immobility-related bone loss.

Embodiment 176. A method of treating a subject having or at risk of developing bone disease, comprising administering to the subject a therapeutically effective amount of the polypeptide of any one of embodiments 1 to 85 or the binding agent of any one of embodiments 103 to 128 or the pharmaceutical composition of any one of embodiments 129 to 131.

Embodiment 177. The method of embodiment 176, wherein the bone disease is primary osteoporosis, secondary osteoporosis, osteopenia, osteopetrosis, bone fracture, bone cancer or cancer metastasis-related bone loss, multiple myeloma, Paget's disease, renal osteodystrophy, treatment-related bone loss, diet-related bone loss, bone loss associated with the treatment of obesity, low gravity-related bone loss, or immobility-related bone loss.

Embodiment 178. A method of treating a subject having or at risk of developing primary osteoporosis (e.g., age-related osteoporosis, hormone-related osteoporosis), secondary osteoporosis (e.g., immobilization-induced osteoporosis, glucocorticoid-induced osteoporosis), osteopenia, Paget's disease, renal osteodystrophy, treatment-related bone loss (e.g., FGF-21 treatment, GLP-1 treatment, cancer therapy, treatment for obesity, treatment for Type-2 diabetes), diet-related bone loss (e.g., rickets), low gravity-related bone loss, immobility-related bone loss, or bone fracture, comprising administering to the subject a therapeutically effective amount of the polypeptide of any one of embodiments 1 to 85 or the binding agent of any one of embodiments 103 to 128 or the pharmaceutical composition of any one of embodiments 129 to 131.

Embodiment 179. The method of any one of embodiments 170 to 178, wherein the bone is cortical bone or trabecular bone.

Embodiment 180. A method of treating fibrosis in a subject in need thereof, comprising administering to the subject a therapeutically effective amount of the polypeptide of any one of embodiments 1 to 85 or the binding agent of any one of embodiments 103 to 128 or the pharmaceutical composition of any one of embodiments 129 to 131.

Embodiment 181. The method of embodiment 180, wherein the fibrosis is pulmonary fibrosis, idiopathic pulmonary fibrosis, renal fibrosis, liver fibrosis, lung fibrosis, kidney fibrosis, bone marrow fibrosis, systemic sclerosis, skin fibrosis, heart fibrosis, myelofibrosis, corneal fibrosis, mediastinal fibrosis, retroperitoneal fibrosis, osteoarticular fibrosis, arthrofibrosis, tissue fibrosis, a fibroproliferative disorder or a connective tissue disorder.

Embodiment 182. The method of embodiment 180 or 181, wherein the fibrosis is chemotherapeutic drug-induced fibrosis, radiation-induced fibrosis, a tumor stroma, a desmoplastic tumor, a surgical adhesion, a hypertrophic scar, or a keloid.

Embodiment 183. The method of embodiment 181, wherein the tissue fibrosis is fibrosis affecting a tissue selected from the group consisting of muscle tissue, skin epidermis, skin dermis, tendon, cartilage, pancreatic tissue, uterine tissue, neural tissue, testis, ovary, adrenal gland, artery, vein, colon, small intestine, large intestine, biliary tract, and gut.

Embodiment 184. The method of any one of embodiments 149, 154, 155, and 180 to 183, wherein the fibrosis is fibrosis associated with wounds, burns, hepatitis B or C infection, fatty liver disease, *Schistosoma* infection, kidney disease, chronic kidney disease, heart disease, macular degeneration, retinal or vitreal retinopathy, Crohn's disease, systemic or local scleroderma, atherosclerosis, or restenosis.

Embodiment 185. The method of any one of embodiments 136 to 184, wherein the method does not: cause a vascular complication in a subject; increase vascular permeability or leakage in a subject; increase red blood cell mass; increase hemoglobin; cause thrombocytopenia; and/or cause a hematological complication in a subject.

Embodiment 186. A method of increasing red blood cell levels in a subject in need thereof, comprising administering to the subject a therapeutically effective amount of the polypeptide of any one of embodiments 1 to 85, the binding agent of any one of embodiments 103 to 128, or the pharmaceutical composition of any one of embodiments 129 to 131, such that red blood cell levels are increased in the subject.

Embodiment 187. A method of promoting or increasing red blood cell formation in a subject in need thereof, comprising administering to the subject a therapeutically effective amount of the polypeptide of any one of embodiments 1 to 85, the binding agent of any one of embodiments 103 to 128, or the pharmaceutical composition of any one of embodiments 129 to 131, such that red blood cell formation is promoted or increased in the subject.

Embodiment 188. A method of treating a subject having or at risk of developing anemia or blood loss, comprising administering to the subject a therapeutically effective amount of the polypeptide of any one of embodiments 1 to 85, the binding agent of any one of embodiments 103 to 128, or the pharmaceutical composition of any one of embodiments 129 to 131.

Embodiment 189. The method of embodiment 188, wherein the anemia or blood loss is associated with cancer, cancer treatment, chronic kidney disease, acute renal disease or failure, chronic renal disease or failure, myelodysplastic syndrome, thalassemia, nutritional deficits, adverse reaction to medication, an inflammatory or autoimmune disease, splenomegaly, *porphyria*, vasculitis, hemolysis, bone marrow defects, bone marrow transplantation, acute liver disease, chronic liver disease, acute bleeding, chronic bleeding, infection, hemoglobinopathy, drug use, alcohol abuse, Churg-Strauss syndrome, Felty syndrome, graft versus host disease, hematopoietic stem cell transplantation, osteomyelofibrosis, pancytopenia, pure red-cell aplasia, purpura Schoenlein Henoch, Shwachman syndrome, advanced age, contraindication to transfusion, surgery, trauma, a wound, an ulcer, urinary tract bleeding, digestive tract bleeding, frequent blood donation, or heavy menstrual bleeding.

Embodiment 190. The method of embodiment 188 or 189, wherein the anemia is aplastic anemia, iron deficiency anemia, vitamin deficiency anemia, anemia of chronic disease, anemia associated with bone marrow disease, hemolytic anemia, sickle cell anemia, microcytic anemia, hypochromic anemia, sideroblastic anemia, Diamond Blackfan anemia, Fanconi's anemia, or refractory anemia with excess of blasts.

Embodiment 191. The method of any one of embodiments 186 to 190, wherein the subject has or is at risk of developing Shwachman-Bodian-Diamond syndrome.

Embodiment 192. The method of any one of embodiments 186 to 191, wherein the subject does not respond well to treatment with erythropoietin (EPO) or is susceptible to the adverse effects of EPO.

Embodiment 193. A method of treating or preventing pulmonary hypertension (PH) in a subject in need thereof, comprising administering to the subject a therapeutically effective amount of the polypeptide of any one of embodiments 1 to 85 or the binding agent of any one of embodiments 103 to 128 or the pharmaceutical composition of any one of embodiments 129 to 131.

Embodiment 194. The method of embodiment 193, wherein the PH is arterial, venous, hypoxic, thromboembolic, or miscellaneous PH.

Embodiment 195. The method of embodiment 193 or 194, wherein the PH is idiopathic or heritable.

Embodiment 196. The method of any one of embodiments 193 to 195, wherein the PH is pulmonary arterial hypertension (PAH).

Embodiment 197. The method of embodiment 196, wherein the PAH is idiopathic PAH, heritable PAH, PAH associated with an infection, or PAH associated with a congenital heart abnormality, portal hypertension, pulmonary veno-occlusive disease, pulmonary capillary hemangiomatosis, cirrhosis of the liver, a congenital heart abnormality, a connective tissue disorder, chronic obstructive pulmonary disease, an autoimmune disorder (e.g., scleroderma or lupus), or drug use (e.g., use of cocaine or methamphetamine).

Embodiment 198. The method of embodiment 197, wherein the infection is HIV infection or schistosomiasis.

Embodiment 199. The method of embodiment 198, wherein the PH is venous PH associated with left ventricular systolic dysfunction, left ventricular diastolic dysfunction, valvular heart disease, congenital cardiomyopathy, or congenital or acquired pulmonary venous stenosis.

Embodiment 200. The method of embodiment 194, wherein the PH is hypoxic PH associated with chronic obstructive pulmonary disease, interstitial lung disease, sleep-disordered breathing, pulmonary fibrosis, an alveolar hypoventilation disorder, chronic exposure to high altitude, or a developmental abnormality.

Embodiment 201. The method of embodiment 194, wherein the PH is thromboembolic PH associated with chronic thromboembolic pulmonary hypertension, pulmonary emboli, angiosarcoma, arteritis, congenital pulmonary artery stenosis, or parasitic infection.

Embodiment 202. The method of embodiment 194, wherein the PH is miscellaneous PH associated with a hematologic disease, a systemic disease, a metabolic disorder, pulmonary tumoral thrombotic microangiopathy, fibrosing mediastinitis, chronic kidney failure, or segmental pulmonary hypertension.

Embodiment 203. A method of treating or preventing a vascular disease or vasculopathy in a subject in need thereof, comprising administering to the subject a therapeutically effective amount of the polypeptide of any one of embodiments 1 to 85 or the binding agent of any one of embodiments 103 to 128 or the pharmaceutical composition of any one of embodiments 129 to 131.

Embodiment 204. The method of embodiment 203, wherein the vascular disease or vasculopathy is vasculitis, arteriosclerosis, aortic aneurysms or vascular calcification, and/or wherein the subject has chronic kidney disease (CKD), diabetes, sickle cell anemia or Kawasaki disease.

Embodiment 205. A method of treating or preventing a metabolic disorder in a subject in need thereof, comprising administering to the subject a therapeutically effective amount of the polypeptide of any one of embodiments 1 to 85 or the binding agent of any one of embodiments 103 to 128 or the pharmaceutical composition of any one of embodiments 129 to 131.

Embodiment 206. The method of embodiment 205, wherein the metabolic disorder is age-related metabolic disorder.

Embodiment 207. The method of embodiment 205, wherein the metabolic disorder is treatment-related metabolic disorder.

Embodiment 208. The method of embodiment 207, wherein the treatment is treatment with a glucocorticoid (e.g., a corticosteroid, such as prednisone), a selective serotonin reuptake inhibitor (SSRI, e.g., paroxetine, mirtazapine, fluoxetine, escitalopram, or sertraline), a serotonin-norepinephrine reuptake inhibitor (SNRI), a tricyclic antidepressant (e.g., amitriptyline), a mood stabilizer (e.g., valproic acid or lithium), an antipsychotic (e.g., olanzapine, chlorpromazine, or clozapine), or an anti-diabetes medication (e.g., insulin, chlorpropamide).

Embodiment 209. The method of any one of embodiments 205 to 208, wherein the metabolic disorder is obesity, Type 1 diabetes, Type 2 diabetes, or pre-diabetes.

Embodiment 210. A method of reducing body fat in a subject in need thereof, comprising administering to the subject a therapeutically effective amount of the polypeptide of any one of embodiments 1 to 85 or the binding agent of any one of embodiments 103 to 128 or the pharmaceutical composition of any one of embodiments 129 to 131.

Embodiment 211. A method of reducing body weight in a subject in need thereof, comprising administering to the subject a therapeutically effective amount of the polypeptide of any one of embodiments 1 to 85 or the binding agent of any one of embodiments 103 to 128 or the pharmaceutical composition of any one of embodiments 129 to 131.

Embodiment 212. A method of reducing blood glucose in a subject in need thereof, comprising administering to the subject a therapeutically effective amount of the polypeptide of any one of embodiments 1 to 85 or the binding agent of any one of embodiments 103 to 128 or the pharmaceutical composition of any one of embodiments 129 to 131.

Embodiment 213. A method of increasing insulin sensitivity in a subject in need thereof, comprising administering to the subject a therapeutically effective amount of the polypeptide of any one of embodiments 1 to 85 or the binding agent of any one of embodiments 103 to 128 or the pharmaceutical composition of any one of embodiments 129 to 131.

Embodiment 214. The method of any one of embodiments 205 to 213, wherein the subject has or is at risk of developing a metabolic disorder.

Embodiment 215. The method of embodiment 214, wherein the metabolic disorder is obesity, Type 1 diabetes, Type 2 diabetes, or pre-diabetes.

Embodiment 216. The method of any one of embodiments 205 to 215, wherein the polypeptide or the binding agent or the pharmaceutical composition is administered in an amount sufficient to effect one or more of the following: reduce body weight and/or percentage of body weight gain of said subject; reduce amount of body fat and/or percentage of body fat of said subject; reduce adiposity of said subject; reduces the weight of epididymal and perirenal fat pads of said subject; reduce the amount of subcutaneous, visceral, and/or hepatic fat of said subject; lower the level of fasting insulin of said subject; reduce blood glucose levels in said subject; increase insulin sensitivity of said subject; reduce fasting insulin levels; increase the rate of glucose clearance of said subject; improve the serum lipid profile of said subject; delay, reduce, or eliminate the need for insulin treatment in said subject; increase lean mass of said subject; reduce the percentage of body weight gain in said subject; reduce the proliferation of adipose cells in said subject; reduce LDL levels in said subject; reduce triglyceride levels in said subject; improve the serum lipid profile of said subject; regulate insulin biosynthesis and/or secretion from pancreatic beta cells in said subject; increase glucose clearance in said subject; increase muscle mass and/or strength of said subject; and/or increase lean mass of said subject.

Embodiment 217. The method of any one of embodiments 193 to 216, wherein the method does not affect the appetite for food intake of said subject.

Embodiment 218. The method of any one of embodiments 193 to 217, wherein the method does not reduce lean mass in said subject.

Embodiment 219. The method of any one of embodiments 193 to 218, wherein the method does not: cause a vascular complication in a subject; increase vascular permeability or leakage in a subject; increase red blood cell mass; increase hemoglobin; cause thrombocytopenia; and/or cause a hematological complication in a subject.

Embodiment 220. A method of reducing or inhibiting activin A, activin B, GDF-8, GDF-11 and/or BMP10 signaling in a subject in need thereof without substantially reducing or inhibiting BMP9 signaling in the subject, comprising administering the polypeptide of any one of embodiments 1 to 85, the binding agent of any one of embodiments 103 to 128, or the pharmaceutical composition of any one of embodiments 129 to 131 to the subject.

Embodiment 221. The method of embodiment 220, wherein binding of activin A, activin B, GDF-8, GDF-11 and/or BMP10 to its respective endogenous receptor is reduced or inhibited in the subject.

Embodiment 222. The method of embodiment 220 or 221, wherein binding of BMP9 to its endogenous receptor is not substantially reduced or inhibited in the subject.

Embodiment 223. The method of any one of embodiments 220 to 222, wherein the subject is a mammal.

Embodiment 224. The method of embodiment 223, wherein the mammal is a human.

Embodiment 225. The method of any one of embodiments 220 to 224, wherein the subject has, or is suspected of having, or is at risk of developing a disease or condition mediated by activin A, activin B, GDF-8, GDF-11, and/or BMP-10.

Embodiment 226. The method of any one of embodiments 220 to 225, wherein activin A signaling is reduced or inhibited in the subject.

Embodiment 227. The method of any one of embodiments 220 to 226, wherein activin B signaling is reduced or inhibited in the subject.

Embodiment 228. The method of any one of embodiments 220 to 227, wherein GDF-8 signaling is reduced or inhibited in the subject.

Embodiment 229. The method of any one of embodiments 220 to 228, wherein GDF-11 signaling is reduced or inhibited in the subject.

Embodiment 230. The method of any one of embodiments 220 to 229, wherein BMP10 signaling is reduced or inhibited in the subject.

Embodiment 231. The method of any one of embodiments 220 to 230, wherein the disease or condition is characterized by overexpression or overactivation of activin A and/or activin B and/or GDF-8 and/or GDF-11.

Embodiment 232. The method of any one of embodiments 220 to 230, wherein the disease or condition is selected from pulmonary hypertension, fibrosis, muscle weakness or atrophy, metabolic disorders, cardiometabolic disease, bone damage, and low red blood cell levels.

Embodiment 233. The method of any one of embodiments 220 to 232, wherein the disease or condition is pulmonary hypertension (PH).

Embodiment 234. The method of embodiment 233, wherein the PH is arterial, venous, hypoxic, thromboembolic, or miscellaneous PH (also known as WHO groups 1-V).

Embodiment 235. The method of embodiment 233 or 234, wherein the PH is pulmonary arterial hypertension (PAH).

Embodiment 236. The method of embodiment 235, wherein the PAH is idiopathic PAH, heritable PAH, or PAH associated with an infection, a congenital heart abnormality, portal hypertension, pulmonary veno-occlusive disease, pulmonary capillary hemangiomatosis, a connective tissue disorder, chronic obstructive pulmonary disease, an autoimmune disorder (e.g., scleroderma or lupus), or drug use (e.g., use of cocaine or methamphetamine)

Embodiment 237. The method of any one of embodiments 220 to 232, wherein the disease or condition is fibrosis.

Embodiment 238. The method of embodiment 237, wherein the fibrosis is pulmonary fibrosis, idiopathic pulmonary fibrosis, renal fibrosis, liver fibrosis, lung fibrosis, kidney fibrosis, bone marrow fibrosis, systemic sclerosis, skin fibrosis, heart fibrosis, myelofibrosis, corneal fibrosis, mediastinal fibrosis, retroperitoneal fibrosis, osteoarticular fibrosis, arthrofibrosis, tissue fibrosis, a fibroproliferative disorder or a connective tissue disorder.

Embodiment 239. The method of any one of embodiments 220 to 232, wherein the disease or condition is muscle weakness or atrophy.

Embodiment 240. The method of embodiment 239, wherein the disease or condition is Duchenne muscular dystrophy (DMD), facioscapulohumeral muscular dystrophy (FSHD), inclusion body myositis (IBM), amyotrophic lateral sclerosis (ALS), sarcopenia, or cancer cachexia.

Embodiment 241. The method of any one of embodiments 220 to 232, wherein the disease or condition is a metabolic disorder.

Embodiment 242. The method of embodiment 241, wherein the metabolic disorder is obesity, Type 1 diabetes, Type 2 diabetes, or pre-diabetes.

Embodiment 243. The method of any one of embodiments 220 to 232, wherein the disease or condition is a cardiometabolic disease.

Embodiment 244. The method of embodiment 243, wherein the disease or condition is heart failure with a reduced ejection fraction (HFrEF) or heart failure with preserved ejection fraction (HFpEF).

Embodiment 245. The method of any one of embodiments 220 to 232, wherein the disease or condition is bone damage.

Embodiment 246. The method of embodiment 245, wherein the bone damage comprises bone demineralization, osteoporosis (e.g., primary or secondary), osteopenia, osteopetrosis, bone fracture, bone cancer or cancer metastasis-related bone loss, Paget's disease, renal osteodystrophy, treatment-related bone loss, diet-related bone loss, bone loss associated with the treatment of obesity, low gravity-related bone loss, or immobility-related bone loss.

Embodiment 247. The method of any one of embodiments 220 to 232, wherein the disease or condition is low red blood cell levels.

Embodiment 248. The method of embodiment 247, wherein the disease or condition is anemia or blood loss.

Embodiment 249. The method of any one of embodiments 220 to 248, wherein the method does not: cause a vascular complication in a subject; increase vascular permeability or leakage in a subject; increase red blood cell mass; increase hemoglobin; cause thrombocytopenia; and/or cause a hematological complication in a subject.

EXAMPLES

The present invention will be more readily understood by referring to the following examples, which are provided to illustrate the invention and are not to be construed as limiting the scope thereof in any manner.

Unless defined otherwise or the context clearly dictates otherwise, all technical and scientific terms used herein have the same meaning as commonly understood by one of ordinary skill in the art to which this invention belongs. It should be understood that any methods and materials similar or equivalent to those described herein can be used in the practice or testing of the invention.

Example 1. Design and Characterization of ActRIIB-ECD Polypeptide Constructs that Neutralize Activin a, Activin B, GDF-8, and GDF-11, but not BMP-9 Signaling A series of TGFβ superfamily binding agents were investigated to identify those that displayed high potency on disease-driving ligands while harboring low potency on ligands required for homeostasis. Agents were examined that were comprised of amino acid substitutions in the ActRIIB ECD at different positions as well as polypeptide variants that contained varying linker lengths between the ECD and the Fc domain. The results from the testing of these TGFβ superfamily binding agents are described below and highlight those with the desired ligand specificity profile.

Exemplary wild type human activin receptor ectodomain-Fc fusion molecules were produced and characterized and used as benchmark proteins: ActRIIB-ECD-Fc (also referred to as "ACVR2B-Fc") and ActRIIA-ECD-Fc (also referred to as "ACVR2A-Fc"), which are referred to herein as P75 (SEQ ID NO: 174) and P444 (SEQ ID NO: 176), respectively. P75 is comprised of the human wild type ActRIIB ECD (also referred to as the ACVR2B ectodomain) (SEQ ID NO: 2), linked to the human IgG1 Fc domain by a triple glycine linker. P444 was assembled similarly, but the ectodomain is the human wild type ActRIIA ECD (also referred to as the ACVR2A ectodomain) (SEQ ID NO: 3). It is noted that P444 (SEQ ID NO: 176) corresponds to the sequence of sotatercept, an investigational drug candidate which is composed of the extracellular domain of the activin receptor type IIA (ActRIIA) receptor linked to the Fc portion of human IgG1 (see, for example, U.S. Pat. No. 7,612,041). SDS-PAGE analysis of P75 and P444 is shown in FIG. 1. The observed molecular weights and purity were as expected and the disulphide-bonded homodimeric nature of the proteins was confirmed by the difference in size under reducing vs. non-reducing conditions.

Figure 2A:
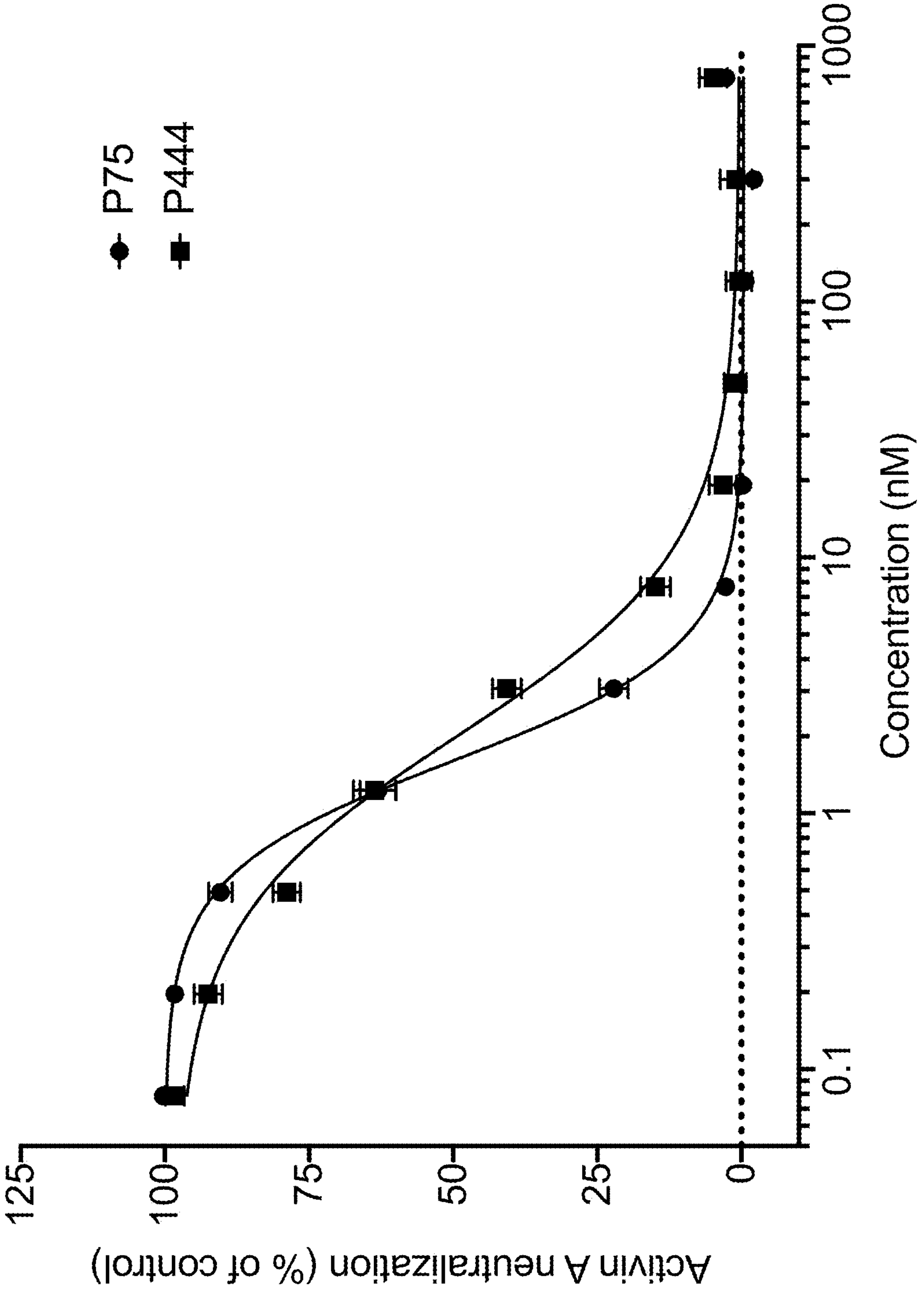
FIG. 2A-FIG. 2D shows representative results in the HEK-Blue cell-based assay for inhibition of TGFβ superfamily ligands for benchmark constructs P75 and P444, as indicated.
Figure 2B:
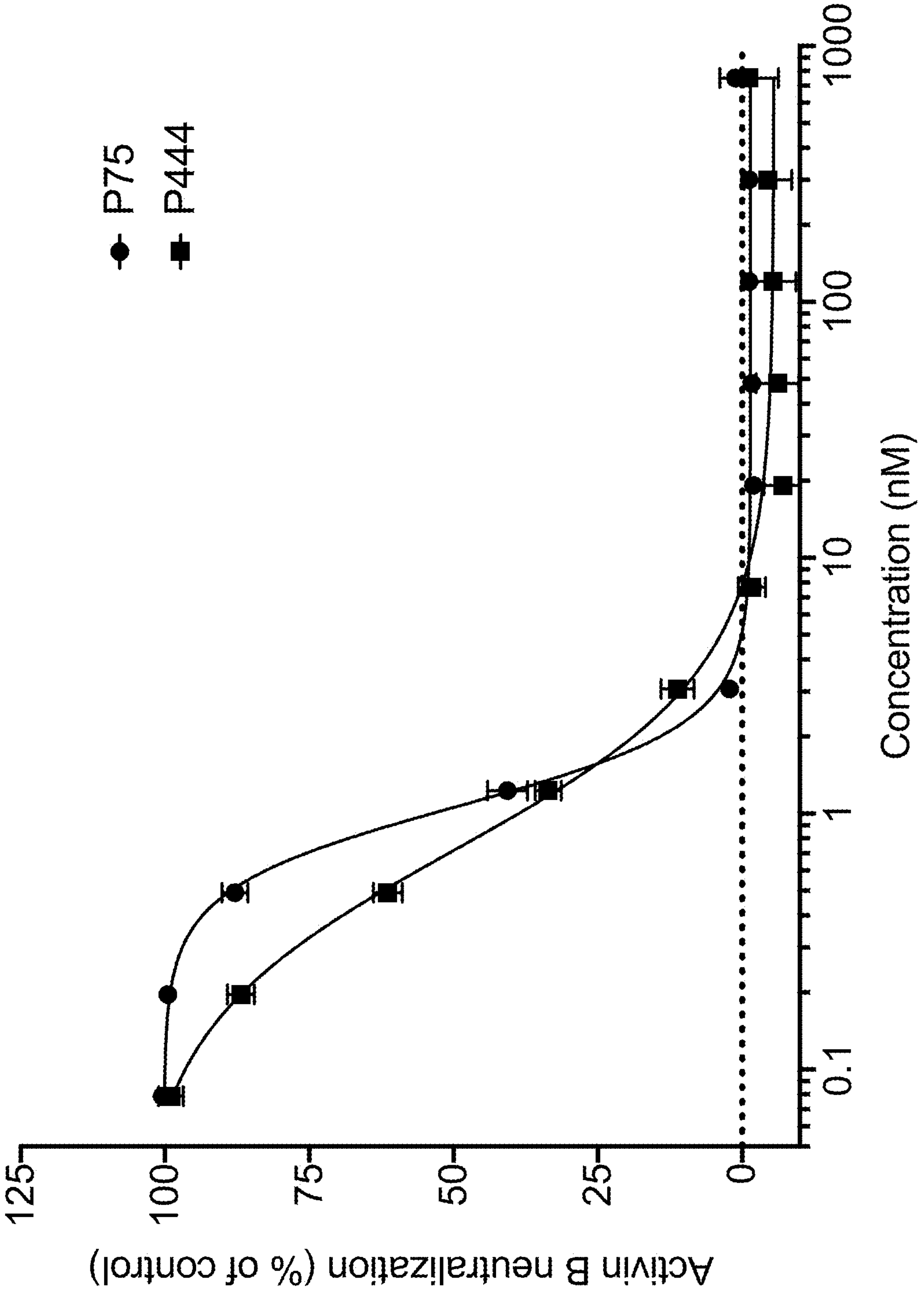
Figure 2C:
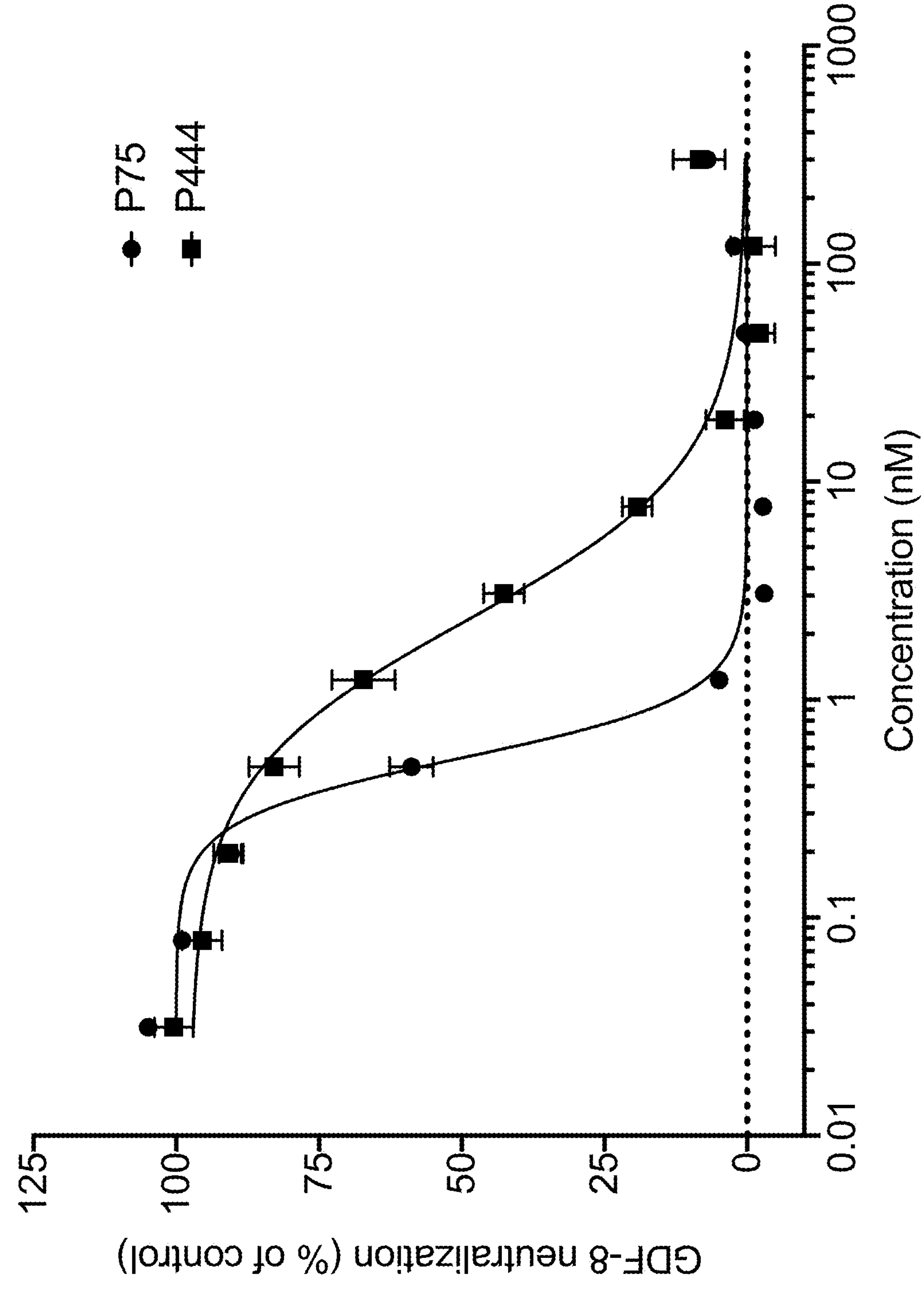
Figure 2D:
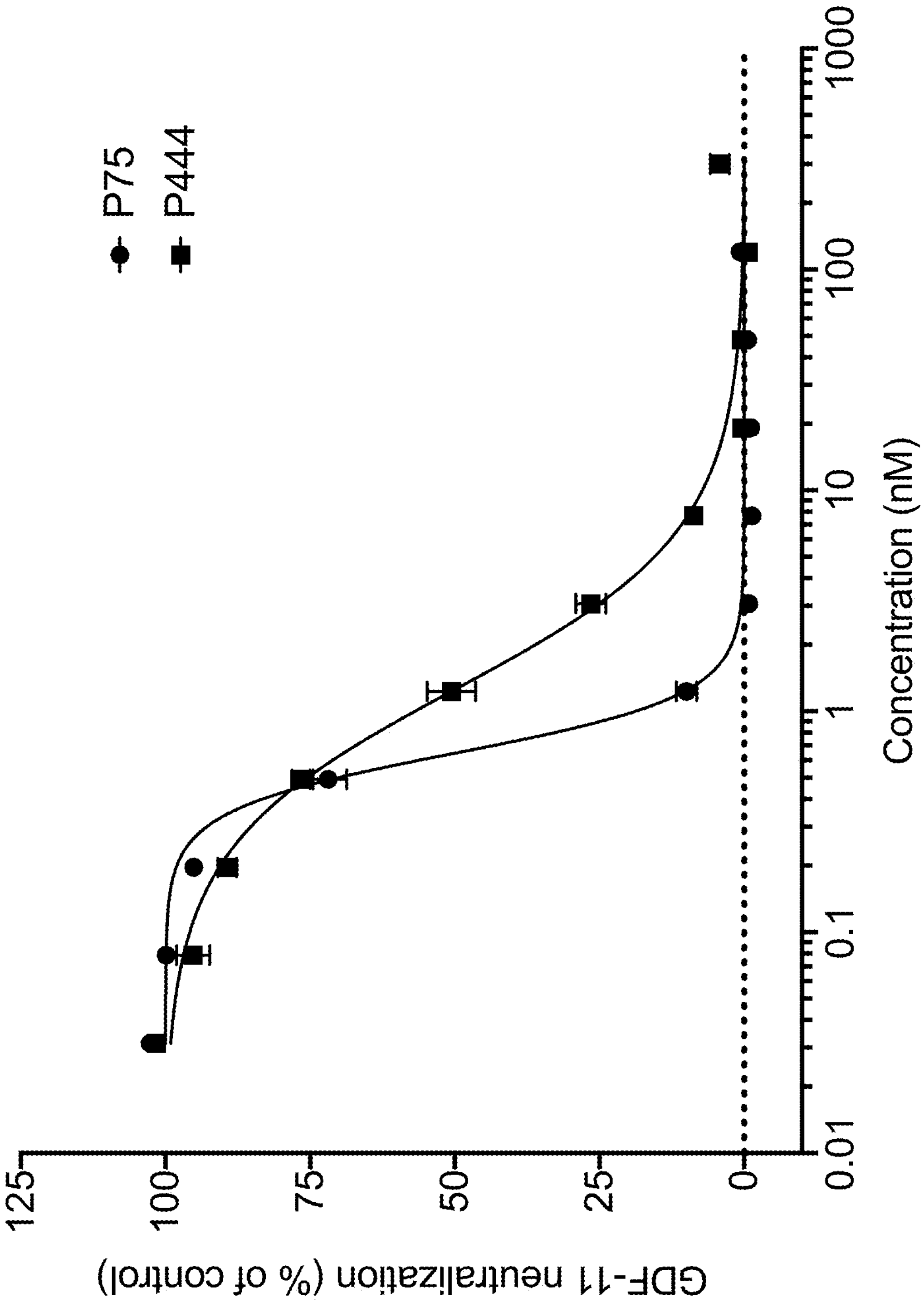

The activin A, activin B, GDF-8, and GDF-11 inhibition potency (IC50) of the benchmark agents P75 (wild type ActRIIB) and P444 (wild type ActRIIA (sotatercept)) were determined using the TGFβ-reporter HEK293 cell-based assay described below. P75 and P444 efficiently neutralized all four cytokines tested (activin A, activin B, GDF-8, and GDF-11) in a dose-dependent manner. The IC50 values represent the mean. Activin A IC50 values: 2.3 and 2.7 nM for P75 and P444, respectively (FIG. 2A). Activin B IC50 values: 1.4 and 0.95 nM for P75 and P444, respectively (FIG. 2B). GDF-8 IC50 values: 0.67 and 3.06 nM for P75 and P444, respectively (FIG. 2C). GDF-11 IC50 values: 0.76 and 1.6 nM for P75 and P444, respectively (FIG. 2D). The IC50 values±SEM are reported in Table 7.

Figure 3A:
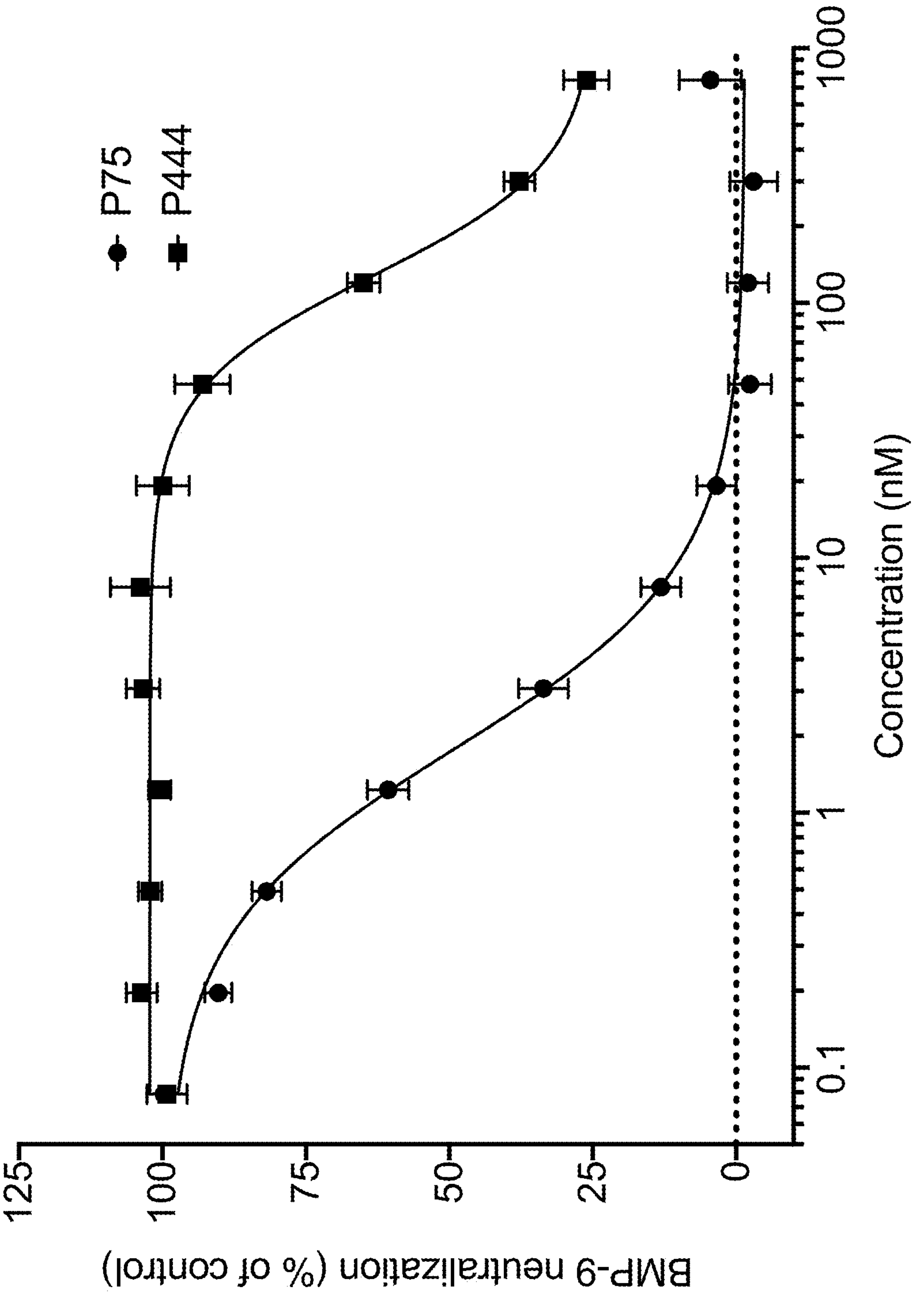
FIG. 3A-FIG. 3B show representative results in the HepG2 cell-based assay for inhibition of TGFβ superfamily ligands for benchmark constructs P75 and P444, as indicated.
Figure 3B:
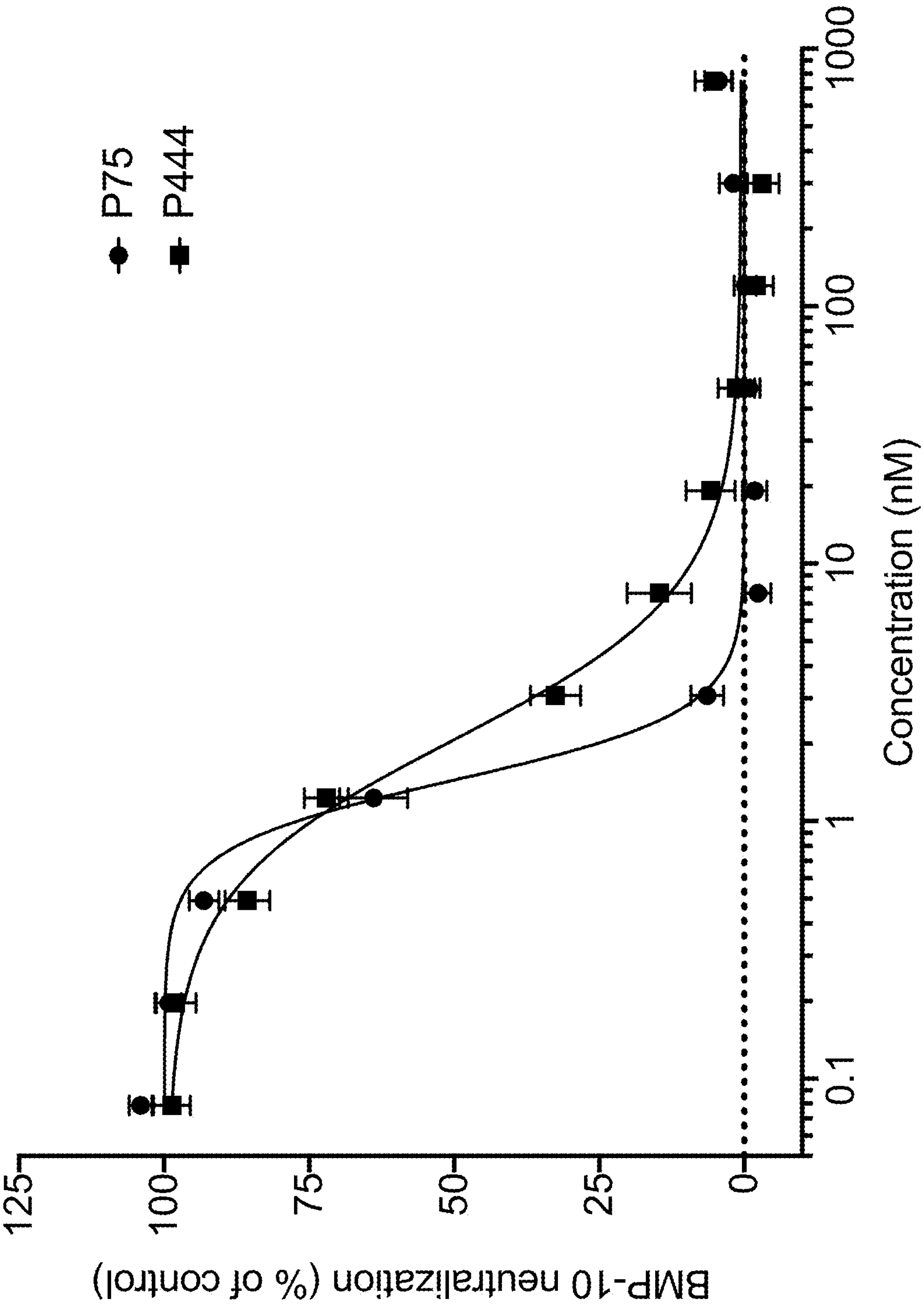
Figure 4A:
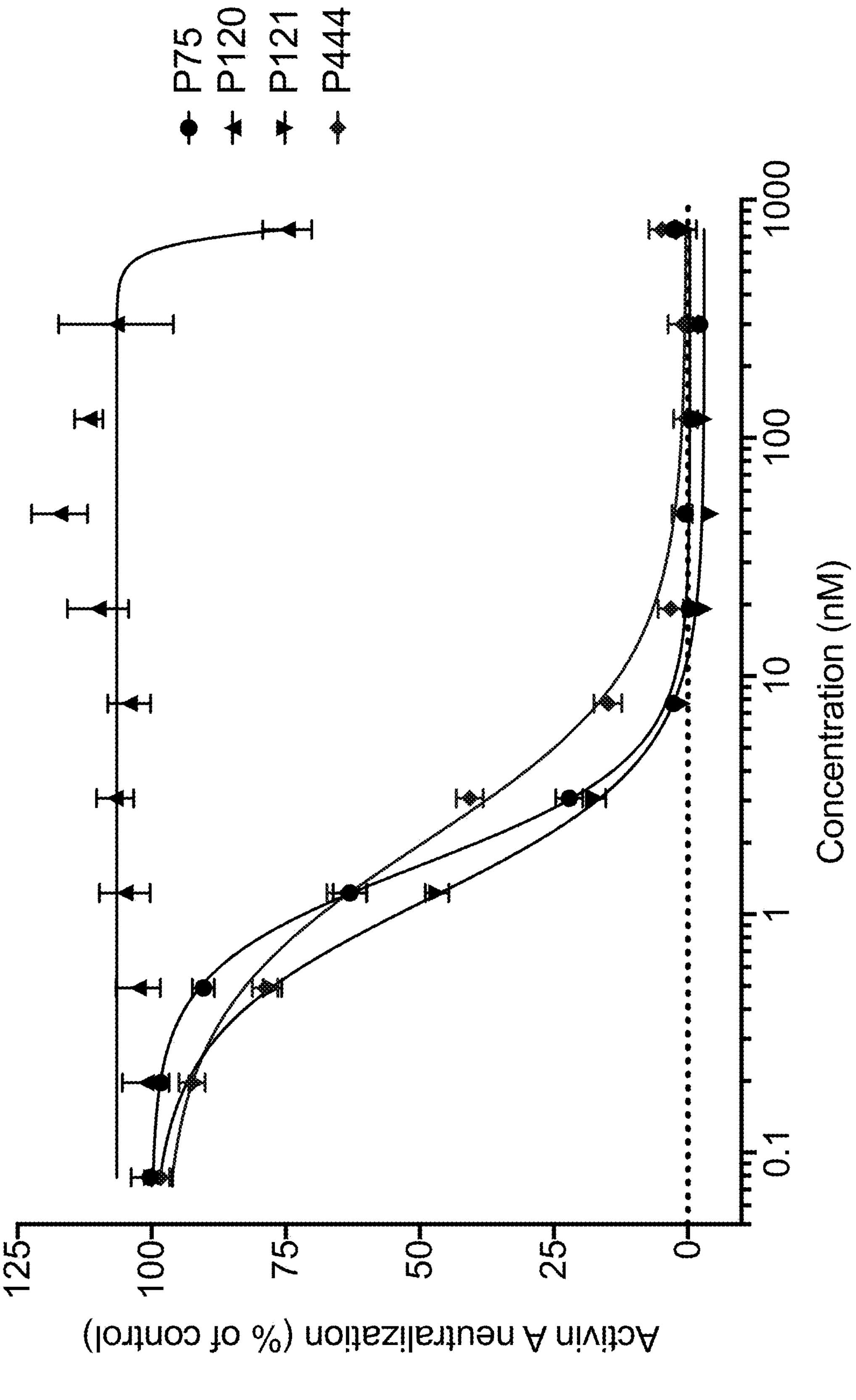
FIG. 4A-FIG. 4D shows representative results in the HEK-Blue cell-based assay for inhibition of activin A for exemplary proteins.
Figure 4B:
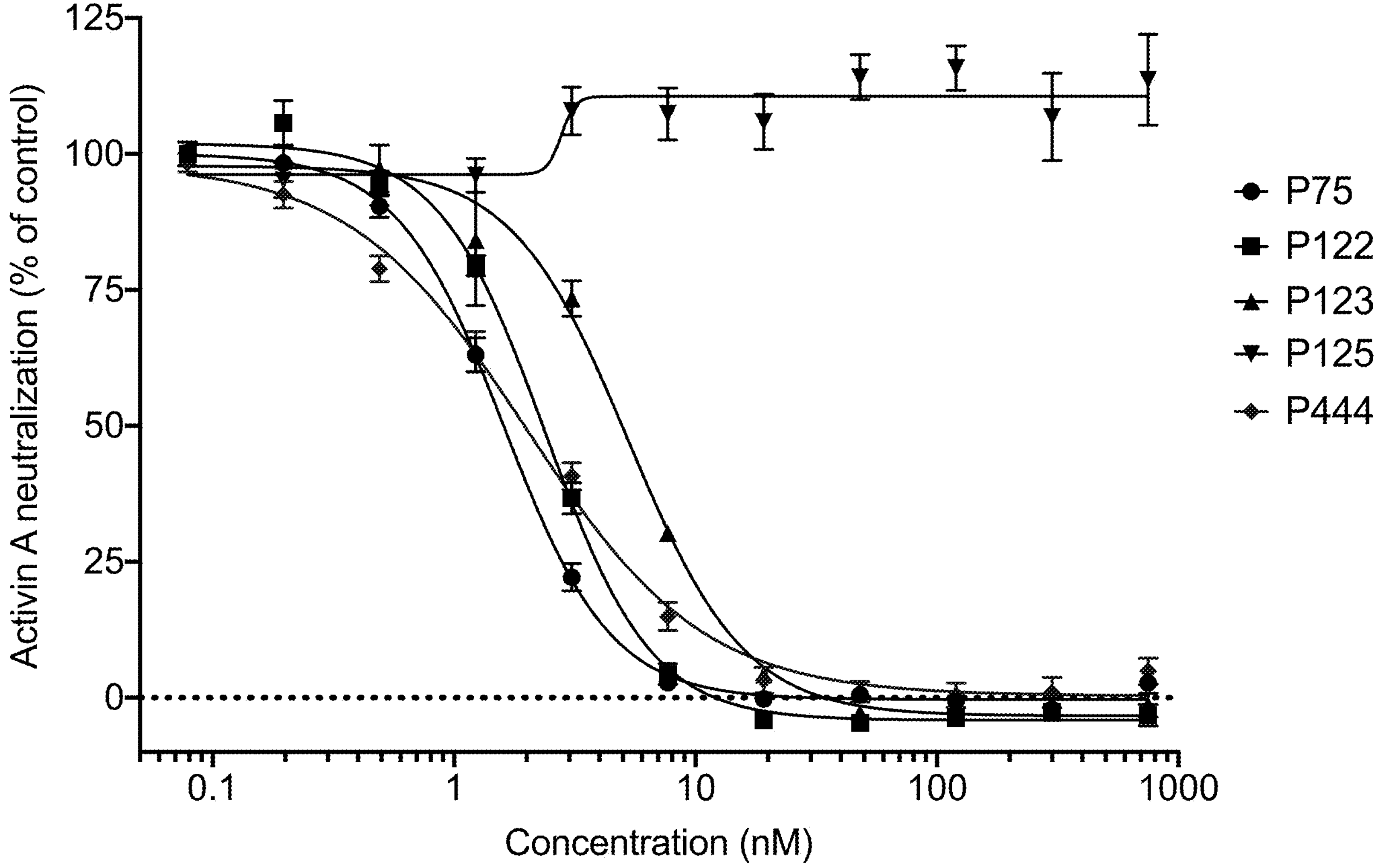
Figure 4C:
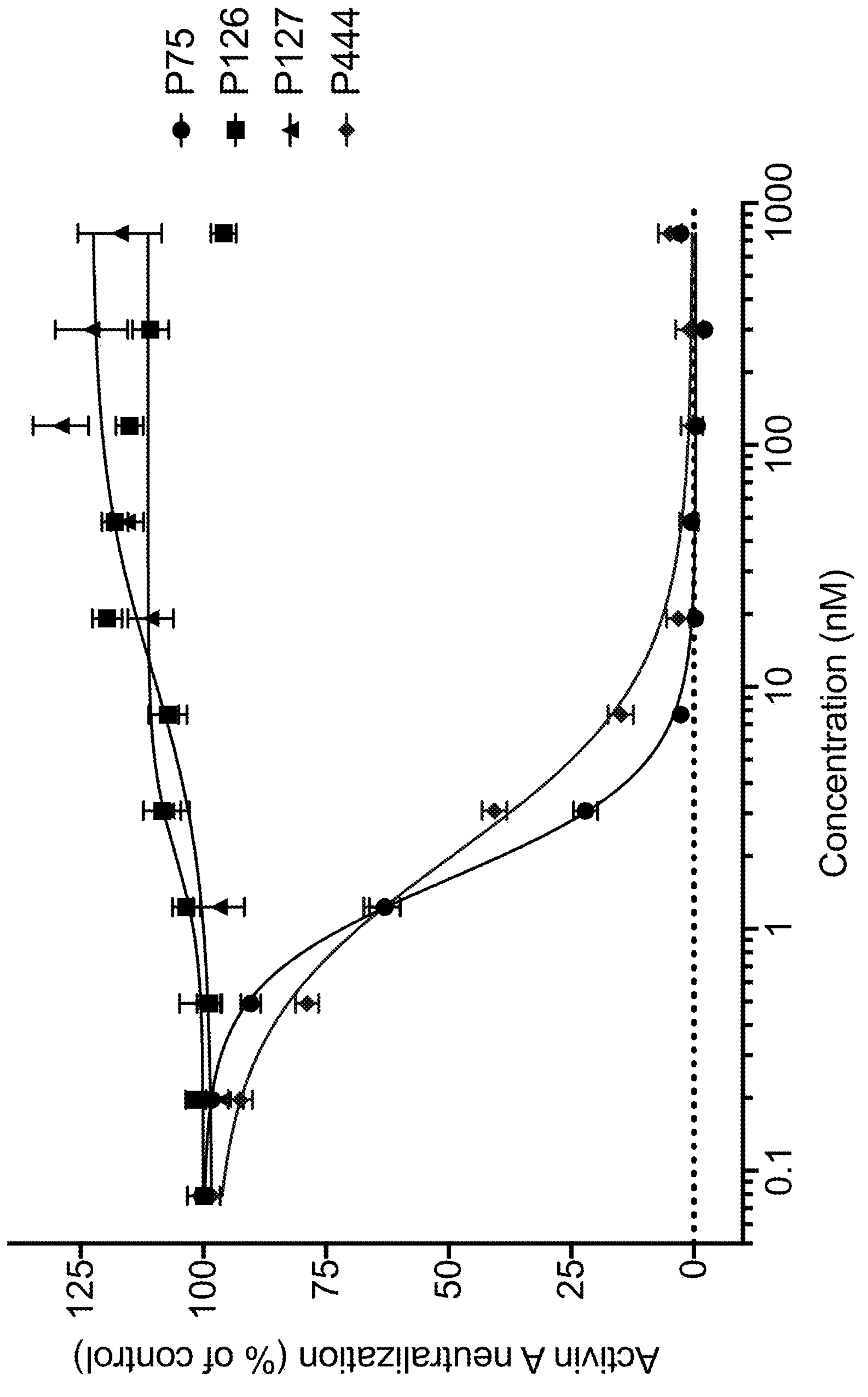
Figure 4D:
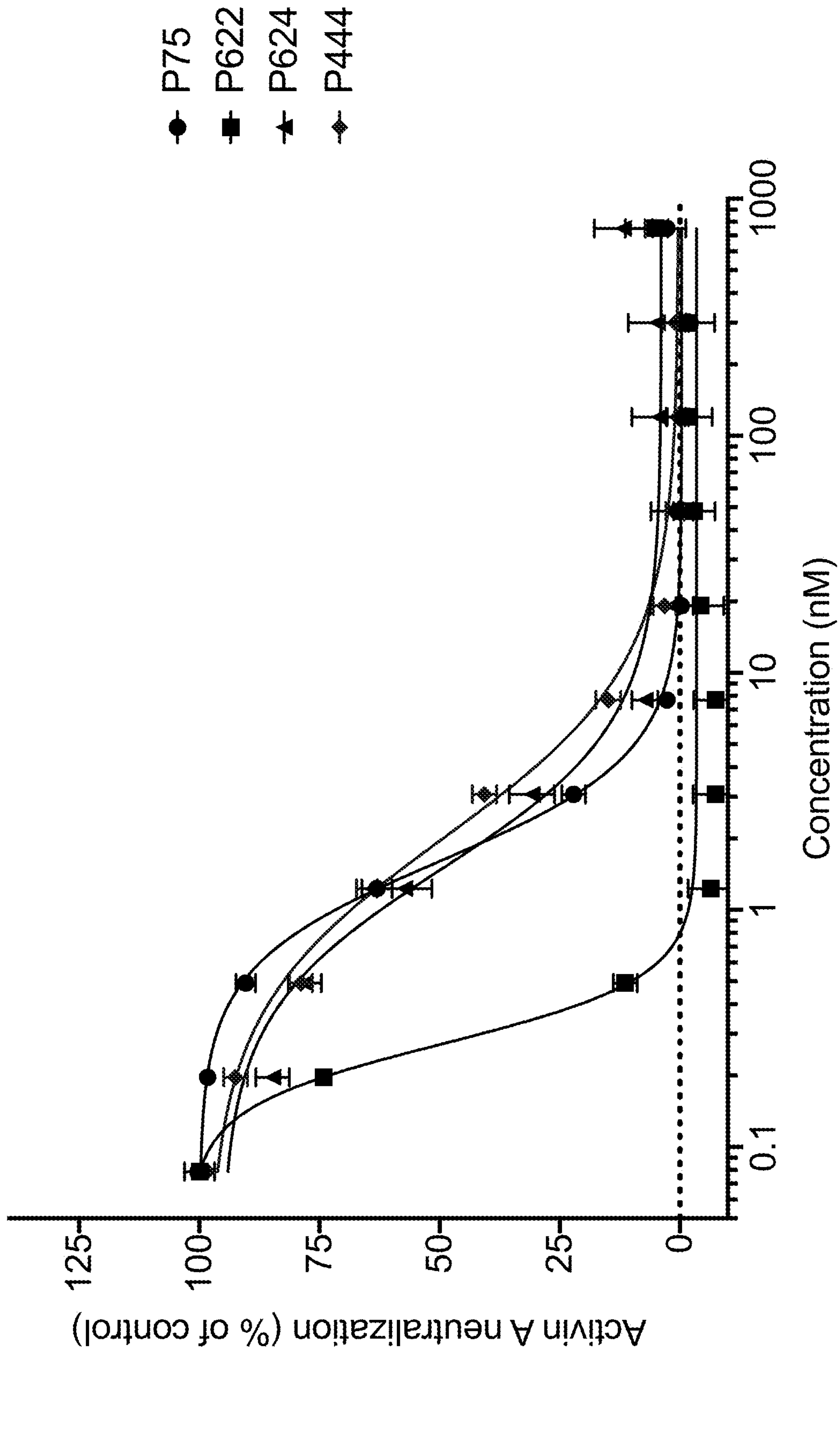
Figure 5A:
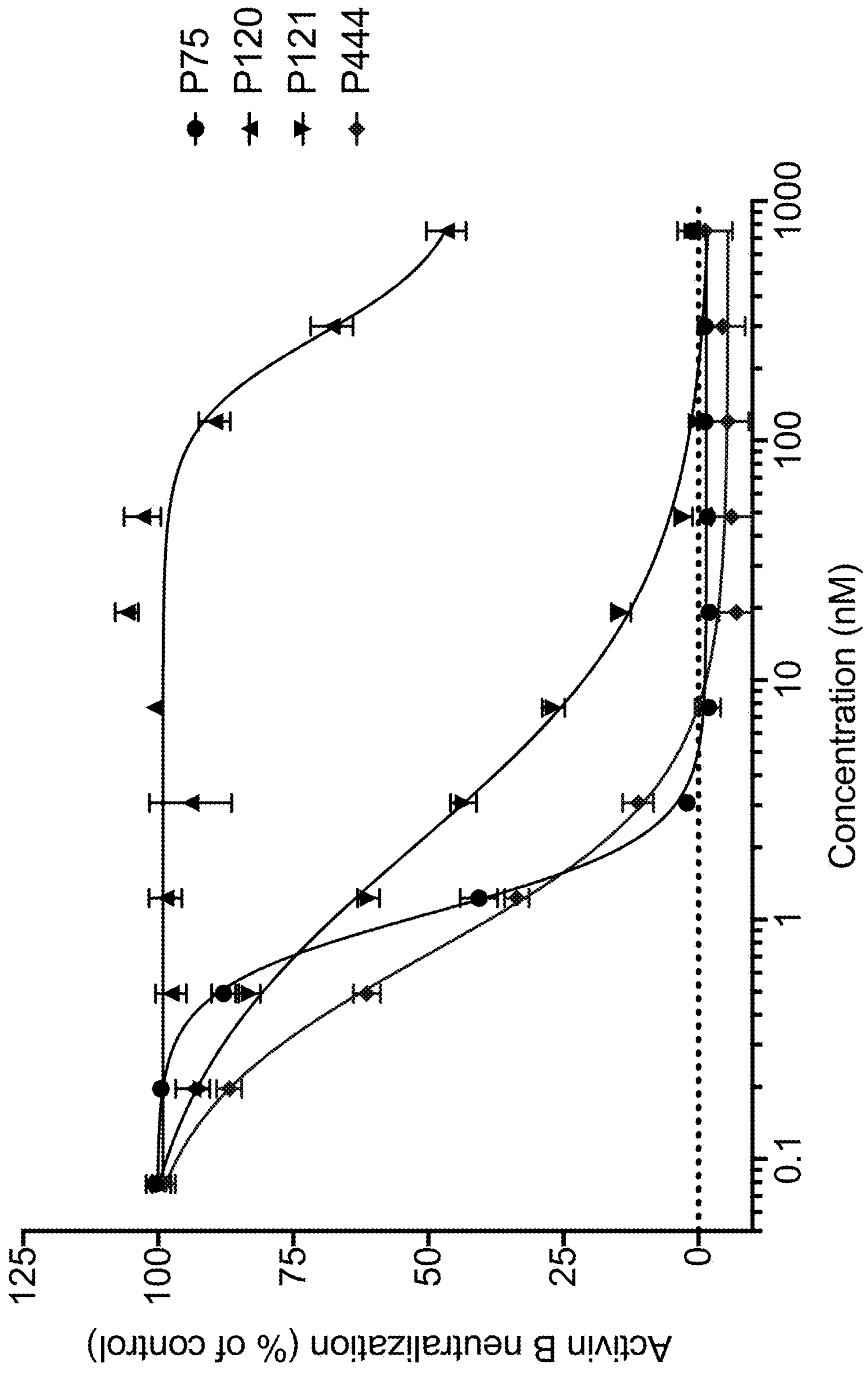
FIG. 5A-FIG. 5D shows representative results in the HEK-Blue cell-based assay for inhibition of activin B for exemplary proteins.
Figure 5B:
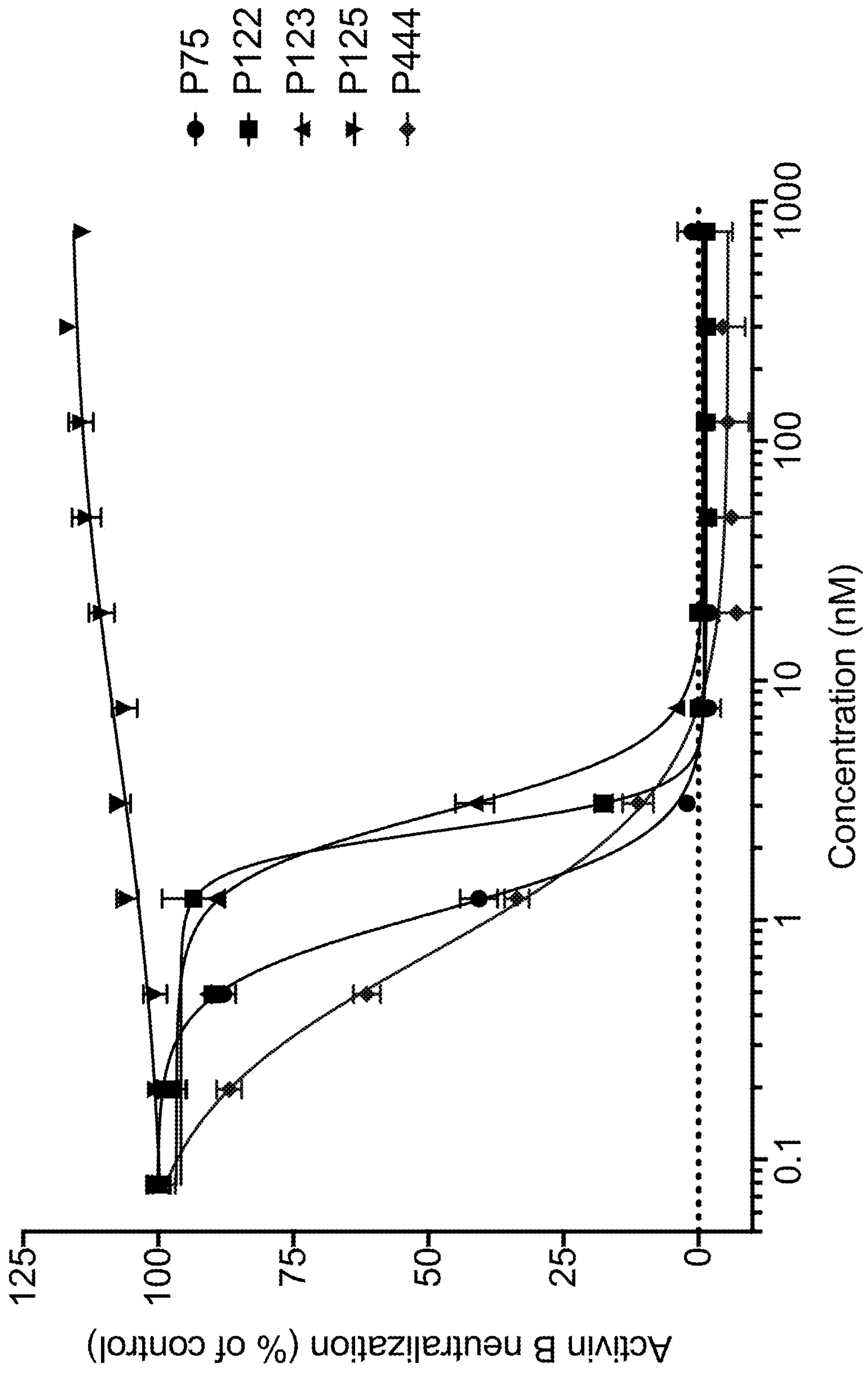
Figure 5C:
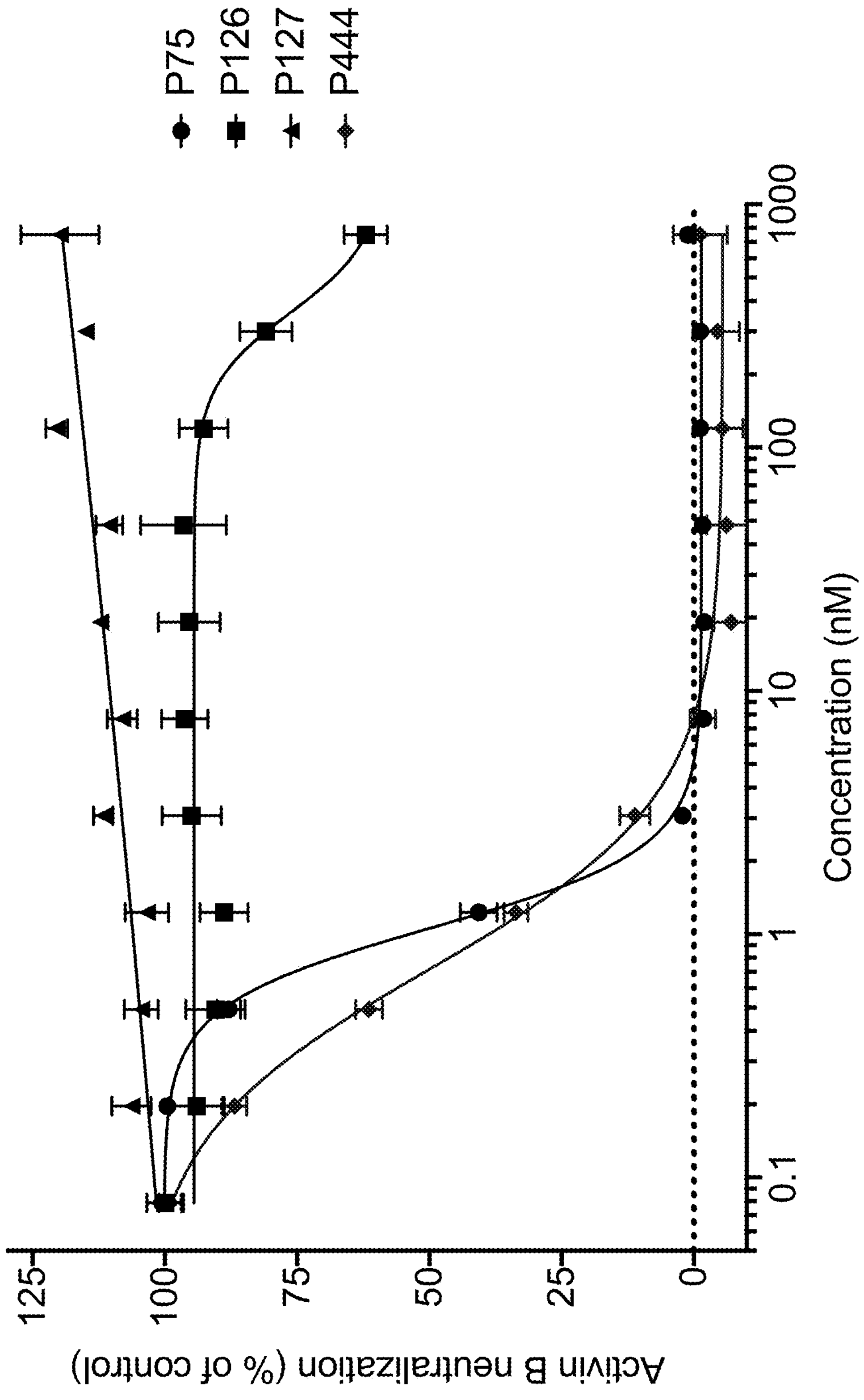
Figure 5D:
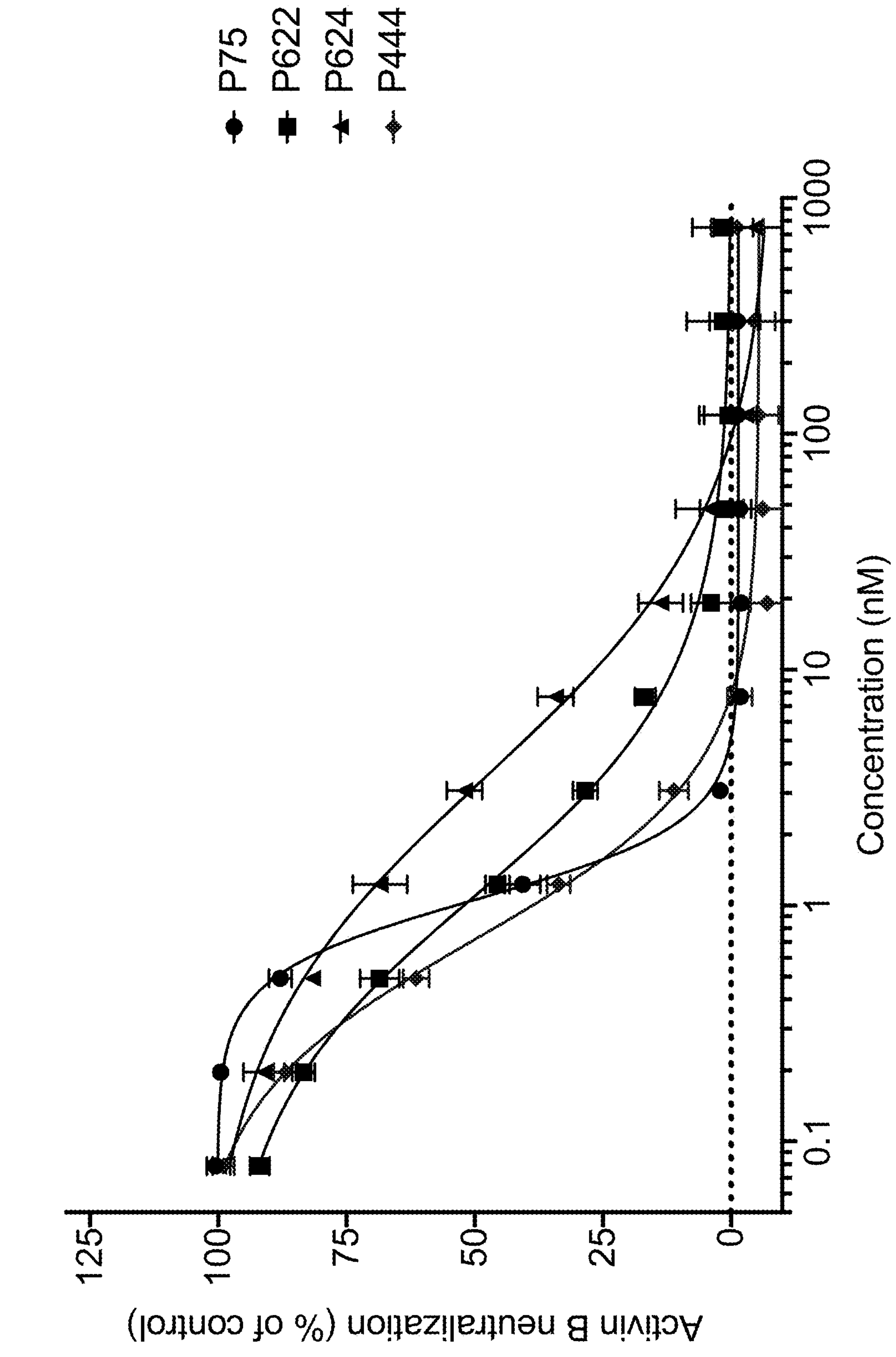
Figure 6A:
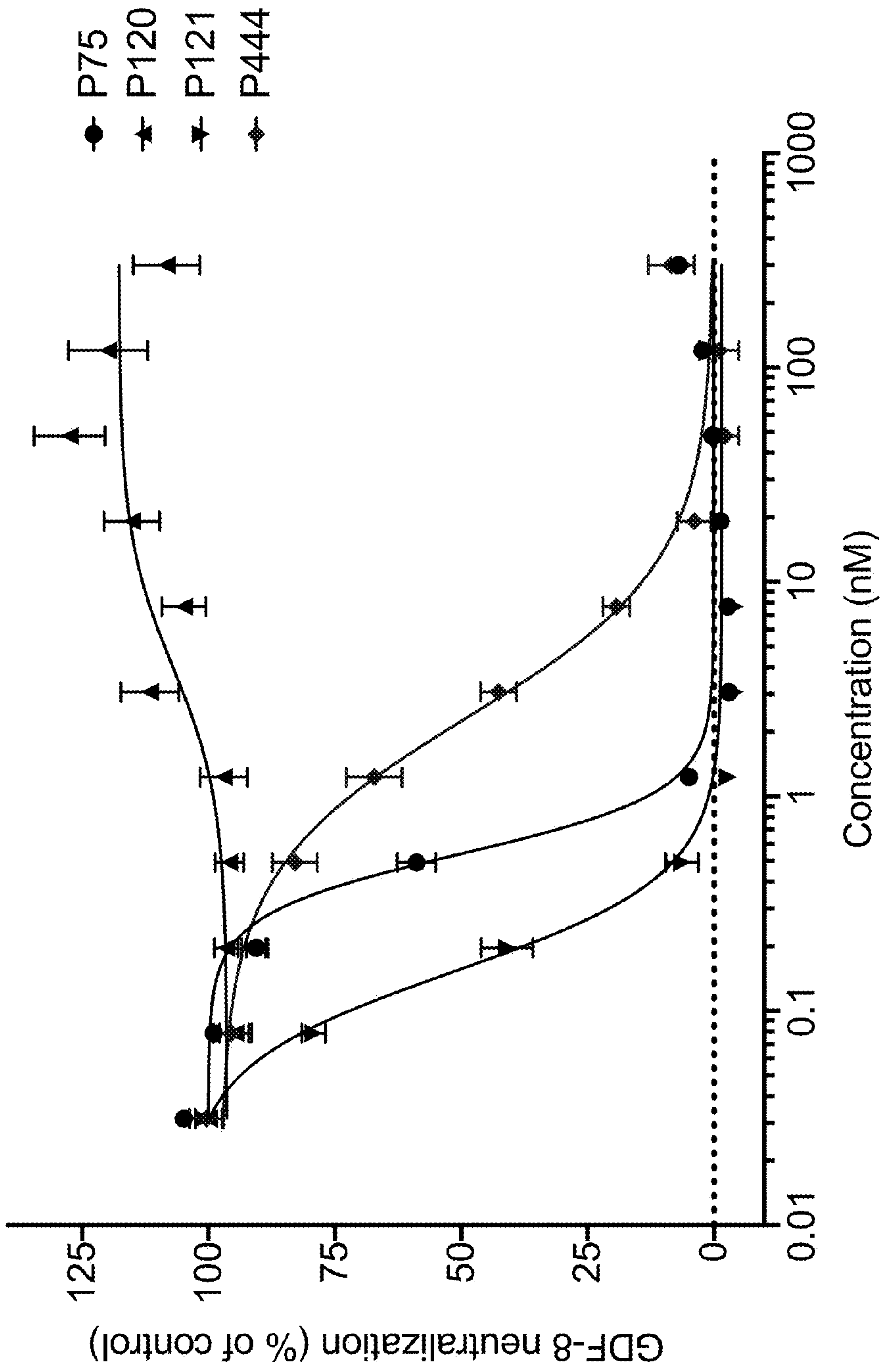
FIG. 6A-FIG. 6D shows representative results in the HEK-Blue cell-based assay for inhibition of GDF-8 for exemplary proteins.
Figure 6B:
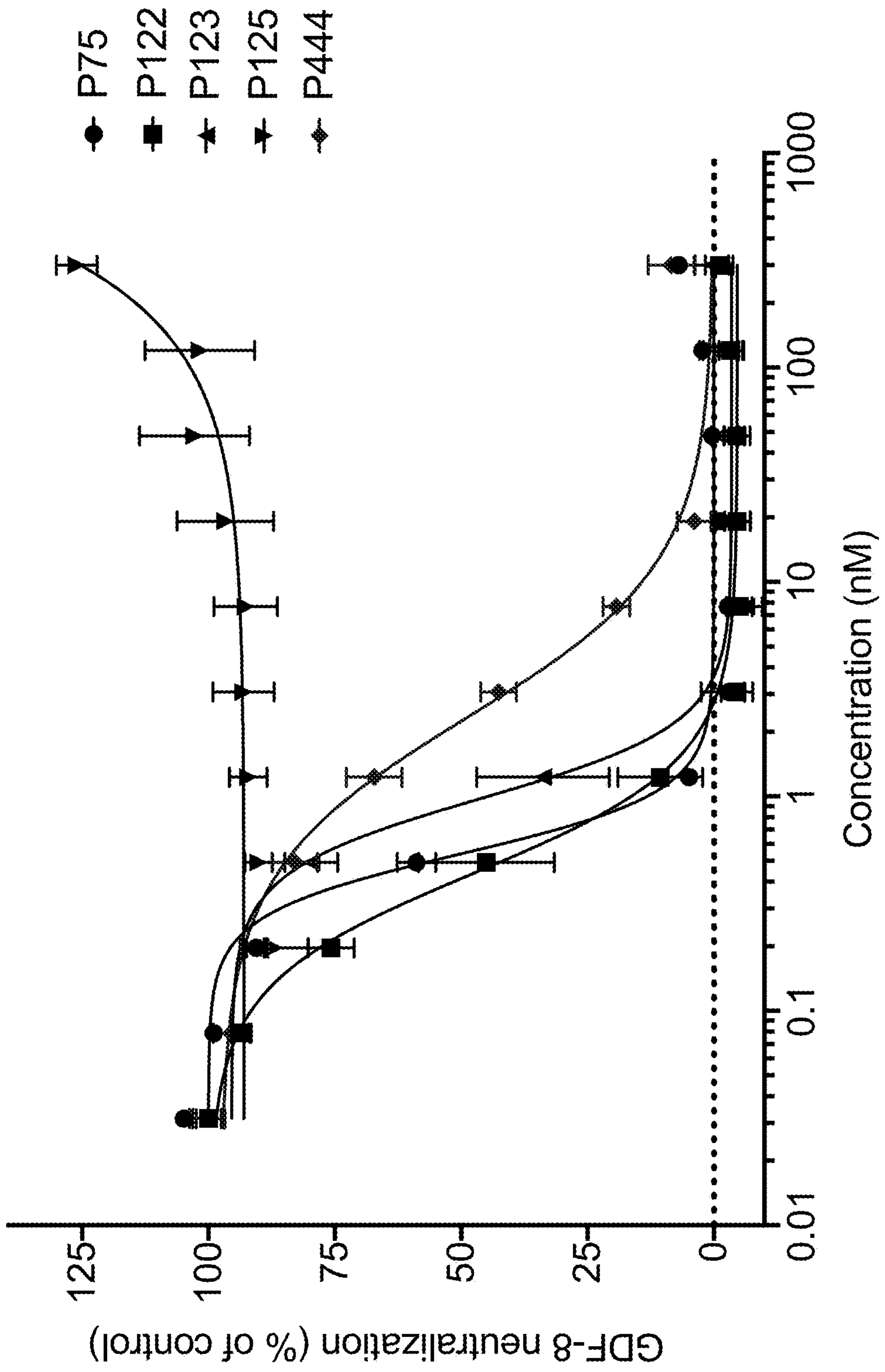
Figure 6C:
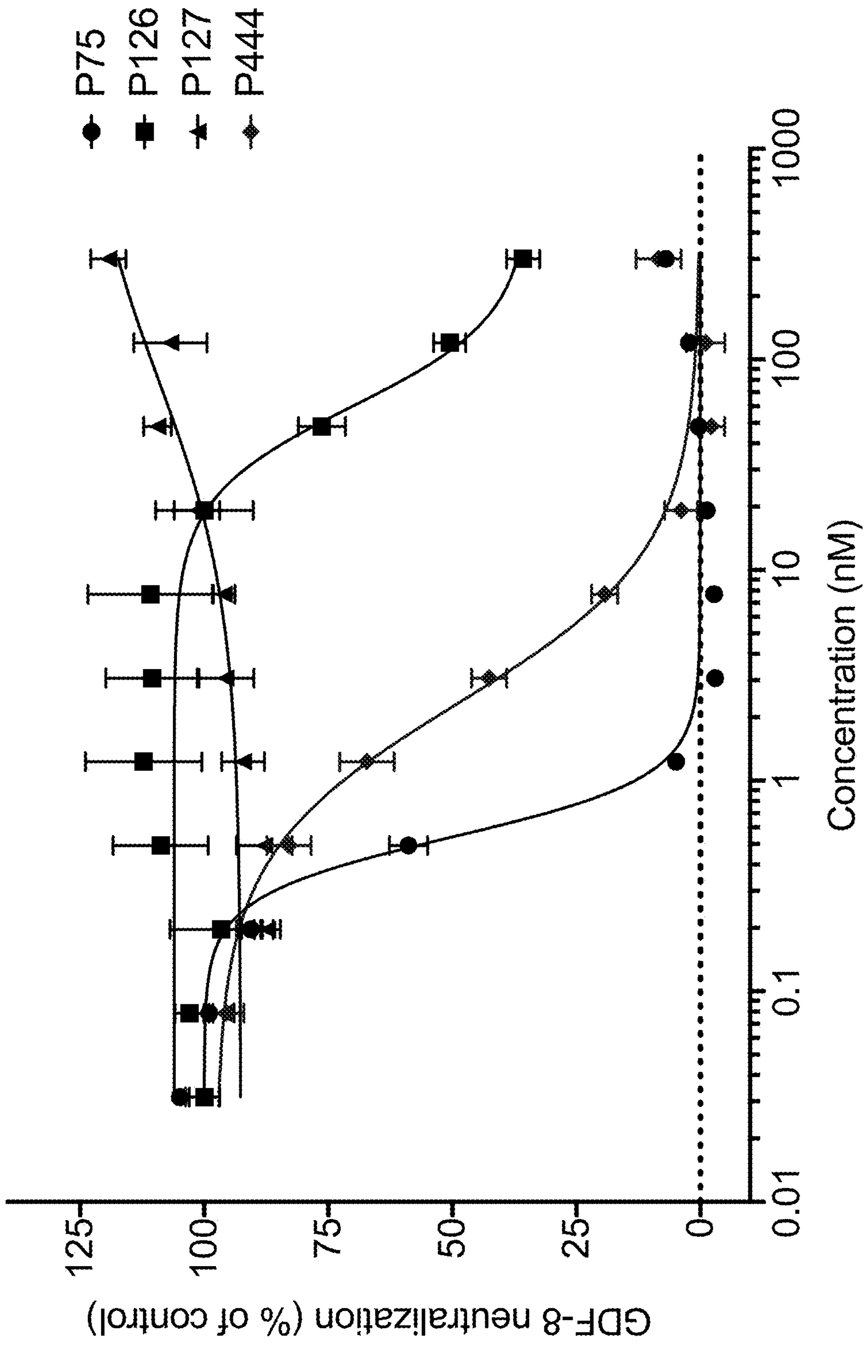
Figure 6D:
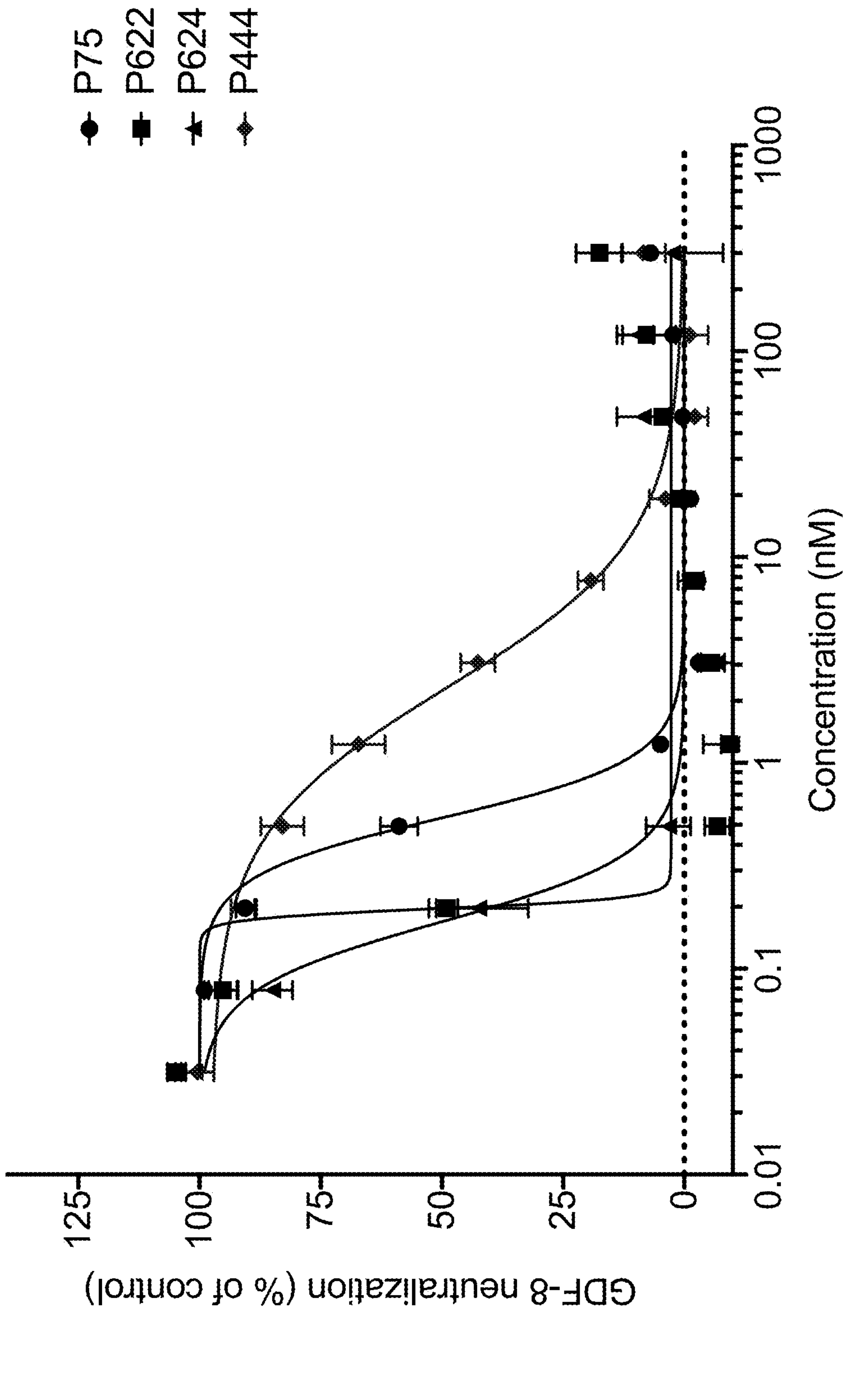

The BMP-9 and BMP-10 inhibition potency (IC50) of the benchmark agents P75 and P444 were determined using the BMP-reporter HepG2 cell-based assay described below. P75 neutralized BMP-9 in a dose-dependent manner, with an average IC50 value of 2.7 nM whereas P444 exhibited much less neutralization activity on BMP-9, with an IC50 value of greater than 100 nM (FIG. 3A). P75 and P444 efficiently neutralized BMP-10 in a dose-dependent manner, with average IC50 values of 2.0 and 3.7 nM for P75 and P444, respectively (FIG. 3B). The IC50 values are reported in Table 8.

TABLE 7

IC50 values for P75 and P444 for activin A, activin B, GDF-8, and GDF-11 neutralization.

| | Activin A | | Activin B | | GDF-8 | | GDF-11 | |
|---|---|---|---|---|---|---|---|---|
| ECD construct | Avg IC50 (nM) | SEM | Avg IC50 (nM) | SEM | Avg IC50 (nM) | SEM | Avg IC50 (nM) | SEM |
| P75 | 2.3 | 0.09 | 1.4 | 0.06 | 0.67 | 0.03 | 0.76 | 0.05 |
| P444 | 2.7 | 0.18 | 0.95 | 0.12 | 3.1 | 0.23 | 1.6 | 0.22 |

SEM: standard error of the mean; agents were tested in at least two independent experiments.

TABLE 8

IC50 values for P75 and P444 for BMP-9 and BMP-10 neutralization.

| | BMP-9 | | BMP-10 | |
|---|---|---|---|---|
| Ectodomain construct | Average IC50 (nM) | SEM | Average IC50 (nM) | SEM |
| P75 | 2.7 | 0.20 | 2.0 | 0.10 |
| P444 | 248 | 60 | 3.7 | 0.53 |

SEM: standard error of the mean; agents were tested in at least two independent experiments.

Figure 7A:
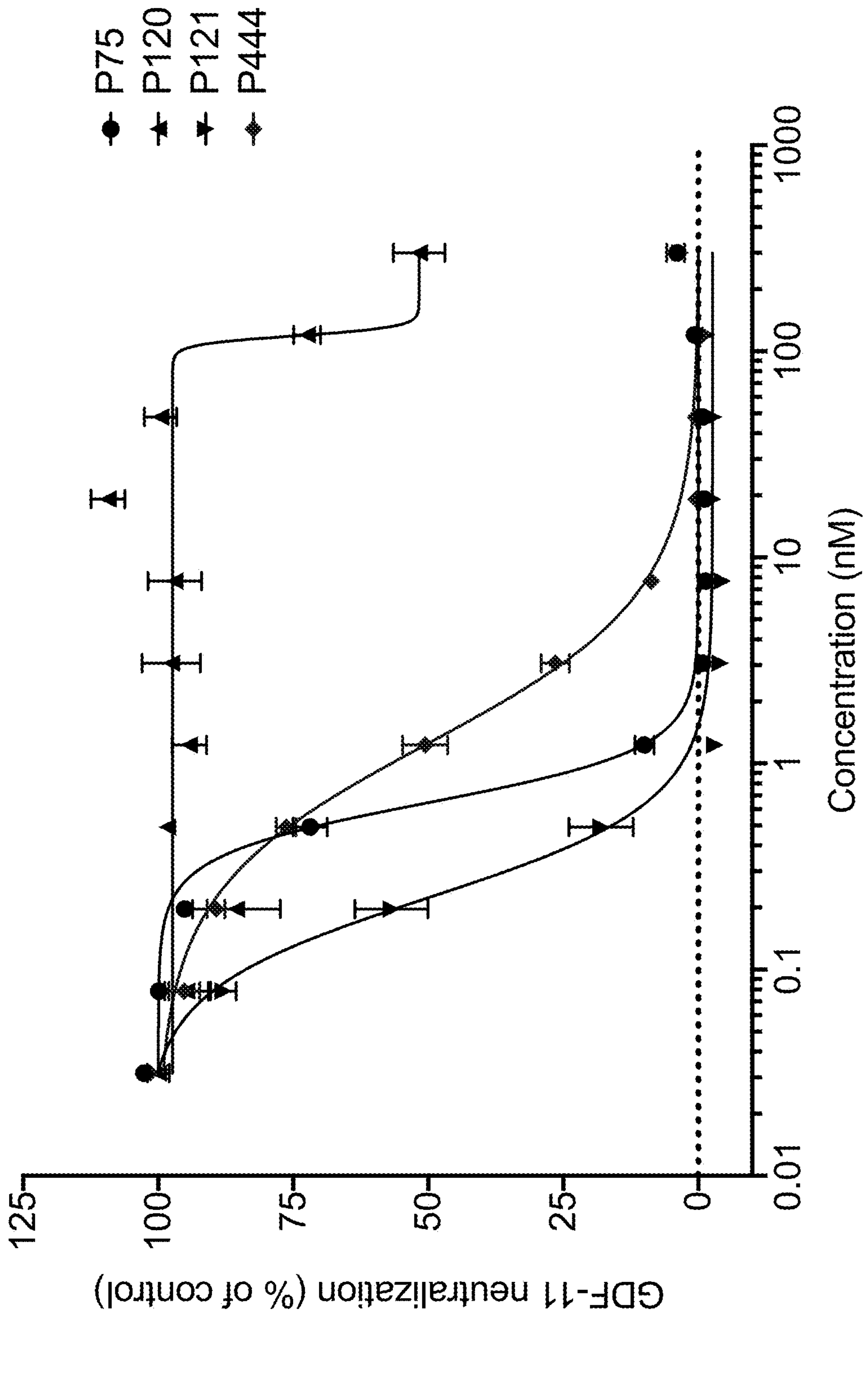
FIG. 7A-FIG. 7D shows representative results in the HEK-Blue cell-based assay for inhibition of GDF-11 for exemplary proteins.
Figure 7B:
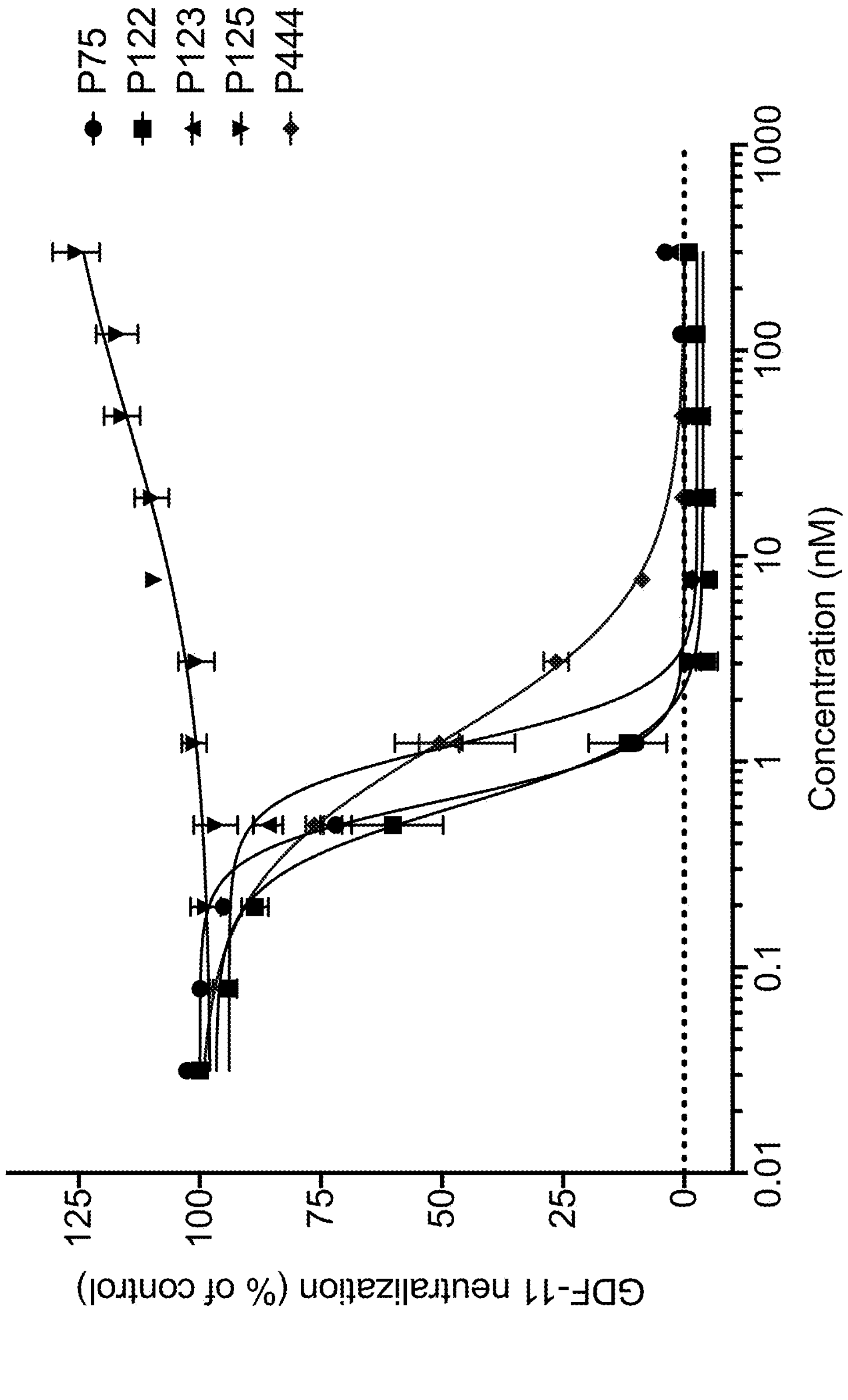
Figure 7C:
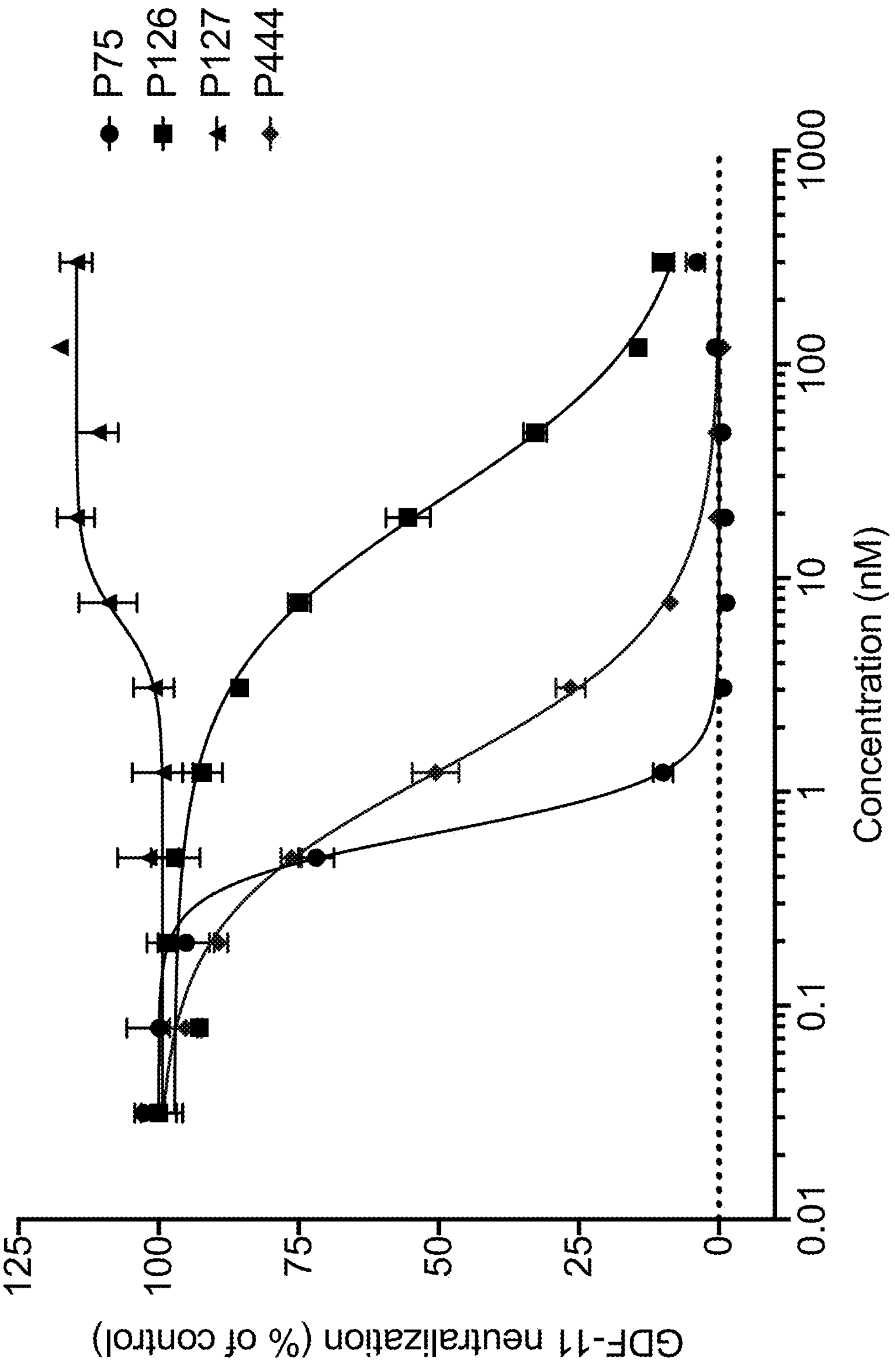
Figure 7D:
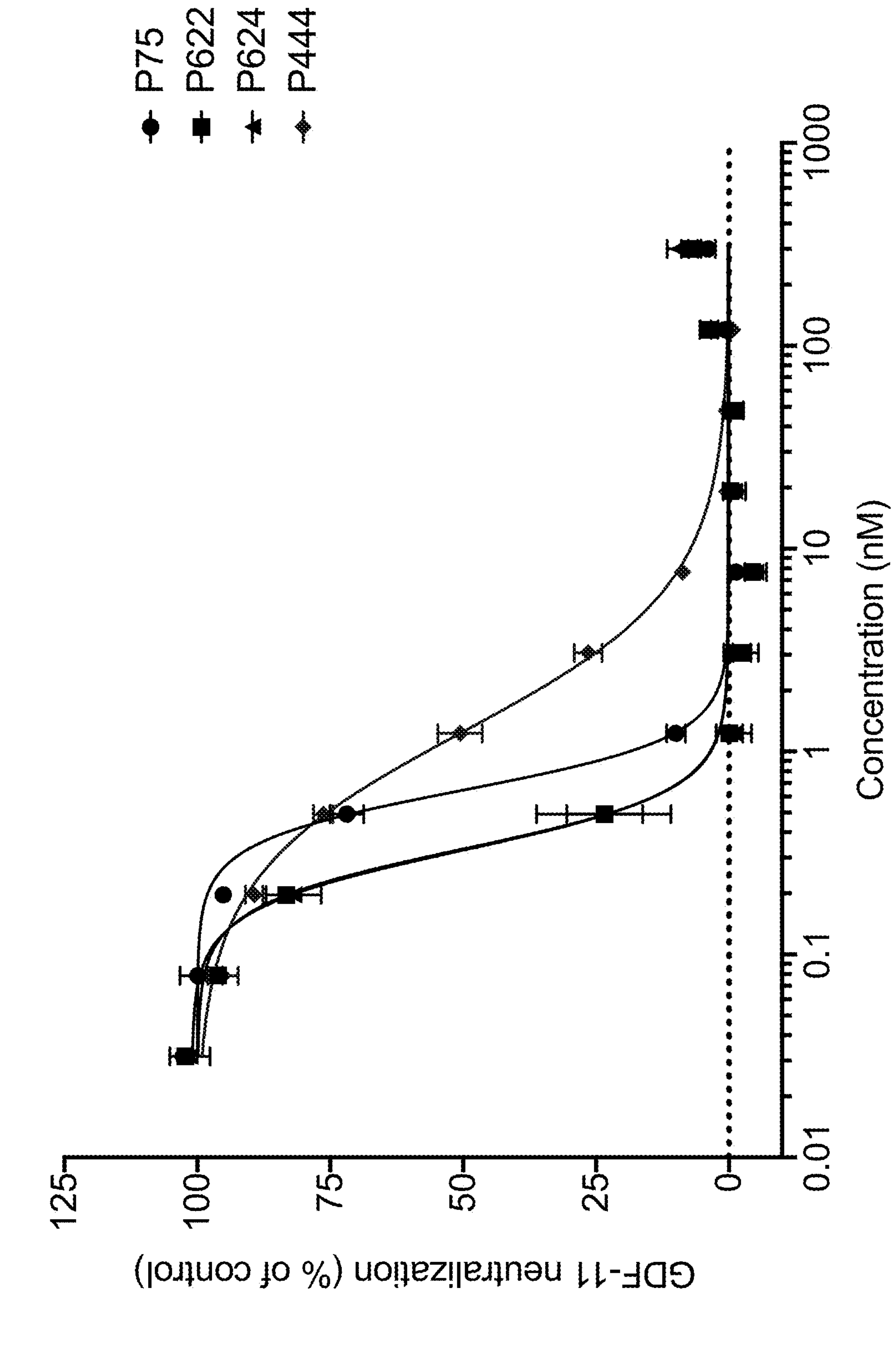

In order to generate agents with high potency inhibition of TGFβ superfamily ligands known to be important in driving disease, ActRIIB-ECD polypeptide variants were examined in the TGFβ-reporter HEK293 cells. The IC50 values obtained in this assay for the entire group of ECD constructs are presented in Table 9 and representative results for exemplary ECD constructs are shown in FIGS. 4-7 and FIGS. 11-14. Among these examples, P122 and P123 had the same or slightly lower potencies relative to P75 (wild type ActRIIB-ECD), i.e., the IC50 values for P122 and P123, respectively on activin A were 2.4 and 5.0 nM (FIG. 4B); on activin B were 2.5 and 2.8 nM (FIG. 5B); on GDF-8 were 0.62 and 1.1 nM (FIG. 6B); on GDF-11 were 0.71 and 1.2 nM (FIG. 7B). Other examples, such as P119, P121, and P126, had slightly increased neutralization profiles on multiple ligands, relative to wild type ActRIIB-ECD (P75), e.g., the potency of P121 was improved 1.7-, 2.3-, and 1.9-fold on activin A, GDF-8, and GDF-11 respectively, relative to P75 (FIGS. 4A, 6A, 7A, 11C, 13C, 14C), whereas on activin B, the neutralization potency of P119 and P121 was slightly lower compared with P75 (see FIGS. 5A and 12C). In the case of P126, the neutralization potencies on all four ligands were significantly decreased compared to wild type ActRIIB-ECD (P75) (see FIGS. 4-7, panel C). The IC50 values for P119, P121, and P126, respectively, on activin A were 0.98, 1.3, and >1,000 nM; on activin B were 1.8, 2.5, and >1,000 nM; on GDF-8 were 0.64, 0.29, and 65 nM; on GDF-11 were 0.97, 0.40, and 23 nM. Some test constructs, notably P120, P125, and P127, lost the ability to neutralize all four ligands (FIGS. 4-7).

The effect of linker length was examined in the context of the wild-type ActRIIB ECD as well as in the context of a series of different mutations in the ActRIIB ECD. Exemplary human activin receptor ectodomain-Fc fusion molecules were produced and characterized as described below. Agents P75 and P757 contain the wild-type ActRIIB ECD fused to Fc through a linker of 3 amino acids or 14 amino acids, respectively. The IC50 values are reported in Table 9 and illustrated in FIGS. 10A-B. Representative neutralization curves are shown in FIGS. 11A, 12A, 13A, and 14A. The potency of P757 was significantly greater on activin A, activin B, GDF-8, and GDF-11, relative to P75 (Table 9 and FIG. 10A), with increases of 389%, 155%, 116%, and 124%, respectively (FIG. 10B).

To examine the effect of linker length in the context of different mutations in the ActRIIB ECD, a series of comparisons were made. One exemplary pair of agents (P624 and P622) contain an F to E substitution at position 58 of the ActRIIB ECD and a 3 amino acid or 14 amino acid linker, respectively. The activin A, activin B, GDF-8, and GDF-11 inhibition potency (IC50) of these agents was determined using the TGFβ-reporter cell-based assay. The IC50 values are reported in Table 9 and illustrated in FIGS. 10C-D. Representative neutralization curves are shown in FIGS. 4D, 5D, 6D, and 7D. The potencies of P622 on activin A and activin B were found to be higher compared to P624 as demonstrated by lower IC50 values (Table 9 and FIG. 10C), i.e., P622 potency on activin A and activin B increased by 295% and 129%, respectively, relative to P624 (FIG. 10D). Interestingly, the IC50 values of P622 and P624 on GDF-8 and GDF-11 were the same (Table 9 and FIGS. 10C-D). The same trend was observed when comparing ligand binding activities of P622 (F58E+14 aa linker+IgG1 DL Fc) and P121 (F58E+3 aa linker+IgG1 EM Fc), demonstrating that the DL and EM Fc polymorphisms do not substantially affect the activity of the fusion proteins described herein (See Table 9).

Another exemplary pair of agents with different linker lengths was P120 (3 amino acid linker) and P759 (14 amino acid linker), each with a D to E substitution at position 57 of the ActRIIB ECD. The IC50 values are reported in Table 9 and illustrated in FIGS. 10E-F. Representative neutralization curves are shown in FIGS. 4A, 5A, 6A, 7A, 11A, 12A, 13A, and 14A. P759 was found to have an increased potency on activin A, activin B, GDF-8 and GDF-11 relative to P120 (Table 9 and FIG. 10E), i.e., P759 potency on activin A, activin B, GDF-8, and GDF-11 increased by 73%, 77%, 60%, and 86%, respectively, relative to P120 (FIG. 10F).

Another exemplary pair of agents with different linker lengths was P124 and P761, each with a K to Y substitution at position 31 of the ActRIIB ECD and a 3 amino acid or 14 amino acid linker, respectively. The IC50 values are reported in Table 9 and illustrated in FIGS. 10G-H. Representative neutralization curves are shown in FIGS. 11A and C, 12A and C, 13A and C, and 14A and C. Surprisingly and in contrast to the effect of increasing linker length presented above, the exemplary agent P761 with the longer 14 amino acid linker exhibited decreased potency (showed higher IC50 values) on both activins and both GDFs (Table 9 and FIG. 10G), i.e., P761 potency on activin A, activin B, GDF-8, and GDF-11 decreased by 58%, 88%, 64%, and 61%, respectively, relative to P124 (FIG. 10H).

Another exemplary pair of agents with different linker lengths was P119 and P758, each with a G to D substitution at position 27 of the ActRIIB ECD and a 3 amino acid or 14 amino acid linker, respectively. The IC50 values are reported in Table 9 and illustrated in FIGS. 10I-J. Representative neutralization curves are shown in FIGS. 11A and C, 12A and C, 13A and C, and 14A and C. Unexpectedly, the potencies on activin A, activin B, GDF-8 and GDF-11 all decreased for the agent with the longer 14 amino acid linker (Table 9 and FIG. 10G), with a more pronounced decrease in potency on GDF-8 (Table 9 and FIG. 10I), i.e., P758 potency on activin A, activin B, GDF-8, and GDF-11 decreased by 11%, 35%, 99%, and 44%, respectively, relative to P119 (FIG. 10J).

Another exemplary pair of agents with different linker lengths was P126 (3 amino acid linker) and P762 (14 amino acid linker), each with a V to Q substitution at position 75 of the ActRIIB ECD. The IC50 values are reported in Table 9 and illustrated in FIGS. 10K-L. Representative neutralization curves are shown in FIGS. 4C, 5C, 6C, 7C, 11A, 12A, 13A, and 14A. Unexpectedly, in the context of this mutation, the change in linker length did not affect potency, i.e., P126 and P762 exhibited the same potencies on activin A, activin B, GDF-8 and GDF-11 (Table 9 and FIGS. 10K-L).

In summary, exemplary agents comprised of the ActRIIB ECD fused to an Fc domain demonstrated different potency profiles depending on the composition and position of amino acid substitutions in the ActRIIB ECD and the length of the linker between the ECD and the Fc domain. Unexpectedly, the linker length had differential effects on the potency profile as, in some instances, potencies increased, decreased, or remained unchanged as linker length increased.

To further demonstrate the unpredictable effects of lengthening the linker on neutralization potency, other linker lengths were examined in the context of different amino acid substitutions in the ActRIIB ECD. First, the F to E substitution at position 58 was examined with linker lengths of 3 amino acids (P624), 14 amino acids (P622 and P1168), 19 amino acids (P666), and 39 amino acids (P667). Increasing the linker length from 3 amino acids to 14, 19 or 39 amino acids increased the potency on activin A from 1.7 nM (P624) to 0.43 (P622), 0.35 (P1168), 0.33 (P666), and 0.48 (P667) nM, respectively (Table 9 and FIG. 10M). Increasing the linker length from 3 amino acids to 14, 19 or 39 amino acids increased the potency on activin B from 2.7 (P624) to 1.2 (P622), 1.1 (P666) and 1.7 (P667) nM, respectively (Table 9 and FIG. 10N). These results show, in the context of this substitution, that potency on both activins increased when the linker was increased from 3 to 14 amino acids and this increase in potency was maintained at longer linker lengths (19, 39 amino acids) as well. The potency on GDF-8 and GDF-11 was maintained with linker lengths of 14, 19, and 39 amino acids (Table 9 and FIGS. 10O-P). It should be noted that the only difference between the two exemplary agents P622 and P1168 is the presence or absence of "APT" at the C-terminus of the ActRIIB ECD sequence; these data confirm that potency was not affected by the presence of the APT sequence at the C-terminus of the ACTRIIB ECD sequence.

The F to Q substitution at position 58 was examined with linker lengths of 6 amino acids (P1218), 10 amino acids (P1219), 14 amino acids (P708), 19 amino acids (P1220), and 39 amino acids (P709). In the context of this substitution, increasing the linker length improved potency on activin A in a stepwise manner (Table 9 and FIG. 10S). Strikingly, and in contrast to the F to E substitution at position 58, the potency on GDF-8 also improved with increasing linker length, from 0.80 nM (6 amino acids) to 0.72 nM (10 amino acids), 0.55 nM (14 amino acids), 0.55 nM (19 amino acids), and 0.29 nM (39 amino acids) (Table 9 and FIG. 10T).

The F to K substitution at position 58 was examined with linker lengths of 3 amino acids (P698), 6 amino acids (P1153), 10 amino acids (P1154), 14 amino acids (P701), 19 amino acids (P1155), and 39 amino acids (P1156). In the context of this substitution, as for the Q substitution, increasing the linker length improved potency on activin A in a mostly stepwise manner (Table 9 and FIG. 10V) and for GDF-8, increasing linker length improved potency from 2.1 nM (3 amino acids) to 1.5 nM (6 amino acids) and 1.0 nM (10 amino acids) (Table 9 and FIG. 10W). Interestingly, whereas the F to K substitution with 3 amino acid linker demonstrated decreased potency on activin A compared to wild type, the F to K substitution with longer linker lengths demonstrated increased potency compared to wild type.

These results demonstrate that both single point amino acid substitutions in the ActRIIB-ECD and changes in the linker length can modulate ligand inhibition potency. Notably, the effect of linker length was unpredictable and had differential effects on different ligands depending on the position of the amino acid mutation in the ActRIIB-ECD as well as the particular substitution at a given position.

Figure 13A:
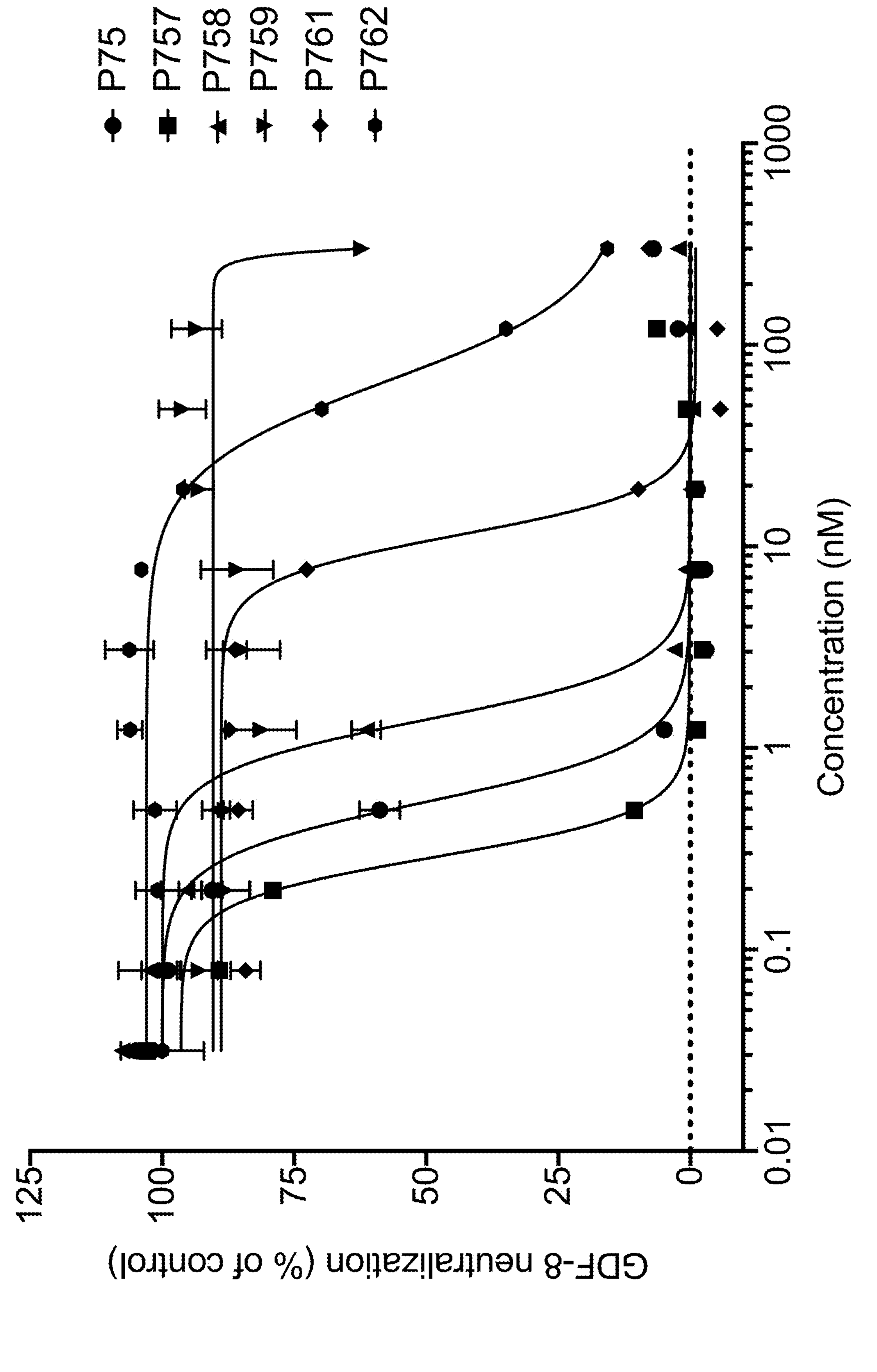
FIG. 13A-FIG. 13D shows representative results in the HEK-Blue cell-based assay for inhibition of GDF-8 for exemplary proteins.
Figure 13B:
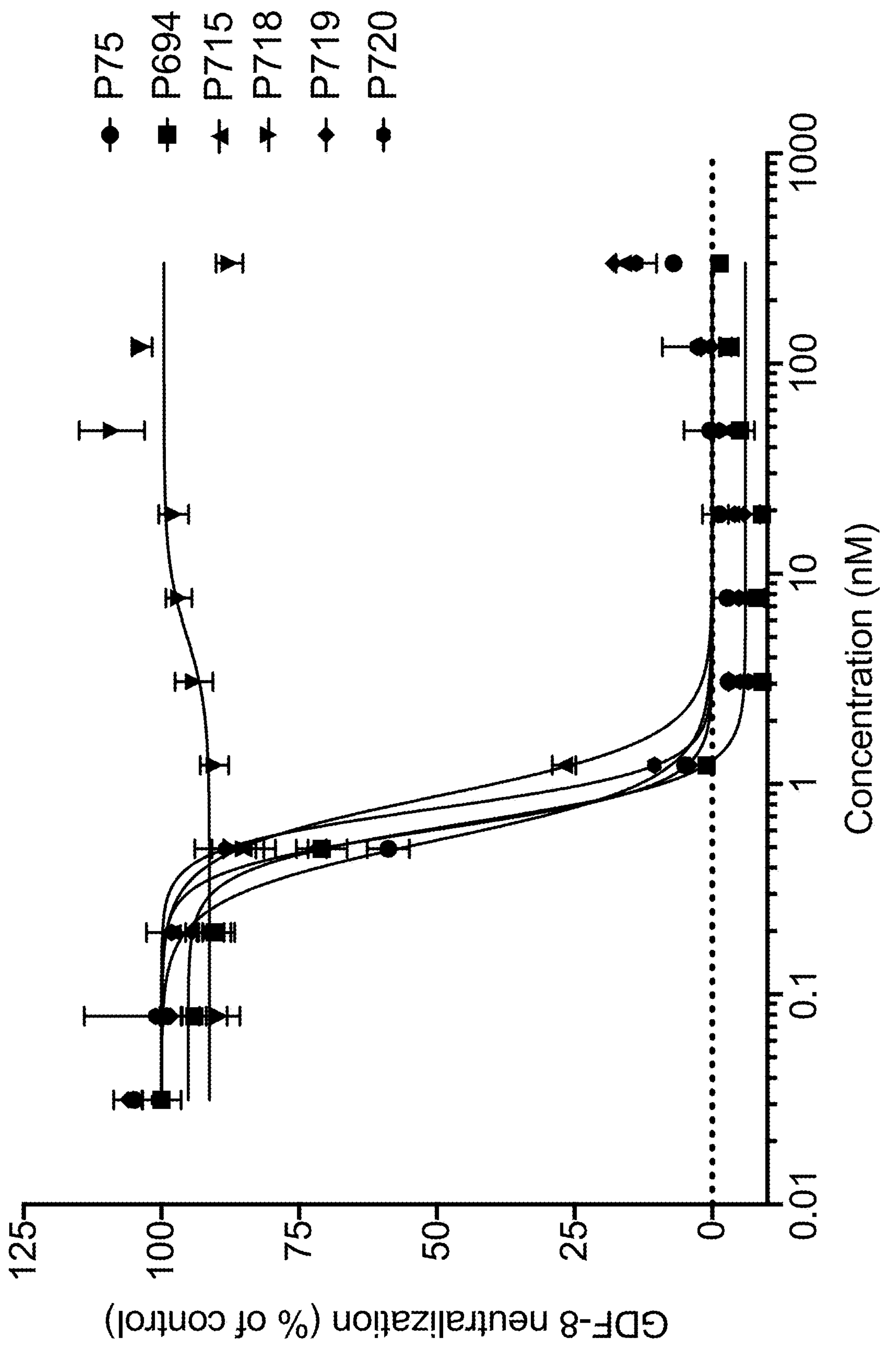
Figure 14A:
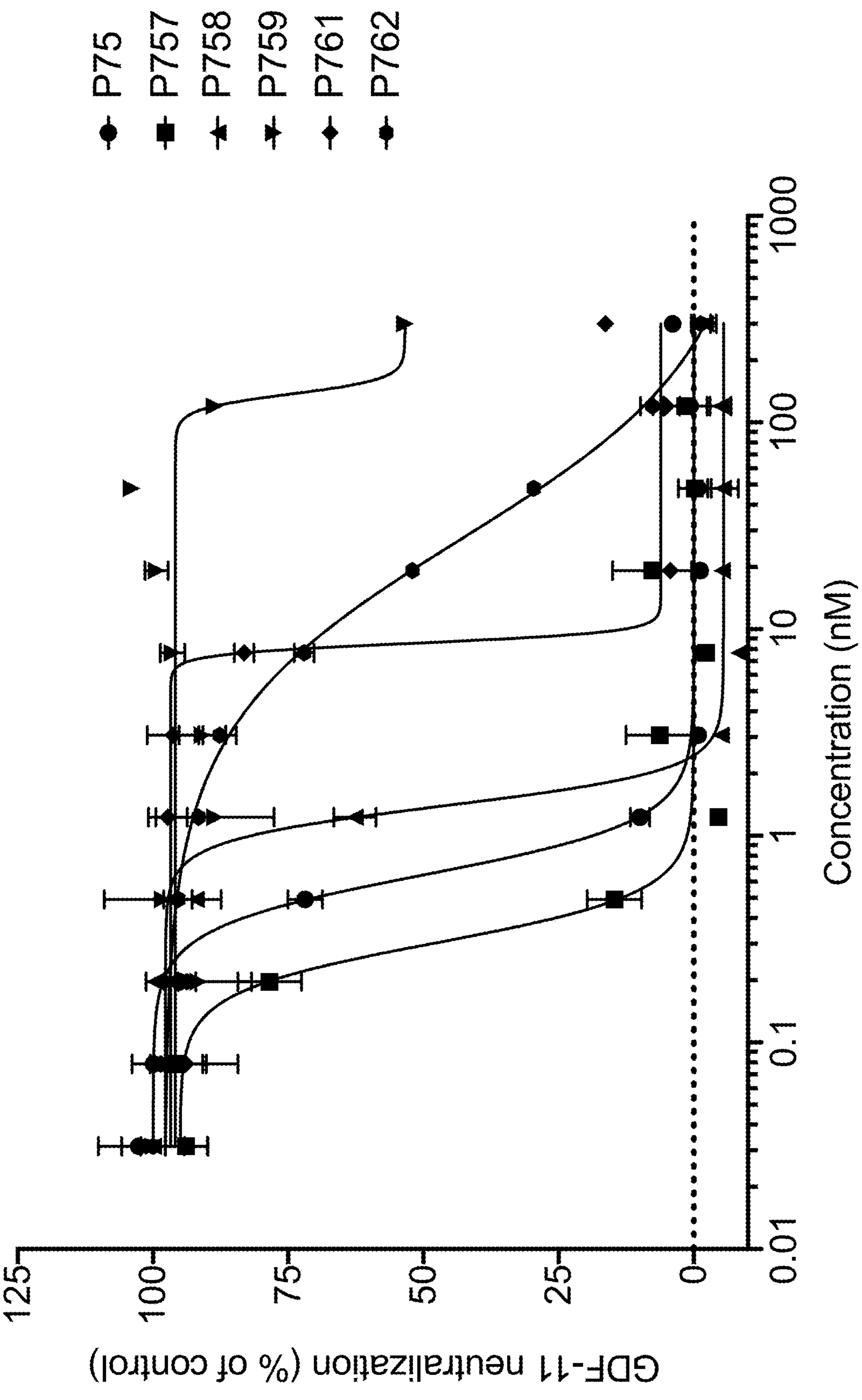
FIG. 14A-FIG. 14D show representative results in the HEK-Blue cell-based assay for inhibition of GDF-11 for exemplary proteins.
Figure 14B:
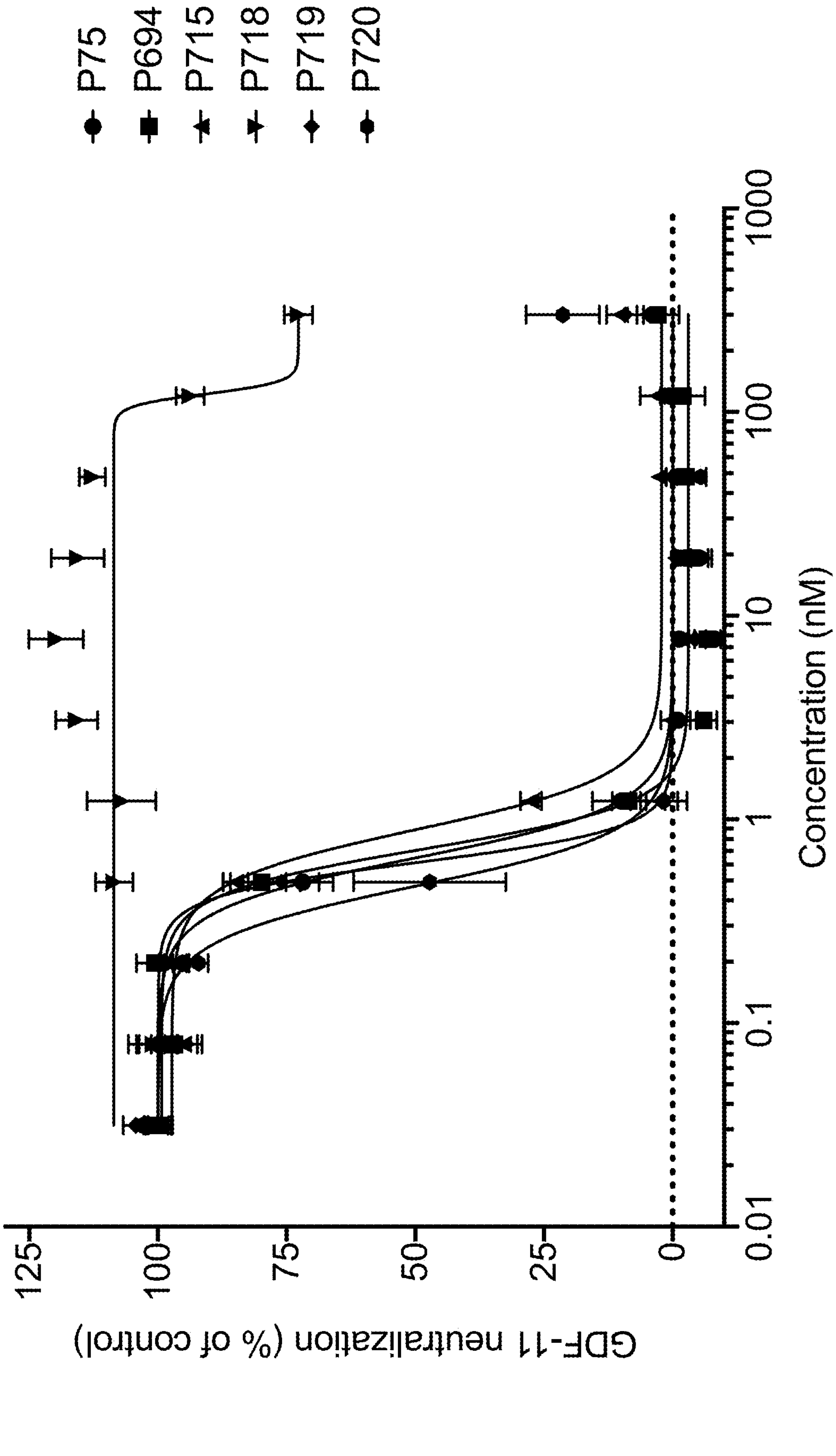
Figure 14C:
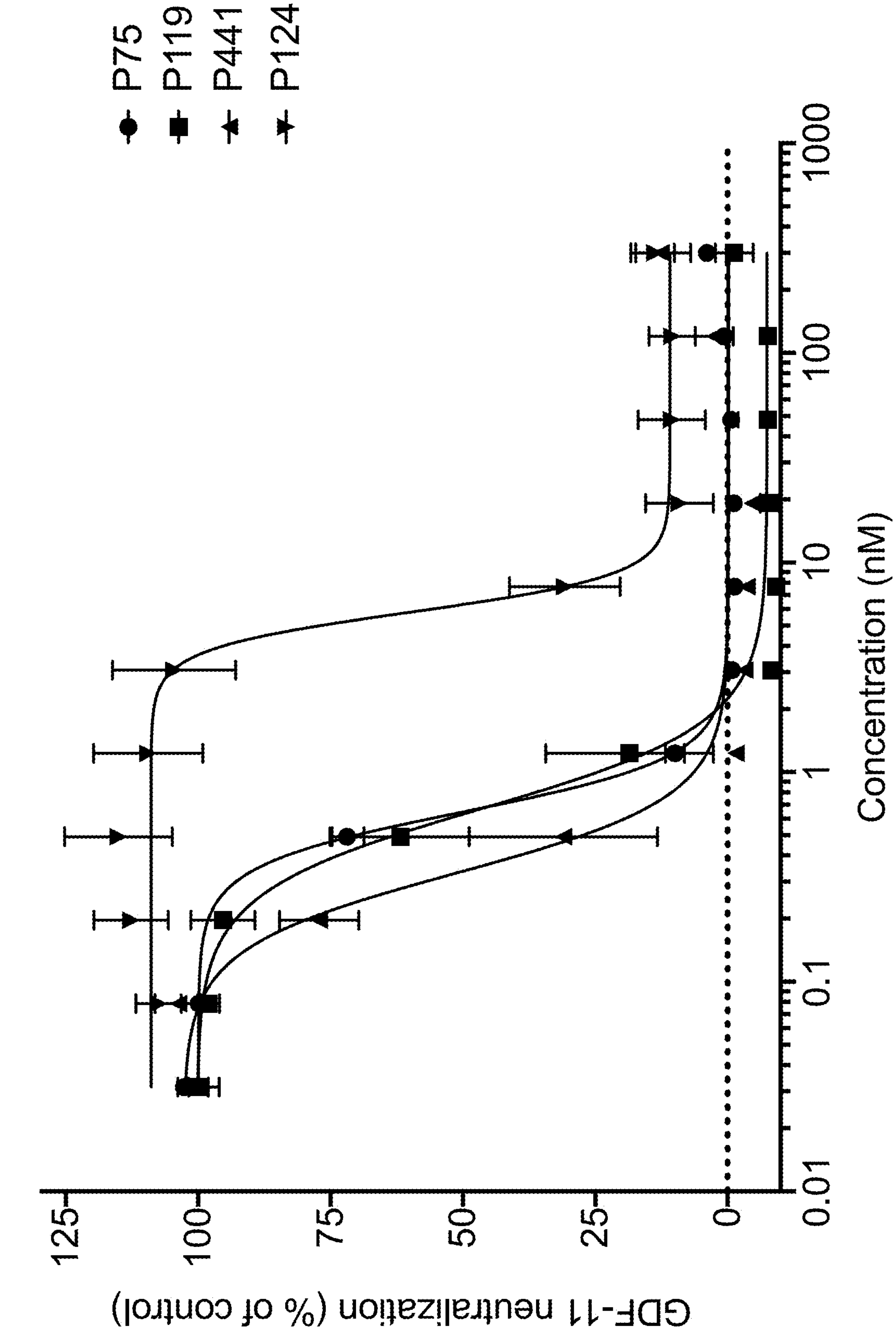
Figure 14D:
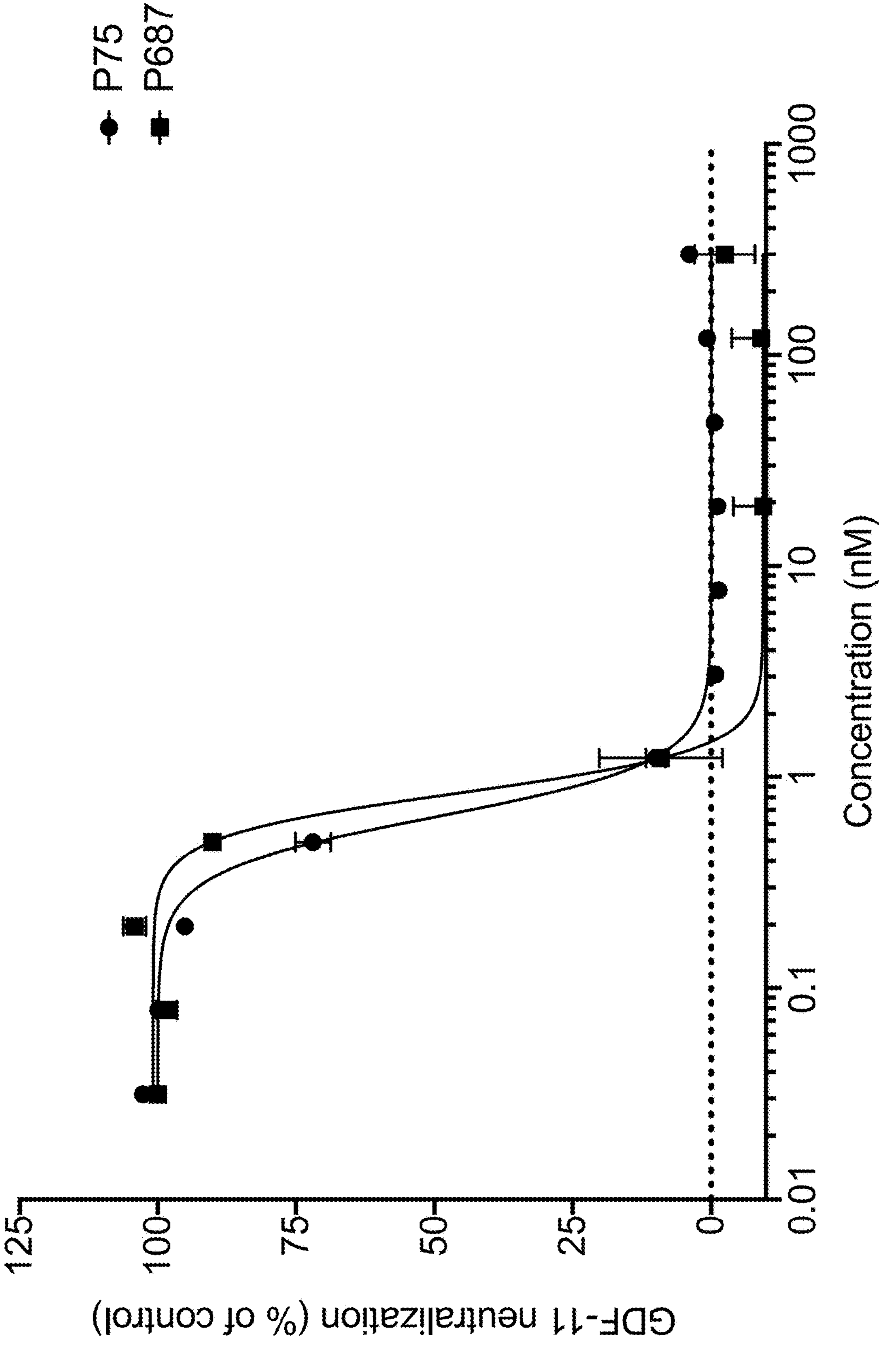

The effects of additional amino acid substitutions at position 58 in the context of a 14 amino acid linker sequence between the ActRIIB-ECD and the Fc domain were also investigated. Exemplary agents comprising substitutions of F to Y (P694) or W (P715) both led to gains in potency on activin A (IC50 values of 0.79 and 0.90 nM, respectively) relative to wild type (P75, 2.3 nM), while maintaining potency on activin B, GDF-8, and GDF-11 (Table 9 and FIGS. 11B, 12B, 13B, and 14B). Exemplary agents comprising substitutions of F to D (P687), F to N (P1213), F to R (P1215) and F to H (P1217) were also investigated. IC50 values on activin A were 2.0, 1.5, 0.58, and 0.59 nM for P687, P1213, P1215, and P1217, respectively (Table 9 and FIG. 11D). The IC50 value on activin B was 8.8 nM for P687 (Table 9 and FIG. 12D). IC50 values on GDF-8 were 1.4, 1.1, 0.99, 0.56 nM for P687, P1213, P1215, and P1217, respectively (Table 9 and FIG. 13D). The IC50 value on GDF-11 was 0.85 nM for P687 (FIG. 14D). These results demonstrate that, in addition to the position of the mutation in the ActRIIB-ECD, the nature of the amino acid substitution at a particular position may decrease, increase, or not change the potency on selected ligands.

Figure 11A:
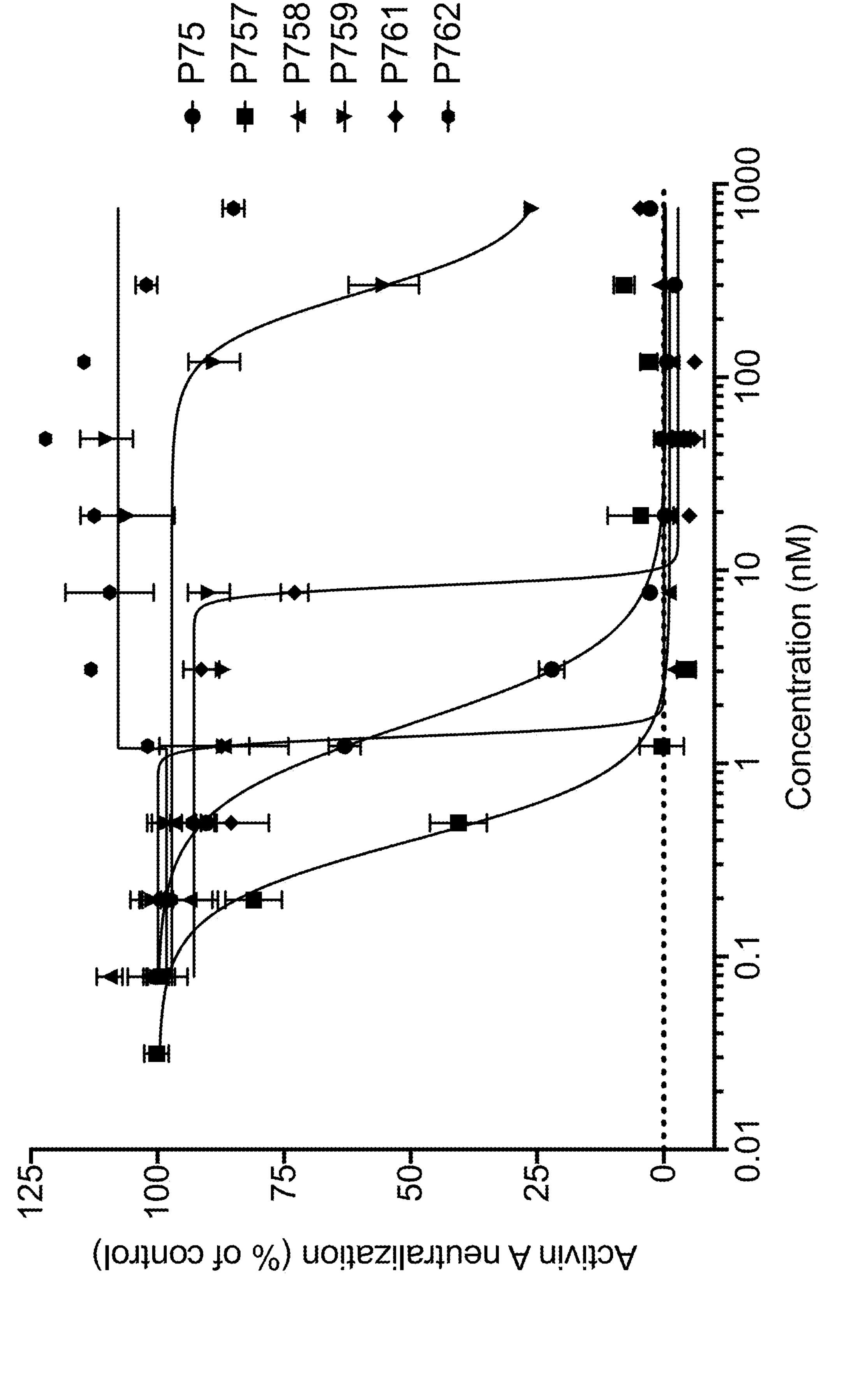
FIG. 11A-FIG. 11D show representative results in the HEK-Blue cell-based assay for inhibition of activin A for exemplary proteins.
Figure 11B:
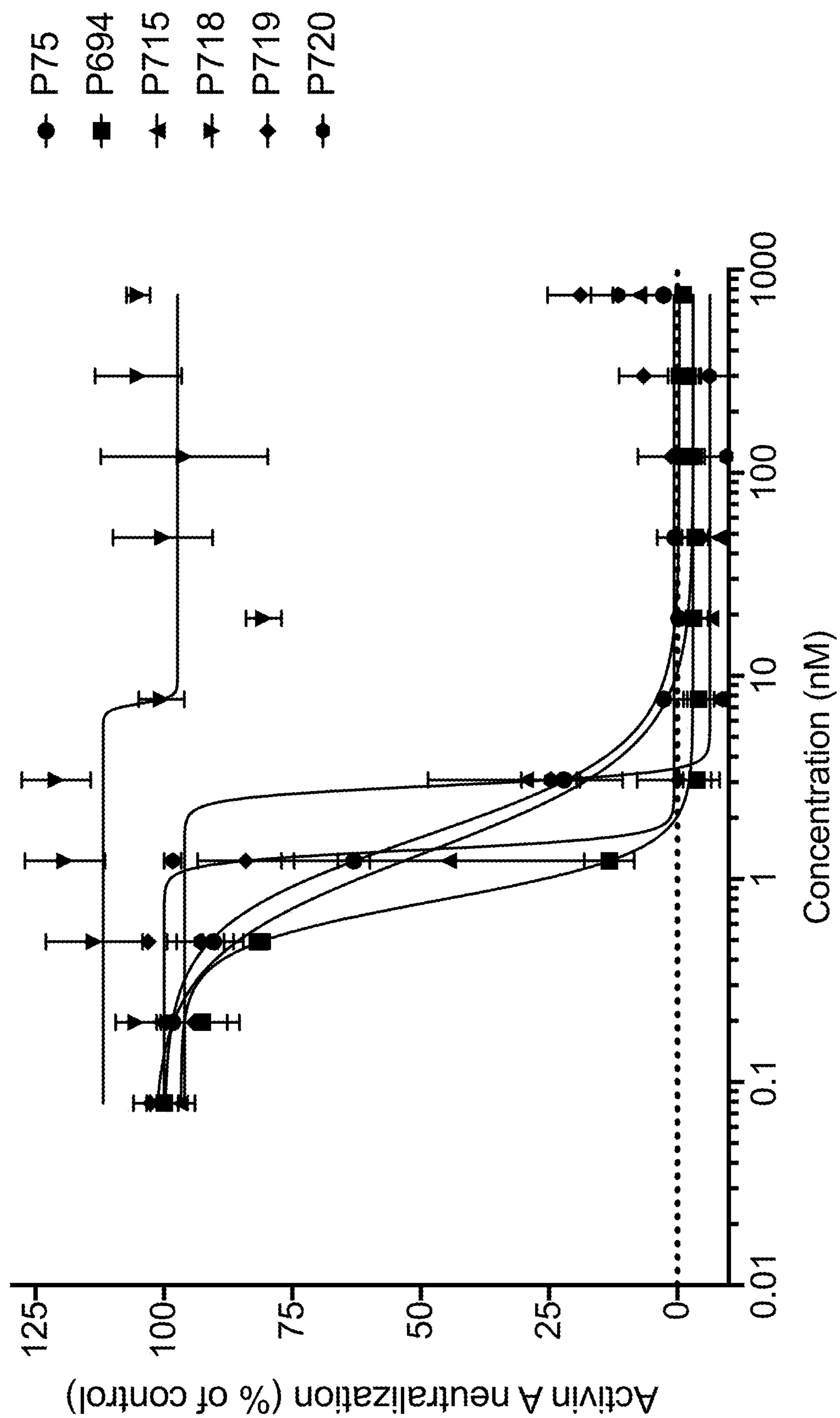
Figure 11C:
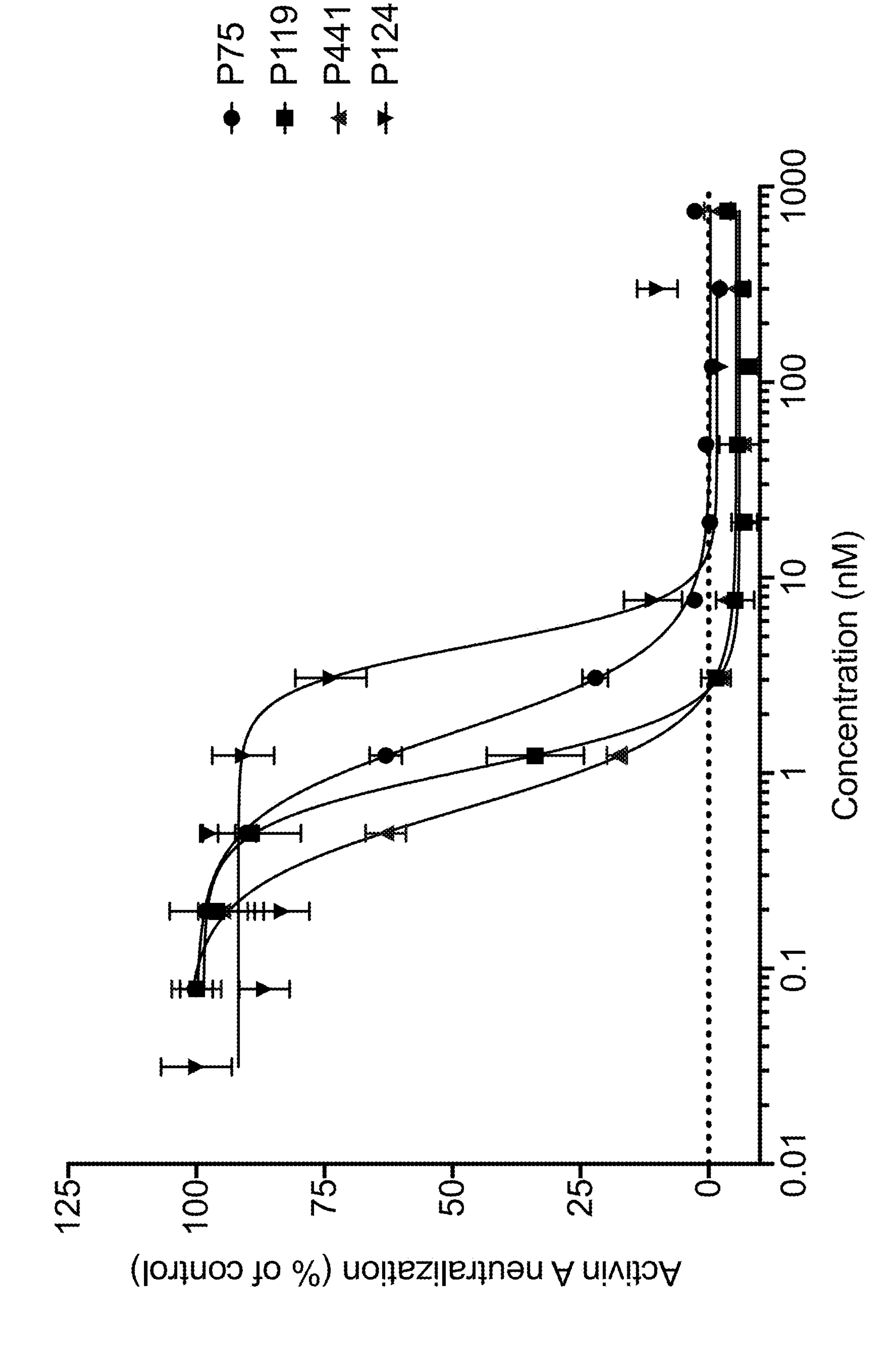
Figure 11D:
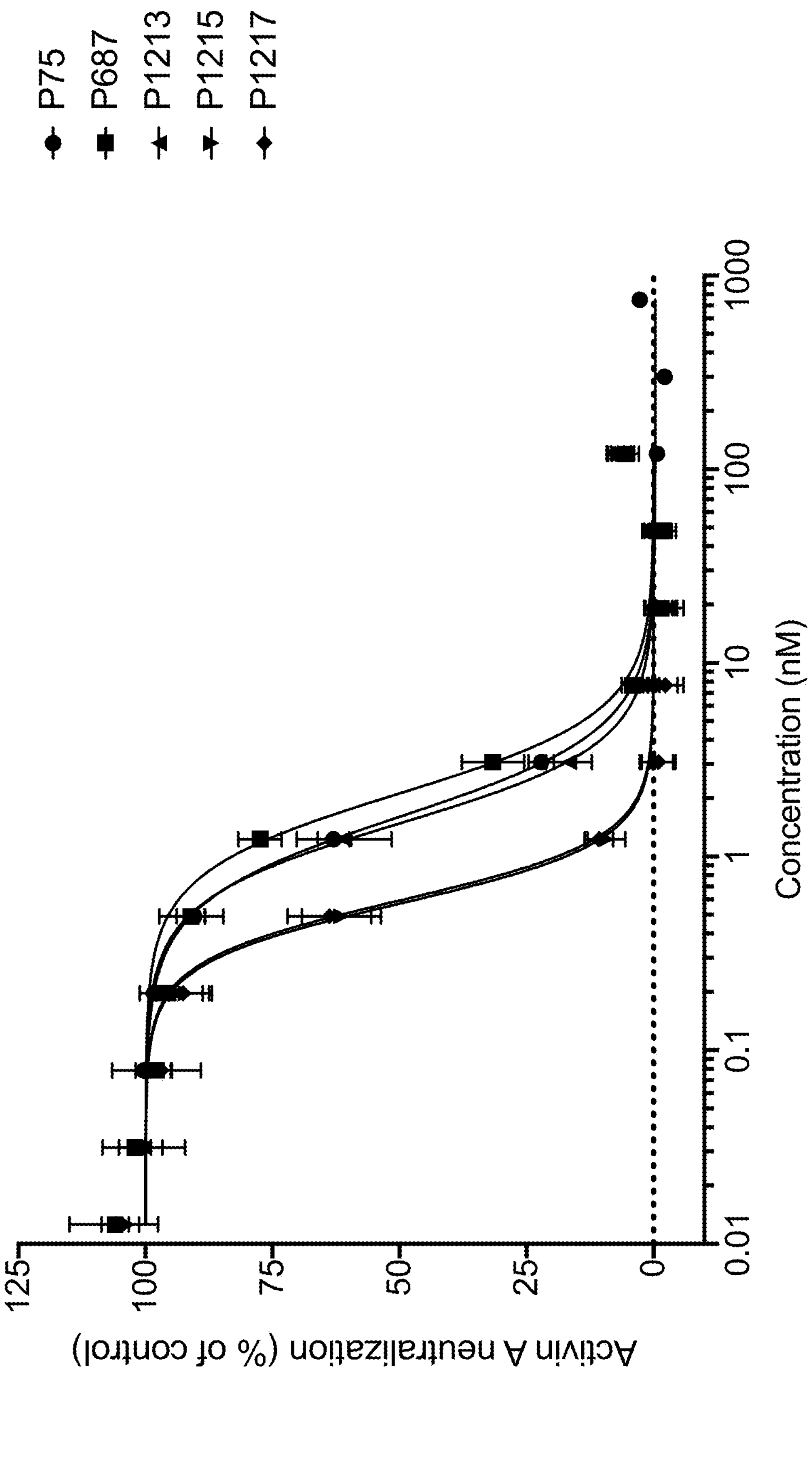
Figure 12A:
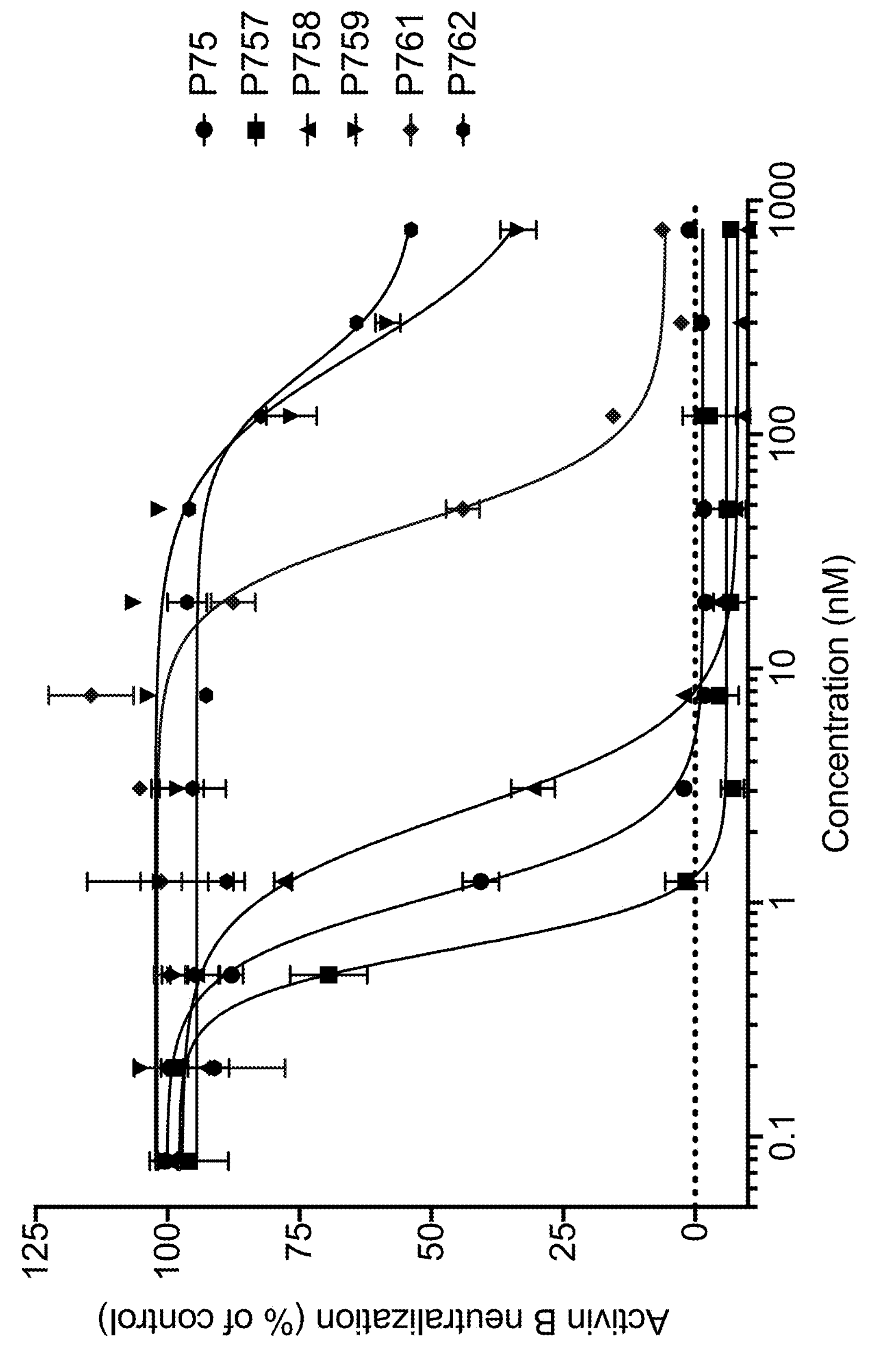
FIG. 12A-FIG. 12D shows representative results in the HEK-Blue cell-based assay for inhibition of activin B for exemplary proteins.
Figure 12B:
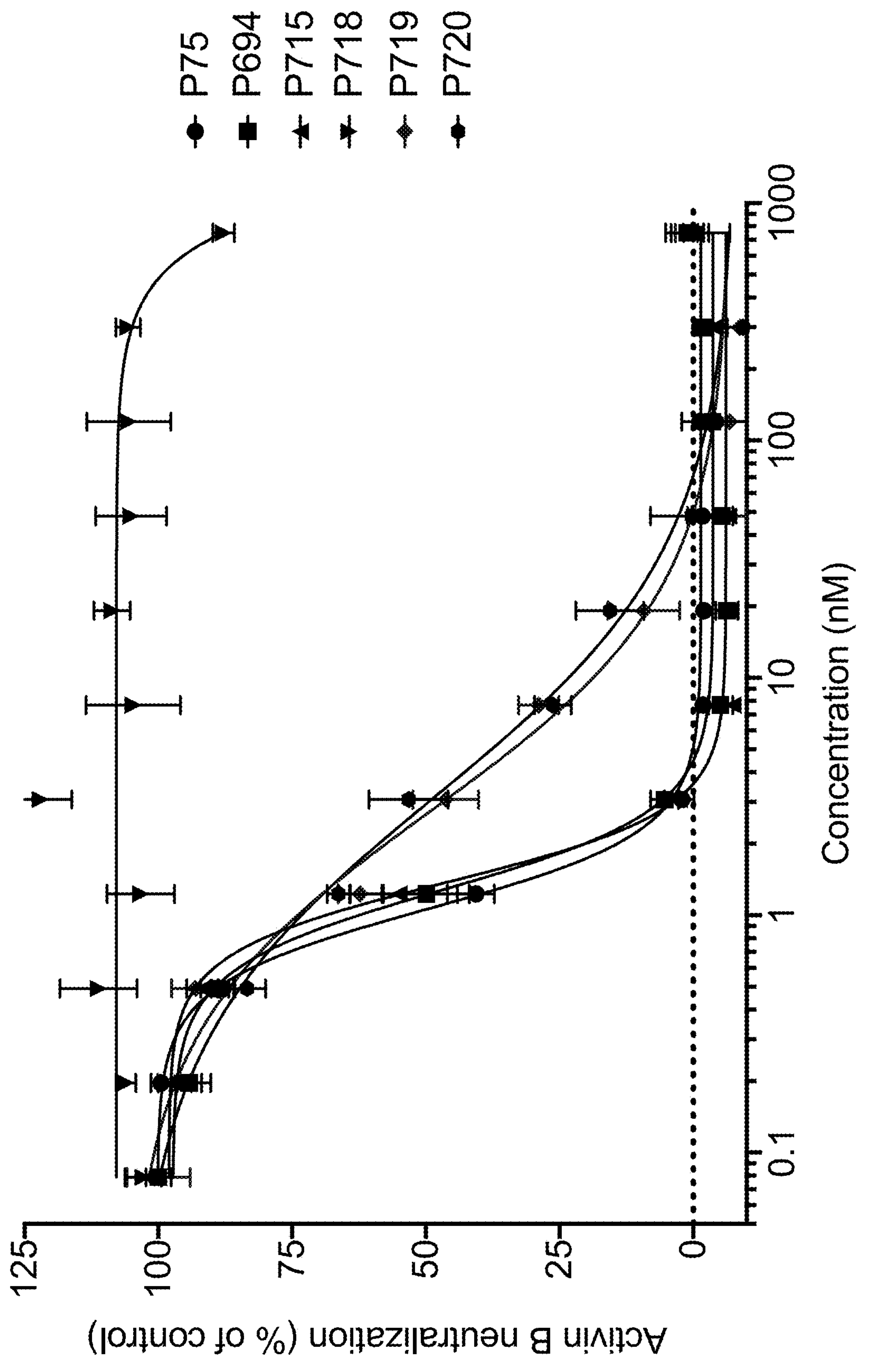
Figure 12C:
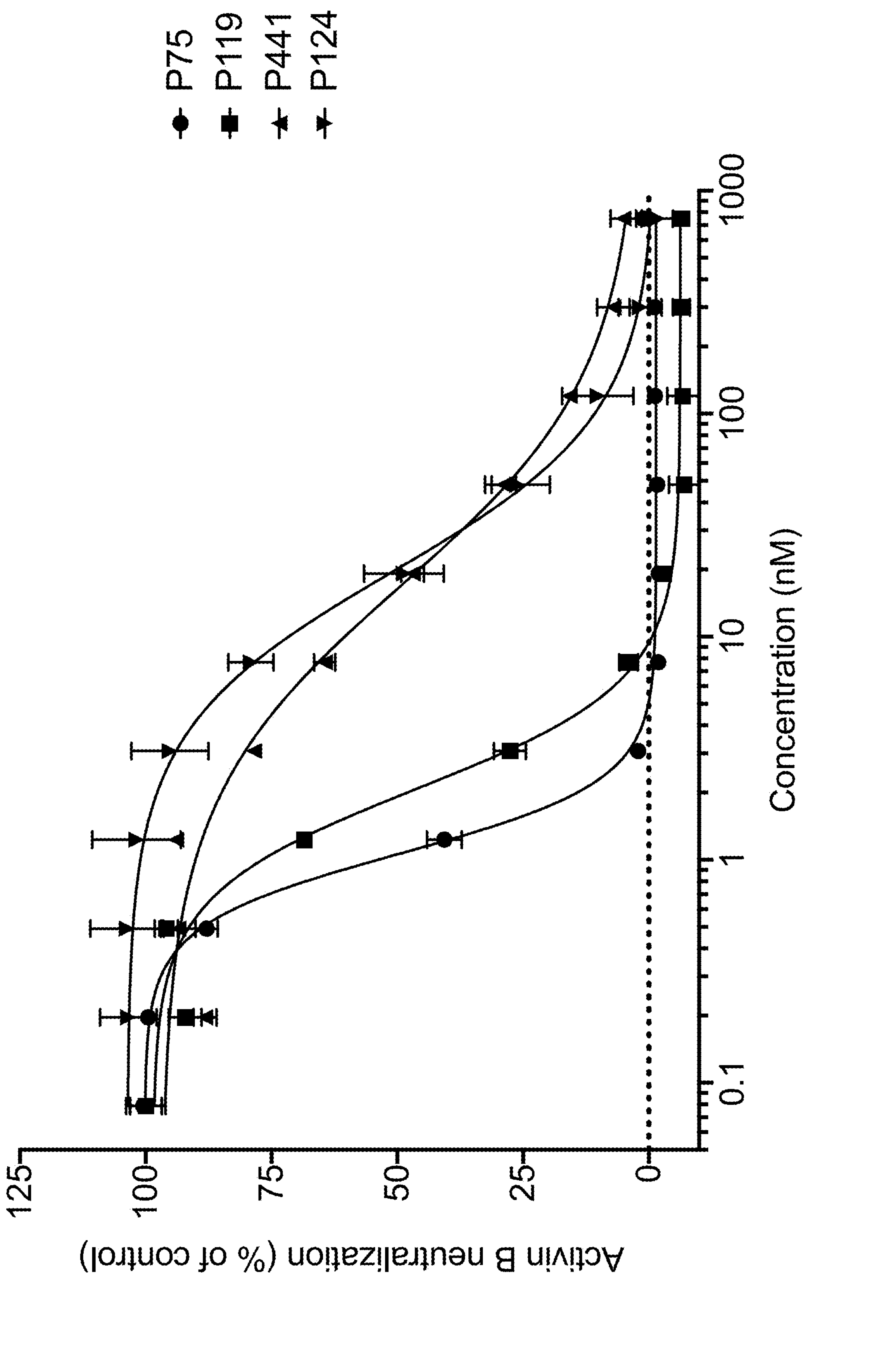
Figure 12D:
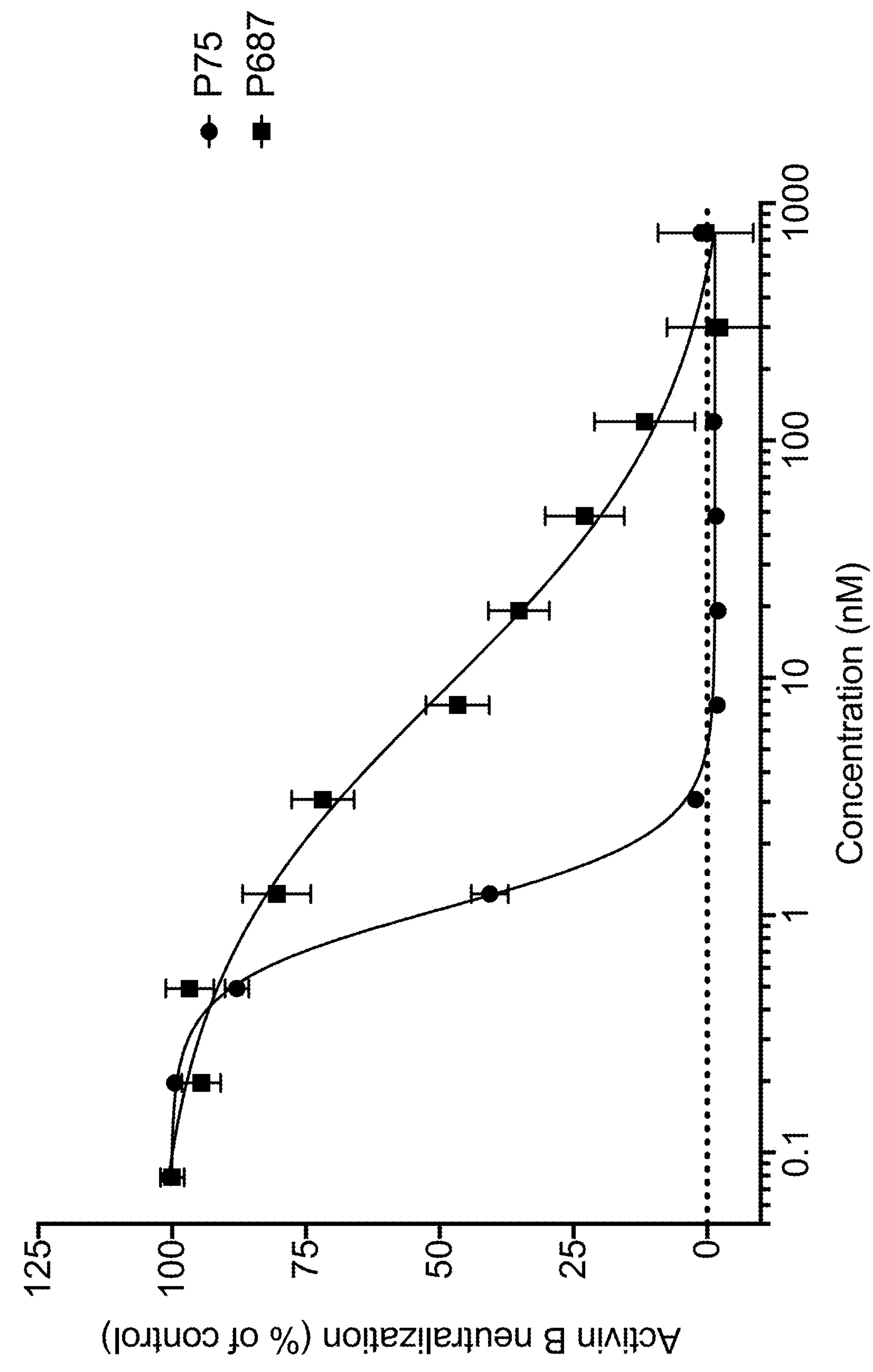
Figure 13C:
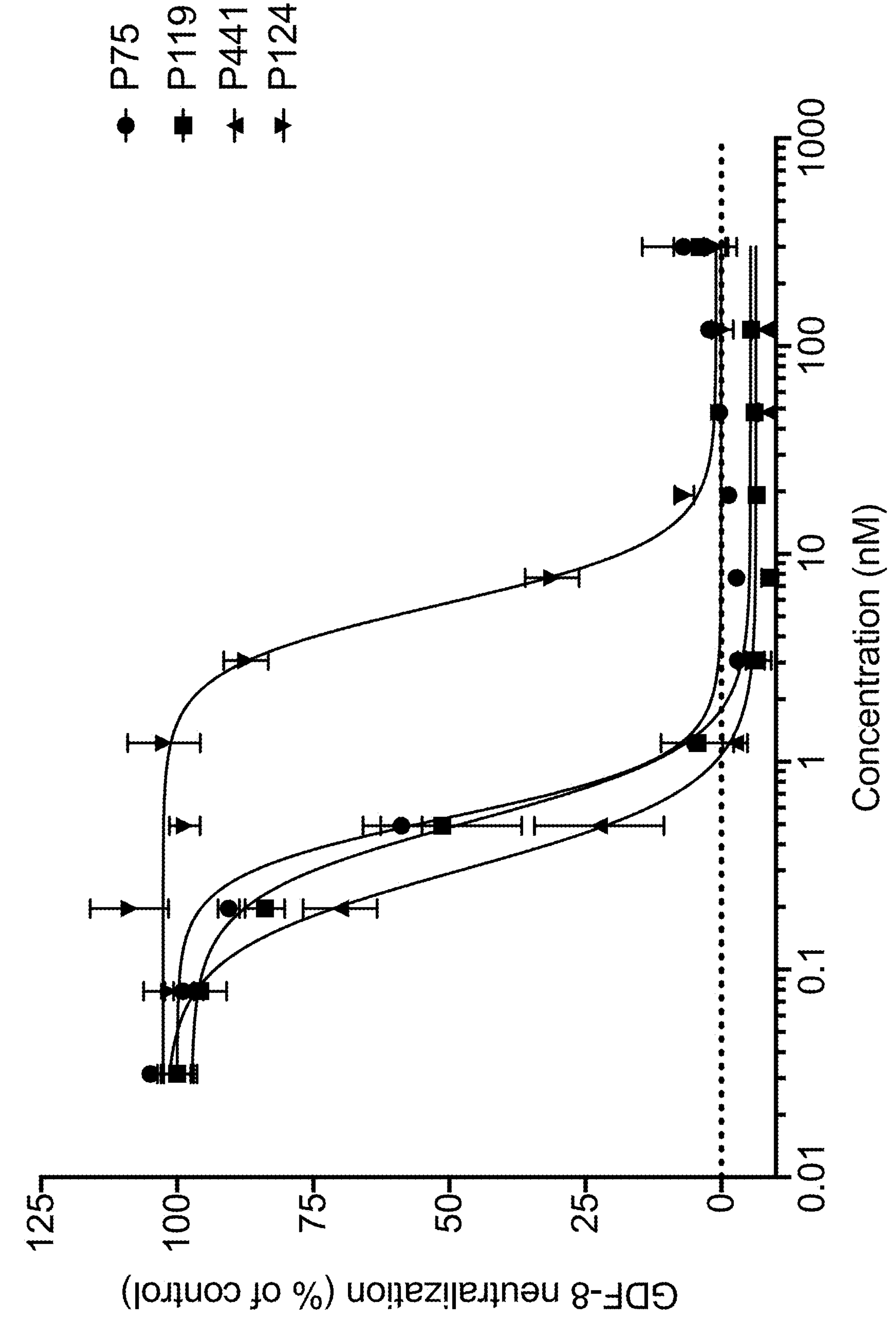
Figure 13D:
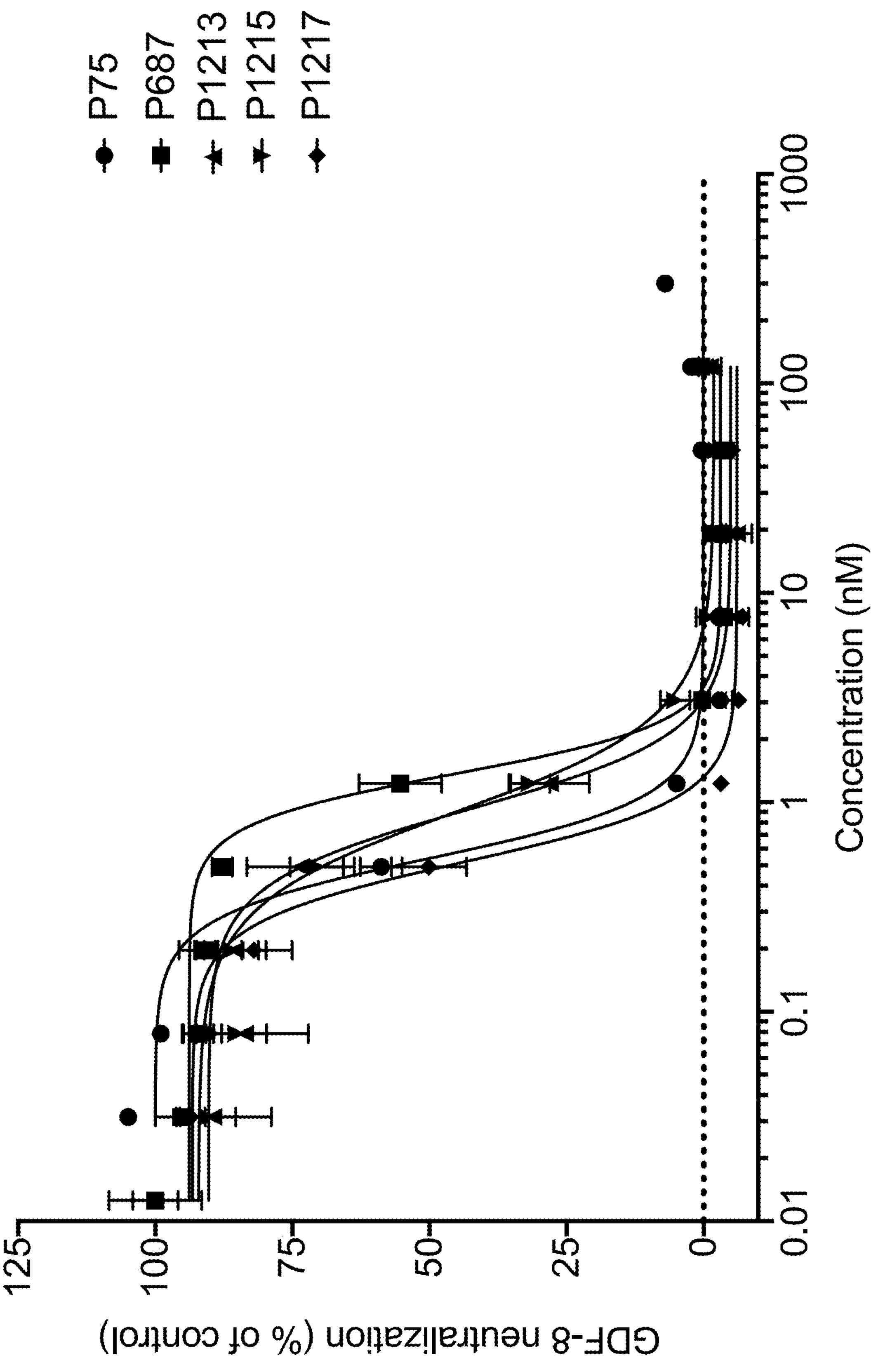

Next, the effects of combining different mutations in the ActRIIB-ECD were investigated. Exemplary agents included P441 (point mutation from P119 combined with the P121 sequence), P718 (point mutation from P120 combined with the P624 sequence), P719 (point mutation from P122 combined with the P622 sequence), and P720 (point mutation from P123 combined with the P622 sequence). IC50 values on activin A were 0.67, >1,000, 0.63, and 0.97 nM for P441, P718, P719, and P720, respectively (FIGS. 11B-C). IC50 values on activin B were 28, >1,000, 2.3, and 2.7 nM for P441, P718, P719, and P720, respectively (FIGS. 12B-C). IC50 values on GDF-8 were 0.60, >1,000, 0.61, and 0.77 nM for P441, P718, P719, and P720, respectively (FIGS. 13B-C). IC50 values on GDF-11 were 0.73, >1,000, 0.58, and 0.54 nM for P441, P718, P719, and P720, respectively (FIGS. 14B-C). These results demonstrate that changes in ligand inhibition potency obtained by mutations at position 58 may be sensitive to other mutations in the ActRIIB-ECD.

Taken together, these results illustrate the different effects of different point mutations in the ActRIIB-ECD combined with different lengths of the linker between the ECD and the Fc domain on inhibition potency for TGFβ superfamily ligands. While some point mutations in the ActRIIB-ECD did not affect inhibition potencies of any ligands, other point mutations significantly altered inhibition potency on select ligands. Still other point mutations abrogated neutralization activity of the ActRIIB-ECD for all the ligands tested. Of note, P119, P121, and P624 showed improved neutralization (inhibition potency) for activin A, GDF-8, and GDF-11 relative to both benchmark proteins tested (ActRIIB-Fc and ActRIIA-Fc). Other exemplary agents P622, P666, P667, P708, P709, P1168, and P1220 showed superior or equal neutralization of activin A, activin B, GDF-8 and/or GDF-11, relative to benchmark proteins. For yet other exemplary agents (P701, P1155, and P1156), potency on activin A and activin B was improved, while potency on GDF-8 and GDF-11 was modestly affected. As activin A, activin B, GDF-8, and GDF-11 are thought to play important roles in PAH pathophysiology, these results suggest that such improved agents, as exemplified by P119, P121, P622, P624, P666, P667, P701, P708, P709, P1155, P1156, P1168, and P1220, may be particularly useful for treatment of PAH and related conditions. Of note, certain exemplary agents, such as e.g. those with position 58 substituted from F to E, K, and Q, showed high neutralization potency on activin A and activin B in the context of longer linker lengths (e.g., 10 amino acids or longer), underscoring that such improved agents may be particularly useful for treatment of PAH and related conditions.

The results also show that lengthening the linker sequence between the ActRIIB-ECD and the Fc domain selectively increased potency on some ligands, but not others. For example, P622, P1168, P666, and P667 (F58E substitution with linkers from 14 amino acids to 39 amino acids) demonstrated increased potencies on activin A and activin B compared to P624 (F58E substitution with 3 amino acid linker), while having no detectable difference in potency on GDF-8 and GDF-11. Notably, in this series, there was no further increase in potency when linker length was increased from 14 to 39 amino acids for any ligand tested, whereas for unpredictable effects on inhibition potencies depending upon the specific mutation in the ActRIIB-ECD and the particular ligand.

Finally, these data also show that the effects of combining other mutations in the ActRIIB-ECD with substitutions at F58 are unpredictable. Notably, P719 and P720 had potencies on activin A, activin B, GDF-8, and GDF-11 intermediate to those of the corresponding single mutants (the corresponding single mutants are P122 and P622 for P719, and P123 and P622 for P720). However, P441 showed lower potency on activin B than either corresponding single mutant (P119 and P121), indicating a compounding effect of both mutations for that particular cytokine. Also, P718 (P622 with the point mutation from P120) showed no activity on any of the cytokines tested, suggesting that the F58E mutation could not rescue the loss of potency observed with P120.

TABLE 9

IC50 values for representative activin receptor ECD constructs for activin A, activin B, GDF-8, and GDF-11 neutralization.

| | Activin A | | Activin B | | GDF-8 | | GDF-11 | |
|---|---|---|---|---|---|---|---|---|
| ECD construct | Avg IC50 (nM) | SEM | Avg IC50 (nM) | SEM | Avg IC50 (nM) | SEM | Avg IC50 (nM) | SEM |
| P75 | 2.3 | 0.09 | 1.4 | 0.06 | 0.67 | 0.03 | 0.76 | 0.05 |
| P120 | >1,000 | — | >1,000 | — | >1,000 | — | >1,000 | — |
| P121 | 1.3 | 0.13 | 2.5 | 0.43 | 0.29 | 0.05 | 0.40 | 0.09 |
| P122 | 2.4 | 0.13 | 2.5 | 0.38 | 0.62 | 0.24 | 0.71 | 0.18 |
| P123 | 5.0 | 0.67 | 2.8 | 0.14 | 1.1 | 0.27 | 1.2 | 0.25 |
| P125 | >1,000 | — | >1,000 | — | >1,000 | — | >1,000 | — |
| P126 | >1,000 | — | >1,000 | — | 65 | 8.7 | 23 | 0.94 |
| P127 | >1,000 | — | >1,000 | — | >1,000 | — | >1,000 | — |
| P444 | 2.7 | 0.18 | 0.95 | 0.12 | 3.1 | 0.23 | 1.6 | 0.22 |
| P622 | 0.43 | 0.02 | 1.2 | 0.18 | 0.29 | 0.02 | 0.31 | 0.02 |
| P624 | 1.7 | 0.1 | 2.7 | 0.31 | 0.32 | 0.02 | 0.30 | 0.03 |
| P666 | 0.33 | 0.03 | 1.1 | 0.23 | 0.25 | 0.04 | 0.21 | 0.05 |
| P667 | 0.48 | 0.06 | 1.7 | 0.57 | 0.47 | 0.05 | 0.38 | 0.06 |
| P687 | 2.0 | 0.24 | 8.8 | 0.6 | 1.4 | 0.17 | 0.85 | 0.08 |
| P694 | 0.79 | 0.05 | 1.3 | 0.23 | 0.65 | 0.02 | 0.73 | 0.1 |
| P701 | 0.52 | 0.05 | 0.55 | 0.07 | 1.1 | 0.13 | 0.75 | 0.09 |
| P708 | 0.62 | 0.04 | 0.66 | 0.01 | 0.55 | 0.05 | 0.42 | 0.03 |
| P715 | 0.90 | 0.37 | 1.4 | 0.3 | 0.83 | 0.04 | 0.90 | 0.01 |
| P718 | >1,000 | — | >1,000 | — | >1,000 | — | >1,000 | — |
| P719 | 0.63 | 0.03 | 2.3 | 0.41 | 0.61 | 0.07 | 0.58 | 0.04 |
| P720 | 0.97 | 0.07 | 2.7 | 0.46 | 0.77 | 0.08 | 0.54 | 0.07 |
| P757 | 0.47 | 0.05 | 0.55 | 0.11 | 0.31 | 0.02 | 0.34 | 0.03 |
| P119 | 0.98 | 0.09 | 1.8 | 0.12 | 0.64 | 0.15 | 0.97 | 0.43 |
| P441 | 0.67 | 0.03 | 28 | 8.3 | 0.60 | 0.22 | 0.73 | 0.31 |
| P124 | 5.3 | 0.61 | 22 | 1.3 | 7.1 | 0.48 | 5.3 | 0.49 |
| P758 | 1.1 | 0.17 | 2.4* | — | 1.3 | 0.12 | 1.4* | — |
| P759 | 274* | — | 227* | — | 397* | — | 137* | — |
| P761 | 8.4* | — | 41* | — | 12* | — | 8.6* | — |
| P762 | >1,000* | — | >1,000* | — | 66* | — | 27* | — |
| P698 | 4.3 | 0.50 | ND | — | 2.1 | 0.20 | ND | — |
| P709 | 0.42 | 0.05 | ND | — | 0.29 | 0.05 | ND | — |
| P1153 | 0.86 | 0.08 | ND | — | 1.5 | 0.10 | ND | — |
| P1154 | 0.53 | 0.05 | ND | — | 1.0 | 0.03 | ND | — |
| P1155 | 0.36 | 0.02 | ND | — | 1.1 | 0.10 | ND | — |
| P1156 | 0.32 | 0.01 | ND | — | 1.3 | 0.04 | ND | — |
| P1168 | 0.35 | 0.17 | ND | — | 0.39 | 0.08 | ND | — |
| P1213 | 1.5 | 0.31 | ND | — | 1.1 | 0.19 | ND | — |
| P1215 | 0.58 | 0.10 | ND | — | 0.99 | 0.12 | ND | — |
| P1217 | 0.59 | 0.12 | ND | — | 0.56 | 0.07 | ND | — |
| P1218 | 1.1 | 0.21 | ND | — | 0.80 | 0.08 | ND | — |
| P1219 | 0.78 | 0.21 | ND | — | 0.72 | 0.10 | ND | — |
| P1220 | 0.54 | 0.12 | ND | — | 0.55 | 0.10 | ND | — |

SEM: standard error of the mean;
>1,000: no detectable neutralization; agents were tested in at least two independent experiments, except for IC50 values marked with *, which indicates testing in only one experiment;
ND: not determined.

Figure 8A:
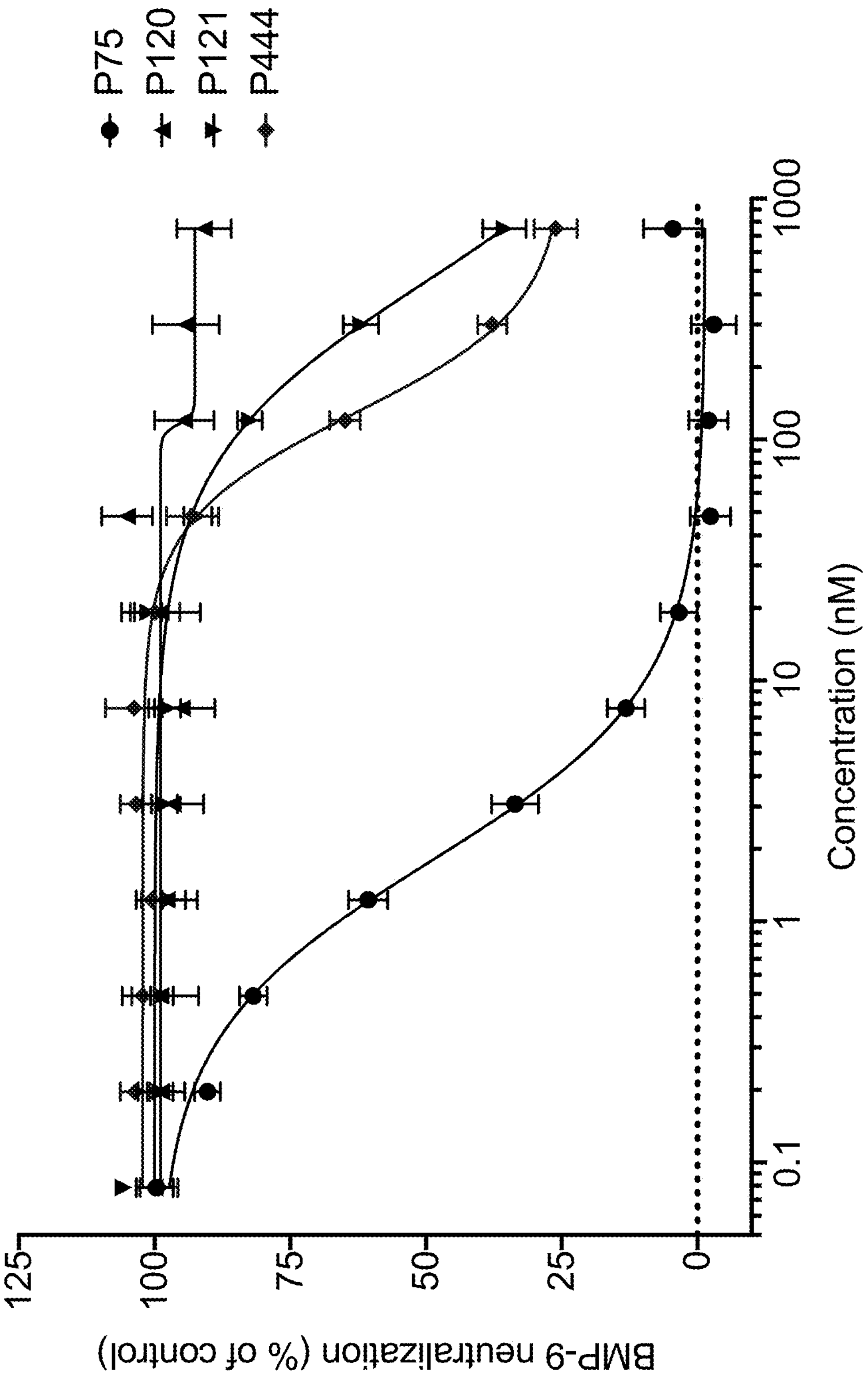
FIG. 8A-FIG. 8D shows representative results in the HepG2 cell-based assay for inhibition of BMP-9 for exemplary proteins.
Figure 8B:
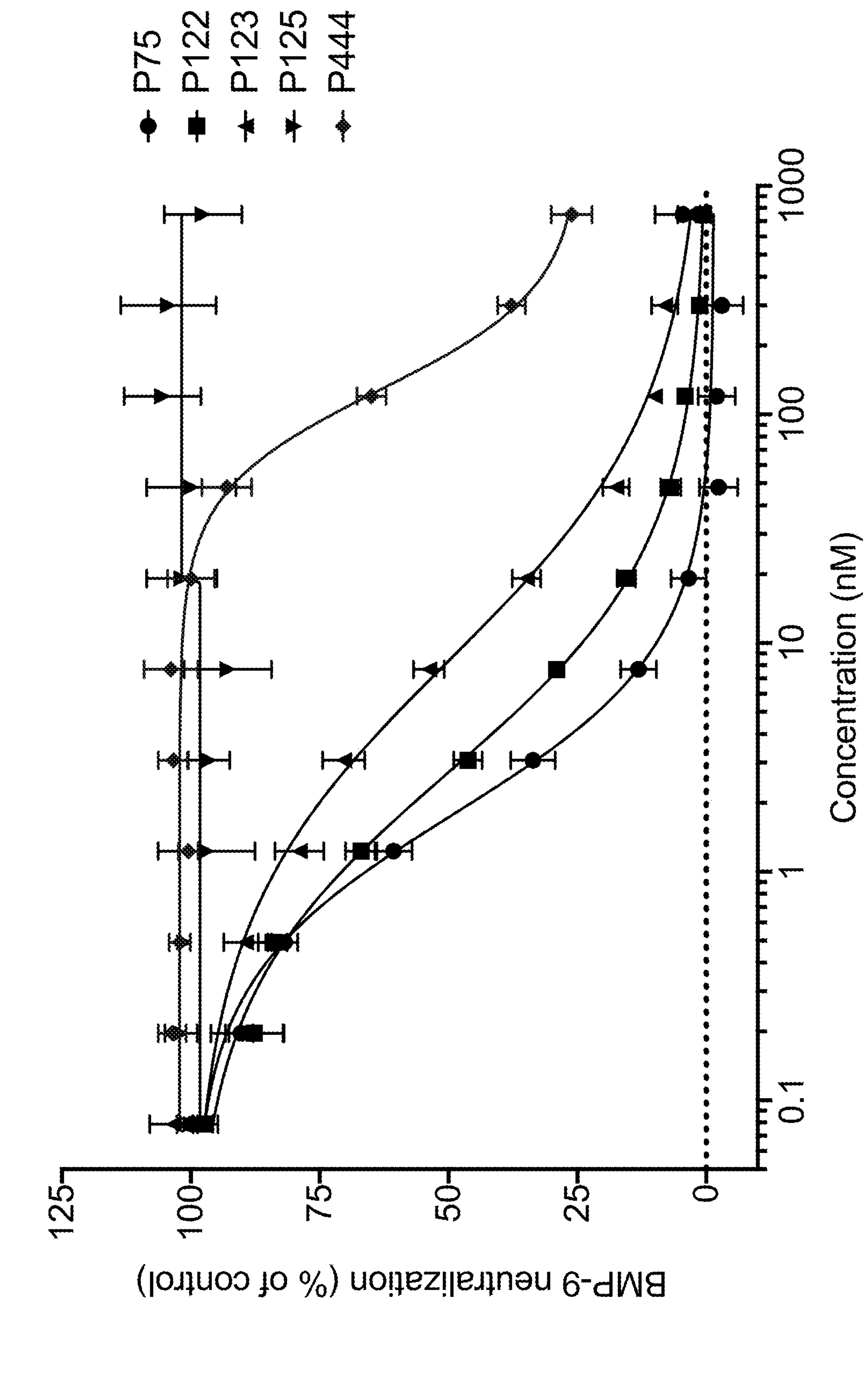
Figure 8C:
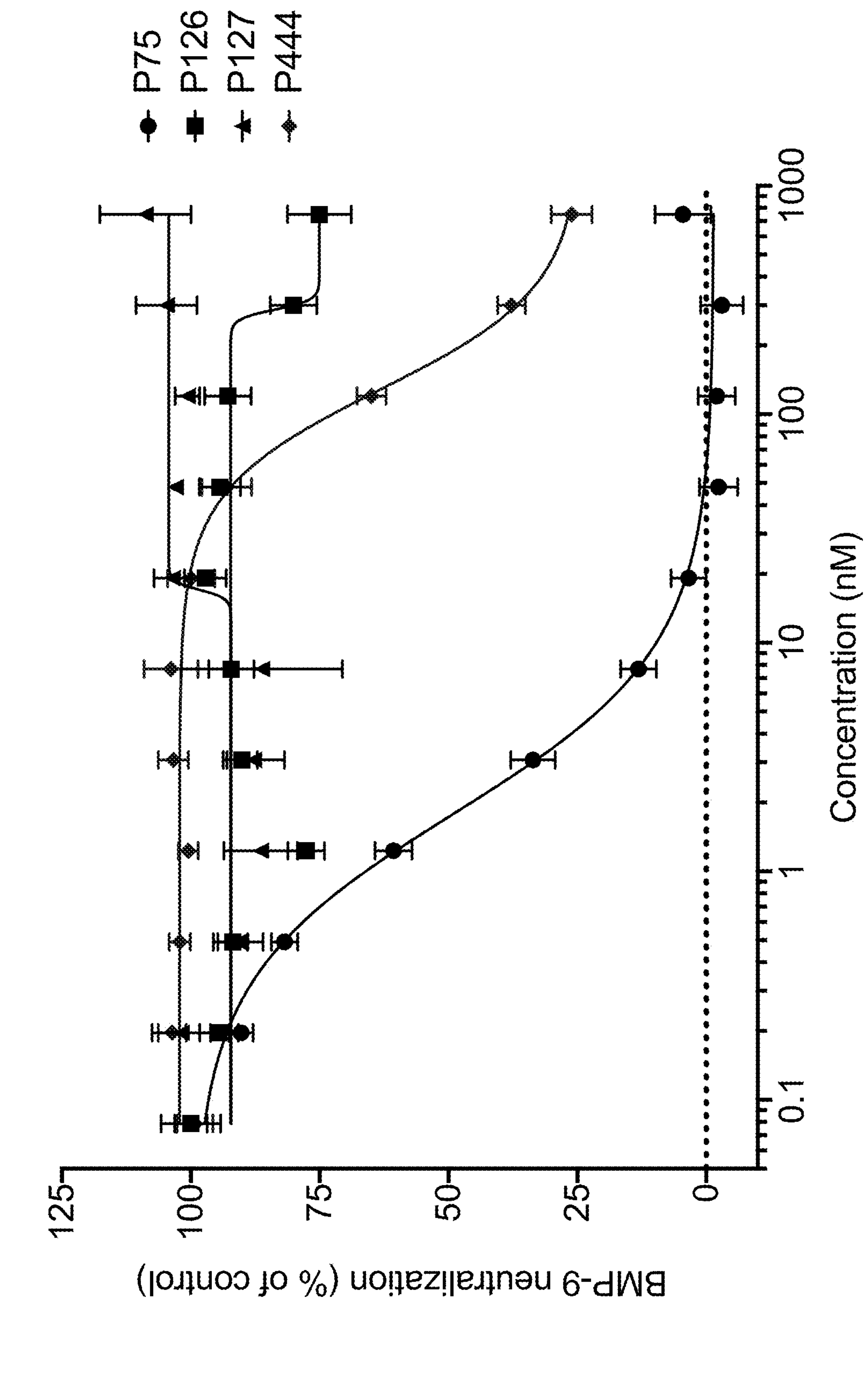
Figure 8D:
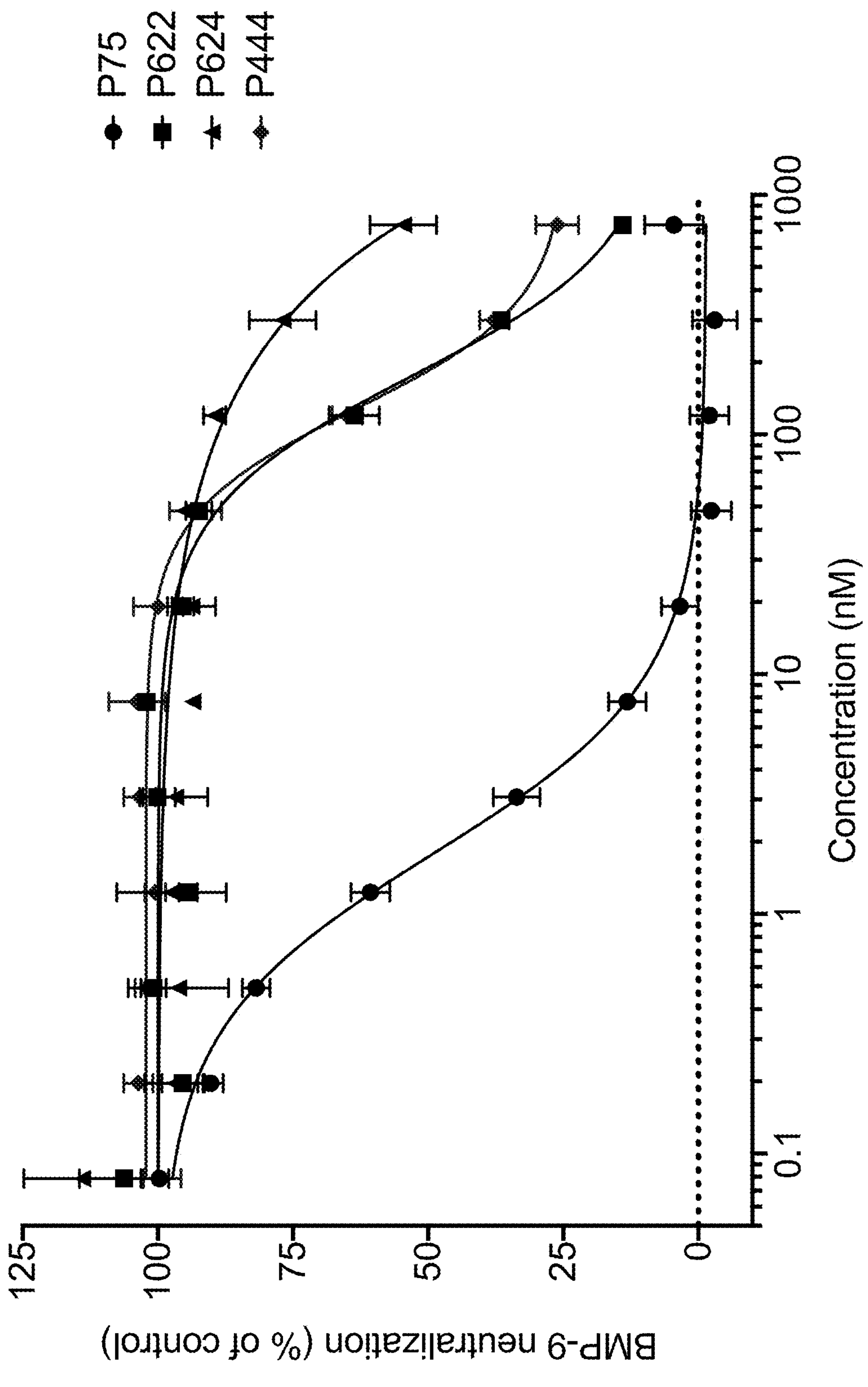
Figure 9A:
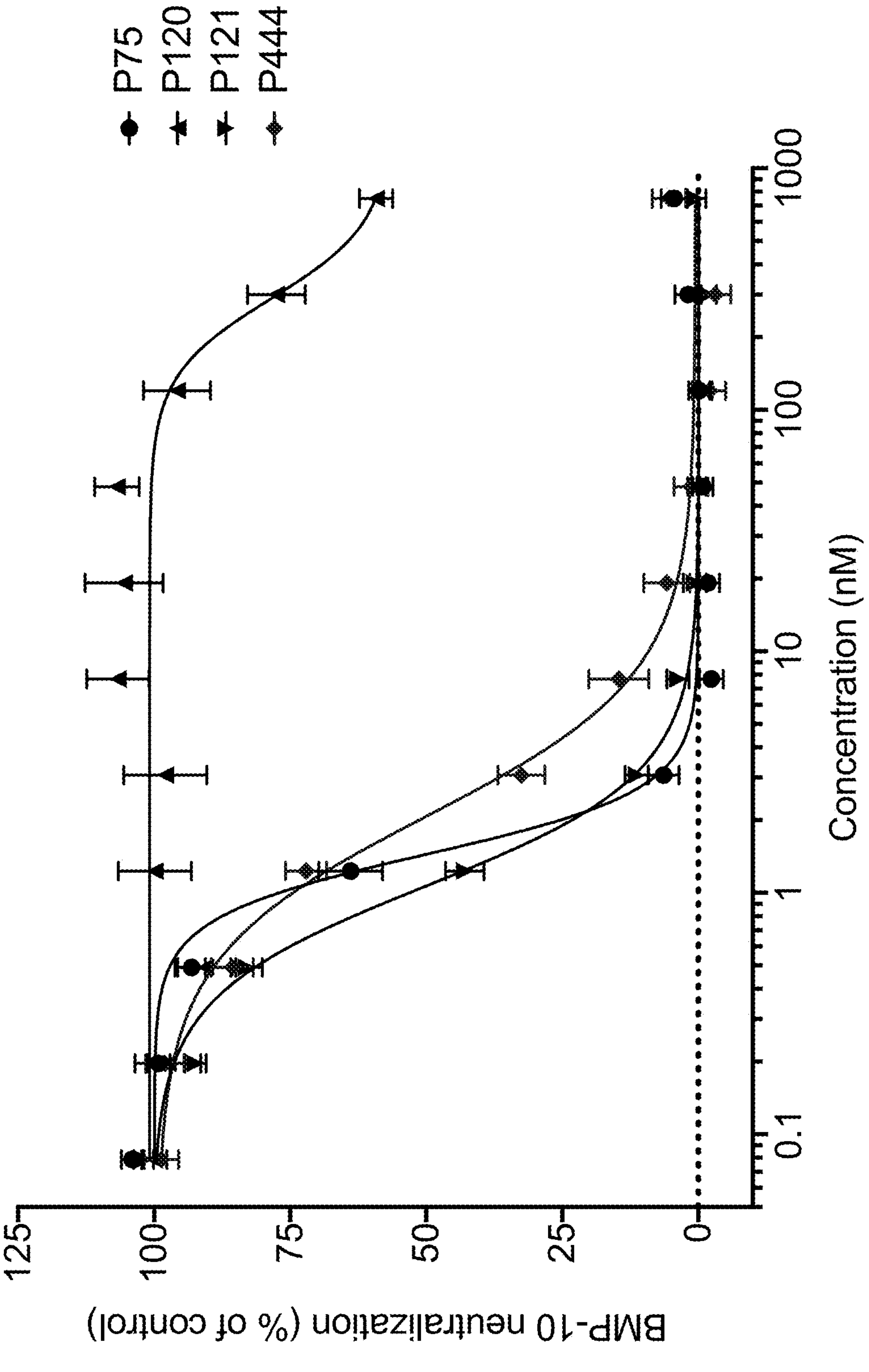
FIG. 9A-FIG. 9D shows representative results in the HepG2 cell-based assay for inhibition of BMP-10 for exemplary proteins.
Figure 9B:
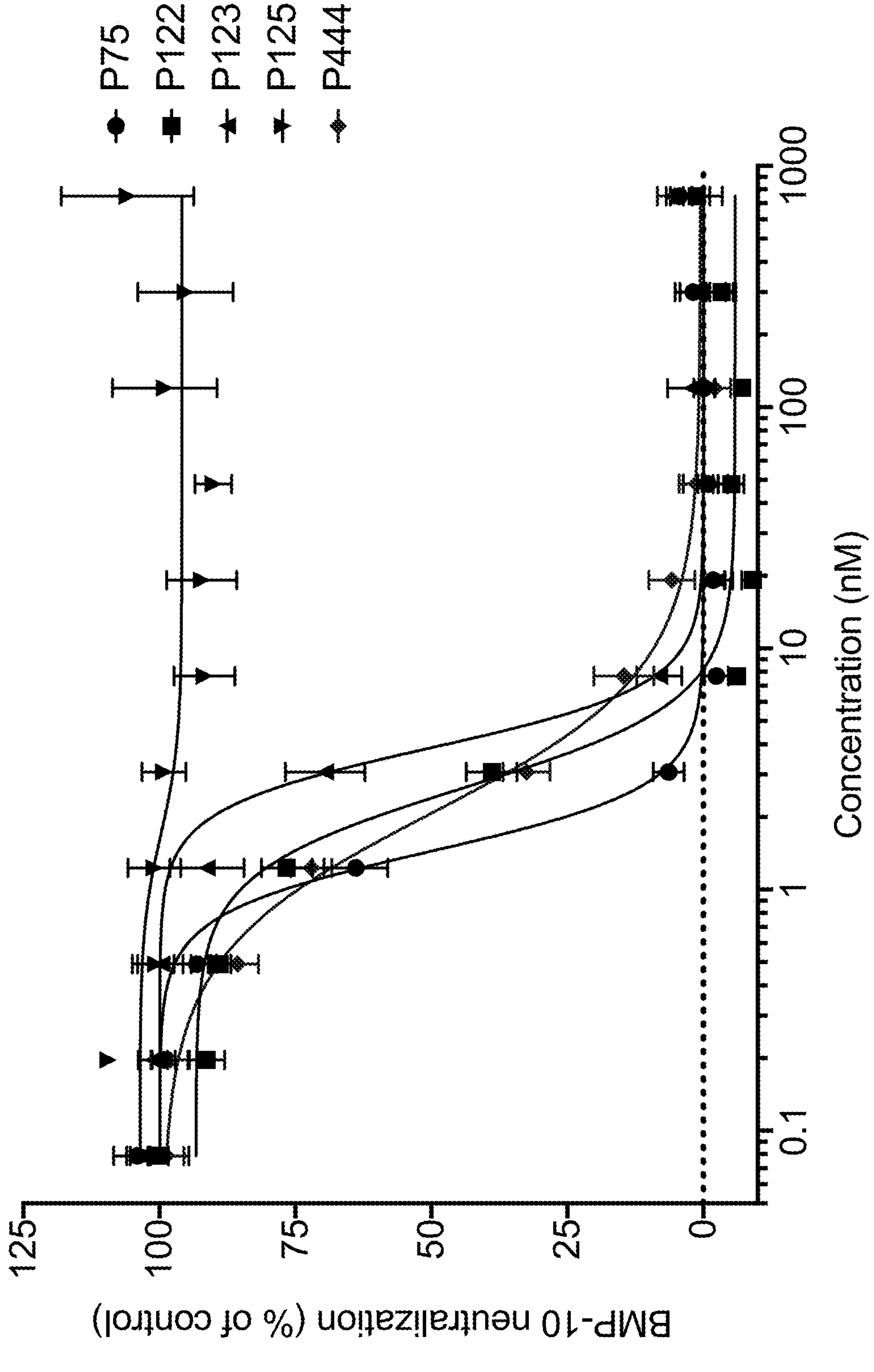
Figure 9C:
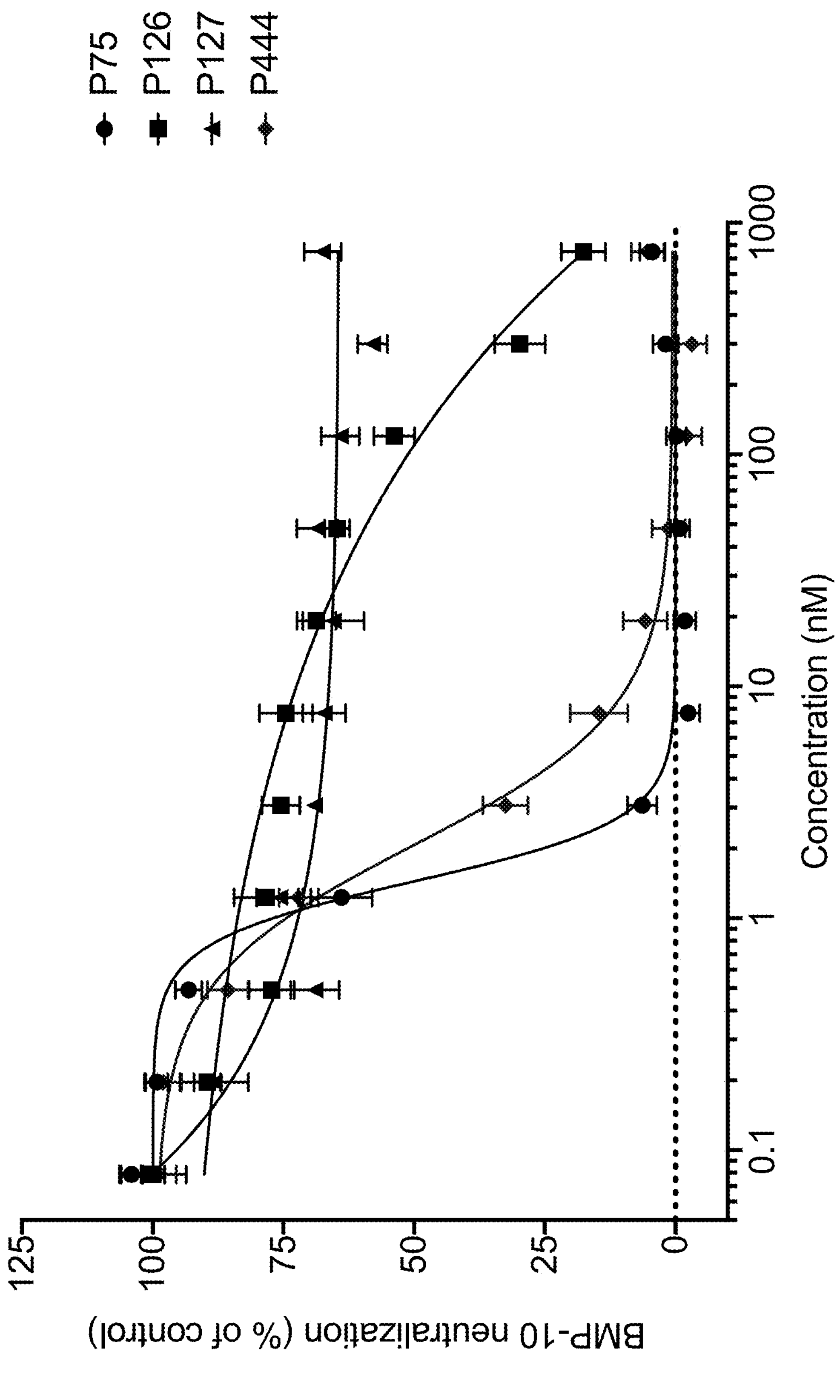
Figure 15C:
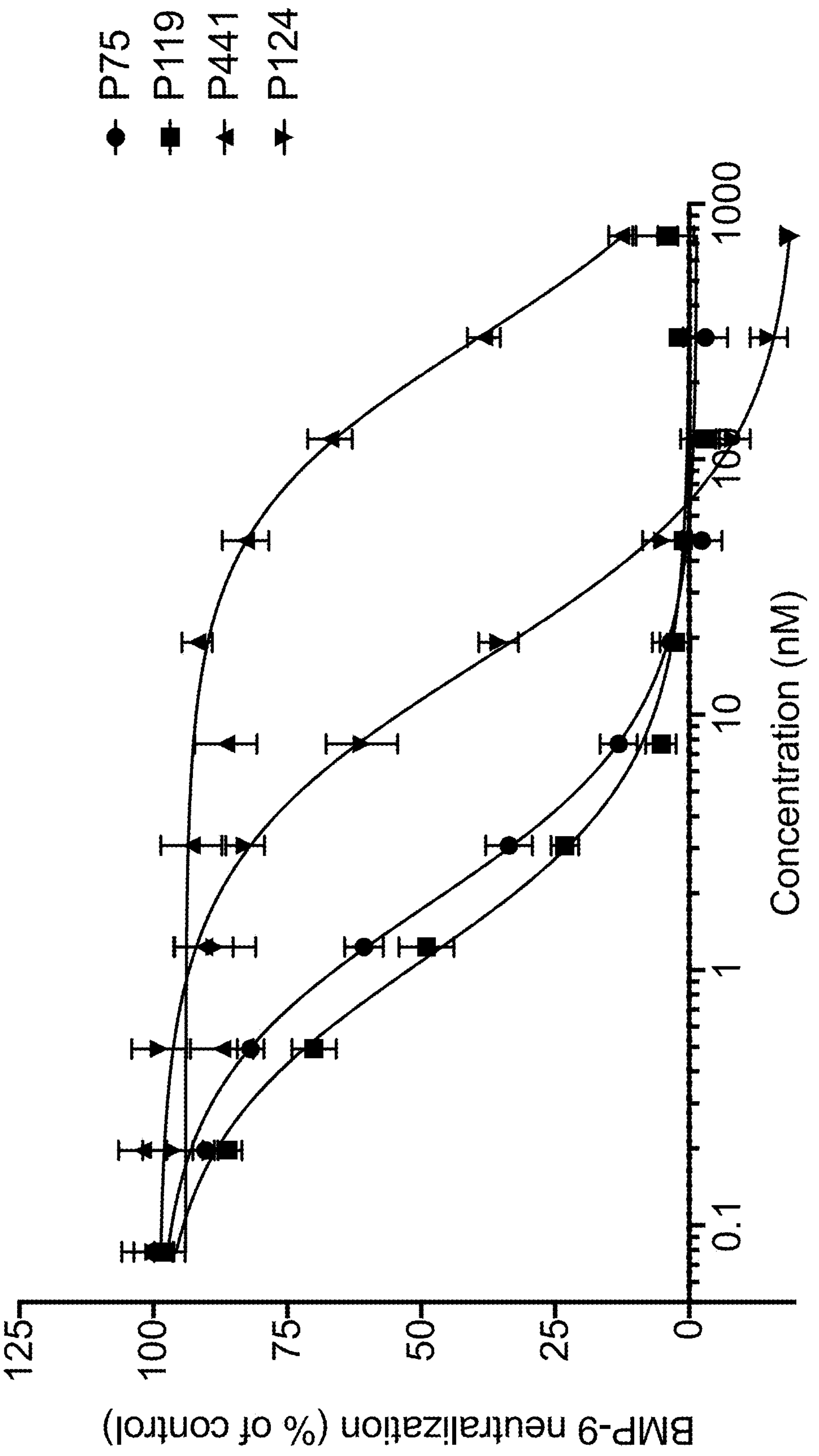
Figure 16A:
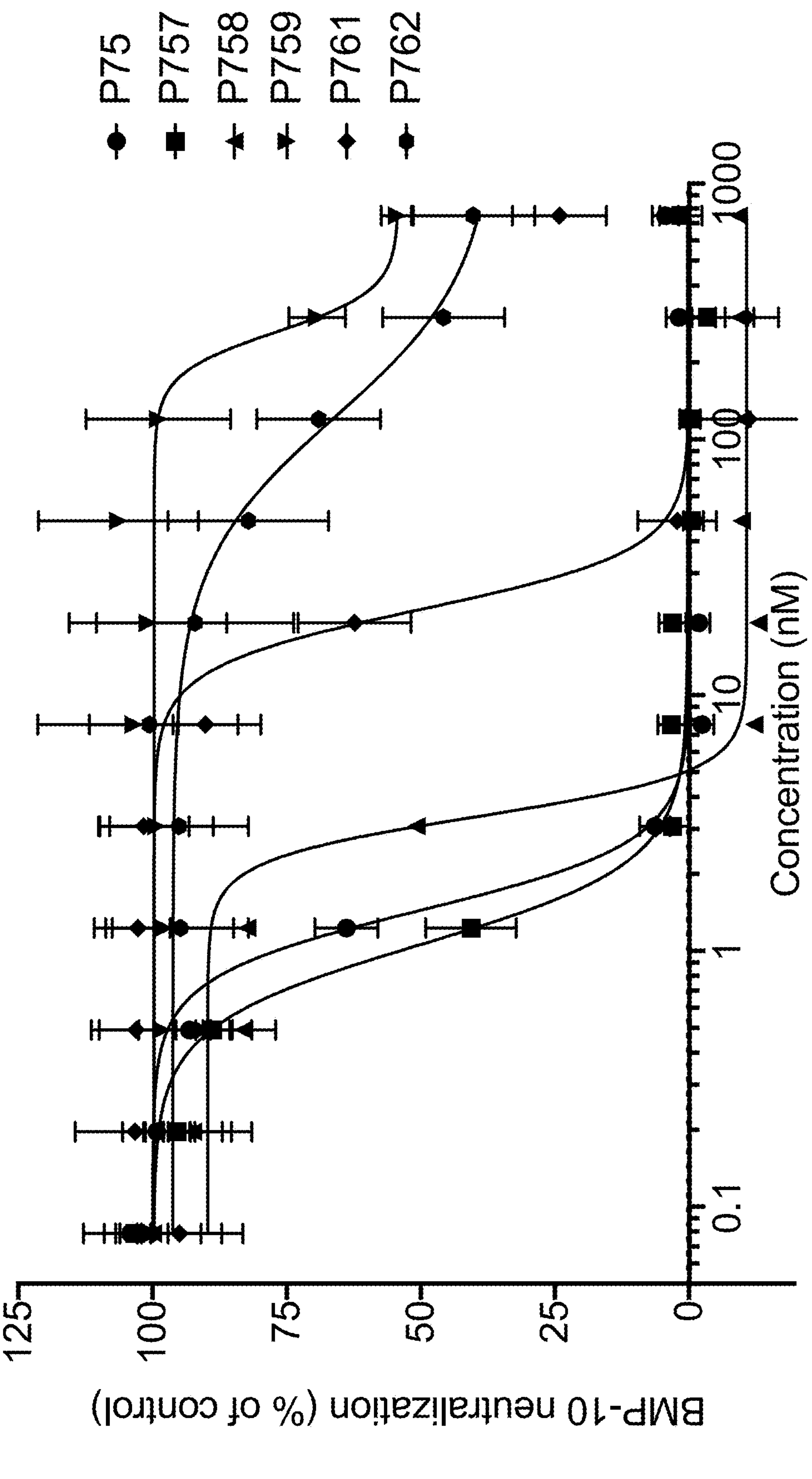
FIG. 16A-FIG. 16D shows representative results in the HepG2 cell-based assay for inhibition of BMP-10 for exemplary proteins.
Figure 16B:
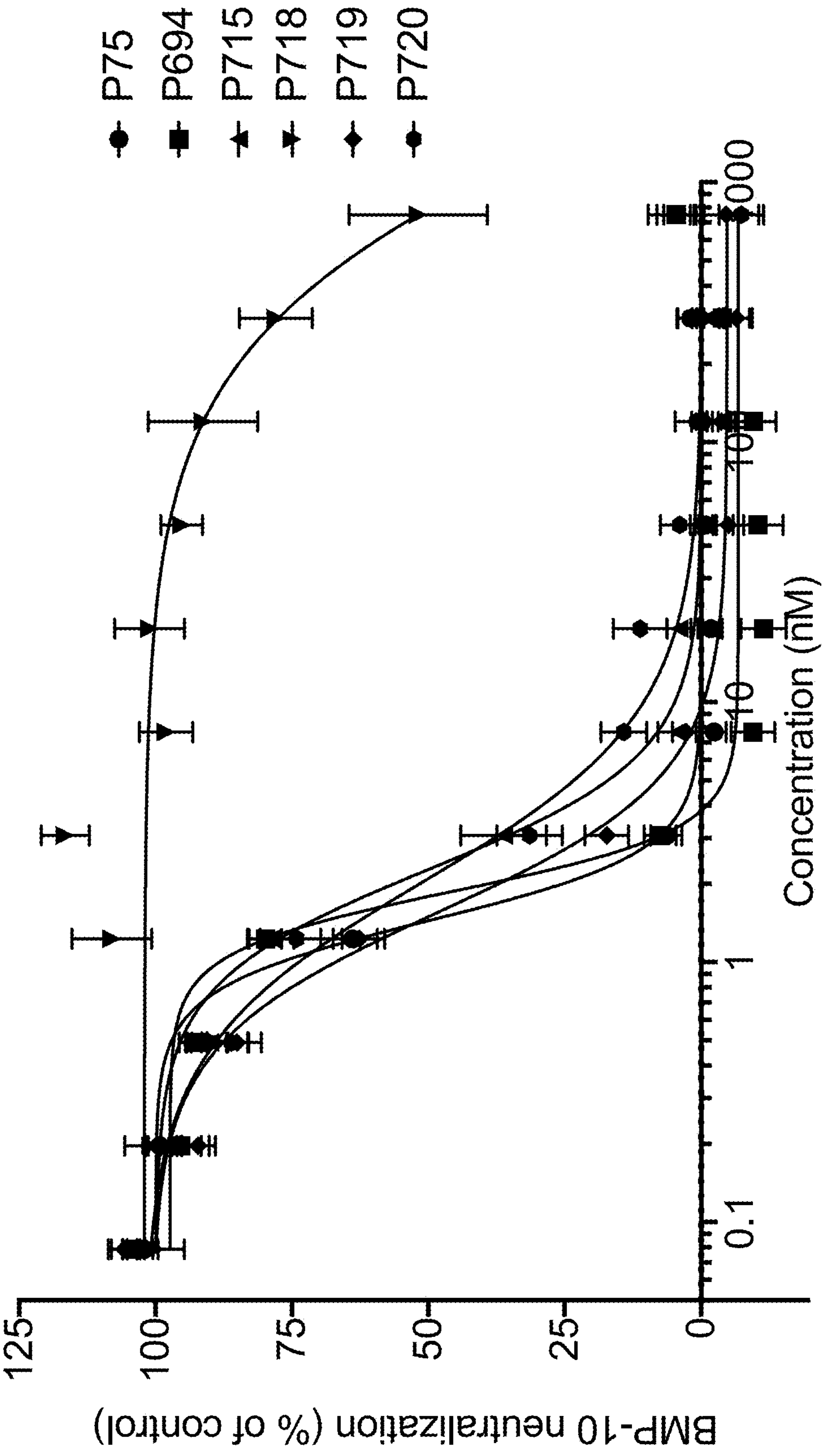
Figure 16C:
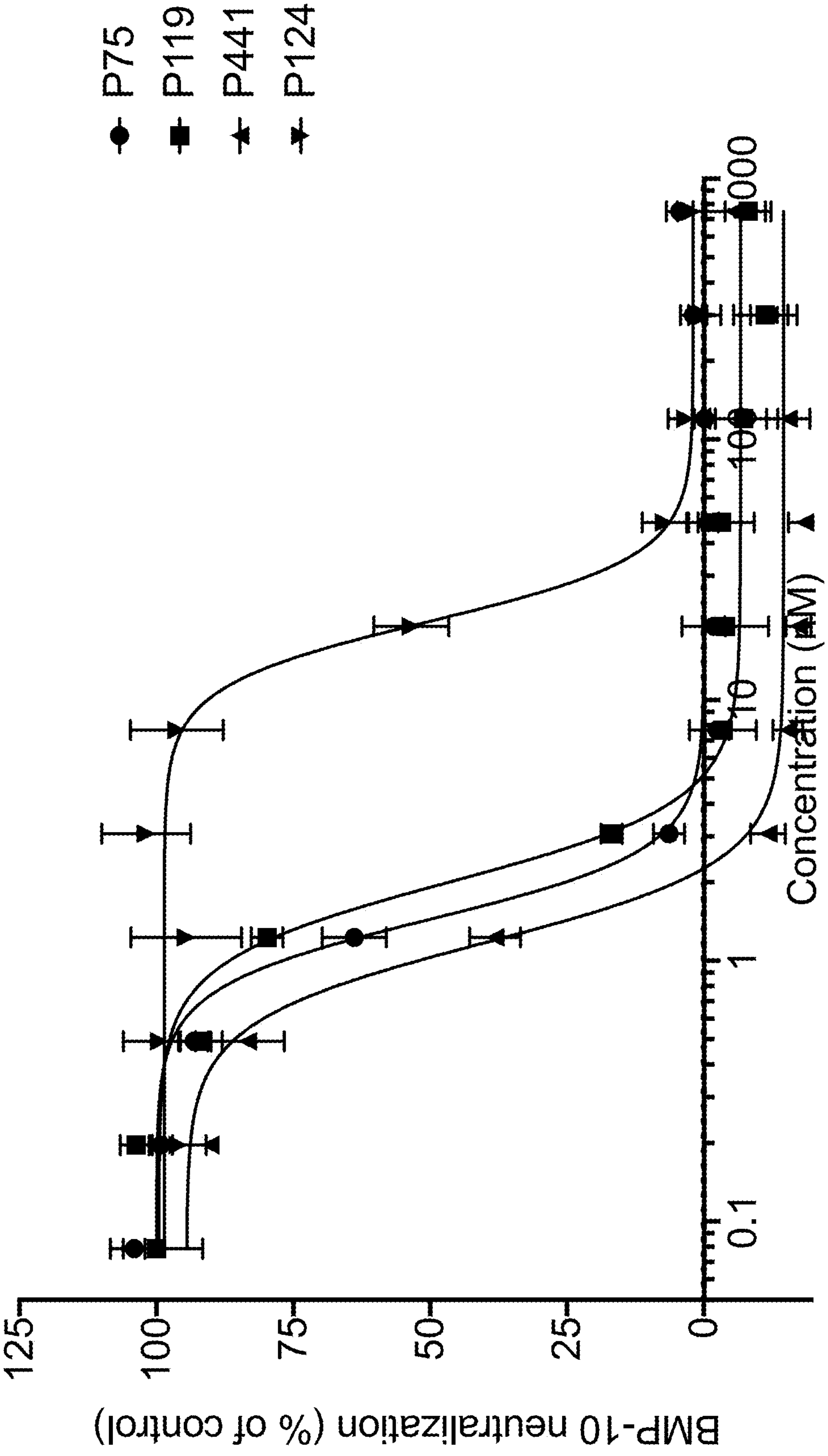
Figure 16D:
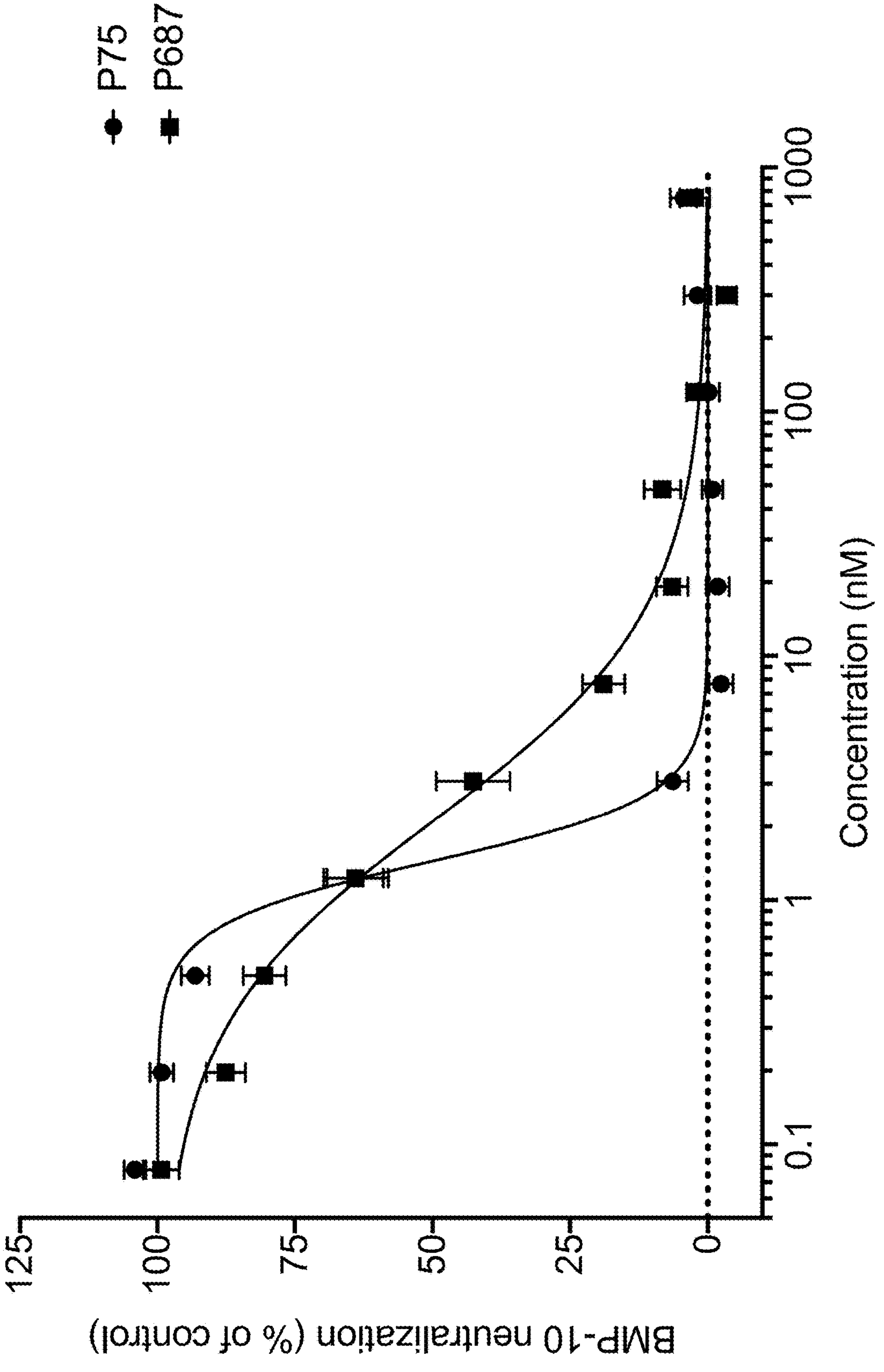

P1156 and P709 (39 amino acid linker with F58K and Q substitution, respectively), potency on activin A increased relative to P701 and P708 (14 amino acid linkers), respectively. These results show that changes in linker length have Characterization of the BMP-9 and BMP-10 neutralization activity of agents. The exemplary binding agents that were assessed for activin A, activin B, GDF-8, and GDF-11 neutralization were also tested in BMP-reporter assays. The IC50 values obtained in these assays for the entire group of binding agents are presented in Table 10 and the results are shown in FIGS. 8-9. Among these examples, P122 and P123 had modest changes in potency relative to P75. IC50 values on BMP-9 were 2.7 and 8.4 nM for P122 and P123, respectively (FIG. 8B). IC50 values on BMP-10 were 2.7 and 3.9 nM for P122 and P123, respectively (FIG. 9B). Exemplary agent P121 significantly reduced the inhibition potency compared to P75 on BMP-9 (FIG. 8A) but not BMP-10 (FIG. 9A). Another agent, P119, significantly increased the inhibition on BMP-9 (FIG. 15C) but not BMP-10 (FIG. 16C). The IC50 value on BMP-9 was 1.3 and 868 for P119 and P121, respectively, while the IC50 value on BMP-10 was 2.1 and 1.0 for P119 and P121, respectively (Table 10). Other exemplary agents, such as P120, P125, P126, and P127, lost the ability to neutralize both BMP-9 and BMP-10.

Figure 15A:
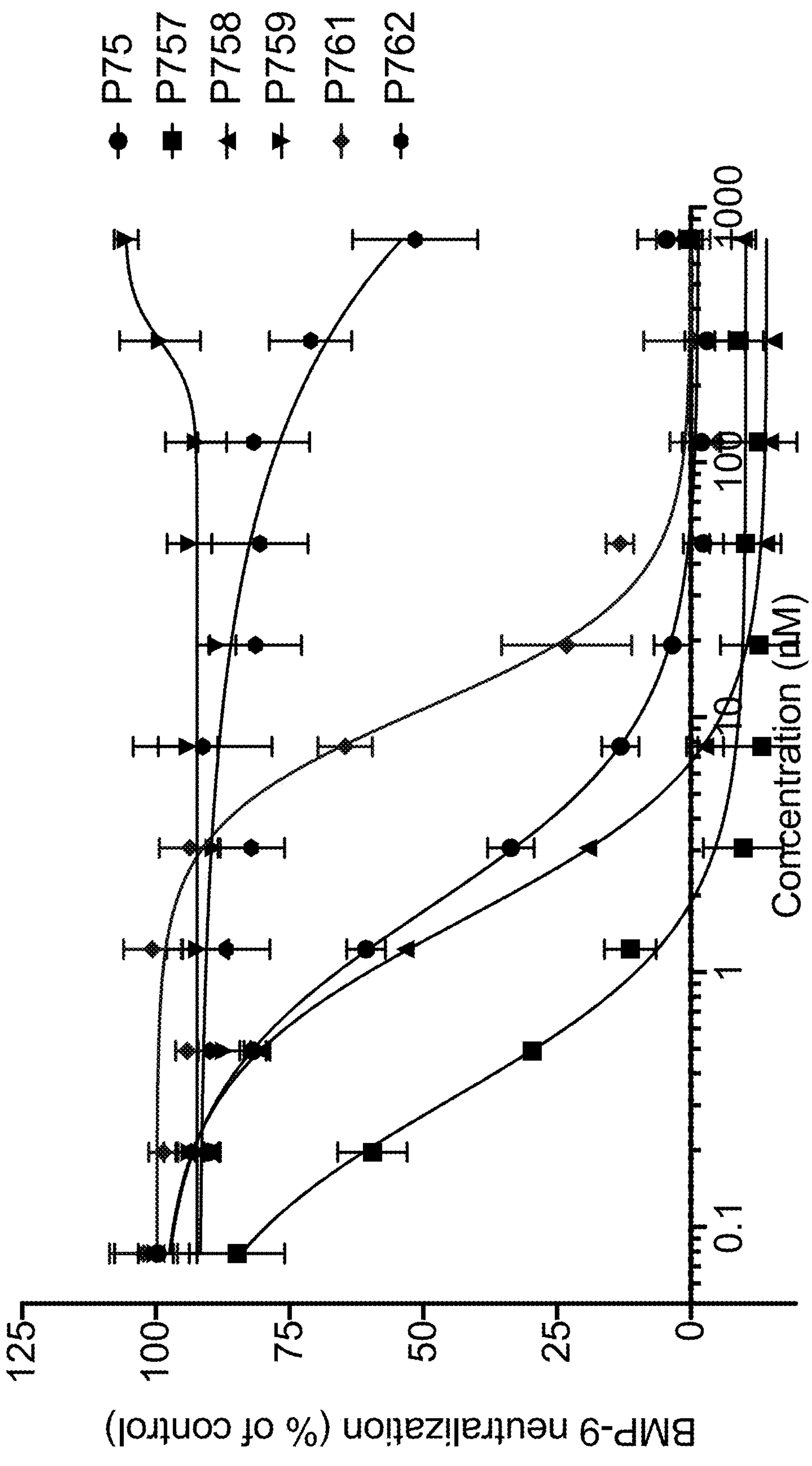
FIG. 15A-FIG. 15D shows representative results in the HepG2 cell-based assay for inhibition of BMP-9 for exemplary proteins.

As was done for the activins and GDFs, the effect of linker length on BMP-9 and BMP-10 potency was examined for a series of different mutations in the ActRIIB ECD. First, the wild-type ectodomain was examined using exemplary agents P75 (3 amino acid linker) and P757 (14 amino acid linker). The IC50 values are reported in Table 10 and illustrated in FIGS. 10A-B. Representative neutralization curves are shown in FIGS. 15A and 16A. The potency of P757 was greater on BMP-9 and BMP-10 relative to P75 (Table 9 and FIG. 10A), with increases of 900%, and 67%, respectively (FIG. 10B). Since BMP9 inhibition is associated with toxicity in patients, this result indicates that increasing linker length in the context of the wild type ActRIIB ECD produced undesirable effects.

Figure 9D:
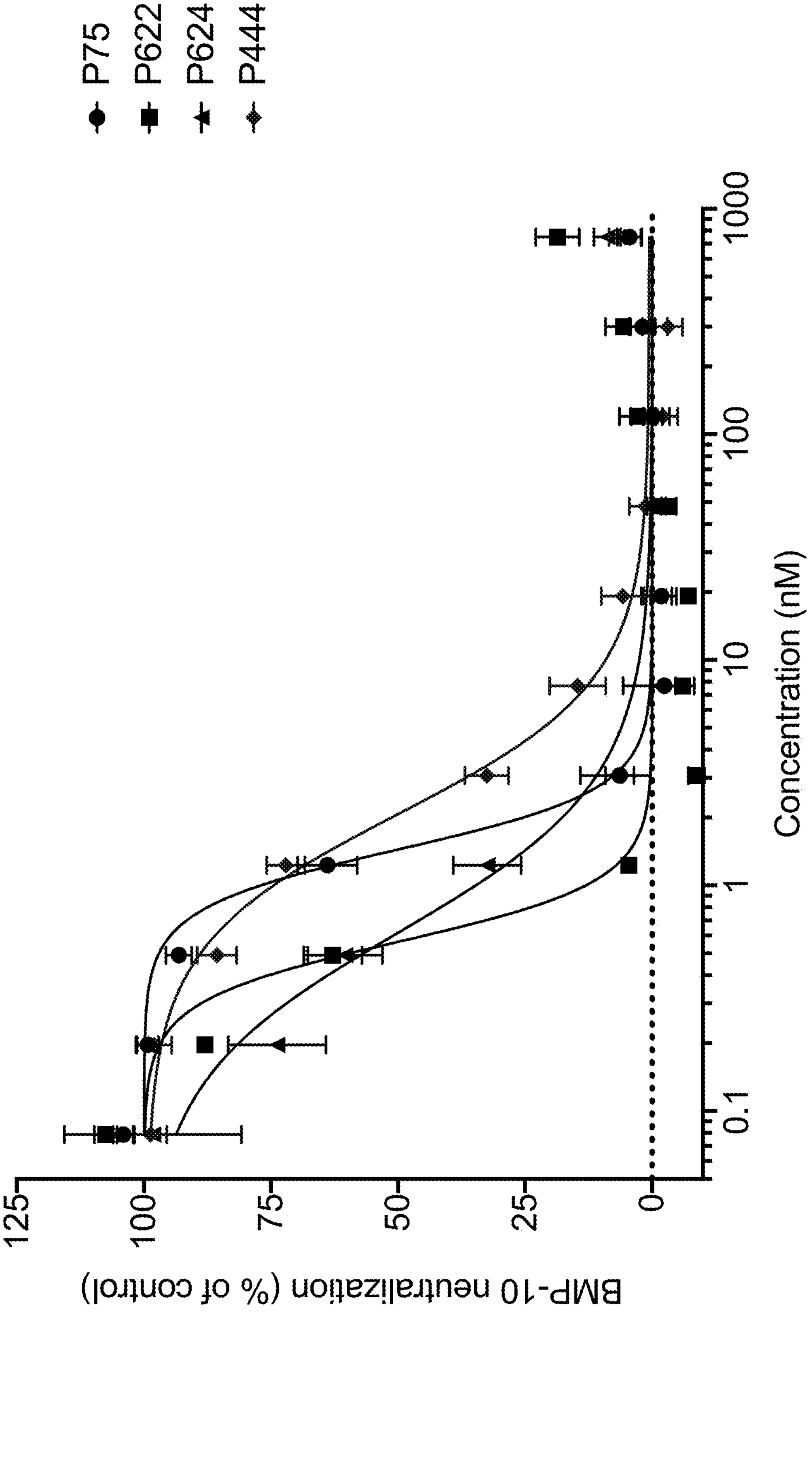
Figure 10C:
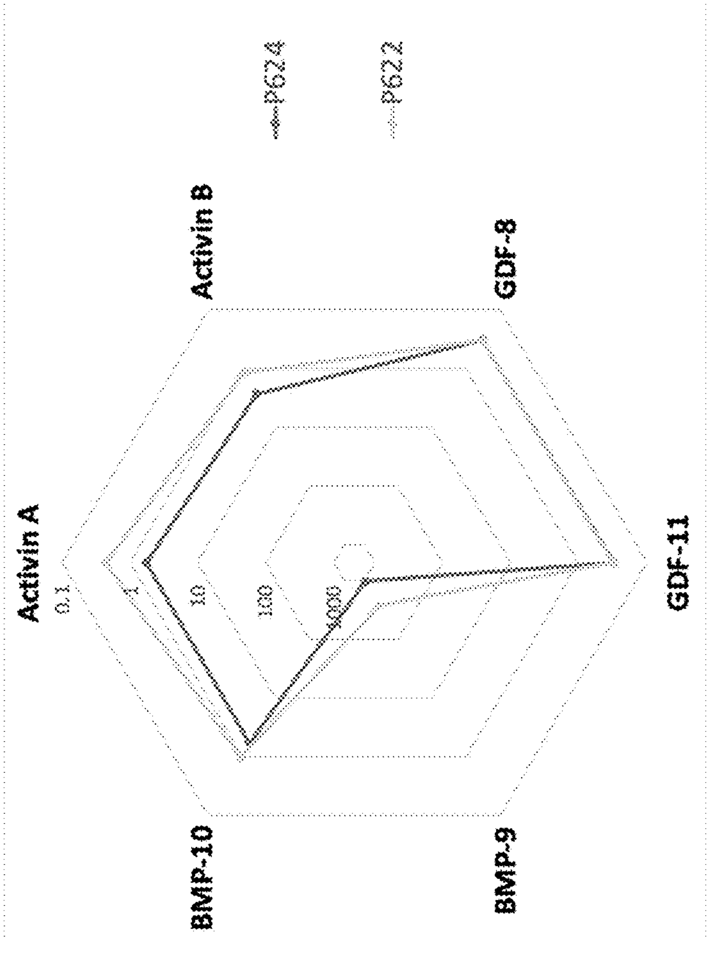
Figure 10D:
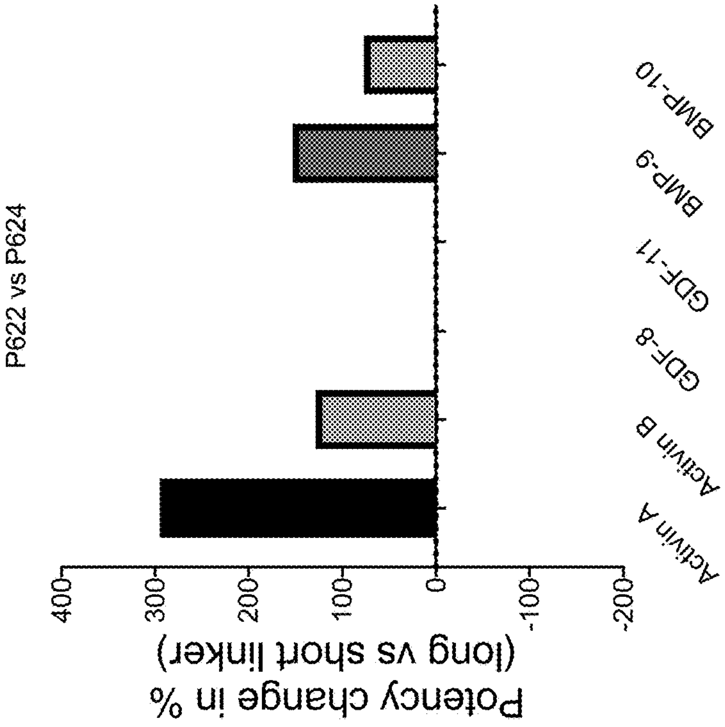
Figure 10F:
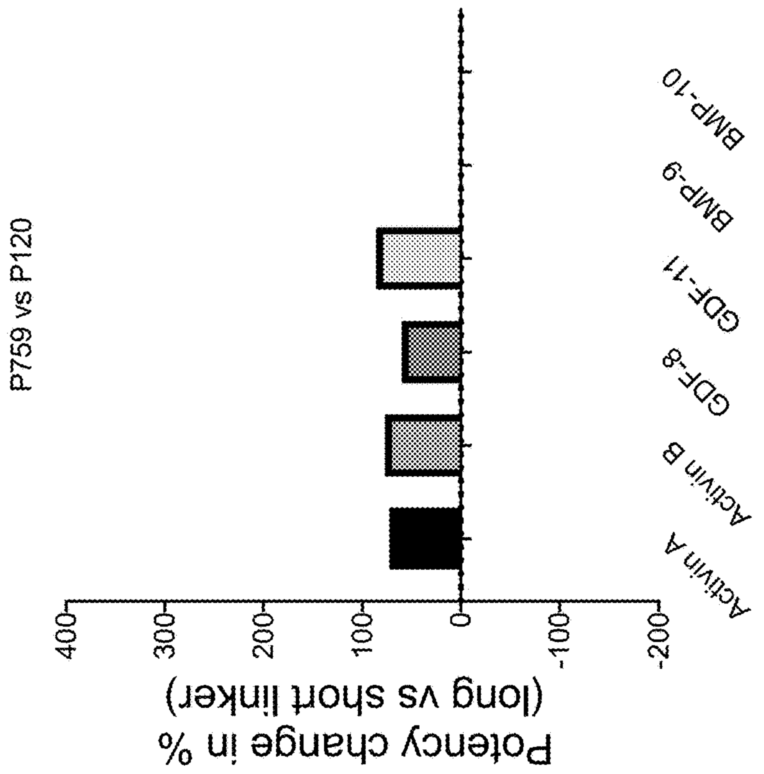

For the next pair of agents (P624 and P622, 3 and 14 amino acid linker, respectively), the IC50 values are reported in Table 10 and illustrated in FIGS. 10C-D. Representative neutralization curves are shown in FIGS. 8D and 9D. In this instance the potency of P622 on BMP-9 and BMP-10 was found to be higher compared to P624 (FIG. 10C) (increasing by 153% and 77%, respectively; FIG. 10D). Notably, this percent increase in potency on BMP-9 was much smaller than in the context of wild-type ActRIIB ECD (P757, discussed above), indicating that the undesirable effect of increasing potency on BMP-9 was reduced in the context of the mutation in the ActRIIB ECD in P624/P622.

Figure 10E:
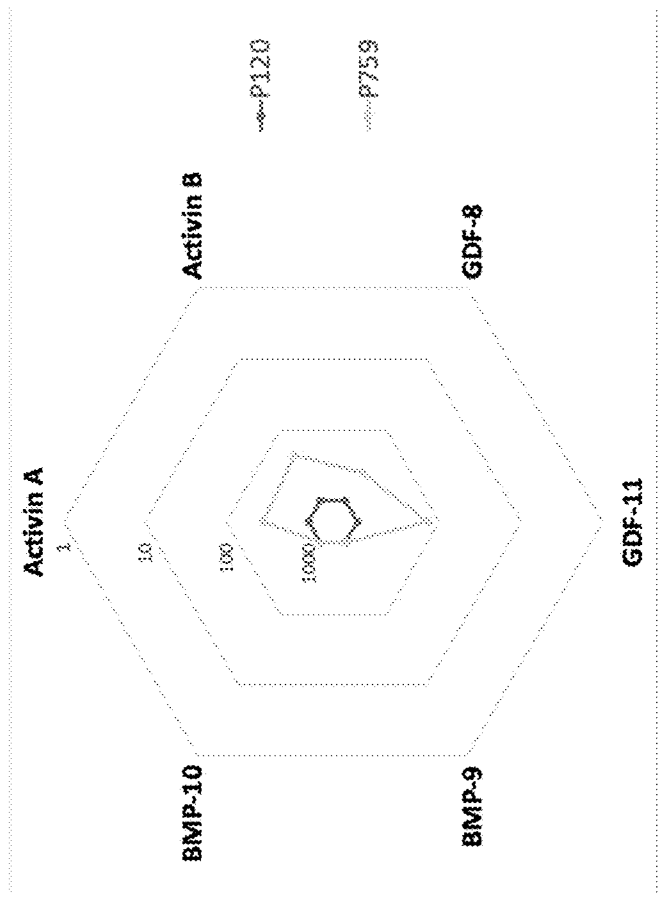
Figure 10H:
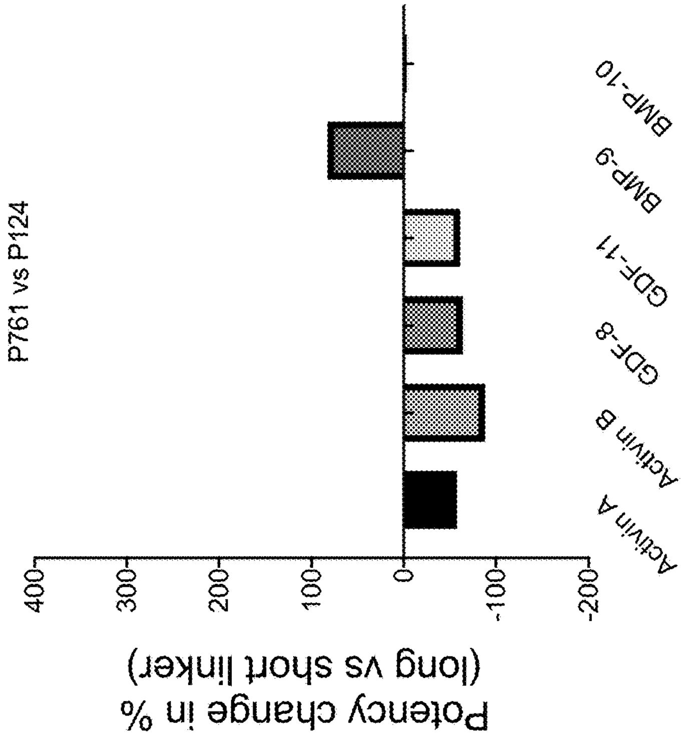

The IC50 values for the next exemplary pair of agents (P120 and P759, 3 and 14 amino acid linker, respectively) are reported in Table 10 and illustrated in FIGS. 10E-F. Representative neutralization curves are shown in FIGS. 8A, 9A, 15A, and 16A. Unexpectedly, in this instance, P759 was found to have the same potency on BMP-9 and BMP-10 as P120 (FIGS. 10E-F). Two other exemplary 3 and 14 amino acid linker pairs, i.e., P119 and P758 (Table 10, FIGS. 10I-J, FIGS. 15A and C, and 16A and C) and P126 and P762 (Table 10, FIGS. 10K-L, FIGS. 8C and 9C, 15A, and 16A) also exhibited the same potencies on BMP-9 and BMP-10.

Figure 10G:
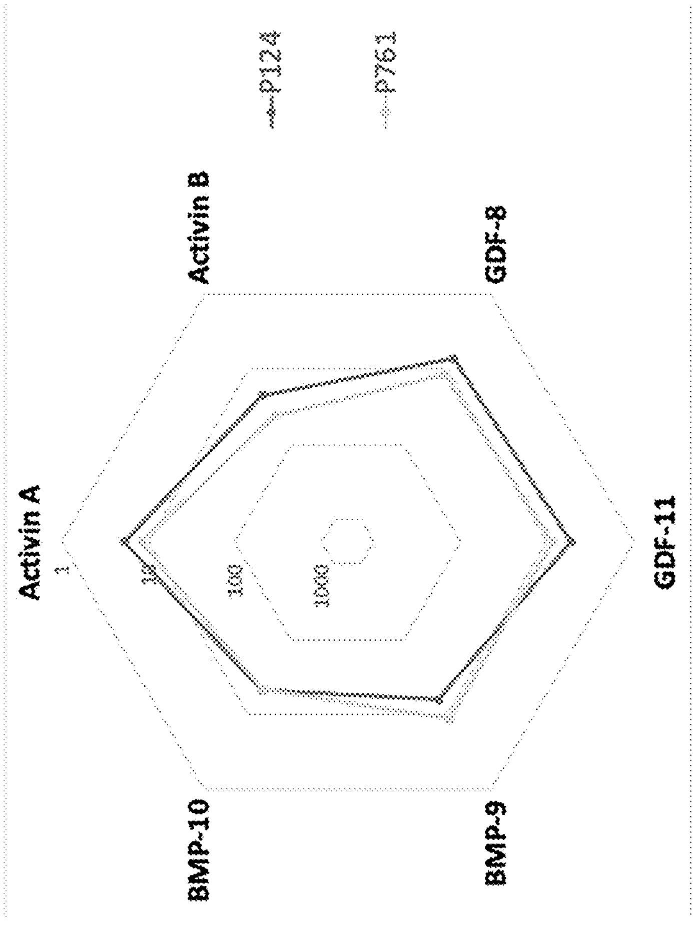
Figure 10I:
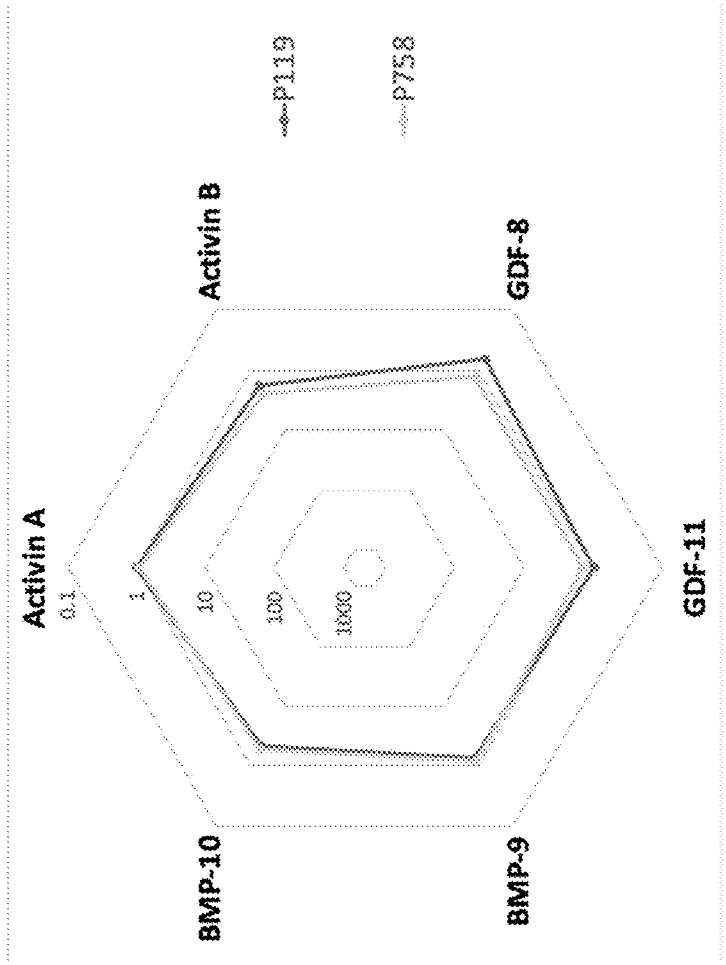
Figure 10J:
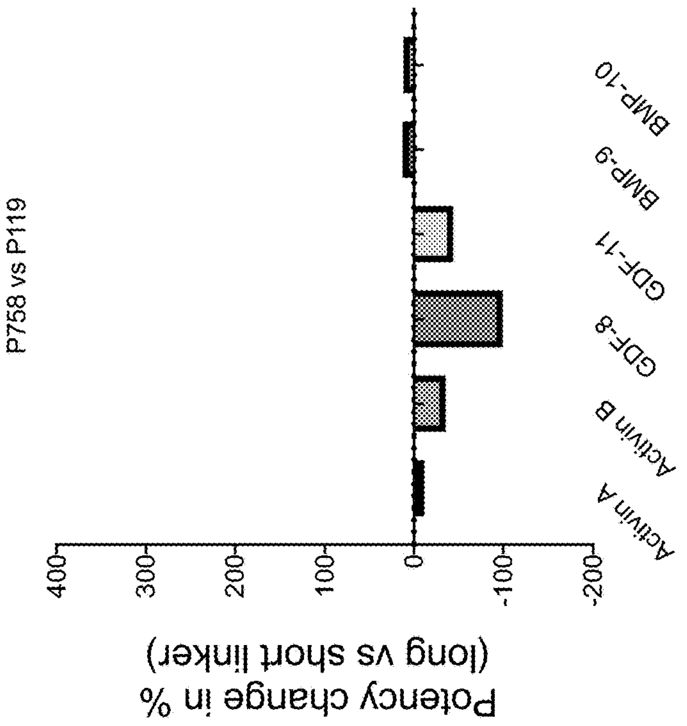
Figure 10L:
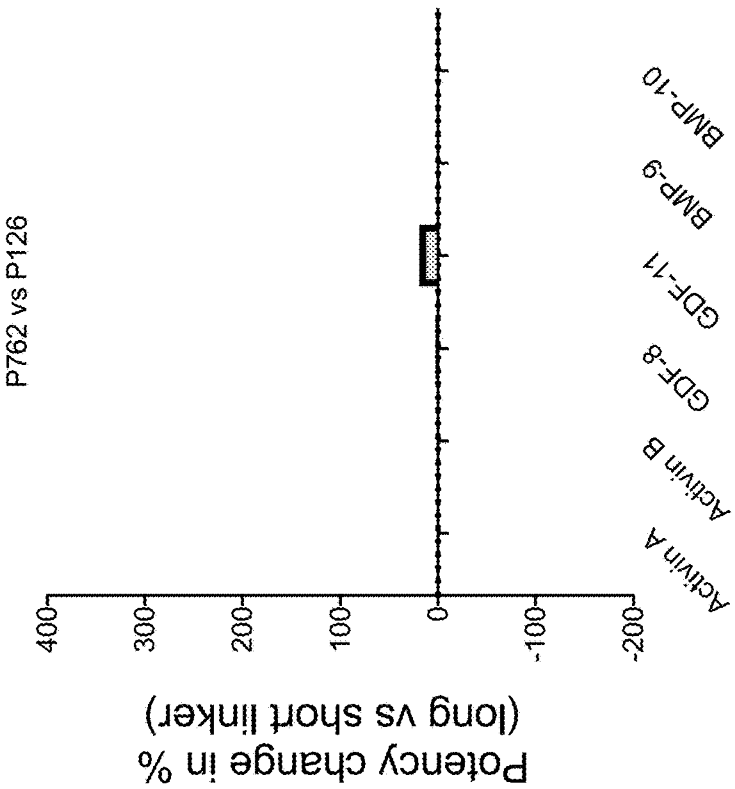
Figure 10K:
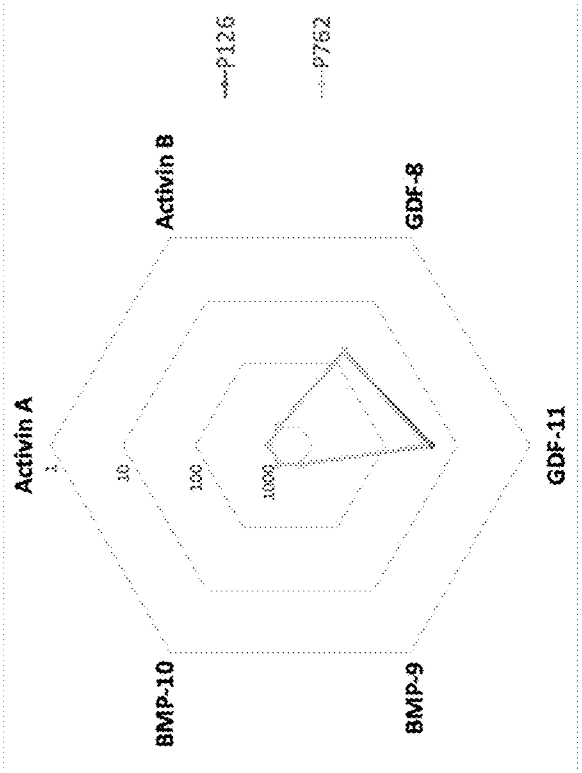
Figure 10M:
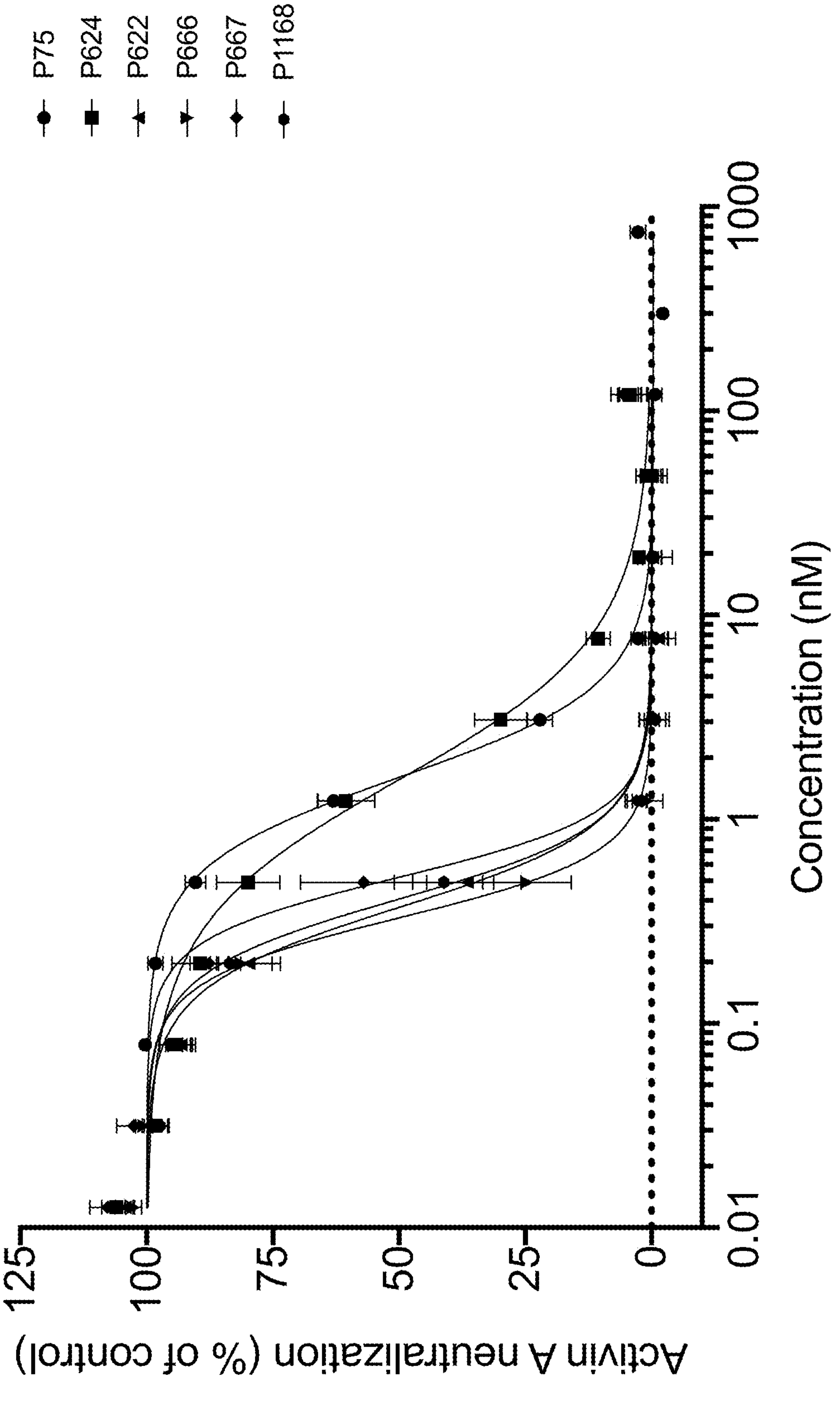
FIGS. 10M-10V show representative results in the HEK-Blue and HepG2 cell-based assays for inhibition of (FIG. 10M, FIG. 10S, and FIG. 10V) activin A, (FIG. 10N) activin B, (FIG. 10O, FIG. 10T, and FIG. 10W) GDF-8, (FIG. 10P) GDF-11, (FIG. 10Q, FIG. 10U, and FIG. 10X) BMP-9, and (FIG. 10R) BMP-10 for exemplary proteins (FIGS. 10M-10R) P624, P622, P666, P667, and P1168, (FIGS. 10S-10U) P1218, P1219, P708, P1220, and P709, and (FIGS. 10V-10X) P698, P1153, P1154, P701, P1155, and P1156, as indicated. Error bars indicate standard error of the mean (SEM).
Figure 10N:
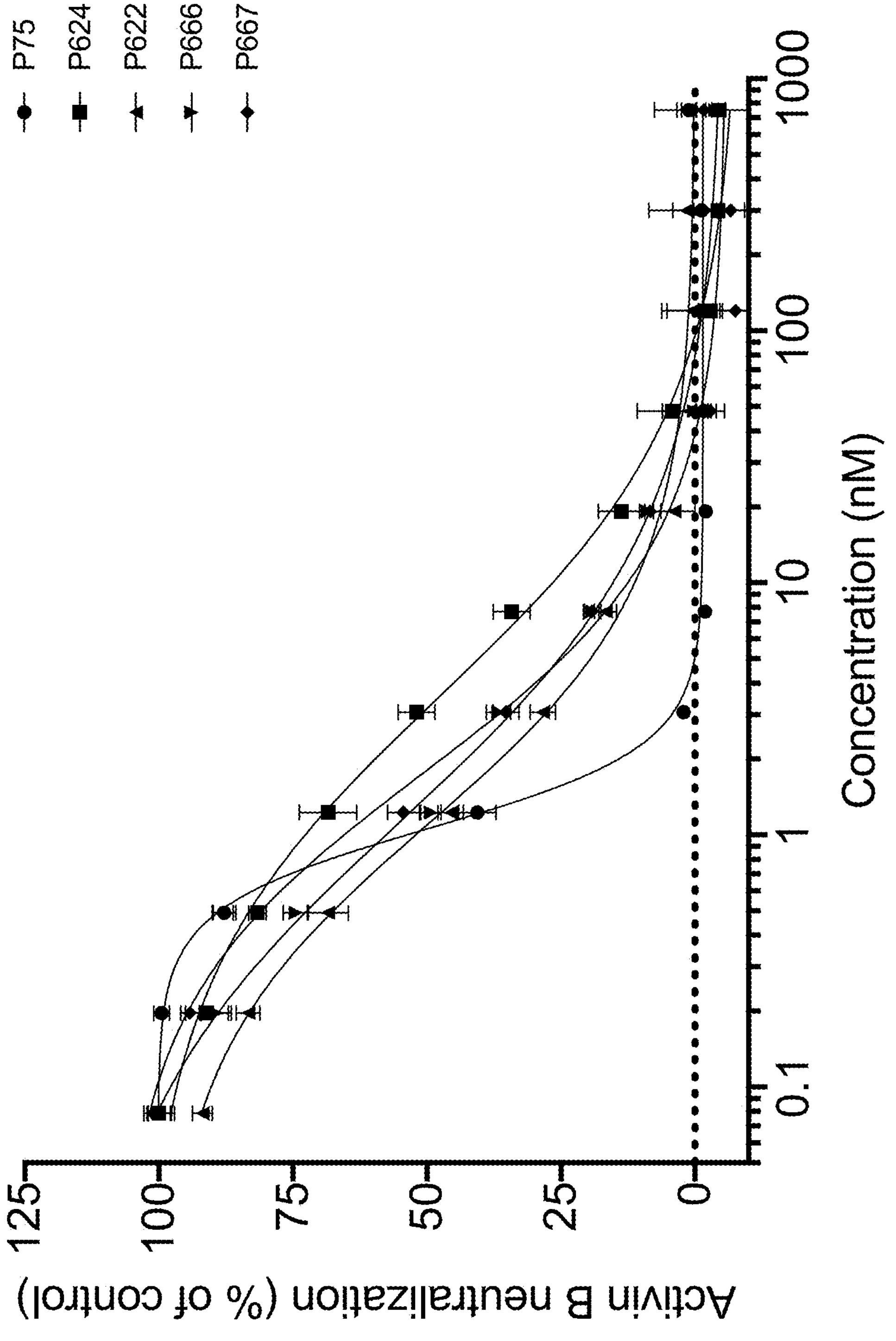
Figure 10O:
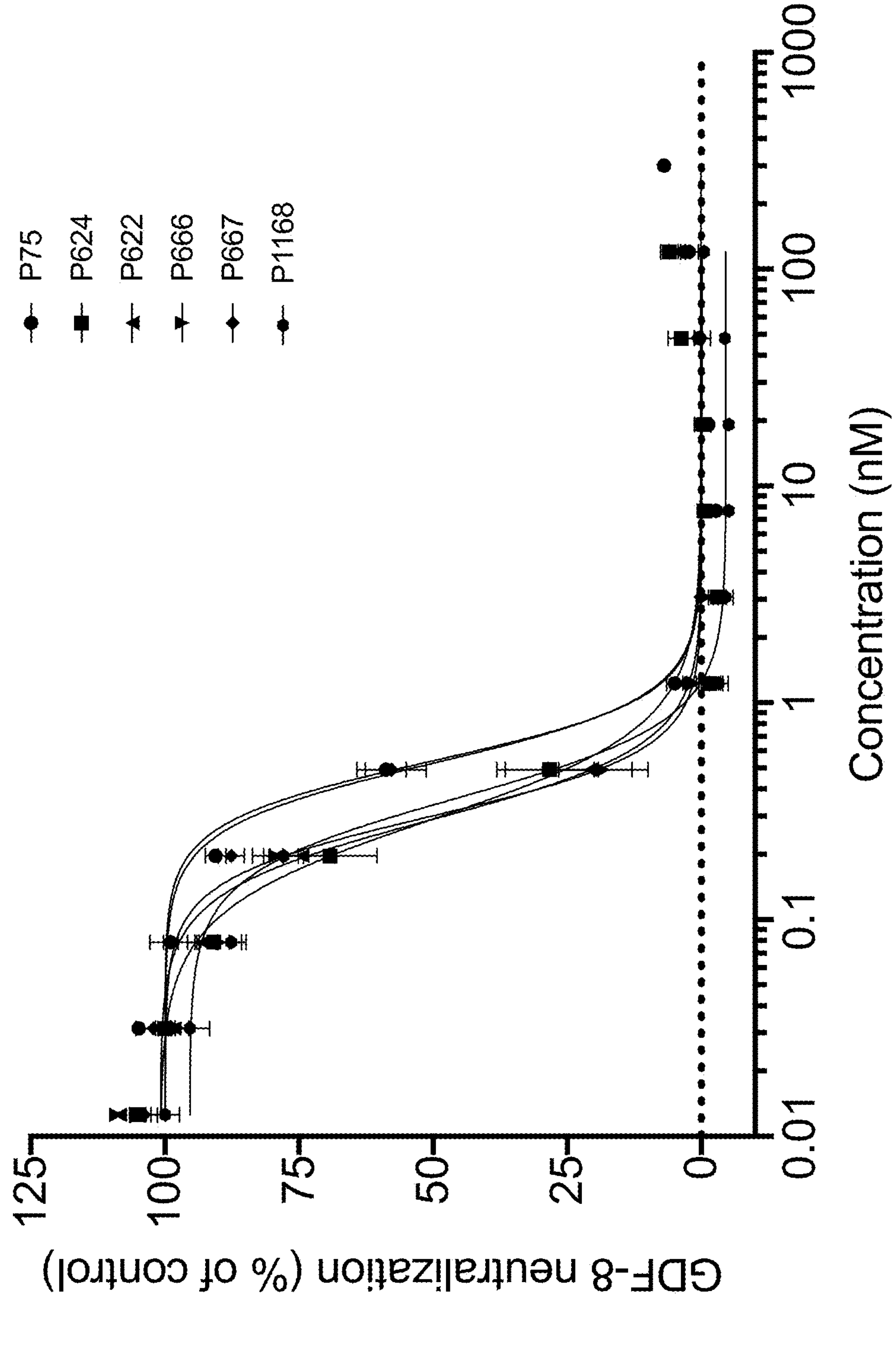
Figure 10P:
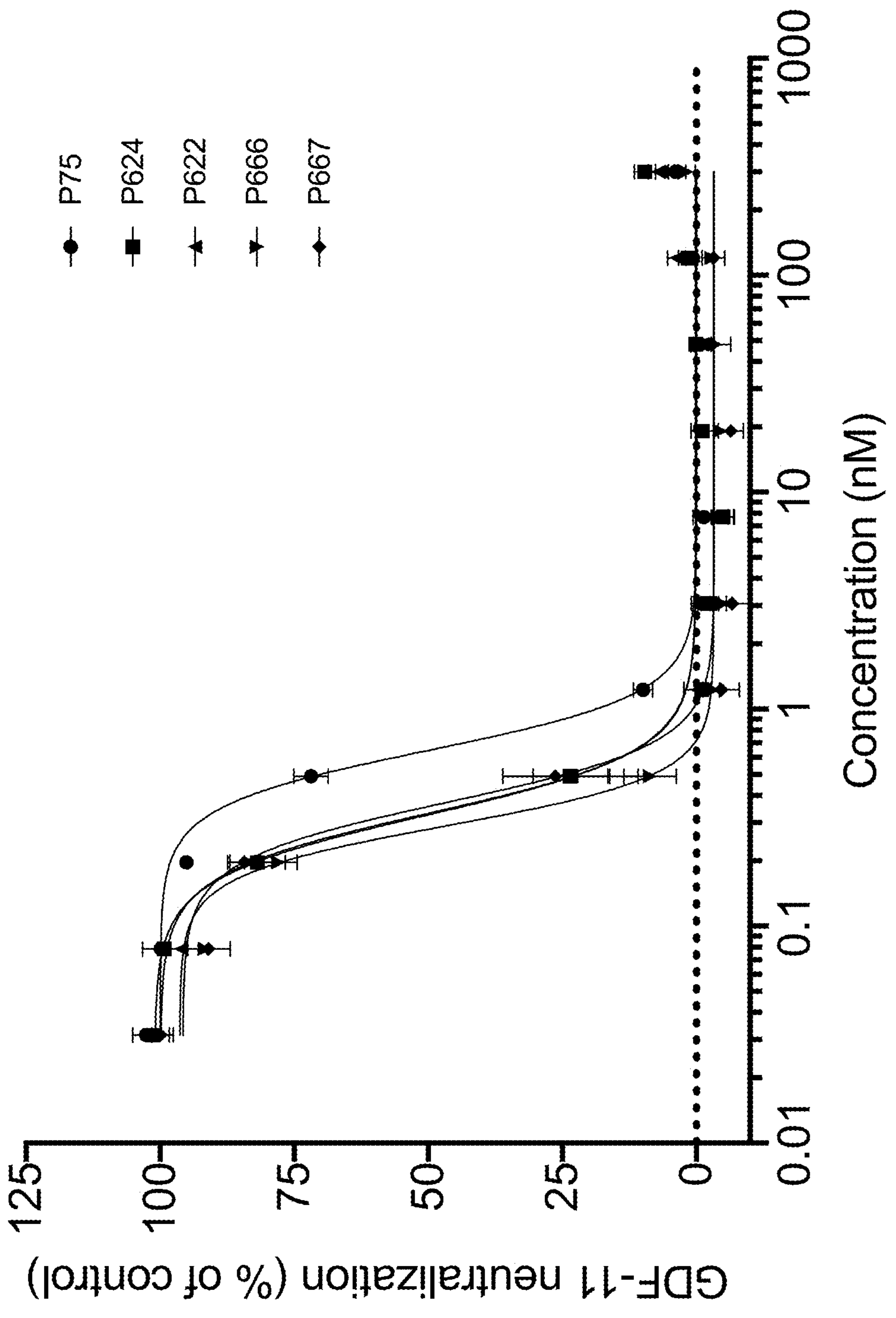

For the next pair (P124 and P761, 3 and 14 amino acid linker, respectively) the IC50 values are reported in Table 10 and illustrated in FIGS. 10G-H. Representative neutralization curves are shown in FIGS. 15A and C, and 16A and C. Surprisingly, in this instance the exemplary agent P761 (longer linker) exhibited no change on BMP-10 relative to P124 (short linker) while showing an increase in potency of 83% on BMP-9 relative to P124 (FIGS. 10G-H).

In summary, as was the case for activin and GDF ligands, exemplary agents comprising the ActRIIB ECD fused to an Fc domain showed different effects of linker length on potency profiles for BMP-9 and BMP-10 ligands depending on the position and the nature of the amino acid substitution in the ActRIIB ECD. As described above, in some instances the potencies were unaffected, whereas in others they were increased.

Figure 10Q:
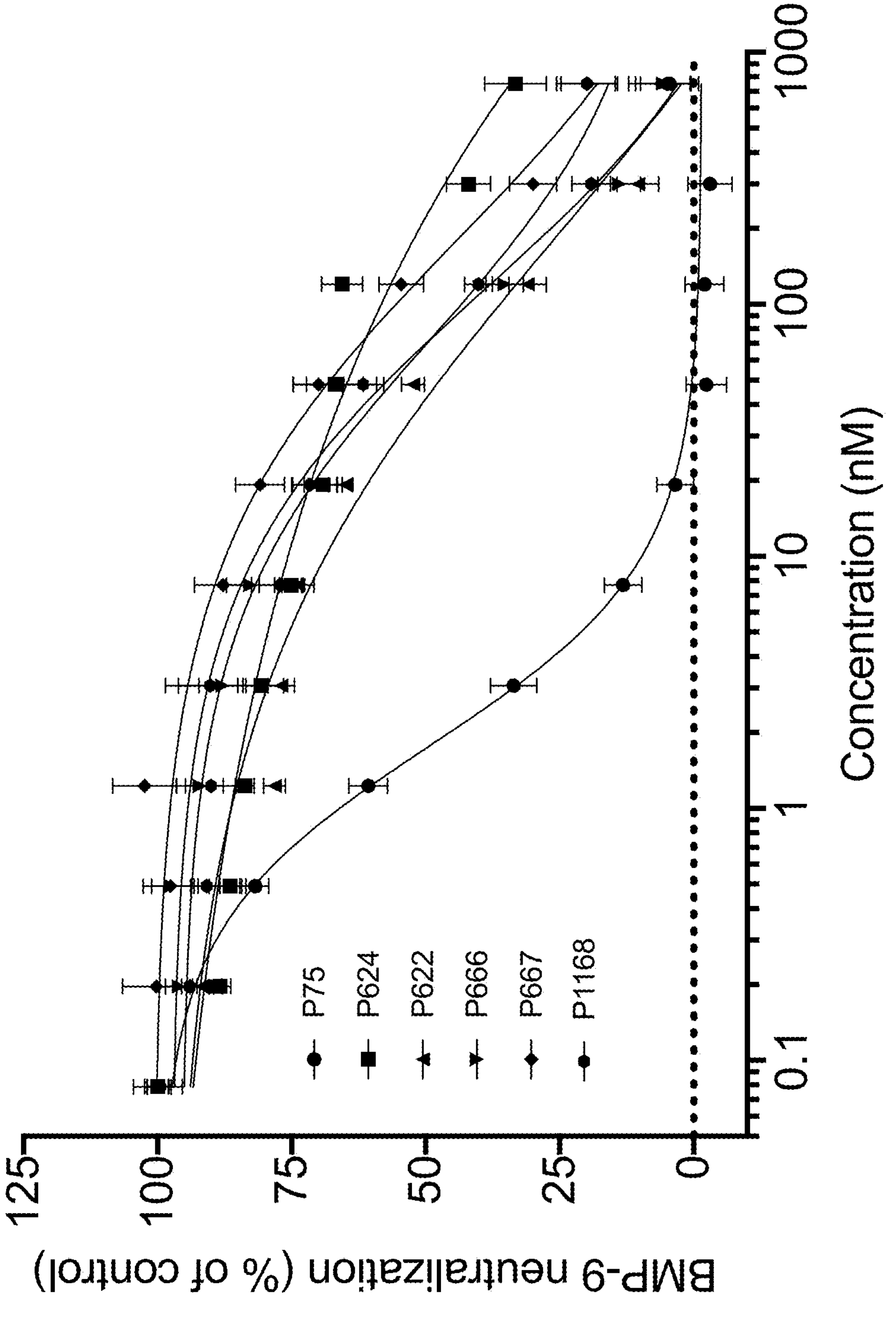
Figure 10R:
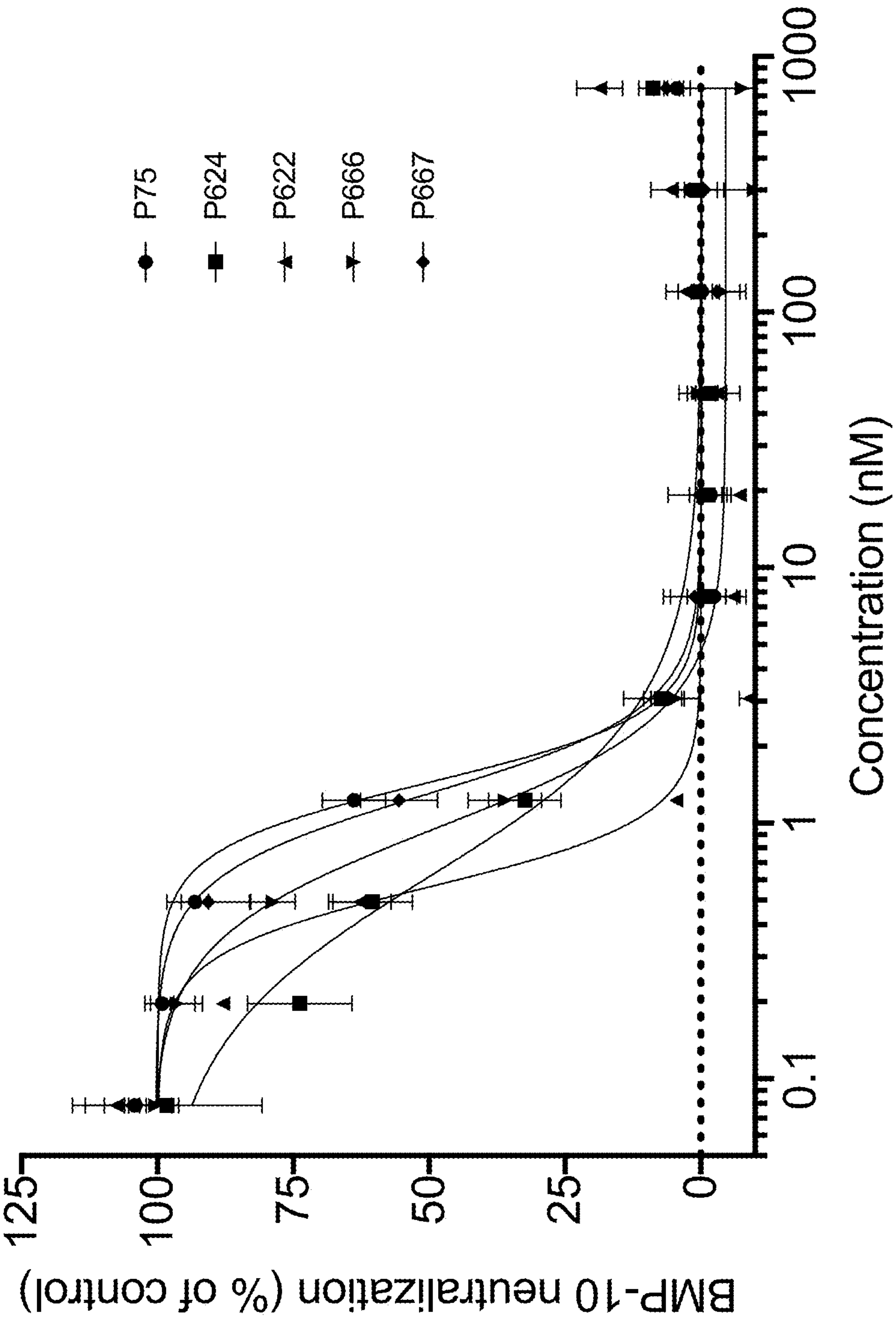
Figure 10S:
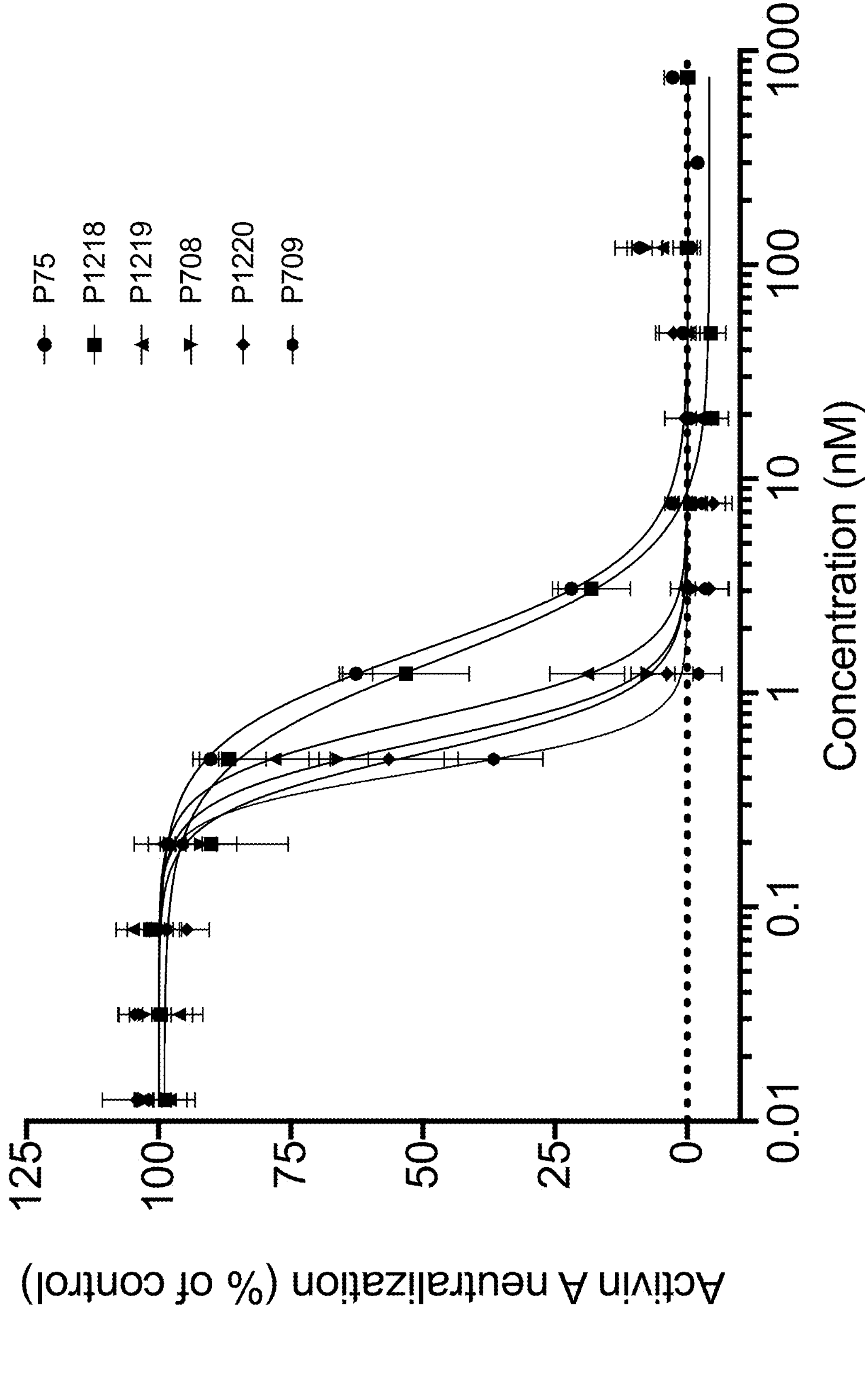
Figure 10T:
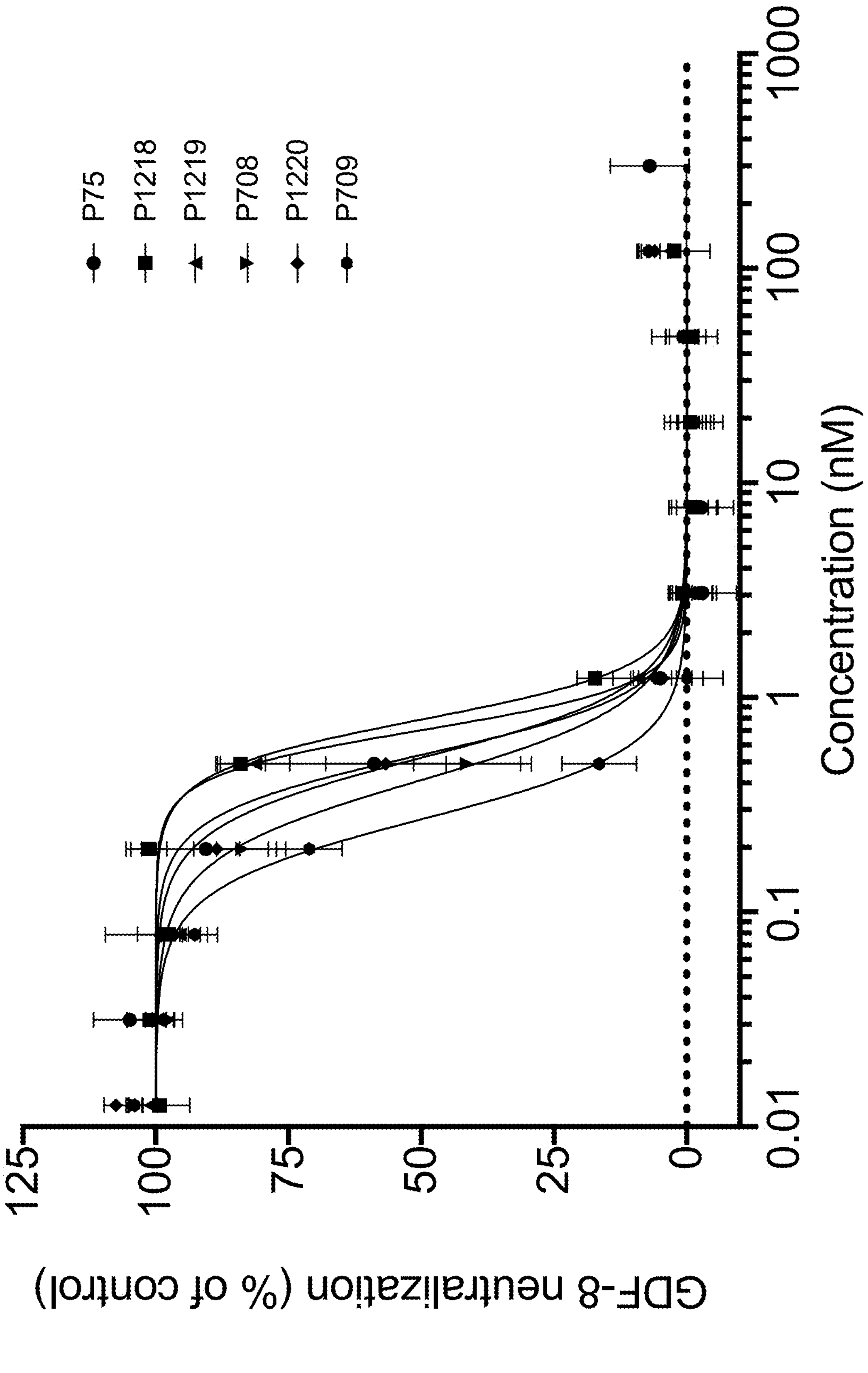
Figure 10U:
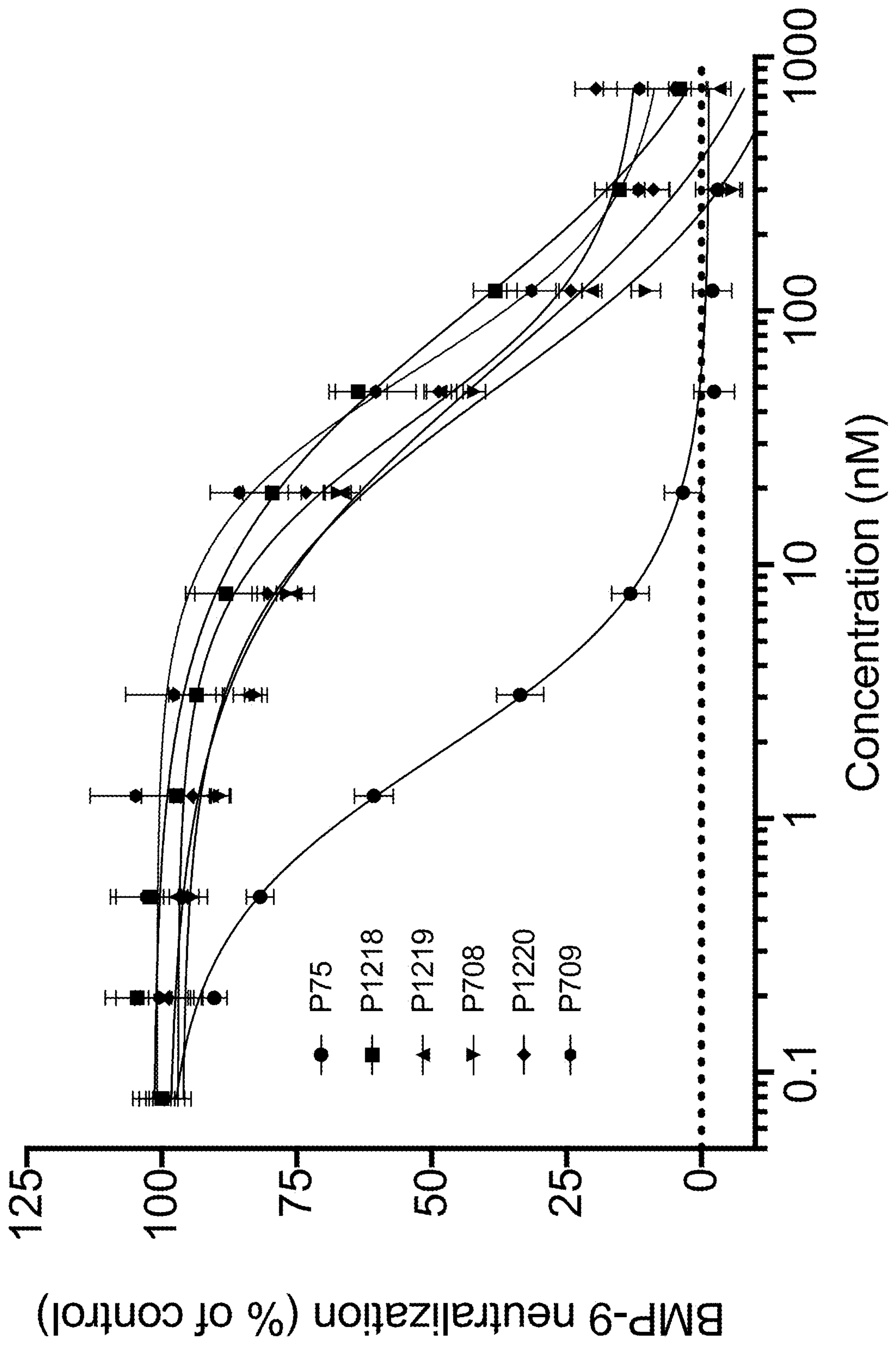
Figure 10V:
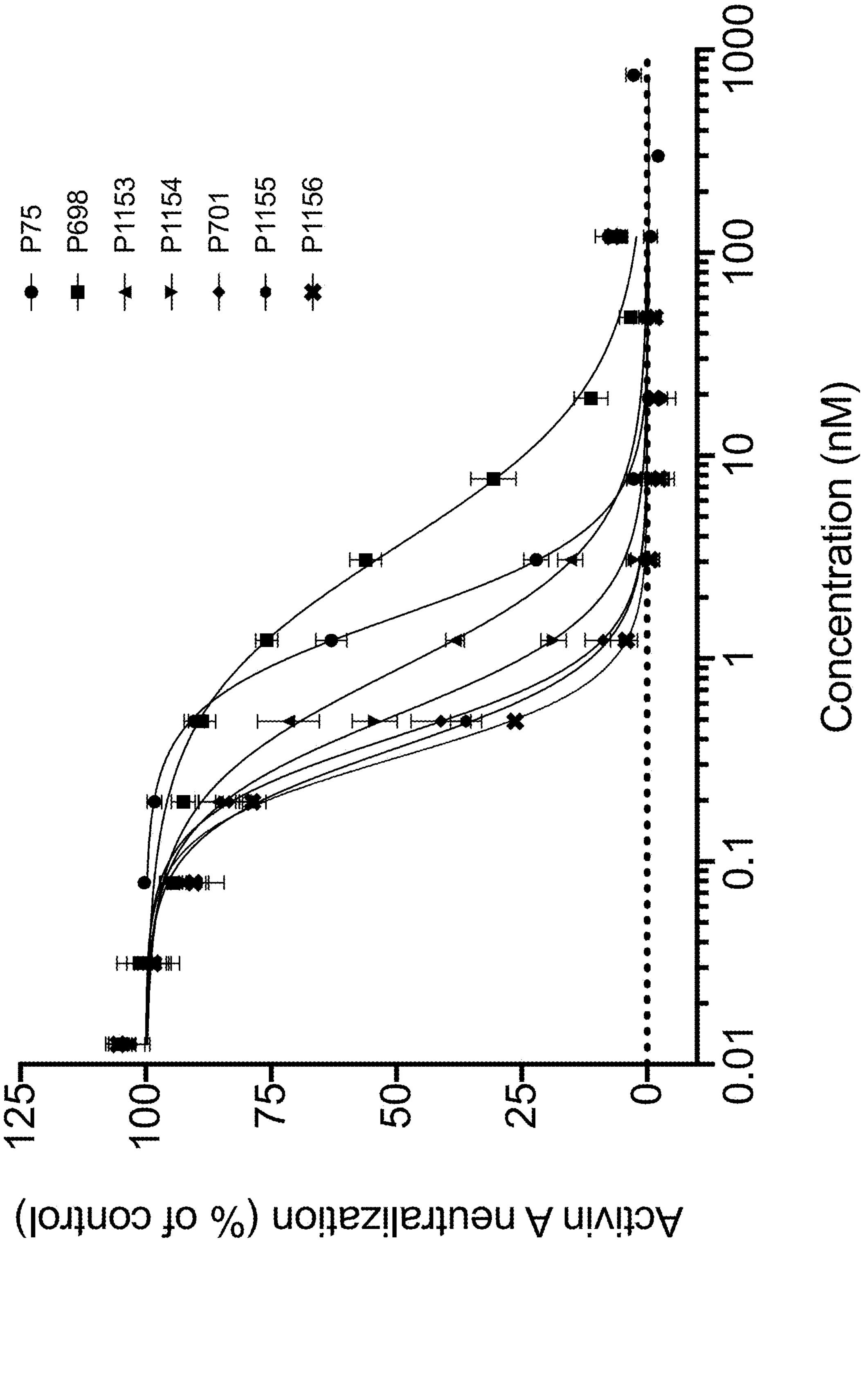
Figure 10W:
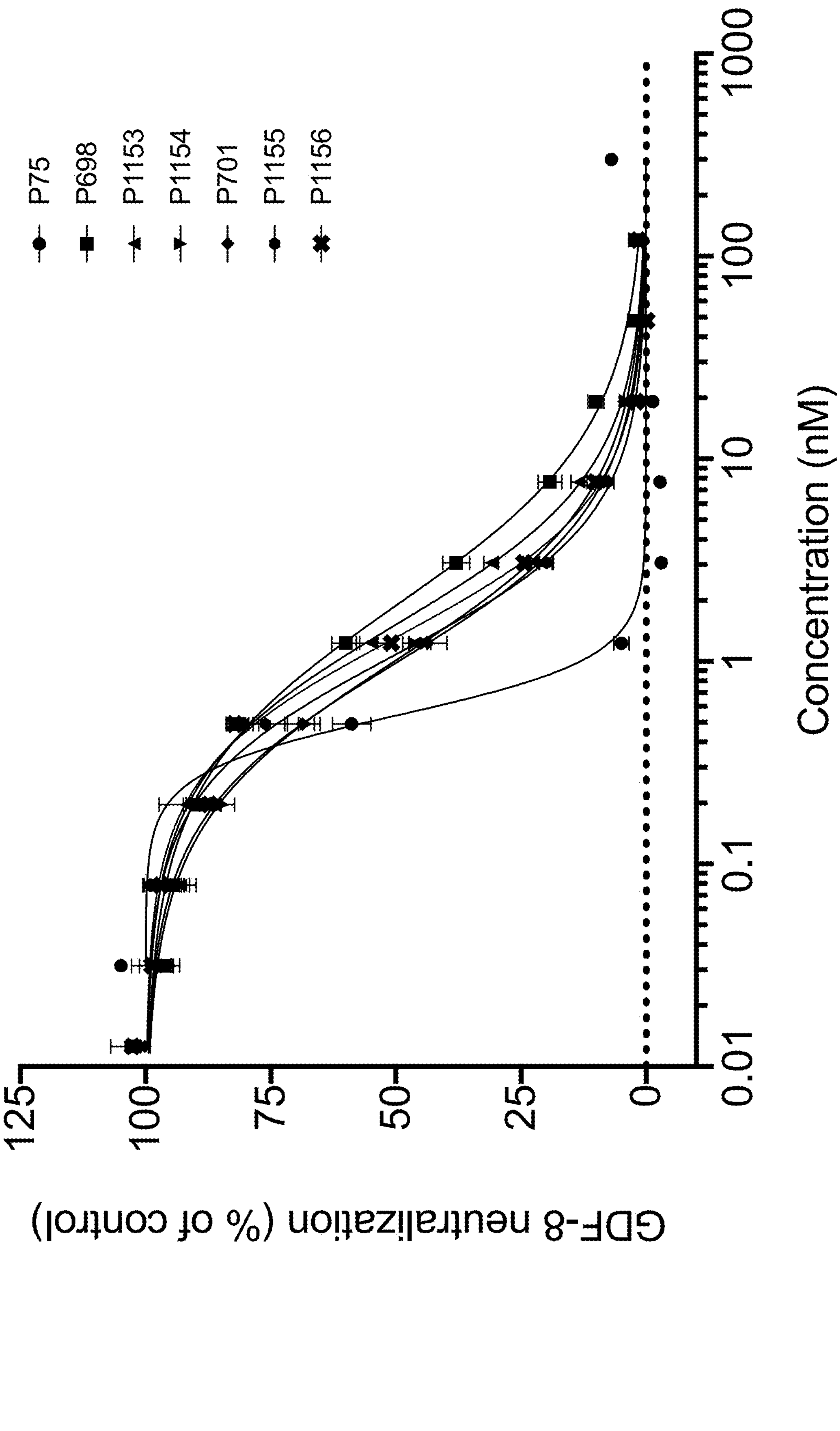
Figure 10X:
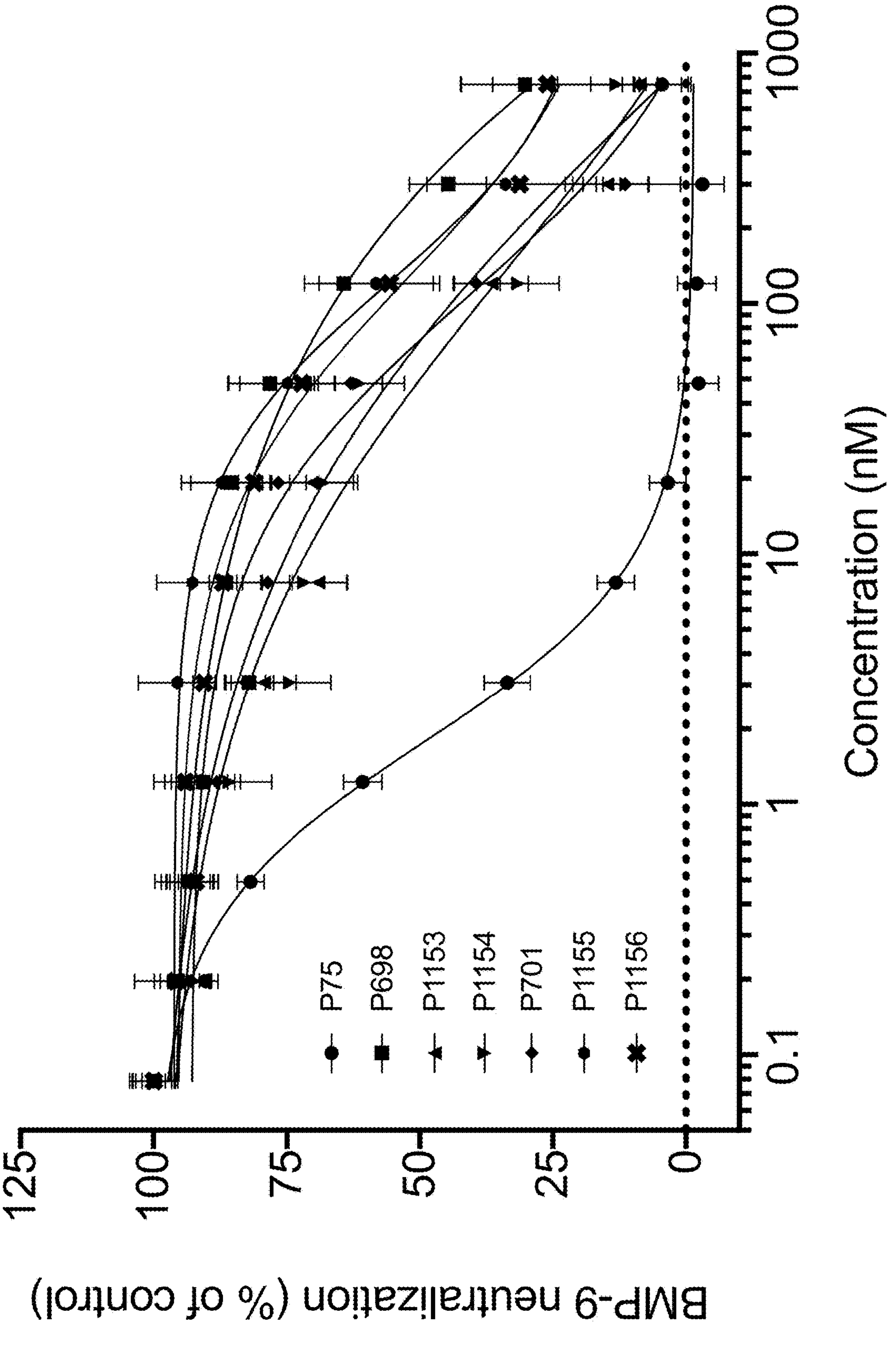

To further investigate the effects of lengthening the linker, other linker lengths were also tested for their effect on BMP-9 and BMP-10 potencies. In the context of the F to E substitution at position 58, increasing the linker length from 3 amino acids to 14, 19, or 39 amino acids demonstrated a moderate increase in potency on BMP-9 and BMP-10 (Table 10 and FIGS. 10Q-R). As mentioned above, this increase was considerably less than that seen in the context of the wild type ActRIIB ECD. In the context of the F to Q substitution at position 58, increasing the linker length had minimal effect on BMP-9 potency (Table 10 and FIG. 10U). In the context of the F to K substitution at position 58, increasing the linker length increased BMP-9 potency from 657 nM (P698) to 170 nM (P1153) (Table 10 and FIG. 10X).

The effects of additional amino acid substitutions at position 58 in the ActRIIB-ECD were also investigated in the BMP-reporter assays. In addition to the substitutions from F to E (P622), K (P701), and Q (P708) described above, substitutions from F to Y (P694), W (P715), D (P687), N (P1213), R (P1215) and H (P1217) were investigated in the context of a 14 amino acid linker. These substitutions all demonstrated a significant decrease in potency on BMP-9 (Table 10 and FIGS. 15B, 15D and 16B) compared to wild type ActRIIB ECD, as was observed with P622, P701, and P708 (F to E, K, or Q, respectively). These results demonstrate varying BMP-9 and BMP-10 potencies depending on the amino acid substitution at position 58, although a significant reduction in BMP-9 potency compared to wild-type was maintained in all instances.

Figure 15B:
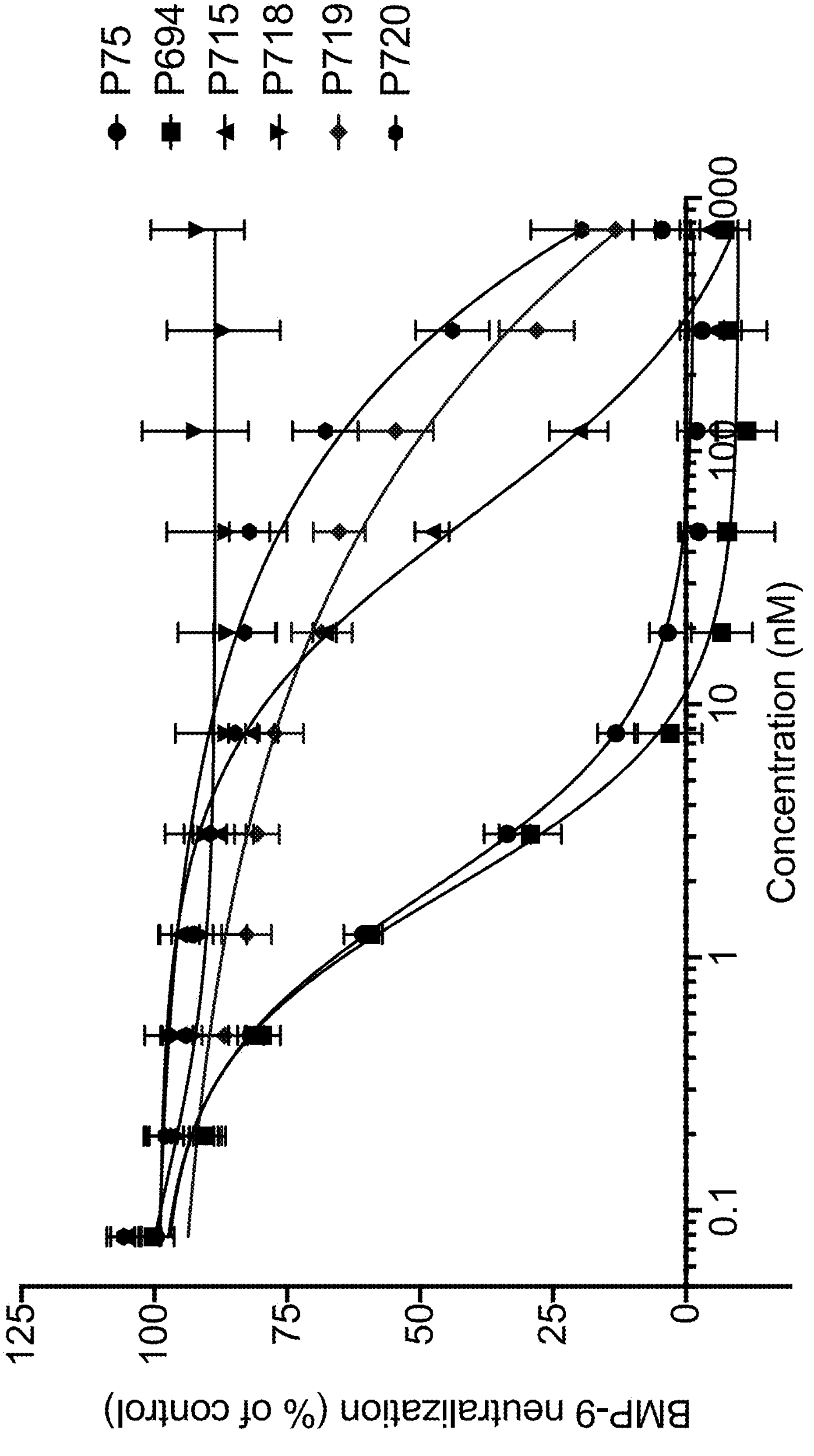
Figure 15D:
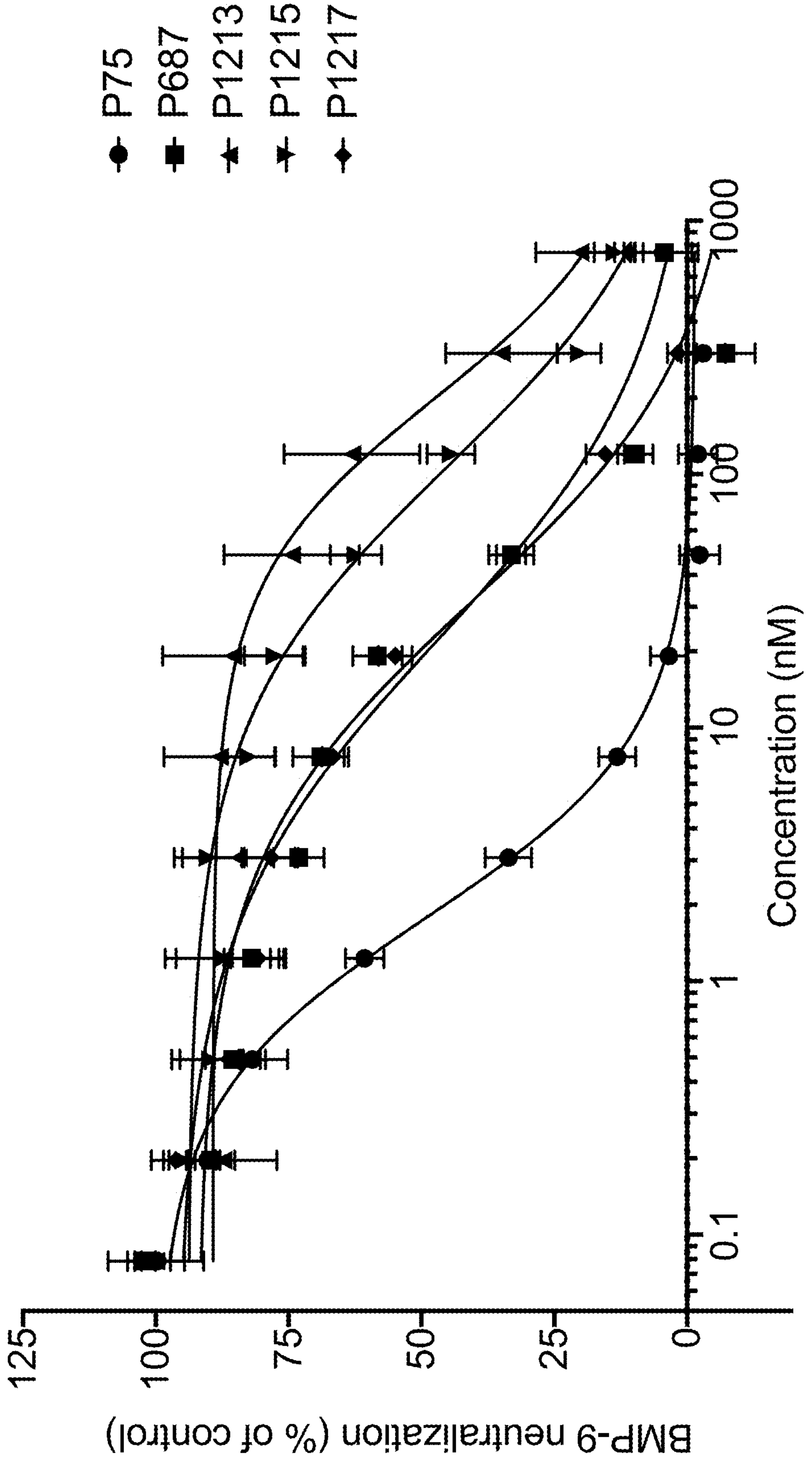

Finally, the effects of combining different mutations in the ActRIIB ECD were investigated (exemplary agents P441, P718, P719, and P720). IC50 values on BMP-9 were 362, >1,000, >100, and 914 nM for P441, P718, P719, and P720, respectively (FIGS. 15B-C). IC50 values on BMP-10 were 1.0, >1,000, 1.7, and 2.3 nM for P441, P718, P719, and P720, respectively (FIGS. 16B-C). These results demonstrate that, as for activin and GDF ligands, the changes in inhibition potency for BMP-9 and BMP-10 obtained by mutations at position 58 are sensitive to other mutations in the ActRIIB ECD.

Taken together, these results illustrate the different effects of various point mutations on the potency profile of the ActRIIB ECD. Some point mutations had no effect on inhibition potency for the ligands tested; some point mutations altered inhibition potency for some ligands but not others; and some point mutations altered inhibition potency for all TGFβ superfamily ligands tested. Of note, P121, P441, P622, P624, P666, P667, P687, P701, P708, P709, P719, P720, P1155, P1156, P1168, P1213, P1215, P1217, and P1218 showed significantly decreased neutralization of BMP-9 relative to P75 (wild-type ActRIIB ECD). As this decreased potency on BMP-9 is desirable to avoid toxicity associated with BMP-9 inhibition, the results suggest that such agents may be particularly useful therapeutically.

TABLE 10

IC50 values for representative ActRIIB-ECD polypeptide constructs for BMP-9 and BMP-10 neutralization.

| Ectodomain construct | BMP-9 Average IC50 (nM) | BMP-9 SEM | BMP-10 Average IC50 (nM) | BMP-10 SEM |
|---|---|---|---|---|
| P75 | 2.7 | 0.19 | 2.0 | 0.1 |
| P120 | >1,000 | — | >1,000 | — |
| P121 | 868 | 181 | 1.0 | 0.09 |
| P122 | 2.7 | 0.35 | 2.7 | 0.31 |
| P123 | 8.1 | 1.8 | 3.9 | 0.46 |
| P125 | >1,000 | — | >1,000 | — |
| P126 | >1,000 | — | >1,000 | — |
| P127 | >1,000 | — | >1,000 | — |
| P444 | 248 | 60 | 3.7 | 0.53 |
| P622 | 373 | 66 | 0.98 | 0.09 |
| P624 | 951 | 391 | 1.7 | 0.22 |
| P666 | 144 | 23 | 0.88 | 0.14 |
| P667 | 498 | 161 | 1.4 | 0.11 |
| P687 | 36 | 6.9 | 2.4 | 0.91 |
| P694 | 1.8 | 0.11 | 1.9 | 0.03 |
| P701 | 386 | 134 | 0.96 | 0.18 |
| P708 | 110 | 44 | 1.4 | 0.23 |
| P715 | 60 | 9.7 | 2.4 | 0.58 |
| P718 | >1,000 | — | >1,000 | — |
| P719 | >100 | — | 1.7 | 0.22 |
| P720 | 914 | 86 | 2.3 | 0.49 |
| P757 | 0.27 | 0.08 | 1.2 | 0.15 |
| P119 | 1.3 | 0.13 | 2.1 | 0.24 |
| P441 | 362 | 60 | 1.0 | 0.08 |
| P124 | 15.9 | 2.2 | 21 | 2.3 |
| P758 | 1.2 | 0.19 | 1.9* | — |
| P759 | >1,000* | — | >1,000* | — |
| P761 | 8.7 | 2.1 | 22 | 23 |
| P762 | >1,000 | — | >1,000 | — |
| P698 | 657 | 197 | ND | — |
| P709 | 58 | 2.6 | ND | — |
| P1153 | 170 | 70 | ND | — |
| P1154 | 210 | 142 | ND | — |
| P1155 | 134 | 16 | ND | — |
| P1156 | 127 | 11 | ND | — |
| P1168 | >100 | — | ND | — |
| P1213 | 192 | 41 | ND | — |
| P1215 | 91 | 25 | ND | — |
| P1217 | 23 | 0.65 | ND | — |
| P1218 | 101 | 10 | ND | — |
| P1219 | 59 | 8.2 | ND | — |
| P1220 | 3 | 3.4 | ND | — |

SEM: standard error of the mean;

>1,000: no detectable neutralization; agents were tested in at least two independent experiments (except for IC50 values marked with *, which indicates testing in only one experiment);

ND: not determined.

In summary, our results show that certain point mutations in the ActRIIB-ECD in the context of particular linker lengths led to significant increases in inhibition potency for certain TGFβ 3 superfamily ligands, particularly those involved in PAH pathophysiology, namely activin A, GDF-8, and GDF-11.

The results also show that the single point mutation in P121, P698, and P1218 resulted in higher neutralization potency on activin A, GDF-8, and GDF-11 relative to wild type ActRIIA (P444, sotatercept). Specifically, the P121 single point mutation resulted in an inhibition potency 2.1-, 11-, and 4.0-fold higher on activin A, GDF-8, and GDF-11 relative to P444. The P698 single point mutation resulted in an inhibition potency 1.5-fold higher on GDF-8 relative to P444. The P1218 single point mutation resulted in an inhibition potency 2.5- and 1.5-fold higher on activin A and GDF-8 relative to P444. Importantly, the single point mutation in P121, P687, P698, P1213, P1215, P1217, and P1218 also led to a significant decrease in inhibition potency on BMP-9 relative to non-mutated (wild type) ActRIIB ECD. This resulted in P121 and P698 having lower neutralization potencies on BMP-9 relative to P444, i.e., the BMP-9 inhibition potency was 3.5- and 2.6-fold lower for P121 and P698, respectively, relative to P444. Taken together, these results suggest a potentially broader therapeutic window for these exemplary agents compared to P444 (sotatercept), i.e., they may have a better safety profile due to their lower potency on BMP-9 while having superior therapeutic efficacy for the treatment of certain diseases due to their higher potency on activin A, GDF-8 and/or GDF-11.

Furthermore, increasing the length of the linker between the ActRIIB ECD and the Fc domain increased neutralization potency on certain ligands. Surprisingly, P622 and P1168 (14 amino acid linkers) exhibited inhibition potencies that were increased by 4.0-fold and 4.9-fold respectively on activin A, and 2.3-fold on activin B, relative to P624 (3 amino acid linker) (Table 9 and FIG. 10C). Another exemplary agent, P1156 (39 amino acid linker), exhibited an inhibition potency that was increased by 13- and 1.6-fold on activin A and GDF-8, relative to P698 (3 amino acid linker). Finally, P709 (39 amino acid linker) exhibited an inhibition potency that was increased by 2.6- and 2.8-fold on activin A and GDF-8, relative to P1218 (6 amino acid linker). Since these pairs of exemplary agents differ only in the linker length, these results underscore the surprising impact of linker length on potency for particular ligands in the context of certain mutations in the ActRIIB ECD.

Notably, the potency results also demonstrate that, although increasing linker length could be beneficial in increasing potency on selected pathological ligands, this approach was not sufficient on its own to obtain an agent with a desirable therapeutic window, i.e. an agent with significantly reduced potency on BMP-9 as well as high potency on pathological ligands. This was achieved only by combining specific mutations in the ActRIIB ECD (e.g., F58E, as in P622, P624, P666, P667, P1168; F58K, as in P698, P701, P1153, P1154, P1155, P1156; or F58Q, as in P708, P709, P1218, P1219, P1220) with a longer linker length (e.g., at least 10 amino acids). This point is illustrated by comparing P622, P701, and P708 to P757 (the wild type ectodomain), which all have a 14 amino acid linker. Although P757 had high potency on the pathological ligands, it also had the highest potency on BMP-9 of any construct tested. Accordingly, P757 is expected to promote toxicity associated with BMP-9 inhibition.

Experimental Procedures for Example 1

Production, Purification, and Characterization of ActRIIB-ECD Fusion Proteins that Neutralize TGFβ Superfamily Ligands.

All constructs included a secretion signal sequence (SEQ ID NO: 1) at the N-terminus when expressed. The complementary cDNAs coding for constructs were prepared synthetically (Genscript, Piscataway, NJ). The cDNAs were cloned into the EcoR1 (5' end) and BamH1 (3' end) of the pTT5 mammalian expression plasmid vector (Durocher et al., 2002). The signal peptide is cleaved off in the cells during expression and was not included in the purified fusion proteins. Representative cDNA sequences used for expression of fusion proteins are summarized below.

TABLE 11

| Fusion protein cDNA sequences | |
|---|---|
| cDNA SEQ ID: | Fusion protein |
| 256 | P75 |
| 257 | P757 |
| 258 | P444 |
| 259 | P119 |
| 260 | P120 |
| 261 | P121 |
| 262 | P122 |
| 263 | P123 |
| 264 | P124 |
| 265 | P125 |
| 266 | P126 |
| 267 | P127 |
| 268 | P622 |
| 269 | P624 |
| 270 | P625 |
| 271 | P626 |
| 272 | P666 |
| 273 | P667 |
| 274 | P671 |
| 275 | P672 |
| 276 | P673 |
| 277 | P674 |
| 278 | P683 |
| 279 | P684 |
| 280 | P685 |
| 281 | P686 |
| 282 | P687 |
| 283 | P688 |
| 284 | P689 |
| 285 | P690 |
| 286 | P691 |
| 287 | P692 |
| 288 | P693 |
| 289 | P694 |
| 290 | P695 |
| 291 | P696 |
| 292 | P697 |
| 293 | P698 |
| 294 | P699 |
| 295 | P700 |
| 296 | P701 |
| 297 | P702 |
| 298 | P703 |
| 299 | P704 |
| 300 | P705 |
| 301 | P706 |
| 302 | P707 |
| 303 | P708 |
| 304 | P709 |
| 305 | P710 |
| 306 | P711 |
| 307 | P712 |
| 308 | P713 |
| 309 | P714 |
| 310 | P715 |
| 311 | P716 |
| 312 | P717 |
| 313 | P758 |
| 314 | P1153 |
| 315 | P1154 |
| 316 | P1155 |
| 317 | P1156 |
| 318 | P1163 |
| 319 | P1164 |
| 320 | P1168 |
| 321 | P1213 |
| 322 | P1215 |
| 323 | P1217 |
| 324 | P1218 |
| 325 | P1219 |
| 326 | P1220 |
| 327 | P718 |
| 328 | P719 |
| 329 | P720 |
| 330 | P441 |
| 334 | P759 |

TABLE 11-continued

| Fusion protein cDNA sequences | |
|---|---|
| cDNA SEQ ID: | Fusion protein |
| 342 | P761 |
| 343 | P762 |
| 344 | P670 |

TABLE 12

Production and purification details for ActRIIB-ECD polypeptide constructs.

| Ectodomain construct | SEQ ID NO: | Transfection duration (days) | Titer (mg/L) | % Monomer |
|---|---|---|---|---|
| P75 | 49 | 8 | 179 | 85 |
| P120 | 51 | 4 | 52 | 78 |
| P121 | 52 | 4 | 56 | 96 |
| P122 | 53 | 4 | 33 | 82 |
| P123 | 54 | 5 | 57 | 73 |
| P125 | 56 | 5 | 70 | 81 |
| P126 | 57 | 5 | 70 | 85 |
| P127 | 58 | 5 | 77 | 86 |
| P444 | 50 | 6 | 117 | 99 |
| P622 | 59 | 4 | 273 | 95 |
| P624 | 60 | 4 | 124 | 99 |
| P666 | 63 | 4 | 261 | 98 |
| P667 | 64 | 4 | 322 | 99 |
| P687 | 73 | 4 | 342 | 88 |
| P694 | 80 | 4 | 376 | 91 |
| P701 | 87 | 4 | 385 | 97 |
| P708 | 94 | 4 | 295 | 98 |
| P715 | 101 | 4 | 224 | 91 |
| P718 | 147 | 4 | 221 | 96 |
| P719 | 148 | 4 | 289 | 96 |
| P720 | 149 | 4 | 237 | 94 |
| P757 | 156 | 4 | 219 | 93 |

All proteins expressed efficiently in CHO and/or 293 cells and purification of each using Protein A affinity chromatography was similar. Although many of the properties were very similar between variants, the potential for aggregation, as measured by SEC-HPLC, and which is indicative of improper folding, revealed some distinctions. For the benchmark proteins (i.e., wild type ActRIIA-ECD-Fc (P444) and wild type ActRIIB-ECD-Fc (P75)), the purity (i.e., percent monomer content) was 99% and 85% monomer content for P444 and P75, respectively. Several exemplary agents had aggregate levels comparable to those of P75, namely P122, P125, P126, P127, and P687 with 82, 81, 85, 86, and 88% monomer content, respectively. Other agents displayed a slightly lower monomer content compared to P75 as exemplified by P120 and P123 with 78 and 73% monomer content, respectively. Strikingly, several variants, P121, P622, P624, P666, P667, P694, P701, P708, P715, P718, P719, and P720 which all contain a mutation at the same position in the ActRIIB-ECD compared to P75, showed a significantly higher monomer content, with 96, 95, 99, 98, 99, 91, 97, 98, 91, 96, 96, and 94% monomer content, respectively.

Figure 1A:
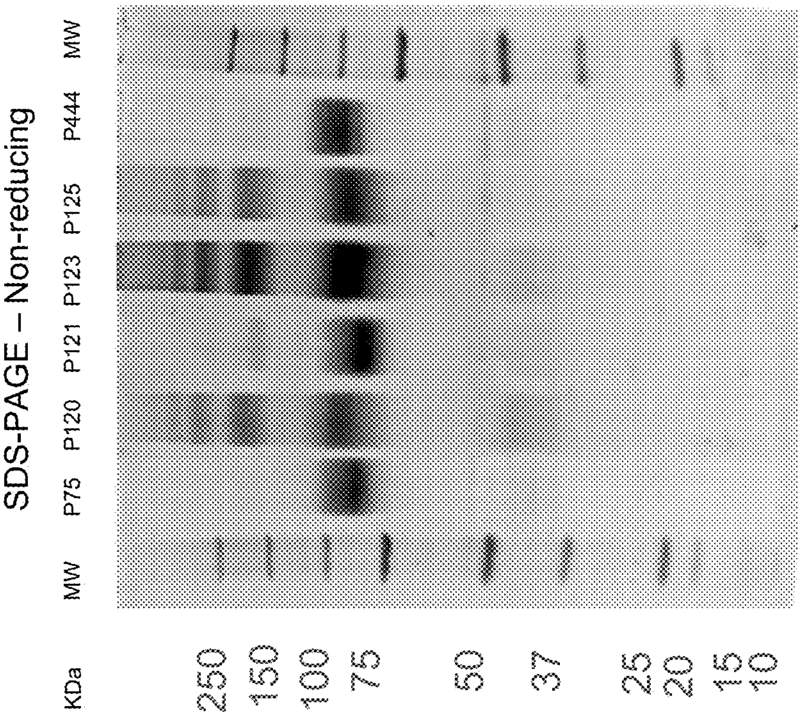

FIGS. 1A and 1B show polyacrylamide gel electrophoresis analysis of exemplary purified Proteins (P) 120, 121, 123, and 125 (see the lanes indicated as P120, P121, P123, and P125, respectively), under both non-reducing (FIG. 1A) and reducing (FIG. 1B) conditions. The observed molecular weight and purity of each protein were as expected and the disulphide-bonded homodimeric nature of the proteins was confirmed by the difference in size under reducing vs. non-reducing conditions. In line with the SEC-HPLC results some agents, for example P120 and P123, showed high molecular weight bands that likely represent aggregation. Conversely, other agents had very low high molecular weight bands.

These results demonstrate that point mutations in the ActRIIB ectodomain had unpredictable and unexpected consequences on the manufacturability profile of the construct. In particular, P121, P622, P624, P666, and P667 (containing the ActRIIB-ECD variant in SEQ ID NO: 5) showed a superior monomer content compared to the Fc fusion containing the wild type receptor ectodomain (P75).

Analysis of ActRIIB-ECD Fusion Proteins that Neutralize TGFβ Superfamily Ligands in Cell-Based Assays.

Characterization of the activin A, activin B, GDF-8, and GDF-11 inhibition potency (IC50) of the fusion proteins was performed using a cell-based reporter assay. TGFβ-reporter HEK293 cells were obtained from InvivoGen (San Diego, CA, cat. no. hkb-tgfb) and were maintained following the manufacturer's instructions. Briefly, cells were grown in high-glucose DMEM, containing 10% heat-inactivated FBS, 30 μg/mL blasticidin, 250 μg/mL hygromycin B, and 100 μg/mL zeocin (hereafter, "growth medium"). Once the cells reached 70-80% confluence, they were detached in growth medium by gently tapping on the flask. For all assays, cells were seeded in 96-well plates at a density of 20,000 cells per well in growth medium. Cells were left to attach for 10 minutes at room temperature (RT) prior to being transferred to a 37° C. incubator (5% CO2) overnight. The next day, treatments were prepared by combining the appropriate concentration of agent with activin A, activin B, GDF-8, or GDF-11 for 30 min at RT (shaking at 150 rpm). Treatments were conducted in high-glucose DMEM (serum-free and with no selection agents), and the final concentration of cytokine (ligand) was 0.3 nM. Growth medium was removed from the culture plates, and cells were treated with the appropriate mixes of fusion protein and cytokine. Treatment duration was for 18-22 h at 37° C. (5% CO2). All treatments were performed in technical duplicates and at least two independent experiments were conducted for each cytokine. At the end of the treatment period, supernatants were transferred to anew plate, and centrifuged at 300 RPM for 3 min. Forty μL of supernatant from each condition was transferred to a new plate, into which 180 μL of Quanti-Blue reagent (InvivoGen, cat. no. rep-qbs) was added. Quanti-Blue reagent was prepared following the manufacturer's instructions. Samples were incubated for 45 min at 37° C. At the end of the incubation, absorbance was read at 650 nm. The data were plotted in GraphPad Prism, which was used to calculate IC50 values as a non-linear regression.

Characterization of the BMP-9 and BMP-10 inhibition potency (IC50) of the fusion proteins was performed using a second cell-based reporter assay. Human hepatic HepG2 cells were transfected with a SEAP-encoding plasmid, in which SEAP expression is under the control of the murine Id1 promoter. A stable pool was generated from this transfection. Cells were grown in EMEM, containing 10% heat-inactivated FBS and 200 ug/mL zeocin (hereafter, "HepG2 growth medium"). Once cells reached 70% confluence, they were washed with PBS and detached using 0.25% trypsin. For all assays, cells were seeded in 96-well plates at a confluence of 100,000 cells per well in HepG2 growth medium. Cells were left to attach for 10 minutes at RT prior to being transferred to a 37° C. incubator (5% CO2) overnight. The next day, treatments were prepared in EMEM (2.5% heat-inactivated FBS and with no selection agents) by combining the appropriate concentration of agent with BMP-9 or BMP-10 for 30 min at RT (shaking at 150 rpm). Treatments were conducted in EMEM (2.5% heat-inactivated FBS and with no selection agents), and the final concentration of BMP-9 and BMP-10 was 2 ng/mL and 40 ng/mL, respectively. HepG2 growth medium was removed from the culture plates, and cells were treated with the appropriate mixes of fusion protein and cytokine. Treatment duration was for 22-24 h at 37° C. (5% CO2). All treatments were performed in technical duplicates and at least two independent experiments were conducted for each cytokine. At the end of the treatment period, supernatants were transferred to a new plate, and centrifuged at 300 RPM for 3 min. Forty μL of supernatant from each condition was transferred to a new plate, onto which 180 μL of Quanti-Blue reagent was added. Quanti-Blue reagent was prepared following the manufacturer's instructions. Samples were incubated for 5 h with Quanti-Blue reagent at 37° C. At the end of the incubation, absorbance was read at 650 nm. The data were plotted in GraphPad Prism, which was used to calculate IC50 values as a non-linear regression.

Example 2: ActRIIB-ECD Polypeptide Constructs with Improved Pharmacokinetic (PK) Properties The PK properties of selected TGFβ superfamily ligand binding and neutralization agents were examined to determine if mutations in the ActRIIB ECD could have an impact on exposure in vivo. An exemplary agent, P121, was injected intraperitoneally in Wild Type (WT) mice at a dose of 10 mg/kg or 50 mg/kg, and blood was collected at 3 hours and 96 hours post-injection for serum preparation. For comparison, the benchmark agent wild type ActRIIB-ECD-Fc (P75) was injected in a second group of WT mice. The concentration of each protein in serum was determined using an ELISA-based method described as follows. A 96-well plate was coated overnight at 4° C. with a 100 μL/well solution of an anti-human IgG antibody (Sigma #12136) at a dilution of 1/6,000 in a carbonate-bicarbonate buffer. After washing three times with buffer, 300 μL of blocking buffer (1% BSA in PBS) was added to each well and the plate was incubated for 1 hour at RT. A standard curve for each agent was prepared by preparing a 900 ng/ml stock of the agent from which 12 serial dilutions (3-fold) were prepared. 100 μL of each dilution was added to the 96-well plate in duplicate. For the serum samples, these were thawed on ice, diluted appropriately in assay diluent (0.5% BSA, 0.05% Tween-20 in PBS), and 100 μL of each dilution was added to the 96-well plate in duplicate. After a 1.5-hour incubation at RT, the plate was washed with assay diluent three times. For detection of bound agent, a 100 μL/well solution of a second anti-human IgG antibody conjugated to biotin (Thermo A18821) at a dilution of 1/6,000 in assay diluent was added to each well and incubated for 1 hour at RT. After washing three times, binding was revealed using streptavidin-HRP using a standard calorimetric method.

Figure 17A:
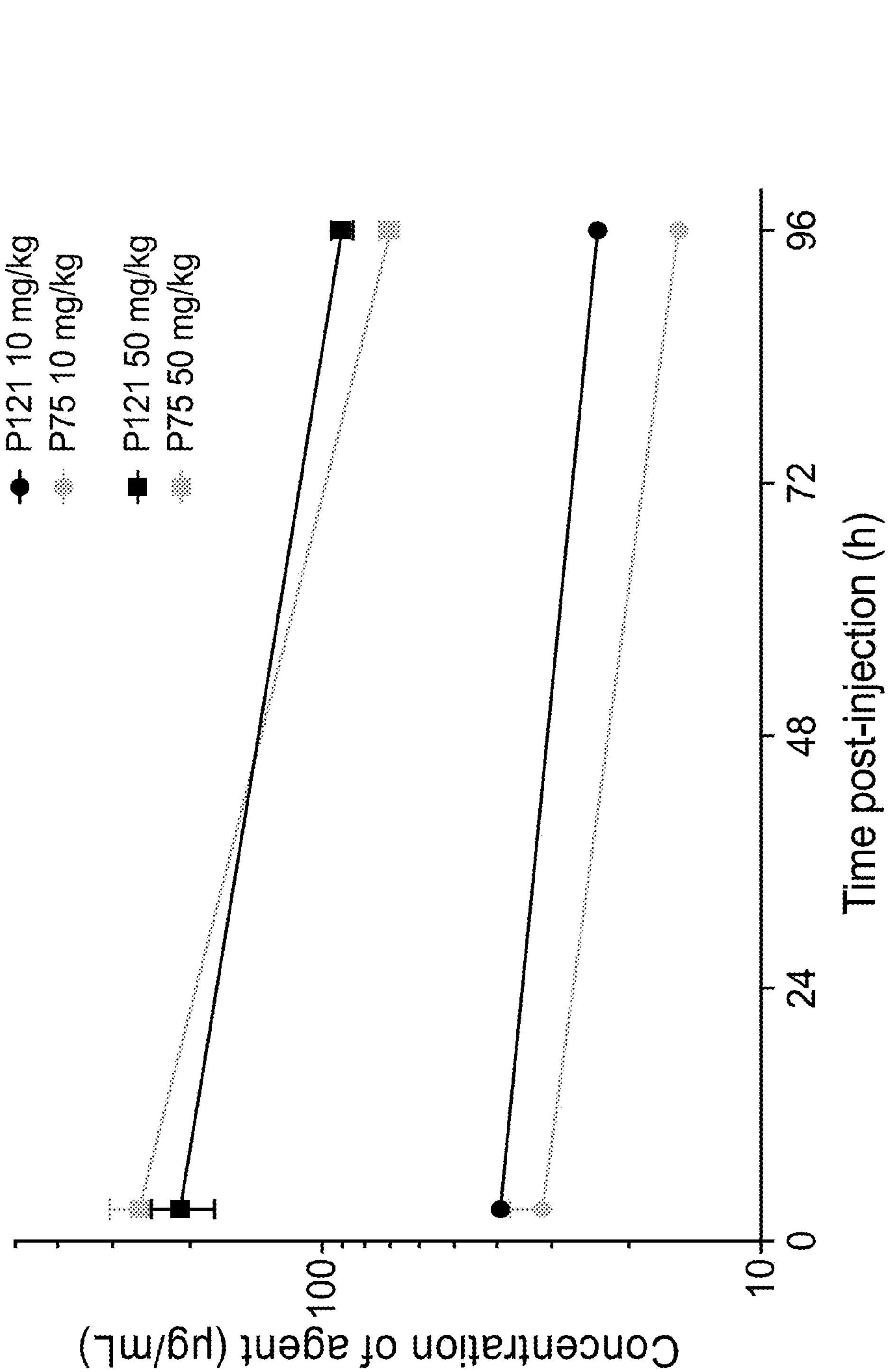
FIG. 17A-FIG. 17B show serum concentration and exposure vs. dose level of P622 and P75.

The results are displayed in FIG. 17A and show that the average serum concentrations of both P75 and P121 following the 10 mg/kg injection were comparable at the 3-hour time point. Similarly, the concentrations of the agents following the 50 mg/kg injection were also comparable after 3 hours. At 96 hours following the injection, a marked difference in the serum concentrations between the agents was observed. For example, the decrease in concentration of P75 administered at 10 mg/kg from the 3 hour to the 96 hour timepoint was 51.1% whereas the concentration of P121 decreased by only 39.9%. A similar difference in the decrease between P75 and P121 was also seen following the 50 mg/kg injections where P75 decreased by 73.3% compared to 57.2% for P121.

In another study, male C57BL/6 WT mice aged between 8-10 weeks were weighed and randomly assigned to either vehicle (n=6) or a test agent treatment group (P622 or P75) of a given dose level (1, 3, 10, 25, or 50 mg/kg; n=6 per dose per test agent). Mice were then treated subcutaneously twice weekly for 21 days, corresponding to days 0, 3, 7, 10, 14, 17, and 21. On each treatment day, body weights were recorded, and the dose was adjusted accordingly. In-life whole blood samples were collected from the facial vein at the specified time points and processed to serum. Test agent serum concentrations were determined as outlined above.

Figure 17B:
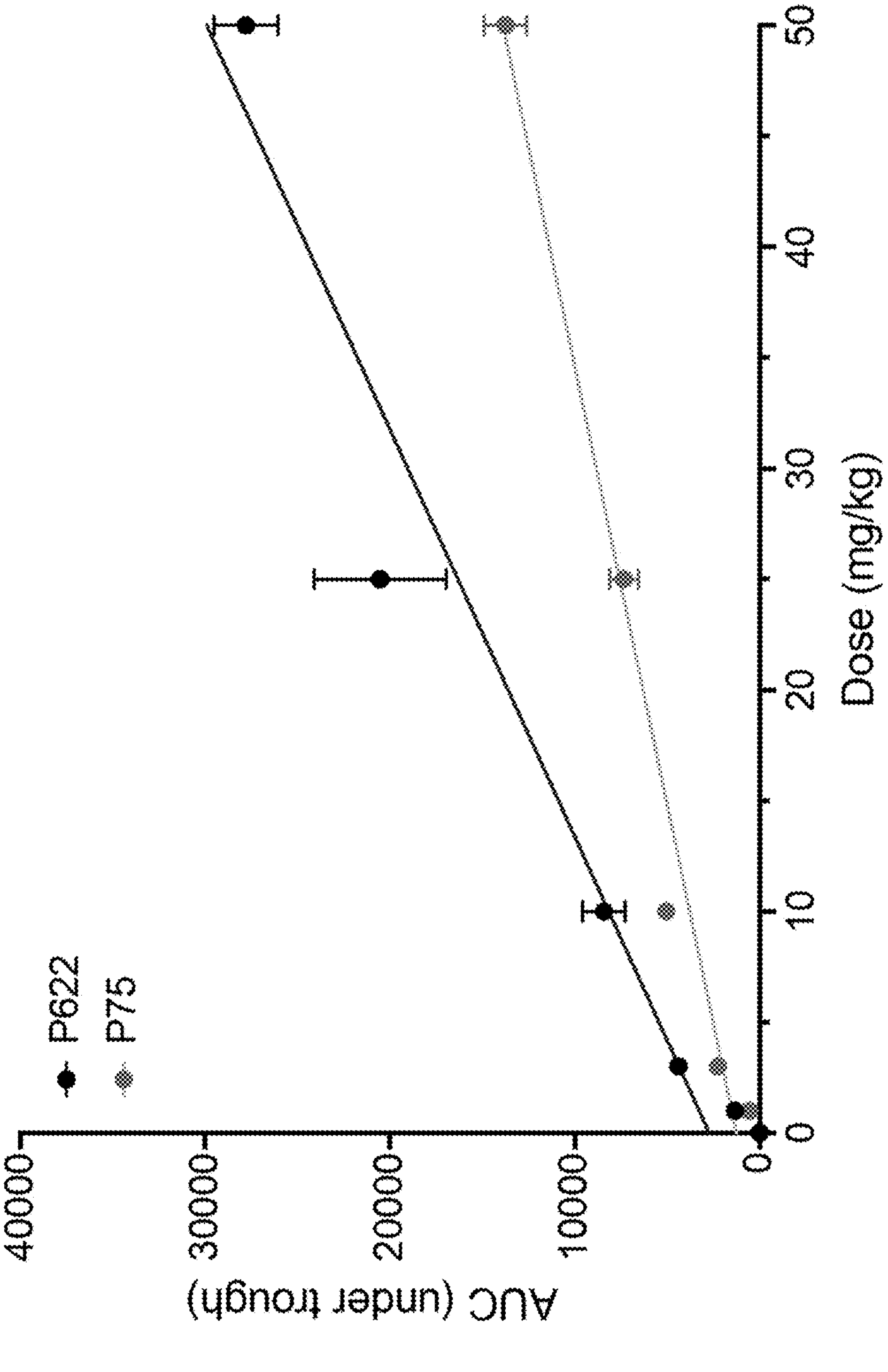

The serum concentrations of P622 and P75 were measured over the course of three weeks (at 3 h post first injection, just prior to each subsequent injection, and at end of life). The estimated exposure was calculated from the PK profiles for each test agent and dose level over the course of the study. Since the agent concentration was measured at the end of each dosing cycle, i.e., at the minimum test agent concentration just prior to the next injection (trough concentration), the exposure estimate is referred to as AUC (under trough). As shown in FIG. 17B, the exposure of P622 was higher than that of P75 at all dose levels, i.e., the AUC (under trough) was an average of 2-fold higher for P622 than for P75. These results indicate that the wild type hActRIIB-ECD-Fc (P75) has a higher clearance and/or lower bioavailability in mice than P622. These results show that, in contrast to previous mutated ActRIIB ectodomains that demonstrate either the same or worse PK properties compared to wild type (see Attie et al., 2014; Tao et al., 2019), the mutated ectodomain in exemplary agent P622 unexpectedly resulted in improved exposure.

These results demonstrate that in addition to having an improved therapeutic efficacy profile (see Examples above), agents such as those exemplified by P121 and P622 harboring a single amino acid mutation in the ActRIIB ECD exhibited improved PK properties in vivo.

Example 3: ActRIIB-ECD Polypeptide Constructs can Increase Body Weight and Muscle Mass Selected agents were tested to examine their effect on body weight and muscle mass, and to investigate how they compared to ActRIIB-Fc (P75) in vivo. Two exemplary agents, P622 and P624, were injected intraperitoneally twice weekly for two weeks in WT C57BL/6 female mice (8-10 weeks) at doses of 4 mg/kg or 16 mg/kg. The control agent, P75, was injected similarly at 16 mg/kg only. Body weights were recorded in all animals twice weekly, and five different muscle groups were collected at the end of the study (skeletal muscle: gastrocnemius, quadriceps, pectoralis, and triceps; and cardiac muscle: heart).

Figure 18:
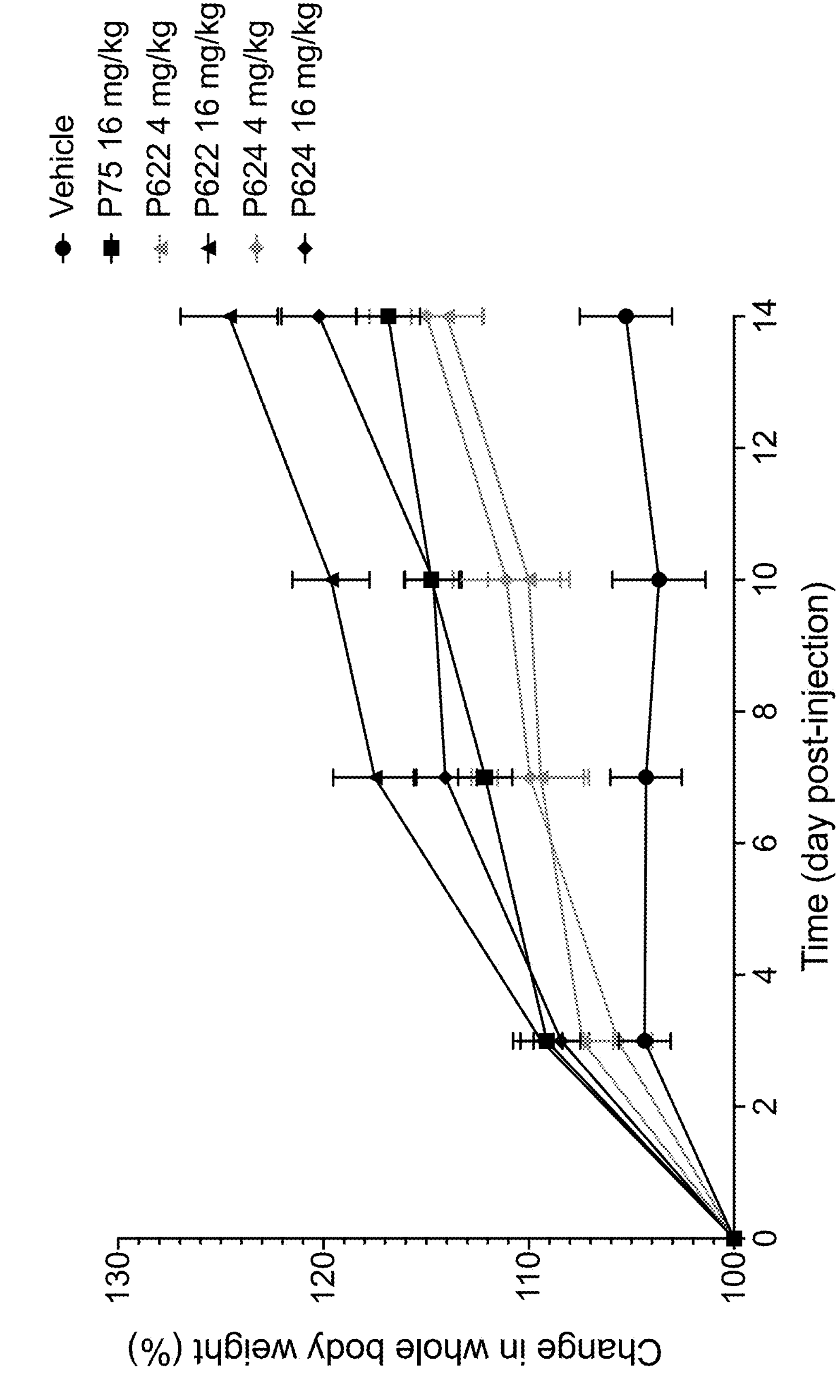
FIG. 18 shows the increase in body weights in C57BL/6 mice (n=6-7 per group) injected with vehicle, P75 (16 mg/kg), P622 (4 and 16 mg/kg), and P624 (4 and 16 mg/kg) twice weekly for two weeks. Error bars indicate standard error of the mean (SEM).

At 4 mg/kg, P622 and P624 displayed similar increases in whole body weight compared to the vehicle treated mice (FIG. 18). At 16 mg/kg, P624 caused an additional increase in whole body weight (compared to P624 at 4 mg/kg) and this increase was similar to that caused by P75 at 16 mg/kg. In contrast, P622 at 16 mg/kg throughout the entire duration of the study consistently induced a greater increase in body weight compared to all other groups. These data highlight that the improved potency profile of P622 (long linker) relative to P624 (short linker) translated to better in vivo efficacy with regards to body weight.

The effect on muscle mass was also examined in this study. When administered at 4 mg/kg, both P622 and P624 produced similar increases in all skeletal muscle groups analyzed (FIG. 19). These increases were only slightly lower compared to P75 administered at 16 mg/kg demonstrating that P622 and P624 had almost the same effect on muscle growth even if they were administered at a lower dose level compared to wild type ActRIIB-Fc (P75). At 16 mg/kg, P624 caused only a small additional increase in skeletal muscle growth compared to when it was injected at 4 mg/kg. In contrast, P622 induced a very high and significant additional increase across all muscle groups at 16 mg/kg compared to 4 mg/kg, demonstrating its superior efficacy to P624. These data demonstrate the beneficial impact of increased linker length in P622 compared to P624 and show that the potency profile of P624 is not sufficient to maximally induce muscle hypertrophy. These results are especially surprising considering that GDF-8 is considered to be a major regulator of muscle mass in rodents, and that the potency of P622 and P624 on GDF-8 is approximately the same.

Figure 19B:
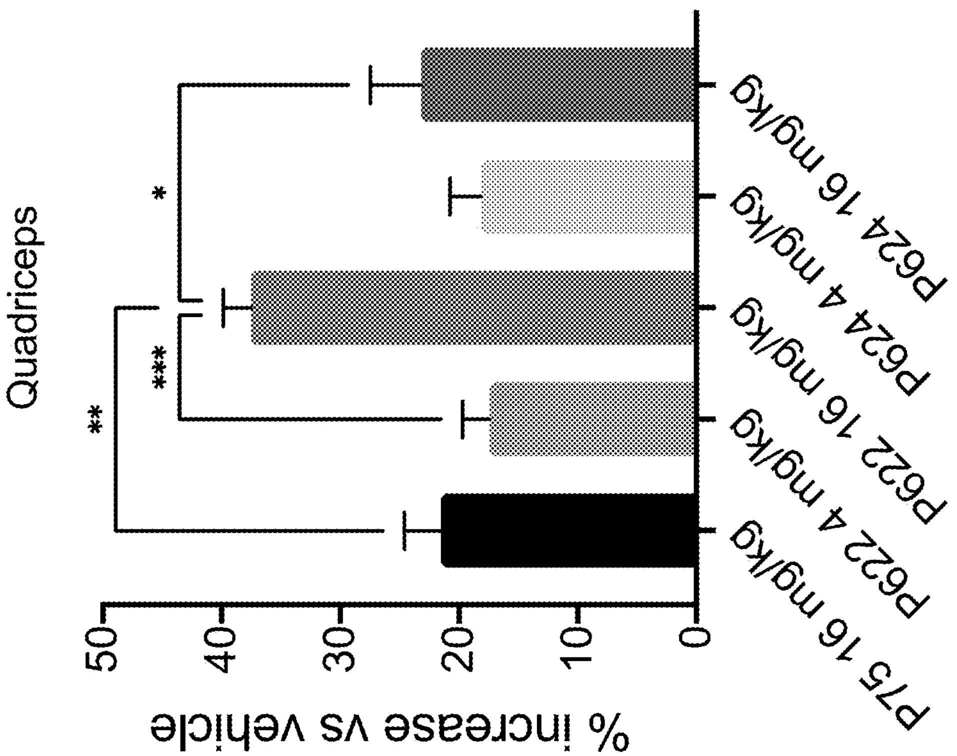
FIG. 19A-FIG. 19F shows the increase in muscle weight and gene expression changes in C57BL/6 female mice (n=6-7 per group; 8-10 weeks of age) injected with P75 (16 mg/kg), P622 (4 and 16 mg/kg), and P624 (4 and 16 mg/kg) twice weekly for two weeks.
Figure 19A:
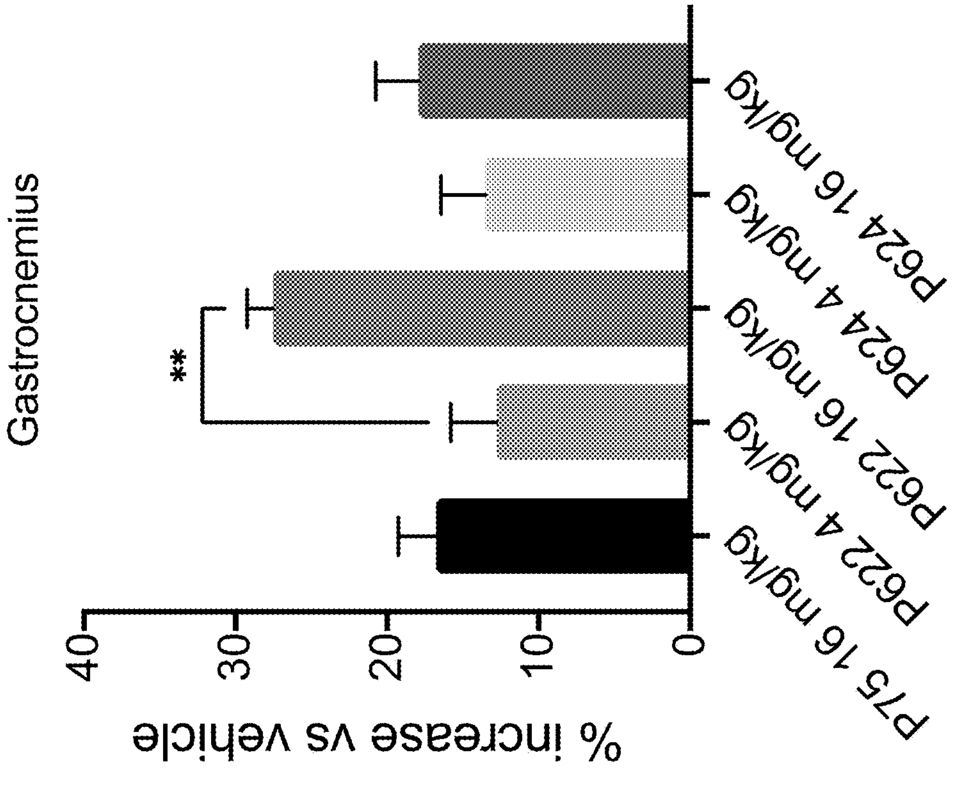
Figure 19C:
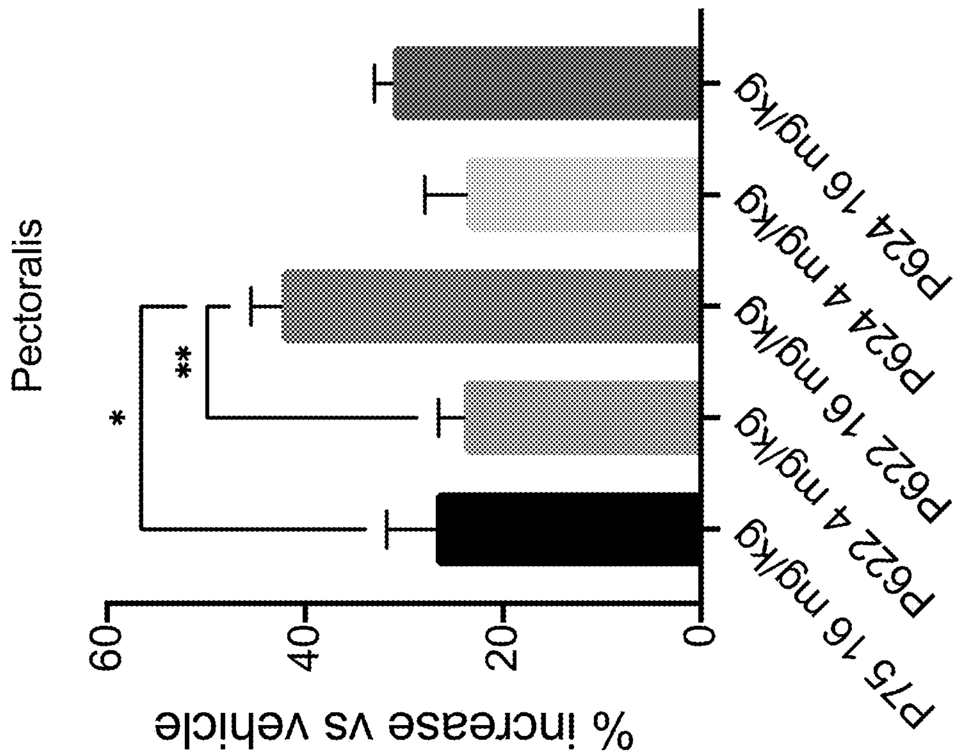
Figure 19D:
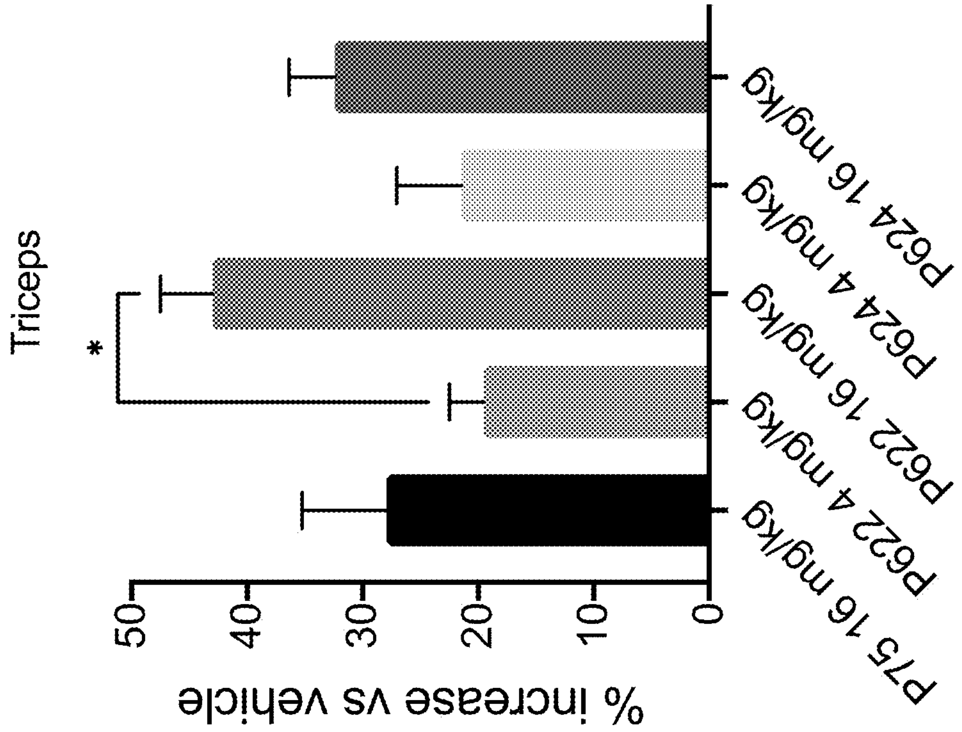
Figure 19E:
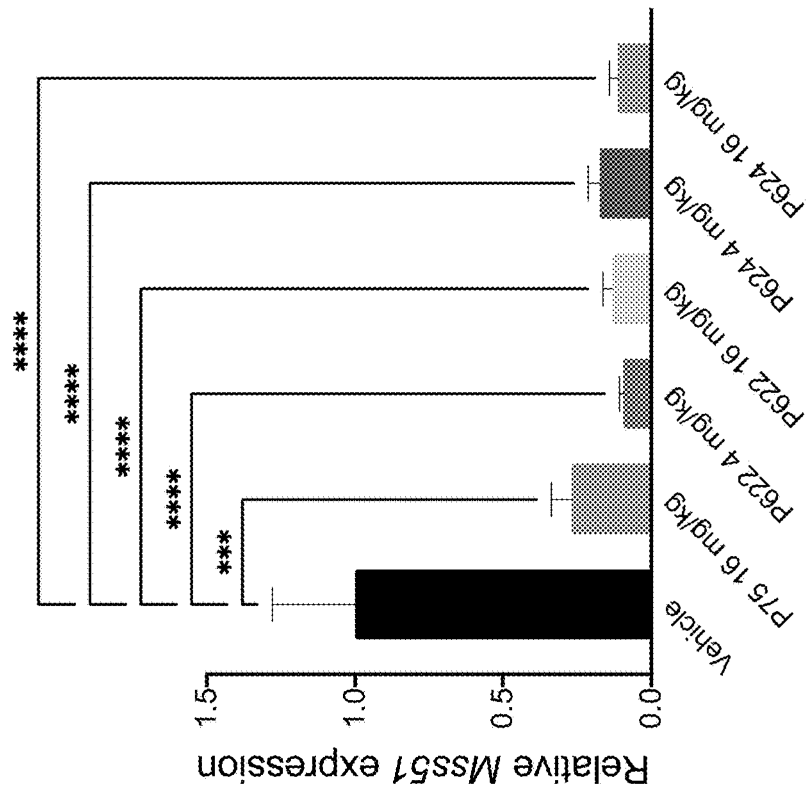
Figure 19F:
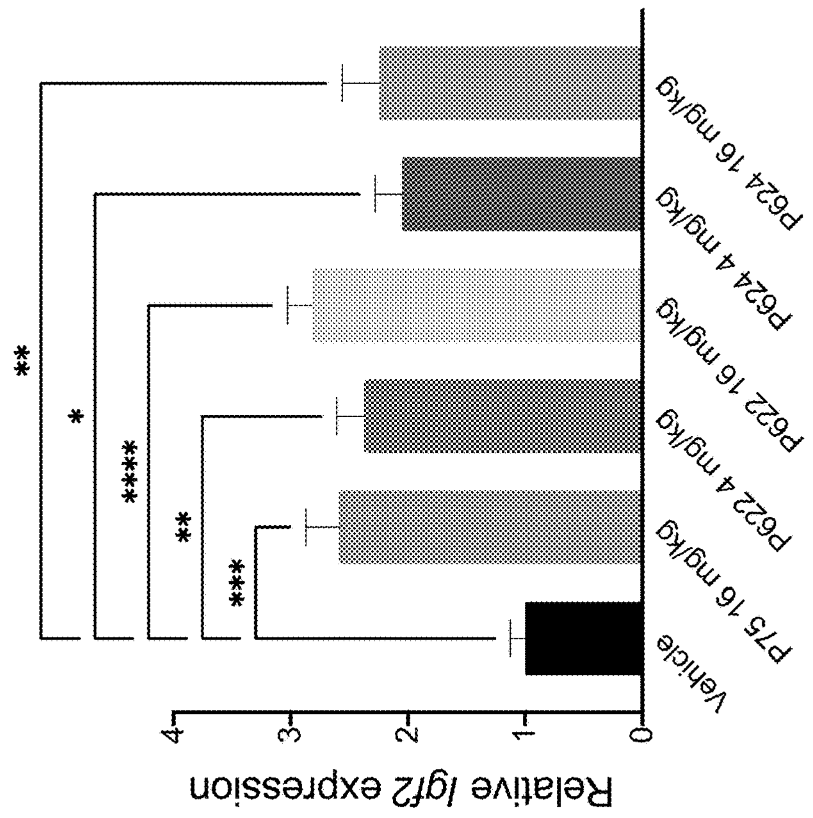

The effects of the exemplary agents on muscle gene expression were also investigated. In the quadriceps, P75, P622, and P624 at all doses (4 or 16 mg/kg) significantly decreased Mss51 mRNA levels (FIG. 19E), and significantly increased Igf2 gene expression levels (FIG. 19F). Mss51 is downregulated by GDF-8 inhibition, and Mss51 loss of function leads to increased skeletal muscle fatty acid oxidation, glycolysis, and oxidative phosphorylation, as well as resistance to diet-induced weight gain in mice (Moyer and Wagner, 2015; Yazmin, 2019). IGF-2 and its signaling effectors are positive regulators of skeletal muscle growth (Torrente et al., 2020).

Taken together, these effects on muscle mass and gene expression support the positive effect on body composition of P75, P622, and P624, with P622 displaying better efficacy overall compared to P75 or P624. Overall, these data indicate that 1) the mutation used in P622 and P624 improves efficacy of the trap in vivo, as evidenced by the muscle hypertrophy effects, and 2) the longer linker used in P622 provides an advantage over P624 on inducing muscle anabolic effects.

Figure 20:
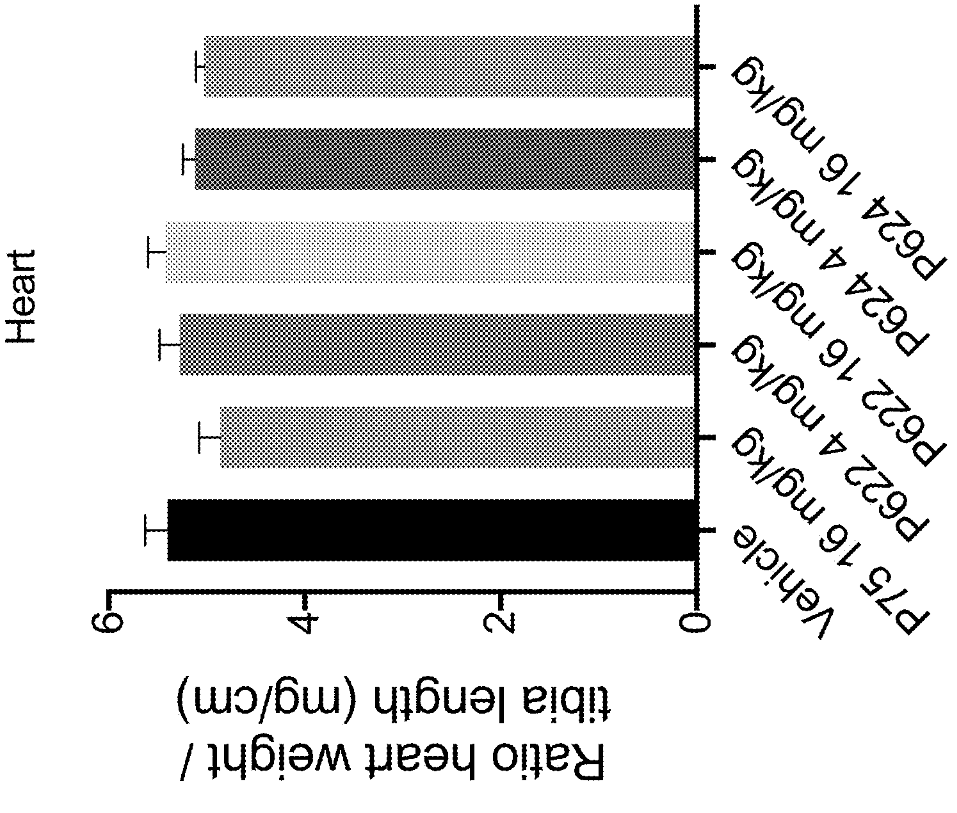
FIG. 20 shows the heart weight normalized by tibia length in C57BL/6 female mice (n=6-7 per group; 8-10 weeks of age) injected with P75 (16 mg/kg), P622 (4 and 16 mg/kg), and P624 (4 and 16 mg/kg) twice weekly for two weeks. Error bars indicate standard error of the mean (SEM). Results were analyzed by one-way ANOVA followed by post-hoc Bonferroni-corrected multiple comparison test.

The observed anabolic effects were specific to skeletal muscle, as none of the agents tested induced significant changes in heart weight relative to vehicle (FIG. 20).

Example 4: Exemplary ActRIIB-ECD Polypeptide Constructs Did not Demonstrate Hematological Effects Two exemplary agents, P622 and P624, were tested to examine their effect on hematological parameters. P622 and P624 were injected subcutaneously in female cynomolgus monkeys at doses of 3 mg/kg and 30 mg/kg (n=3 per group). P622 was injected once, and hematology parameters were assessed at baseline and at the end of the study 14 days after the injection. P624 was injected every two weeks for four weeks (total of two injections), and hematology parameters were assessed at baseline, before the second injection, and at the end of the study.

Figure 21B:
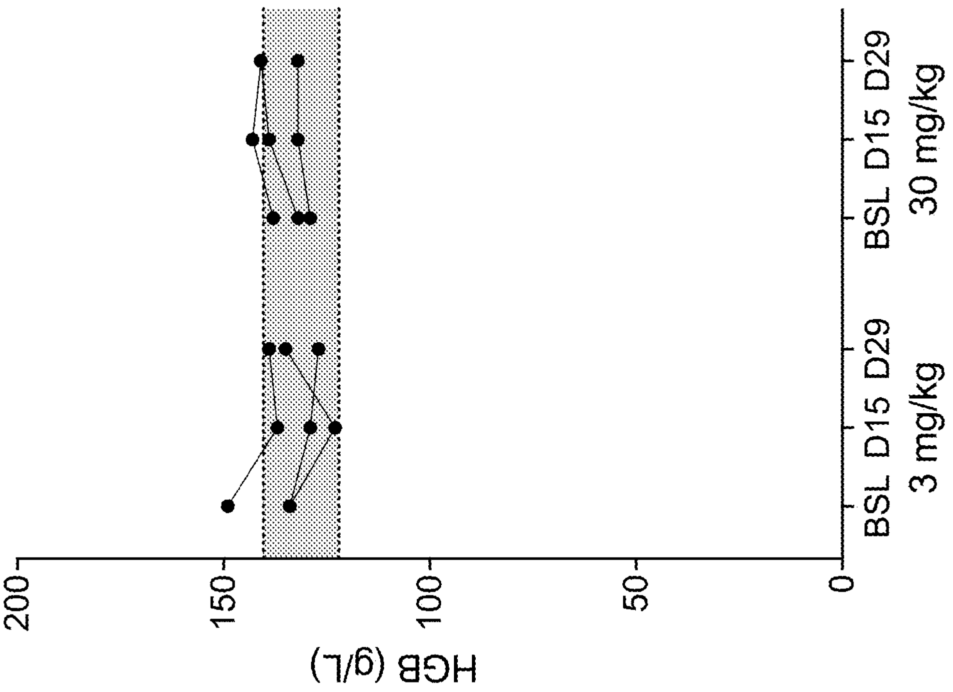
FIG. 21A-FIG. 21F shows the hematological parameters of female cynomolgus monkeys injected with P622 and P624 at 3 or 30 mg/kg (n=3 per group).
Figure 21A:
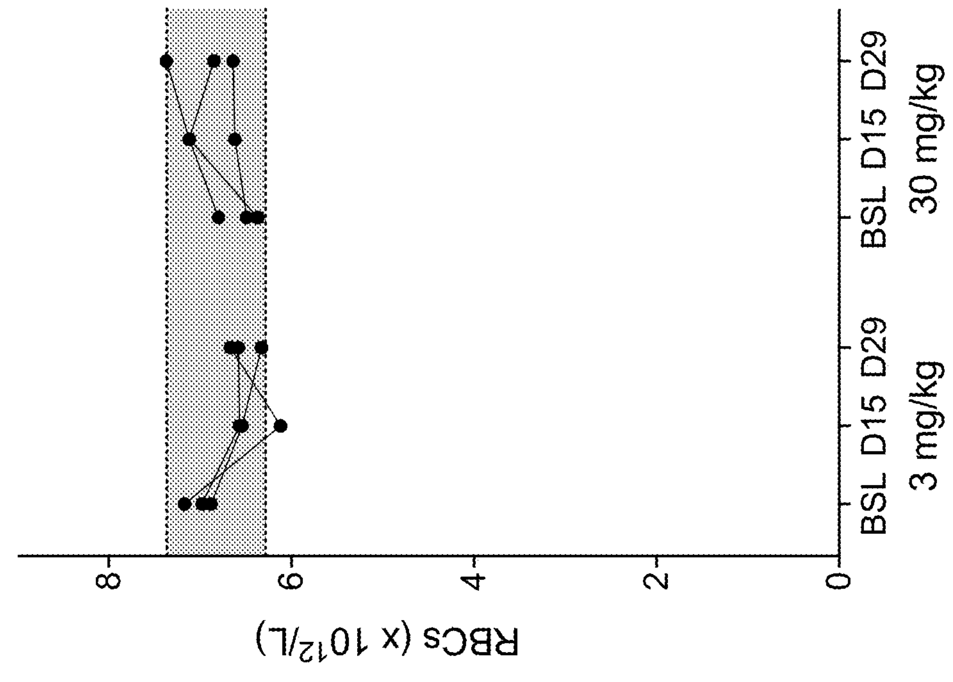
Figure 21C:
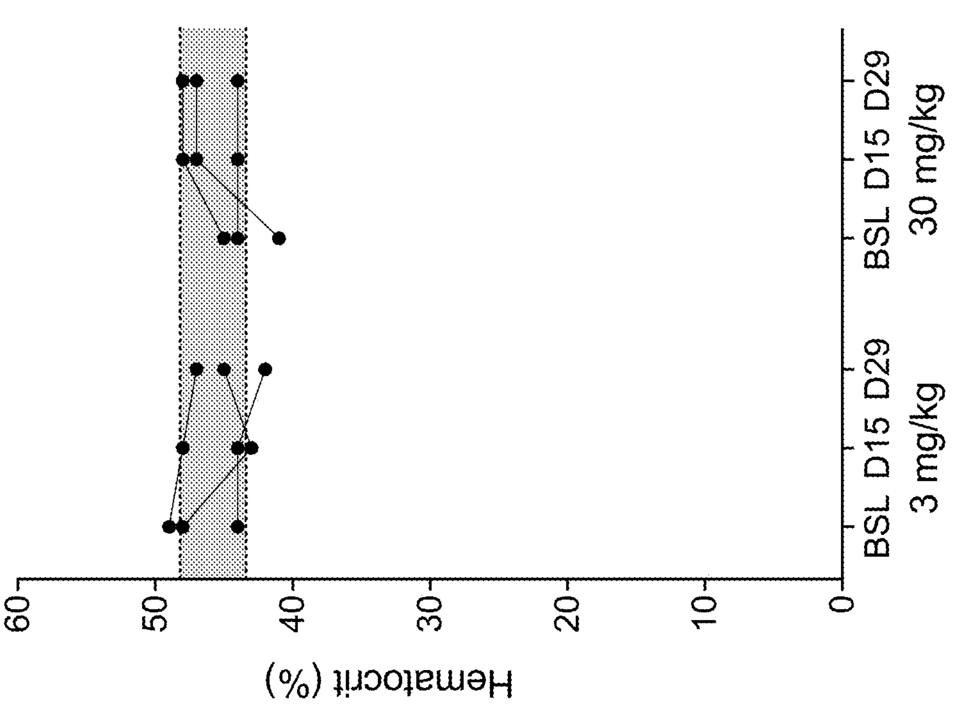
Figure 21D:
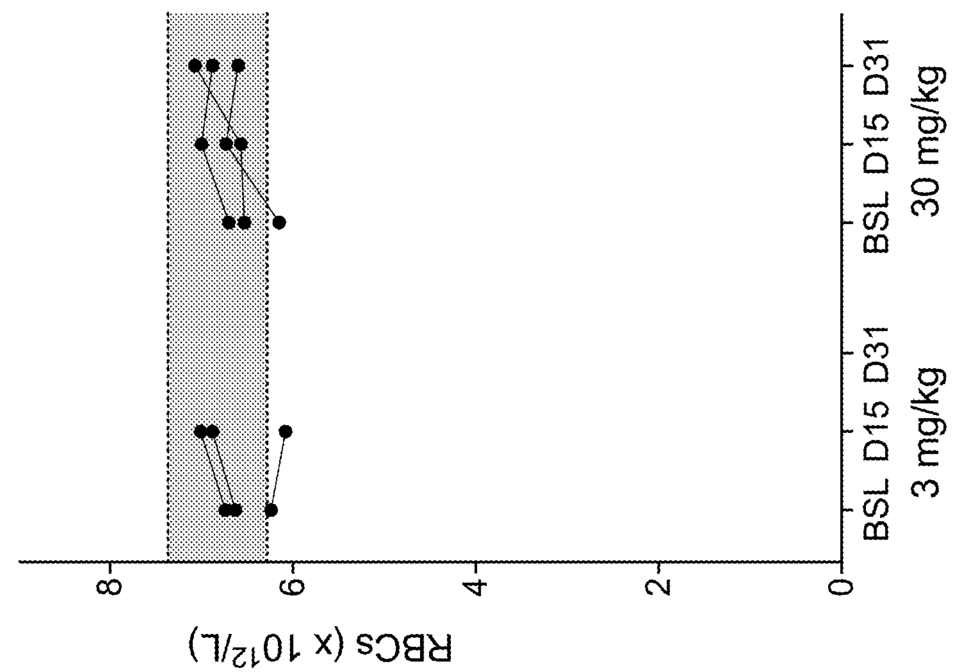
Figure 21E:
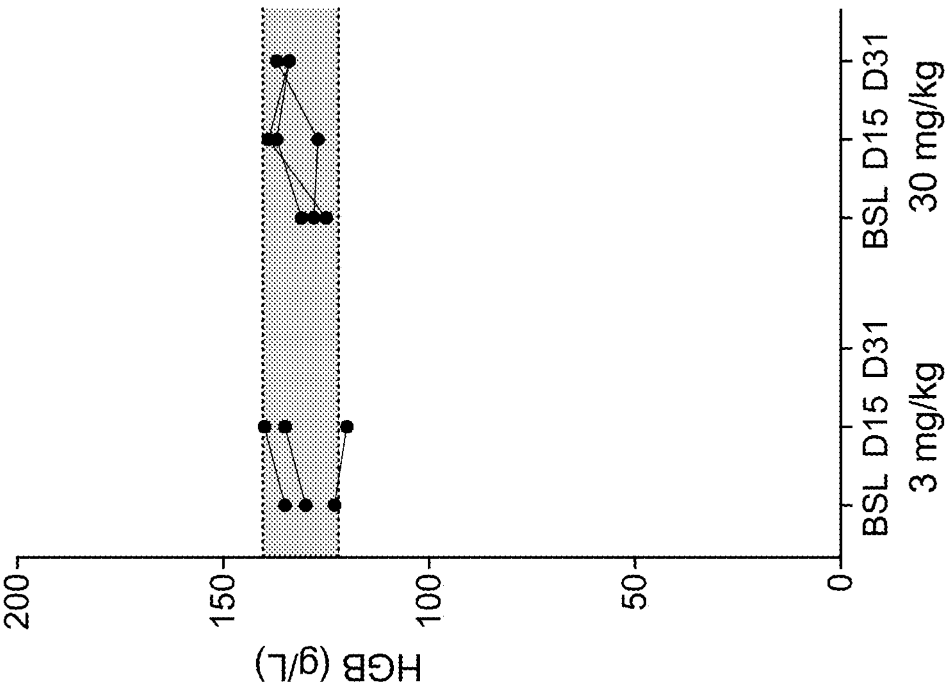
Figure 21F:
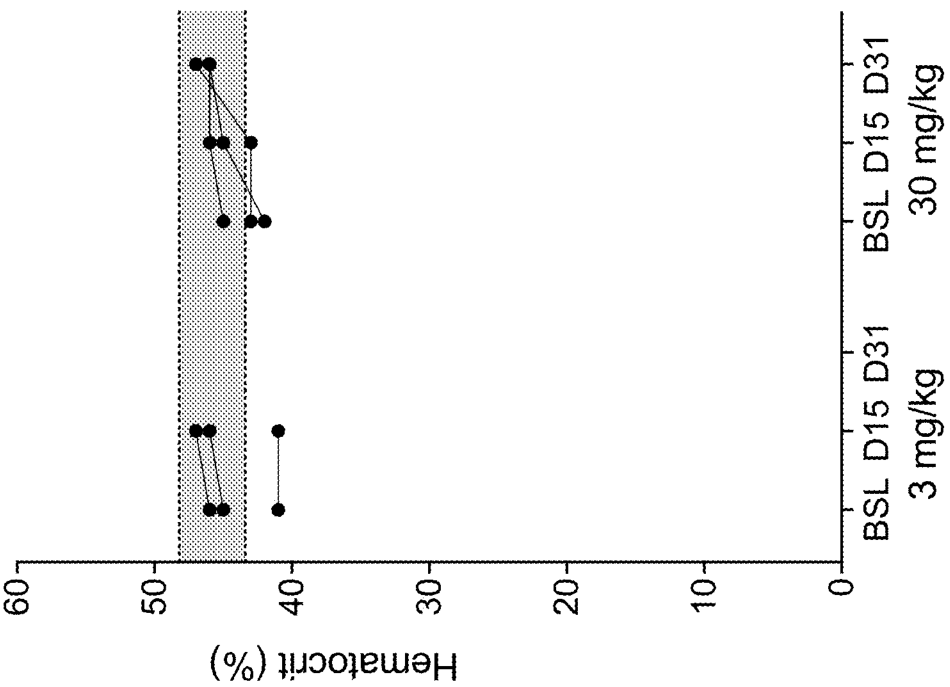

Neither P622 nor P624 induced a significant increase in red blood cell (RBC) count (FIGS. 21A and 21D), hemoglobin (FIGS. 21B and 21E), or hematocrit (FIGS. 21C and 21F) throughout the study. The grey area in each graph shows the normal range for each parameter in this type of cynomolgus monkey. The results show that hematological parameters in the monkeys treated with P622 and P624 remained generally within the normal ranges throughout the duration of the dosing period. No noticeable clinical signs or adverse events were reported. These results demonstrate that agents such as those exemplified by P622 and P624, harboring a single amino acid mutation in the ActRIIB ECD, did not induce an increase in red cell mass in vivo. The results indicate that the agents did not induce hematological effects in non-human primates, suggesting that for these agents dosing in humans may not be restricted by undesired hematological effects, as has been observed with ActRIIA-Fc polypeptides (e.g., sotatercept).

Figure 22A:
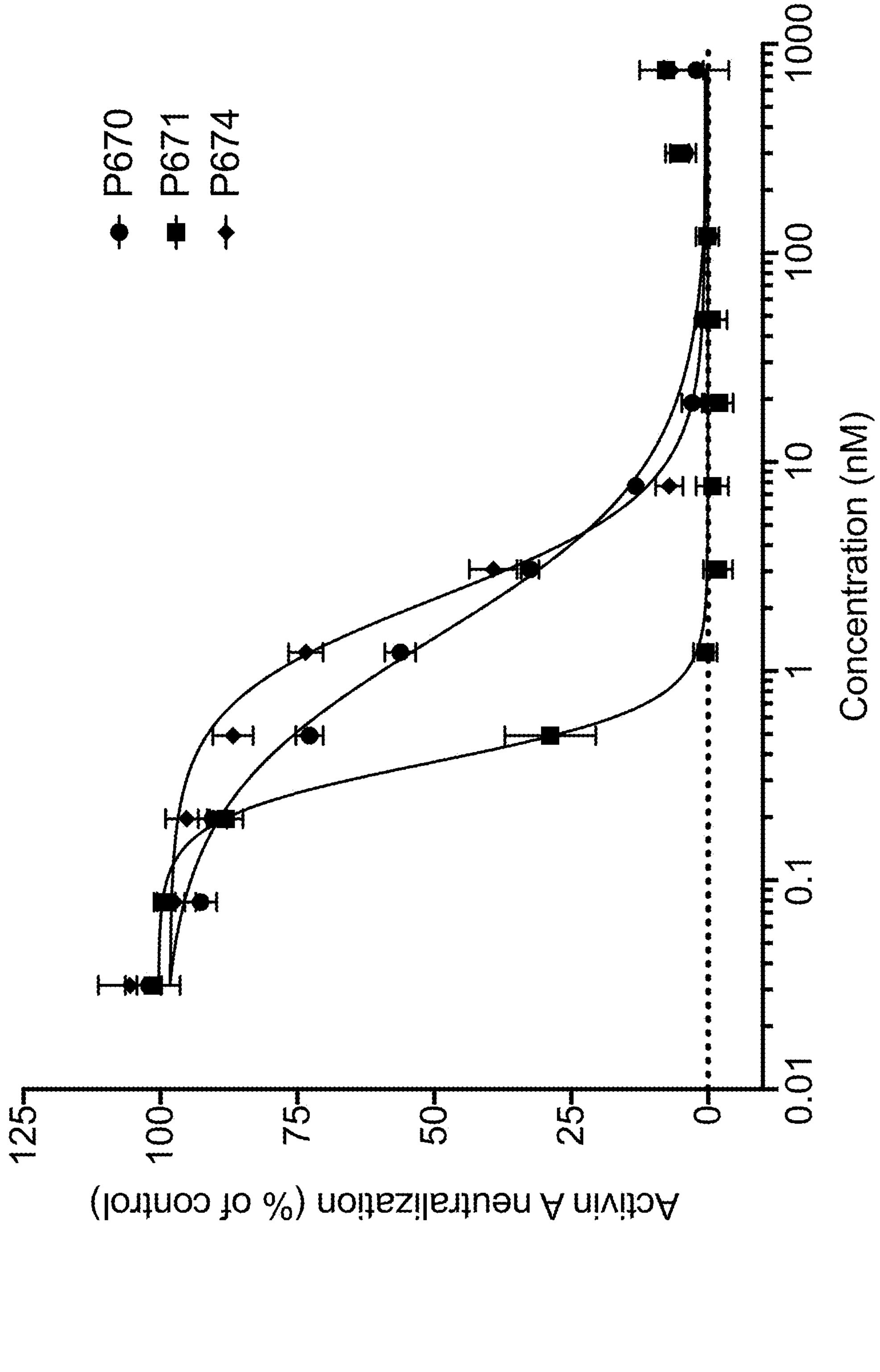
FIG. 22A-FIG. 22F shows representative results in the HEK-Blue cell-based assay for inhibition of activin A (FIG. 22A), activin B (FIG. 22B), GDF-8 (FIG. 22C), and GDF-11 (FIG. 22D), and in the HepG2 cell-based assay for inhibition of BMP-9 (FIG. 22E) and BMP-10 (FIG. 22F) for exemplary proteins P670, P671, and P674. Error bars indicate standard error of the mean (SEM).
Figure 22B:
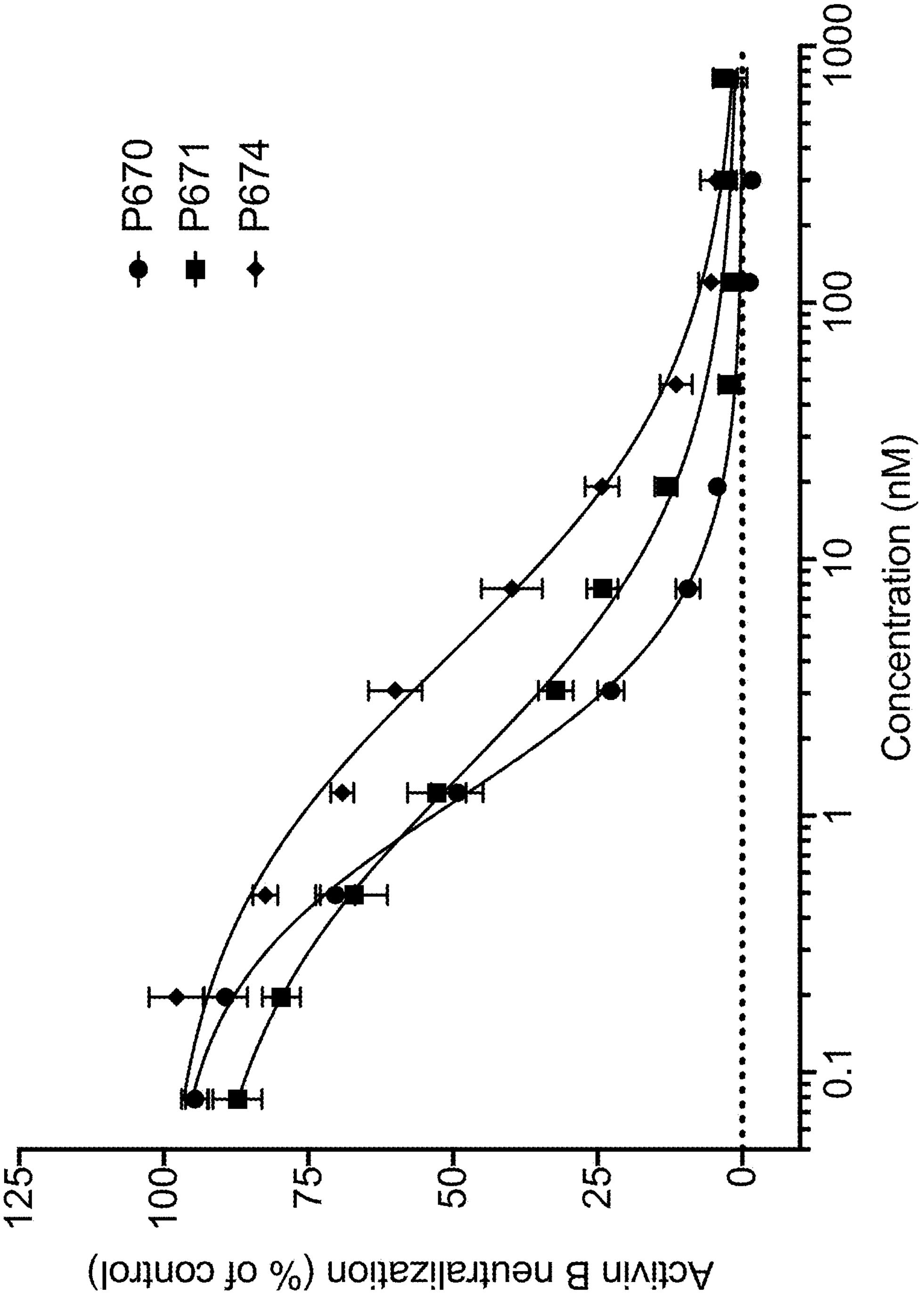
Figure 22C:
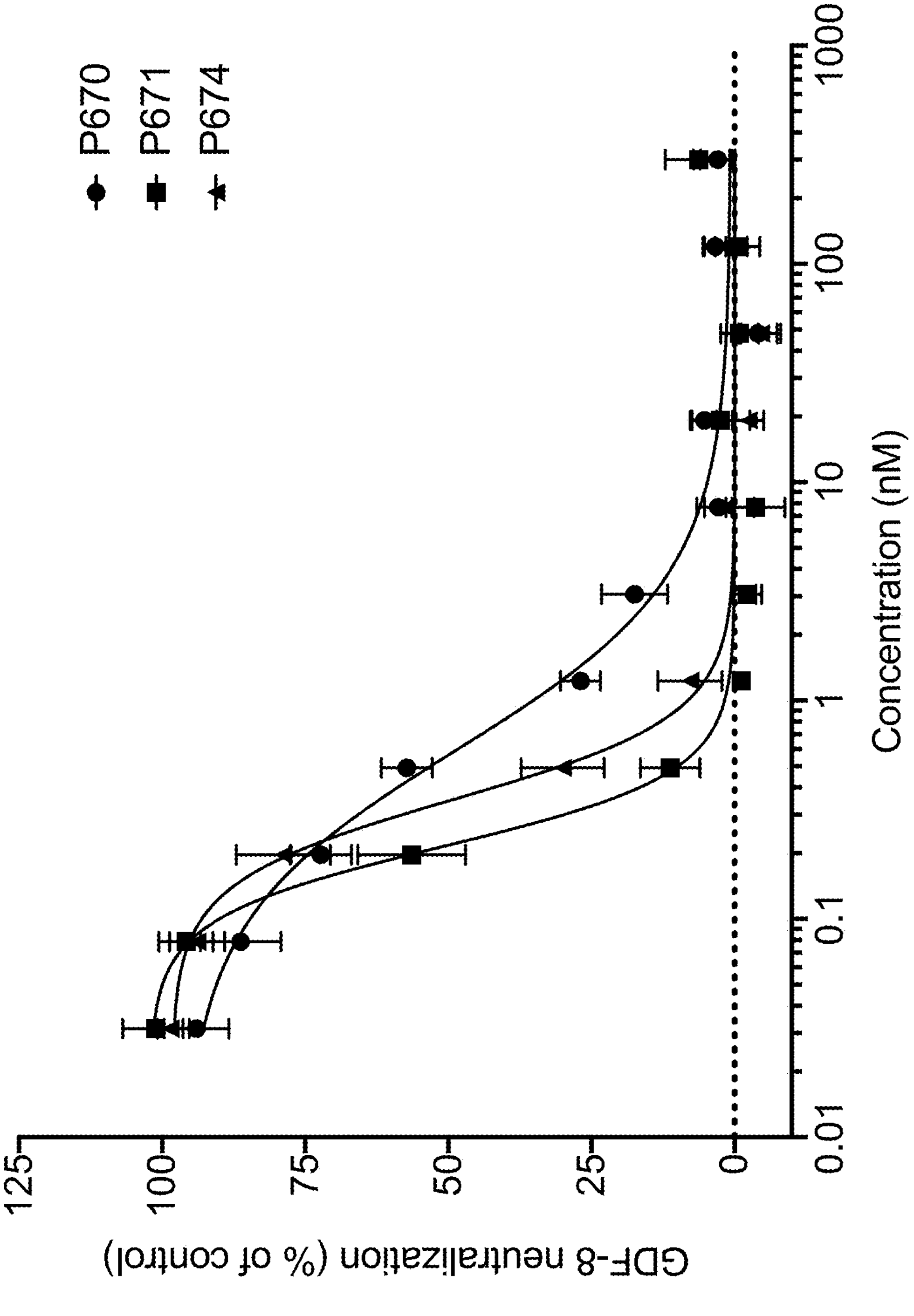
Figure 22D:
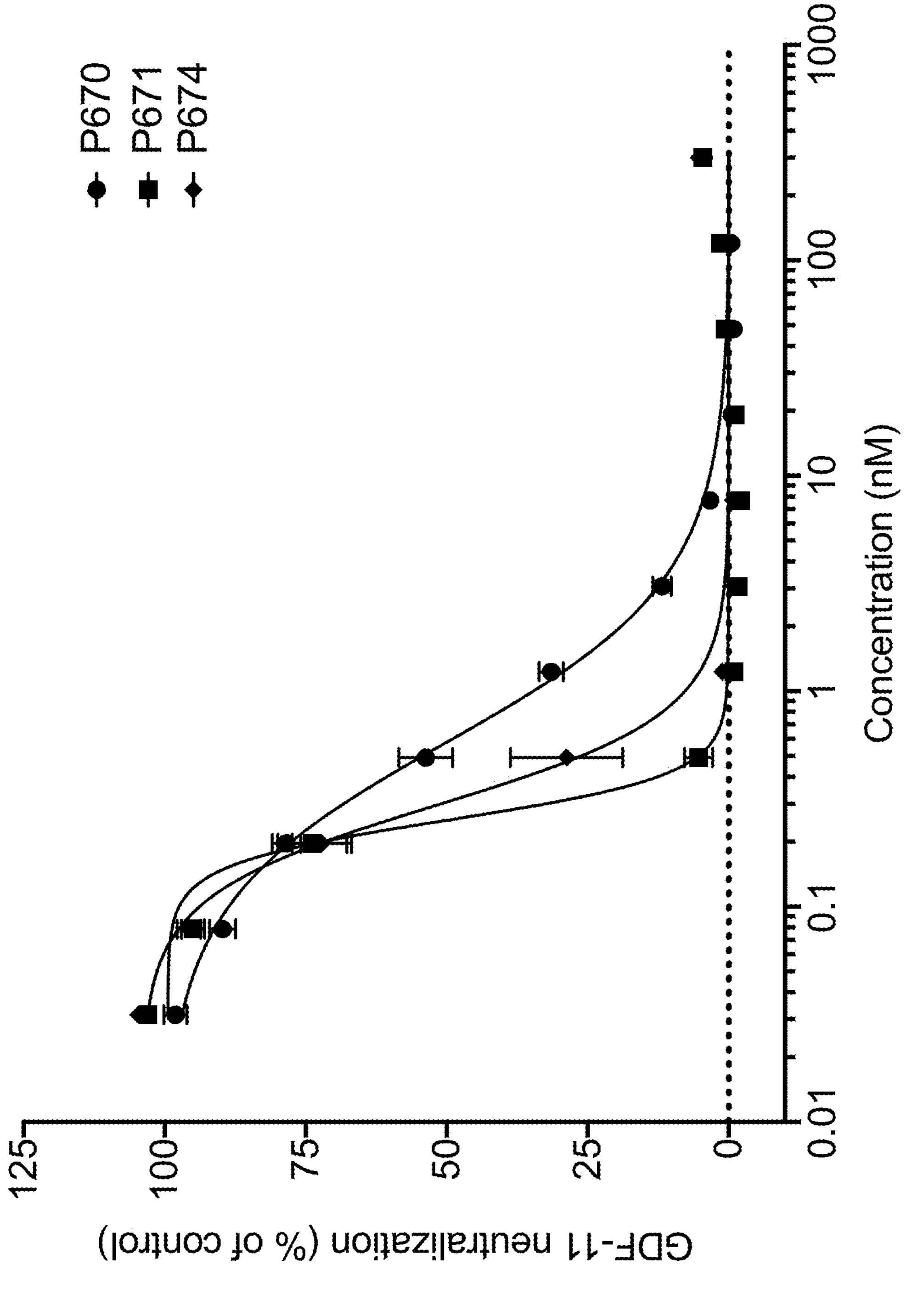
Figure 22E:
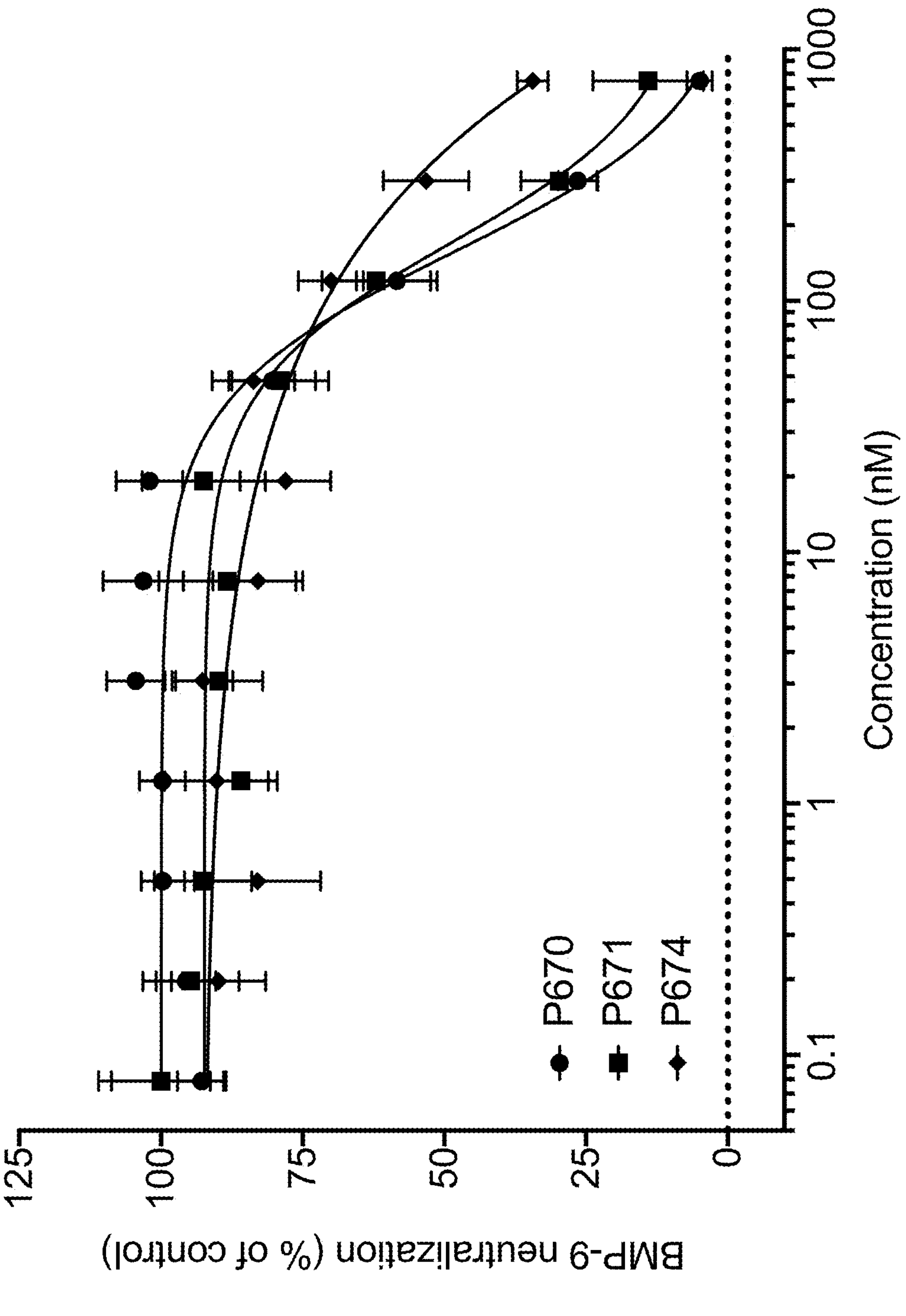
Figure 22F:
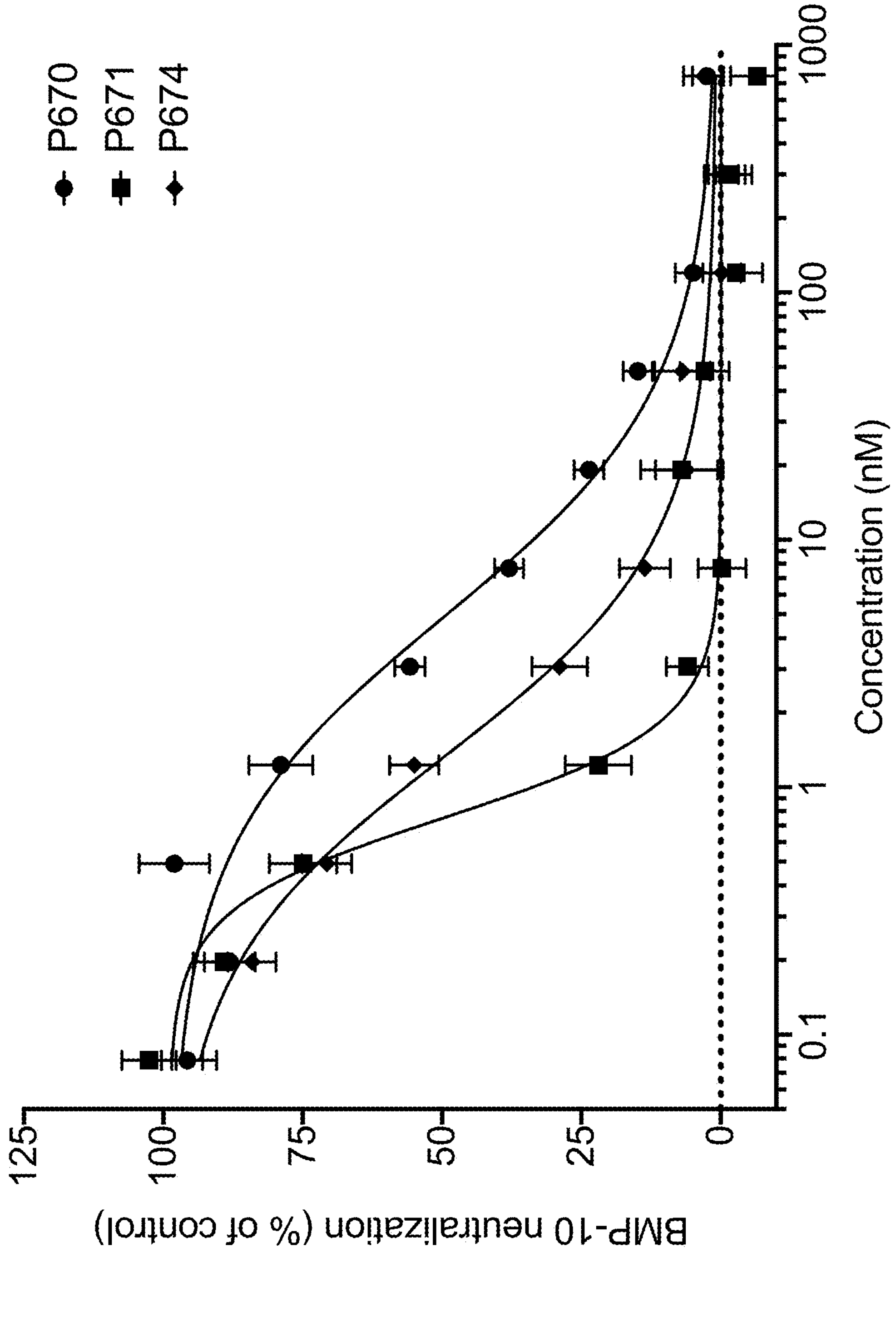
Figure 23B:
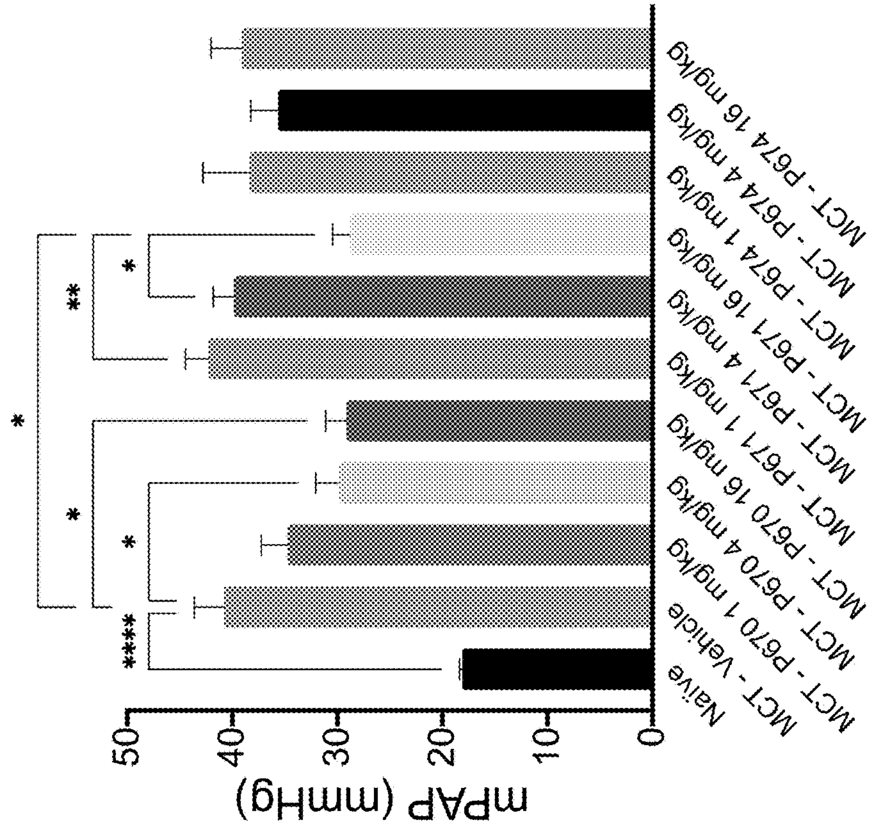
FIG. 23A-FIG. 23F show the efficacy of P670, P671, and P674 in a rat PAH model. Rats were injected with monocrotaline (MCT; 60 mg/kg) on day 0, followed by bi-weekly injections of P670, P671, and P674 (1, 4, or 16 mg/kg) starting on day 1. On day 29, animals were sacrificed, and parameters assessed were (FIG. 23A) Fulton index (ratio of right ventricle mass over left ventricle and septum mass [RV/LV+S]), (FIG. 23B) mean pulmonary arterial pressure (mPAP), (FIG. 23C) right ventricular systolic pressure (RVSP), (FIG. 23D) right ventricular free-wall thickness (RVFWT), (FIG. 23E) velocity time integral (VTI), and (FIG. 23F) pulmonary artery acceleration time (PAAT). Error bars indicate standard error of the mean (SEM). Results were analyzed by one-way ANOVA followed by post-hoc Bonferroni-corrected multiple comparison test.
Figure 23A:
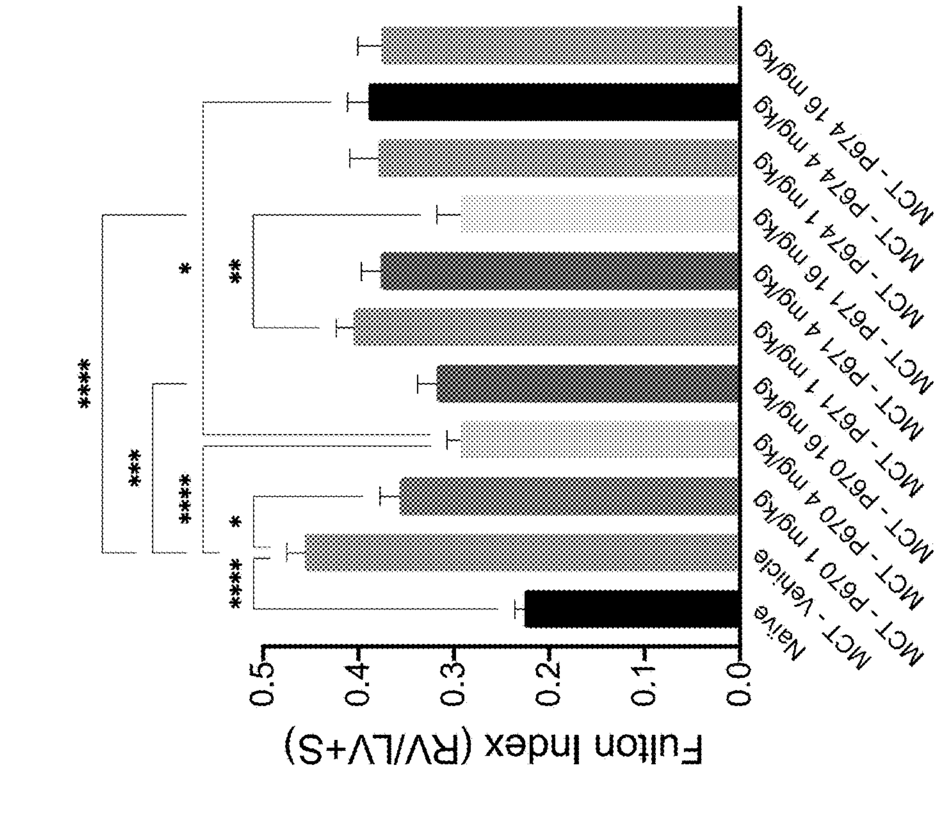
Figure 23C:
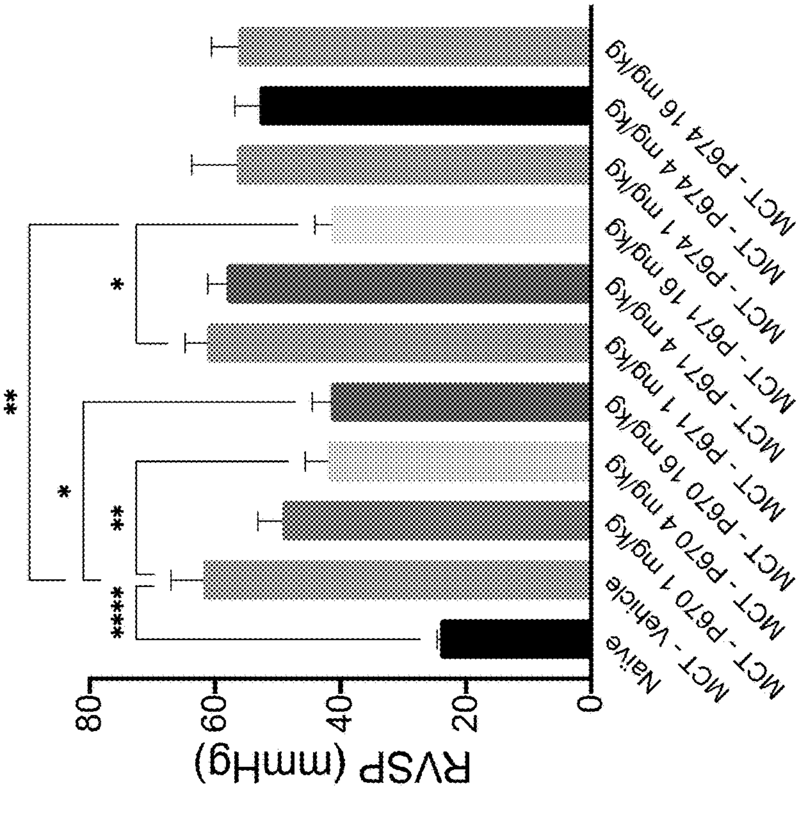
Figure 23D:
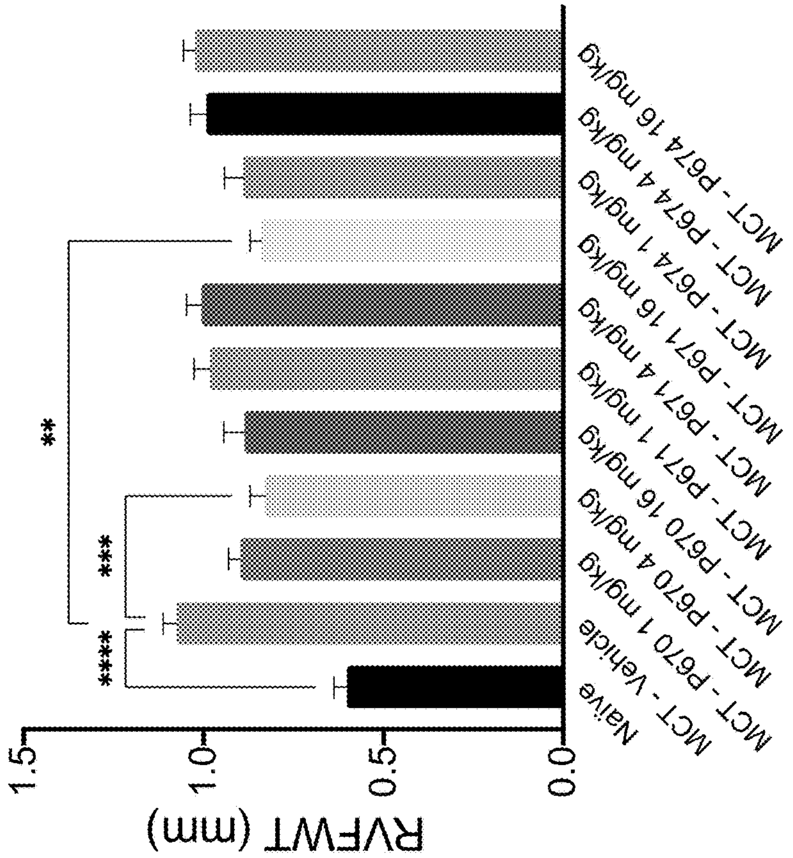
Figure 23E:
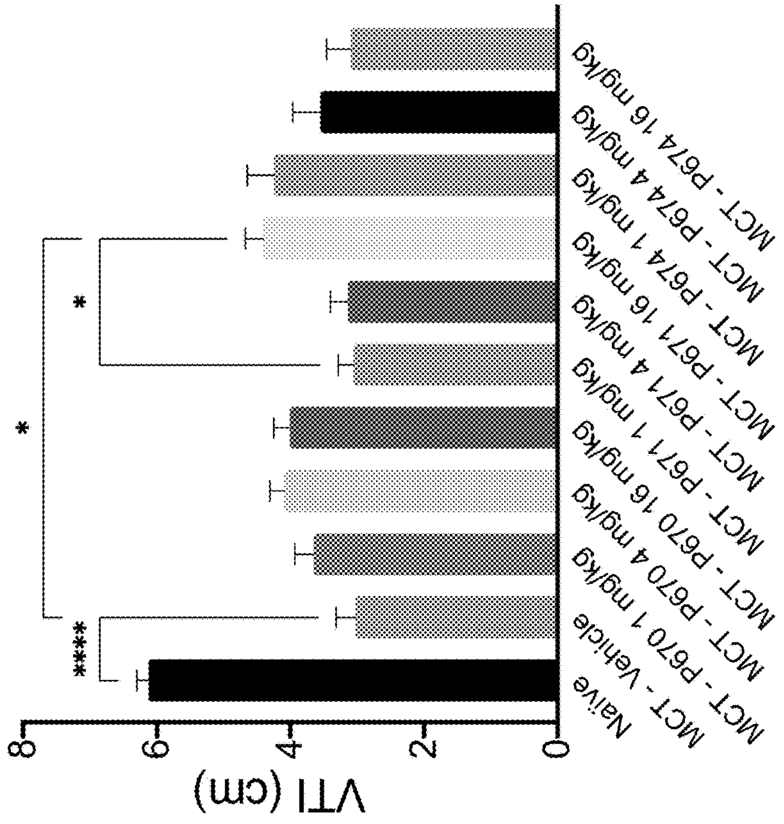
Figure 23F:
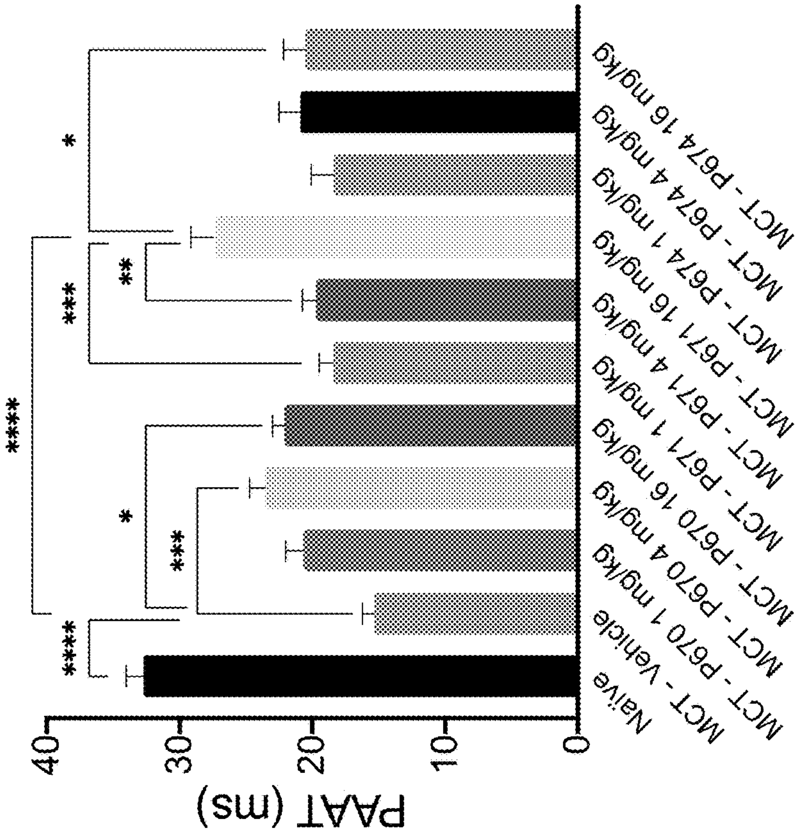

Example 5: Exemplary ActRIIB-ECD Polypeptide Constructs Demonstrate Efficacy in a Rat PAH Model To test the efficacy of three exemplary agents, P444, P622, and P624 in rats, their corresponding human ECD sequences were fused to a murine Fc (in place of a human Fc), to generate P670, P671, and P674 (P670, P671, and P674 correspond to P444, P622, and P624 respectively). Ligand inhibition potency for P670, P671, and P674 was tested using cell-based assays on activin A (FIG. 22A), activin B (FIG. 22B), GDF-8 (FIG. 22C), GDF-11 (FIG. 22D), BMP-9 (FIG. 22E), and BMP-10 (FIG. 22F). The results confirmed that the potencies of P670, P671, and P674 were comparable to those of their human Fc fused counterparts, P444, P622, and P624, respectively.

P670, P671, and P674 were then tested for their effects on rescuing a PAH-like phenotype in a rat PAH model. Male Sprague-Dawley rats (7-9 weeks of age, 225-275 g) were injected with monocrotaline (MCT; 60 mg/kg) on day 0. The next day, animals were randomly distributed between treatment groups with P670, P671, and P674 (1, 4, and 16 mg/kg; n=16 per group), injected i.p. twice weekly. Some animals were injected with MCT and vehicle, and others remained naïve (no MCT). At the end of the study (day 29, four weeks after the first injection), echocardiographic and hemodynamic assessments were made for all animals. Fulton index (FIGS. 23A-24A), mean pulmonary arterial pressure (mPAP; FIGS. 23B-24B), right ventricular systolic pressure (RVSP; FIGS. 23C-24C), right ventricular free-wall thickness (RVFWT; FIGS. 23D-24D), velocity time integral (FIGS. 23E-24E), and pulmonary artery acceleration time (FIGS. 23F-24F) were assessed.

MCT induced the expected hallmarks of PAH in this model: right ventricle hypertrophy (as measured by the Fulton index [FIGS. 23A-24A] and RVFWT [FIGS. 23D-24D]), and increased mPAP (FIGS. 23B-24B) and RVSP (FIG. 23C-24C). Heart contractility was also affected, as assessed by VTI (FIGS. 23E-24E) and PAAT (FIGS. 23F-24F). P670 significantly decreased the Fulton index at 1, 4, and 16 mg/kg, mPAP, and RVSP at 4 and 16 mg/kg, RVFWT at 4 mg/kg (FIGS. 23A-D). P670 did not significantly affect VTI relative to animals exposed to MCT alone (FIG. 23E), and partially rescued PAAT at 4 and 16 mg/kg (FIG. 23F). P671 (mutated ActRIIB-Fc, long linker) significantly decreased the Fulton index, mPAP, RVSP, and RVFWT at 16 mg/kg (FIGS. 23A-D). In contrast to P670, P671 also significantly increased VTI at 16 mg/kg (FIG. 23E). Also, P671 significantly increased PAAT at 16 mg/kg, more so than P670 (FIG. 23F). Surprisingly, P674 (mutated ActRIIB-Fc, short linker) did not have any significant effects on any of the hemodynamic or echocardiography parameters investigated (FIGS. 23A-F).

Animals injected with 16 mg/kg of P670, P671, or P674 were sub-categorized based on their exposure to the test agent. Exposure was assessed by calculating the area under the curve (AUC) of the PK profile for each animal, between day 7 and day 29. Based on this exposure analysis, animals were sub-grouped into tertiles: tertile 1 (T1) represents animals with lowest exposure, tertile 2 (T2) represents animals with mid-exposure, and tertile 3 (T3) represents animals with highest exposure. Tertiles were established such that animals were equally distributed for a given test agent.

Figure 24B:
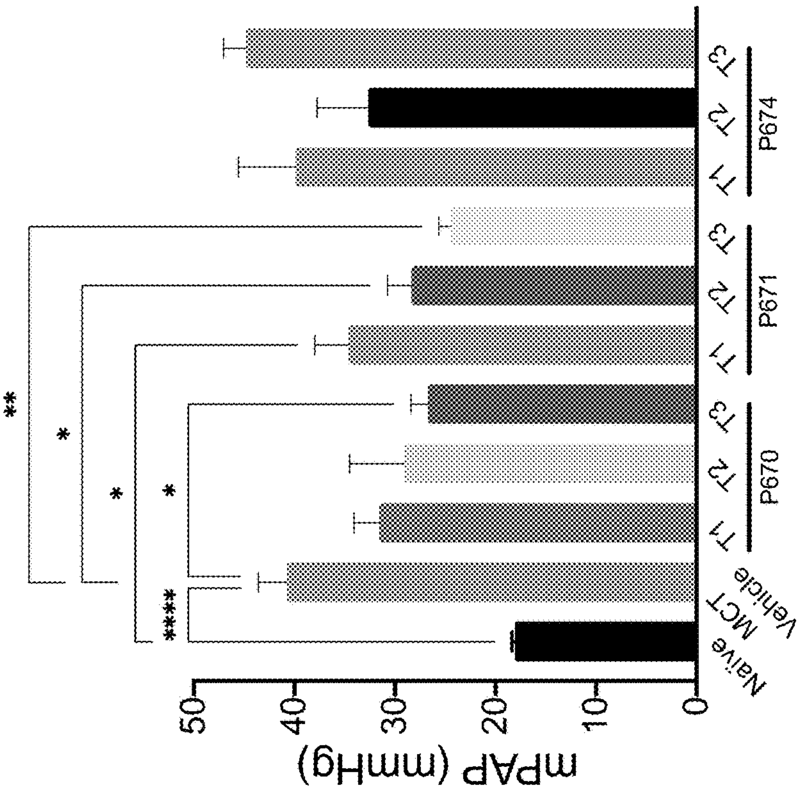
FIG. 24A-FIG. 24F show the efficacy of P670, P671, and P674 in a rat PAH model. Using the 16 mg/kg data from FIG. 23 for each agent, rats were divided into sub-groups based on their exposure to the drug between days 7 and 29. T1: lowest exposure levels, T2: mid-exposure levels, T3: highest exposure levels. Parameters assessed were (FIG. 24A) Fulton index, (FIG. 24B) mPAP, (FIG. 24C) RVSP, (FIG. 24D) RVFWT, (FIG. 24E) VTI, and (FIG. 24F) PAAT. Error bars indicate standard error of the mean (SEM). Results were analyzed by one-way ANOVA followed by post-hoc Bonferroni-corrected multiple comparison test.
Figure 24A:
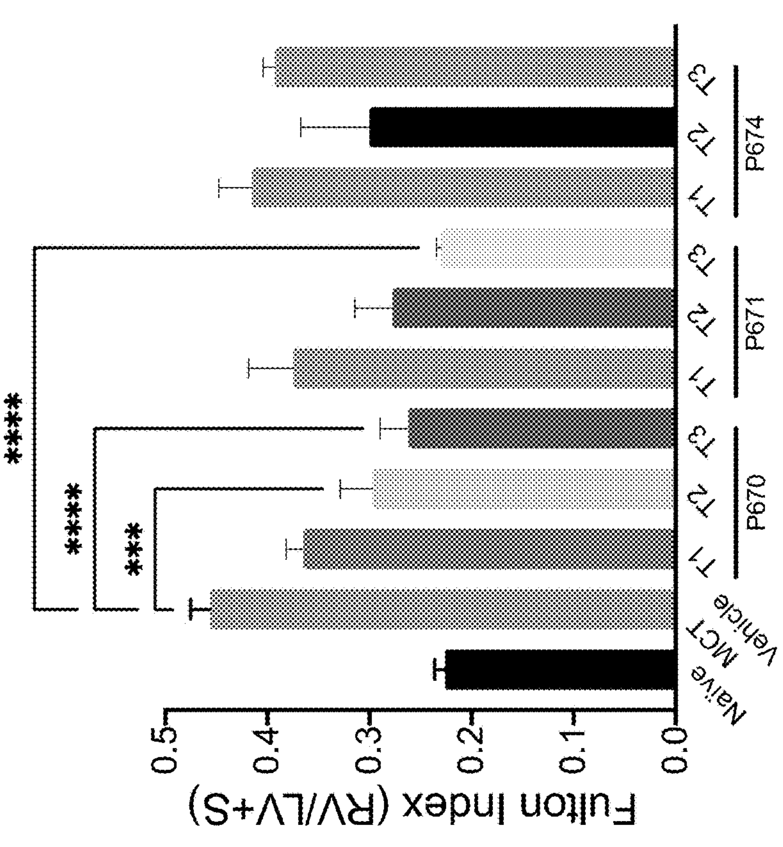
Figure 24C:
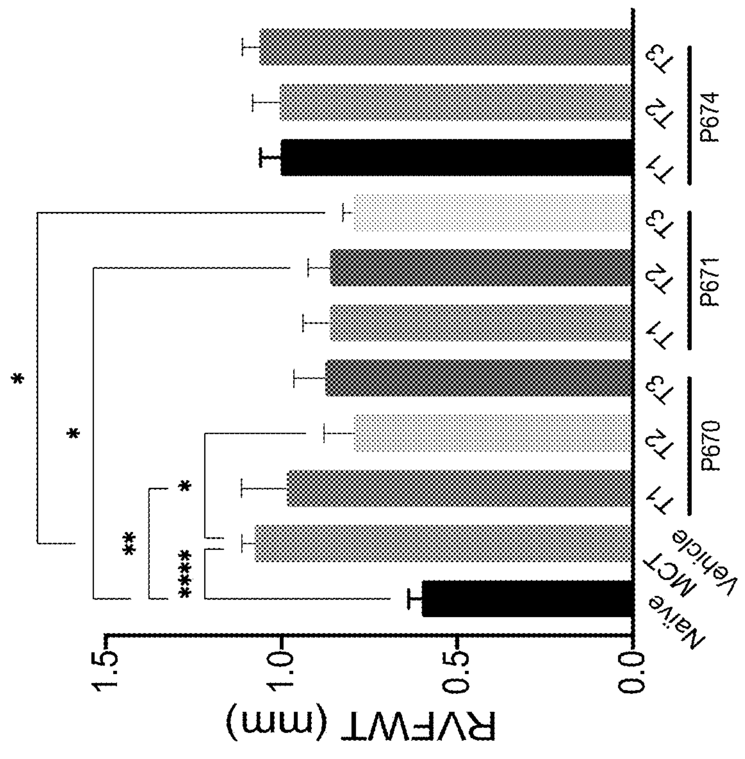
Figure 24D:
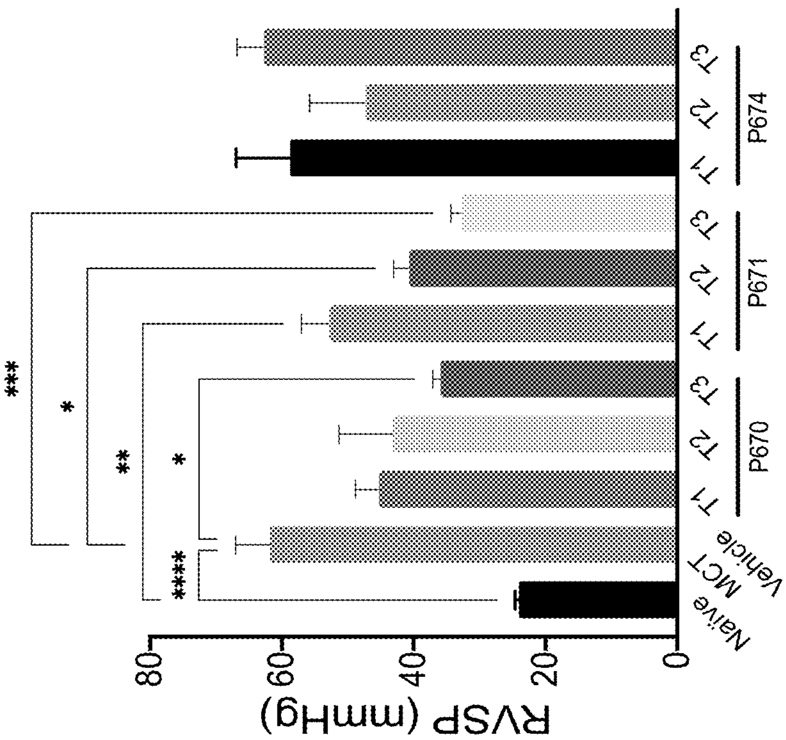
Figure 24E:
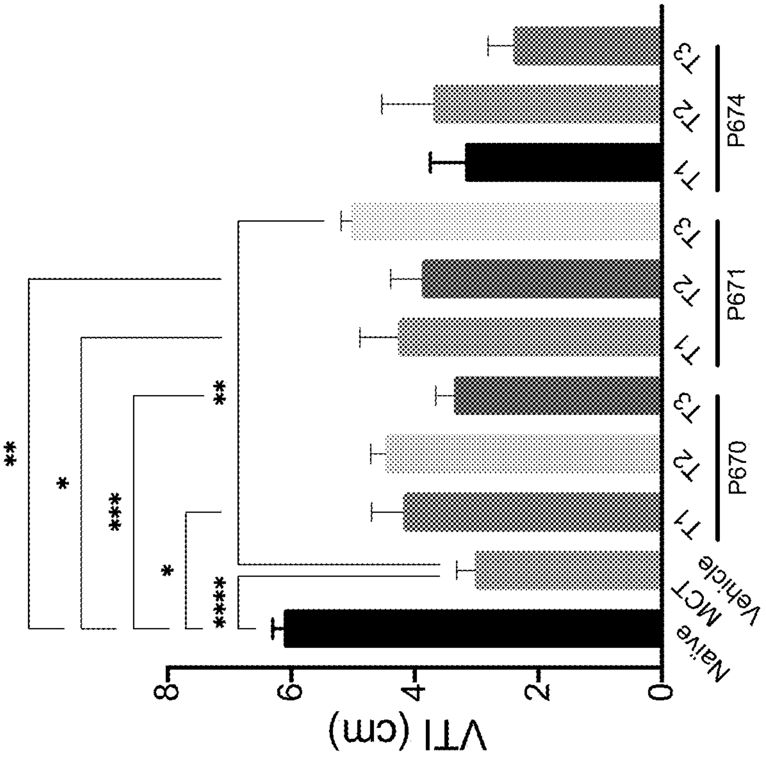
Figure 24F:
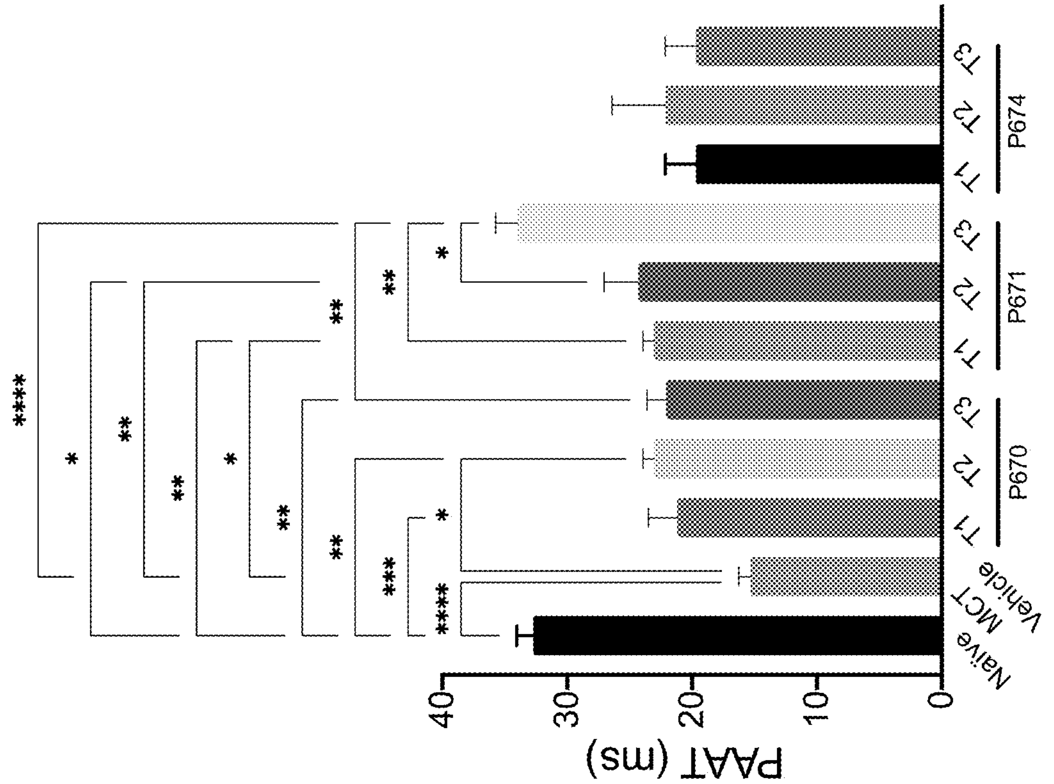

Based on this stratification, P670 and P671 showed comparable responses between T1, T2, and T3 across the two groups (FIGS. 24A-F), with some notable exceptions. First, the Fulton Index in the rats from P671-T3 was comparable to naïve animals (FIG. 24A). Second, the increase in PAAT was stronger in P671-T3 rats relative to P670-T3 rats. Both observations suggest that the maximal possible response from P671 is greater than that from P670. Surprisingly, with regards to P674, there were no apparent efficacy differences between exposure tertiles, and none of these sub-groups showed a significant improvement in the parameters assessed (FIGS. 24A-F).

Overall, these data suggest that exemplary agents P670 and P671 were efficacious in a preclinical PAH rat model, with P671 rescuing several parameters back to naïve levels. This indicates that, overall, the exemplary agent P671 was more efficacious than P670. Unexpectedly, P674 did not show any significant effects on any of the parameters investigated. Given that the only difference between P671 and P674 is the length of the linker between the ectodomain and the Fc, these results highlight the importance of this linker.

Figure 25A:
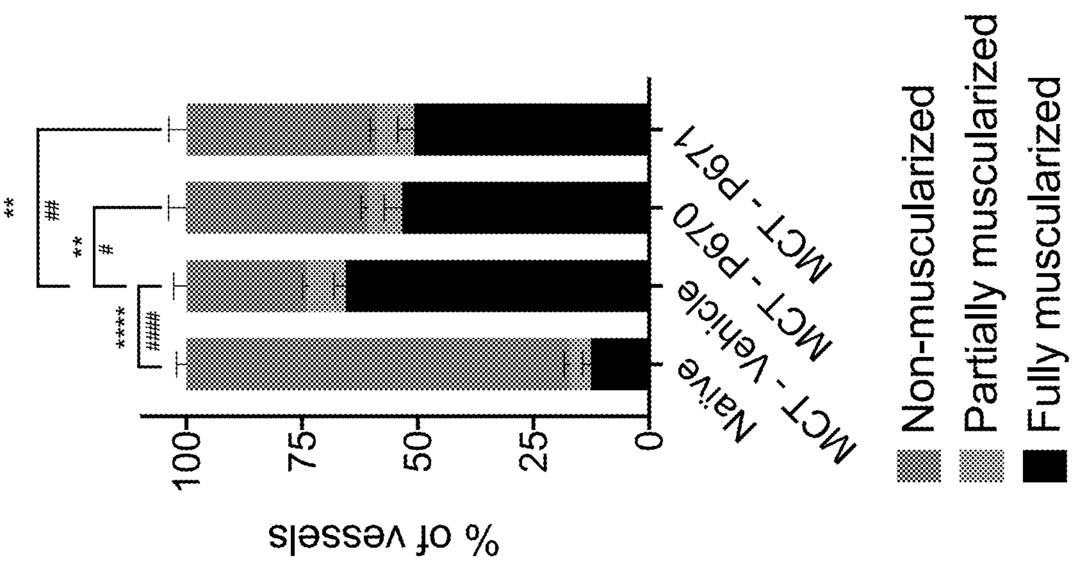
FIG. 25A-FIG. 25O shows the efficacy of P670, P671, and P674 at 16 mg/kg in a rat PAH model. Rats were divided into sub-groups based on their exposure to the drug between days 7 and 29. T1: lowest exposure levels, T2: mid-exposure levels, T3: highest exposure levels. Lungs were collected at day 29, inflated, and perfused with 10% neutral buffered formalin for further histological analyses. Following paraffin embedding, sections were cut and stained with H&E.
Figure 25B:
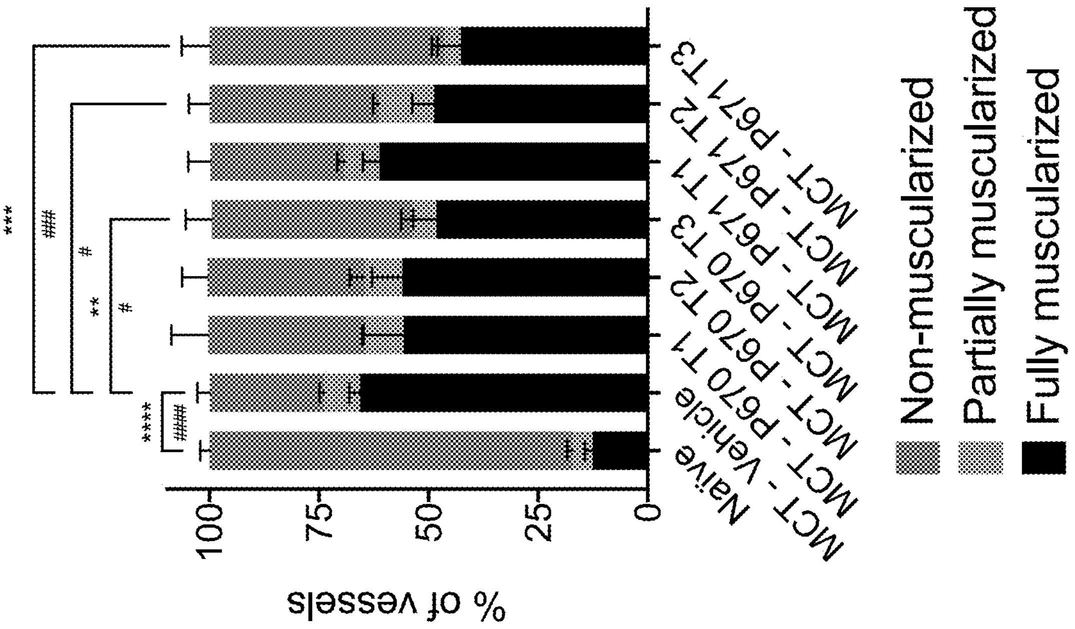
Figure 25C:
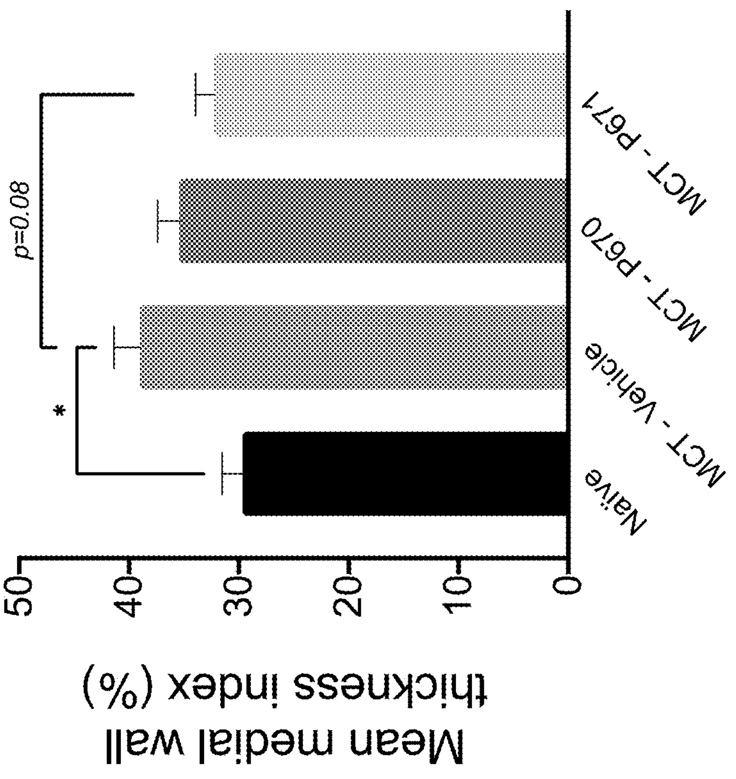
(FIG. 25C-FIG. 25D) Internal and external mural diameter was measured from muscularized blood vessels, and an average percent of luminal occlusion and wall thickness was calculated for each animal (medial wall thickness index, MTI).
Figure 25D:
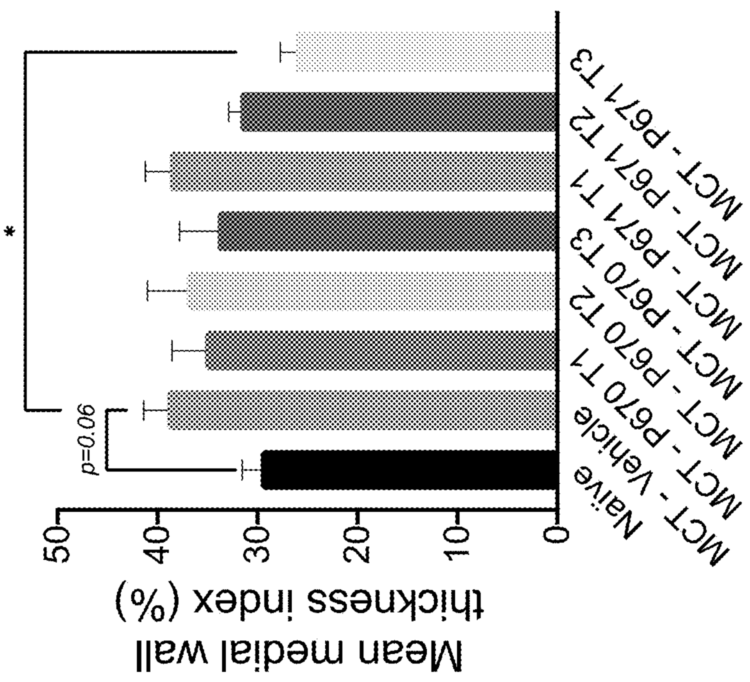
Figure 25E:
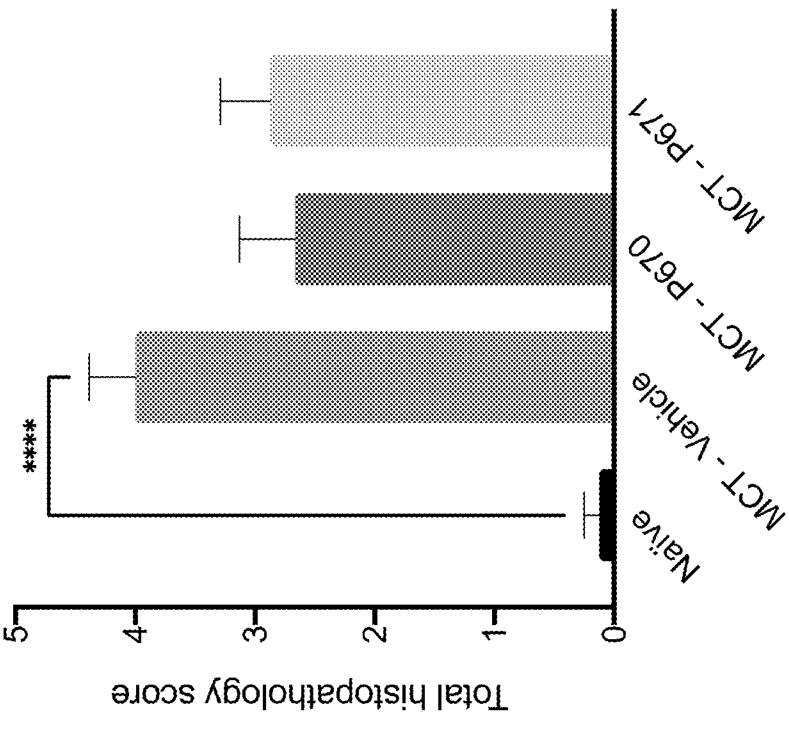
(FIG. 25E-FIG. 25F) Each animal was also attributed a score based on fibrin levels in the interstitium, alveolar hemorrhage, and cellular infiltration, herein referred to as total histopathology score.
Figure 25F:
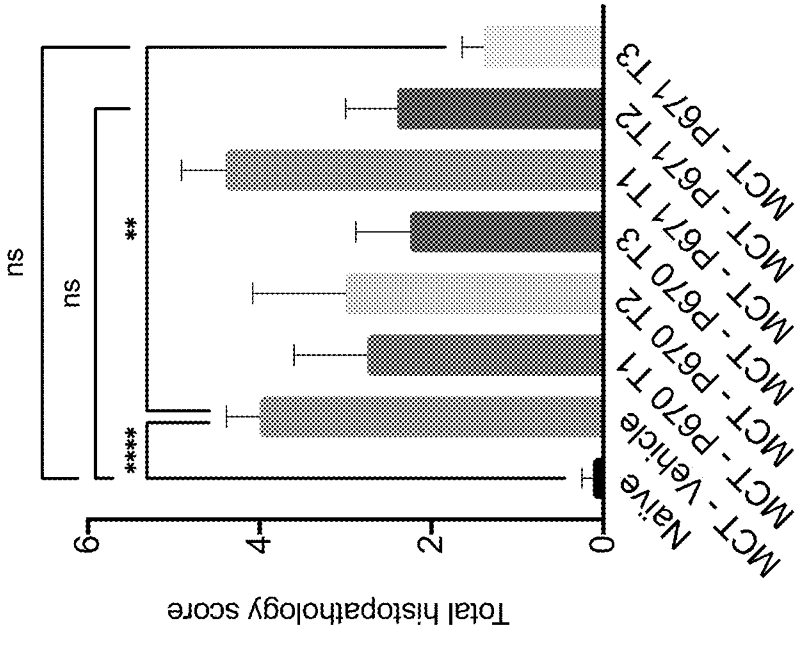
Figure 25H:
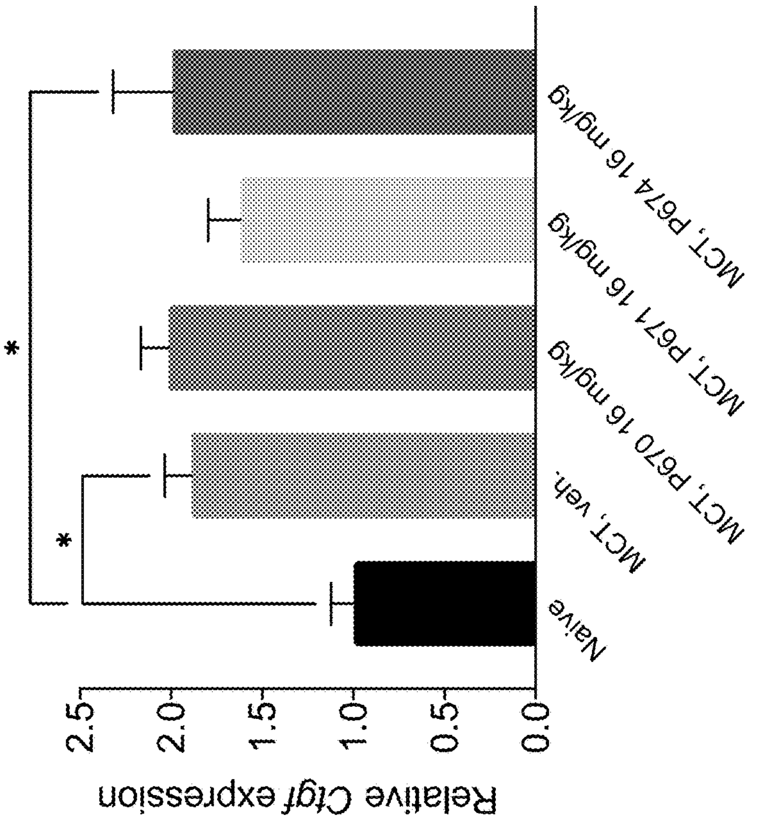
(FIG. 25G-FIG. 25K) Inhba and Ctgf expression levels in lung (FIG. 25G-FIG. 25H), and Nppb, Ctgf, and Nppa expression levels in right ventricle (FIG. 25I-FIG. 25K) were assessed. Tissues were snap-frozen after collection and lysed using the gentleMACS™ Octo Dissociator (Miltenyi Biotech). RNA was extracted and reverse transcribed, and gene expression was assessed by qPCR as per manufacturer's instructions (Qiagen). Actb, Rpl13a, and B2m were used as housekeeping genes. Error bars indicate standard error of the mean (SEM). Results were analyzed by one-way ANOVA followed by post-hoc Bonferroni-corrected multiple comparison test.
Figure 25G:
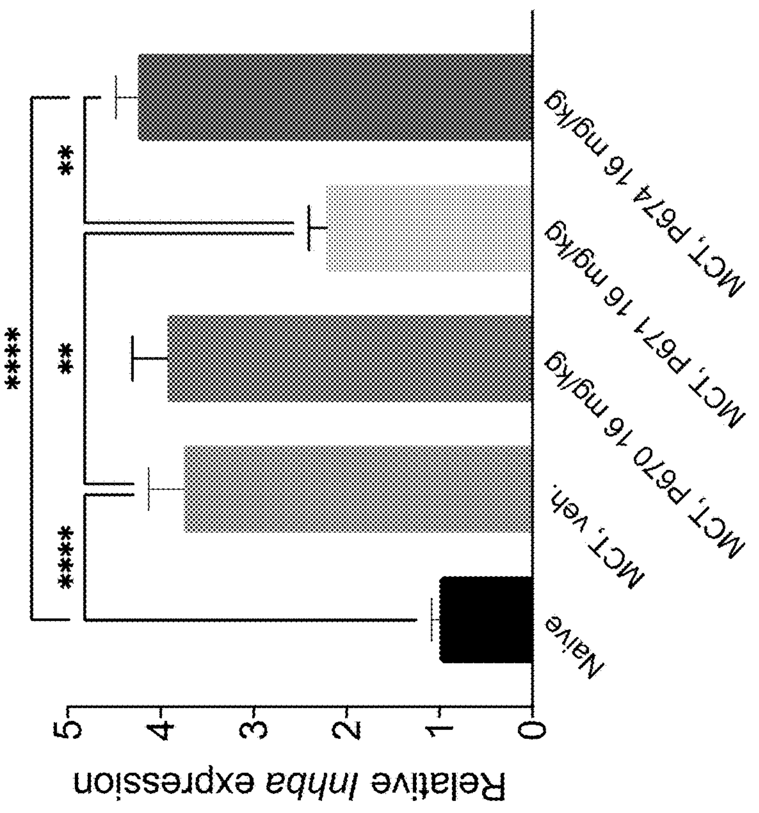

A hallmark of PAH is pulmonary vessel muscularization, which reduces the size of the lumen (as measured by the mean medial wall thickness, MTI). MCT significantly induced vessel muscularization in the rats (FIGS. 25A-B), and this effect was reduced by P670 and P671 at 16 mg/kg (FIG. 25A). When stratified by exposure, P671 appeared to reduce muscularization levels more than P670 in the highest exposure tertile, though this difference was not statistically significant (FIG. 25B). The MTI was also increased by MCT (FIGS. 25C-D), and this effect was significantly reduced by P671, but not by P670 (FIG. 25C), even when stratifying the animals by exposure (FIG. 25D). Finally, a histopathological score was given to each individual rat, based on fibrin levels in the interstitium, alveolar hemorrhage, and cellular infiltration. MCT significantly increased this score (FIGS. 25E-F), and this increase was not significantly changed by either P670 or P671 at 16 mg/kg (FIG. 25E). Based on stratification, the highest exposure tertile of P671, but not P670, significantly reduced the histopathological score (FIG. 25F).

Figure 25I:
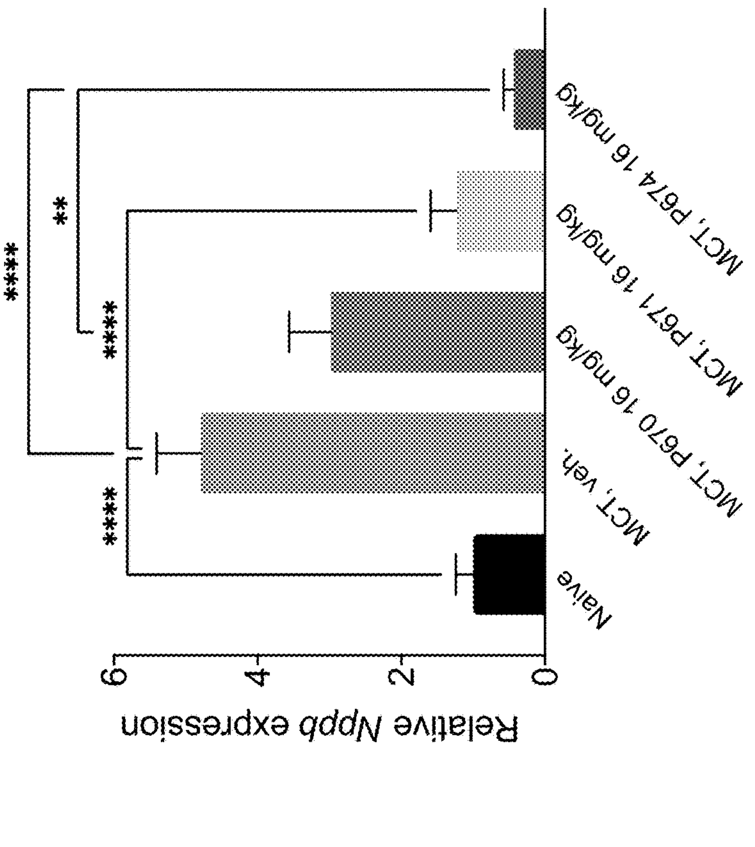
Figure 25J:
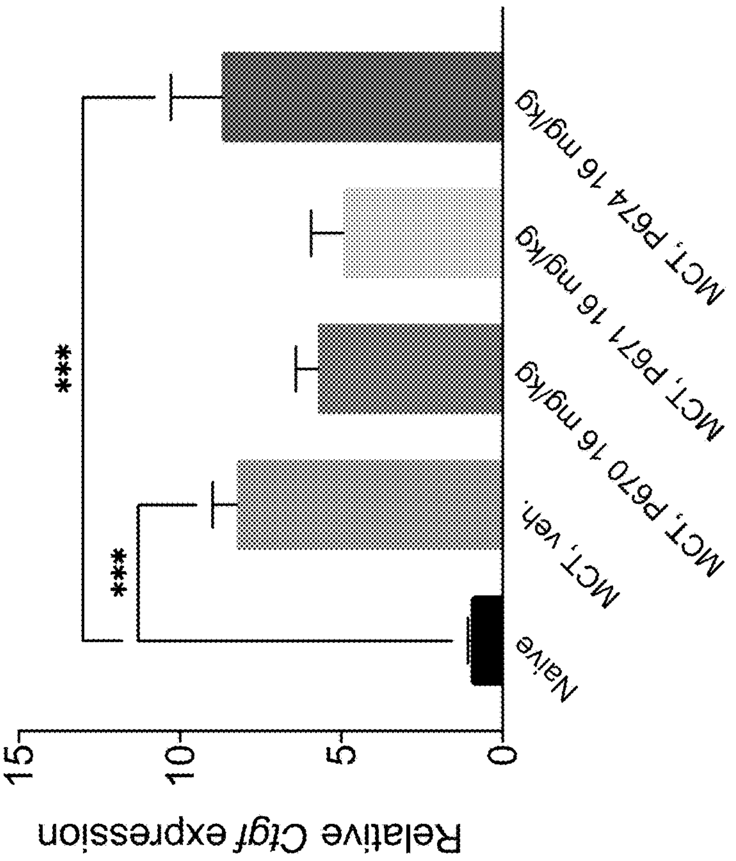
Figure 25K:
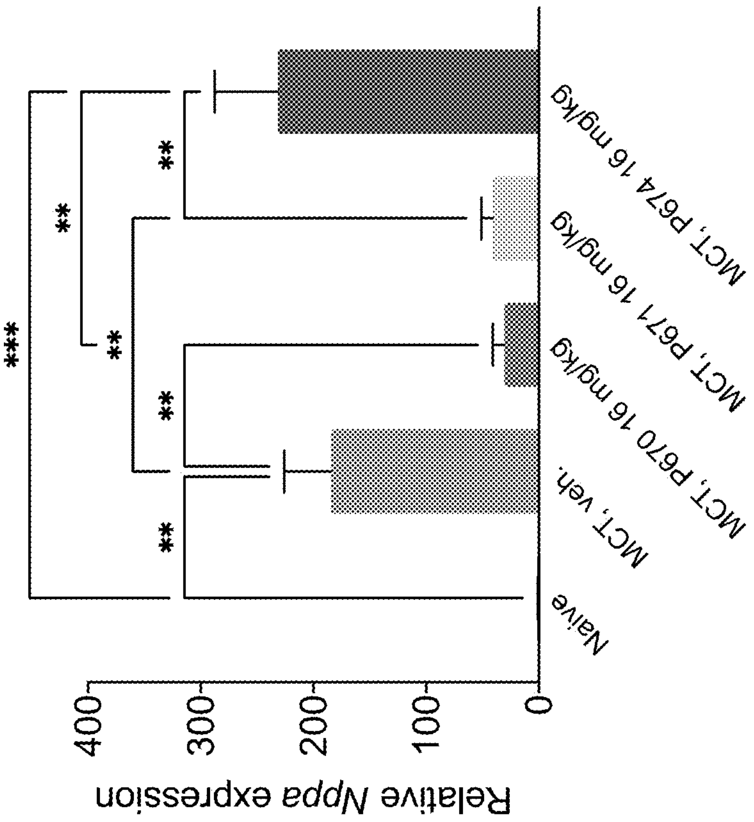

The effects of P670 and P671 on PAH-relevant gene expression changes were also investigated. MCT induction significantly increased Inhba (encoding activin A) and Ctgf (encoding CTGF) gene expression in the lung (FIGS. 25G-H), and Nppb (encoding BNP) and Ctgf gene expression in the right ventricle (FIGS. 25I-J). P670 had no effect on expression of Inhba and Ctgf in the lung and only a modest effect on Nppb and Ctgf expression in the right ventricle (FIGS. 25G-J). P671 did not significantly affect Ctgf expression levels in the lung (FIG. 25H), but significantly decreased expression levels of Inhba in the lung, and Nppb and Ctgf in the right ventricle (FIGS. 25G-J). In the case of Nppb in the right ventricle, these levels were brought back to naïve levels with P671 (FIG. 25I). Nppa expression was also investigated and it was observed that both P670 and P671 significantly and comparably decreased MCT-induced Nppa expression (FIG. 25K). With respect to P674, again unexpectedly, it did not affect Inhba or Ctgf expression in lung (FIGS. 25G-H), nor Ctgf or Nppa expression in the right ventricle (FIGS. 25J-K). P674 did significantly decrease Nppb mRNA levels in the right ventricle (FIG. 25I).

These results demonstrate that agents such as those exemplified by P671, harboring a single amino acid mutation in the ActRIIB ECD in addition to a longer linker length, can rescue a PAH-like phenotype in vivo in an animal model. The results strongly support the potential therapeutic use of such agents in the treatment of pulmonary hypertension.

To further compare the effects of exemplary agents P670 and P671 in this rodent PAH model, RNA-sequencing was performed on samples from the right ventricle (RV). Three animals per group (naïve, MCT alone, MCT+P670 [16 mg/kg], and MCT+P671 [16 mg/kg]) were selected: for the MCT alone group, those animals that had the worst disease state (as assessed by mPAP and RVSP), and for the P670 and P671 groups, those animals that had the best exposure to the agent, were selected. RNA was extracted from RV and sequenced by paired-end 150 bp sequencing with Illumina NGS. FastQC (v0.11.9) was used to verify the quality of the raw data. All bases had a quality score of at least Q34. Reads were aligned to reference genome m6 using HISAT2 (v. 2.2.1) (Kim et al., 2015) then summarized with featureCounts (v2.0.3)(Liao et al., 2014). Differential expression analysis was performed using DESeq2 (version 1.36.0) (Love et al., 2014). Genes with adjusted p-value<0.05 (Benjamini-Hochberg method) were categorized as differentially expressed genes (DEGs).

Figure 25L:
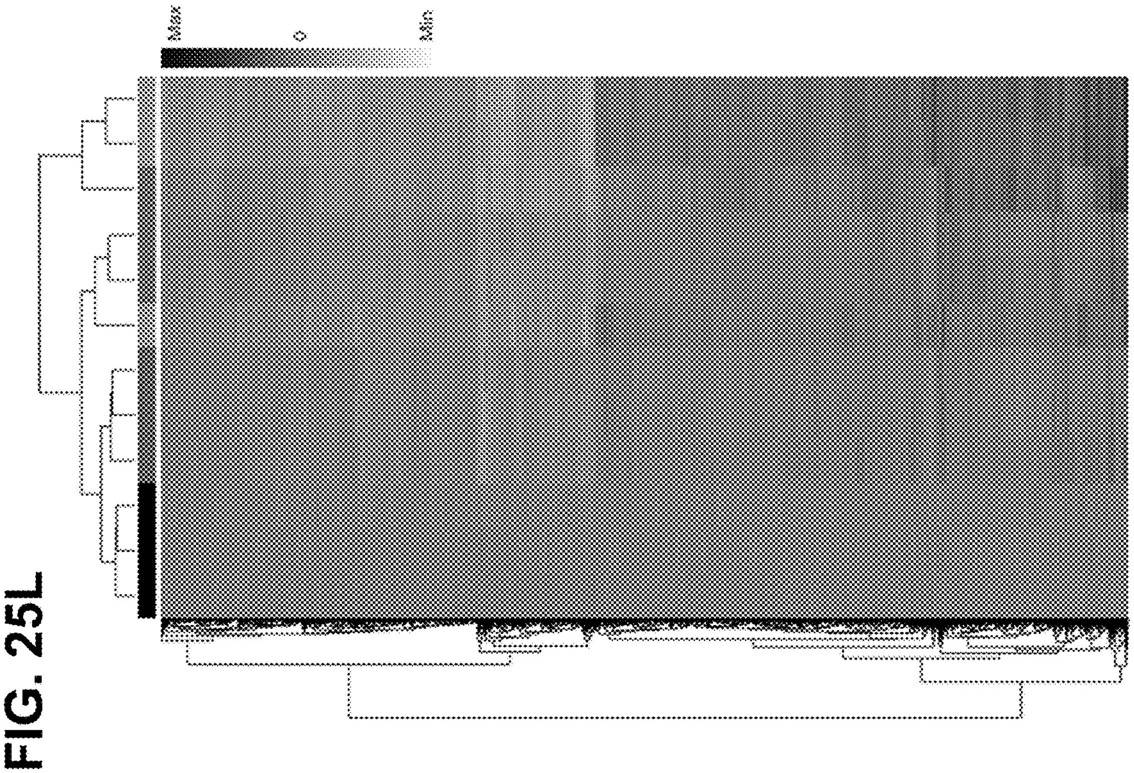
Figure 25M:
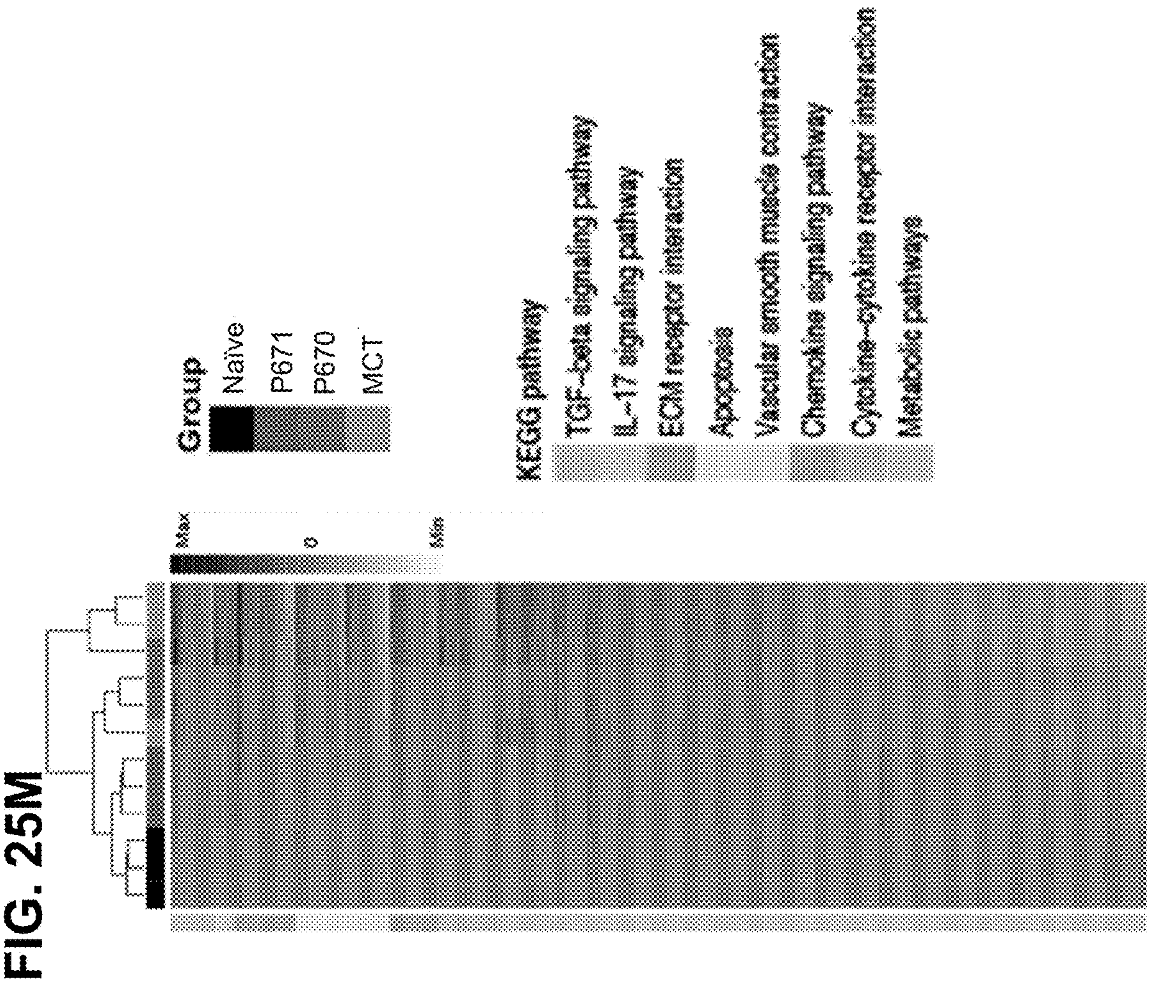

When looking at all DEGs (between naïve and MCT-vehicle groups; FIG. 25L), unbiased clustering showed that the P671-treated group clustered closer to the naïve group, while the P670-treated group clustered closer to the MCT-vehicle treated group. These data suggest that P671 had more pronounced reverse remodeling effects at the gene expression level compared to P670. Moreover, when specifically looking at given KEGG pathways (Kyoto Encyclopedia of Genes and Genomes, a reference database for pathway mapping) relevant to PAH pathophysiology (FIG. 25M), similar observations could be made: the P671-treated animals had a comparable heatmap signature to naïve animals, while P670-treated animals resembled more the MCT-vehicle animals.

Figure 25N:
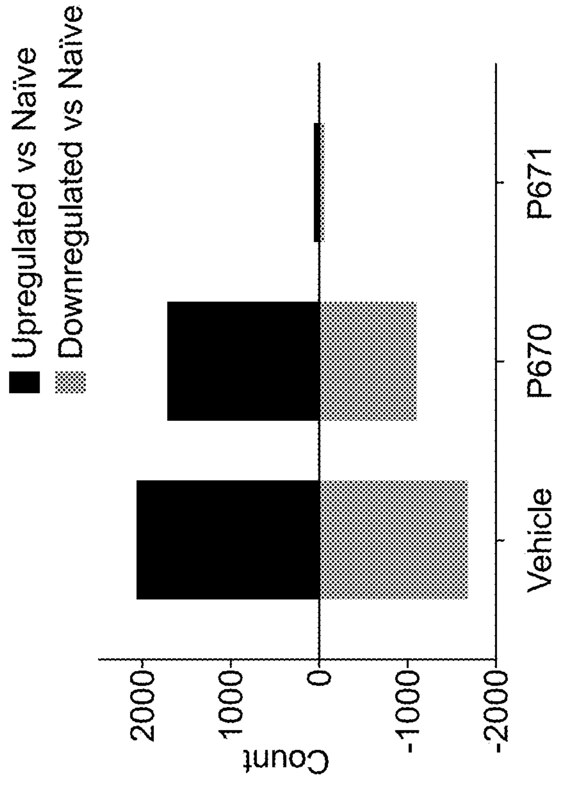
Figure 25O:
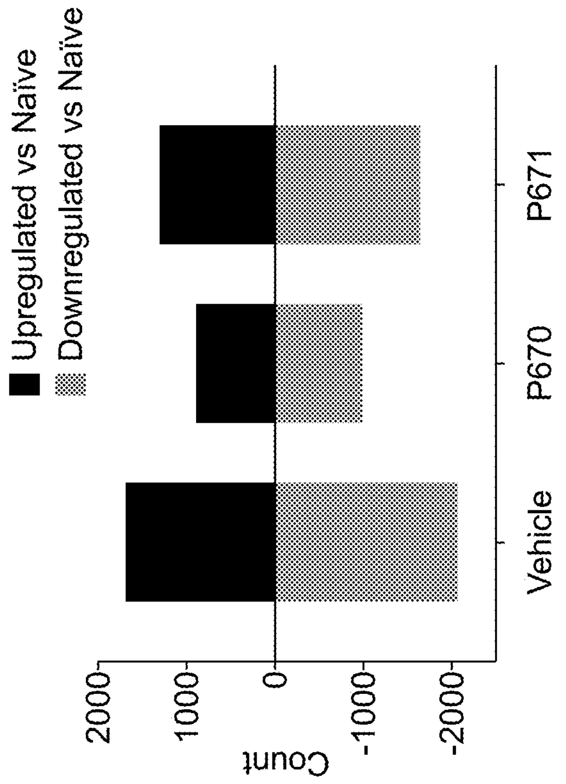

Furthermore, if using naïve animals as the reference group, MCT-treated animals displayed 2,068 upregulated and 1,687 downregulated genes in the RV (FIG. 25N). P670 had modest effects on this profile, with 1,720 upregulated and 1,103 downregulated genes relative to naïve animals (FIG. 25N). P671 displayed a near-complete rescue of the gene expression signature of MCT-treated animals, with only 58 upregulated and 60 downregulated genes relative to naïve animals (FIG. 25N). Similar conclusions are reached if using the MCT-vehicle group as the reference (FIG. 25O), with naïve and P671-treated animals showing the most differences with MCT-vehicle animals.

Taken together, these gene expression results again illustrate superior in vivo efficacy of the exemplary agent P671 (murine variant of P622) compared to ActRIIA-Fc (P670, the murine variant of P444). The results suggest that such exemplary agents may provide increased therapeutic benefit in patients.

To further understand the effect of exemplary agents P670, P671 and P674 on signaling pathways driving the MCT phenotype, volcano plots were generated displaying the genes associated with the top 8 KEGG terms known to be de-regulated in MCT treated animals (i.e., significantly up- or down-regulated relative to naïve). As shown in FIG. 35, P670 and P674 had only modest effects on MCT-driver genes, particularly genes related to the TGF-β pathway (e.g. TGF-β1, TGF-β2, Inhbb) and gene pathways related to heart failure (for example, Nppa, Nppb, Sppl). P671, conversely, normalized the expression levels of these pathways to near naïve levels. These data show that the superior in vitro potency profile of P671 relative to P674 translated into a surprisingly different in vivo pharmacological profile, i.e., P671 and P674 differentially affected pathways associated with TGF-β superfamily signaling and pathological conditions such as PH and heart failure. These results further underscore the potential therapeutic benefits of exemplary agents of the disclosure with respect to achieving improved inhibition of ligands and increased in vivo efficacy.

Example 6: Exemplary ActRIIB-ECD Polypeptide Constructs Efficiently Prevent Cytokine-Induced Changes in Gene Expression in a PAH-Relevant In Vitro Model Exemplary agents P444, P622, and P624 were examined in the context of a PAH-relevant cellular model. Primary human pulmonary arterial smooth muscle cells (PASMCs; Lonza CC-2581) were maintained in culture and treated with cytokines in the presence or absence of P444, P622, and P624. The next day, RNA was extracted to generate cDNA. mRNA expression levels of ACTA2, CTGF, and INHBA (which encodes the activin A subunit of dimeric activin and inhibin protein complexes) were assessed relative to GAPDH (which is a housekeeping gene).

ACTA2 and CTGF are two key genes reported to be highly inducible by Activins and GDFs in human PASMCs in vitro (Yung et al., 2020). Both genes are relevant to PAH as they are upregulated in preclinical PAH models and in PAH patients (Calvier et al., 2019; Li et al., 2016; Pi et al., 2018; Sevilla-Perez et al., 2008; Tam et al., 2021).

Figure 26A:
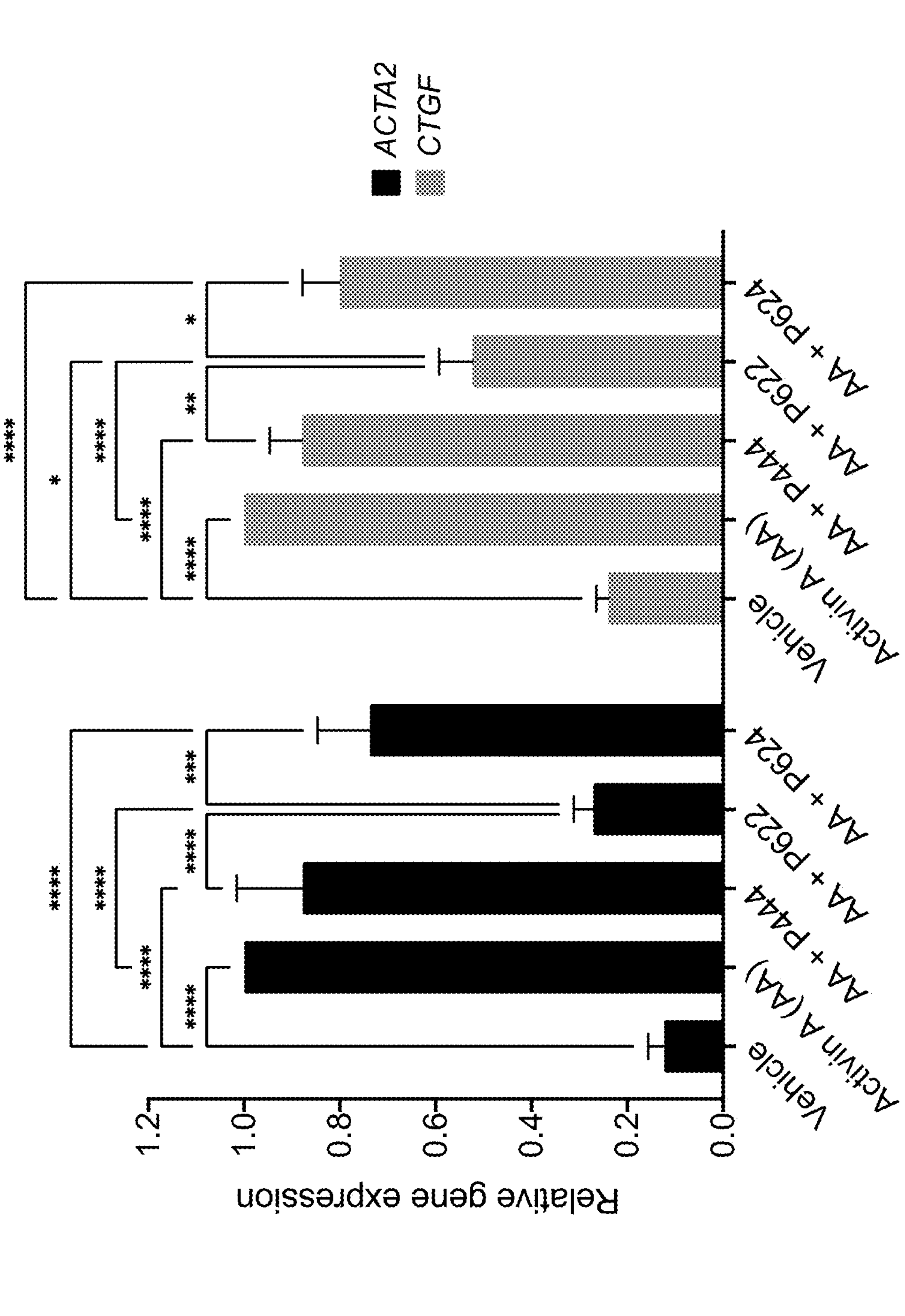
FIG. 26A-FIG. 26D shows the efficacy of P444, P622, and P624 in primary human pulmonary arterial smooth muscle cells (PASMCs). On day 1, 50,000 cells were seeded in growth medium in a 96-well plate. On day 2, exemplary agents (3.7 nM) were incubated with the cells in serum-free medium for 30 minutes, following which the relevant cytokine (50 ng/mL, except for activin AB at 25 ng/mL) was added.
Figure 26B:
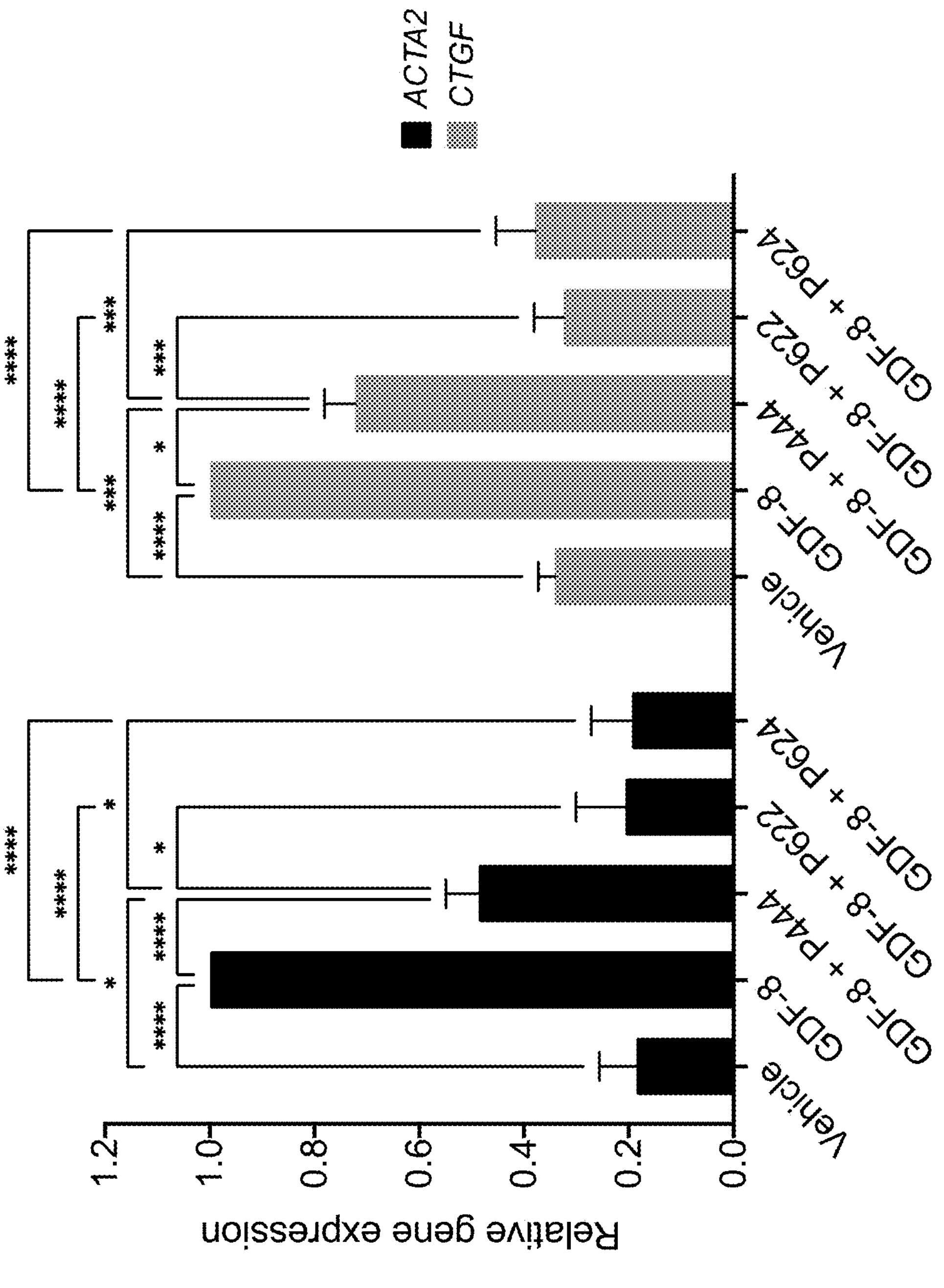
Figure 26C:
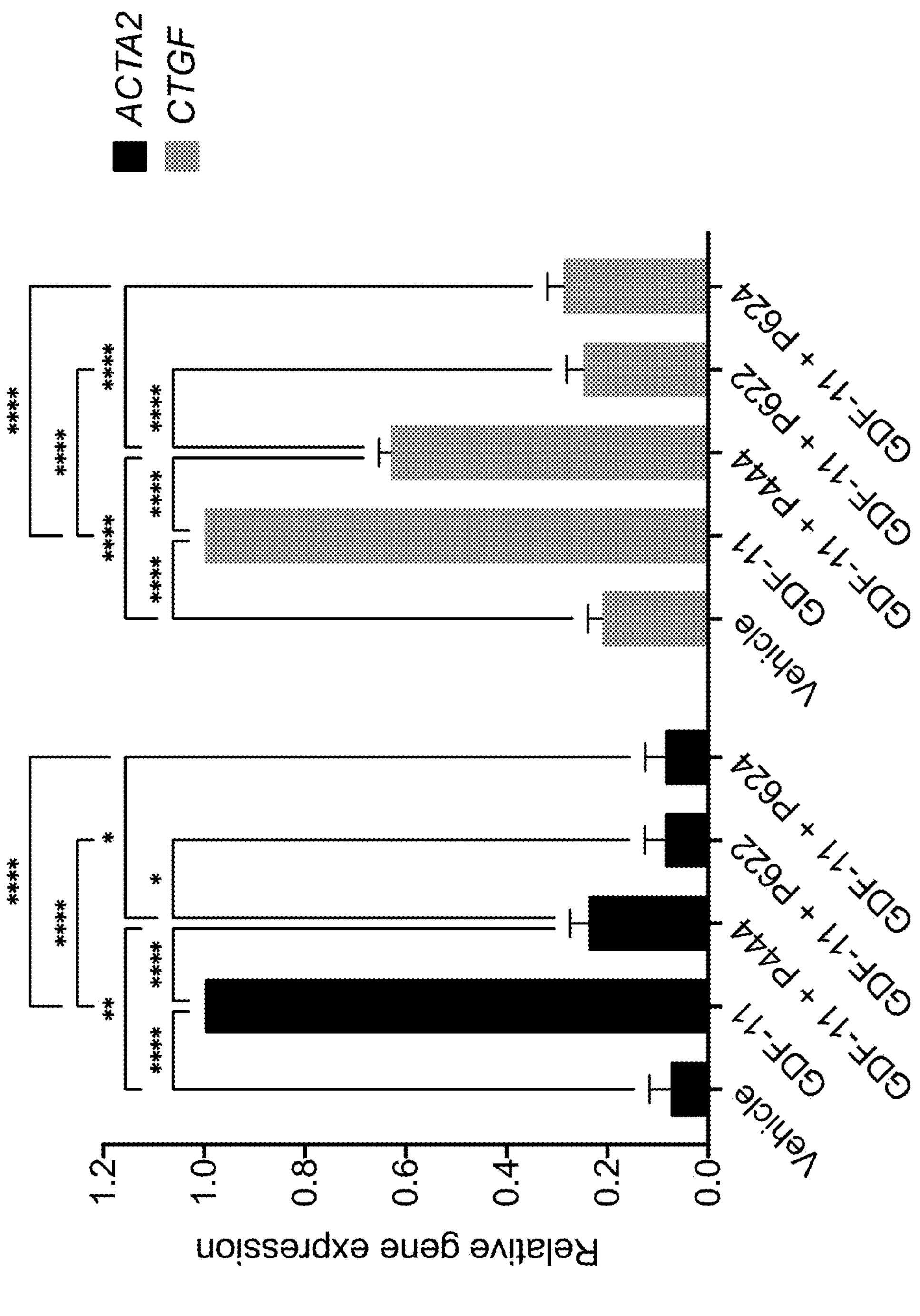
Figure 26D:
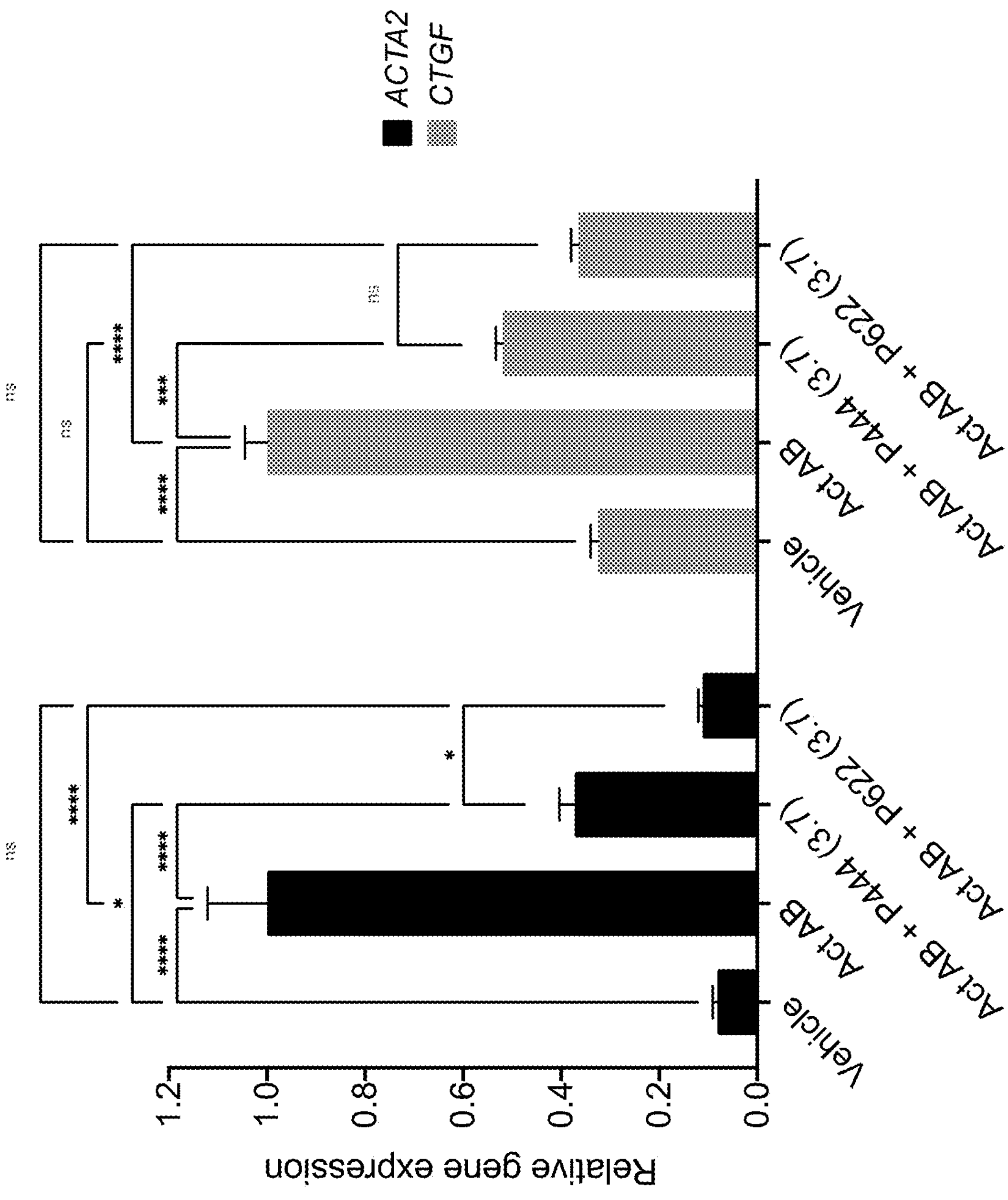
Figure 27B:
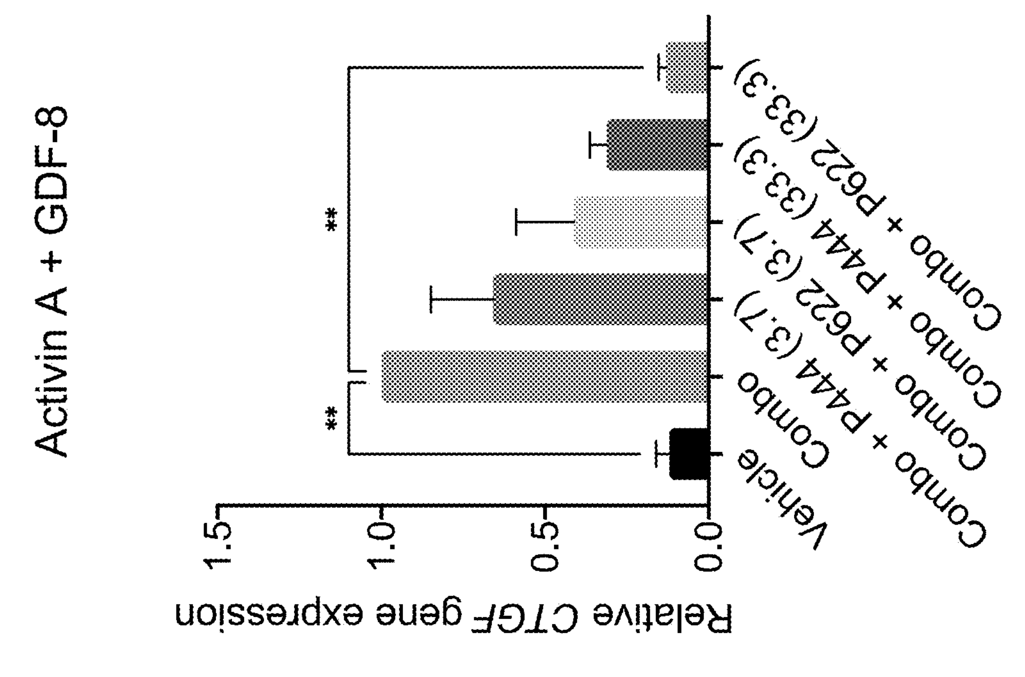
FIG. 27A-FIG. 27F shows the efficacy of P444 and P622 in primary human pulmonary arterial smooth muscle cells (PASMCs). On day 1, 50,000 cells were seeded in growth medium in a 96-well plate. On day 2, exemplary agents (3.7 or 33.3 nM) were incubated with the cells in serum-free medium for 30 minutes, following which the relevant cytokine combination (50 ng/mL per cytokine) was added.
Figure 27A:
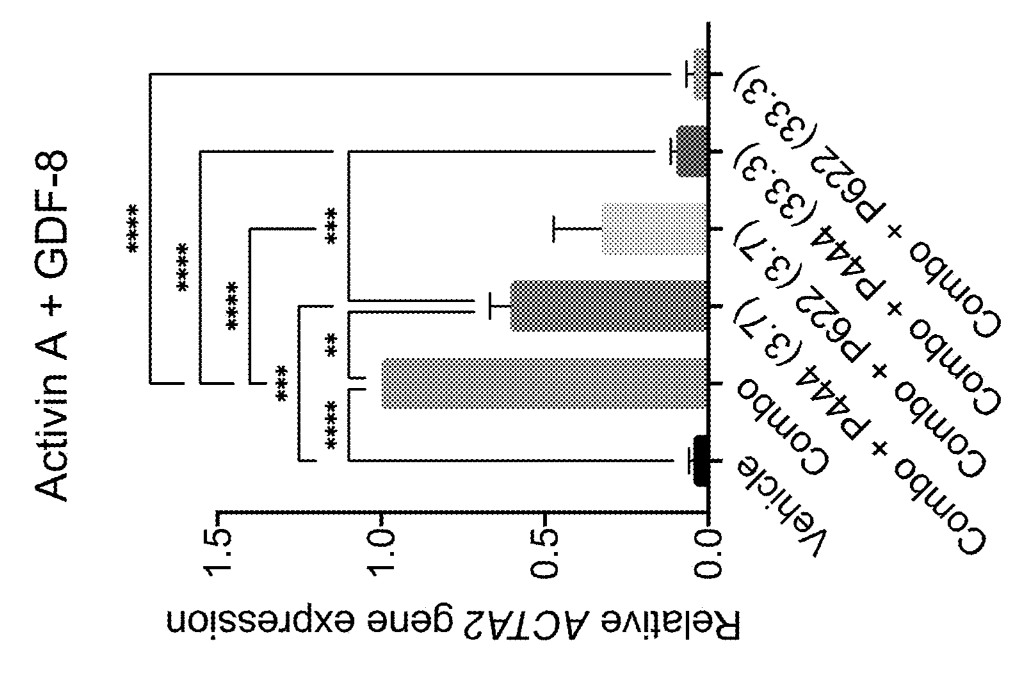
Figure 27D:
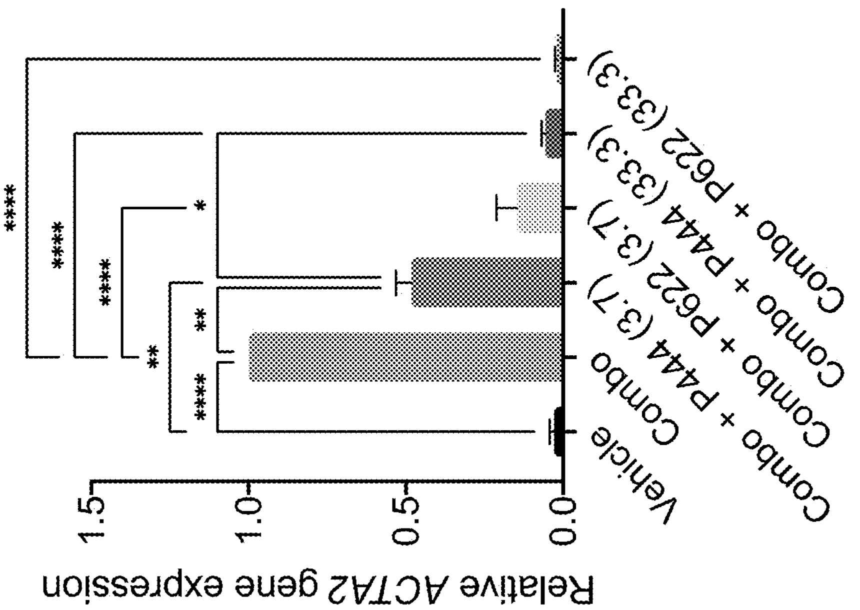
Figure 27C:
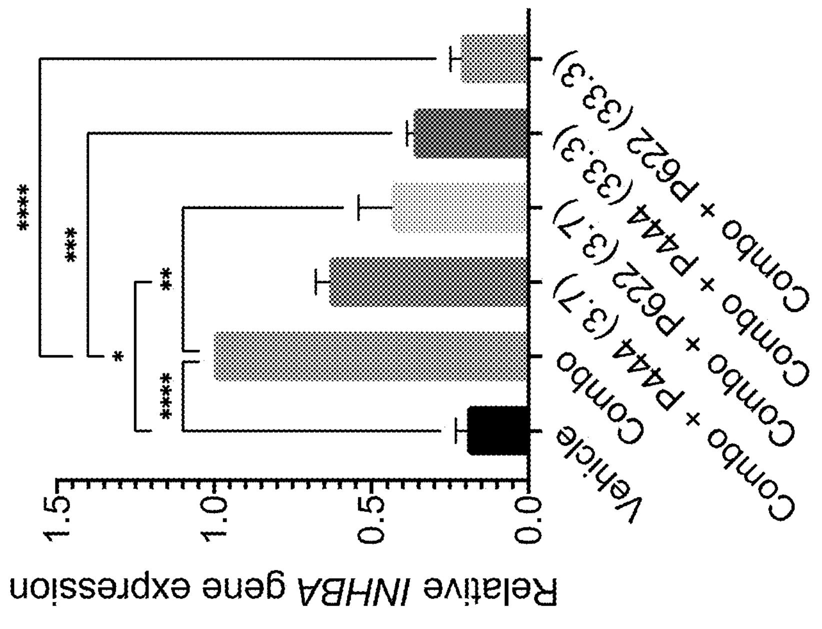
Figure 27E:
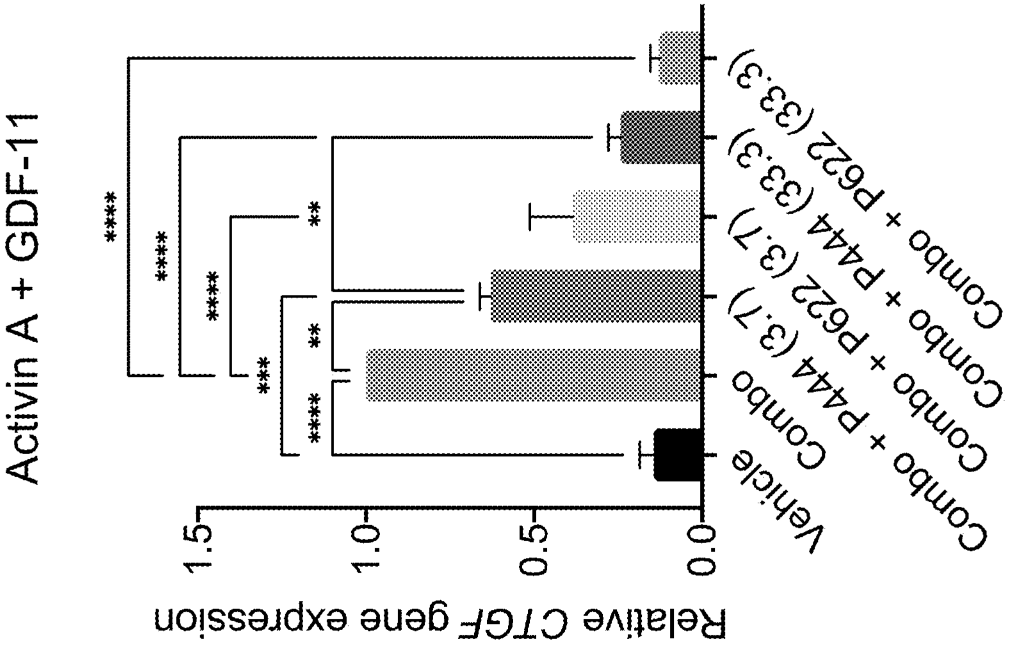
Figure 27F:
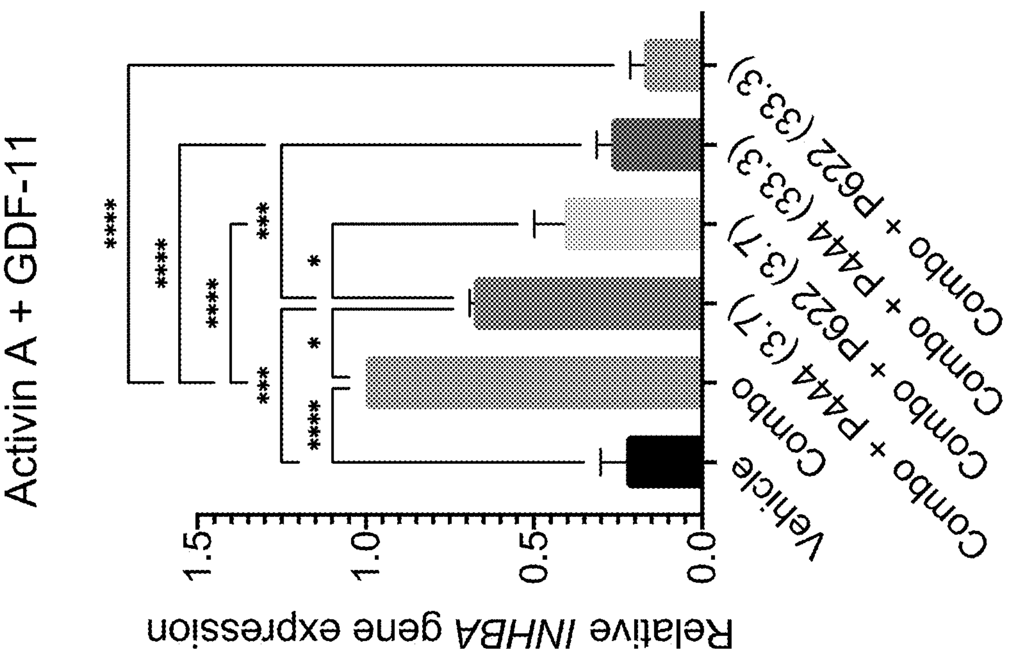

All cytokines tested (activin A, GDF-8, GDF-11, and activin AB) significantly induced ACTA2 and CTGF expression in PASMCs (FIGS. 26A-D). (Note activin AB is a heterodimer composed of an inhibin βA and an inhibin PB subunit, as compared to activin A, which is a homodimer of two inhibin βA subunits [INHBA], and activin B, which is a homodimer of two inhibin PB subunits [INHBB]). Induction of INHBA was not consistently assessed in these experiments, due to the modest induction observed (data not shown). P444 (3.7 nM) significantly reduced GDF-8-, GDF-11, and activin AB-induced ACTA2 and CTGF mRNA levels, although they were still higher compared to vehicle (FIGS. 26B-D). P444 did not significantly affect activin A-induced gene expression (FIG. 26A). On the other hand, P622 (3.7 nM) significantly inhibited activin A-, GDF-8-, GDF-11-, and activin AB-induced ACTA2 and CTGF mRNA levels, which were not significantly different from vehicle (FIGS. 26A-D) (activin A-induced CTGF expression, which was only partially inhibited by P622) (FIG. 26A). P624 was not as efficacious on activin A-induced gene expression compared to P622 (FIG. 26A), but had comparable effects on GDF-8- and GDF-11-induced gene expression (FIGS. 26B-C). These results are in agreement with those from cell-based reporter assays (see Example 1). These data further demonstrate that the longer linker used in P622 (relative to P624) is necessary to maximize potency on certain ligands such as activin A.

Figure 28A:
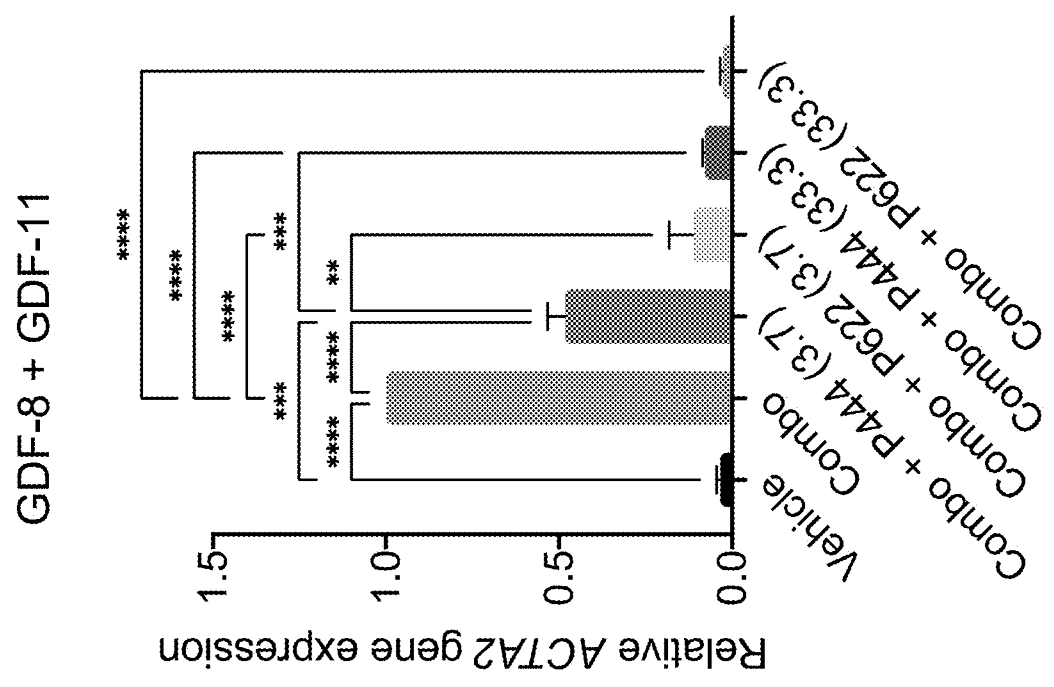
FIG. 28A-FIG. 28F shows the efficacy of P444 and P622 in primary human pulmonary arterial smooth muscle cells (PASMCs). On day 1, 50,000 cells were seeded in growth medium in a 96-well plate. On day 2, exemplary agents (3.7 or 33.3 nM) were incubated with the cells in serum-free medium for 30 minutes, following which the relevant cytokine combination (50 ng/mL per cytokine) was added.
Figure 28B:
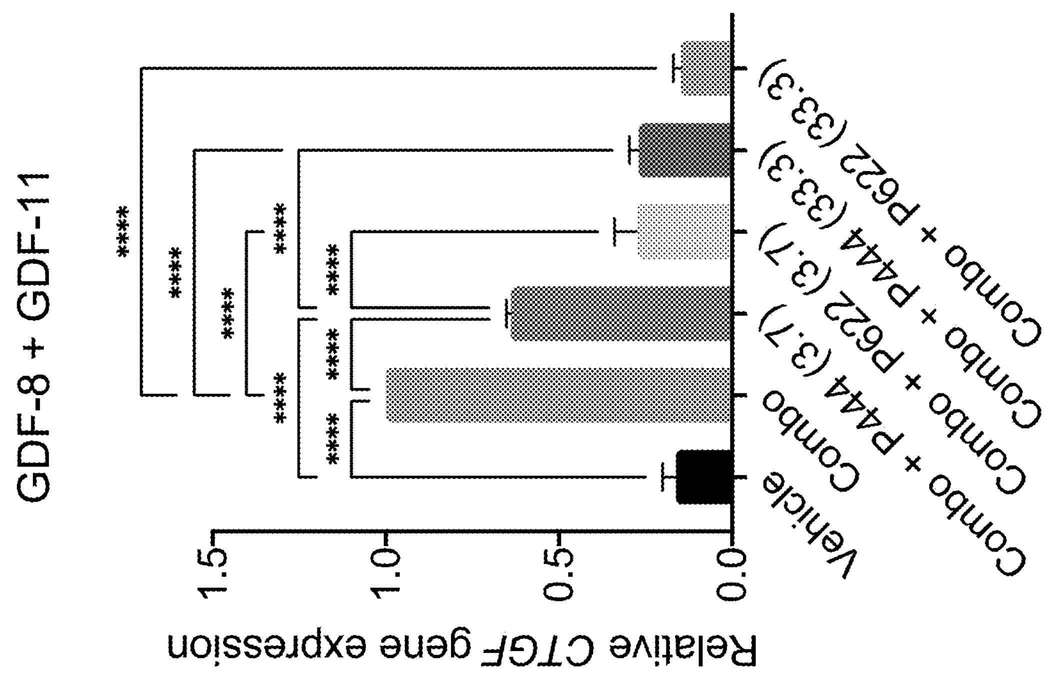
Figure 28D:
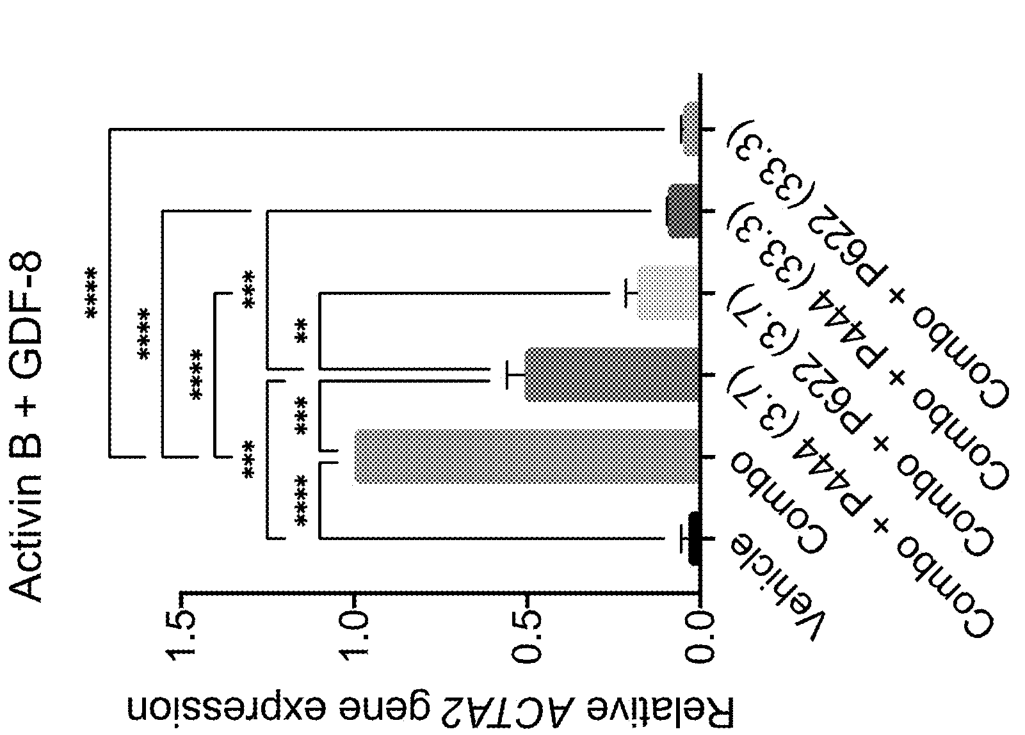
Figure 28C:
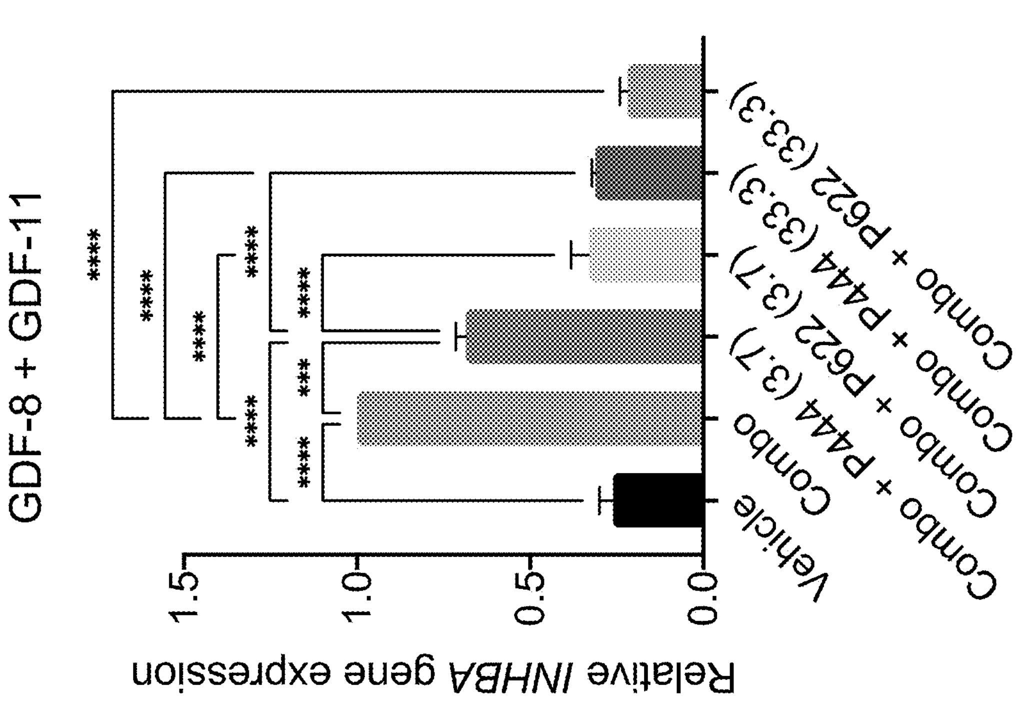
Figure 28E:
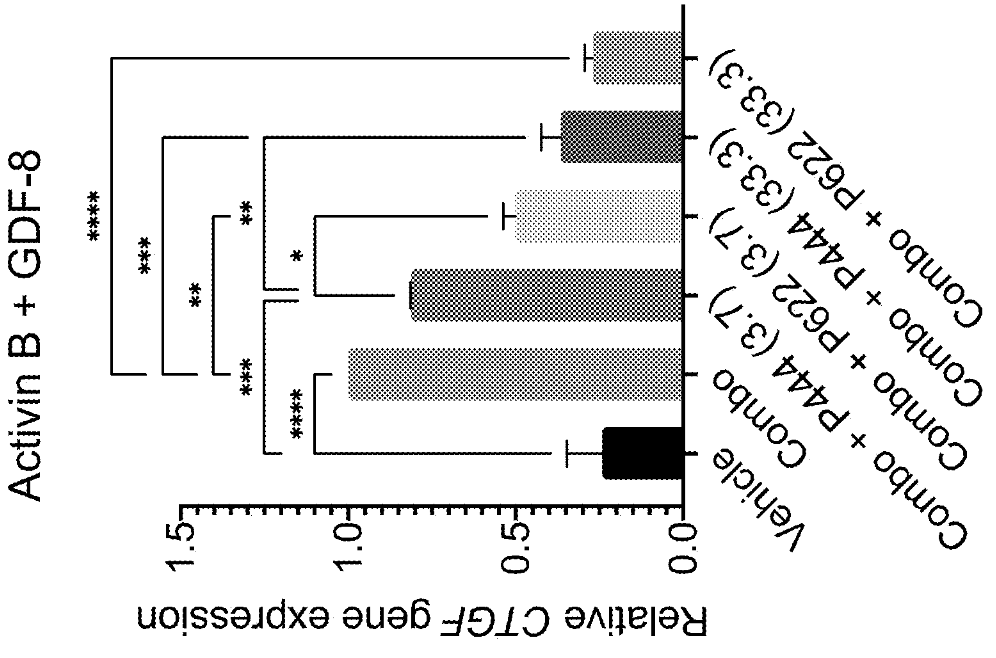
Figure 28F:
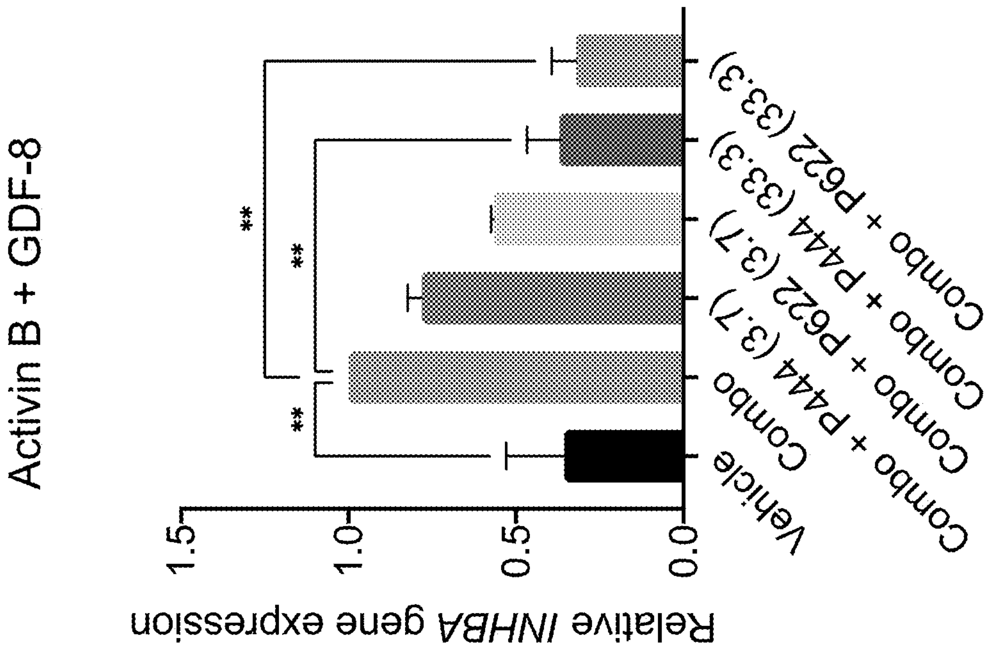

Similar experiments were conducted using cytokine combinations: a) activin A+GDF-8 (FIGS. 27A-C), b) activin A+GDF-11 (FIGS. 27D-F), c) GDF-8+GDF-11 (FIGS. 28A-C), and d) activin B+GDF-8 (FIGS. 28D-F). For these experiments, two different concentrations of P444 and P622 were used (3.7 and 33.3 nM). On average, P622 at 3.7 nM consistently reduced induction of ACTA2, CTGF, and INHBA more than P444 at the same concentration, for any combination of cytokines tested (FIGS. 27 and 28). At 33.3 nM, the two agents were comparable to each other and significantly reduced induction, yielding expression levels similar to vehicle-treated conditions.

These results demonstrate that P622, which harbors a single amino acid mutation in the ActRIIB ECD, was efficacious in inhibiting induction of disease-relevant gene targets in a relevant PAH-related cellular system in vitro. These data also illustrate the superiority of P622 over P444 in this context, whether cytokines were used alone or in combination.

Figure 29B:
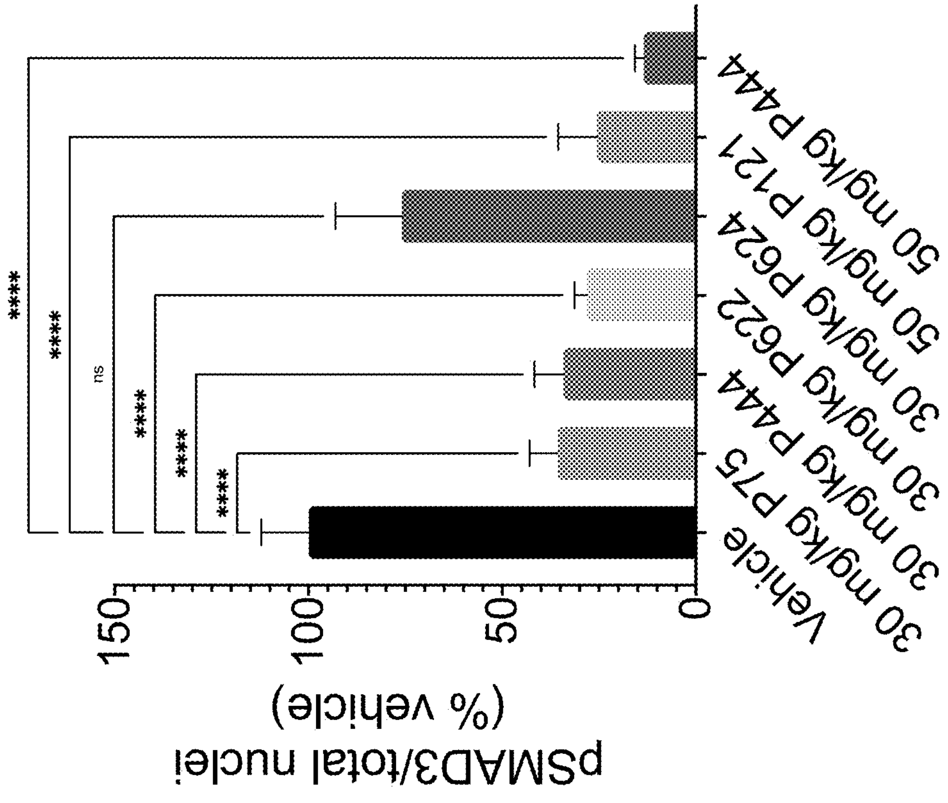
FIG. 29A-FIG. 29C shows the efficacy of exemplary agents P75, P121, P444, P622, and P624 (30 and/or 50 mg/kg) in vivo. 6-8 week-old male mice were injected with exemplary agents, and lungs were collected 4 days later, and fixed in neutral buffered formalin.
Figure 29A:
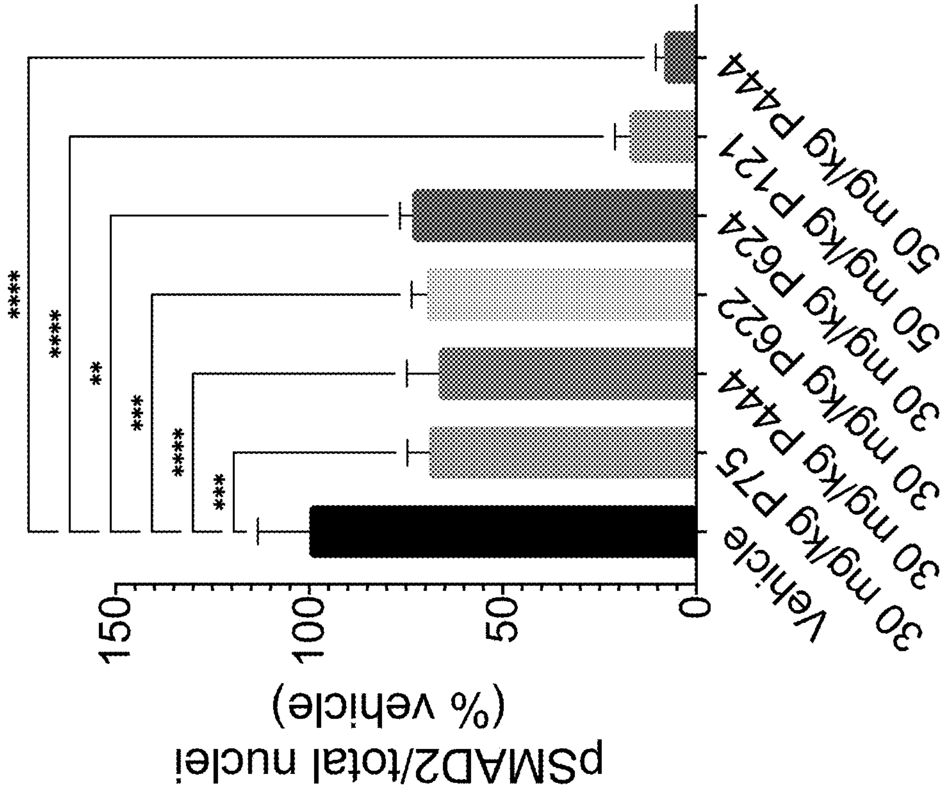
Figure 29C:
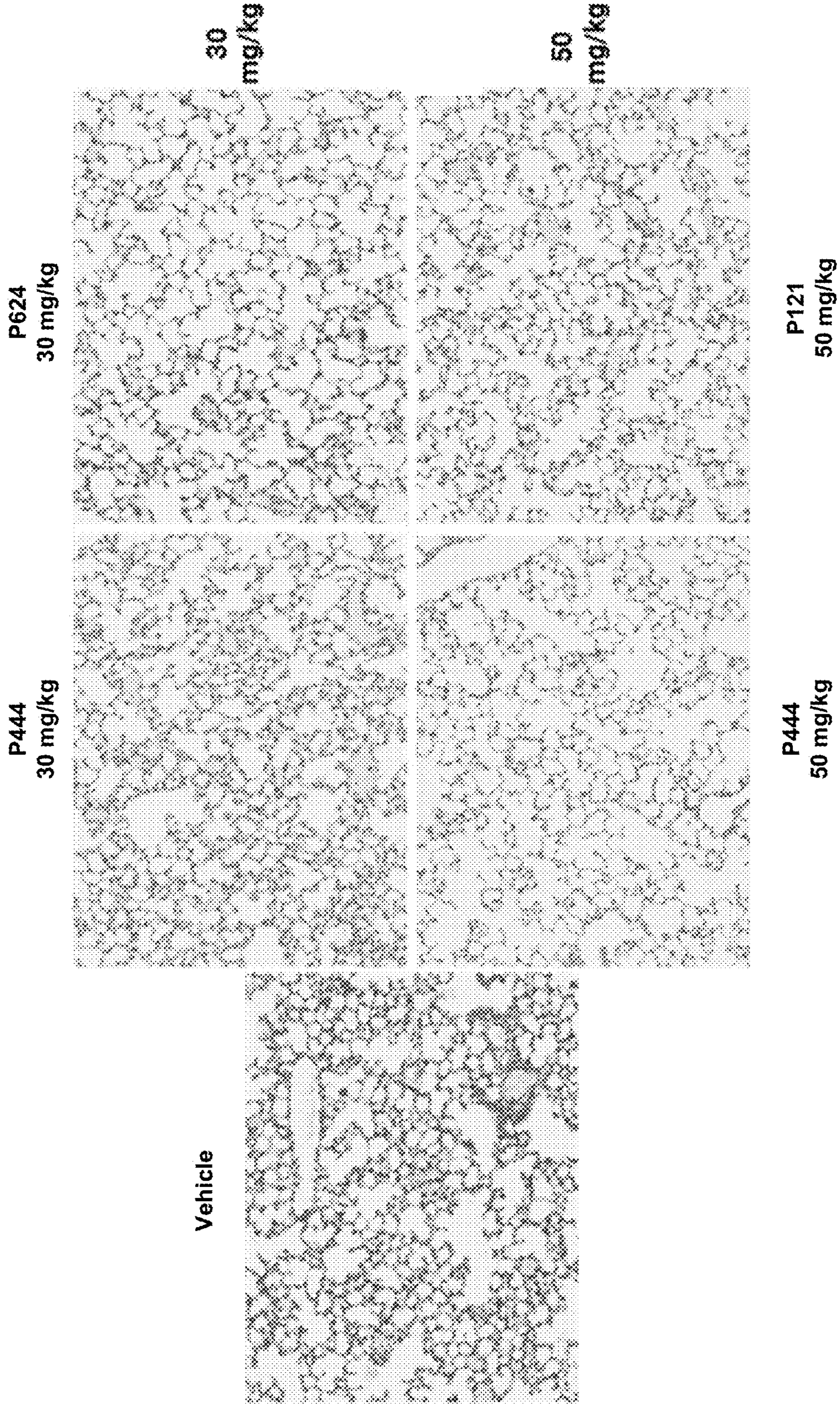

Example 7: Exemplary ActRIIB-ECD Polypeptide Constructs Decrease SMAD Phosphorylation and TGF-β-Related Gene Expression Levels To test whether the ActRIIB-ECD polypeptide constructs can engage their targets in a relevant tissue (e.g., lung), exemplary agents P75, P121, P444, P622, and P624 were injected in mice at concentrations of 30 and/or 50 mg/kg. Four days after a single injection, a dose-dependent decrease in both phosphorylated SMAD2 (pSMAD2; FIG. 29A) and SMAD3 (pSMAD3; FIG. 29B-C) levels was observed in murine lungs. At each respective dose, all test agents were comparable except, surprisingly, for P624 on pSMAD3 at 30 mg/kg (FIG. 29B). These data further indicate that the superior potency profile exhibited by P622 relative to P624 is necessary to carry out maximal target engagement in vivo.

Figure 30B:
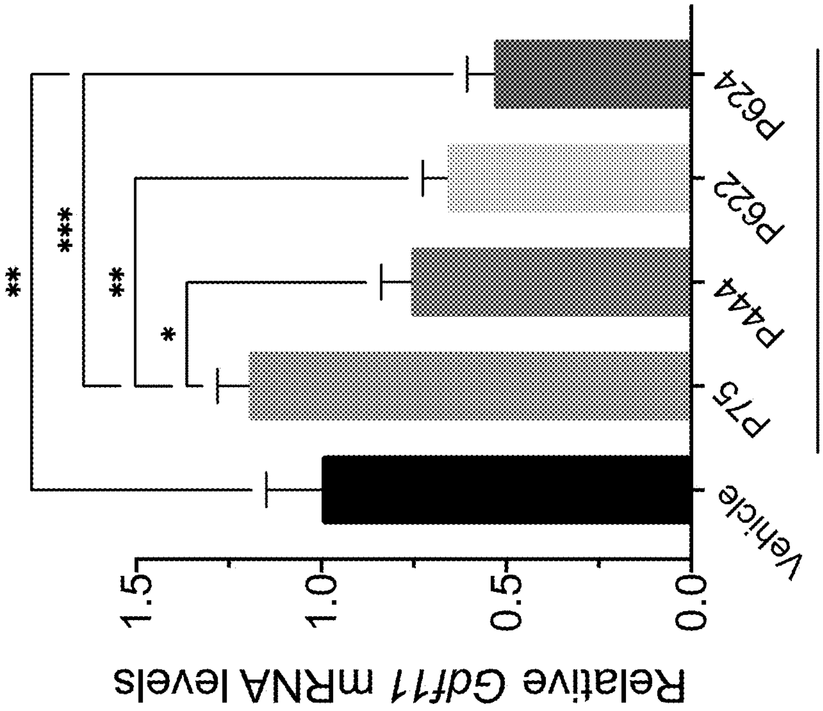
FIG. 30A-FIG. 30C shows the efficacy of exemplary agents P75, P444, P622, and P624 (30 mg/kg) in vivo. 6-8 week-old male mice were injected with exemplary agents, and lungs were collected 4 days later, and RNA was extracted for RT-qPCR analyses.
Figure 30A:
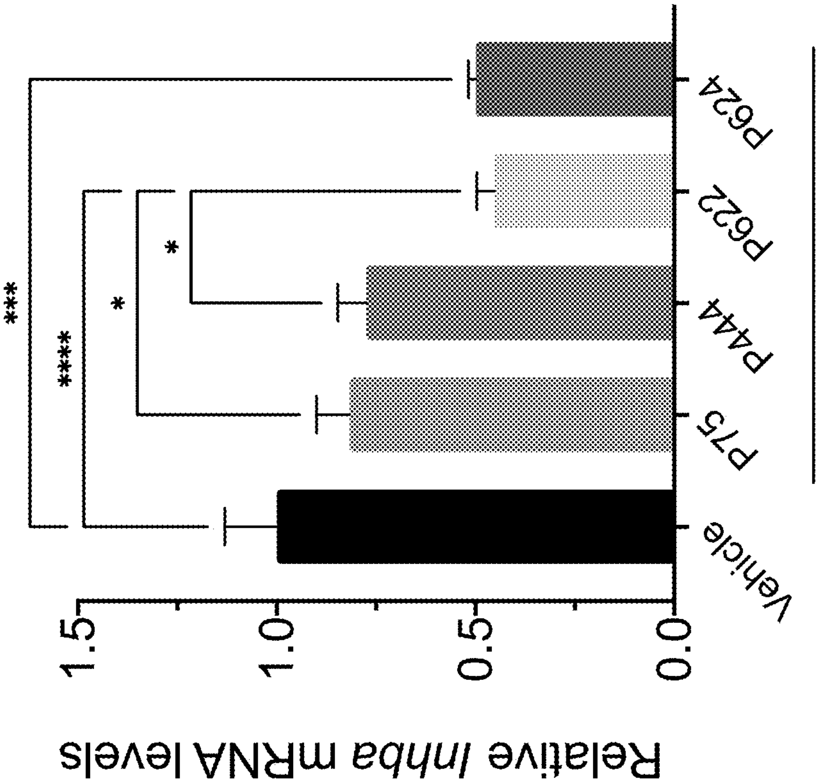
Figure 30C:
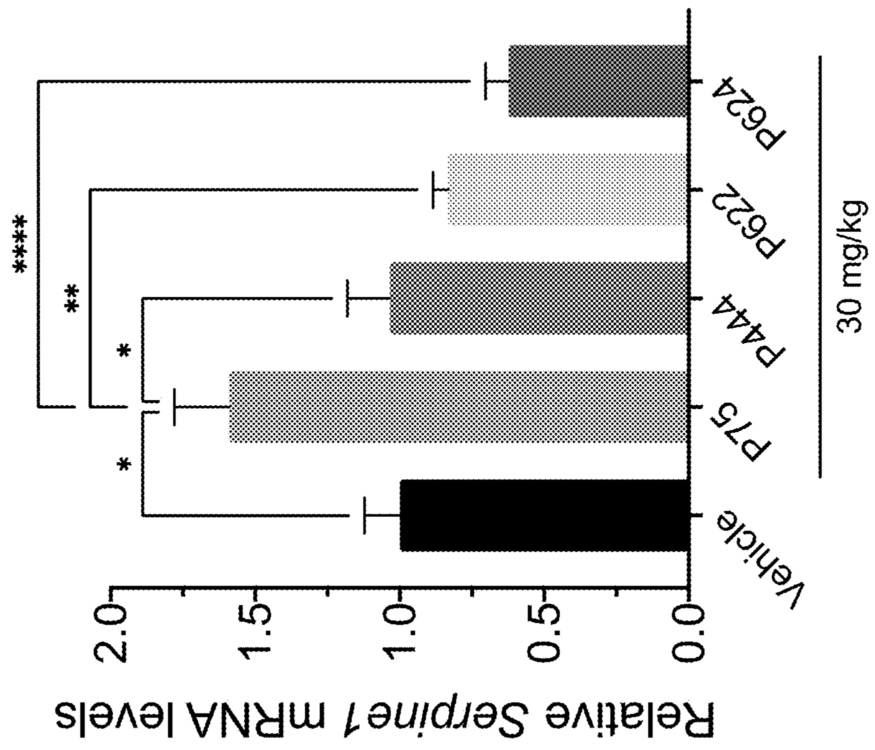

In addition, gene expression levels were assessed in murine lungs 4 days following injection of 30 mg/kg of exemplary agents P75, P444, P622, and P624 (FIG. 30). Both P622 and P624, but neither P75 nor P444, significantly reduced Inhba gene expression levels relative to vehicle (FIG. 30A). Moreover, P624 significantly decreased Gdfl1 gene expression levels relative to vehicle (FIG. 30B), and P622 displayed similar trends. None of the exemplary agents significantly affected Serpine1 mRNA levels relative to vehicle (FIG. 30C).

These results demonstrate that P121, P622, and P624, which include a mutated ActRIIB ECD, displayed signs of target engagement in a disease-relevant tissue (lung). Notably, P622 and P624 were superior to P75 and P444 in inhibiting Inhba gene expression. This result shows that, in addition to neutralizing activin A ligand more potently than P75 and P44, P622 and P624 reduce endogenous activin A gene expression in vivo more efficaciously than P75 and P444.

Example 8: Exemplary ActRIIB-ECD Polypeptide Constructs Successfully Engage Activins and GDFs In Vivo and Demonstrate Superior Potency Wild-type C57BL/6 male mice (8-10 weeks of age) were injected subcutaneously twice weekly for three weeks with exemplary test agents P75, P444, P622 and P624 at doses of 1, 3, 10, 25, or 50 mg/kg. Body weights were recorded in all animals twice weekly, and muscles (gastrocnemius and tibialis anterior), plasma, and pituitary gland were collected at the end of the study.

Figure 31A:
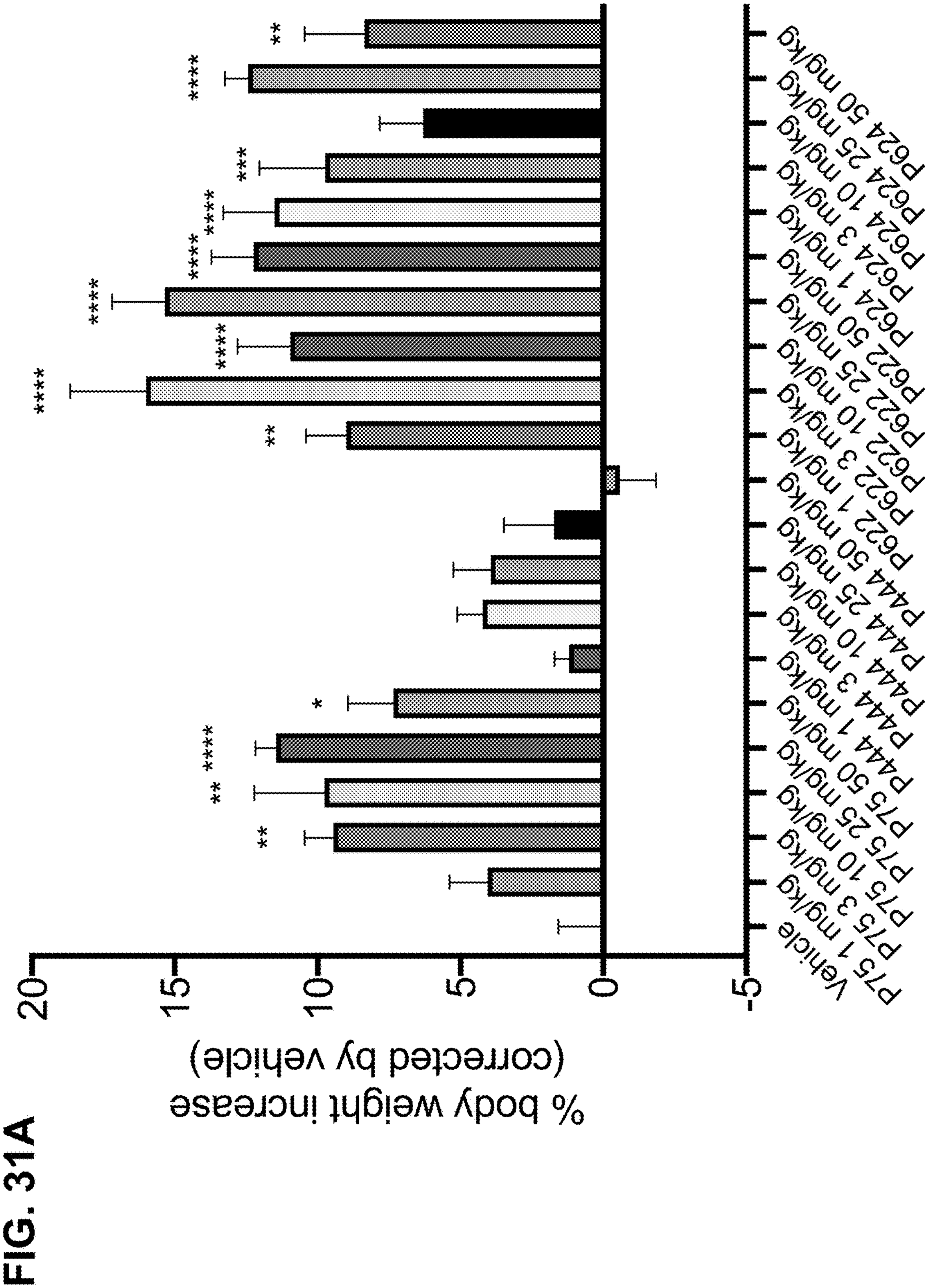
FIG. 31A-FIG. 31E shows the efficacy of exemplary agents P75, P444, P622, and P624 (1, 3, 10, 25, and 50 mg/kg) in vivo. Wild-type C57BL/6 male mice were injected with vehicle or exemplary agents twice weekly (subcutaneously), and body weights, organs, and plasma were collected 21 days later.
Figure 31B:
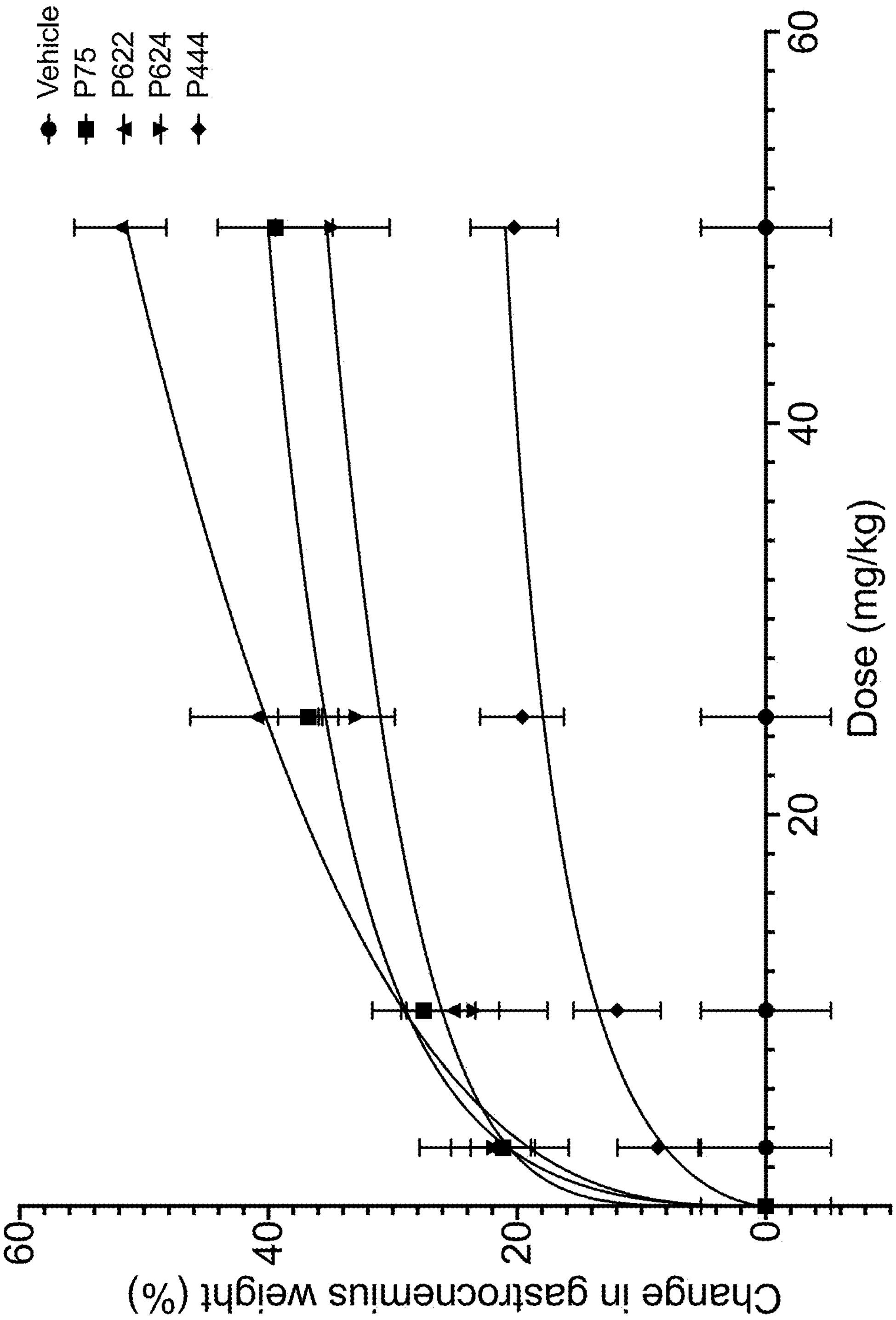
Figure 31C:
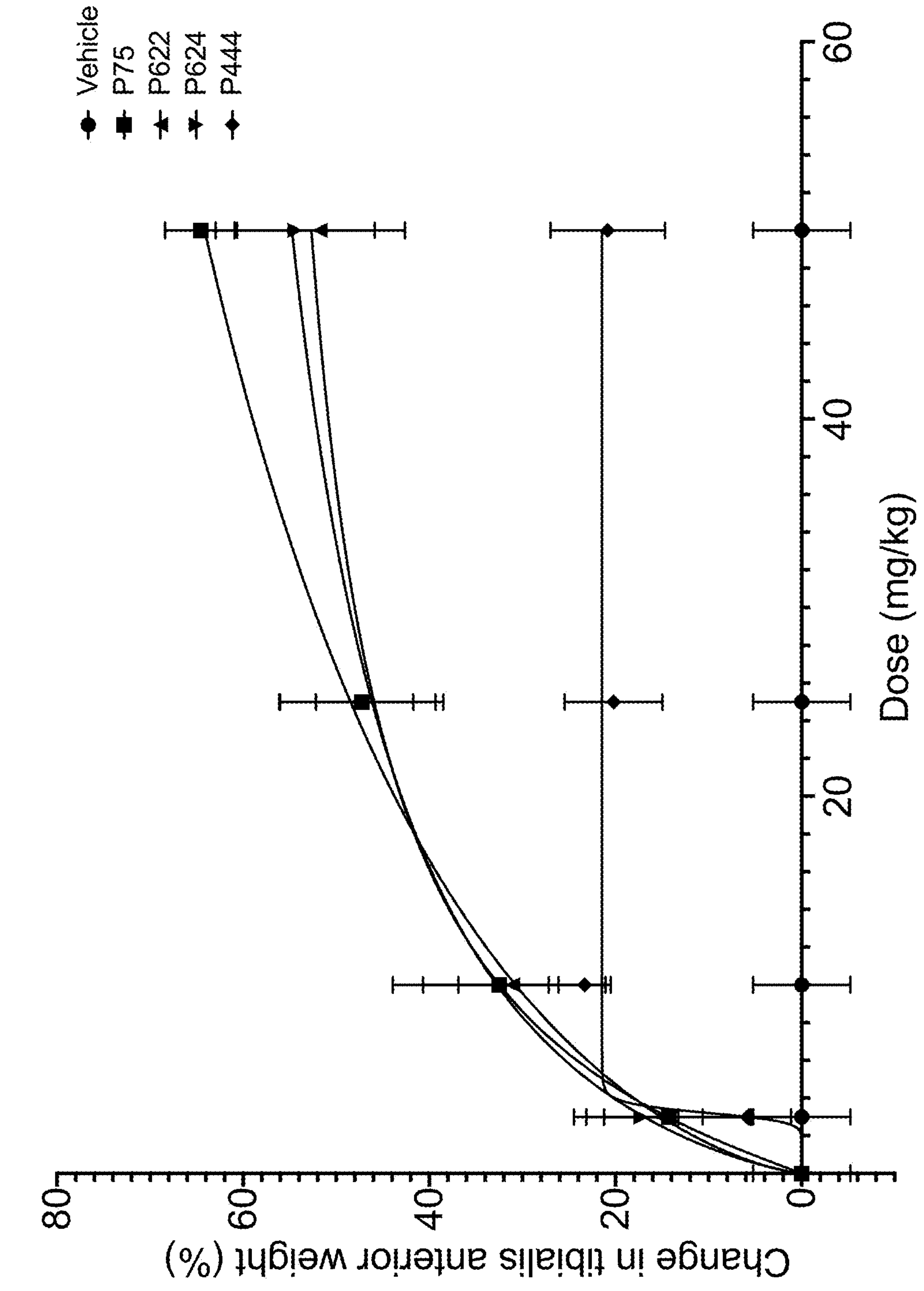

P75 caused an increase in whole body weight (FIG. 31A) and induced muscle hypertrophy (FIGS. 31B-C) at doses of 3 mg/kg and higher. P444 (ActRIIA-Fc) did not have any significant effect on whole body weight, up to 50 mg/kg (FIG. 31A), while it significantly induced muscle hypertrophy at doses of 25 and 50 mg/kg (FIGS. 31B-C). Both P622 and P624 had significant effects on whole body weight including at the lowest dose tested (1 mg/kg; FIG. 31A), as well as on muscle weights at 3 mg/kg and above (FIGS. 31B-C). As was observed in other in vivo efficacy studies, P622 demonstrated overall greater efficacy on whole body weights (FIG. 31A) and gastrocnemius hypertrophy (FIG. 31B) relative to P75 and P624. These data confirm the advantage of a longer linker sequence between the ActRIIB ECD and the Fc domain as in exemplary agent P622.

Figure 31D:
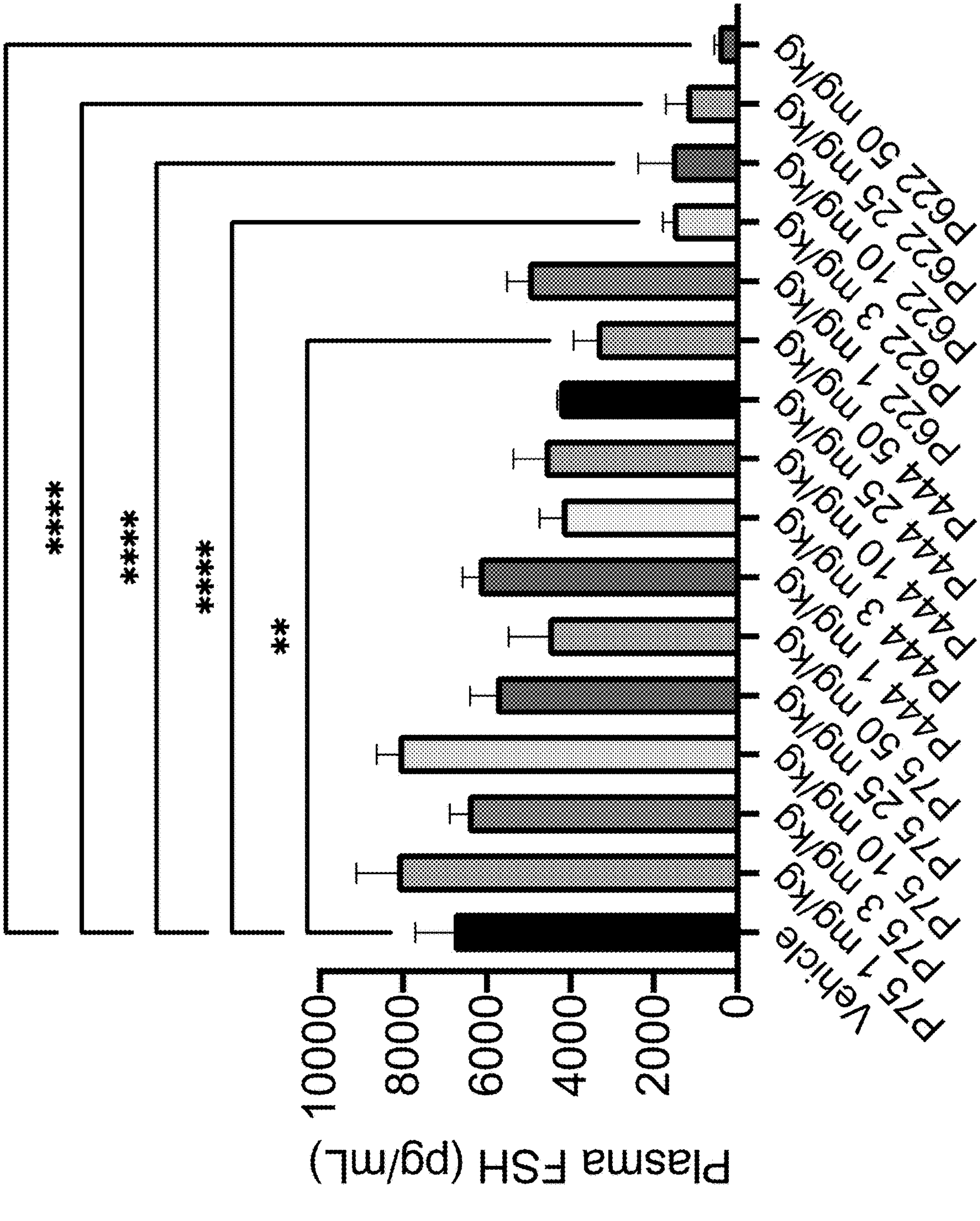
Figure 31E:
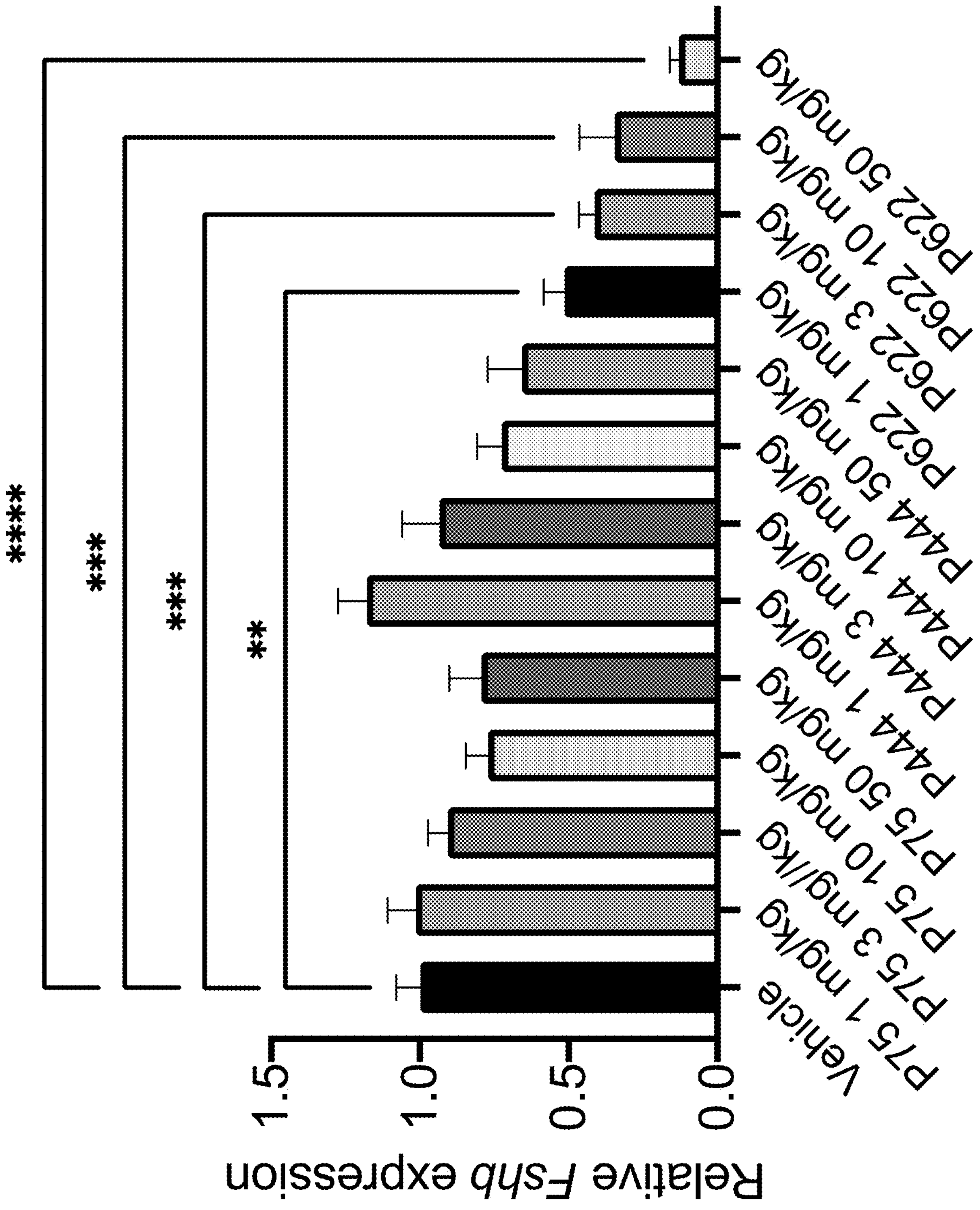

Reductions in plasma follicle stimulating hormone (FSH) levels have been observed following administration of ActRIIA-Fc, ActRIIB-Fc and bimagrumab in humans (Garito et al., 2018; Ruckle et al., 2009; Attie et al., 2013) which has been linked to inhibition of Activin signalling. The effect on plasma FSH levels was examined in mice following administration of exemplary agents. P75 had no significant effects on plasma FSH levels (FIG. 31D) or pituitary Fshb (encoding the FSHβ subunit) mRNA levels (FIG. 31E). P444 significantly decreased plasma FSH levels at 50 mg/kg (~50% decrease; FIG. 31D) but had no significant effect on Fshb mRNA levels (FIG. 31E). P622 significantly decreased plasma FSH levels at doses of 3 mg/kg and higher (FIG. 31D), reaching an ~93% decrease in FSH level at 50 mg/kg compared to control. P622 also decreased pituitary Fshb mRNA levels at doses as low as 1 mg/kg (FIG. 31E).

The exposure-target engagement relationship of P622, P75, and P444 was further investigated by correlating reductions in plasma FSH and pituitary Fshb expression with the corresponding exposure (area under the curve [AUC] of the respective agent in each animal). Exposure analysis was performed by non-compartmental analysis (NCA) using the WinNonlin Software (Cetera, Princeton, NJ). The exposure was calculated from the complete PK profiles for each test article and dose level over the course of the study. All animals were included in this analysis.

For each exemplary agent, a model comparison analysis between linear regression and 4-parameter logarithmic regression was conducted (GraphPad Prism 9.0) using Akaike's Information Criterion (AICc). The vehicle group was set at 1 (+/−SEM at x=0), and each regression was constrained to cross that point. The model that best fit the data was chosen for a given readout.

Figure 32A:
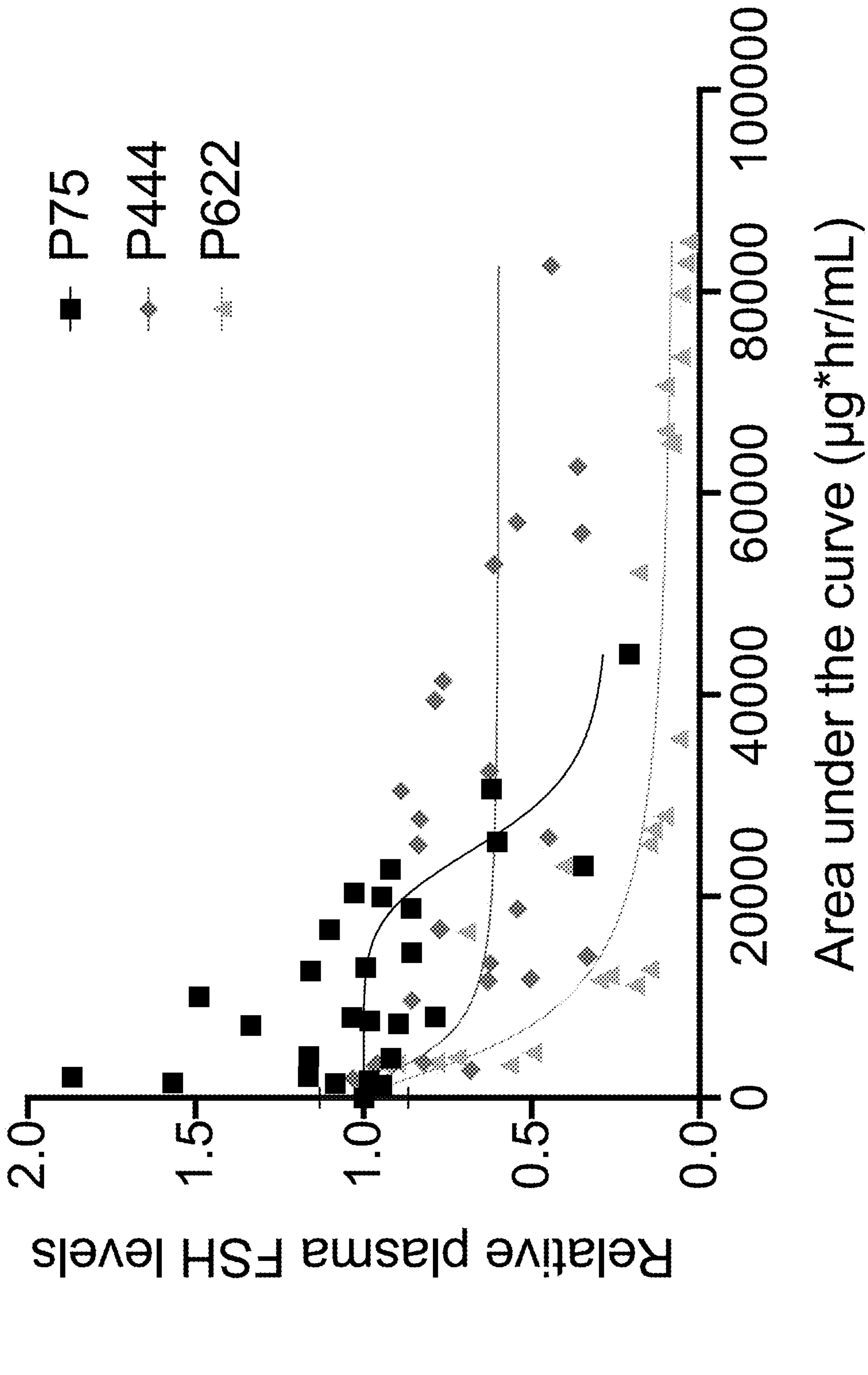
FIG. 32A-FIG. 32B shows the efficacy of exemplary agents P75, P444, and P622 in vivo in relation to the exposure of each animal. (A-B) Data from FIGS. 31D-E were plotted against the exposure of each animal (area under the curve [AUC]), and a linear or non-linear fit was plotted using GraphPad Prism 9.0.
Figure 32B:
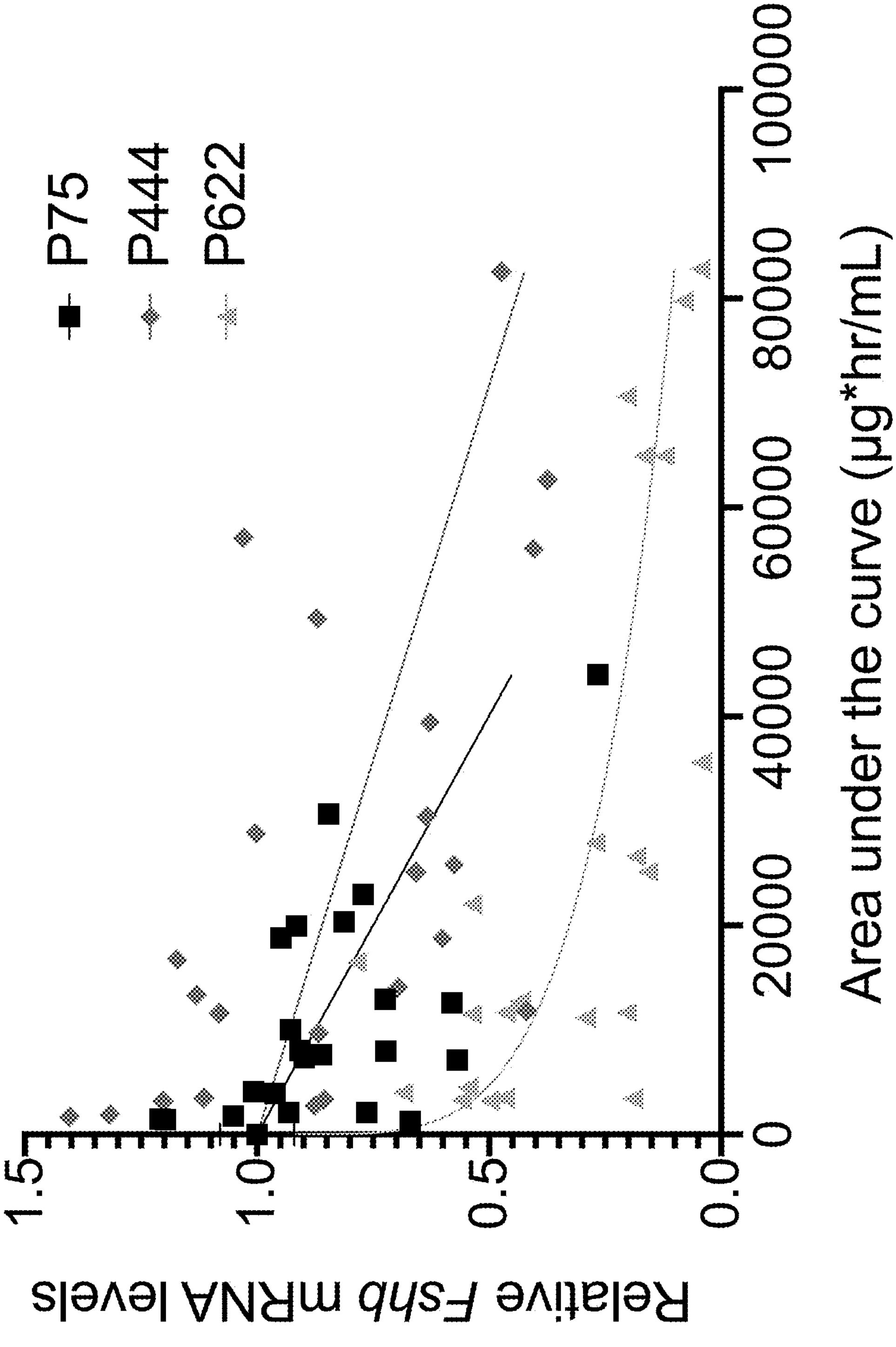

P622 at similar exposures to P75 and P444 induced a greater decrease in FSH levels and Fshb mRNA levels (FIGS. 32A-B) reaching an overall lower plateau which corresponds to near total suppression of FSH at both the plasma protein and gene expression level.

Overall, these data indicate that P622 successfully engaged the relevant TGF-β superfamily members in a dose-dependent fashion in vivo and demonstrated superior potency compared to P75 and P444.

Figure 33A:
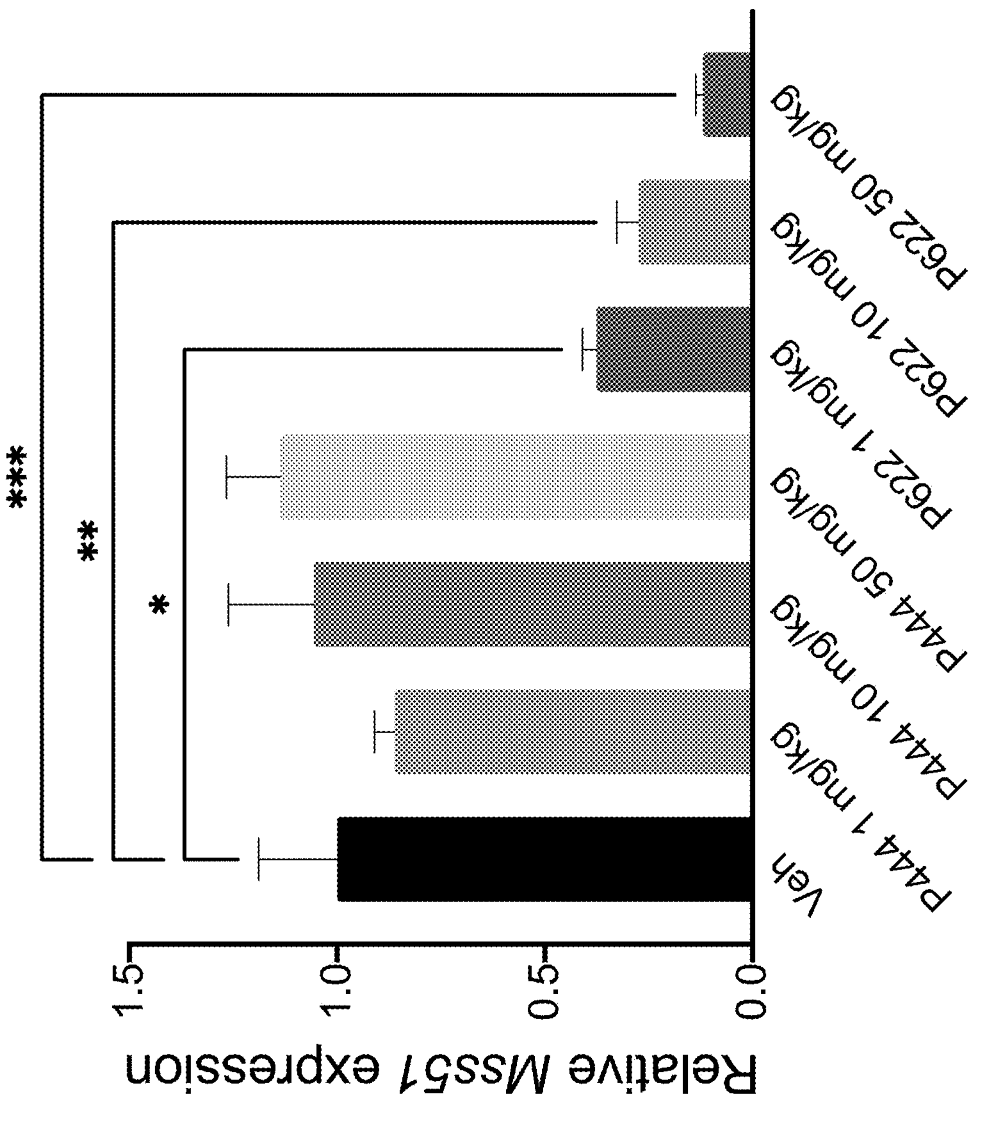
FIG. 33A-FIG. 33B shows the efficacy of exemplary agents P444 and P622 (1, 10, and 50 mg/kg) in vivo. Wild-type C57BL/6 male mice were injected with vehicle or exemplary agents twice weekly (subcutaneously), and muscle tissues were collected 21 days later. (A-B) Mss51 and Igf2 expression levels in right gastrocnemius. Tissues were snap-frozen after collection and lysed using the gentleMACS™ Octo Dissociator (Miltenyi Biotech). RNA was extracted and reverse transcribed, and gene expression was assessed by qPCR as per manufacturer's instructions (Qiagen). Actb, Gapdh, and Rpl13 were used as housekeeping genes. Error bars indicate standard error of the mean (SEM). Results were analyzed by one-way ANOVA followed by post-hoc Bonferroni-corrected multiple comparison test. *$p<0.05$, $p<0.01$, *$p<0.001$.
Figure 33B:
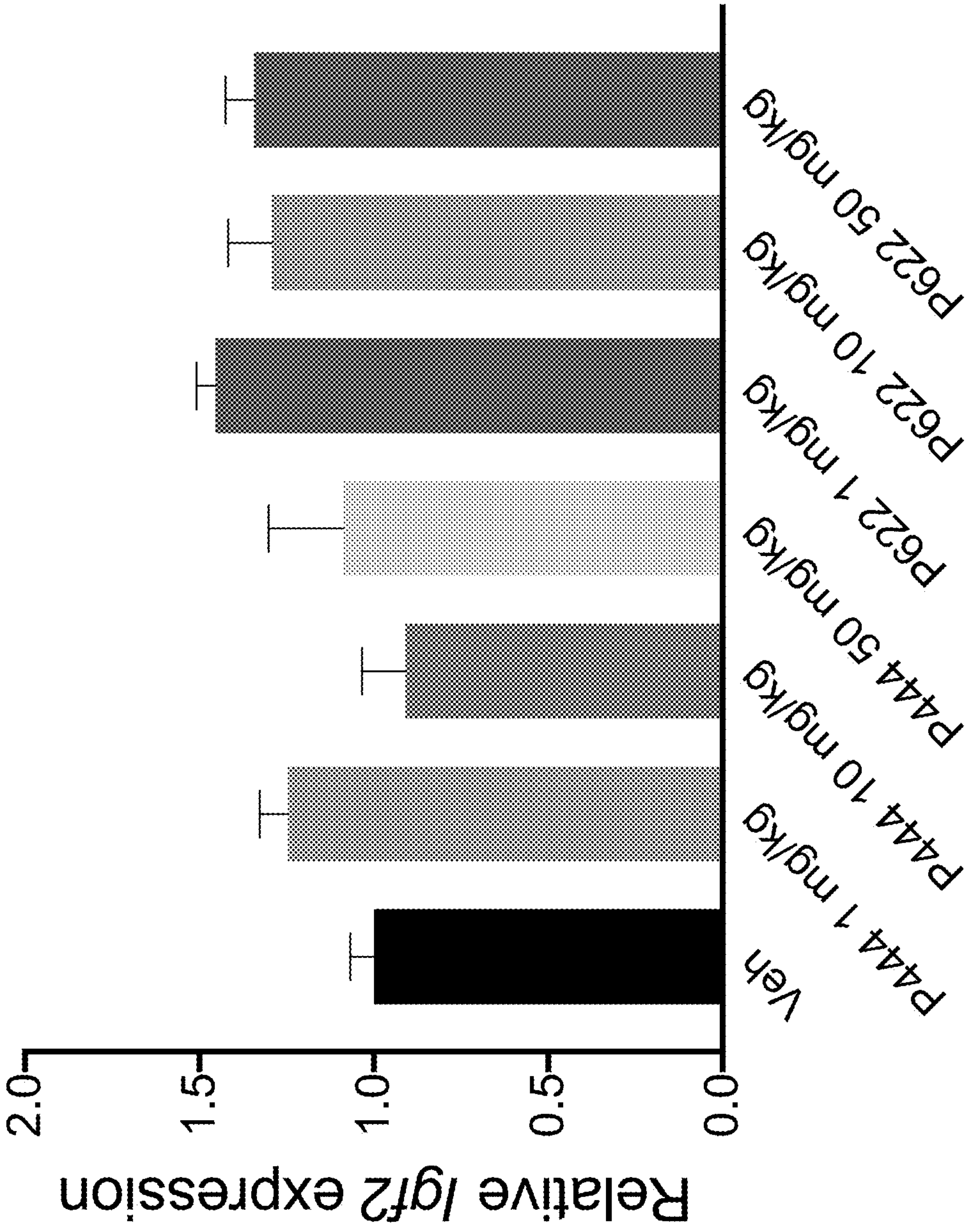

Further analyses were conducted on the effects of exemplary agents P444 and P622 on Mss51 and Igf2 gene expression in the gastrocnemius muscle (FIG. 33). P444 had no effect on either Mss51 (FIG. 33A) or Igf2 (FIG. 33B). On the other hand, P622 significantly and dose-dependently decreased Mss51 gene expression levels (FIG. 33A), which was comparable to what was previously observed in quadriceps (FIG. 19E). In the gastrocnemius, P622 had a modest effect on Igf2 mRNA levels (FIG. 33B).

Figure 34:
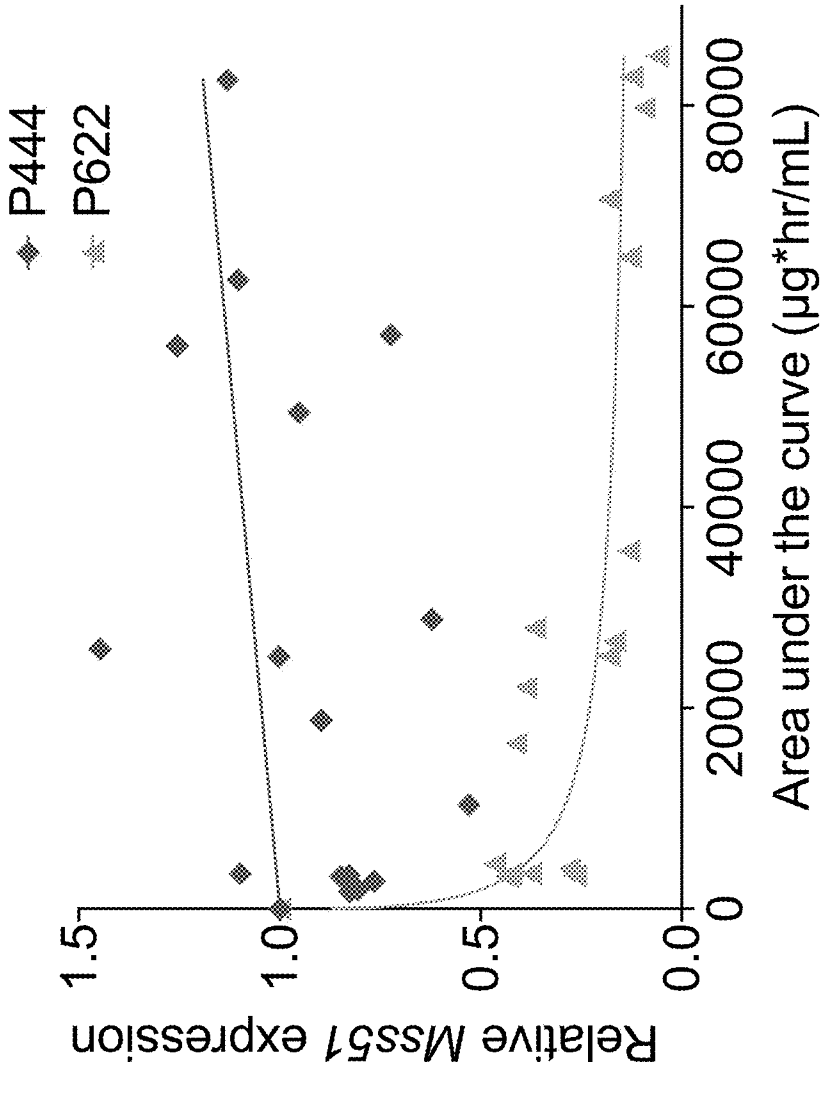
FIG. 34 shows the efficacy of exemplary agents P444 and P622 in vivo in relation to the exposure of each animal. Data from FIGS. 33A-33B were plotted against the exposure of each animal (area under the curve [AUC]), and a linear or non-linear fit was plotted using GraphPad Prism 9.0.
Figure 35A:
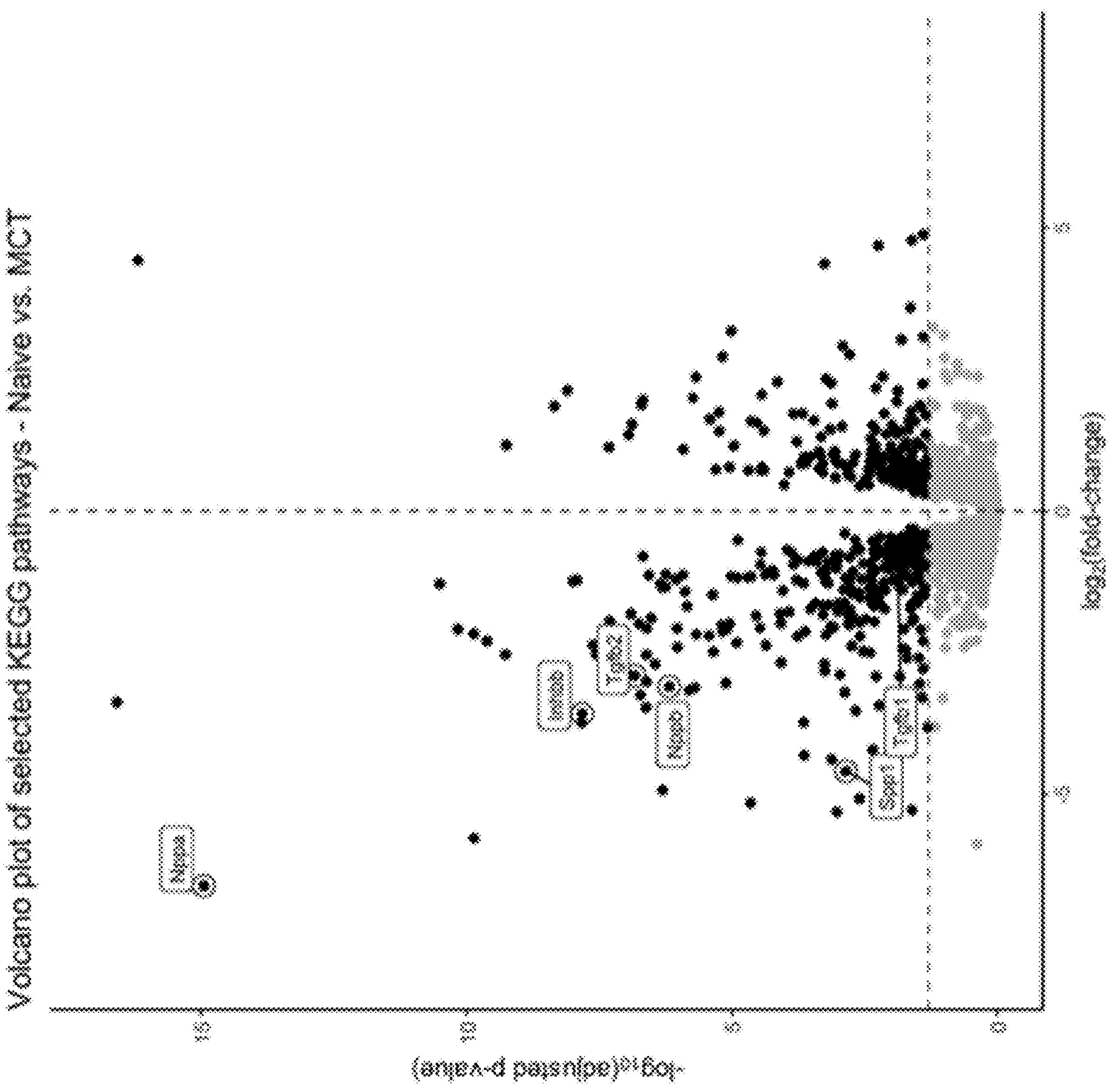
FIG. 35A-FIG. 35D shows volcano plots of genes associated with eight KEGG pathways, selected for their relevance to PH pathophysiology, and their expression levels in RV relative to MCT for naive animals (see FIG. 35A). Results for gene expression changes following treatment with exemplary agents P671, P674, and P670 are shown in FIG. 35B, FIG. 35C, and FIG. 35D, respectively. All genes are plotted as a function of their fold change expression (down- or up-regulated as log 2 fold change) and statistical significance (as −log 10 of adjusted p-value). Exemplary genes of interest related to the TGFβ signaling pathway and associated with heart failure are highlighted for each graph. Horizontal dashed lines denote a significance level of $p=0.05$.
Figure 35B:
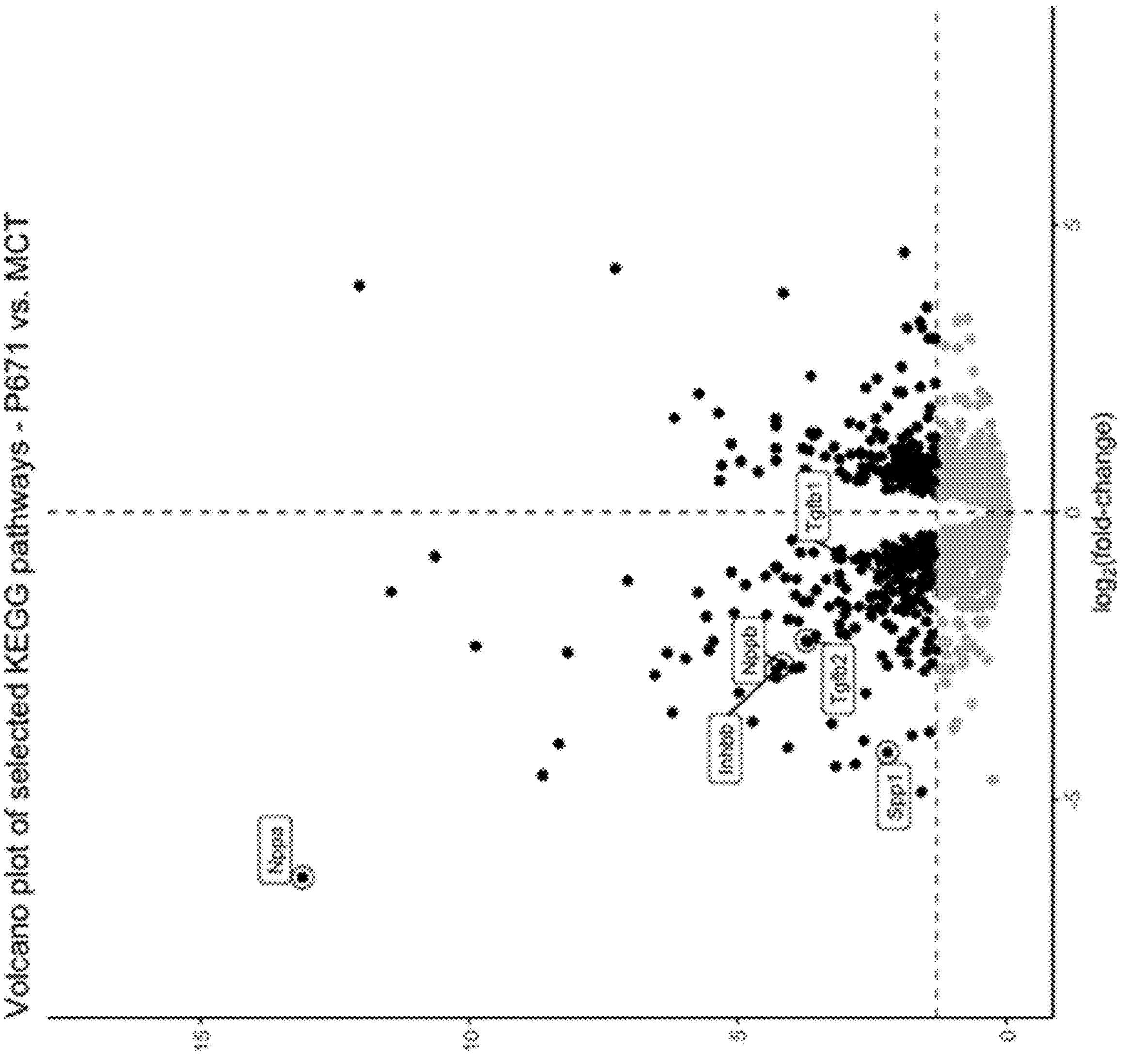
Figure 35C:
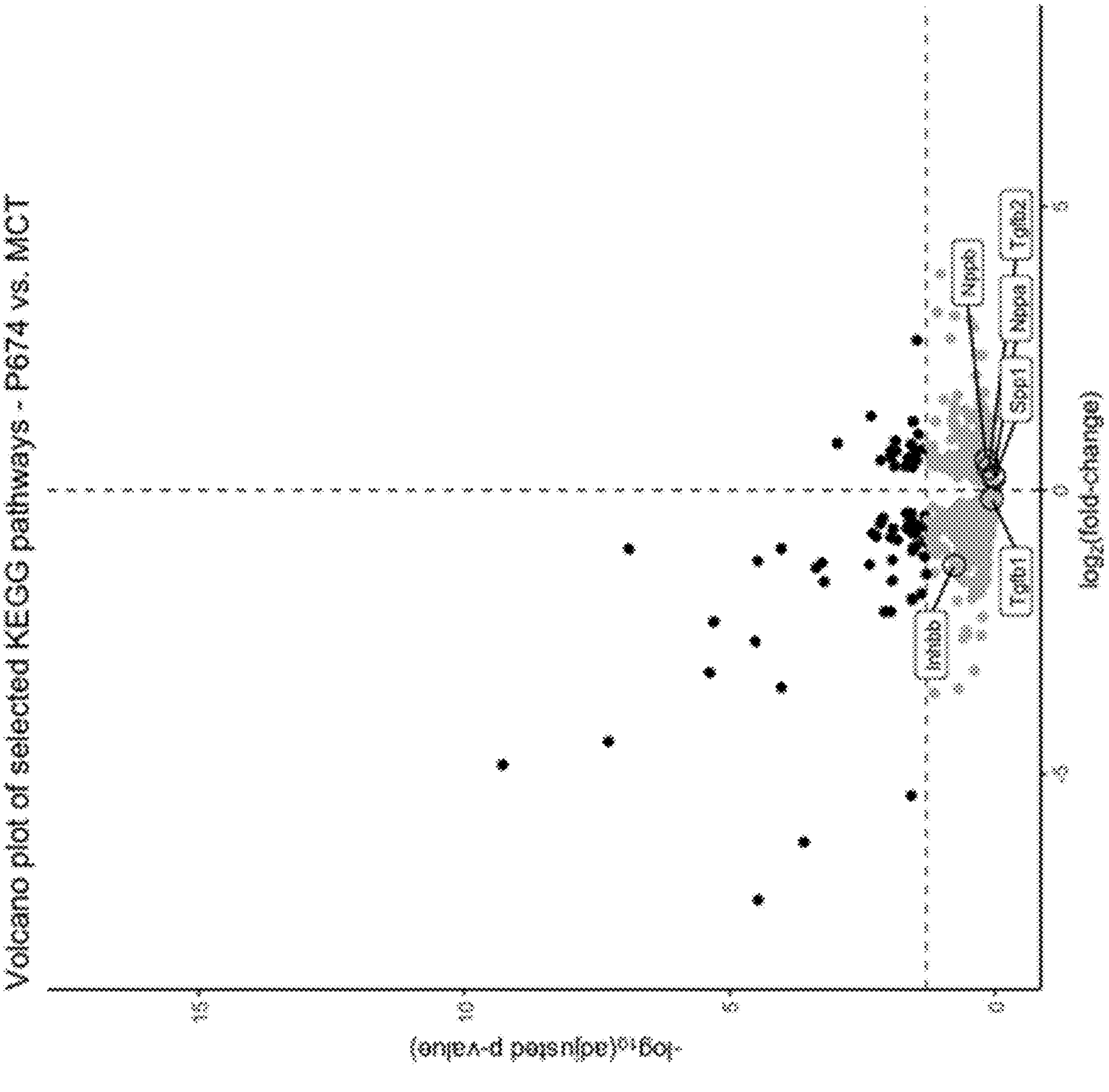
Figure 35D:
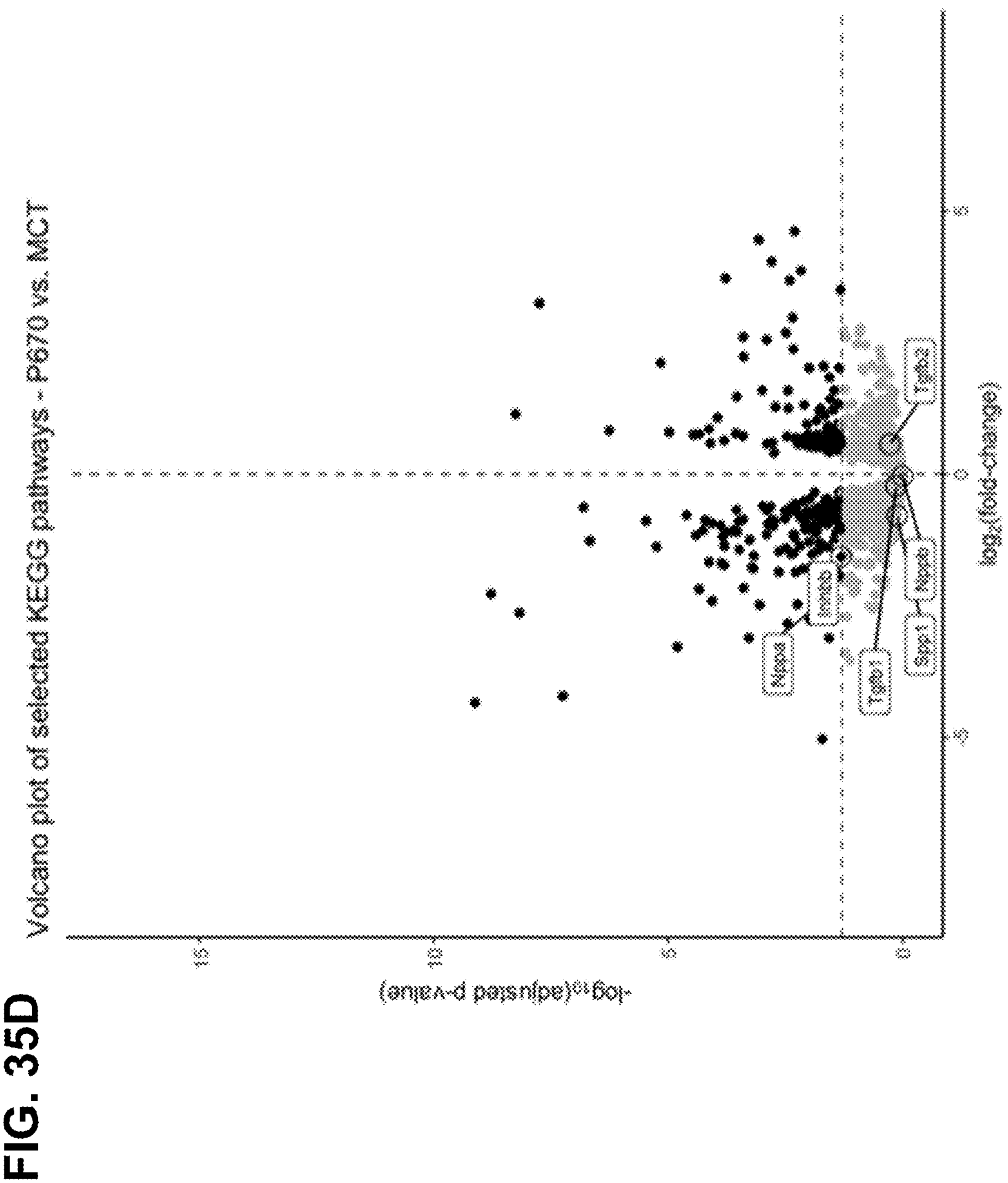

The exposure-target engagement relationship of P622 and P444 was further investigated (as described above) by correlating changes in Mss51 gene expression with the corresponding exposure (AUC) of the respective agent in each animal. P622 at similar exposures to P444 induced a greater decrease in Mss51 mRNA levels (FIG. 34) reaching an overall lower plateau which corresponds to near total suppression of Mss51 expression. These Mss51 and Igf2 gene expression data further demonstrate the superior potency of P622 compared to P444.

Although this invention is described in detail with reference to embodiments thereof, these embodiments are offered to illustrate but not to limit the invention. It is possible to make other embodiments that employ the principles of the invention and that fall within its spirit and scope as defined by the claims appended hereto.

The invention claimed is:

1. A polypeptide comprising:

(a) an Activin receptor type IIB (ActRIIB) ectodomain (ECD) variant comprising the amino acid sequence that is at least 85% identical to the amino acid sequence of SEQ ID NO: 2, wherein the ActRIIB-ECD variant comprises a substitution F58Q relative to the human wild type ActRIIB-ECD of SEQ ID NO: 2;

(b) a peptide linker comprising at least 10 amino acids; and (c) an immunoglobulin (Ig) Fc domain monomer.

2. The polypeptide of claim 1, wherein the ActRIIB ECD comprises the amino acid sequence that is at least 95% identical to SEQ ID NO: 9.

3. The polypeptide of claim 1, wherein the ActRIIB-ECD variant further comprises GRGEA (SEQ ID NO: 23) at the N terminus.

4. The polypeptide of claim 1, wherein the polypeptide comprises from N- to C-terminus: the ActRIIB-ECD-the peptide linker-the Ig Fc domain monomer.

5. The polypeptide of claim 1, wherein the Ig Fc domain monomer is an IgG1, IgG2, IgG3 or IgG4 isotype.

6. The polypeptide of claim 5, wherein the Ig Fc domain monomer comprises D at position 356 and L at position 358 (DL).

7. The polypeptide of claim 5, wherein the Ig Fc domain monomer comprises E at position 356 and M at position 358 (EM).

8. The polypeptide of claim 5, wherein the Ig Fc domain monomer further comprises lysine residue (K) at the C terminus.

9. The polypeptide of claim 1, wherein the Ig Fc domain monomer is engineered to reduce aggregation or to modulate stability of a dimer of the polypeptide.

10. The polypeptide of claim 9, wherein the Ig Fc domain monomer comprises the amino acid substitutions of M252Y, S254T, and T256E (YTE).

11. The polypeptide of claim 9, wherein the Ig Fc domain monomer comprises the M252Y amino acid substitution.

12. The polypeptide of claim 1, wherein the Ig Fc domain monomer comprises the amino acid sequence that is at least 85% identical to any one of SEQ ID NOs: 134-173 and 338.

13. The polypeptide of claim 12, wherein the Ig Fc domain monomer is:

(a) an IgG1 isotype and comprises the amino acid sequence of SEQ ID NO: 135 or SEQ ID NO: 134; or (b) an IgG2 isotype and comprises the amino acid sequence of SEQ ID NO: 157.

14. The polypeptide claim 1, wherein the peptide linker is between 10 and 40 amino acids in length.

15. The polypeptide of claim 14, wherein the peptide linker is 10 amino acids in length, 14 amino acids in length, 19 amino acids in length, or 39 amino acids in length.

16. The polypeptide of claim 14, wherein the peptide linker comprises the amino acid sequence of any one of SEQ ID NOs: 34, 54, or 59.

17. The polypeptide of claim 1, wherein the polypeptide comprises the amino acid sequence that is at least 95% identical to any one selected from the group consisting of SEQ ID NOs: 220-223 and 253.

18. The polypeptide of claim 1, wherein the polypeptide comprises the amino acid sequence selected from the group consisting of SEQ ID NOs: 220-223 and 253.

19. The polypeptide of claim 1, wherein the polypeptide further comprises an albumin-binding domain, a fibronectin domain, or a human serum albumin domain fused to the N- or C-terminus of the ActRIIB-ECD variant via a linker.

20. The polypeptide of claim 1, further comprising a signal peptide of SEQ ID NO: 1 at the N-terminus of the ActRIIB-ECD variant.

21. The polypeptide of claim 1, wherein the polypeptide binds to human activin A, activin B, growth differentiation factor (GDF)-8, GDF-11, and/or bone morphogenetic protein (BMP)-10; and has reduced binding to human BMP-9 relative to the binding of a human wild type ActRIIB-ECD to human BMP-9.

22. The polypeptide of claim 21, wherein the polypeptide does not substantially bind to human BMP-9.

23. The polypeptide of claim 21, wherein the polypeptide inhibits signaling of one or more of human activin A, activin B, GDF-8, GDF-11, and BMP-10.

24. The polypeptide of claim 21, wherein the polypeptide does not inhibit human BMP-9 signaling.

25. A pharmaceutical composition comprising the polypeptide of claim 1 and a pharmaceutically acceptable carrier, diluent or excipient.

26. The pharmaceutical composition of claim 25, wherein the composition is formulated for intravenous, subcutaneous, intraperitoneal, or intramuscular administration.

27. A transforming growth factor beta (TGFβ) superfamily ligand binding agent comprising a first polypeptide and a second polypeptide, wherein each of the first and second polypeptide comprises:

(a) an Activin receptor type IIB (ActRIIB) ectodomain (ECD) variant comprising the amino acid sequence that is at least 85% identical to the amino acid sequence of SEQ ID NO: 2, wherein the ActRIIB-ECD variant comprises F58Q substitution relative to the human wild type ActRIIB-ECD of SEQ ID NO: 2;

(b) a peptide linker comprising at least 10 amino acids; and (c) an immunoglobulin (Ig) Fc domain monomer, wherein the first and second polypeptides are linked by at least one disulfide bond between the Ig Fc domain monomer of the first polypeptide and the Ig Fc domain monomer of the second polypeptide.

28. The binding agent of claim 27, wherein each of the first polypeptide and the second polypeptide comprises the amino acid sequence that is at least 95% identical to a sequence selected from the group consisting of SEQ ID NOs: 220-223 and 253.

29. A method of treating a disease or condition associated with TGFβ-superfamily ligand signaling in a subject in need thereof, wherein the method comprises administering to said subject a therapeutically effective amount of the polypeptide of claim 1.

30. The method of claim 29, wherein the subject is a human.

31. The method of claim 29, wherein the disease or condition is selected from the group consisting of pulmonary hypertension (PH), fibrosis, muscle weakness or atrophy, metabolic disorders, cardiometabolic disease, bone damage, and low red blood cell levels.

32. The method of claim 31, wherein the PH is pulmonary arterial hypertension (PAH).

33. The method of claim 32, wherein the PAH is idiopathic PAH; heritable PAH; or PAH associated with an infection, a congenital heart abnormality, portal hypertension, pulmonary veno-occlusive disease, pulmonary capillary hemangiomatosis, connective tissue disorder, chronic obstructive pulmonary disease, autoimmune disorder, or drug use.

* * * * *